US008383637B2

(12) United States Patent
Baxter et al.

(10) Patent No.: US 8,383,637 B2
(45) Date of Patent: Feb. 26, 2013

(54) 2-AMINO-QUINAZOLINE DERIVATIVES USEFUL AS INHIBITORS OF β-SECRETASE (BACE)

(75) Inventors: Ellen Baxter, Glenside, PA (US); Francois Paul Bischoff, Vosselaar (BE); Robert E. Boyd, Horsham, PA (US); Mirielle Braeken, Vlimmeren (BE); Steve Coats, Quakertown, PA (US); Yifang Huang, Lansdale, PA (US); Alfonzo D. Jordan, North Wales, PA (US); Chi Luo, New Hope, PA (US); Marc Hubert Mercken, Turnhout (BE); Serge Maria Aloysius Pieters, AR Hulst (NL); Allen B. Reitz, Lansdale, PA (US); Charles H. Reynolds, Lansdale, PA (US); Tina Morgan Ross, Royersford, PA (US); Brett A. Tounge, Blue Bell, PA (US); Mark J. Schulz, Skippack, PA (US); Hans Louis Jos De Winter, Schilde (BE)

(73) Assignee: Janssen Pharmaceutica N.V., Beerse (BE)

( * ) Notice: Subject to any disclaimer, the term of this patent is extended or adjusted under 35 U.S.C. 154(b) by 1446 days.

(21) Appl. No.: 11/197,669

(22) Filed: Aug. 4, 2005

(65) Prior Publication Data

US 2006/0079687 A1    Apr. 13, 2006

Related U.S. Application Data

(60) Provisional application No. 60/599,811, filed on Aug. 6, 2004, provisional application No. 60/599,317, filed on Aug. 6, 2004, provisional application No. 60/599,810, filed on Aug. 6, 2004.

(51) Int. Cl.
| *A61K 31/517* | (2006.01) |
| *C07D 239/88* | (2006.01) |
| *C07D 239/94* | (2006.01) |
| *C07D 401/06* | (2006.01) |
| *A61K 31/535* | (2006.01) |
| *C07D 265/30* | (2006.01) |

(52) U.S. Cl. ............. 514/266.4; 514/266.2; 514/266.22; 514/231.5; 544/284; 544/292; 544/106
(58) Field of Classification Search ............... 514/231.5, 514/266.2, 266.22, 266.4; 544/106, 284, 544/292
See application file for complete search history.

(56) References Cited

U.S. PATENT DOCUMENTS

| 3,138,595 | A | | 6/1964 | Osdene et al. |
| 3,932,407 | A | | 1/1976 | Beverung, Jr. et al. |
| 3,983,120 | A | | 9/1976 | Beverung et al. |
| 3,988,340 | A | | 10/1976 | Partyka et al. |
| 4,001,237 | A | * | 1/1977 | Partyka et al. ................ 544/284 |
| 4,256,748 | A | | 3/1981 | Chodnekar et al. |
| 4,455,311 | A | | 6/1984 | Kienzle |
| 4,610,987 | A | | 9/1986 | Ishikawa |
| 4,675,047 | A | | 6/1987 | Serban et al. |
| 4,739,056 | A | | 4/1988 | Venuti et al. |
| 4,761,416 | A | | 8/1988 | Fried et al. |
| 4,783,467 | A | | 11/1988 | Campbell et al. |
| 5,387,742 | A | | 2/1995 | Cordell |
| 5,580,003 | A | | 12/1996 | Malone et al. |
| 5,612,486 | A | | 3/1997 | McConlogue et al. |
| 5,672,805 | A | | 9/1997 | Neve |
| 5,720,936 | A | | 2/1998 | Wadsworth et al. |
| 5,811,633 | A | | 9/1998 | Wadsworth et al. |
| 5,877,015 | A | | 3/1999 | Hardy et al. |
| 5,877,399 | A | | 3/1999 | Hsiao et al. |
| 6,037,521 | A | | 3/2000 | Sato et al. |
| 6,071,903 | A | * | 6/2000 | Albright et al. ................ 514/221 |
| 6,184,435 | B1 | | 2/2001 | Benson et al. |
| 6,187,922 | B1 | | 2/2001 | Geen et al. |
| 6,211,428 | B1 | | 4/2001 | Singh et al. |
| 6,340,783 | B1 | | 1/2002 | Snow |
| 7,531,545 | B2 | | 5/2009 | Baxter et al. |
| 2004/0087548 | A1 | | 5/2004 | Salvati et al. |
| 2004/0209905 | A1 | | 10/2004 | Kubo et al. |
| 2005/0171111 | A1 | | 8/2005 | Angibaud et al. |
| 2006/0074105 | A1 | | 4/2006 | Ware et al. |
| 2006/0079686 | A1 | | 4/2006 | Baxter et al. |
| 2006/0178383 | A1 | | 8/2006 | Bischoff et al. |
| 2007/0232642 | A1 | | 10/2007 | Baxter et al. |
| 2008/0194624 | A1 | | 8/2008 | Baxter et al. |
| 2009/0227581 | A1 | | 9/2009 | Baxter et al. |
| 2009/0227627 | A1 | | 9/2009 | Baxter et al. |

FOREIGN PATENT DOCUMENTS

| CA | 1131631 | 9/1982 |
| EP | 0406958 | 1/1991 |
| EP | 0371564 | 7/1995 |
| EP | 1407774 | 4/2004 |
| JP | 54-041894 | 4/1979 |
| JP | 56-007786 | 1/1981 |
| JP | 57-123184 | 7/1982 |
| JP | 58-46088 | 6/1984 |
| JP | 60-028979 | 2/1985 |
| JP | 61-282385 | 12/1986 |
| JP | 63-196573 | 8/1988 |

(Continued)

OTHER PUBLICATIONS

Database Caplus "Online!" Chemical Abstracts Service, Columbus, Ohio, US. Ishikawa, Fumyoshi et al.: "Quinazolineacetic acid derivatives as platelet aggregation inhibitors". XP00236713, 1989.

(Continued)

*Primary Examiner* — Alexander R Pagano
(74) *Attorney, Agent, or Firm* — Hal B. Woodrow

(57) ABSTRACT

The present invention is directed to novel 2-amino-3,4-dihydro-quinazoline derivatives, pharmaceutical compositions containing them and their use in the treatment of Alzheimer's disease (AD) and related disorders. The compounds of the invention are inhibitors of β-secretase, also known as β-site cleaving enzyme and BACE.

13 Claims, No Drawings

FOREIGN PATENT DOCUMENTS

| | | |
|---|---|---|
| JP | 64-61468 | 3/1989 |
| JP | 04 011255 | 1/1992 |
| JP | 8-151377 | 6/1996 |
| WO | 01/38314 | 5/2001 |
| WO | 01/38315 | 5/2001 |
| WO | WO 01/88314 | 5/2001 |
| WO | 02/100399 | 12/2002 |
| WO | WO 2004/022523 | 3/2004 |
| WO | 2004/063172 | 7/2004 |
| WO | WO 2004/058686 | 7/2004 |
| WO | 2004/082616 | 9/2004 |
| WO | WO 2005/049585 | 6/2005 |
| WO | 2006/017836 | 2/2006 |
| WO | 2006/017844 | 2/2006 |
| WO | 2006/024932 | 3/2006 |
| WO | 2006/078577 | 7/2006 |
| WO | 2007/050612 | 5/2007 |
| WO | 2007/092846 | 8/2007 |
| WO | 2007/092854 | 8/2007 |

OTHER PUBLICATIONS

Bakke, J. M.; Lorentzen, G. B. *Acta Chem. Scand. B* 1974, 28, 650.
Baumgarth, M.; Beier, N.; Gericke, R. *J. Med. Chem.* 1998, 41, 3736.
Burk, M. J.; Gross, M. F.; Martinez, J. P. *J. Am. Chem. Soc.* 1995, 117, 9375.
Deloux, L.; Srebnik, M. *J. Org. Chem.* 1994, 59, 6871.
Fernandez et al., Org. Biomol. Chem., 2003, 1, 767-771.
Ford et al., J. Med. Chem. 1985, 28, 164.
Hintermann, T.; Gademann, K.; Jaun, B. Seebach, D. *Helv. Chim. Acta* 1998, 81, 983.
Hu, Y.-Z., Zhang, G., and Thummel, R.P., Org. Lett., vol. 5, 2003, p. 2251.
Jung, M. E.; Lam, P. Y.-S.; Mansuri, M. M.; Speltz, L. M. *J. Org. Chem.* 1985, 50, 1087.
Jung, M.E. and Dansereau, S.M.K., Heterocycles, vol. 39, 1994, p. 767.
Katritzky, A.R., Chassaing, C., Toader D. and Gill, K., J. Chem. Research, (S), 1999, pp. 504-505.
Katritzky, A.R., Lang, H., Wang, Z., Zhang, Z. and Song, H., J. Org. Chem., 60, 1990, pp. 7619-7624.
Lhermitte, F.; Carboni, B. *Synlett*, 1996, 377.
Matsubara, S.; Otake, Y.; Hashimoto, Y.; Utimoto, K. *Chem. Lett.* 1999, 747.
Miyaura, N.; Suzuki, A. *Chem. Rev.* 1995, 95, 2457.
Osdene, Thomas S. et al. Journal of Medicinal Chemistry (1967), 10(2), 165-7.
Smrcina, M.; Majer, P.; Majerová, E.; Guerassiná, T. A.; Eissenstat, M. A. *Tetrahedron* 1997, 53, 12867.
Suzuki, A. *J. Organomet. Chem.* 1999, 576, 147.
Takai, K.; Shinomiya, N.; Kaihara, H.; Yoshida, N.; Moriwake, T. *Synlett* 1995, 963.
Vetelino, M.G. and Coe, J.W., Tetrahedron Lett., 35(2), 1994, pp. 219-222.
Yang, D.; Yip, Y.-C.; Jiao, G.-S.; Wong, M.-K. *Org. Synth.* 2000, 78, 225.
Citron, Trends in Pharm. Sci., vol. 25, Issue 2, Feb. 2004, 92-97.
Cole, et al., Molecular Neurodegeneration 2007, 2:22.
Hamaguchi, et al., Cell. Mol. Life Sci. 63 (2006) 1538-1552.
Kienzle, Frank et al: "I,5-Dihydroimidazoquinazolinones as blood platelet aggregation inhibitors", European Journal of Medicinal Chemistry, 17(6), S47-S6 Coden: EJMCAS; ISSN: 0009-4374, 1982.
Larner, A.J.: "Secretases as Therapeutic Targets in Alzheimer's Disease: Patents 2000 2004". Expert Opinion on Therapeutic Patents, Ashley Publications, GB, vol. 14, No. 10, 2004, pp. 1403-1420, XP002404250.
Venuti, M., et al. Inhibitors of Cyclic AMP Phosphodiestrase 2 Structural Variations of N-Cyclohexyl-N-Methyl-4-(1,2,3,5-Tetrahydro-2-Oxoimidazo 2,1-B Quinazo-7-yl-Oxybutyramids J. Medicinal Chemistry, American Chemical Society, vol. 30, No. 2, 1987, pp. 303-318.
Webb, Thomas Hand Wilcox: "Improved Synthesis of Symmetrical and Unsymmterical 5,11-methandibenzo'b,f!'1,5!-diazocines. Readily Available Nanoscale Structural Units" Journal of Organic Chemistry, vol. 55, No. 1, 1990, pp. 363-365.
Office Action mailed Jun. 19, 2009 in U.S. Appl. No. 11/671,681.
Office Action mailed Sep. 29, 2009 in U.S. Appl. No. 11/671,681.
Office Action mailed Jun. 19, 2008 in U.S. Appl. No. 11/671,703.
Office Action mailed Aug. 20, 2008 in U.S. Appl. No. 11/671,703.
Office Action mailed Feb. 12, 2009 in U.S. Appl. No. 11/671,703.
Office Action mailed Jun. 9, 2009 in U.S. Appl. No. 11/671,703.
Notice of Allowance mailed Nov. 19, 2009 in U.S. Appl. No. 11/671,703.
Office Action mailed Mar. 24, 2009 in U.S. Appl. No. 11/671,732.
Notice of Allowance mailed Sep. 25, 2009 in U.S. Appl. No. 11/671,732.
Notice of Allowance mailed Jan. 6, 2010 in U.S. Appl. No. 11/671,732.
Office Action mailed May 30, 2008 in U.S. Appl. No. 11/197,608.
Office Action mailed Aug. 20, 2008 in U.S. Appl. No. 11/197,608.
Office Action mailed Apr. 30, 2009 in U.S. Appl. No. 11/197,608.
Notice of Allowance mailed Dec. 8, 2009 in U.S. Appl. No. 11/197,608.
Office Action mailed May 29, 2008 in U.S. Appl. No. 11/197,615.
Office Action mailed Jan. 27, 2009 in U.S. Appl. No. 11/197,615.
Office Action mailed Sep. 10, 2009 in U.S. Appl. No. 12/362,020.
Notice of Allowance mailed Dec. 24, 2009 in U.S. Appl. No. 12/362,020.
Ermolieff et al., Biochemistry, (2000) vol. 39, p. 12450.
El Mouedden, M. et al., (Johnson & Johnson Pharmaceutical Research and Development, Division of Janssen Pharmaceutica N.V., Turnhoutseweg 30, Beerse, Belg.), Development of a specific ELISA for the quantitative study of amino-terminally truncated beta-amyloid peptides,. Journal of Neuroscience Methods (2005), 145(1-2), pp. 97-105.
Games, D. et al., (Athena Neurosciences, Inc., South San Francisco, CA, USA), Alzheimer-type neuropathology in transgenic mice overexpressing V717F b-amyloid precursor protein, Nature (London) (1995), 373(6514), pp. 523-527 (V717F mice).
Hsiao, K. et al., (Dep. Neurology, Univ. Minnesota, Minneapolis, MN, USA), Correlative memory deficits, Ab elevation, and amyloid plaques in transgenic mice, Science (Washington, D.C.) (1996), 274(5284), pp. 99-102 (Tg2576 mice).
Patent Abstracts of Japan, Vo. 016, No. 160 (p-1340) Apr. 20, 1992, JP 04 011255 (Fuji Photo Film Co.. td.) Jan. 16, 1992, p. 5, compound 20.
Kienzle, F. et. al., Chemical Abstract, 1983, vol. 98, Abstract No. 143363, (or CAPLUS Accession No. 1983:143363).
Lewczuk, P. et al., (Department of Psychiatry and Psychotherapy, Molecular Neurobiology Lab, University of Erlangen-Nuremberg, Erlangen, Germany), Neurochemical diagnosis of Alzheimer's dementia by CSF Ab42, Ab42/Ab40 ratio and total tau, Neurobiology of Aging (2004), 25(3), pp. 273-281.
Lins, H. et al., (Department of Neurology, Otto-von-Guericke-University, Magdeburg, Germany), Immunoreactivities of amyloid b peptide(1-42) and total t protein in lumbar cerebrospinal fluid of patients with normal pressure hydrocephalus, Journal of Neural Transmission (2004), 111(3), pp. 273-280.
Neve, R. L. et al., (Dep. Genetics, Harvard Medical School and McLean Hospital, Belmont, MA, USA), Transgenic mice expressing APP-C100 in the brain, Neurobiology of Aging (1996), 17(2), pp. 191-203 (APP-C100 mice).
Notice of Allowance mailed May 4, 2010 in U.S. Appl. No. 11/671,681.
Notice of Allowance mailed Aug. 23, 2010 in U.S. Appl. No. 11/671,681.
Notice of Allowance mailed Mar. 17, 2010 in U.S. Appl. No. 11/671,703.
Notice of Allowance mailed Apr. 16, 2010 in U.S. Appl. No. 11/671,732.
Notice of Allowance mailed Jul. 26, 2010 in U.S. Appl. No. 11/671,732.
Notice of Allowance mailed Dec. 15, 2010 in U.S. Appl. No. 11/671,732.

Notice of Allowance mailed Apr. 19, 2010 in U.S. Appl. No. 11/197,615.
Oddo, S. et al, (Department of Neurobiology and Behavior, University of California, Irvine, Irvine, CA, USA), Triple-transgenic model of Alzheimer's disease with plaques and tangles: Intracellular Ab and synaptic dysfunction, Neuron (2003), 39(3), pp. 409-421 (APP Triple Transgenic Mice).
Office Action mailed Sep. 29, 2009 in U.S. Appl. No. 11/197,615.
Olsson, A. et al., (Sahlgrenska University Hospital, Experimental Neuroscience Section, Institute of Clinical Neuroscience, Goteborg University, Moelndal, Sweden), Measurement of a- and b-secretase cleaved amyloid precursor protein in cerebrospinal fluid from Alzheimer patients, Experimental Neurology (2003), 183(1), pp. 74-80.
Ruberti et al., (Neuroscience Program, International School for Advanced Studies (SISSA), Trieste, Italy), Phenotypic knockout of nerve growth factor in adult transgenic mice reveals severe deficits in basal forebrain cholinergic neurons, cell death in the spleen, and skeletal muscle dystrophy, Journal of Neuroscience (2000), 20(7), pp. 2589-2601 (AD11 mice).
Schoonenboom, N.S. et al., Amyloid b 38, 40, and 42 species in cerebrospinal fluid: More of the same?, Annals of Neurology (2005), 58(1), pp. 139-142.
Sirinathsinghji, D. J. S. (Merck Sharp and Dohme Research Laboratories, Neuroscience Research Centre, Essex, UK.), Transgenic mouse models of Alzheimer's disease, Biochemical Society Transactions (1998), 26(3), pp. 504-508.
Van Leuven, F. (Experimental Genetics Group, Center for Human Genetics, Flemish Institute for Biotechnology (VIB), K.U.Leuven, Louvain, Belg.), Single and multiple transgenic mice as models for Alzheimer's disease, Progress in Neurobiology (Oxford) (2000), 61(3), pp. 305-312.
Vanderstichele, H. et al., (Innogenetics NV, Ghent, Belg.), Standardization of measurement of b-amyloid(1-42) in cerebrospinal fluid and plasma, Amyloid (2000), 7(4), pp. 245-258.
Wahlund, L.-O et al., (Karolinska Institute, Section of Geriatric Medicine, Department of Clinical Neuroscience and Family Medicine, Huddinge University Hospital, Stockholm, Sweden), Cerebrospinal fluid biomarkers for disease stage and intensity in cognitively impaired patients, Neuroscience Letters (2003), 339(2), pp. 99-102.
Office Action mailed Apr. 28, 2011 in U.S. Appl. No. 11/197,608.
Notice of Allowance mailed Feb. 15, 2012 in U.S. Appl. No. 11/197,608.
Notice of Allowance mailed Feb. 28, 2012 in U.S. Appl. No. 11/197,615.
Office Action mailed Jan. 7, 2011 in U.S. Appl. No. 12/360,611.
Notice of Allowance mailed Mar. 11, 2011 in U.S. Appl. No. 12/360,611.
Notice of Allowance mailed Jul. 13, 2011 in U.S. Appl. No. 12/360,611.
Notice of Allowance mailed Jun. 11, 2012 in U.S. Appl. No. 11/197,608.
Notice of Allowance mailed Jun. 25, 2012 in U.S. Appl. No. 11/197,615.
Notice of Allowance mailed Apr. 14, 2010 in U.S. Appl. No. 12/362,020.

* cited by examiner

SEQUENCE LISTING

```
<160> NUMBER OF SEQ ID NOS: 4

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Glu-Aedens
<220> FEATURE:
<221> NAME/KEY: MOD_RES
<222> LOCATION: (13)..(13)
<223> OTHER INFORMATION: Lys-Dabcyl

<400> SEQUENCE: 1

Arg Glu Glu Glu Val Asn Leu Asp Ala Glu Phe Lys Lys Arg
```

```
1               5                  10

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu-Aedens
<220> FEATURE:
<221> NAME/KEY: MOD_RES
<222> LOCATION: (9)..(9)
<223> OTHER INFORMATION: Lys-Dabcyl
<220> FEATURE:
<223> OTHER INFORMATION: C-term amidated

<400> SEQUENCE: 2

Glu Val Asn Leu Asp Ala Glu Phe Lys
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Methyl cumaryl amide-Ser
<220> FEATURE:
<223> OTHER INFORMATION: C-term amidated

<400> SEQUENCE: 3

Ser Glu Val Asn Leu
1               5

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Methyl cumaryl amide-Ser
<220> FEATURE:
<221> NAME/KEY: MOD_RES
<222> LOCATION: (11)..(11)
<223> OTHER INFORMATION: Dinitrophenyl-Lys
<220> FEATURE:
<223> OTHER INFORMATION: C-term amidated

<400> SEQUENCE: 4

Ser Glu Val Asn Leu Asp Ala Glu Phe Arg Lys Arg Arg
1               5                  10
```

2-AMINO-QUINAZOLINE DERIVATIVES USEFUL AS INHIBITORS OF β-SECRETASE (BACE)

CROSS REFERENCE TO RELATED APPLICATIONS

This application claims the benefit of U.S. Provisional Application Ser. No. 60/599,811, filed on Aug. 6, 2004, U.S. Provisional Application Ser. No. 60/599,317, filed on Aug. 6, 2004, and U.S. Provisional Application Ser. No. 60/599,810, filed on Aug. 6, 2004, which are incorporated by reference herein in their entirety.

FIELD OF THE INVENTION

The present invention is directed to novel 2-amino-3,4-dihydro-quinazoline derivatives, pharmaceutical compositions containing them and their use in the treatment of Alzheimer's disease (AD), mild cognitive impairment, senility and/or dementia. The compounds of the present invention are inhibitors of β-secretase, also known as β-site amyloid cleaving enzyme, BACE, BACE1, Asp2, or memapsin2.

BACKGROUND OF THE INVENTION

Alzheimer's Disease (AD) is a neurodegenerative disease associated with aging. AD patients suffer from cognition deficits and memory loss as well as behavioral problems such as anxiety. Over 90% of those afflicted with AD have a sporadic form of the disorder while less than 10% of the cases are familial or hereditary. In the United States, about 1 in 10 people at age 65 have AD while at age 85, 1 out of every two individuals are affected with AD. The average life expectancy from the initial diagnosis is 7-10 years, and AD patients require extensive care either in an assisted living facility which is very costly or by family members. With the increasing number of elderly in the population, AD is a growing medical concern. Currently available therapies for AD merely treat the symptoms of the disease and include acetylcholinesterase inhibitors to improve cognitive properties as well as anxiolytics and antipsychotics to control the behavioral problems associated with this ailment.

The hallmark pathological features in the brain of AD patients are neurofibrillary tangles which are generated by hyperphosphorylation of tau protein and amyloid plaques which form by aggregation of β-amyloid$_{1-42}$ (Aβ$_{1-42}$) peptide. Aβ$_{1-42}$ forms oligomers and then fibrils, and ultimately amyloid plaques. The fibrils are believed to be especially neurotoxic and may cause most of the neurological damage associated with AD. Agents that prevent the formation of Aβ$_{1-42}$ have the potential to be disease-modifying agents for the treatment of AD. Aβ$_{1-42}$ is generated from the amyloid precursor protein (APP), comprised of 770 amino acids. The N-terminus of Aβ$_{1-42}$ is cleaved by β-secretase (BACE), and then γ-secretase cleaves the C-terminal end. In addition to Aβ$_{1-42}$, γ-secretase also liberates Aβ$_{1-40}$ which is the predominant cleavage product as along with Aβ$_{1-38}$ and Aβ$_{1-43}$. Thus, inhibitors of BACE would be expected to prevent the formation of Aβ$_{1-42}$ and would be potential therapeutic agents in the treatment of AD.

SUMMARY OF THE INVENTION

The present invention is directed to compounds of formula (I)

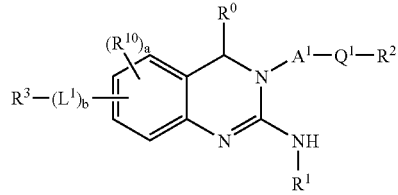

(I)

wherein $R^0$ is selected from the group consisting of hydrogen, methyl and $CF_3$;

$R^1$ is selected from the group consisting of hydrogen, hydroxy, methyl, ethyl, trifluoromethyl, 2,2,2-trifluoroethyl, methoxy, ethoxy and methyl-carbonyl;

$A^1$ is selected from the group consisting of $C_{1-4}$alkyl; wherein the $C_{1-4}$alkyl is optionally substituted with one or more $R^X$ substituents;

wherein each $R^X$ is independently selected from the group consisting of hydroxy, oxo, $C_{1-8}$alkyl, $C_{1-8}$alkoxy, hydroxy substituted $C_{1-6}$alkyl, amino substituted $C_{1-6}$alkyl, cycloalkyl, cycloalkyl-$C_{1-4}$alkyl-, biphenyl, aryl, $C_{1-4}$aralkyl, heteroaryl, heteroaryl-$C_{1-4}$alkyl-, heterocycloalkyl, heterocycloalkyl-$C_{1-4}$alkyl-, spiro-heterocyclyl and —($C_{1-4}$alkyl)$_n$-$Q^2$-$R^4$;

wherein the cycloalkyl, aryl, heteroaryl, heterocycloalkyl or spiro-heterocyclyl group, whether alone or as part of a substituent group is optionally substituted with one or more substituents independently selected from the group consisting of fluoro, chloro, hydroxy, oxo, carboxy, $C_{1-4}$alkyl, $C_{1-4}$alkoxy, —C(O)O—($C_{1-4}$alkyl), hydroxy substituted $C_{1-4}$alkyl, fluoro substituted $C_{1-4}$alkyl, fluoro substituted $C_{1-4}$alkoxy, 5-tetrazolyl and 1-(1,4-dihydro-tetrazol-5-one);

wherein n is an integer from 0 to 1;

wherein $Q^2$ is selected from the group consisting of —O—, —S—, —C(O)—, —C(S)—, —C(O)O—, —OC(O)—, —NR$^G$—, —NR$^G$—C(O)—, —C(O)—NR$^G$—, —NR$^G$—SO$_2$—, —SO$_2$—NR$^G$—, —NR$^G$—SO—, —SO—NR$^G$—, —NR$^G$—C(O)O—, —OC(O)—NR$^G$—, —O—SO$_2$—NR$^G$—, —NR$^G$—SO$_2$—O—, —NR$^G$—C(O)—NR$^H$—, —NR$^G$—C(S)—NR$^H$— and —NR$^G$—SO$_2$—NR$^H$—;

wherein each $R^G$ and $R^H$ is independently selected from the group consisting of hydrogen, $C_{1-8}$alkyl, hydroxy substituted $C_{1-4}$alkyl, $C_{1-4}$aralkyloxy substituted $C_{1-4}$alkyl, cycloalkyl, aryl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;

wherein the cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, $C_{1-4}$alkyl, $C_{1-4}$alkoxy, $C_{1-4}$alkoxy-carbonyl, nitro, cyano, amino, $C_{1-4}$alkylamino, di($C_{1-4}$alkyl) amino, —SO$_2$—N($R^J R^K$), 5-tetrazolyl and 1-(1,4-dihydro-tetrazol-5-one);

wherein each $R^J$ and $R^K$ is independently selected from from the group consisting of hydrogen and $C_{1-4}$alkyl;

wherein $R^4$ is selected from the group consisting of hydrogen, $C_{1-4}$alkyl, hydroxy substituted $C_{1-4}$alkyl, fluoro substituted $C_{1-4}$alkyl, cycloalkyl, aryl, biphenyl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;

wherein the cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, —C(O)O—$C_{1-4}$alkyl, —C(O)—$C_{1-4}$alkyl, $C_{1-4}$alkyl, fluoro substituted $C_{1-4}$alkyl, $C_{1-4}$alkoxy, nitro, cyano, amino, $C_{1-4}$alkylamino, di($C_{1-4}$alkyl)amino and phenyl;

wherein the phenyl is optionally substituted with one or more substituent independently selected from the group consisting of halogen, hydroxy, oxo, carboxy, —C(O)O—$C_{1-4}$alkyl, —C(O)—$C_{1-4}$alkyl, $C_{1-4}$alkyl, fluoro substituted $C_{1-4}$alkyl, $C_{1-4}$alkoxy, nitro, cyano, amino, $C_{1-4}$alkylamino, di($C_{1-4}$alkyl)amino and —$SO_2$—N($R^E R^F$);

wherein each $R^E$ and $R^F$ is independently selected from the group consisting of hydrogen and $C_{1-4}$alkyl;

$Q^1$ is selected from the group consisting of —O—, —S—, —C(O)—, —C(S)—, —C(O)O—, —OC(O)—, —$NR^A$—, —$NR^A$—C(O), —C(O)—$NR^A$—, —$NR^A$—C(S)—, —C(S)—$NR^A$—, —$NR^A$—$SO_2$—, —$SO_2$—$NR^A$—, —$NR^A$—SO—, —SO—$NR^A$—, —$NR^A$—C(O)O—, —OC(O)—$NR^A$—, —O—$SO_2$—$NR^A$—, —$NR^A$—$SO_2$—O—, —$NR^A$—C(O)—$NR^B$—, —$NR^A$—C(S)—$NR^B$— and —$NR^A$—$SO_2$—$NR^B$—;

wherein each $R^A$ and $R^B$ is independently selected from the group consisting of hydrogen, $C_{1-8}$alkyl, hydroxy substituted $C_{1-4}$alkyl, $C_{1-4}$aralkyloxy substituted $C_{1-4}$alkyl, cycloalkyl, aryl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;

wherein the cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, $C_{1-4}$alkyl, $C_{1-4}$alkoxy, $C_{1-4}$alkoxycarbonyl, nitro, cyano, amino, $C_{1-4}$alkylamino, di($C_{1-4}$alkyl)amino, —$SO_2$—N($R^C R^D$), 5-tetrazolyl and 1-(1,4-dihydro-tetrazol-5-one);

wherein each $R^C$ and $R^D$ is independently selected from the group consisting of hydrogen and $C_{1-4}$alkyl;

$R^2$ is selected from the group consisting of $C_{1-10}$alkyl, cycloalkyl, aryl, biphenyl, partially unsaturated carbocyclyl, heteroaryl, heterocycloalkyl, cycloalkyl-$C_{1-4}$alkyl-, $C_{1-4}$aralkyl, partially unsaturated carbocyclyl-$C_{1-4}$alkyl-, heteroaryl-$C_{1-4}$alkyl-, heterocycloalkyl-$C_{1-4}$alkyl- and spiro-heterocyclyl;

wherein the $C_{1-10}$alkyl, cycloalkyl, aryl, partially unsaturated carbocyclyl, heteroaryl, heterocycloalkyl or spiro-heterocyclyl, whether alone or as part of a substituent group is optionally substituted with one or more substituents independently selected from the group consisting of halogen, hydroxy, oxo, carboxy, —C(O)—$C_{1-4}$alkyl, —C(O)—$C_{1-4}$aralkyl, —C(O)O—$C_{1-4}$alkyl, —C(O)O—$C_{1-4}$aralkyl, —$C_{1-4}$alkyl-C(O)O—$C_{1-4}$alkyl, —$C_{1-4}$alkyl-S—$C_{1-4}$alkyl, —C(O)—N($R^L R^M$), —$C_{1-4}$alkyl-C(O)—N($R^L R^M$), —$NR^L$—C(O)—$C_{1-4}$alkyl, —$SO_2$—N($R^L R^M$), —$C_{1-4}$alkyl-$SO_2$—N($R^L R^M$), $C_{1-6}$alkyl, fluoro substituted $C_{1-4}$alkyl, hydroxy substituted $C_{1-4}$alkyl, carboxy substituted $C_{1-4}$alkyl, $C_{1-4}$alkoxy, —O—$C_{1-4}$aralkyl, —O-(tetrahydropyranyl), —NH—C(O)O—$CH_2$—-(tetrahydropyranyl), —N($CH_3$)—C(O)O—$CH_2$—-(tetrahydropyranyl), nitro, cyano, amino, $C_{1-4}$alkylamino, di($C_{1-4}$alkyl)amino, phenyl, 5-tetrazolyl and 1-(1,4-dihydro-tetrazol-5-one);

wherein the phenyl or tetrahydropyranyl is optionally substituted with one or more substituent independently selected from the group consisting of halogen, hydroxy, oxo, carboxy, —C(O)O—$C_{1-4}$alkyl, —C(O)—$C_{1-4}$alkyl, —OC(O)—$C_{1-4}$alkyl, —$C_{1-4}$alkyl-OC(O)—$C_{1-4}$alkyl, —O—$C_{1-4}$aralkyl, $C_{1-4}$alkyl, fluoro substituted $C_{1-4}$alkyl, hydroxy substituted $C_{1-4}$alkyl, $C_{1-4}$alkoxy, nitro, cyano, amino, $C_{1-4}$alkylamino and di($C_{1-4}$alkyl)amino;

wherein each $R^L$ and $R^M$ is independently selected from the group consisting of hydrogen and $C_{1-4}$alkyl;

b is an integer from 0 to 1;

$L^1$ is selected from the group consisting of —O—, —$S(O)_{0-2}$—, —$NR^N$—, —C(O)—, —C(S)—, —$C_{1-4}$alkyl-, -(hydroxy substituted $C_{1-4}$alkyl)- and —($C_{2-4}$alkenyl)-;

wherein $R^N$ is selected from the group consisting of hydrogen and $C_{1-4}$alkyl;

$R^3$ is selected from the group consisting of $C_{1-6}$alkyl, $C_{2-6}$alkenyl, cycloalkyl, partially unsaturated carbocyclyl, aryl, biphenyl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;

wherein the $C_{1-6}$alkyl, cycloalkyl, partially unsaturated carbocyclyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, $C_{1-4}$alkyl, hydroxy substituted $C_{1-4}$alkyl, halogen substituted $C_{1-4}$alkyl, cyano substituted $C_{1-4}$alkyl, $C_{2-4}$alkenyl, $C_{2-4}$alkynyl, $C_{1-4}$alkoxy, halogen substituted $C_{1-4}$alkoxy, nitro, cyano, —$R^5$, —O—$R^5$, —S—$R^5$, —$SO_2$—$R^5$, —$SO_2$—$NR^P$—$R^5$, —$NR^P$—$SO_2$—$R^5$, —$NH_2$, —N($R^P$)—$R^5$, —C(O)—$R^5$, —C(O)—$NH_2$, —C(O)—$NR^P$—$R^5$, —$NR^P$—C(O)—$R^5$ and —$NR^P$—C(O)O—$R^5$;

wherein $R^5$ is selected from the group consisting of $C_{1-4}$alkyl, aryl, $C_{1-4}$aralkyl, partially unsaturated carbocyclyl, cycloalkyl, cycloalkyl-$C_{1-4}$alkyl-, partially unsaturated carbocyclyl-$C_{1-4}$alkyl-, heteroaryl, heteroaryl-$C_{1-4}$alkyl-, heterocycloalkyl and heterocyclyl-$C_{1-4}$alkyl-;

wherein the aryl, partially unsaturated carbocyclyl, cycloalkyl, heteroaryl or heterocycloalkyl, whether alone or as part of a substituent group is optionally substituted with one or more substituent independently selected from the group consisting of $C_{1-4}$alkyl, $C_{1-4}$alkoxy, halogen, hydroxy, carboxy, amino, $C_{1-4}$alkylamino, di($C_{1-4}$alkyl)amino, cyano and nitro;

wherein $R^P$ is selected from the group consisting of hydrogen, $C_{1-8}$alkyl, hydroxy substituted $C_{1-4}$alkyl, $C_{1-4}$aralkyloxy substituted $C_{1-4}$alkyl, cycloalkyl, aryl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;

wherein the cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, $C_{1-4}$alkyl, $C_{1-4}$alkoxy, $C_{1-4}$alkoxycarbonyl, nitro, cyano, amino, $C_{1-4}$alkylamino, di($C_{1-4}$alkyl)amino, —$SO_2$—N($R^S R^T$), 5-tetrazolyl and 1-(1,4-dihydro-tetrazol-5-one);

wherein each $R^S$ and $R^T$ is independently selected from the group consisting of hydrogen and $C_{1-4}$alkyl;

a is an integer from 0 to 3;

each $R^{10}$ is independently selected from the group consisting of hydroxy, halogen, $C_{1-4}$alkyl, $C_{1-4}$alkoxy, halogen substituted $C_{1-4}$alkyl, halogen substituted $C_{1-4}$alkoxy, —C(O)—$NR^V R^W$, —$SO_2$—$NR^V R^W$, —C(O)—$C_{1-4}$alkyl and —$SO_2$—$C_{1-4}$alkyl;

wherein each $R^V$ and $R^W$ is independently selected from the group consisting of hydrogen and $C_{1-4}$alkyl; alternatively $R^V$ and $R^W$ are taken together with the N atom to which they are bound to form a 5 to 6 membered saturated, partially unsaturated or aromatic ring structure;

provided that the halogens on the halogen substituted $C_{1-4}$alkyl or the halogen substituted $C_{1-4}$alkoxy are selected from the group consisting of chloro and fluoro;

provided that when $R^0$ is hydrogen, $R^1$ is hydrogen, b is 1, $L^1$ is —O—, $R^3$ is $C_3$alkyl, wherein the $C_3$alkyl is substituted with —C(O)—$NR^P$—$R^5$, wherein $R^P$ is methyl and $R^5$ is cyclohexyl, $A^1$ is —$CH_2$— and $Q^1$ is —C(O)—O—, then $R^2$ is other than $C_{1-6}$alkyl, cycloalkyl or $C_{1-4}$aralkyl;

provided further that when $R^0$ is hydrogen, $R^1$ is hydrogen, b is 1, $L^1$ is —O—, $R^3$ is $C_3$alkyl, wherein the $C_3$alkyl is substituted with —C(O)—$NR^P$—$R^5$ wherein $R^P$ is methyl and $R^5$ is cyclohexyl, $A^1$ is —$CH_2$— and $Q^1$ is —C(O)—, then $R^2$ is other than morpholinyl or piperidinyl;

provided further that when $R^0$ is hydrogen, $R^1$ is hydrogen, b is 1, $L^1$ is —O—, $R^3$ is $C_3$alkyl, wherein the $C_3$alkyl is substituted with —C(O)—$NR^P$—$R^5$, wherein $R^P$ is methyl and $R^5$ is cyclohexyl, $A^1$ is —$CH_2$— and $Q^1$ is —C(O)—NH—, then $R^2$ is other than phenyl;

and pharmaceutically acceptable salts thereof.

The present invention is further directed to compounds of formula (II)

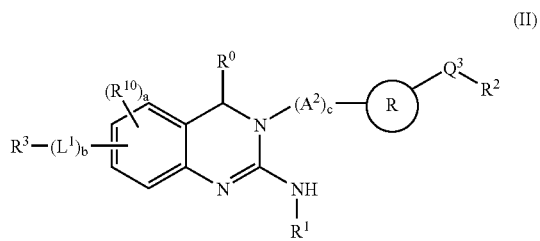

(II)

wherein $R^0$ is selected from the group consisting of hydrogen, methyl, and $CF_3$;

$R^1$ is selected from the group consisting of hydrogen, hydroxy, methyl, ethyl, trifluoromethyl, 2,2,2-trifluoroethyl, methoxy, ethoxy and methyl-carbonyl;

c is an integer from 0 to 1;

$A^2$ is selected from the group consisting of $C_{1-4}$alkyl; wherein the $C_{1-4}$alkyl is optionally substituted with one or more $R^Y$ substituents;

wherein each $R^Y$ is independently selected from the group consisting of hydroxy, oxo, $C_{1-4}$alkyl, $C_{1-4}$alkoxy, hydroxy substituted $C_{1-4}$alkyl, amino substituted $C_{1-6}$alkyl, cycloalkyl, cycloalkyl-$C_{1-4}$alkyl-, biphenyl, aryl, $C_{1-4}$aralkyl, heteroaryl, heteroaryl-$C_{1-4}$alkyl-, heterocycloalkyl, heterocycloalkyl-$C_{1-4}$alkyl- and spiro-heterocyclyl;

wherein the cycloalkyl, aryl, heteroaryl, heterocycloalkyl or spiro-heterocyclyl group, whether alone or as part of a substituent group is optionally substituted with one or more substituents independently selected from the group consisting of fluoro, chloro, hydroxy, oxo, carboxy, $C_{1-4}$alkyl, $C_{1-4}$alkoxy, —C(O)O—($C_{1-4}$alkyl), hydroxy substituted $C_{1-4}$alkyl, fluoro substituted $C_{1-4}$alkyl, fluoro substituted $C_{1-4}$alkoxy, 5-tetrazolyl and 1-(1,4-dihydro-tetrazol-5-one);

is selected from the group consisting of aryl, $C_{1-4}$aralkyl, cycloalkyl, partially unsaturated carbocyclyl, heteroaryl, heterocycloalkyl and spiro-heterocyclyl;

wherein the aryl, cycloalkyl, partially unsaturated carbocyclyl, heteroaryl, heterocycloalkyl or spiro-heterocyclyl group, whether alone or as part of a substituent group, is optionally substituted with one or more substituents independently selected from the group consisting of $C_{1-4}$alkyl, $C_{1-4}$alkoxy, halogen substituted $C_{1-4}$alkyl, halogen substituted $C_{1-4}$alkoxy, hydroxy substituted $C_{1-4}$alkyl, hydroxy, carboxy, cyano, nitro, amino, $C_{1-4}$alkylamino and di($C_{1-4}$alkyl)amino;

provided that when c is 0 (i.e. $A^1$ is absent), then

is other than aryl or heteroaryl;

$Q^3$ is selected from the group consisting of —O—, —S—, —C(O)—, —C(S)—, —C(O)O—, —OC(O)—, —C(O)—$NR^A$, —$NR^A$—C(O)—, —C(S)—$NR^A$, —$SO_2$—$NR^A$—, —SO—$NR^A$, —OC(O)—$NR^A$—, —$NR^A$—C(O)O— and —O—$SO_2$—$NR^A$—;

wherein each $R^A$ is independently selected from the group consisting of hydrogen, $C_{1-8}$alkyl, hydroxy substituted $C_{1-4}$alkyl, $C_{1-4}$aralkyloxy substituted $C_{1-4}$alkyl, cycloalkyl, aryl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;

wherein the cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, $C_{1-4}$alkyl, $C_{1-4}$alkoxy, $C_{1-4}$alkoxy-carbonyl-, nitro, cyano, amino, $C_{1-4}$alkylamino, di($C_{1-4}$alkyl)amino, —$SO_2$—N($R^C R^D$), 5-tetrazolyl and 1-(1,4-dihydro-tetrazol-5-one);

wherein each $R^C$ and $R^D$ is independently selected from the group consisting of hydrogen and $C_{1-4}$alkyl;

$R^2$ is selected from the group consisting of $C_{1-10}$alkyl, cycloalkyl, aryl, biphenyl, partially unsaturated carbocyclyl, heteroaryl, heterocycloalkyl, cycloalkyl-$C_{1-4}$alkyl-, $C_{1-4}$aralkyl, partially unsaturated carbocyclyl-$C_{1-4}$alkyl-, heteroaryl-$C_{1-4}$alkyl-, heterocycloalkyl-$C_{1-4}$alkyl- and spiro-heterocyclyl;

wherein the $C_{1-10}$alkyl, cycloalkyl, aryl, partially unsaturated carbocyclyl, heteroaryl, heterocycloalkyl or spiro-heterocyclyl, whether alone or as part of a substituent group is optionally substituted with one or more substituents independently selected from the group consisting of halogen, hydroxy, oxo, carboxy, —C(O)—$C_{1-4}$alkyl, —C(O)—$C_{1-4}$aralkyl, —C(O)O—$C_{1-4}$alkyl, —C(O)O—$C_{1-4}$aralkyl, —$C_{1-4}$alkyl-C(O)O—$C_{1-4}$alkyl, —$C_{1-4}$alkyl-S—$C_{1-4}$alkyl, —C(O)—N($R^L R^M$), —$C_{1-4}$alkyl-C(O)—N($R^L R^M$), —$NR^L$—C(O)—$C_{1-4}$alkyl, —$SO_2$—N($R^L R^M$), —$C_{1-4}$alkyl-$SO_2$—N($R^L R^M$), $C_{1-6}$alkyl, fluoro substituted $C_{1-4}$alkyl, hydroxy substituted $C_{1-4}$alkyl, carboxy substituted $C_{1-4}$alkyl, $C_{1-4}$alkoxy, —O—$C_{1-4}$aralkyl, —O-(tetrahydropyranyl), —NH—C(O)O—$CH_2$-(tetrahydropyranyl), —N($CH_3$)—C(O)O—$CH_2$-(tetrahydropyranyl), nitro, cyano, amino, $C_{1-4}$alkylamino, di($C_{1-4}$alkyl)amino, phenyl, 5-tetrazolyl and 1-(1,4-dihydro-tetrazol-5-one);

wherein the phenyl or tetrahydropyranyl is optionally substituted with one or more substituent independently selected from the group consisting of halogen, hydroxy, oxo, carboxy, C(O)O—C$_{1-4}$alkyl, C(O)—C$_{1-4}$alkyl, —O—C(O)—C$_{1-4}$alkyl, —C$_{1-4}$alkyl-OC(O)—C$_{1-4}$alkyl, —O—C$_{1-4}$aralkyl, C$_{1-4}$alkyl, fluoro substituted C$_{1-4}$alkyl, hydroxy substituted C$_{1-4}$alkyl, C$_{1-4}$alkoxy, nitro, cyano, amino, C$_{1-4}$alkylamino and di(C$_{1-4}$alkyl)amino;

wherein each R$^L$ and R$^M$ is independently selected from the group consisting of hydrogen and C$_{1-4}$alkyl;

b is an integer from 0 to 1;

L$^1$ is selected from the group consisting of —O—, —S(O)$_{0-2}$—, —NR$^N$—, —C(O)—, —C(S)—, —C$_{1-4}$alkyl-, -(hydroxy substituted C$_{1-4}$alkyl)- and —(C$_{2-4}$alkenyl)-;

wherein R$^N$ is selected from the group consisting of hydrogen and C$_{1-4}$alkyl;

R$^3$ is selected from the group consisting of C$_{1-6}$alkyl, C$_{2-6}$alkenyl, cycloalkyl, partially unsaturated carbocyclyl, aryl, biphenyl, heteroaryl, heterocycloalkyl, cycloalkyl-C$_{1-4}$alkyl-, C$_{1-4}$aralkyl, heteroaryl-C$_{1-4}$alkyl-, heterocycloalkyl-C$_{1-4}$alkyl- and spiro-heterocyclyl;

wherein the C$_{1-6}$alkyl, cycloalkyl, partially unsaturated carbocyclyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, C$_{1-4}$alkyl, hydroxy substituted C$_{1-4}$alkyl, halogen substituted C$_{1-4}$alkyl, cyano substituted C$_{1-4}$alkyl, C$_{2-4}$alkenyl, C$_{2-4}$alkynyl, C$_{1-4}$alkoxy, halogen substituted C$_{1-4}$alkoxy, nitro, cyano, —R$^5$, —O—R$^5$, —S—R$^5$, —SO$_2$—R$^5$, —SO$_2$—NR$^P$—R$^5$, —NR$^A$ SO$_2$—R$^5$, —NH$_2$, —N(R$^P$)—R$^5$, —C(O)—R$^5$, —C(O)—NH$_2$, —C(O)—NR$^P$—R$^5$, —NR$^P$—C(O)—R$^5$ and —NR$^P$—C(O)O—R$^5$;

wherein R$^5$ is selected from the group consisting of C$_{1-4}$alkyl, aryl, C$_{1-4}$aralkyl, partially unsaturated carbocyclyl, cycloalkyl, cycloalkyl-C$_{1-4}$alkyl-, partially unsaturated carbocyclyl-C$_{1-4}$alkyl-, heteroaryl, heteroaryl-C$_{1-4}$alkyl-, heterocycloalkyl and heterocyclyl-C$_{1-4}$alkyl-;

wherein the aryl, partially unsaturated carbocyclyl, cycloalkyl, heteroaryl or heterocycloalkyl, whether alone or as part of a substituent group is optionally substituted with one or more substituent independently selected from the group consisting of C$_{1-4}$alkyl, C$_{1-4}$alkoxy, halogen, hydroxy, carboxy, amino, C$_{1-4}$alkylamino, di(C$_{1-4}$alkyl)amino, cyano and nitro;

wherein R$^P$ is selected from the group consisting of hydrogen, C$_{1-8}$alkyl, hydroxy substituted C$_{1-4}$alkyl, C$_{1-4}$aralkyloxy substituted C$_{1-4}$alkyl, cycloalkyl, aryl, heteroaryl, heterocloalkyl, cycloalkyl-C$_{1-4}$alkyl-, C$_{1-4}$aralkyl, heteroaryl-C$_{1-4}$alkyl-, heterocycloalkyl-C$_{1-4}$alkyl- and spiro-heterocyclyl;

wherein the cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, C$_{1-4}$alkyl, C$_{1-4}$alkoxy, C$_{1-4}$alkoxycarbonyl, nitro, cyano, amino, C$_{1-4}$alkylamino, di(C$_{1-4}$alkyl)amino, —SO$_2$—N(R$^S$R$^T$), 5-tetrazolyl and 1-(1,4-dihydrotetrazol-5-one);

wherein each R$^S$ and R$^T$ is independently selected from the group consisting of hydrogen and C$_{1-4}$alkyl;

a is an integer form 0 to 3;

each R$^{10}$ is independently selected from the group consisting of hydroxy, halogen, C$_{1-4}$alkyl, C$_{1-4}$alkoxy, halogen substituted C$_{1-4}$alkyl, halogen substituted C$_{1-4}$alkoxy, —C(O)—NR$^V$R$^W$, —SO$_2$—NR$^V$R$^W$, —C(O)—C$_{1-4}$alkyl and —SO$_2$—C$_{1-4}$alkyl;

wherein each R$^V$ and R$^W$ is independently selected from the group consisting of hydrogen and C$_{1-4}$alkyl; alternatively R$^V$ and R$^W$ are taken together with the N atom to which they are bound to form a 5 to 6 membered saturated, partially unsaturated or aromatic ring structure;

provided that the halogens on the halogen substituted C$_{1-4}$alkyl and the halogen substituted C$_{1-4}$alkoxy are selected from the group consisting of chloro and fluoro;

provided that when R$^0$ is hydrogen, R$^1$ is hydrogen, A$^1$ is —CH$_2$—,

is phenyl, Q$^3$ is —O—, R$^2$ is methyl, b is an integer selected from 0 to 1 and L$^1$ is selected from —O—, —NH— or —N(CH$_3$)—, then R$^3$ is other than methyl;

and pharmaceutically acceptable salts thereof.

The present invention is further directed to compounds of formula (III)

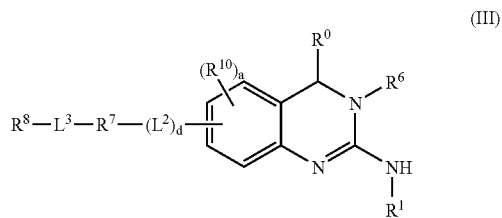

(III)

wherein

R$^0$ is selected from the group consisting of hydrogen, methyl and CF$_3$;

R$^1$ is selected from the group consisting of hydrogen, hydroxy, methyl, ethyl, trifluoromethyl, 2,2,2-trifluoroethyl, methoxy, ethoxy and methyl-carbonyl;

R$^6$ is selected from the group consisting of C$_{1-6}$alkyl and hydroxy substituted C$_{1-8}$alkyl;

d is an integer from 0 to 1;

L$^2$ is selected from the group consisting of —O—, —S(O)$_{0-2}$—, —NR$^Q$—;

wherein R$^Q$ is selected from the group consisting of hydrogen and C$_{1-4}$alkyl;

R$^7$ is selected from the group consisting of cycloalkyl, cycloalkyl-C$_{1-4}$alkyl, aryl, C$_{1-4}$alkyl-aryl, aryl-C$_{1-4}$alkyl, partially unsaturated carbocyclyl, partially unsaturated carbocyclyl-C$_{1-4}$alkyl, heteroaryl, heteroaryl-C$_{1-4}$alkyl, heterocycloalkyl and heterocycloalkyl-C$_{1-4}$alkyl;

wherein the aryl, cycloalkyl, partially unsaturated carbocyclyl, heteroaryl or heterocycloalkyl group, whether alone or as part of a substituent group, is optionally substituted with one or more substituents independently selected from the group consisting of C$_{1-4}$alkyl, C$_{1-4}$alkoxy, halogen substituted C$_{1-4}$alkyl, halogen substituted C$_{1-4}$alkoxy, hydroxy substituted C$_{1-4}$alkyl, hydroxy, carboxy, cyano, nitro, amino, C$_{1-4}$alkylamino, di(C$_{1-4}$alkyl)amino, 5-tetrazolyl and 1-(1,4-dihydro-tetrazol-5-one);

L$^3$ is selected from the group consisting of —O—, —S—, —C(O)—, —C(S)—, —C(O)O—, —OC(O)—, —NR$^A$—, —N(CN)—, —NR$^A$—C(O)—, —C(O)—NR$^A$—, NR$^A$—C(S)—, —C(S)—NR$^A$—, —NR$^A$—SO$_2$—, —SO$_2$—NR$^A$—, —NR$^A$—SO—, —SO—NR$^A$—, —NR$^A$ C(O)O—, —OC(O)—NR$^A$—, —O—SO$_2$—NR$^A$—, —NR$^A$—SO$_2$—O—, NR$^A$—C(O)—NR$^B$—, —NR$^A$—C(S)—NR$^B$— and —NR$^A$—SO$_2$—NR$^B$—;

wherein each $R^A$ and $R^B$ is independently selected from the group consisting of hydrogen, $C_{1-8}$alkyl, hydroxy substituted $C_{1-4}$alkyl, $C_{1-4}$aralkyloxy substituted $C_{1-4}$alkyl, cycloalkyl, aryl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;

wherein the cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, $C_{1-4}$alkyl, $C_{1-4}$alkoxy, $C_{1-4}$alkoxycarbonyl, nitro, cyano, amino, $C_{1-4}$alkylamino, di($C_{1-4}$alkyl)amino, —$SO_2$—$N(R^C R^D)$, 5-tetrazolyl and 1-(1,4-dihydrotetrazol-5-one);

wherein each $R^C$ and $R^D$ is independently selected from the group consisting of hydrogen and $C_{1-4}$alkyl;

$R^8$ is selected from the group consisting of $C_{1-10}$alkyl, cycloalkyl, aryl, biphenyl, partially unsaturated carbocyclyl, heteroaryl, heterocycloalkyl, cycloalkyl-$C_{1-4}$alkyl-, $C_{1-4}$aralkyl, partially unsaturated carbocyclyl-$C_{1-4}$alkyl-, heteroaryl-$C_{1-4}$alkyl-, heterocycloalkyl-$C_{1-4}$alkyl- and spiro-heterocyclyl;

wherein the $C_{1-10}$alkyl, cycloalkyl, aryl, partially unsaturated carbocyclyl, heteroaryl, heterocycloalkyl or spiro-heterocyclyl, whether alone or as part of a substituent group is optionally substituted with one or more substituents independently selected from the group consisting of halogen, hydroxy, oxo, carboxy, —C(O)—$C_{1-4}$alkyl, —C(O)—$C_{1-4}$aralkyl, —C(O)O—$C_{1-4}$alkyl, —C(O)O—$C_{1-4}$aralkyl, —$C_{1-4}$alkyl-C(O)O—$C_{1-4}$alkyl, —$C_{1-4}$alkyl-S—$C_{1-4}$alkyl, —C(O)—$N(R^L R^M)$, —$C_{1-4}$alkyl-C(O)—$N(R^L R^M)$, —$NR^L$—C(O)—$C_{1-4}$alkyl, —$SO_2$—$C_{1-4}$alkyl, —$SO_2$-aryl, —$SO_2$—$N(R^L R^M)$, —$C_{1-4}$alkyl-$SO_2$—$N(R^L R^M)$, $C_{1-4}$alkyl, fluoro substituted $C_{1-4}$alkyl, hydroxy substituted $C_{1-4}$alkyl, carboxy substituted $C_{1-4}$alkyl, $C_{1-4}$alkoxy, fluoro substituted $C_{1-4}$alkoxy, nitro, cyano, amino, $C_{1-4}$alkylamino, di($C_{1-4}$alkyl)amino, phenyl and heteroaryl;

wherein the phenyl or heteroaryl is optionally substituted with one or more substituent independently selected from the group consisting of halogen, hydroxy, oxo, carboxy, —C(O)O—$C_{1-4}$alkyl, —C(O)—$C_{1-4}$alkyl, $C_{1-4}$alkyl, fluoro substituted $C_{1-4}$alkyl, $C_{1-4}$alkoxy, nitro, cyano, amino, $C_{1-4}$alkylamino and di($C_{1-4}$alkyl)amino;

wherein each $R^L$ and $R^M$ is independently selected from the group consisting of hydrogen, $C_{1-4}$alkyl and cycloalkyl;

a is an integer from 0 to 3;

each $R^{10}$ is independently selected from the group consisting of hydroxy, halogen, $C_{1-4}$alkyl, $C_{1-4}$alkoxy, halogen substituted $C_{1-4}$alkyl, halogen substituted $C_{1-4}$alkoxy, —C(O)—$NR^V R^W$, —$SO_2$—$NR^V R^W$, —C(O)—$C_{1-4}$alkyl and —$SO_2$—$C_{1-4}$alkyl;

wherein each $R^V$ and $R^W$ is independently selected from the group consisting of hydrogen and $C_{1-4}$alkyl; alternatively $R^V$ and $R^W$ are taken together with the N atom to which they are bound to form a 5 to 6 membered saturated, partially unsaturated or aromatic ring structure;

provided that the halogens on the halogen substituted $C_{1-4}$alkyl and the halogen substituted $C_{1-4}$alkoxy are selected from the group consisting of chloro and fluoro;

or a pharmaceutically acceptable salt thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating a disorder mediated by the β-secretase enzyme, comprising administering to a subject in need thereof, a therapeutically effective amount of any of the compounds or pharmaceutical compositions described above.

An example of the invention is a method of treating a disorder selected from the group consisting of Alzheimer's disease (AD), mild cognitive impairment, senility, dementia, dementia with Lewy bodies, Down's syndrome, dementia associated with Parkinson's disease and dementia associated with beta-amyloid, comprising administering to a subject in need thereof, a therapeutically effective amount of any of the compounds or pharmaceutical compositions described above.

Another example of the invention is the use of any of the compounds described above in the preparation of a medicament for treating: (a) Alzheimer's Disease (AD), (b) mild cognitive impairment, (c) senility, (d) dementia, (e) dementia with Lewy bodies, (f) Down's syndrome, (g) dementia associated with Parkinson's disease and (h) dementia associated with beta-amyloid, in a subject in need thereof.

DETAILED DESCRIPTION OF THE INVENTION

The present invention is directed to compounds of formula (I), (II) and (III)

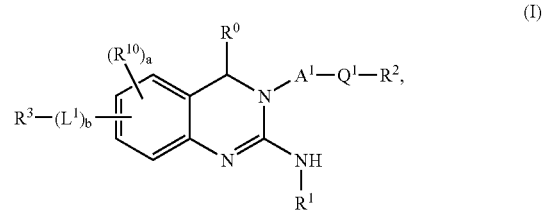

(I)

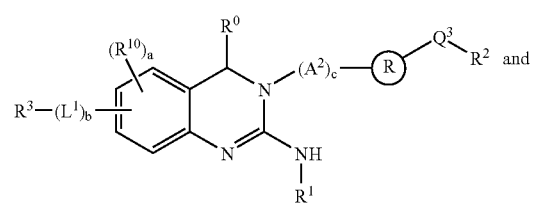

(II)

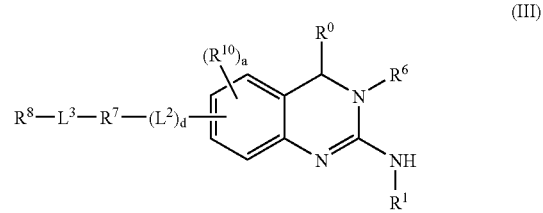

(III)

wherein $R^0$, $R^1$, $R^2$, $R^3$, $R^6$, $R^7$, $R^8$, $R^{10}$, $L^1$, $L^2$, $L^3$, a, b, c, d, $A^1$, $A^2$, $Q^1$, $Q^3$ and (R)

are as herein defined. The compounds of formula (I), formula (II) and formula (III) are inhibitors of the β-secretase enzyme (also known as β-site cleaving enzyme, BACE, BACE1, Asp2 or memapsin2), and are useful in the treatment of Alzheimer's disease (AD), mild cognitive impairment (MCI), senility, dementia, dementia with Lewy bodies, Down's syndrome, dementia associated with Parkinson's disease and dementia associated with beta-amyloid, preferably Alzheimer's disease.

One skilled in the art will recognize that some of the variables (e.g. $R^0$, $R^1$, $L^1$, $R^2$, $R^{10}$, etc.) appear in compounds of formula (I), formula (II) and/or formula (III). One skilled in the art will further recognize that wherein a particular substituent is selected for a given variable for a compound of formula (I), said selection is not intended to limit the scope of said variable for compounds of formula (II) and/or compounds of formula (III). Similarly, the selection of a particular substituent for a given variable for a compound of formula (II), is not intended to limit the scope of said variable for compounds of formula (I) and/or compounds of formula (III). Similarly, the selection of a particular substituent for a given variable for a compound of formula (III), is not intended to limit the scope of said variable for compounds of formula (I) and/or compounds of formula (II).

In an embodiment, the present invention is directed to compounds of formula (I)

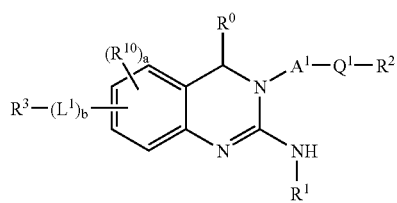

(I)

wherein $R^0$ is selected from the group consisting of hydrogen, methyl and $CF_3$;

$R^1$ is selected from the group consisting of hydrogen, hydroxy, methyl, ethyl, trifluoromethyl, 2,2,2-trifluoroethyl, methoxy, ethoxy and methyl-carbonyl;

$A^1$ is selected from $C_{1-4}$alkyl; wherein the $C_{1-4}$alkyl is optionally substituted with one or more $R^X$ substituents;

wherein each $R^X$ is independently selected from the group consisting of hydroxy, oxo, $C_{1-8}$alkyl, $C_{1-8}$alkoxy, hydroxy substituted $C_{1-6}$alkyl, amino substituted $C_{1-6}$alkyl, cycloalkyl, cycloalkyl-$C_{1-4}$alkyl-, biphenyl, aryl, $C_{1-4}$aralkyl, heteroaryl, heteroaryl-$C_{1-4}$alkyl-, heterocycloalkyl, heterocycloalkyl-$C_{1-4}$alkyl-, spiro-heterocyclyl and —($C_{1-4}$alkyl)$_n$-$Q^2$-$R^4$;

wherein the cycloalkyl, aryl, heteroaryl, heterocycloalkyl or spiro-heterocyclyl group, whether alone or as part of a substituent group is optionally substituted with a substituent selected from the group consisting of fluoro, chloro, hydroxy, oxo, carboxy, $C_{1-4}$alkyl, $C_{1-4}$alkoxy, —C(O)—($C_{1-4}$alkyoxy), hydroxy substituted $C_{1-4}$alkyl, fluoro substituted $C_{1-4}$alkyl, fluoro substituted $C_{1-4}$alkoxy, 5-tetrazolyl and 1-(1,4-dihydro-tetrazol-5-one);

wherein n is an integer from 0 to 1;

wherein $Q^2$ is selected from the group consisting of —O—, —S—, —C(O)—, —C(S)—, —C(O)O—, —OC(O)—, —$NR^G$—, —$NR^G$—C(O)—, —C(O)—$NR^G$—, —$NR^G$—$SO_2$—, —$SO_2$—$NR^G$—, —$NR^G$—SO—, —SO—$NR^G$, —$NR^G$—C(O)O—, —OC(O)—$NR^G$—, —O—$SO_2$—$NR^G$—, —$NR^G$—$SO_2$—O—, —$NR^G$—C(O)$NR^H$—, —$NR^G$—C(S)—$NR^H$— and —$NR^G$—$SO_2$—$NR^H$—;

wherein each $R^G$ and $R^H$ is independently selected from the group consisting of hydrogen, $C_{1-8}$alkyl, hydroxy substituted $C_{1-4}$alkyl, $C_{1-4}$aralkyloxy substituted $C_{1-4}$alkyl, cycloalkyl, aryl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;

wherein the cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, $C_{1-4}$alkyl, $C_{1-4}$alkoxy, $C_{1-4}$alkoxycarbonyl, nitro, cyano, amino, $C_{1-4}$alkylamino, di($C_{1-4}$alkyl)amino, —$SO_2$—N($R^J R^K$), 5-tetrazolyl and 1-(1,4-dihydro-tetrazol-5-one);

wherein each $R^J$ and $R^K$ is independently selected from from the group consisting of hydrogen and $C_{1-4}$alkyl;

wherein $R^4$ is selected from the group consisting of hydrogen, $C_{1-4}$alkyl, hydroxy substituted $C_{1-4}$alkyl, fluoro substituted $C_{1-4}$alkyl, cycloalkyl, aryl, biphenyl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;

wherein the cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, —C(O)O—$C_{1-4}$alkyl, —C(O)—$C_{1-4}$alkyl, $C_{1-4}$alkyl, fluoro substituted $C_{1-4}$alkyl, $C_{1-4}$alkoxy, nitro, cyano, amino, $C_{1-4}$alkylamino, di($C_{1-4}$alkyl)amino and phenyl;

wherein the phenyl is optionally substituted with one or more substituent independently selected from the group consisting of halogen, hydroxy, oxo, carboxy, —C(O)O—$C_{1-4}$alkyl, —C(O)—$C_{1-4}$alkyl, $C_{1-4}$alkyl, fluoro substituted $C_{1-4}$alkyl, $C_{1-4}$alkoxy, nitro, cyano, amino, $C_{1-4}$alkylamino, di($C_{1-4}$alkyl)amino and —$SO_2$—N($R^E R^F$);

wherein each $R^E$ and $R^F$ is independently selected from the group consisting of hydrogen and $C_{1-4}$alkyl;

$Q^1$ is selected from the group consisting of —O—, —S—, —C(O)—, —C(S)—, —C(O)O—, —OC(O)—, —$NR^A$—, —$NR^A$—C(O), —C(O)—$NR^A$—, —$NR^A$—C(S), —C(S)—$NR^A$—, —$NR^A$ $SO_2$—, —$SO_2$—$NR^A$—, —$NR^A$—SO—, —SO—$NR^A$, —$NR^A$—C(O)O—, —OC(O)—$NR^A$—, —O—$SO_2$—$NR^A$—, —$NR^A$—$SO_2$—O—, —$NR^A$—C(O)—$NR^B$, $NR^A$—C(S)—$NR^B$ and $NR^A$—$SO_2$—$NR^B$—;

wherein each $R^A$ and $R^B$ is independently selected from the group consisting of hydrogen, $C_{1-8}$alkyl, hydroxy substituted $C_{1-4}$alkyl, $C_{1-4}$aralkyloxy substituted $C_{1-4}$alkyl, cycloalkyl, aryl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;

wherein the cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, $C_{1-4}$alkyl, $C_{1-4}$alkoxy, $C_{1-4}$alkoxycarbonyl, nitro, cyano, amino, $C_{1-4}$alkylamino, di($C_{1-4}$alkyl)amino, —$SO_2$—N($R^C R^D$), 5-tetrazolyl and 1-(1,4-dihydro-tetrazol-5-one);

wherein each $R^C$ and $R^D$ is independently selected from the group consisting of hydrogen and $C_{1-4}$alkyl;

$R^2$ is selected from the group consisting of $C_{1-10}$alkyl, cycloalkyl, aryl, biphenyl, partially unsaturated carbocyclyl, heteroaryl, heterocycloalkyl, cycloalkyl-$C_{1-4}$alkyl-, $C_{1-4}$aralkyl, partially unsaturated carbocyclyl-$C_{1-4}$alkyl-, heteroaryl-$C_{1-4}$alkyl-, heterocycloalkyl-$C_{1-4}$alkyl- and spiro-heterocyclyl;

wherein the $C_{1-10}$alkyl, cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, —C(O)—$C_{1-4}$alkyl, —C(O)—$C_{1-4}$aralkyl, —C(O)O—$C_{1-4}$alkyl, —C(O)O—$C_{1-4}$aralkyl, —$C_{1-4}$alkyl-C(O)O—$C_{1-4}$alkyl, —$C_{1-4}$alkyl-S—$C_{1-4}$alkyl, —C(O)—N($R^L R^M$), —$C_{1-4}$alkyl-C(O)—N($R^L R^M$), —$NR^L$—C(O)—$C_{1-4}$alkyl, —$SO_2$—N($R^L R^M$), —$C_{1-4}$alkyl-$SO_2$—N($R^L R^M$), $C_{1-6}$alkyl, fluoro substituted $C_{1-4}$alkyl, hydroxy substituted $C_{1-4}$alkyl, carboxy substituted $C_{1-4}$alkyl, $C_{1-4}$alkoxy, nitro, cyano, amino, $C_{1-4}$alkylamino, di($C_{1-4}$alkyl)amino, phenyl, 5-tetrazolyl and 1-(1,4-dihydrotetrazol-5-one);

wherein the phenyl is optionally substituted with one or more substituent independently selected from the group consisting of halogen, hydroxy, oxo, carboxy, —C(O)O—$C_{1-4}$alkyl, —C(O)—$C_{1-4}$alkyl, $C_{1-4}$alkyl, fluoro substituted $C_{1-4}$alkyl, $C_{1-4}$alkoxy, nitro, cyano, amino, $C_{1-4}$alkylamino and di($C_{1-4}$alkyl)amino;

wherein each $R^L$ and $R^M$ is independently selected from the group consisting of hydrogen and $C_{1-4}$alkyl;

b is an integer from 0 to 1;

$L^1$ is selected from the group consisting of —O—, —S(O)$_{0-2}$—, —$NR^N$—, —C(O)—, —C(S)—, —$C_{1-4}$alkyl-, -(hydroxy substituted $C_{1-4}$alkyl) and —($C_{2-4}$alkenyl)-;

wherein $R^N$ is selected from the group consisting of hydrogen and $C_{1-4}$alkyl;

$R^3$ is selected from the group consisting of $C_{1-6}$alkyl, $C_{2-6}$alkenyl, cycloalkyl, partially unsaturated carbocyclyl, aryl, biphenyl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;

wherein the $C_{1-6}$alkyl, cycloalkyl, partially unsaturated carbocyclyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, $C_{1-4}$alkyl, hydroxy substituted $C_{1-4}$alkyl, halogen substituted $C_{1-4}$alkyl, cyano substituted $C_{1-4}$alkyl, $C_{2-4}$alkenyl, $C_{2-4}$alkynyl, $C_{1-4}$alkoxy, halogen substituted $C_{1-4}$alkoxy, nitro, cyano, —$R^5$, —O—$R^5$, —S—$R^5$, —$SO_2$—$R^5$, —$SO_2$—$NR^P$—$R^5$, —$NR^P$—$SO_2$—$R^5$, —$NH_2$, —N($R^P$)—$R^5$, —C(O)—$R^5$, —C(O)—$NH_2$, —C(O)—$NR^P$—$R^5$, —$NR^P$—C(O)—$R^5$ and —$NR^P$—C(O)O—$R^5$;

wherein $R^5$ is selected from the group consisting of $C_{1-4}$alkyl, aryl, $C_{1-4}$aralkyl, partially unsaturated carbocyclyl, cycloalkyl, cycloalkyl-$C_{1-4}$alkyl-, partially unsaturated carbocyclyl-$C_{1-4}$alkyl-, heteroaryl, heteroaryl-$C_{1-4}$alkyl-, heterocycloalkyl and heterocyclyl-$C_{1-4}$alkyl-;

wherein the aryl, $C_{1-4}$aralkyl, partially unsaturated carbocyclyl, cycloalkyl, heteroaryl or heterocycloalkyl, whether alone or as part of a substituent group may be optionally substituted with one or more substituent independently selected from the group consisting of $C_{1-4}$alkyl, $C_{1-4}$alkoxy, halogen, hydroxy, carboxy, amino, $C_{1-4}$alkylamino, di($C_{1-4}$alkyl)amino, cyano and nitro;

wherein $R^P$ is selected from the group consisting of hydrogen, $C_{1-8}$alkyl, hydroxy substituted $C_{1-4}$alkyl, $C_{1-4}$aralkyloxy substituted $C_{1-4}$alkyl, cycloalkyl, aryl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;

wherein the cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, $C_{1-4}$alkyl, $C_{1-4}$alkoxy, $C_{1-4}$alkoxycarbonyl, nitro, cyano, amino, $C_{1-4}$alkylamino, di($C_{1-4}$alkyl)amino, —$SO_2$—N($R^S R^T$), 5-tetrazolyl and 1-(1,4-dihydrotetrazol-5-one);

wherein each $R^S$ and $R^T$ is independently selected from the group consisting of hydrogen and $C_{1-4}$alkyl;

a is an integer from 0 to 3;

each $R^{10}$ is independently selected from the group consisting of hydroxy, halogen, $C_{1-4}$alkyl, $C_{1-4}$alkoxy, halogenated $C_{1-4}$alkyl, halogenated $C_{1-4}$alkoxy, —C(O)—$NR^V R^W$, —$SO_2$—$NR^V R^W$, —C(O)—$C_{1-4}$alkyl and —$SO_2$—$C_{1-4}$alkyl;

wherein each $R^V$ and $R^W$ is independently selected from the group consisting of hydrogen and $C_{1-4}$alkyl; alternatively $R^V$ and $R^W$ are taken together with the N atom to which they are bound to form a 5 to 6 membered saturated, partially unsaturated or aromatic ring structure;

provided that the halogens on the halogenated $C_{1-4}$alkyl or the halogenated $C_{1-4}$alkoxy are selected from chloro or fluoro;

provided that when $R^0$ is hydrogen, $R^1$ is hydrogen, b is 1, $L^1$ is —O—, $R^3$ is $C_3$alkyl, wherein the $C_3$alkyl is substituted with —C(O)—$NR^P$—$R^5$, wherein $R^P$ is methyl and $R^5$ is cyclohexyl, $A^1$ is —$CH_2$—, $Q^1$ is —C(O)—O— then $R^2$ is other than $C_{1-6}$alkyl, cycloalkyl or $C_{1-4}$aralkyl;

provided further that when $R^0$ is hydrogen, $R^1$ is hydrogen, b is 1, $L^1$ is —O—, $R^3$ is $C_3$alkyl, wherein the $C_3$alkyl is substituted with —C(O)—$NR^P$—$R^5$, wherein $R^P$ is methyl and $R^5$ is cyclohexyl, $A^1$ is —$CH_2$—, $Q^1$ is —C(O)— then $R^2$ is other than morpholinyl or piperidinyl;

provided further that when $R^0$ is hydrogen, $R^1$ is hydrogen, b is 1, $L^1$ is —O—, $R^3$ is $C_3$alkyl, wherein the $C_3$alkyl is substituted with —C(O)—$NR^P$—$R^5$, wherein $R^P$ is methyl and $R^5$ is cyclohexyl, $A^1$ is —$CH_2$—, $Q^1$ is —C(O)—NH— then $R^2$ is other than phenyl;

and pharmaceutically acceptable salts thereof.

In an embodiment, the present invention is directed to compounds of formula (II)

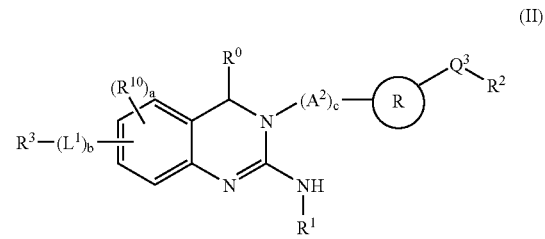

wherein $R^0$ is selected from the group consisting of hydrogen, methyl, and $CF_3$;

$R^1$ is selected from the group consisting of hydrogen, hydroxy, methyl, ethyl, trifluoromethyl, 2,2,2-trifluoroethyl, methoxy, ethoxy and methyl-carbonyl;

c is an integer from 0 to 1;

$A^2$ is selected from $C_{1-4}$alkyl; wherein the $C_{1-4}$alkyl is optionally substituted with one or more $R^Y$ substituents;

wherein each $R^Y$ is independently selected from the group consisting of hydroxy, oxo, $C_{1-4}$alkyl, $C_{1-4}$alkoxy, hydroxy substituted $C_{1-4}$alkyl, amino substituted $C_{1-6}$alkyl, cycloalkyl, cycloalkyl-$C_{1-4}$alkyl-, biphenyl, aryl, $C_{1-4}$aralkyl, heteroaryl, heteroaryl-$C_{1-4}$alkyl-, heterocycloalkyl, heterocycloalkyl-$C_{1-4}$alkyl- and spiro-heterocyclyl;

wherein the cycloalkyl, aryl, heteroaryl, heterocycloalkyl or spiro-heterocyclyl group, whether alone or as part of a substituent group is optionally substituted with a substituent selected from the group consisting of fluoro, chloro, hydroxy, oxo, carboxy, $C_{1-4}$alkyl, $C_{1-4}$alkoxy, —C(O)—($C_{1-4}$alkoxy), hydroxy substituted $C_{1-4}$alkyl, fluoro substituted $C_{1-4}$alkyl, fluoro substituted $C_{1-4}$alkoxy, 5-tetrazolyl and 1-(1,4-dihydro-tetrazol-5-one);

is selected from the group consisting of aryl, aryl-$C_{1-4}$alkyl, cycloalkyl, partially unsaturated carbocyclyl, heteroaryl, heterocycloalkyl and spiro-heterocyclyl;

wherein the aryl, cycloalkyl, partially unsaturated carbocyclyl, heteroaryl, heterocycloalkyl or spiro-heterocyclyl group is optionally substituted with one or more substituents independently selected from the group consisting of $C_{1-4}$alkyl, $C_{1-4}$alkoxy, halogen substituted $C_{1-4}$alkyl, halogen substituted $C_{1-4}$alkoxy, hydroxy substituted $C_{1-4}$alkyl, hydroxy, carboxy, cyano, nitro, amino, $C_{1-4}$alkylamino and di($C_{1-4}$alkyl)amino;

provided that when c is 0 (i.e. $A^1$ is absent), then

is other than aryl or heteroaryl;

$Q^3$ is selected from the group consisting of —O—, —S—, —C(O)—, —C(S)—, —C(O)O—, —OC(O)—, —C(O)—$NR^A$—, —$NR^A$—C(O), —C(S)—$NR^A$—, —$SO_2$—$NR^A$—, —SO—$NR^A$—, —OC(O)—$NR^A$—, —$NR^A$—C(O)O— and —O—$SO_2$—$NR^A$—;

wherein each $R^A$ is independently selected from the group consisting of hydrogen, $C_{1-8}$alkyl, hydroxy substituted $C_{1-4}$alkyl, $C_{1-4}$aralkyloxy substituted $C_{1-4}$alkyl, cycloalkyl, aryl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;

wherein the cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, $C_{1-4}$alkyl, $C_{1-4}$alkoxy, $C_{1-4}$alkoxycarbonyl-, nitro, cyano, amino, $C_{1-4}$alkylamino, di($C_{1-4}$alkyl)amino, —$SO_2$—N($R^C R^D$), 5-tetrazolyl and 1-(1,4-dihydrotetrazol-5-one);

wherein each $R^C$ and $R^D$ is independently selected from the group consisting of hydrogen and $C_{1-4}$alkyl;

$R^2$ is selected from the group consisting of $C_{1-10}$alkyl, cycloalkyl, aryl, biphenyl, partially unsaturated carbocyclyl, heteroaryl, heterocycloalkyl, cycloalkyl-$C_{1-4}$alkyl-, $C_{1-4}$aralkyl, partially unsaturated carbocyclyl-$C_{1-4}$alkyl-, heteroaryl-$C_{1-4}$alkyl-, heterocycloalkyl-$C_{1-4}$alkyl- and spiro-heterocyclyl;

wherein the $C_{1-10}$alkyl, cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, —C(O)—$C_{1-4}$alkyl, —C(O)—$C_{1-4}$aralkyl, —C(O)O—$C_{1-4}$alkyl, —C(O)O—$C_{1-4}$aralkyl, —$C_{1-4}$alkyl-C(O)O—$C_{1-4}$alkyl, —$C_{1-4}$alkyl-S—$C_{1-4}$alkyl, —C(O)—N($R^L R^M$), —$C_{1-4}$alkyl-C(O)—N(R LM), —$NR^L$—C(O)—$C_{1-4}$alkyl, —$SO_2$—N($R^L R^M$), —$C_{1-4}$alkyl-$SO_2$—N($R^L R^M$), $C_{1-6}$alkyl, fluoro substituted $C_{1-4}$alkyl, hydroxy substituted $C_{1-4}$alkyl, carboxy substituted $C_{1-4}$alkyl, $C_{1-4}$alkoxy, nitro, cyano, amino, $C_{1-4}$alkylamino, di($C_{1-4}$alkyl)amino, phenyl, 5-tetrazolyl and 1-(1,4-dihydrotetrazol-5-one);

wherein the phenyl is optionally substituted with one or more substituent independently selected from the group consisting of halogen, hydroxy, oxo, carboxy, C(O)O—$C_{1-4}$alkyl, C(O)—$C_{1-4}$alkyl, $C_{1-4}$alkyl, fluoro substituted $C_{1-4}$alkyl, $C_{1-4}$alkoxy, nitro, cyano, amino, $C_{1-4}$alkylamino and di($C_{1-4}$alkyl)amino;

wherein each $R^L$ and $R^M$ is independently selected from the group consisting of hydrogen and $C_{1-4}$alkyl;

b is an integer from 0 to 1;

$L^1$ is selected from the group consisting of —O—, —$S(O)_{0-2}$—, —$NR^N$—, —C(O)—, —C(S)—, —$C_{1-4}$alkyl-, -(hydroxy substituted $C_{1-4}$alkyl)- and —($C_{2-4}$alkenyl)-;

wherein $R^N$ is selected from the group consisting of hydrogen and $C_{1-4}$alkyl;

$R^3$ is selected from the group consisting of $C_{1-6}$alkyl, $C_{2-6}$alkenyl, cycloalkyl, partially unsaturated carbocyclyl, aryl, biphenyl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;

wherein the $C_{1-6}$alkyl, cycloalkyl, partially unsaturated carbocyclyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, $C_{1-4}$alkyl, hydroxy substituted $C_{1-4}$alkyl, halogen substituted $C_{1-4}$alkyl, cyano substituted $C_{1-4}$alkyl, $C_{2-4}$alkenyl, $C_{2-4}$alkynyl, $C_{1-4}$alkoxy, halogen substituted $C_{1-4}$alkoxy, nitro, cyano, —$R^5$, —O—$R^5$, —S—$R^5$, —$SO_2$—$R^5$, —$SO_2$—$NR^P$—$R^5$, —$NR^A$ $SO_2$—$R^5$, —$NH_2$, —N($R^P$)—$R^5$, —C(O)—$R^5$, —C(O)—$NH_2$, —C(O)—$NR^P$—$R^5$, —$NR^P$—C(O)—$R^5$ and —$NR^P$—C(O)O—$R^5$;

wherein $R^5$ is selected from the group consisting of $C_{1-4}$alkyl, aryl, $C_{1-4}$aralkyl, partially unsaturated carbocyclyl, cycloalkyl, cycloalkyl-$C_{1-4}$alkyl-, partially unsaturated carbocyclyl-$C_{1-4}$alkyl-, heteroaryl, heteroaryl-$C_{1-4}$alkyl-, heterocycloalkyl and heterocyclyl-$C_{1-4}$alkyl-;

wherein the aryl, $C_{1-4}$aralkyl, partially unsaturated carbocyclyl, cycloalkyl, heteroaryl or heterocycloalkyl, whether alone or as part of a substituent group may be optionally substituted with one or more substituent independently selected from the group consisting of $C_{1-4}$alkyl, $C_{1-4}$alkoxy, halogen, hydroxy, carboxy, amino, $C_{1-4}$alkylamino, di($C_{1-4}$alkyl)amino, cyano and nitro;

wherein $R^P$ is selected from the group consisting of hydrogen, $C_{1-8}$alkyl, hydroxy substituted $C_{1-4}$alkyl, $C_{1-4}$aralkyloxy substituted $C_{1-4}$alkyl, cycloalkyl, aryl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;

wherein the cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, $C_{1-4}$alkyl, $C_{1-4}$alkoxy, $C_{1-4}$alkoxycarbonyl, nitro, cyano, amino, $C_{1-4}$alkylamino, di($C_{1-4}$alkyl)amino, —$SO_2$—N($R^S R^T$), 5-tetrazolyl and 1-(1,4-dihydrotetrazol-5-one);

wherein each $R^S$ and $R^T$ is independently selected from the group consisting of hydrogen and $C_{1-4}$alkyl;

a is an integer form 0 to 3;

each $R^{10}$ is independently selected from the group consisting of hydroxy, halogen, $C_{1-4}$alkyl, $C_{1-4}$alkoxy, halogenated $C_{1-4}$alkyl, halogenated $C_{1-4}$alkoxy, —C(O)—NR$^V$R$^W$, —SO$_2$—NR$^V$R$^W$, —C(O)—C$_{1-4}$alkyl and —SO$_2$—C$_{1-4}$alkyl;

wherein each $R^V$ and $R^W$ is independently selected from the group consisting of hydrogen and $C_{1-4}$alkyl; alternatively $R^V$ and $R^W$ are taken together with the N atom to which they are bound to form a 5 to 6 membered saturated, partially unsaturated or aromatic ring structure;

provided that the halogens on the halogenated $C_{1-4}$alkyl and the halogenated $C_{1-4}$alkoxy are selected from chloro or fluoro;

provided that when $R^0$ is hydrogen, $R^1$ is hydrogen, $A^1$ is —CH$_2$—,

is phenyl, $Q^3$ is —O—, $R^2$ is methyl, b is an integer selected from 0 to 1 and $L^1$ is selected from —O—, —NH— or —N(CH$_3$)—, then $R^3$ is other than methyl;

and pharmaceutically acceptable salts thereof.

In an embodiment, the present invention is directed to compounds of formula (I-AA)

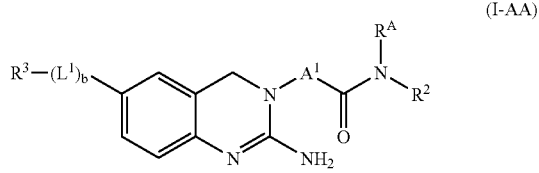

(I-AA)

wherein $A^1$, $R^A$, $R^2$, b, $L^1$ and $R^3$ are as herein defined. Preferably, in the compound of formula (I-AA), the $A^1$ group is substituted at the carbon atom bound to nitrogen atom of the quinazoline core (i.e. at the alpha carbon atom).

In another embodiment, the present invention is directed to compounds of formula (I-BB)

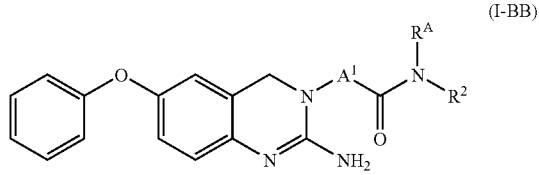

(I-BB)

wherein $A^1$, $R^A$ and $R^2$ are as herein defined. Preferably, in the compound of formula (I-BB), the $A^1$ group is substituted at the carbon atom bound to nitrogen atom of the quinazoline core (i.e. at the alpha carbon atom).

In an embodiment, the present invention is directed to compounds of formula (II-AA)

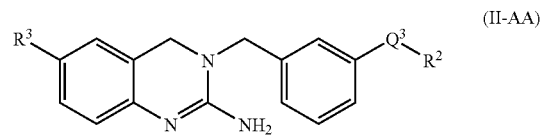

(II-AA)

wherein $R^3$, $Q^3$ and $R^2$ are as herein defined.

In an embodiment of the present invention are compounds of formula (I) wherein the -(L$^1$)$_b$-R$^3$ substituent group is bound at the 6 or 7 position, preferably at the 6-position.

In an embodiment of the present invention are compounds of formula (II) wherein the -(L$^1$)$_b$-R$^3$ substituent group is bound at the 6 or 7 position, preferably at the 6-position. In another embodiment of the present invention, are compounds of formula (II) wherein the -Q$^3$-R$^2$ substituent group is bound at the 2-, 3-, 4- or 5-position of the

substituent, preferably at the 3-position of the

substituent.

In an embodiment of the present invention is a compound of formula (III) wherein the -(L$^2$)$_d$-R$^7$-L$^3$-R$^8$ substituent group is bound at the 6 or 7 position, preferably at the 6-position. In another embodiment of the present invention, is a compound of formula (III) wherein the -L$^3$-R$^8$ substituent group is bound at the 2-, 3- or 4-position of the R$^7$ substituent, preferably, at the 3-position of the R$^7$ substituent.

In an embodiment of the present invention, $R^0$ is selected from the group consisting of hydrogen and methyl. In another embodiment of the present invention, $R^0$ is hydrogen.

In an embodiment of the present invention, $R^1$ is selected from the group consisting of hydrogen, hydroxy, methyl, trifluoromethyl, methoxy and methyl-carbonyl. In another embodiment of the present invention $R^1$ is selected from the group consisting of hydrogen, hydroxy and methoxy. In yet another embodiment of the present invention, $R^1$ is hydrogen.

In an embodiment of the present invention, $A^1$ is selected from the group consisting of $C_{1-4}$alkyl; wherein the $C_{1-4}$alkyl is optionally substituted with one to two R$^X$ substituents; wherein each R$^X$ is independently selected from hydroxy, oxo, $C_{1-8}$alkyl, $C_{1-8}$alkoxy, hydroxy substituted $C_{1-4}$alkyl, cycloalkyl, cycloalkyl-$C_{1-4}$alkyl, biphenyl, aryl, $C_{1-4}$aralkyl, heteroaryl, heteroaryl-$C_{1-4}$alkyl-, heterocycloalkyl, heterocycloalkyl-$C_{1-4}$alkyl-, spiro-heterocyclyl and —(C$_{1-4}$alkyl)$_n$— Q$^2$-R$^4$; and wherein the cycloalkyl, aryl, heteroaryl or heterocycloalkyl group, whether alone or as part of a substituent group is optionally substituted with fluoro, chloro, hydroxy, oxo, carboxy, $C_{1-4}$alkyl, $C_{1-4}$alkoxy, hydroxy substituted $C_{1-4}$alkyl, fluoro substituted $C_{1-4}$alkyl, fluoro substituted $C_{1-4}$alkoxy, 5-tetrazolyl or 1-(1,4-dihydrotetrazol-5-one).

In another embodiment of the present invention, $A^1$ is selected from the group consisting of $C_{1-4}$alkyl; wherein the $C_{1-4}$alkyl is optionally substituted with one to two R$^X$ substituents; wherein each R$^X$ is independently selected from the group consisting of $C_{1-8}$alkyl, hydroxy substituted $C_{1-4}$alkyl, cycloalkyl, aryl, $C_{1-4}$aralkyl, biphenyl, heterocycloalkyl, spiro-heterocyclyl and —$(C_{1-4}alkyl)_n$-$Q^2$-$R^4$; wherein the cycloalkyl, aryl, whether alone or as part of a substituent group is optionally substituted with fluoro, chloro, hydroxy, oxo, $C_{1-4}$alkyl or $C_{1-4}$alkoxy.

In another embodiment of the present invention, $A^1$ is selected from the group consisting of methyl, ethyl, 1-methyl-ethyl, (1)-(R)-methyl-ethyl, (1)-(S)-methyl-ethyl, 1-n-propyl-ethyl, (1)-(R)-n-propyl-ethyl, (1)-(S)-n-propyl-ethyl, 1-isopropyl-ethyl, (1)-(R)-isopropyl-ethyl, (1)-(S)-isopropyl-ethyl, 1-cyclohexyl-ethyl, (1)-(R)-cyclohexyl-ethyl, (1)-(S)-cyclohexyl-ethyl, 1-phenyl-ethyl, 1-(4-hydroxybenzyl)-ethyl, (1)-(R)-(4-hydroxybenzyl)-ethyl, (1)-(S)-(4-hydroxybenzyl)-ethyl, 1-(1-carboxy-2-hydroxy-ethyl), 1-(S)-(1-carboxy-2-hydroxy-ethyl), 1-(R)-(1-carboxy-2-hydroxy-ethyl), 1-(1-carboxy-2-t-butoxy-ethyl), 1-(R)-(1-carboxy-2-t-butoxy-ethyl), 1-(1-carboxy-2-benzyloxy-ethyl), 1-(S)-(1-carboxy-2-benzyloxy-ethyl), 1-(R)-(1-carboxy-2-benzyloxy-ethyl), 1-(1-methoxy-carbonyl-2-benzyloxy-ethyl), 1-(S)-(1-methoxy-carbonyl-2-benzyloxy-ethyl), 1-(R)-(1-methoxy-carbonyl-2-benzyloxy-ethyl), n-propyl, 1-hydroxymethyl-n-propyl, (1)-(R)-hydroxymethyl-n-propyl, (1)-(S)-hydroxymethyl-n-propyl, 1-(dimethyl)-n-propyl, 1-(n-propyl)-n-propyl, 1-isopropyl-n-propyl, (1)-(S)-isopropyl-n-propyl, (1)-(R)-isopropyl-n-propyl, 1-(n-pentyl)-n-propyl, 1-n-octyl-n-propyl, 1-cyclohexyl-n-propyl, (1)-(R)-cyclohexyl-n-propyl, (1)-(S)-cyclohexyl-n-propyl, 1-phenyl-n-propyl, 1-(4-chlorophenyl)-n-propyl, 1-(4-methylphenyl)-n-propyl, 1-(4-methoxyphenyl)-n-propyl, 1-(4-biphenyl)-n-propyl, 1-(N-piperidiny-carbonyl-n-propyl)-n-propyl, 1-(4-tetrahydropyranyl)-n-propyl, (1)-(R)-(4-tetrahydropyranyl)-n-propyl, (1)-(S)-(4-tetrahydropyranyl)-n-propyl, 1-(4-hydroxy-cyclohexyl)-n-propyl, 1-(N-methyl-N-cyclohexyl-aminocarbonyl)-n-propyl, (1)-(R)-(N-methyl-N-cyclohexyl-aminocarbonyl)-n-propyl, (1)-(S)-(N-methyl-N-cyclohexyl-aminocarbonyl)-n-propyl, 1-(1,4-dioxaspiro[4.5]decane)-n-propyl, (1)-(R)-(1,4-dioxaspiro[4.5]decane)-n-propyl, (1)-(S)-(1,4-dioxaspiro[4.5]dec-8-yl)-n-propyl, (1)-(R)-((4R)-hydroxycyclohexyl)-n-propyl, 1-(cylcohexan-4-one)-n-propyl, (1)-(R)-(cylcohexan-4-one)-n-propyl, (1)-(S)-(cylcohexan-4-one)-n-propyl, 1-pyranyl-n-propyl, (1)-(S)-pyranyl-n-propyl, n-butyl, 1-propyl-n-butyl, 1-phenyl-n-butyl, 1-(cyclohexyl-carbonylaminomethyl)-ethyl, 1-(N-cyclohexyl-N-methyl-aminocarbonylethyl)-n-propyl, 1-(2-methyl-piperidinylcarbonyl-n-propyl)-n-propyl and 1-(4-methyl-piperidinylcarbonyl-n-propyl)-n-propyl.

In another embodiment of the present invention, $A^1$ is selected from the group consisting of methyl, ethyl, 1-methyl-ethyl, (1)-(R)-methyl-ethyl, (1)-(S)-methyl-ethyl, 1-n-propyl-ethyl, (1)-(R)-n-propyl-ethyl, (1)-(S)-n-propyl-ethyl, 1-isopropyl-ethyl, (1)-(R)-isopropyl-ethyl, (1)-(S)-isopropyl-ethyl, 1-cyclohexyl-ethyl, (1)-(R)-cyclohexyl-ethyl, (1)-(S)-cyclohexyl-ethyl, 1-phenyl-ethyl, 1-(4-hydroxybenzyl)-ethyl, (1)-(R)-(4-hydroxybenzyl)-ethyl, (1)-(S)-(4-hydroxybenzyl)-ethyl, n-propyl, 1-hydroxymethyl-n-propyl, (1)-(R)-hydroxymethyl-n-propyl, (1)-(S)-hydroxymethyl-n-propyl, 1-(dimethyl)-n-propyl, 1-(n-propyl)-n-propyl, 1-isopropyl-n-propyl, (1)-(S)-isopropyl-n-propyl, (1)-(R)-isopropyl-n-propyl, 1-(n-pentyl)-n-propyl, 1-n-octyl-n-propyl, 1-cyclohexyl-n-propyl, (1)-(R)-cyclohexyl-n-propyl, (1)-(S)-cyclohexyl-n-propyl, 1-phenyl-n-propyl, 1-(4-chlorophenyl)-n-propyl, 1-(4-methylphenyl)-n-propyl, 1-(4-methoxyphenyl)-n-propyl, 1-(4-biphenyl)-n-propyl, 1-(N-piperidiny-carbonyl-n-propyl)-n-propyl, 1-(4-tetrahydropyranyl)-n-propyl, (1)-(R)-(4-tetrahydropyranyl)-n-propyl, (1)-(S)-(4-tetrahydropyranyl)-n-propyl, 1-(4-hydroxy-cyclohexyl)-n-propyl, 1-(N-methyl-N-cyclohexyl-aminocarbonyl)-n-propyl, (1)-(R)-(N-methyl-N-cyclohexyl-aminocarbonyl)-n-propyl, (1)-(S)-(N-methyl-N-cyclohexyl-aminocarbonyl)-n-propyl, 1-(1,4-dioxaspiro[4.5]decane)-n-propyl, (1)-(R)-(1,4-dioxaspiro[4.5]decane)-n-propyl, (1)-(S)-(1,4-dioxaspiro[4.5]dec-8-yl)-n-propyl, (1)-(R)-((4R)-hydroxycyclohexyl)-n-propyl, 1-(cylcohexan-4-one)-n-propyl, (1)-(R)-(cylcohexan-4-one)-n-propyl, (1)-(S)-(cylcohexan-4-one)-n-propyl, 1-pyranyl-n-propyl, (1)-(S)-pyranyl-n-propyl, n-butyl, 1-propyl-n-butyl, 1-phenyl-n-butyl, 1-(cyclohexylcarbonylaminomethyl)-ethyl, 1-(N-cyclohexyl-N-methyl-aminocarbonylethyl)-n-propyl, 1-(2-methyl-piperidinylcarbonyl-n-propyl)-n-propyl and 1-(4-methyl-piperidinylcarbonyl-n-propyl)-n-propyl.

In an embodiment of the present invention, $A^1$ is selected from the group consisting of -ethyl-, -n-butyl-, -n-propyl-, 1-(R)-methyl-ethyl-, 1-n-propyl-ethyl-, 1-cyclohexyl-ethyl-, 1-(R)-cyclohexyl-ethyl-, 1-cyclohexyl-n-propyl-, 1-(S)-cyclohexyl-n-propyl, 1-(R)-cyclohexyl-n-propyl-, 1-(n-propyl)-n-propyl, 1-(n-propyl)-n-butyl-, 1-(R)-isopropyl-n-propyl, 1-(S)-isopropyl-n-propyl, 1-(4-chlorophenyl)-n-propyl, 1-(4-methylphenyl)-n-propyl, 1-(4-methoxyphenyl)-n-propyl, 1-(phenyl)-ethyl-, 1-(cyclohexyl-carbonyl-amino-methyl)-ethyl and 1-(N-cyclohexyl-N-methyl-amino-carbonyl-ethyl)-n-propyl.

In another embodiment of the present invention, $A^1$ is selected from the group consisting of -ethyl-, -n-butyl-, 1-(R)-methyl-ethyl-, 1-n-propyl-ethyl-, 1-cyclohexyl-ethyl-, 1-(R)-cyclohexyl-ethyl-, 1-cyclohexyl-n-propyl, 1-(S)-cyclohexyl-n-propyl, 1-(n-propyl)-n-propyl, 1-(n-propyl)-n-butyl-, 1-(R)-isopropyl-n-propyl, 1-(S)-isopropyl-n-propyl, 1-(4-chlorophenyl)-n-propyl, 1-(4methylphenyl)-n-propyl and 1-(4-methoxyphenyl)-n-propyl.

In another embodiment of the present invention, $A^1$ is selected from the group consisting of -ethyl-, 1-n-propyl-ethyl-, 1-cyclohexyl-ethyl-, 1-(R)-cyclohexyl-ethyl-, 1-cyclohexyl-n-propyl, 1-(S)-cyclohexyl-n-propyl, 1-(n-propyl)-n-propyl, 1-(R)-isopropyl-n-propyl and 1-(S)-isopropyl-n-propyl.

In another embodiment of the present invention, $A^1$ is selected from the group consisting of -ethyl-, -n-butyl-, -n-propyl-, 1-(R)-methyl-ethyl, 1-n-propyl-ethyl, 1-(R)-n-propyl-ethyl-, 1-(n-propyl)-n-propyl-, 1-(n-propyl)-n-butyl-, 1-isopropyl-ethyl-, 1-(n-pentyl)-n-propyl-, 1-cyclohexyl-ethyl-, 1-(R)-cyclohexyl-ethyl, 1-(S)-cyclohexyl-ethyl, 1-phenyl-ethyl, 1-(4-chlorophenyl)-n-propyl-, 1-(4-methoxyphenyl)-n-propyl, 1-cyclohexyl-n-propyl-, 1-phenyl-n-propyl-, 1-(R)-isopropyl-n-propyl, 1-(S)-isopropyl-n-propyl, 1-(R)-cyclohexyl-n-propyl-, 1-(S)-(cyclohexyl)-n-propyl-, 1-(S)-(hydroxymethyl)-n-propyl-, 1-(4-tetrahydropyranyl)-n-propyl-, 1-(S)-(4-tetrahydropyranyl)-n-propyl-, 1-(4-hydroxy-cyclohexyl)-n-propyl-, 1-(S)-(4-oxo-cyclohexyl)-n-propyl, 1-(S)-(cis-4-hydroxy-cyclohexyl)-n-propyl, 1-(S)-(N-cyclohexyl-N-methyl-amino-carbonyl)-n-propyl-, 1-(N-cyclohexyl-N-methyl-amino-carbonyl-ethyl)-n-propyl- and 1-(S)-(1,4-dioxa-spiro[4.5]dec-8-yl)-n-propyl.

In another embodiment of the present invention, $A^1$ is selected from the group consisting of -ethyl-, -n-propyl-, 1-(R)-methyl-ethyl, 1-n-propyl-ethyl, 1-(R)-n-propyl-ethyl-, 1-(n-propyl)-n-propyl-, 1-(n-propyl)-n-butyl-, 1-(n-pentyl)-n-propyl-, 1-cyclohexyl-ethyl-, 1-(R)-cyclohexyl-ethyl, 1-phenyl-ethyl, 1-(4-chlorophenyl)-n-propyl-, 1-(4-methoxyphenyl)-n-propyl, 1-cyclohexyl-n-propyl-, 1-phenyl-n-propyl-, 1-(R)-isopropyl-n-propyl, 1-(S)-isopropyl-n-propyl, 1-(R)-cyclohexyl-n-propyl-, 1-(S)-(cyclohexyl)-n-propyl-, 1-(S)-hydroxymethyl)-n-propyl-, 1-(4-tetrahydropyranyl)-n- propyl-, 1-(S)-(4-tetrahydropyranyl)-n-propyl-, 1-(4-hydroxy-cyclohexyl)-n-propyl-, 1-(S)-(4-oxo-cyclohexyl)-n-propyl, 1-(S)-(cis-4-hydroxy-cyclohexyl)-n-propyl, 1-(S)-(N-cyclohexyl-N-methyl-amino-carbonyl)-n-propyl- and 1-(S)-(1,4-dioxa-spiro[4.5]dec-8-yl)-n-propyl.

In another embodiment of the present invention, $A^1$ is selected from the group consisting of -ethyl-, 1-cyclohexyl-ethyl-, 1-(R)-cyclohexyl-ethyl, 1-cyclohexyl-n-propyl-, 1-(R)-isopropyl-n-propyl, 1-(S)-isopropyl-n-propyl, 1-(R)-cyclohexyl-n-propyl-, 1-(S)-(cyclohexyl)-n-propyl-, 1-(4-tetrahydropyranyl)-n-propyl-, 1-(S)-(4-tetrahydropyranyl)-n-propyl-, 1-(4-hydroxy-cyclohexyl)-n-propyl- and 1-(S)-(4-oxo-cyclohexyl)-n-propyl.

In an embodiment of the present invention, $Q^2$ is selected from the group consisting of —O—, —C(O)—, —C(O)O—, —OC(O)—, —NR$^G$, —NR$^G$—C(O)— and —C(O)—NR$^G$—; wherein R$^G$ is selected from the group consisting of hydrogen, $C_{1-8}$alkyl, hydroxy substituted $C_{1-4}$alkyl, $C_{1-4}$aralkyloxy substituted $C_{1-4}$alkyl, cycloalkyl, aryl, heteroaryl, heterocycloalkyl and $C_{1-4}$aralkyl; wherein the cycloalkyl, aryl, heteroaryl, heterocycloalkyl or spiro-heterocyclyl, whether alone or as part of a substituent group is optionally substituted with one to two substituents independently selected from halogen, hydroxy, oxo, carboxy, $C_{1-4}$alkyl, $C_{1-4}$alkoxy, $C_{1-4}$alkoxy-carbonyl, nitro, cyano, amino, $C_{1-4}$alkylamino, di($C_{1-4}$alkyl)amino, —SO$_2$—N(R$^J$R$^K$), 5-tetrazolyl or 1-(1,4-dihydro-tetrazol-5-one); and wherein each R$^J$ and R$^K$ is independently selected from hydrogen or $C_{1-4}$alkyl.

In another embodiment of the present invention, $Q^2$ is selected from the group consisting of —C(O)—, —C(O)—NR$^G$— and —NR$^G$—C(O)—; wherein R$^G$ is selected from the group consisting of hydrogen and $C_{1-4}$alkyl.

In a embodiment of the present invention, $R^4$ is selected from the group consisting of $C_{1-4}$alkyl, hydroxy substituted $C_{1-4}$alkyl, fluoro substituted $C_{1-4}$alkyl, cycloalkyl, aryl, biphenyl, heteroaryl, heterocycloalkyl and $C_{1-4}$aralkyl; wherein the cycloalkyl, aryl, heteroaryl or heterocycloalkyl, whether alone or as part of a substituent group is optionally substituted with one to two substituents independently selected from halogen, hydroxy, oxo, carboxy, C(O)O—$C_{1-4}$alkyl, C(O)—$C_{1-4}$alkyl, $C_{1-4}$alkyl, fluoro substituted $C_{1-4}$alkyl, $C_{1-4}$alkoxy, nitro, cyano, amino, $C_{1-4}$alkylamino, di($C_{1-4}$alkyl)amino or phenyl; wherein the phenyl is optionally substituted with one to two substituent independently selected from halogen, hydroxy, oxo, carboxy, —C(O)O—$C_{1-4}$alkyl, —C(O)—$C_{1-4}$alkyl, $C_{1-4}$alkyl, fluoro substituted $C_{1-4}$alkyl, $C_{1-4}$alkoxy, nitro, cyano, amino, $C_{1-4}$alkylamino and di($C_{1-4}$alkyl)amino.

In another embodiment of the present invention, $R^4$ is selected from the group consisting of cycloalkyl and heterocycloalkyl.

In an embodiment of the present invention, $Q^1$ is selected from the group consisting of —O—, —S—, —C(O)—, —C(S)—, —C(O)O—, —OC(O)—, —C(O)—NH—, —C(O)—N(CH$_3$)—, —C(O)—N(CH$_2$CH$_3$)—, —C(O)—N(CH$_2$CH$_2$OH)—, —C(O)—N($C_{1-4}$alkyl))-, —C(O)—N(cycloalkyl)-, —C(O)—N(CH$_2$CH$_2$—O—$C_{1-4}$aralkyl)-, —NH—, —N($C_{1-4}$alkyl)-, —NH—C(O)—, —N($C_{1-4}$alkyl)-C(O)—, —NH—C(O)O—, —N($C_{1-4}$alkyl)-C(O)O—, —NH—SO$_2$—, —SO$_2$—NH—, —NH—C(O)—NH—, NH—C(S)—NH— and —NH—SO$_2$—NH—.

In another embodiment of the present invention, $Q^1$ is selected from the group consisting of —O—, —C(O)—, —C(O)O—, —C(O)—NH—, —C(O)—N(CH$_3$)—, —C(O)—N(CH$_2$CH$_3$)—, —C(O)—N(CH$_2$CH$_2$OH)—, —C(O)—N($C_{1-4}$alkyl))-, —C(O)—N(cycloalkyl)-, —C(O)—N(CH$_2$CH$_2$—O—$C_{1-4}$aralkyl)-, —NH—, —N($C_{1-4}$alkyl)-, —NH—C(O)—, —N($C_{1-4}$alkyl)-C(O)—, —NH—C(O)O—, —N($C_{1-4}$alkyl)-C(O)O—, —NH—SO$_2$—, —NH—C(O)—NH— and NH—C(S)—NH—.

In another embodiment of the present invention, $Q^1$ is selected from the group consisting of —O—, —C(O)—, —C(O)O—, —C(O)—NH—, —C(O)—N(CH$_3$)—, —C(O)—N(CH$_2$CH$_3$)—, —C(O)—N(CH$_2$CH$_2$OH)—, —C(O)—N(isopropyl)-, —C(O)—N(cyclohexyl)-, —C(O)—N(CH$_2$CH$_2$—O-benzyl)-, —NH—, —N(CH$_3$)—, —N(CH$_2$CH$_3$)—, —NH—C(O)—, —N(CH$_3$)—C(O)—, —NH—C(O)O—, —N(CH$_3$)—C(O)$_b$—, —NH—SO$_2$—, —NH—C(O)—NH— and NH—C(S)—NH—.

In an embodiment of the present invention, $Q^1$ is selected from the group consisting of —C(O)—NH—, —C(O)—N(CH$_3$)—, —C(O)—N(cyclohexyl)-, —NH—C(O)—, —NH—C(O)O—, —N(CH$_3$)—C(O)O—, —NH—C(O)—NH—, —NH—C(S)—NH and —NH—SO$_2$—. In another embodiment of the present invention, Q1 is selected from the group consisting of —C(O)—NH—, —C(O)—N(CH$_3$)—, —C(O)—N(cyclohexyl)-, —NH—C(O)—, —NH—C(O)O—, —N(CH$_3$)—C(O)O—, —NH—C(O)—NH— and —NH—C(S)—NH. In yet another embodiment of the present invention, $Q^1$ is selected from the group consisting of —C(O)—NH—, —C(O)—N(CH$_3$)— and —NH—C(O)—.

In an embodiment of the present invention, $Q^1$ is selected from the group consisting of —C(O)—NH—, —C(O)—N(CH$_3$)—, —C(O)—N(ethyl)-, —C(O)—N(cyclohexyl)-, —C(O)—N(hydroxyethyl)-, —C(O)—N(benzyloxy-ethyl)-, —N(CH$_3$)—, —NH—C(O)—, —N(CH$_3$)—C(O)—, —NH—C(O)O—, —N(CH$_3$)—C(O)O—, —NH—C(O)—NH, —NH—C(S)—NH and —NH—SO$_2$—. In another embodiment of the present invention, $Q^1$ is selected from the group consisting of —C(O)—NH—, —C(O)—N(CH$_3$)—, —C(O)—N(ethyl)-, —C(O)—N(hydroxyethyl)-, —C(O)—N(benzyloxy-ethyl)-, —N(CH$_3$)—, —NH—C(O)—, —NH—C(O)O—, —N(CH$_3$)—C(O)O— and —NH—C(S)—NH. In yet another embodiment of the present invention, $Q^1$ is selected from the group consisting of —C(O)—NH—, —C(O)—N(CH$_3$)—, —C(O)—N(hydroxyethyl)-, —C(O)—N(benzyloxy-ethyl)- and —NH—C(O)—.

In another embodiment of the present invention, $Q^1$ is selected from the group consisting of —C(O)—NH—, —C(O)—N(CH$_3$)—, —C(O)—N(ethyl)-, —C(O)—N(CH$_2$CH$_2$OH)—, —C(O)—N(cyclohexyl)-, —C(O)—N(hydroxyethyl)-, —C(O)—N(benzyloxy-ethyl)-, —N(CH$_3$)—, —NH—C(O)—, —N(CH$_3$)—C(O)—, —NH—C(O)O—, —N(CH$_3$)—C(O)O—, —NH—C(O)—NH, —NH—C(S)—NH and —NH—SO$_2$—.

In another embodiment of the present invention, $Q^1$ is selected from the group consisting of —C(O)—NH—, —C(O)—N(CH$_3$)—, —C(O)—N(ethyl)-, —C(O)—N(CH$_2$CH$_2$OH)—, —C(O)—N(hydroxyethyl)-, —C(O)—N(benzyloxy-ethyl)-, —N(CH$_3$)—, —NH—C(O)—, —NH—C(O)O—, —N(CH$_3$)—C(O)O— and —NH—C(S)—NH.

In another embodiment of the present invention, $Q^1$ is selected from the group consisting of —C(O)—NH—, —C(O)—N(CH$_3$)—, —C(O)—N(hydroxyethyl)-, —C(O)—N(benzyloxy-ethyl)-, —C(O)—N(cyclohexyl)- and —NH—C(O)—.

In an embodiment of the present invention, $R^2$ is selected from the group consisting of $C_{1-10}$alkyl, cycloalkyl, aryl, biphenyl, partially unsaturated carbocyclyl, heteroaryl, heterocycloalkyl, cycloalkyl-$C_{1-4}$alkyl-, $C_{1-4}$aralkyl, partially unsaturated carbocyclyl-$C_{1-4}$alkyl-, heteroaryl-$C_{1-4}$alkyl-, heterocycloalkyl-$C_{1-4}$alkyl- and spiro-heterocyclyl;

wherein the $C_{1-10}$alkyl, cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, —C(O)—$C_{1-4}$alkyl, —C(O)—$C_{1-4}$aralkyl, —C(O)O—$C_{1-4}$alkyl, —C(O)O—$C_{1-4}$aralkyl, —$C_{1-4}$alkyl-C(O)O—$C_{1-4}$alkyl, —$C_{1-4}$alkyl-S—$C_{1-4}$alkyl, —C(O)—N($R^L R^M$), —$C_{1-4}$alkyl-C(O)—N($R^L R^M$), —$NR^L$—C(O)—$C_{1-4}$alkyl, —$SO_2$—N($R^L R^M$), —$C_{1-4}$alkyl-$SO_2$—N($R^L R^M$), $C_{1-6}$alkyl, fluoro substituted $C_{1-4}$alkyl, hydroxy substituted $C_{1-4}$alkyl, carboxy substituted $C_{1-4}$alkyl, $C_{1-4}$alkoxy, nitro, cyano, amino, $C_{1-4}$alkylamino, di($C_{1-4}$alkyl)amino, phenyl, 5-tetrazolyl and 1-(1,4-dihydrotetrazol-5-one);

wherein the phenyl is optionally substituted with one or more substituent independently selected from the group consisting of halogen, hydroxy, oxo, carboxy, C(O)O—$C_{1-4}$alkyl, C(O)—$C_{1-4}$alkyl, $C_{1-4}$alkyl, fluoro substituted $C_{1-4}$alkyl, $C_{1-4}$alkoxy, nitro, cyano, amino, $C_{1-4}$alkylamino and di($C_{1-4}$alkyl)amino;

wherein each $R^L$ and $R^M$ is independently selected from the group consisting of hydrogen and $C_{1-4}$alkyl;

In another embodiment of the present invention, $R^2$ is selected from the group consisting of $C_{1-10}$alkyl, cycloalkyl, aryl, biphenyl, partially unsaturated carbocyclyl, heteroaryl, heterocycloalkyl, cycloalkyl-$C_{1-4}$alkyl-, $C_{1-4}$aralkyl, partially unsaturated carbocyclyl-$C_{1-4}$alkyl-, heteroaryl-$C_{1-4}$alkyl-, heterocycloalkyl-$C_{1-4}$alkyl- and spiro-heterocyclyl;

wherein the $C_{1-10}$alkyl, cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, —C(O)—$C_{1-4}$alkyl, —C(O)—$C_{1-4}$aralkyl, —C(O)O—$C_{1-4}$alkyl, —C(O)O—$C_{1-4}$aralkyl, —C(O)—N($R^L R^M$), —$C_{1-4}$alkyl-C(O)O—$C_{1-4}$alkyl, —$C_{1-4}$alkyl-C(O)—N($R^L R^M$), —$NR^L$—C(O)—$C_{1-4}$alkyl, $C_{1-6}$alkyl, fluoro substituted $C_{1-4}$alkyl, hydroxy substituted $C_{1-4}$alkyl, carboxy substituted $C_{1-4}$alkyl, $C_{1-4}$alkoxy, —O—$C_{1-4}$aralkyl, —O-(tetrahydropyranyl), —NH—C(O)—O—$CH_2$-(tetrahydropyranyl), nitro, cyano, amino, $C_{1-4}$alkylamino, di($C_{1-4}$alkyl)amino phenyl and 5-tetrazolyl;

wherein the phenyl or tetrahydropyranyl is optionally substituted with one to two substituent independently selected from the group consisting of halogen, hydroxy, oxo, carboxy, —OC(O)—$C_{1-4}$alkyl, —$C_{1-4}$alkyl-OC(O)—$C_{1-4}$alkyl, $C_{1-4}$alkyl, fluoro substituted $C_{1-4}$alkyl, hydroxy substituted $C_{1-4}$alkyl, $C_{1-4}$alkoxy, nitro, cyano, amino, $C_{1-4}$alkylamino and di($C_{1-4}$alkyl)amino;

wherein each $R^L$ and $R^M$ is independently selected from the group consisting of hydrogen and $C_{1-4}$alkyl.

In another embodiment of the present invention, $R^2$ is selected from the group consisting of $C_{1-10}$alkyl, cycloalkyl, aryl, biphenyl, partially unsaturated carbocyclyl, heteroaryl, heterocycloalkyl, cycloalkyl-$C_{1-4}$alkyl-, $C_{1-4}$aralkyl, partially unsaturated carbocyclyl-$C_{1-4}$alkyl-, heteroaryl-$C_{1-4}$alkyl-, heterocycloalkyl-$C_{1-4}$alkyl- and spiro-heterocyclyl; wherein the $C_{1-10}$alkyl, cycloalkyl, aryl, heteroaryl, heterocycloalkyl or spiro-heterocyclyl, whether alone or as part of a substituent group is optionally substituted with one or more substituents independently selected from halogen, hydroxy, oxo, carboxy, —C(O)—$C_{1-4}$alkyl, —C(O)—$C_{1-4}$aralkyl, —C(O)O—$C_{1-4}$alkyl, —C(O)O—$C_{1-4}$aralkyl, —C(O)—N($R^L R^M$), —$C_{1-4}$alkyl-C(O)—N($R^L R^M$), —$NR^L$—C(O)—$C_{1-4}$alkyl, $C_{1-6}$alkyl, fluoro substituted $C_{1-4}$alkyl, hydroxy substituted $C_{1-4}$alkyl, carboxy substituted $C_{1-4}$alkyl, $C_{1-4}$alkoxy, nitro, cyano, amino, $C_{1-4}$alkylamino, di($C_{1-4}$alkyl)amino or phenyl; wherein the phenyl is optionally substituted with one to two substituent independently selected from halogen, hydroxy, oxo, carboxy, $C_{1-4}$alkyl, fluoro substituted $C_{1-4}$alkyl, $C_{1-4}$alkoxy, nitro, cyano, amino, $C_{1-4}$alkylamino or di($C_{1-4}$alkyl)amino; and wherein each $R^L$ and $R^M$ is independently selected from the group consisting of hydrogen and $C_{1-4}$alkyl.

In another embodiment of the present invention, $R^2$ is selected from the group consisting of $C_{1-10}$alkyl, cycloalkyl, cycloalkyl-alkyl, aryl, $C_{1-4}$aralkyl, heteroaryl, heterocycloalkyl, spiro-heterocyclyl and heteroaryl-$C_{1-4}$alkyl-;

wherein the $C_{1-10}$alkyl, aryl, cycloalkyl, heteroaryl or heterocycloalkyl, whether alone or as part of a substituent group is optionally substituted with one to two substituent independently selected from the group consisting of $C_{1-5}$alkyl, $C_{1-4}$alkoxy, —O—$C_{1-2}$aralkyl, —O-(tetrahydropyranyl), —NH—C(O)—O—$CH_2$-(tetrahydropyranyl), halogen, trifluoromethyl, amino, cyano, hydroxy, oxo, carboxy, phenyl, —C(O)—$C_{1-4}$alkyl, —C(O)O—$C_{1-2}$aralkyl, —C(O)—N($R^L R^M$), —C(O)—N($C_{1-4}$alkyl)(cycloalkyl), —NH—C(O)—$C_{1-4}$alkyl, —C(O)O—$C_{1-4}$alkyl, —$C_{1-2}$alkyl-C(O)O—$C_{1-4}$alkyl, carboxy substituted $C_{1-2}$alkyl and 5-tetrazolyl;

wherein the phenyl or tetrahydropyranyl is optionally substituted with one to two substituents independently selected from the group consisting of hydroxy, halogen, cyano, $C_{1-4}$alkyl, $C_{1-4}$alkoxy, hydroxy substituted $C_{1-2}$alkyl, —OC(O)—$C_{1-2}$alkyl, —$C_{1-12}$alkyl-OC(O)—$C_{1-2}$alkyl, amino, $C_{1-4}$alkylamino and di($C_{1-4}$alkyl)amino;

wherein $R^L$ and $R^M$ are each independently selected from the group consisting of hydrogen, methyl and ethyl.

In another embodiment of the present invention, $R^2$ is selected from the group consisting of $C_{1-10}$alkyl, cycloalkyl, cycloalkyl-alkyl, aryl, $C_{1-4}$aralkyl, heteroaryl, heterocycloalkyl and spiro-heterocyclyl; wherein the $C_{1-10}$alkyl, aryl, cycloalkyl, heteroaryl or heterocycloalkyl, whether alone or as part of a substituent group is optionally substituted with one to two substituent independently selected from $C_{1-5}$alkyl, $C_{1-4}$alkoxy, halogen, trifluoromethyl, amino, cyano, hydroxy, oxo, carboxy, phenyl, —C(O)—$C_{1-4}$alkyl, —C(O)—$NH_2$, —C(O)—N($C_{1-4}$alkyl)(cycloalkyl), —NH—C(O)—$C_{1-4}$alkyl or —C(O)O—$C_{1-4}$alkyl; wherein the phenyl is optionally substituted with one to two substituents independently selected from the group consisting of halogen, cyano, $C_{1-4}$alkyl, $C_{1-4}$alkoxy, amino, $C_{1-4}$alkylamino and di($C_{1-4}$alkyl)amino.

In another embodiment of the present invention, $R^2$ is selected from the group consisting of methyl, ethyl, n-propyl, isopropyl, t-butyl, isobutyl, isopentyl, 3-n-heptyl, n-nonyl, amino-methyl, carboxy-methyl-, 2-amino-ethyl, 2-cyano-ethyl, 4-carboxy-n-butyl, 3-n-heptyl, 4-n-heptyl, 3-amino-n-propyl, 3,3,3-trifluoro-n-propyl, 3,3,3-trifluoro-isobutyl, 1-(1-carboxy-2-hydroxy-ethyl), 1-(1-(S)-carboxy-2-hydroxy-ethyl), 1-(1-(R)-carboxy-2-hydroxy-ethyl), 1-(1-carboxy-2-t-butoxy-ethyl), 1-(1-(R)-carboxy-2-t-butoxy-ethyl), 1-(1-carboxy-2-benzyloxy-ethyl), 1-(1-(S)-carboxy-2-benzyloxy-ethyl), 1-(1-(R)-carboxy-2-benzyloxy-ethyl), 1-(1-methoxy-carbonyl-2-benzyloxy-ethyl), 1-(1-(S)-methoxy-carbonyl-2-benzyloxy-ethyl), 1-(1-(R)-methoxy-carbonyl-2-benzyloxy-ethyl), cyclopropyl, cyclobutyl, cyclopentyl, cyclohexyl, cycloheptyl, 2-phenyl-cyclopropyl, cyclopentyl-methyl, cyclopentyl-ethyl, 1-(1-aminocarbonyl-cyclopropyl), 4-hydroxy-cyclohexyl, 4-carboxy-cyclohexyl, cis-(4-carboxy)-cyclohexyl, trans-(4-carboxy)-cyclohexyl, 3-carboxy-cyclohexyl, cis-(3-carboxy)-cyclohexyl, 4-cyano-cyclohexyl, 4-methoxy-carbonyl-cyclohexyl, 3-methoxy-carbonyl-cyclohexyl, cis-(3-methoxy-carbonyl)-cyclohexyl, 4-ethoxy-carbonyl-cyclohexyl, (1)-(S)-((4R)-methoxy-carbonyl-cyclohexyl, (1)-(R)-((4S)-methoxy-carbonyl-cyclohexyl, 2-methyl-cyclohexyl, 4-methyl-cyclohexyl, 4-n-pentyl-cyclohexyl, 4-t-butyl-cyclohexyl, (1)-(S)-2-(R)-methyl-cyclopentyl, 3-methoxy-cyclohexyl, 1-(1-(4-chlorophenyl)-cyclopentyl), 4-trifluoromethyl-cyclohexyl, 4-oxo-cyclohexyl, 1-(4-benzyloxy-carbonyl-cyclohexyl), 1-(S)-(4-(S)-benzyloxy-carbonyl-cyclohexyl), 1-(4-amino-carbonyl-cyclohexyl), 1-(S)-(4-(S)-amino-carbonyl-cyclohexyl), 1-(4-methylamino-carbonyl-cyclohexyl), 1-(S)-(4-(S)-methylamino-carbonyl-cyclohexyl), 1-(4-(5-tetrazolyl)-cyclohexyl), phenyl, benzyl, phenyl-ethyl, 3-carboxy-methyl-benzyl, 3-methoxy-carbonyl-methyl-benzyl, 4-carboxy-phenyl, 3-cyano-phenyl, 4-methyl-phenyl, 4-t-butyl-phenyl, 4-n-butyl-phenyl, 2-methoxy-phenyl, 3-methoxy-phenyl, 4-dimethylamino-phenyl, 4-(methylcarbonylamino)-phenyl, 1-naphthyl-methyl, 1-(1,2,3,4-tetrahydronaphthyl), 4-biphenyl, benzhydryl, 1-adamantyl, 2-adamantyl, 2-(R)-adamantyl, 2-(S)-adamantyl, N-piperidinyl, 1-(2-carboxy-piperidinyl), 1-(S)-2-carboxy-piperidinyl), 1-(2-methoxy-carbonyl-piperidinyl), 1-(S)-2-methoxy-carbonyl-piperidinyl), 1-(2-methyl-piperidinyl), 1-(4-methyl-piperidinyl), 1-(4-isopropyl-piperidinyl), 4-(1-methylcarbonyl)-piperidinyl), 3-(2,5-dimethyl-furyl), 4-tetrahydropyranyl, 4-(2-phenyl-thiazolyl)-methyl, 4-(1-phenyl-pyrazolyl)-methyl, 5-(3-methyl-isoxazolyl)-methyl, 3-(5-phenyl-isoxazolyl)-methyl, 1-(2-carboxy-pyrrolidinyl), 1-(S)-(2-carboxy-pyrrolidinyl), 1-(2-(N-methyl-N-cyclohexylaminocarbonyl)-pyrrolidinyl), 1,4-dioxaspiro[4.5]dec-8-yl, 2-(bicyclo[2.2.1]heptyl), 1-(3-n-pentyl-bicyclo[2.2.2]-octyl, 2-bicyclo[2.2.2]octyl, 2-(R)-bicyclo[2.2.2]octyl, 2-(S)-bicyclo[2.2.2]octyl, 5-tetrazolyl-methyl, 2-imidazolyl-methyl, 5-imidazolyl-methyl, 4-pyridyl-methyl, 3-(1,2,4-triazolyl)-methyl, 1-(2-carboxy-octahydroindolyl), 1-(S)-(2-carboxy-octahydroindolyl), 1-(2-methoxy-carbonyl-octahydroindolyl), 1-(S)-2-methoxy-carbonyl-octahydroindolyl), 2R-(3R,4S,5R-tri(methyl-carbonyloxy)-6R-(methyl-carbonyloxy-methyl)-tetrahydropyranyl)oxy-ethyl, 2R-(3S,4S,5R-trihydroxy-6R-(hydroxy-methyl)-tetrahydropyranyl)oxy-ethyl and 3-(2R-(3S,4S,5R,6R-tetrahydroxy-tetrahydropyrantl)-methoxy-carbonyl-amino)-n-propyl.

In another embodiment of the present invention, $R^2$ is selected from the group consisting of methyl, ethyl, n-propyl, isopropyl, t-butyl, isobutyl, isopentyl, 3-n-heptyl, n-nonyl, amino-methyl, 2-amino-ethyl, 2-cyano-ethyl, 4-carboxy-n-butyl, 3-n-heptyl, 4-n-heptyl, 3-amino-n-propyl, 3,3,3-trifluoro-n-propyl, 3,3,3-trifluoro-isobutyl, cyclopropyl, cyclobutyl, cyclopentyl, cyclohexyl, cycloheptyl, 2-phenyl-cyclopropyl, cyclopentyl-methyl, cyclopentyl-ethyl, 1-(1-aminocarbonyl-cyclopropyl), 4-hydroxy-cyclohexyl, 4-carboxy-cyclohexyl, cis-(4-carboxy)-cyclohexyl, trans-(4-carboxy)-cyclohexyl, 4-methoxy-carbonyl-cyclohexyl, 4-ethoxy-carbonyl-cyclohexyl, (1)-(S)-((4R)-methoxy-carbonyl-cyclohexyl, (1)-(R)-((4S)-methoxy-carbonyl-cyclohexyl, 2-methyl-cyclohexyl, 4-methyl-cyclohexyl, 4-n-pentyl-cyclohexyl, 4-t-butyl-cyclohexyl, (1)-(S)-2-(R)-methyl-cyclopentyl, 3-methoxy-cyclohexyl, 1-(1-(4-chlorophenyl)-cyclopentyl), 4-trifluoromethyl-cyclohexyl, 4-oxo-cyclohexyl, phenyl, benzyl, phenyl-ethyl, 3-cyano-phenyl, 4-methyl-phenyl, 4-t-butyl-phenyl, 4-n-butyl-phenyl, 2-methoxy-phenyl, 3-methoxy-phenyl, 4-dimethylamino-phenyl, 4-(methylcarbonylamino)-phenyl, 1-naphthyl-methyl, 1-(1,2,3,4-tetrahydro-naphthyl), 4-biphenyl, benzhydryl, 1-adamantyl, 2-adamantyl, 2-(R)-adamantyl, 2-(S)-adamantyl, N-piperidinyl, 1-(2-methyl-piperidinyl), 1-(4-methyl-piperidinyl), 1-(4-isopropyl-piperidinyl), 4-(1-methylcarbonyl)-piperidinyl), 3-(2,5-dimethyl-furyl), 4-tetrahydropyranyl, 4-(2-phenyl-thiazolyl)-methyl, 4-(1-phenyl-pyrazolyl)-methyl, 5-(3-methyl-isoxazolyl)-methyl, 3-(5-phenyl-isoxazolyl)-methyl, 1-(2-(N-methyl-N-cyclohexylaminocarbonyl)-pyrrolidinyl), 1,4-dioxaspiro[4.5]dec-8-yl, 2-(bicyclo[2.2.1]heptyl), 1-(3-n-pentyl-bicyclo[2.2.2]-octyl, 2-bicyclo[2.2.2]octyl, 2-(R)-bicyclo[2.2.2]octyl and 2-(S)-bicyclo[2.2.2]octyl.

In an embodiment of the present invention, $R^2$ is selected from the group consisting of isopropyl, n-butyl, t-butyl, 1-ethyl-n-pentyl, isopentyl, 3-n-heptyl, 4-n-heptyl, cyclobutyl, cyclopentyl, cyclohexyl, cycloheptyl, cyclopentyl-methyl-, 2-methyl-cyclohexyl, 3-methoxy-cyclohexyl, phenyl, phenylethyl-, 4-(1-methyl-piperidinyl), 1-(1-(4-chlorophenyl)-cyclopentyl), 1-adamantyl and 2-adamantyl.

In another embodiment of the present invention, $R^2$ is selected from the group consisting of isopropyl, t-butyl, 1-ethyl-n-pentyl, isopentyl, 3-n-heptyl, 4-n-heptyl, cyclopentyl, cyclohexyl, cycloheptyl, cyclopentyl-methyl-, 2-methyl-cyclohexyl, phenyl, 4-(1-methyl-piperidinyl), 1-(1-(4-chlorophenyl)-cyclopentyl), 1-adamantyl and 2-adamantyl.

In another embodiment of the present invention, $R^2$ is selected from the group consisting of isopentyl, 4-n-heptyl, cyclopentyl, cyclohexyl, cyclopentyl-methyl-, 1-(1-(4-chlorophenyl)-cyclopentyl), 1-adamantyl and 2-adamantyl.

In another embodiment of the present invention, $R^2$ is selected from the group consisting of carboxy-methyl, 2-cyanoethyl-, n-propyl, isopropyl, n-butyl, isobutyl, t-butyl, isopentyl, 3-n-heptyl, 4-n-heptyl, 4-carboxy-n-butyl, cyclopropyl, cyclobutyl, cyclopentyl, cyclohexyl, cycloheptyl, cyclopentyl-methyl-, cyclopentyl-ethyl-, 1-(S)-(1-carboxy-2-hydroxy-ethyl), 1-(R)-(1-carboxy-2-hydroxy-ethyl), 1-(R)-(1-carboxy-2-t-butoxy-ethyl), 1-(S)-(1-methoxy-carbonyl-2-benzyloxy-ethyl), 1-(R)-(1-methoxy-carbonyl-2-benzyloxy-ethyl), 1-(S)-(1-carboxy-2-benzyloxy-ethyl), 1-(R)-(-carboxy-2-benzyloxy-ethyl), trans-2-methyl-cyclohexyl-, 1-(1-(4-chlorophenyl)-cyclopentyl), 3-methoxy-cyclohexyl, 4-hydroxy-cyclohexyl, 1-cis-(3-carboxy-cyclohexyl), 4-carboxy-cyclohexyl, (1)-(S)-((4R)-carboxy-cyclohexyl), (1)-(R)-((4S)-carboxy-cyclohexyl), 4-(ethoxy-carbonyl)-cyclohexyl, cis-(4-methoxy-carbonyl)-cyclohexyl, trans-(4-methoxy-carbonyl)-cyclohexyl, 1-4-oxo-cyclohexyl, 1-cis-(4-amino-carbonyl-cyclohexyl), phenyl, 2-methoxyphenyl, 2-methylphenyl, benzyl, phenylethyl-, benzhydryl, 4-(1-isopropyl)-piperidinyl, 4-(1-methyl-piperidinyl), 1-adamantyl, 2-adamantyl, 4-(tetrahydropyranyl), 5-(3-methyl-isoxazolyl)-methyl, 1,4-oxaspiro[4.5]dec-8-yl and 5-tetrazolyl-methyl.

In an embodiment of the present invention, $R^2$ is selected from the group consisting of 2-cyanoethyl-, n-propyl, isopropyl, n-butyl, isobutyl, t-butyl, isopentyl, 3-n-heptyl, 4-n-heptyl, 4-carboxy-n-butyl, cyclopropyl, cyclobutyl, cyclopentyl, cyclohexyl, cycloheptyl, cyclopentyl-methyl-, cyclopentyl-ethyl-, trans-2-methyl-cyclohexyl-, 1-(1-(4-chlorophenyl)-cyclopentyl), 3-methoxy-cyclohexyl, 4-hydroxy-cyclohexyl, 4-carboxy-cyclohexyl, (1)-(S)-((4R)-carboxy-cyclohexyl), (1)-(R)-((4S)-carboxy-cyclohexyl), 4-(ethoxy-carbonyl)-cyclohexyl, cis-(4-methoxy-carbonyl)-cyclohexyl, trans-(4-methoxy-carbonyl)-cyclohexyl, 1-4-oxo-cyclohexyl, phenyl, 2-methoxyphenyl, 2-methylphenyl, benzyl, phenylethyl-, benzhydryl, 4-(1-isopropyl)-piperidinyl, 4-(1-methyl-piperidinyl), 1-adamantyl, 2-adamantyl, 4-(tetrahydropyranyl), 5-(3-methyl-isoxazolyl)-methyl and 1,4-oxaspiro[4.5]dec-8-yl.

In another embodiment of the present invention, $R^2$ is selected from the group consisting of carboxy-methyl, isopropyl, isobutyl, t-butyl, isopentyl, 3-n-heptyl, 4-n-heptyl, 4-carboxy-n-butyl, cyclobutyl, cyclopentyl, cyclohexyl, cycloheptyl, cyclopentyl-methyl-, cyclopentyl-ethyl-, 1-(S)-(1-carboxy-2-hydroxy-ethyl), 1-(R)-(1-carboxy-2-hydroxy-ethyl), 1-(R)-(1-carboxy-2-t-butoxy-ethyl), 1-(S)-(1-methoxy-carbonyl-2-benzyloxy-ethyl), 1-(R)-(1-methoxy-carbonyl-2-benzyloxy-ethyl), 1-(S)-(1-carboxy-2-benzyloxy-ethyl), trans-2-methyl-cyclohexyl-, 1-(1-(4-chlorophenyl)-cyclopentyl), 3-methoxy-cyclohexyl, 4-hydroxy-cyclohexyl, 1-cis-(3-carboxy-cyclohexyl), 4-carboxy-cyclohexyl, (1)-(S)-((4R)-carboxy-cyclohexyl), (1)-(R)-((4S)-carboxy-cyclohexyl), cis-(4-methoxy-carbonyl)-cyclohexyl, trans-(4-methoxy-carbonyl)-cyclohexyl, 1-cis-(4-amino-carbonyl-cyclohexyl), phenyl, 2-methylphenyl, phenylethyl-, 4-(1-methyl-piperidinyl), 1-adamantyl, 2-adamantyl, 4-(tetrahydropyranyl), 5-(3-methyl-isoxazolyl)-methyl and 5-tetrazolyl-methyl.

In another embodiment of the present invention, $R^2$ is selected from the group consisting of isopropyl, isobutyl, t-butyl, isopentyl, 3-n-heptyl, 4-n-heptyl, 4-carboxy-n-butyl, cyclobutyl, cyclopentyl, cyclohexyl, cycloheptyl, cyclopentyl-methyl-, cyclopentyl-ethyl-, trans-2-methyl-cyclohexyl-, 1-(1-(4-chlorophenyl)-cyclopentyl), 3-methoxy-cyclohexyl, 4-hydroxy-cyclohexyl, 4-carboxy-cyclohexyl, (1)-(S)-((4R)-carboxy-cyclohexyl), (1)-(R)-((4S)-carboxy-cyclohexyl), cis-(4-methoxy-carbonyl)-cyclohexyl, trans-(4-methoxy-carbonyl)-cyclohexyl, phenyl, 2-methylphenyl, phenylethyl-, 4-(1-methyl-piperidinyl), 1-adamantyl, 2-adamantyl, 4-(tetrahydropyranyl) and 5-(3-methyl-isoxazolyl)-methyl.

In another embodiment of the present invention, $R^2$ is selected from the group consisting of carboxy-methyl, isobutyl, isopentyl, 1-(1-(R)-carboxy-2-hydroxy-ethyl), 1-(1-(R)-carboxy-2-t-butoxy-ethyl), 1-(1-(S)-carboxy-2-benzyloxy-ethyl), cyclopentyl, cyclohexyl, 4-carboxy-cyclohexyl, (1)-(S)-((4R)-carboxy-cyclohexyl), 1-adamantyl and 2-adamantyl.

In another embodiment of the present invention, $R^2$ is selected from the group consisting of isobutyl, isopentyl, cyclopentyl, cyclohexyl, 4-carboxy-cyclohexyl, (1)-(S)-((4R)-carboxy-cyclohexyl), 1-adamantyl and 2-adamantyl.

In an embodiment of the present invention, $L^1$ is selected from the group consisting of —O—, —S(O)$_{0-2}$—, —C(O)—, —C(S)—, —C$_{1-4}$alkyl- and (hydroxy substituted C$_{1-4}$alkyl)-. In another embodiment of the present invention, $L^1$ is selected from the group consisting of —O—, —C(O)—, —CH$_2$— and —C(OH)—. In another embodiment of the present invention, $L^1$ is selected from the group consisting of —O—, —C(O)—, —CH$_2$— and —C(OH)—.

In an embodiment of the present invention, $L^1$ is selected from the group consisting of —C(O)— and —O—. In another embodiment of the present invention, $L^1$ is —O—.

In an embodiment of the present invention, $L^1$ is selected from the group consisting of —C(O)— and —(O)—. In another embodiment of the present invention, $L^1$ is —(O)—;

In an embodiment of the present invention, $R^3$ is selected from the group consisting of C$_{1-6}$alkyl, C$_{2-6}$alkenyl, cycloalkyl, partially unsaturated carbocyclyl, aryl, C$_{1-4}$aralkyl, biphenyl, heteroaryl and heterocycloalkyl; wherein the cycloalkyl, partially unsaturated carbocyclyl, aryl, heteroaryl or heterocycloalkyl, whether alone or as part of a substituent group is optionally substituted with one to two substituents independently selected from halogen, hydroxy, oxo, carboxy, C$_{1-4}$alkyl, hydroxy substituted C$_{1-4}$alkyl, halogen substituted C$_{1-4}$alkyl, cyano substituted C$_{1-4}$alkyl, C$_{2-4}$alkenyl, C$_{2-4}$alkynyl, C$_{1-4}$alkoxy, halogen substituted C$_{1-4}$alkoxy, nitro, cyano, —R$^5$, —O—R$^5$, —S—R$^5$, —NH$_2$, —N(R$^P$)—R$^5$, —C(O)—R$^5$, —C(O)—NH$_2$, —C(O)—NR$^P$—R$^5$, —NR$^P$—C(O)—R$^5$, —NR$^P$—C(O)O—R$^5$ and —SO$_2$—NR$^P$—R$^5$.

In another embodiment of the present invention, $R^3$ is selected from the group consisting of C$_{2-6}$alkenyl, aryl, biphenyl, partially unsaturated carbocyclyl and heteroaryl; wherein the aryl or heteroaryl group is optionally substituted with one to two substituents independently selected from hydroxy, halogen, C$_{1-4}$alkyl, C$_{1-4}$alkoxy, —S—C$_{1-4}$alkyl, hydroxy substituted C$_{1-4}$alkyl, halogen substituted C$_{1-4}$alkyl, —C(O)—NH$_2$, —C(O)—C$_{1-4}$alkyl, —NH—C$_{1-4}$alkyl-cycloalkyl, —NH—C(O)—C$_{1-4}$alkyl, —NH—C(O)—O—C$_{1-4}$aralkyl, —SO$_2$—NH—C$_{1-4}$alkyl or —SO$_2$—NH-phenyl.

In another embodiment of the present invention, $R^3$ is selected from the group consisting of n-penten-1-yl, phenyl, 2-hydroxy-phenyl, 2-chloro-phenyl, 3-chloro-phenyl, 4-chloro-phenyl, 2-fluoro-phenyl, 4-fluorophenyl, 2,6-difluoro-phenyl, 2-methyl-phenyl, 3-methyl-phenyl, 4-methyl-phenyl, 2-methoxy-phenyl, 4-methoxy-phenyl, 3,5-dimethoxy-phenyl, 2,6-dimethoxy-phenyl, 2-isopropyl-phenyl, 2-methylthio-phenyl, 2-fluoro-6-methoxy-phenyl, 2-methoxy-5methyl-phenyl, 2-methoxy-5-fluoro-phenyl, 3-(hydroxymethyl)-phenyl, 3-trifluoromethyl-phenyl, 2-(methylcarbonylamino)-phenyl, 2-(t-butylaminosulfonyl)-phenyl, 2-(aminocarbonyl)-phenyl, 2-(methylsulfonylamino)-phenyl, 3-(methylcarbonyl)-phenyl, 3-(benzyloxycarbonylamino)-phenyl, 3-(N-(cyclohexylmethyl)-amino)-phenyl, 3-(phenylsulfonylamino)-phenyl, 2-naphthyl, 1-cyclohexenyl, 1-cyclopentenyl, 2-biphenyl, 5-pyrimidinyl, 4-pyridyl, 3-quinolinyl and 3-(6-fluoro-benzo[d]isoxazolyl).

In an embodiment of the present invention, $R^3$ is selected from the group consisting of phenyl, 2-methoxyphenyl, 3-(benzyloxy-carbonyl-amino)-phenyl, 3-(N-(cyclohexylmethyl)-amino)-phenyl and 3-(phenyl-sulfonyl-amino)-phenyl. In another embodiment of the present invention, $R^3$ is selected from the group consisting of phenyl, 2-methoxyphenyl, 3-(benzyloxy-carbonyl-amino)-phenyl and 3-(phenyl-sulfonyl-amino)-phenyl. In yet another embodiment of the present invention, $R^3$ is selected from the group consisting of phenyl and 2-methoxyphenyl.

In an embodiment of the present invention, $R^3$ is selected from the group consisting of phenyl, 2-hydroxyphenyl, 2-fluorophenyl, 2,6-difluorophenyl, 2-chlorophenyl, 3-chlorophenyl, 2-methylphenyl, 3-methylphenyl, 2-methoxy-phenyl, 2-fluoro-6-methoxyphenyl, 3-hydroxymethyl-phenyl and 3-(phenyl-sulfonyl-amino)-phenyl. In another embodiment of the present invention, $R^3$ is selected from the group consisting of phenyl, 2-fluorophenyl, 2,6-difluorophenyl, 2-chlorophenyl, 2-methylphenyl, 3-methylphenyl, 2-methoxy-phenyl and 2-fluoro-6-methoxyphenyl. In another embodiment of the present invention, $R^3$ is selected from the group consisting of phenyl, 2-fluorophenyl and 2-methoxyphenyl.

In an embodiment of the present invention, $R^5$ is selected from the group consisting of C$_{1-4}$alkyl, aryl, C$_{1-4}$aralkyl, cycloalkyl and cycloalkyl-C$_{1-4}$alkyl-; wherein the aryl, whether alone or as part of a substituent group is optionally substituted with one to two substituent independently selected from C$_{1-4}$alkyl, C$_{1-4}$alkoxy, halogen, hydroxy, carboxy, amino, C$_{1-4}$alkylamino, di(C$_{1-4}$alkyl)amino, cyano or nitro.

In an embodiment of the present invention, $R^P$ is selected from the group consisting of hydrogen, C$_{1-8}$alkyl, hydroxy substituted C$_{1-4}$alkyl, C$_{1-4}$aralkyloxy substituted C$_{1-4}$alkyl, cycloalkyl, aryl, heteroaryl, heterocycloalkyl and C$_{1-4}$aralkyl; wherein the cycloalkyl, aryl, heteroaryl, heterocycloalkyl or spiro-heterocyclyl, whether alone or as part of a substituent group is optionally substituted with one to two substituents independently selected from halogen, hydroxy, oxo, carboxy, $C_{1-4}$alkyl, $C_{1-4}$alkoxy, $C_{1-4}$alkoxy-carbonyl, nitro, cyano, amino, $C_{1-4}$alkylamino, di($C_{1-4}$alkyl)amino, —$SO_2$—N($R^S R^T$), 5-tetrazolyl or 1-(1,4-dihydro-tetrazol-5-one); and wherein each $R^S$ and $R^T$ is independently selected from hydrogen or $C_{1-4}$alkyl.

In an embodiment of the present invention, $R^{10}$ is selected from the group consisting of hydroxy, halogen, $C_{1-4}$alkyl, $C_{1-4}$alkoxy, halogen substituted $C_{1-4}$alkyl, halogen substituted $C_{1-4}$alkoxy; provided that the halogens on the halogen substituted $C_{1-4}$alkyl and the halogen substituted $C_{1-4}$alkoxy are selected from fluoro or chloro. In another embodiment of the present invention, $R^{10}$ is selected from the group consisting of halogen. In another embodiment of the present invention, $R^{10}$ is fluoro.

In an embodiment of the present invention, $R^1$ is selected from the group consisting of hydrogen, methyl and methylcarbonyl. In another embodiment of the present invention, $R^1$ is hydrogen. In another embodiment of the present invention, $R^1$ is selected from the group consisting of hydrogen and methoxy.

In an embodiment of the present invention, c is an integer from 0 to 1. In another embodiment of the present invention, c is 1.

In an embodiment of the present invention, $A^2$ is selected from the group consisting of $C_{1-4}$alkyl; wherein the $C_{1-4}$alkyl is optionally substituted with an $R^Y$ substituent; wherein $R^Y$ is selected from the group consisting of $C_{1-4}$alkyl, aryl, $C_{1-4}$aralkyl and cycloalkyl-$C_{1-4}$alkyl-. In another embodiment of the present invention, $A^2$ is selected from the group consisting of —$CH_2$—, —CH($CH_2CH_3$)—, —CH(phenyl)-, —CH(benzyl)- and —CH(cyclohexylmethyl)-.

In another embodiment of the present invention, $A^2$ is selected from the group consisting of —$CH_2$— and —CH($CH_2CH_3$)—. In another embodiment of the present invention, $A^2$ is —$CH_2$—.

In another embodiment of the present invention, $A^2$ is selected from the group consisting of —$CH_2$—, —CH($CH_2CH_3$)—, —CH(phenyl)- and —CH(cyclohexyl)-. In yet another embodiment of the present invention, $A^2$ is selected from the group consisting of —$CH_2$—, —CH($CH_2CH_3$)— and —CH(cyclohexyl)-. In another embodiment of the present invention, $A^2$ is —$CH_2$—.

In an embodiment of the present invention,

is selected from the group consisting of aryl, aryl-$C_{1-4}$alkyl-, cycloalkyl, heteroaryl and heterocycloalkyl; wherein the aryl, cycloalkyl, heteroaryl or heterocycloalkyl group, whether alone or as part of a substituent group, is optionally substituted with one to two substituents independently selected from $C_{1-4}$alkyl, $C_{1-4}$alkoxy, halogen substituted $C_{1-4}$alkyl, halogen substituted $C_{1-4}$alkoxy, hydroxy substituted $C_{1-4}$alkyl, hydroxy, carboxy, cyano, nitro, amino, $C_{1-4}$alkylamino or di($C_{1-4}$alkyl)amino; provided that when c is 0, then is other than aryl or heteroaryl.

In an embodiment of the present invention,

is selected from the group consisting of cycloalkyl, aryl, aryl-$C_{1-4}$alkyl-, heteroaryl, and heterocycloalkyl; wherein the aryl, heteroaryl or heterocycloalkyl, whether alone or as part of a substituent group, is optionally substituted with one to two substituents independently selected from $C_{1-4}$alkyl or $C_{1-4}$alkoxy; provided that when c is 0, then

is other than aryl or heteroaryl.

In another embodiment of the present invention,

is selected from the group consisting of cyclopentyl, (S)-cyclopentyl, (R)-cyclopentyl, cyclohexyl, (R)-cyclohexyl, (S)-cyclohexyl, trans-cyclohexyl, phenyl, benzyl, 9-fluorenyl, 3-pyrrolidinyl, 1-indanyl, 1-(5-methoxy-indanyl)-methyl, 3-piperidinyl, 4-piperidinyl, 3-azepinyl, 2-pyridyl, 4-pyridyl, 2-furyl, 2-thienyl and 5-oxazolyl; provided that when c is 0, then

is other than phenyl.

In an embodiment of the present invention,

is selected from the group consisting of phenyl, 4-piperidinyl and 4-pyridyl; provided that when c is 0, then

is other than phenyl. In another embodiment of the present invention,

is selected from the group consisting of phenyl and 4-piperidinyl; provided that when c is 0, then

is 4-piperidinyl. In yet another embodiment of the present invention, c is 1 and

is phenyl.

In an embodiment of the present invention,

is selected from the group consisting of phenyl, 2-pyridyl and 2-furyl. In another embodiment of the present invention,

is selected from the group consisting of phenyl and 2-pyridyl.

In an embodiment of the present invention, $Q^3$ is selected from the group consisting of —C(O)—, —C(O)O—, —C(O)—NH—, —C(O)—N($C_{1-8}$alkyl)-, —C(O)—N(cycloalkyl)-, —NH—C(O)— and —NH—C(O)O—; wherein the cycloalkyl is optionally substituted with $C_{1-4}$alkyl.

In another embodiment of the present invention, $Q^3$ is selected from the group consisting of —C(O)—, —C(O)—NH—, —C(O)—N(CH$_3$)—, —(R)—C(O)—N(CH$_3$), —(S)—C(O)—N(CH$_3$), —C(O)—N(isopropyl)-, —C(O)—N(n-propyl)-, —C(O)—N(isobutyl)-, —C(O)—N(2-ethyl-n-hexyl)-, —C(O)—N(cyclohexyl)-, —C(O)—N(4-methyl-cyclohexyl)-, —C(O)O—, —NH—C(O)— and —NH—C(O)O—.

In an embodiment of the present invention, $Q^3$ is selected from the group consisting of -1-C(O)O—, -3-C(O)O—, -2-C(O)—N(CH$_3$)— and -3-C(O)—N(CH$_3$)—. In another embodiment of the present invention, $Q^3$ is selected from the group consisting of -1-C(O)O—, -3-C(O)O— and -3-C(O)—N(CH$_3$)—. In another embodiment of the present invention, $Q^3$ is -3-C(O)—N(CH$_3$)—.

In an embodiment of the present invention, $Q^3$ is selected from the group consisting of -3-C(O)—N(CH$_3$)—, -3-C(O)—N(isopropyl)-, -3-C(O)—N(isobutyl)-, -3-C(O)—N(cyclohexyl)-, -4-C(O)—N(CH$_3$)— and 5-C(O)—N(CH$_3$)—. In another embodiment of the present invention, $Q^3$ is selected from the group consisting of -3-C(O)—N(CH$_3$)—, -3-C(O)—N(isopropyl)-, -3-C(O)—N(cyclohexyl)- and -4-C(O)—N(CH$_3$)—. In another embodiment of the present invention, $Q^3$ is -3-C(O)—N(CH$_3$)—

In an embodiment of the present invention, $R^2$ is selected from the group consisting of $C_{1-8}$alkyl, cycloalkyl, cycloalkyl-$C_{1-4}$alkyl-, aryl, $C_{1-4}$aralkyl, heteroaryl, heteroaryl-$C_{1-4}$alkyl-, heterocycloalkyl and heterocycloalkyl-$C_{1-4}$alkyl-; wherein the $C_{1-8}$alkyl, cycloalkyl, aryl or heterocycloalkyl, whether alone or as part of a substituent group is optionally substituted with one to three halogen, $C_{1-4}$alkyl, —SO$_2$—NH$_2$ or phenyl.

In another embodiment of the present invention, $R^2$ is selected from the group consisting of trifluoromethyl, methyl, ethyl, isobutyl, t-butyl, 3-n-heptyl, 4-n-heptyl, 2-ethyl-n-hexyl, cyclopentyl, cyclohexyl, 4-methyl-cyclohexyl, cyclopropyl-methyl, 4-aminosulfonyl-phenylethyl, benzhydryl, 1-adamantyl, 2-adamantyl, 2-(R)-adamantyl, 2-(S)-adamantyl, 2-decahydro-isoquinolinyl, 2-(1-methyl-pyrrolidinyl)-ethyl, 1-piperidinyl and 4-(1-methyl-piperidinyl).

In another embodiment of the present invention, $R^2$ is selected from the group consisting of methyl, ethyl, t-butyl and cyclohexyl. In an embodiment of the present invention, $R^2$ is selected from the group consisting of isobutyl and cyclohexyl. In another embodiment of the present invention, $R^2$ is cyclohexyl.

In an embodiment of the present invention, $L^1$ is selected from the group consisting of —O—, —S—, —NH—, —$C_{1-4}$alkyl- and —$C_{2-4}$alkenyl-. In another embodiment of the present invention, $L^1$ is selected from the group consisting of —O—, —S—, —NH—, —CH(CH$_3$)— and —CH=CH—. In another embodiment of the present invention, $L^1$ is selected from the group consisting of —O—, —S— and —NH—. In another embodiment of the present invention, $L^1$ is selected from the group consisting of —O— and —S—.

In an embodiment of the present invention, $R^3$ is selected from the group consisting of $C_{1-4}$alkyl, cycloalkyl, cycloalkyl-$C_{1-4}$alkyl-, aryl, heteroaryl and heterocycloalkyl; wherein the cycloalkyl or aryl, whether alone or as art of a substituent group is optionally substituted with one to two substituents independently selected from halogen, hydroxy, carboxy, cyano, nitro, amino, $C_{1-4}$alkylamino, di($C_{1-4}$alkylamino), $C_{1-4}$alkyl, $C_{2-4}$alkenyl, $C_{1-4}$alkoxy, hydroxy substituted $C_{1-4}$alkyl, halogen substituted $C_{1-4}$alkyl, cyano substituted $C_{1-4}$alkyl, halogen substituted $C_{1-4}$alkoxy, —O-aryl, —O—$C_{1-4}$aralkyl, —S—$C_{1-4}$alkyl, —SO$_2$—$C_{1-4}$alkyl, —C(O)—$C_{1-4}$alkyl, —C(O)—NH$_2$, —C(O)—NH($C_{1-4}$alkyl), —C(O)—N($C_{1-4}$alkyl)$_2$, —NH—C(O)—$C_{1-4}$alkyl, —C(O)—NH—$C_{1-4}$alkyl, —NH—SO$_2$—$C_{1-4}$alkyl, —NH—SO$_2$-phenyl, aryl, $C_{1-4}$aralkyl, cycloalkyl, cycloalkyl-$C_{1-4}$alkyl-, heteroaryl, heteroaryl-$C_{1-4}$alkyl-heterocycloalkyl or heterocycloalkyl-$C_{1-4}$alkyl-; and wherein the aryl, cycloalkyl, heteroaryl or heterocycloalkyl substituent, whether alone or as part of a substituent group, is optionally substituted with one to three substituents independently selected from $C_{1-4}$alkyl or $C_{1-4}$alkoxy.

In another embodiment of the present invention, $R^3$ is selected from the group consisting of n-pentyl, isopentyl, isobutyl, isopropyl, cyclopentyl, cyclopentyl-methyl, phenyl, 2-hydroxy-phenyl, 3-carboxy-phenyl, 2-cyano-phenyl, 2-nitro-phenyl, 2-bromo-phenyl, 2-fluoro-phenyl, 2-chloro-phenyl, 2,6-dichloro-phenyl, 2-methyl-phenyl, 3-methyl-phenyl, 2-ethyl-phenyl, 4-isopropyl-phenyl, 3,4-dimethyl-phenyl, 3,5-dimethyl-phenyl, 2,6-dimethyl-phenyl, 2-methoxy-phenyl, 3-methoxy-phenyl, 4-methoxy-phenyl, 3,4-dimethoxy-phenyl, 2,6-dimethoxy-phenyl, 2-ethoxy-phenyl, 3-ethoxy-phenyl, 2-isopropoxy-phenyl, 2-methoxy-5-methyl-phenyl, 2-methoxy-6-methyl-phenyl, 2-trifluoromethyl-phenyl, 2-trifluoromethoxy-phenyl, 2-methylthio-phenyl, 4-methylthio-phenyl, 2-hydroxymethyl-phenyl, 2-cyanomethyl-phenyl, 2-(aminocarbonyl)-phenyl, 4-(aminocarbonyl)-phenyl, 2-(dimethylaminocarbonyl)-phenyl, 3-(dimethylamino)-phenyl, 4-(dimethylamino)-phenyl, 2-allyl-6-methyl-phenyl, 2-allyl-6-ethoxy-phenyl, 2-methyl-6-n-propyl-phenyl, 3-(methylcarbonylamino)-phenyl, 2-(methylaminocarbonyl)-phenyl, 2-(methylcarbonyl)-phenyl, 4-(methylcarbonylamino)-phenyl, 2-(aminocarbonylmethyl)-phenyl, 2-(methylsulfonyl)-phenyl, (3-(2-methoxy-4-methyl-phenyl)-sulfonylamino)-phenyl, 3-(2,4,6-trimethylphenylsulfonylamino)-phenyl, 3-(phenylsulfonylamino)-phenyl, 2-(t-butylaminosulfonyl)-phenyl, 2-(t-butylcarbonylamino)-5-methoxy-phenyl, 3-(phenylsulfonylamino)-phenyl, 2-phenoxy-phenyl, 3-phenoxy-phenyl, 2-benzyloxy-phenyl, 2-(2-benzthiazolyl)-5- methoxy-phenyl, 2-(2-benzthiazolyl)-phenyl, 2-(1-pyrrolyl)-phenyl, 3-(2-quinolinyl)-phenyl, 2-(1-pyrrolidinyl-methyl)-phenyl, 2-cyclopentyl-phenyl, 4-cyclohexyl-phenyl, 4-(4-morpholinyl)-phenyl, 3-methoxy-benzyl, 1-naphthyl, 2-naphthyl, 2-(5,6,7,8-tetrahydro-naphthyl), 2-biphenyl, 3-biphenyl, 2-biphenyl-methyl, 3-pyridyl, 3,4-methylenedioxyphenyl, 4(3,5-dimethyl-isoxazolyl), 4-pyrazolyl, 3-thienyl, 3-pyridyl, 4-pyridyl, 5-indolyl and 3-benzothienyl.

In an embodiment of the present invention, $R^3$ is selected from the group consisting of phenyl, 2-bromophenyl, 2-chlorophenyl, 2,6-dichlorophenyl, 2-hydroxy-phenyl, 2-hydroxymethyl-phenyl, 2-methoxy-phenyl, 3-methoxy-phenyl, 2-ethoxy-phenyl, 2-methylthio-phenyl, 2-cyanomethyl-phenyl, 3-(phenyl-sulfonyl-amino)-phenyl, 3-(2,4,6-trimethylphenyl-sulfonyl-amino)-phenyl, (3-(2-methoxy-4-methylphenyl)-sulfonyl-amino)-phenyl, 2-(t-butyl-carbonyl-amino)-5-methoxy-phenyl, 1-naphthyl, 3-thienyl and 4-(3,5-dimethylisoxazolyl).

In another embodiment of the present invention, $R^3$ is selected from the group consisting of phenyl, 2-bromophenyl, 2-chlorophenyl, 2,6-dichlorophenyl, 2-hydroxy-phenyl, 2-hydroxymethyl-phenyl, 2-methoxy-phenyl, 3-methoxy-phenyl, 2-ethoxy-phenyl, 2-methylthio-phenyl, 2-cyanomethyl-phenyl, 3-(phenyl-sulfonyl-amino)-phenyl, 1-naphthyl and 3-thienyl. In another embodiment of the present invention, $R^3$ is selected from the group consisting of phenyl, 2-methoxy-phenyl, 2-ethoxy-phenyl and 1-naphthyl.

In an embodiment of the present invention, $R^3$ is selected from the group consisting of phenyl, 2-bromophenyl, 2-fluorophenyl, 2-chlorophenyl, 2,6-dichlorophenyl, 2-hydroxyphenyl, 2-hydroxymethyl-phenyl, 2-methylphenyl, 3-methylphenyl, 2,6-dimethylphenyl, 2-methoxyphenyl, 3-methoxyphenyl, 2,6-dimethoxyphenyl, 2-ethoxyphenyl, 2-trifluoromethylphenyl, 2-trifluoromethoxyphenyl, 2-methylthio-phenyl, 2-nitrophenyl, 2-cyanophenyl, 2-cyanomethyl-phenyl, 2-phenoxy-phenyl, 2-(methyl-carbonyl-amino)-phenyl, 2-(amino-carbonyl)-phenyl, 3-(phenyl-sulfonyl-amino)-phenyl, 2-(t-butyl-amino-sulfonyl)-phenyl, 2-(t-butyl-carbonyl-amino)-5-methoxy-phenyl, 4-(3,5-dimethyl-soxazolyl), 1-naphthyl, 3-thienyl and 3-pyridyl.

In another embodiment of the present invention, $R^3$ is selected from the group consisting of phenyl, 2-bromophenyl, 2-fluorophenyl, 2-chlorophenyl, 2-hydroxyphenyl, 2-hydroxymethyl-phenyl, 3-methylphenyl, 2-methoxyphenyl, 2-ethoxyphenyl, 2-cyanomethyl-phenyl, 2-(t-butyl-carbonyl-amino)-5-methoxy-phenyl, 1-naphthyl and 3-thienyl.

In another embodiment of the present invention, $R^3$ is selected from the group consisting of 2-methoxyphenyl and 2-ethoxyphenyl.

In an embodiment of the present invention, $R^6$ is selected from the group consisting of $C_{1-6}$alkyl and hydroxy substituted $C_{1-6}$alkyl. In another embodiment of the present invention, $R^6$ is selected from the group consisting of n-propyl, 4-hydroxy-n-butyl and 5-hydroxy-n-pentyl.

In an embodiment of the present invention, $R^6$ is selected from the group consisting of n-propyl, 4-hydroxy-n-butyl and 5-hydroxy-n-pentyl. In another embodiment of the present invention, $R^6$ is selected from the group consisting of n-propyl and 4-hydroxy-n-butyl. In another embodiment of the present invention, $R^6$ is n-propyl.

In an embodiment of the present invention d is an integer from 0 to 1. In another embodiment of the present invention, d is 1.

In an embodiment of the present invention, $L^2$ is selected from the group consisting of —O—, —S(O)$_{0-2}$— and —NH—. In another embodiment of the present invention, $L^2$ is selected from the group consisting of —O—, —S—, —SO— and —SO—. In yet another embodiment of the present invention, $L^2$ is selected from the group consisting of —O—, —S— and —SO—. In another embodiment of the present invention, $L^2$ is selected from the group consisting of —O— and —S—. In yet another embodiment of the present invention, $L^2$ is —O—.

In an embodiment of the present invention, $R^7$ is selected from the group consisting of cycloalkyl, cycloalkyl-$C_{1-4}$alkyl, aryl, $C_{1-4}$alkyl-aryl, aryl-$C_{1-4}$alkyl, heteroaryl, heteroaryl-$C_{1-4}$alkyl, heterocycloalkyl and heterocycloalkyl-$C_{1-4}$alkyl; wherein the aryl, cycloalkyl, partially unsaturated carbocyclyl, heteroaryl or heterocycloalkyl group is optionally substituted with one to two substituents independently selected from $C_{1-4}$alkyl, $C_{1-4}$alkoxy, halogen substituted $C_{1-4}$alkyl, halogen substituted $C_{1-4}$alkoxy, hydroxy substituted $C_{1-4}$alkyl, hydroxy, carboxy, cyano, nitro, amino, $C_{1-4}$alkylamino or di($C_{1-4}$alkyl)amino.

In another embodiment of the present invention, $R^7$ is selected from the group consisting of aryl, $C_{1-4}$alkyl-aryl and aryl-$C_{1-4}$alkyl. In another embodiment of the present invention, $R^7$ is selected from the group consisting of phenyl, —CH$_2$-phenyl-, -phenyl-3-CH$_2$— and -phenyl-2-CH$_2$—CH$_2$—.

In an embodiment of the present invention, $R^7$ is selected from the group consisting of -phenyl-, -phenyl-3-CH$_2$— and phenyl-2-CH$_2$—CH$_2$—. In another embodiment of the present invention, $R^7$ is selected from the group consisting of -phenyl- and -phenyl-3-CH$_2$—. In another embodiment of the present invention, $R^7$ is phenyl.

In an embodiment of the present invention, $L^3$ is selected from the group consisting of —C(O)—, —C(O)O—, —OC(O)—, —NR$^A$—, —N(CN)—, —NR$^A$—C(O)—, —C(O)—NR$^A$—, —NR$^A$—SO$_2$—, —SO$_2$—NR$^A$—, —NR$^A$C(O)O— and —OC(O)—NR$^A$.

In another embodiment of the present invention, $L^3$ is selected from the group consisting of —NH—, —N(CN)—, —N(C$_{1-4}$alkyl)-, —NH—C(O)—, —C(O)—NH—, —NH—SO$_2$—, —N(C$_{1-4}$alkyl)-C(O)O— and —N(cycloalkyl)-C(O)O—. In yet another embodiment of the present invention, $L^3$ is selected from the group consisting of —NH—, —N(CN)—, —N(CH$_3$)—, —NH—C(O)—, —C(O)—NH—, —NH—SO$_2$— and —N(cyclohexyl)-C(O)O—; wherein the $L^3$ group is bound at the 3-position of the $R^7$ group.

In an embodiment of the present invention, $L^3$ is selected from the group consisting of —NH—, —N(CN)—, —NH—C(O)—, —NH—C(O)O—, —N(cyclohexyl)-C(O)O— and —NH—SO$_2$—; wherein the $L^3$ is bound to the $R^7$ phenyl at the 3-position. In another embodiment of the present invention, $L^3$ is selected from the group consisting of —NH—, —NH—C(O)— and —NH—SO$_2$—; wherein the $L^3$ is bound to the $R^7$ phenyl at the 3-position. In another embodiment of the present invention, $L^3$ is —NH—SO$_2$—; wherein the $L^3$ is bound to the $R^7$ phenyl at the 3-position.

In an embodiment of the present invention, $L^3$ is selected from the group consisting of —NH—C(O)O—, —N(cyclohexyl)-C(O)O—, —NH—, —N(CN)— and —NH—SO$_2$; wherein the $L^3$ is bound to $R^7$ phenyl at the 3-position.

In an embodiment of the present invention, $R^A$ is selected from the group consisting of hydrogen, $C_{1-4}$alkyl, hydroxy substituted $C_{1-4}$alkyl, $C_{1-4}$aralkyloxy substituted $C_{1-4}$alkyl, cycloalkyl, aryl, heteroaryl, heterocycloalkyl, cycloalkyl-$C_{1-4}$alkyl-, $C_{1-4}$aralkyl, heteroaryl-$C_{1-4}$alkyl- and heterocycloalkyl-$C_{1-4}$alkyl-; wherein the cycloalkyl, aryl, heteroaryl or heterocycloalkyl, whether alone or as part of a substituent group is optionally substituted with one to two substituents independently selected from halogen, hydroxy, oxo, carboxy, $C_{1-4}$alkyl, $C_{1-4}$alkoxy, $C_{1-4}$alkoxy-carbonyl, nitro, cyano, amino, $C_{1-4}$alkylamino or di($C_{1-4}$alkyl)amino.

In an embodiment of the present invention, $R^8$ is selected from the group consisting of $C_{1-6}$alkyl, cycloalkyl, aryl, heteroaryl, heterocycloalkyl, cycloalkyl-$C_{1-4}$alkyl-, $C_{1-4}$aralkyl, heteroaryl-$C_{1-4}$alkyl- and heterocycloalkyl-$C_{1-4}$alkyl-; wherein the $C_{1-6}$alkyl, cycloalkyl, aryl, heteroaryl or heterocycloalkyl, whether alone or as part of a substituent group is optionally substituted with one to two substituents independently selected from halogen, hydroxy, carboxy, —C(O)—$C_{1-4}$alkyl, —C(O)—$C_{1-4}$aralkyl, —C(O)O—$C_{1-4}$alkyl, —C(O)O—$C_{1-4}$aralkyl, —C(O)—N($R^L R^M$), —$NR^L$—C(O)—$C_{1-4}$alkyl, —$SO_2$—$C_{1-4}$alkyl, —$SO_2$-aryl, —$SO_2$—N($R^L R^M$), $C_{1-4}$alkyl, fluoro substituted $C_{1-4}$alkyl, hydroxy substituted $C_{1-4}$alkyl, carboxy substituted $C_{1-4}$alkyl, $C_{1-4}$alkoxy, fluoro substituted $C_{1-4}$alkoxy, nitro, cyano, amino, $C_{1-4}$alkylamino, di($C_{1-4}$alkyl)amino, phenyl or heteroaryl; wherein the phenyl or heteroaryl substituent is optionally substituted with one or more substituent independently selected from halogen, hydroxy, carboxy, $C_{1-4}$alkyl, fluoro substituted $C_{1-4}$alkyl, $C_{1-4}$alkoxy, nitro, cyano, amino, $C_{1-4}$alkylamino or di($C_{1-4}$alkyl)amino; and wherein each $R^L$ and $R^M$ is independently selected from the group consisting of hydrogen, $C_{1-4}$alkyl and $C_{5-8}$cycloalkyl.

In another embodiment of the present invention, $R^8$ is selected from the group consisting of $C_{1-4}$alkyl, cycloalkyl, cycloalkyl-$C_{1-4}$alkyl, aryl, $C_{1-4}$aralkyl, heteroaryl and heterocycloalkyl; wherein the aryl or heteroaryl, whether alone or as part of a substituent group is optionally substituted with one to three substituents independently selected from halogen, hydroxy, carboxy, $C_{1-4}$alkyl, $C_{1-4}$alkoxy, fluoro substituted $C_{1-4}$alkyl, fluoro substituted $C_{1-4}$alkoxy, cyano, amino, $C_{1-4}$alkylamino, di($C_{1-4}$alkyl)amino, —C(O)O—$C_{1-4}$alkyl, —C(O)—N($R^L R^M$)—$SO_2$—$C_{1-4}$alkyl, —$SO_2$-aryl, —NH—C(O)—$C_{1-4}$alkyl, phenyl or heteroaryl; wherein the phenyl or heteroaryl substituent is optionally substituted with a substituent selected from fluoro substituted $C_{1-4}$alkyl; and wherein each $R^L$ and $R^M$ is independently selected from hydrogen, $C_{1-4}$alkyl or $C_{5-6}$cycloalkyl.

In yet another embodiment of the present invention, $R^8$ is selected from the group consisting of methyl, isopropyl, n-butyl, cyclohexyl, cyclohexyl-methyl, phenyl, phenyl-ethyl, phenyl-n-propyl, 3-(N-methyl-N-cyclohexyl-amino-carbonyl)-n-propyl, 3-bromo-phenyl, 3-methoxy-phenyl, 4-methoxy-phenyl, 2-methoxy-4-methyl-phenyl, 2,4,6-trimethyl-phenyl, 2,5-dimethoxy-phenyl, 3,4-dimethoxy-phenyl, 3-trifluoromethoxy-phenyl, 4-trifluoromethoxy-phenyl, 3-cyano-phenyl, 2-(methyl-sulfonyl)-phenyl, 4-(methyl-carbonyl-amino)-phenyl, 5-carboxy-2-methoxy-phenyl, benzyl, 3-hydroxy-benzyl, 4-methyl-benzyl, 2-methoxy-benzyl, 4-methoxy-benzyl, 2,6-dimethoxy-benzyl, 2,4,6-trimethyl-benzyl, 1-naphthyl, 2-naphthyl, 1-naphthyl-methyl, 1-(5-dimethylamino)-naphthyl, 4-biphenyl, 2-thienyl, 3-thienyl, 4-(3,5-dimethyl-isoxazolyl), 3-benzothienyl, 4-benzo[2,3,1]thiadiazolyl, 2-(5-(2-pyridyl)-thienyl), 2-(5-(3-(2-methyl-thiazolyl)-thienyl)), 2-(5-(3-(5-trifluoromethyl)-isoxazolyl)-thienyl), 6-(2,3-dihydro-benzo[1,4]dioxanyl), 3-(2-methoxy-carbonyl)-thienyl, 2-(5-(5-isoxazolyl)-thienyl)), 2-(5-bromo-thienyl) and 2-(4-phenyl-sulfonyl)-thienyl.

In an embodiment of the present invention, $R^8$ is selected from the group consisting of n-butyl, 3-(N-methyl-N-cyclohexyl-amino-carbonyl)-n-propyl, cyclohexyl, cyclohexyl-methyl-, phenyl, 2-trifluoromethylphenyl, 3-trifluoromethoxyphenyl, 3-cyanophenyl, 3-methoxyphenyl, 4-methoxyphenyl, 2-methoxy-4-methylphenyl, 2,4,6-trimethylphenyl, benzyl, 2-methoxybenzyl, 4-methoxbenzyl, 2,4,6-trimethylbenzyl, phenylethyl-, 2-thienyl, 3-thienyl, 2-(5-bromo-thienyl) and 3-benzothienyl. In another embodiment of the present invention, $R^8$ is selected from the group consisting of 3-(N-methyl-N-cyclohexyl-amino-carbonyl)-n-propyl, phenyl, 2-methoxy-4-methylphenyl, 2,4,6-trimethylphenyl, benzyl, 2-methoxybenzyl, 4-methoxybenzyl, 2,4,6-trimethylbenzyl and 3-benzothienyl. In yet another embodiment of the present invention, $R^8$ is 2,4,6-trimethylphenyl.

In an embodiment of the present invention, $R^8$ is selected from the group consisting of 3-(N-methyl-N-cyclohexyl-amino-carbonyl)-n-propyl, cyclohexyl, cyclohexyl-methyl-, phenyl and benzyl.

In an embodiment of the present invention, $R^{10}$ is selected from the group consisting of hydroxy, halogen, $C_{1-4}$alkyl, $C_{1-4}$alkoxy, halogen substituted $C_{1-4}$alkyl and halogen substituted $C_{1-4}$alkoxy; provided that the halogens on the halogen substituted $C_{1-4}$alkyl or the halogen substituted $C_{1-4}$alkoxy are selected from the group consisting of chloro and fluoro.

In an embodiment of the present invention are compounds of formula (I) wherein $R^3$ is other than $C_{1-6}$alkyl. In another embodiment of the present invention $R^3$ is other than $C_{1-6}$alkyl, wherein the $C_{1-6}$alkyl is substituted with —C(O)—$NR^P$-cycloalkyl, preparaby, $R^3$ is other than $C_{1-6}$alkyl, wherein the $C_{1-6}$alkyl is substituted with —C(O)—$NR^P$—$R^5$. In another embodiment of the present invention $R^3$ is unsubstituted cycloalkyl, partially unsaturated carbocyclyl, aryl, heteroaryl or heterocycloalkyl. In another embodiment of the present invention $R^3$ is a substituted or unsubstituted aryl or heteroaryl, wherein the substituents are as herein defined.

In an embodiment of the present invention are compounds of formula (I) selected from the group consisting of the compounds listed in Tables 1-6 below. In another embodiment of the present invention are compounds of formula (II) selected from the group consisting of the compounds listed in Tables 9-13 below. In another embodiment of the present invention are compounds of formula (III) selected from the group consisting of the compounds listed in Tables 7-8 below.

In an embodiment of the present invention are compounds of formula (I) whose Ki, as measured according to the procedure described in Example 159, is less than or equal to about 1 µM, preferably, less than or equal to about 250 nM, more preferably, less than or equal to about 100 nM, more preferably still, less than or equal to about 50 nM. In another embodiment of the present invention are compounds of formula (II) whose Ki, as measured according to the procedure described in Example 159, is less than or equal to about 1 µM, preferably, less than or equal to about 250 nM, more preferably, less than or equal to about 100 nM, more preferably still, less than or equal to about 50 nM. In another embodiment of the present invention are compounds of formula (III) whose Ki, as measured according to the procedure described in Example 159, is less than or equal to about 1 µM, preferably, less than or equal to about 250 nM, more preferably, less than or equal to about 100 nM, more preferably still, less than or equal to about 50 nM.

In an embodiment of the present invention are compounds of formula (I), whose $IC_{50}$, as measured according to the procedure described in Example 158, is less than or equal to about 1 µM, preferably, less than or equal to about 250 nM, more preferably, less than or equal to about 50 nM. In another embodiment of the present invention are compounds of formula (II), whose $IC_{50}$, as measured according to the procedure described in Example 158, is less than or equal to about 1 µM, preferably, less than or equal to about 250 nM, more preferably, less than or equal to about 50 nM. In another embodiment of the present invention are compounds of formula (III), whose IC$_{50}$, as measured according to the procedure described in Example 158, is less than or equal to about 1 μM, preferably, less than or equal to about 250 nM, more preferably, less than or equal to about 50 nM.

Additional embodiments of the present invention, include those wherein the substituents selected for one or more of the variables defined herein (e.g. R$^0$, R$^1$, R$^2$, R$^3$, R$^6$, R$^7$, R$^8$, R$^{10}$, L$^1$, L$^2$, L$^3$, a, b, c, d, A$^1$, A$^2$, Q$^1$, Q$^3$

etc.) are independently selected to be any individual substituent or any subset of substituents selected from the complete list as defined herein.

Representative compounds of the present invention are as listed in Tables 1 through 13, below. Unless otherwise noted, all compounds were prepared as mixtures of stereo-isomers. Representative compounds of formula (I) are as listed in Tables 1-6; compounds of formula (III) are as listed in Tables 7 and 8; and compounds of formula (II) are as listed in Tables 9-13 below.

For substituent groups bound through two points within the structures in the Tables below, for example R$^7$, A$^1$, A$^2$, Q$^1$, Q$^3$, L$^1$, L$^2$, L$^3$, etc., the substituent group is identified as it would be incorporated into the structure heading the table. Thus, for example in Table 1 wherein A$^1$ is 1-(cyclohexyl)-n-propyl-, the 1- and 3-carbon atoms of the n-propyl are bound to the nitrogen and Q$^1$ groups respectively, and the cyclohexyl is bound to the 1-carbon of the n-propyl. Similarly, when Q$^1$ is —C(O)—N(CH$_3$)—, the carbonyl is bound to A$^1$ and the nitrogen of the methylamino is bound to the R$^2$ group. Similarly, in Table 7, wherein R$^7$ is —CH$_2$-phenyl-, the carbon of the CH$_2$— is bound to the L$^3$ group and the phenyl is bound to the (L$^2$)$_d$ group whereas when R$^7$ is -phenyl-3-CH$_2$—, the phenyl is bound to the L$^3$ group and the carbon of the CH$_2$— is bound to the (L$^2$)$_d$ group. Further, unless otherwise noted, any terminal substituent group is bound at the 1-position. Thus for example, 4-fluorophenyl corresponds to a phenyl group bound at the 1-position and substituted with a fluoro group at the 4-position, and could alternatively be defined as 1-(4-fluorophenyl). Further, for compounds of formula (II) listed in Tables 9-13, unless otherwise noted, the

substituent shall be assumed to be bound at the 1-position, unless otherwise noted, with the Q$^3$ substituent bound as indicated by the numbering listed in the Q$^3$ substituent column.

TABLE 1

Compounds of Formula (I)

| ID No | A$^1$ | Q$^1$ | R$^2$ | R$^3$ |
|---|---|---|---|---|
| 1 | -ethyl- | —C(O)—N(CH$_3$)— | cyclohexyl | phenyl |
| 2 | -ethyl- | —C(O)—N(CH$_3$)— | cyclohexyl | 4-fluoro-phenyl |
| 3 | -ethyl- | —C(O)—N(CH$_2$CH$_3$)— | cyclohexyl | phenyl |
| 4 | -ethyl- | —C(O)—N(CH$_3$)— | cycloheptyl | phenyl |
| 5 | -ethyl- | —C(O)—N(CH$_3$)— | cycloheptyl | 4-fluoro-phenyl |
| 6 | -ethyl- | —C(O)—N(CH$_2$CH$_3$)— | cyclohexyl | 4-fluoro-phenyl |
| 7 | -ethyl- | —NH—C(O)— | cyclohexyl | phenyl |
| 8 | -n-propyl- | —O— | phenyl | phenyl |
| 10 | -n-propyl- | —C(O)—N(CH$_3$)— | cyclohexyl | phenyl |
| 12 | -ethyl- | —C(O)—N(cyclohexyl)- | phenyl | phenyl |
| 13 | -ethyl- | —C(O)—N(CH$_3$)— | phenyl | phenyl |
| 15 | -n-propyl- | —N(CH$_3$)— | cyclohexyl | phenyl |
| 18 | -ethyl- | —O— | methyl | phenyl |
| 22 | -ethyl- | —C(O)—N(CH$_3$)— | isopropyl | phenyl |
| 23 | -ethyl- | —N(CH$_3$)—C(O)— | cyclohexyl | phenyl |
| 24 | -ethyl- | —C(O)—N(CH$_3$)— | cyclopentyl | phenyl |
| 25 | -ethyl- | —C(O)—N(CH$_3$)— | cyclopentyl | 4-fluoro-phenyl |
| 27 | -n-butyl- | —C(O)—N(CH$_3$)— | cyclohexyl | phenyl |
| 30 | -n-butyl- | —NH—C(O)— | cyclohexyl | phenyl |
| 31 | -n-butyl- | —C(O)—NH— | cyclohexyl | phenyl |
| 39 | -ethyl- | —C(O)—N(cyclohexyl)- | cyclohexyl | phenyl |
| 40 | -ethyl- | —C(O)—N(CH$_3$)— | phenylethyl- | phenyl |
| 41 | -ethyl- | —C(O)—N(CH$_3$)— | 1-adamantyl | phenyl |
| 42 | -ethyl- | —C(O)—N(CH$_3$)— | 1-naphthyl-methyl- | phenyl |
| 43 | -ethyl- | —C(O)—N(CH$_3$)— | benzyl | phenyl |
| 45 | -ethyl- | —C(O)—N(CH$_3$)— | 1-(1,2,3,4-tetrahydro-naphthyl) | phenyl |
| 46 | -n-butyl- | —C(O)—N(cyclohexyl)- | cyclohexyl | phenyl |
| 47 | -n-butyl- | —C(O)—N(CH$_3$)— | benzyl | phenyl |
| 48 | -n-butyl- | —C(O)—N(CH$_3$)— | 1-adamantyl | phenyl |
| 50 | -n-butyl- | —C(O)—N(CH$_3$)— | phenylethyl- | phenyl |
| 51 | -n-butyl- | —C(O)—N(CH$_3$)— | 1-naphthyl-methyl- | phenyl |

TABLE 1-continued

| | | | | |
|---|---|---|---|---|
| 54 | -n-butyl- | —C(O)—N(CH$_3$)— | 1-(1,2,3,4-tetrahydro-naphthyl) | phenyl |
| 57 | -ethyl- | —SO$_2$—N(CH$_3$)— | cyclohexyl | phenyl |

TABLE 2

Compound of formula (I)

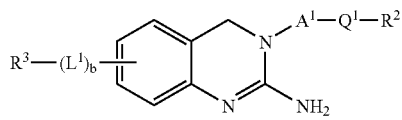

| ID No | A$^1$ | Q$^1$ | R$^2$ | (L$^1$)$_b$ | R$^3$ |
|---|---|---|---|---|---|
| 35 | -ethyl- | —C(O)—N(CH$_3$)— | cyclohexyl | 7-C(O)— | phenyl |
| 753 | 1-(S)-(cyclohexyl)-n propyl- | —C(O)—N(CH$_3$)— | cyclohexyl | 5-O— | phenyl |
| 754 | 1-(S)-(cyclohexyl)-n propyl- | —C(O)—N(CH$_3$)— | cyclohexyl | 7-O— | phenyl |

TABLE 3

Compounds of Formula (I)

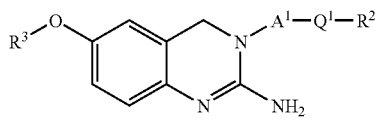

| ID No | A$^1$ | Q$^1$ | R$^2$ | R$^3$ |
|---|---|---|---|---|
| 19 | -n-butyl- | —C(O)—N(cyclohexyl)- | cyclohexyl | phenyl |
| 20 | -ethyl- | —C(O)—N(CH$_3$)— | cyclohexyl | phenyl |
| 65 | -ethyl- | —C(O)O— | ethyl | phenyl |
| 71 | -ethyl- | —SO$_2$—N(CH$_3$)— | cyclohexyl | 3-(benzyloxy-carbonyl-amino)-phenyl |
| 75 | -n-butyl- | —C(O)—N(cyclohexyl)- | cyclohexyl | 3-(benzyloxy-carbonyl-amino)-phenyl |
| 79 | -ethyl- | —N(ethyl)- | ethyl | phenyl |
| 80 | -ethyl- | —NH—C(O)O— | t-butyl | phenyl |
| 84 | 1-(N-cyclohexyl-N-methyl-amino-carbonyl-ethyl)-n-propyl- | —C(O)—N(CH$_3$)— | cyclohexyl | phenyl |
| 85 | 1-cyclohexyl-n-propyl- | —C(O)—N(CH$_3$)— | cyclohexyl | phenyl |
| 86 | 1-(n-propyl)-n-propyl- | —C(O)—N(CH$_3$)— | cyclohexyl | phenyl |
| 88 | -methyl- | —C(O)— | 1-(2-(S)-(N-methyl-N-cyclohexyl-aminocarbonyl)-pyrrolidinyl) | phenyl |
| 90 | 1-(n-propyl)-n-butyl | —C(O)—N(CH$_3$)— | cyclohexyl | phenyl |
| 91 | 1-(n-propyl)-n-butyl | —C(O)—NH— | cyclohexyl | phenyl |
| 96 | -n-butyl- | —C(O)—N(CH$_3$)— | cyclohexyl | 3-(N-(cyclohexyl-methyl)-amino)-phenyl |
| 101 | -n-butyl- | —NH—C(O)O— | t-butyl | phenyl |
| 103 | -n-propyl- | —NH—C(O)O— | t-butyl | phenyl |
| 105 | 1-(n-propyl)-n-butyl- | —C(O)—N(ethyl)- | cyclohexyl | phenyl |
| 106 | 1-(n-propyl)-n-butyl- | —C(O)—N(CH$_3$)— | 4-(1-methyl-piperidinyl) | phenyl |
| 107 | 1-(cyclohexyl-carbonylamino-methyl)-ethyl- | —NH—C(O)— | cyclohexyl | phenyl |

TABLE 3-continued

| | | | | |
|---|---|---|---|---|
| 108 | -n-propyl- | —NH—C(O)— | cyclohexyl | phenyl |
| 109 | -ethyl- | —NH—SO$_2$— | 4-methyl-phenyl | phenyl |
| 111 | -ethyl- | —NH—C(O)— | cyclohexyl | phenyl |
| 112 | -ethyl- | —NH—C(O)— | cyclopentyl | phenyl |
| 113 | -n-butyl- | —C(O)—N(cyclohexyl)- | cyclohexyl | 3-(phenyl-sulfonyl-amino)-phenyl |
| 114 | -n-butyl- | —C(O)—N(CH$_3$)— | cyclohexyl | 3-(phenyl-sulfonyl-amino)-phenyl |
| 115 | -n-butyl- | —NH—C(O)— | cyclohexyl | phenyl |
| 116 | -n-butyl- | —NH—C(O)— | cyclopentyl | phenyl |
| 121 | -ethyl- | —NH—C(O)— | isopropyl | phenyl |
| 122 | -ethyl- | —NH—C(O)— | 1-ethyl-n-pentyl | phenyl |
| 123 | -ethyl- | —NH—C(O)— | cyclopropyl | phenyl |
| 127 | 1-(n-propyl)-n-propyl- | —C(O)—N(ethyl)- | cyclohexyl | phenyl |
| 128 | 1-(n-propyl)-n-propyl- | —C(O)—NH— | cycloheptyl | phenyl |
| 129 | 1-(n-propyl)-n-propyl- | —C(O)—NH— | cyclohexyl | phenyl |
| 130 | -ethyl- | —NH—C(O)— | cyclobutyl | phenyl |
| 131 | -ethyl- | —NH—C(O)— | 1-adamantyl | phenyl |
| 133 | -n-butyl- | —C(O)—N(CH$_3$)— | cyclohexyl | 3-(benzyloxy-carbonyl-amino)-phenyl |
| 134 | -ethyl- | —NH—SO$_2$— | n-propyl | phenyl |
| 135 | -ethyl- | —NH—SO$_2$— | n-butyl | phenyl |
| 137 | 1-(n-propyl)-n-butyl- | —C(O)—NH— | cycloheptyl | phenyl |
| 139 | -ethyl- | —NH—C(O)— | 2-phenyl-cyclopropyl | phenyl |
| 140 | -ethyl- | —NH—C(O)— | cyclopentyl-ethyl- | phenyl |
| 141 | -ethyl- | —NH—C(O)— | t-butyl | phenyl |
| 142 | -ethyl- | —NH—C(O)— | n-nonyl | phenyl |
| 143 | -n-propyl- | —NH—C(O)— | cyclopropyl | phenyl |
| 144 | -n-propyl- | —NH—C(O)— | cyclobutyl | phenyl |
| 148 | 1-(n-pentyl)-n-propyl- | —C(O)—N(CH$_3$)— | cyclohexyl | phenyl |
| 149 | 1-(n-pentyl)-n-propyl- | —C(O)—NH— | cyclohexyl | phenyl |
| 150 | 1-(n-pentyl)-n-propyl- | —C(O)—NH— | cycloheptyl | phenyl |
| 151 | 1-phenyl-n-propyl- | —C(O)—N(CH$_3$)— | cyclohexyl | phenyl |
| 152 | 1-phenyl-n-butyl- | —C(O)—N(CH$_3$)— | cyclohexyl | phenyl |
| 154 | -ethyl- | —NH—C(O)— | phenyl | phenyl |
| 155 | -ethyl- | —NH—C(O)— | phenylethyl- | phenyl |
| 156 | -ethyl- | —NH—C(O)— | 4-t-butyl-phenyl | phenyl |
| 157 | -ethyl- | —NH—C(O)— | 4-n-butyl-phenyl | phenyl |
| 177 | -n-propyl- | —C(O)—N(CH$_3$)— | cyclohexyl | phenyl |
| 178 | -ethyl- | —C(O)—NH— | cyclohexyl | phenyl |
| 179 | -ethyl- | —C(O)—N(isopropyl)- | cyclohexyl | phenyl |
| 180 | -ethyl- | —C(O)—N(cyclohexyl)- | cyclohexyl | phenyl |
| 181 | -ethyl- | —C(O)—N(isopropyl)- | isopropyl | phenyl |
| 182 | -ethyl- | —NH—C(O)— | 4-n-pentyl-cyclohexyl | phenyl |
| 183 | -ethyl- | —NH—C(O)— | 4-n-heptyl | phenyl |
| 184 | -ethyl- | —NH—C(O)— | 4-t-butyl-cyclohexyl | phenyl |
| 189 | -ethyl- | —NH—C(O)— | 4-dimethylamino-phenyl | phenyl |
| 190 | -ethyl- | —NH—C(O)— | isobutyl | phenyl |
| 191 | -ethyl- | —NH—C(O)— | 4-methyl-cyclohexyl | phenyl |
| 194 | -ethyl- | —NH—C(O)— | 1-(3-n-pentyl-bicyclo[2.2.2]-octyl) | phenyl |
| 195 | -ethyl- | —NH—C(O)— | 4-biphenyl | phenyl |
| 196 | -ethyl- | —NH—C(O)— | 1-(1-(4-chlorophenyl)cyclopentyl) | phenyl |
| 199 | 1-cyclohexyl-ethyl- | —C(O)—N(CH$_3$)— | cyclohexyl | phenyl |
| 200 | 1-cyctohexyl-ethyl- | —C(O)—N(isopropyl)- | cyclohexyl | phenyl |
| 201 | 1-isopropyl-ethyl- | —C(O)—N(CH$_3$)— | cyclohexyl | phenyl |
| 202 | 1-isopropyl-ethyl- | —C(O)—N(isopropyl)- | cyclohexyl | phenyl |
| 205 | -ethyl- | —NH—C(O)—NH— | phenyl | phenyl |
| 206 | -ethyl- | —NH—C(O)—NH— | 1-adamantyl | phenyl |
| 207 | -ethyl- | —NH—C(O)— | benzhydryl | phenyl |
| 208 | 1-(n-octyl)-n-propyl- | —C(O)—NH— | cycloheptyl | phenyl |
| 210 | 1-(n-octyl)-n-propyl- | —C(O)—N(CH$_3$)— | cyclohexyl | phenyl |
| 214 | -ethyl- | —NH—C(S)—NH— | 1-adamantyl | phenyl |

TABLE 3-continued

| | | | | |
|---|---|---|---|---|
| 215 | -ethyl- | —NH—C(O)—NH— | cyclohexyl | phenyl |
| 216 | -ethyl- | —NH—C(O)— | 2-methoxy-phenyl | phenyl |
| 217 | -ethyl- | —NH—C(O)— | 3-methoxy-phenyl | phenyl |
| 218 | -ethyl- | —NH—C(O)— | 2-methyl-cyclohexyl | phenyl |
| 219 | -ethyl- | —NH—C(O)— | 3-methoxy-cyclohexyl | phenyl |
| 220 | -ethyl- | —NH—C(O)O— | isopropyl | phenyl |
| 221 | -ethyl- | —C(O)—NH— | 2-adamantyl | phenyl |
| 257 | 1-cyclohexyl-ethyl- | —NH—C(O)O— | t-butyl | phenyl |
| 258 | 1-phenyl-ethyl- | —NH—C(O)O— | t-butyl | phenyl |
| 288 | -n-butyl- | —C(O)—N(CH$_3$)— | cyclohexyl | 3,5-dimethoxy-phenyl |
| 294 | 1-cyclohexyl-ethyl- | —NH—C(O)— | cyclohexyl | phenyl |
| 295 | 1-cyclohexyl-ethyl- | —NH—C(O)— | cyclopentyl | phenyl |
| 297 | 1-(4-chloro-phenyl)-n-propyl- | —C(O)—N(CH$_3$)— | cyclohexyl | phenyl |
| 298 | 1-(4-methoxy-phenyl)-n-propyl- | —C(O)—N(CH$_3$)— | cyclohexyl | phenyl |
| 299 | 1-phenyl-ethyl- | —C(O)—NH— | cyclohexyl | phenyl |
| 300 | 1-cyclohexyl-ethyl- | —C(O)—NH— | cyclohexyl | phenyl |
| 301 | 1-cyclohexyl-ethyl- | —NH—C(O)— | isopropyl | phenyl |
| 302 | 1-cyclohexyl-ethyl- | —NH—C(O)— | 4-n-heptyl | phenyl |
| 303 | 1-cyclohexyl-ethyl- | —NH—C(O)— | 3-n-heptyl | phenyl |
| 304 | 1-cyclohexyl-ethyl- | —NH—C(O)— | benzhydryl | phenyl |
| 311 | 1-cyclohexyl-ethyl- | —NH—C(O)— | cyclopentyl-methyl- | phenyl |
| 312 | 1-cyclohexyl-ethyl- | —NH—C(O)— | 1-adamantyl | phenyl |
| 313 | 1-cyclohexyl-ethyl- | —C(O)—NH— | cyclohexyl | 2-isopropyl-phenyl |
| 314 | 1-cyclohexyl-ethyl- | —C(O)—NH— | 2-adamantyl | phenyl |
| 317 | 1-cyclohexyl-ethyl- | —NH—C(O)— | t-butyl | phenyl |
| 318 | 1-(n-propyl)-ethyl- | —NH—C(O)O— | t-butyl | phenyl |
| 319 | 1-cyclohexyl-ethyl- | —NH—C(O)— | phenyl | phenyl |
| 341 | 1-phenyl-ethyl- | —NH—C(O)— | 3-n-heptyl | phenyl |
| 342 | 1-phenyl-ethyl- | —NH—C(O)— | cyclohexyl | phenyl |
| 343 | 1-(n-propyl)-ethyl | —NH—C(O)— | cyclohexyl | phenyl |
| 346 | 1-(S)-cyclohexyl-n-propyl- | —C(O)—N(CH$_3$)— | cyclohexyl | phenyl |
| 365 | -ethyl- | —C(O)—NH— | 1-adamantyl | phenyl |
| 366 | 1-cyclohexyl-ethyl- | —NH—C(O)— | cyclopentyl-ethyl- | phenyl |
| 367 | 1-cyclohexyl-ethyl- | —NH—C(O)O— | t-butyl | phenyl |
| 386 | 1-(R)-cyclohexyl-n-propyl- | —C(O)—N(CH$_3$)— | cyclohexyl | phenyl |
| 388 | 1-cyclohexyl-ethyl | NH—C(O) | isopentyl | phenyl |
| 389 | 1-cyclohexyl-ethyl- | —NH—C(O)— | isobutyl | phenyl |
| 390 | 1-cyclohexyl-ethyl- | —NH—C(O)— | 1-(1-(4-chloro-phenyl)-cyclopentyl) | phenyl |
| 391 | 1-cyclohexyl-n-propyl- | —NH—C(O)— | cyclohexyl | phenyl |
| 392 | 1-cyclohexyl-n-propyl- | —NH—C(O)— | cyclopentyl | phenyl |
| 393 | 1-cyclohexyl-n-propyl- | —NH—C(O)— | cyclopentyl-methyl- | phenyl |
| 394 | -ethyl- | —NH—C(O)O— | t-butyl | 3-(phenyl-sulfonyl-amino)-phenyl |
| 400 | 1-cyclohexyl-ethyl- | —C(O)—NH— | 2-(bicyclo[2.2.1]heptyl) | phenyl |
| 401 | 1-isopropyl-ethyl- | —C(O)—NH— | cyclohexyl | phenyl |
| 402 | 1-isopropyl-ethyl- | —C(O)—NH— | 2-adamantyl | phenyl |
| 403 | -n-propyl- | —NH— | cyclohexyl | phenyl |
| 420 | 1-(4-biphenyl)-n-propyl- | —C(O)—N(CH$_3$)— | cyclohexyl | phenyl |
| 421 | 1-(4-methyl-phenyl)-n-propyl- | —C(O)—N(CH$_3$)— | cyclohexyl | phenyl |
| 425 | -ethyl- | —N(CH$_3$)—C(O)O— | t-butyl | phenyl |
| 426 | -ethyl- | —N(CH$_3$)—C(O)— | cyclohexyl | phenyl |
| 427 | -ethyl- | —NH— | cyclohexyl-methyl- | phenyl |
| 428 | -n-propyl- | —N(CH$_3$)— | cyclohexyl | phenyl |
| 429 | -ethyl- | —N(CH$_3$)— | cyclohexyl | phenyl |
| 444 | 1-(R)-isopropyl-n-propyl- | —C(O)—N(CH$_3$)— | cyclohexyl | phenyl |
| 450 | 1-(S)-isopropyl-n-propyl- | —C(O)—N(CH$_3$)— | cyclohexyl | phenyl |
| 452 | 1-(1-piperidinyl-carbonyl-n-propyl)-n-propyl- | —C(O)— | N-piperidinyl | phenyl |

TABLE 3-continued

| | | | | |
|---|---|---|---|---|
| 465 | -ethyl- | —C(O)—NH— | 2-adamantyl | 2,6-dimethoxy-phenyl |
| 466 | -ethyl- | —C(O)—NH— | 2-adamantyl | 2-isopropyl-phenyl |
| 484 | 1-(S)-cyclohexyl-ethyl- | —NH—C(O)— | cyclohexyl | phenyl |
| 485 | 1-(R)-cyclohexyl-ethyl- | —NH—C(O)— | cyclohexyl | phenyl |
| 486 | 1-(S)-methyl-ethyl- | —NH—C(O)— | cyclohexyl | phenyl |
| 495 | 1-(R)-methyl-ethyl- | —NH—C(O)— | cyclohexyl | phenyl |
| 504 | 1-(2-methyl-piperidinyl-carbonyl-n-propyl)-n-propyl- | —C(O)— | 2-methyl-piperidinyl | phenyl |
| 511 | -ethyl- | —C(O)—NH— | trans-2-methyl-cyclohexyl- | phenyl |
| 528 | 1-(S)-isopropyl-ethyl- | —NH—C(O)— | cyclohexyl | phenyl |
| 529 | -ethyl- | —C(O)—NH— | 2-adamantyl | 2,6-difluoro-phenyl |
| 532 | 1-(4-methyl-piperidinyl carbonyl-n-propyl)-n-propyl- | —C(O)— | 4-methyl-piperidinyl | phenyl |
| 553 | 1-(S)-isopropyl-ethyl- | —NH—C(O)— | 1-adamantyl | phenyl |
| 554 | 1-(S)-n-propyl-ethyl- | —NH—C(O)— | cyclohexyl | phenyl |
| 555 | 1-(S)-n-propyl-ethyl- | —NH—C(O)— | 1-adamantyl | phenyl |
| 557 | 1-(R)-hydroxy-methyl-n-propyl- | —C(O)—N(CH$_3$)— | cyclohexyl | phenyl |
| 558 | 1-(S)-hydroxy-methyl)-n-propyl- | —C(O)—N(CH$_3$)— | cyclohexyl | phenyl |
| 561 | 1-(R)-isopropyl-ethyl- | —NH—C(O)— | cyclohexyl | phenyl |
| 562 | 1-(R)-isopropyl-ethyl- | —NH—C(O)— | 1-adamantyl | phenyl |
| 563 | 1-(R)-isopropyl-ethyl- | —NH—C(O)— | isobutyl | phenyl |
| 564 | 1-(R)-isopropyl-ethyl- | —NH—C(O)— | isopentyl | phenyl |
| 601 | 1-(R)-n-propyl-ethyl- | —NH—C(O)— | cyclohexyl | phenyl |
| 602 | 1-(R)-n-propyl-ethyl- | —NH—C(O)— | 1-adamantyl | phenyl |
| 603 | 1-(R)-n-propyl-ethyl- | —NH—C(O)— | isopentyl | phenyl |
| 614 | 1-(R)-(4-hydroxy-benzyl)-ethyl- | —NH—C(O)— | cyclohexyl | phenyl |
| 615 | 1-(R)-(4-hydroxy-benzyl)-ethyl- | —NH—C(O)— | isopentyl | phenyl |
| 616 | 1-(S)-(4-hydroxy-benzyl)-ethyl- | —NH—C(O)— | cyclohexyl | phenyl |
| 618 | -ethyl- | —C(O)—N(CH$_3$)— | 2-adamantyl | phenyl |
| 619 | 1-(4-tetrahydro-pyranyl)-n-propyl- | —C(O)—N(CH$_3$)— | cyclohexyl | phenyl |
| 632 | 1-(4-hydroxy-cyclohexyl)-n-propyl- | —C(O)—N(CH$_3$)— | cyclohexyl | phenyl |
| 633 | 1-(R)-cyclohexyl-n-propyl- | —C(O)—N(CH$_3$)— | 4-tetrahydro-pyranyl | phenyl |
| 634 | 1-(S)-(N-methyl-N-cyclohexyl-aminocarbonyl)-n-propyl- | —C(O)—N(CH$_3$)— | cyclohexyl | phenyl |
| 636 | 2-(S)-cyclohexyl-ethyl- | —NH—C(O)— | cyclohexyl | phenyl |
| 637 | 2-(R)-cyclohexyl-ethyl- | —NH—C(O)— | cyclohexyl | phenyl |
| 638 | 1-(S)-cyclohexyl-n-propyl- | —C(O)—N(CH$_3$)— | 4-tetrahydro-pyranyl | phenyl |
| 639 | 1-(R)-cyclohexyl-n-propyl- | —C(O)—N(CH$_3$)— | 4-hydroxy-cyclohexyl | phenyl |
| 709 | 1-(S)-tetrahydro-pyranyl-n-propyl- | —C(O)—N(CH$_3$)— | cyclohexyl | phenyl |
| 710 | 1-(S)-cyclohexyl-n-propyl- | —C(O)—N(CH$_3$)— | 1,4-dioxa-spiro[4.5]dec-8-yl | phenyl |
| 711 | 1-(S)-cyclohexyl-n-propyl- | —C(O)—N(CH$_3$)— | 1-4-oxo-cyclohexyl | phenyl |

TABLE 3-continued

| | | | | |
|---|---|---|---|---|
| 712 | 1-(S)-cyclohexyl-n-propyl- | —C(O)—N(CH$_3$)— | 4-hydroxy-cyclohexyl | phenyl |
| 714 | 1-(S)-cyclohexyl-n-propyl- | —C(O)—N(CH$_3$)— | 4-carboxy-cyclohexyl | phenyl |
| 728 | 1-(S)-cyclohexyl-n-propyl- | —C(O)—N(CH$_3$)— | 4-(1-isopropyl)-piperidinyl | phenyl |
| 730 | 1-(S)-(1,4-dioxa-spiro[4.5]dec-8-yl)-n-propyl- | —C(O)—N(CH$_3$)— | cyclohexyl | phenyl |
| 731 | 1-(S)-(cis-4-hydroxy-cyclohexyl)-n-propyl- | —C(O)—N(CH$_3$)— | cyclohexyl | phenyl |
| 732 | 1-(S)-(4-oxo-cyclohexyl)-n-propyl- | —C(O)—N(CH$_3$)— | cyclohexyl | phenyl |
| 736 | 1-(S)-cyclohexyl-n-propyl- | —C(O)—N(hydroxyethyl)- | cyclohexyl | phenyl |
| 737 | 1-(S)-cyclohexyl-n-propyl- | —C(O)—N(CH$_3$)— | 4-ethoxy-carbonyl-cyclohexyl | phenyl |
| 738 | 1-(dimethyl)-n propyl- | —C(O)—N(CH$_3$)— | cyclohexyl | phenyl |
| 739 | 1-(S)-cyclohexyl-n-propyl- | —C(O)—N(CH$_3$)— | cis-(4-carboxy)-cyclohexyl | phenyl |
| 740 | 1-(S)-cyclohexyl-n-propyl- | —C(O)—N(CH$_3$)— | trans-(4-carboxy)-cyclohexyl | phenyl |
| 741 | 1-(S)-cyclohexyl-n-propyl- | —C(O)—N(CH$_3$)— | 1-carboxy-cyclohexyl | phenyl |
| 742 | 1-(S)-(4-tetrahydropyranyl)-n-propyl- | —C(O)—N(CH$_3$)— | 4-(ethoxy-carbonyl)-cyclohexyl | phenyl |
| 743 | 1-(S)-(4-tetrahydropyranyl)-n-propyl- | —C(O)—N(CH$_3$)— | 4-carboxy-cycohexyl | phenyl |
| 744 | 1-(S)-(4-tetrahydropyranyl)-n-propyl- | —C(O)—N(CH$_3$)— | cis-(4-methoxy-carbonyl)-cyclohexyl | phenyl |
| 745 | 1-(S)-(4-tetrahydropyranyl)-n-propyl- | —C(O)—N(CH$_3$)— | cis-(4-carboxy)-cyclohexyl | phenyl |
| 746 | 1-(S)-(4-tetrahydropyranyl)-n-propyl- | —C(O)—N(CH$_3$)— | trans-(4-carboxy)-cyclohexyl | phenyl |
| 747 | 1-(S)-(4-tetrahydropyranyl)-n-propyl- | —C(O)—NH— | trans-(4-methoxy-carbonyl)-cyclohexyl | phenyl |
| 748 | 1-(S)-(4-tetrahydropyranyl)-n-propyl- | —C(O)—N(CH$_3$)— | cis-(4-carboxy)-cyclohexyl | phenyl |
| 749 | 1-(S)-(cyclohexyl)-n-propyl- | —C(O)—N(hydroxyethyl)- | cis-(4-carboxy)-cyclohexyl | phenyl |
| 750 | 1-(S)-(4-tetrahydropyranyl)-n-propyl- | —C(O)—N(hydroxyethyl)- | cis-(4-carboxy)-cyclohexyl | phenyl |
| 751 | 1-(S)-(4-tetrahydropyranyl)-n-propyl- | —C(O)—N(benzyloxy-ethyl)- | cis-(4-carboxy)-cyclohexyl | phenyl |
| 752 | 1-(S)-(cyclohexyl)-n-propyl- | —C(O)—N(CH$_3$)— | 4-(carboxy)-n-butyl | phenyl |
| 760 | 1-(S)-(cyclohexyl)-n-propyl | —C(O)—N(CH$_3$)— | 1-cis-(4-benzyloxy-carbonyl-cyclohexyl) | phenyl |
| 761 | 1-(S)-(cyclohexyl)-n-propyl | —C(O)—N(CH$_3$)— | 1-cis-(4-methoxy-carbonyl-cyclohexyl) | phenyl |
| 762 | 1-(S)-(cyclohexyl)-n-propyl | —C(O)—N(CH$_2$CH$_2$OH)— | 1-cis-(4-methoxy-carbonyl-cyclohexyl) | phenyl |
| 763 | 1-(S)-(cyclohexyl)-n-propyl | —C(O)—N(CH$_3$)— | 1-cis-(4-ethoxy-carbonyl-cyclohexyl) | phenyl |
| 764 | 1-(S)-(cyclohexyl)-n-propyl | —C(O)—N(CH$_3$)— | 1-cis-(4-amino-carbonyl-cyclohexyl) | phenyl |
| 765 | 1-(S)-(cyclohexyl)-n-propyl | —C(O)—N(CH$_3$)— | 1-cis-(4-methylamino-carbonyl-cyclohexyl) | phenyl |

TABLE 3-continued

| 766 | 1-(S)-(cyclohexyl)-n-propyl | —C(O)—N(CH₃)— | 1-(4-carboxy-phenyl) | phenyl |
| 767 | 1-(S)-(cyclohexyl)-n-propyl | —C(O)—N(CH₃)— | carboxy-methyl- | phenyl |
| 768 | 1-(S)-(cyclohexyl)-n-propyl | —C(O)—N(cyclohexyl)- | carboxy-methyl- | phenyl |
| 769 | 1-(S)-(cyclohexyl)-n-propyl | —C(O)—N(CH₃)— | 1-(4-cyano-cyclohexyl) | phenyl |
| 770 | 1-(S)-(cyclohexyl)-n-propyl | —C(O)—N(CH₃)— | 1-(4-(5-tetrazolyl)-cyclohexyl) | phenyl |
| 771 | 1-(S)-(4-tetrahydro-pyranyl)-n-propyl | —C(O)—NH— | 1-(S)-(1-carboxyl-2-hydroxy-ethyl) | phenyl |
| 773 | 1-(S)-(4-tetrahydro-pyranyl)-n-propyl | —C(O)—NH— | 1-(R)-(1-carboxyl-2-hydroxy-ethyl) | phenyl |
| 774 | 1-(S)-(4-tetrahydro-pyranyl)-n-propyl | —C(O)—NH— | 1-(R)-(1-carboxyl-2-t-butoxy-ethyl) | phenyl |
| 775 | 1-(S)-(cyclohexyl)-n-propyl | —C(O)—N(CH₃)— | 3-(methoxy-carbonyl-methyl)-benzyl | phenyl |
| 776 | 1-(S)-(cyclohexyl)-n-propyl | —C(O)—N(CH₃)— | 1-cis-(3-carboxy)-cyclohexyl | phenyl |
| 777 | 1-(S)-(cyclohexyl)-n-propyl | —C(O)—N(CH₃)— | 1-cis-(3-methoxy-carbonyl)-cyclohexyl | phenyl |
| 778 | 1-(S)-(cyclohexyl)-n-propyl | —C(O)—N(CH₃)— | 3-(carboxy-methyl)-benzyl | phenyl |
| 779 | 1-(S)-(cyclohexyl)-n-propyl | —C(O)—N(CH₃)— | 1-(R)-(1-methoxy-carbonyl-2-benzyloxy-ethyl) | phenyl |
| 780 | 1-(S)-(cyclohexyl)-n-propyl | —C(O)—N(CH₃)— | 1-(S)-(1-methoxy-carbonyl-2-benzyloxy-ethyl) | phenyl |
| 781 | 1-(S)-(cyclohexyl)-n-propyl | —C(O)—N(CH₃)— | 1-(S)-(1-carboxy-2-benzyloxy-ethyl) | phenyl |
| 782 | 1-(S)-(4-tetrahydro-pyranyl)-n-propyl | —C(O)—NH— | 1-(S)-(1-carboxy-2-benzyloxy-ethyl) | phenyl |
| 783 | 1-(S)-(4-tetrahydro-pyranyl)-n-propyl | —C(O)—N(CH₃)— | 1-(R)-(1-methoxy-carbonyl-2-benzyloxy-ethyl) | phenyl |
| 784 | 1-(S)-(4-tetrahydro-pyranyl)-n-propyl | —C(O)—N(CH₃)— | 1-(R)-(1-carboxy-2-benzyloxy-ethyl) | phenyl |
| 785 | 1-(S)-(4-tetrahydro-pyranyl)-n-propyl | —C(O)—NH— | 1-(S)-(1-methoxy-carbonyl-2-benzyloxy-ethyl) | phenyl |
| 786 | 1-(S)-(4-tetrahydro-pyranyl)-n-propyl | —C(O)—N(CH₃)— | 1-(S)-(1-methoxy-carbonyl-2-benzyloxy-ethyl) | phenyl |
| 787 | 1-(S)-(cyclohexyl-n-propyl) | —C(O)—N(cyclohexyl)- | 5-tetrazolyl-methyl- | phenyl |
| 788 | 1-(S)-(cyclohexyl)-n-propyl | —C(O)—N(cyclohexyl)- | 2-imidazolyl-methyl- | phenyl |
| 789 | 1-(S)-(cyclohexyl)-n-propyl | —C(O)—N(cyclohexyl)- | 4-pyridyl-methyl- | phenyl |
| 790 | 1-(S)-(cyclohexyl)-n-propyl | —C(O)—N(cyclohexyl)- | 3-(1,2,4-triazolyl)-methyl- | phenyl |
| 791 | 1-(S)-(cyclohexyl)-n-propyl | —C(O)— | 1-(S)-(2-carboxy-pyrrolidinyl) | phenyl |
| 792 | 1-(S)-(cyclohexyl)-n-propyl | —C(O)— | 1-(S)-(2-methoxy-carbonyl-piperidinyl) | phenyl |
| 793 | 1-(S)-(cyclohexyl)-n-propyl | —C(O)— | 1-(S)-(2-methoxy-carbonyl-octahydroindolyl) | phenyl |
| 794 | 1-(S)-(cyclohexyl)-n-propyl | —C(O)— | 1-(S)-(2-carboxy-piperidinyl) | phenyl |
| 795 | 1-(S)-(cyclohexyl)-n-propyl | —C(O)— | 1-(S)-(2-carboxy-octahydroindolyl) | phenyl |
| 796 | 1-(S)-(cyclohexyl)-n-propyl | —C(O)—N(cyclohexyl)- | 5-imidazolyl-methyl- | phenyl |
| 797 | 1-(S)-(cyclohexyl)-n-propyl | —C(O)—N(cyclohexyl)- | 2R-(3R,4S,5R-tri(methyl-carbonyloxy)-6R-(methyl-carbonyloxy-methyl)-tetrahydro- | phenyl |

TABLE 3-continued

| 798 | 1-(S)-(cyclohexyl)-n-propyl | —C(O)—N(cyclohexyl)- | pyranyl)oxy-ethyl-2R-(3S,4S,5R-trihydroxy-6R-(hydroxy-methyl)-tetrahydro-pyranyl)oxy-ethyl- | phenyl |
| 799 | 1-(S)-(cyclohexyl)-n-propyl | —C(O)—N(cyclohexyl)- | 3-(2R-(3S,4S,5R,6R-tetrahydroxy-tetrahydro-pyranyl)-methoxy-carbonyl-amino)-n-propyl- | phenyl |

TABLE 4

Compounds of Formula (I)

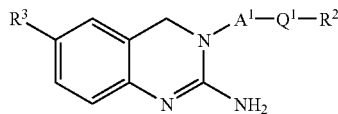

| ID No | A¹ | Q¹ | R² | R³ |
|---|---|---|---|---|
| 37 | -ethyl- | —C(O)—N(CH₃)— | cyclohexyl | 3-(6-fluoro-benzo[d]isoxazole) |
| 226 | 1-cyclohexyl-n-propyl- | —C(O)—N(CH₃)— | cyclohexyl | 4-methoxy-phenyl |
| 227 | 1-cyclohexyl-n-propyl- | —C(O)—N(CH₃)— | cyclohexyl | 2-methoxy-phenyl |
| 487 | -ethyl- | —NH—C(O)— | cyclohexyl | 2-methoxy-phenyl |
| 488 | -ethyl- | —NH—C(O)— | 1-(amino carbonyl)-cyclopropyl | 2-methoxy-phenyl |
| 490 | -ethyl- | —NH—C(O)— | amino-methyl- | 2-methoxy-phenyl |
| 491 | -ethyl- | —NH—C(O)— | 4-(1-(methyl-carbonyl)-piperidinyl) | 2-methoxy-phenyl |
| 493 | -ethyl- | —NH—C(O)— | amino-ethyl- | 2-methoxy-phenyl |
| 494 | -ethyl- | —NH—C(O)— | 3-amino-n-propyl | 2-methoxy-phenyl |
| 506 | 1-(S)-cyclohexyl-n-propyl- | —C(O)—N(CH₃)— | cyclohexyl | 2-methoxy-phenyl |
| 515 | -ethyl- | —NH—C(O)— | cyclohexyl | phenyl |
| 530 | 1-(R)-cyclohexyl-n-propyl- | —C(O)—N(CH₃)— | cyclohexyl | 2-methoxy-phenyl |
| 535 | -ethyl- | —NH—C(O)— | cyclohexyl | 2-fluoro-phenyl |
| 536 | -ethyl- | —NH—C(O)— | cyclohexyl | 2-chloro-phenyl |
| 537 | -ethyl- | —NH—C(O)— | cyclohexyl | 2-methyl-phenyl |
| 538 | -ethyl- | —NH—C(O)— | cyclohexyl | 2-hydroxy-phenyl |
| 539 | -ethyl- | —NH—C(O)— | cyclohexyl | 2-(methyl-sulfonyl-amino)-phenyl |
| 540 | -ethyl- | —NH—C(O)— | cyclohexyl | 2-methylthio-phenyl |
| 541 | -ethyl- | —NH—C(O)— | cyclohexyl | 2-(methyl-carbonyl-amino)-phenyl |
| 542 | -ethyl- | —NH—C(O)— | cyclohexyl | 2-(t-butyl-amino-sulfonyl)-phenyl |
| 543 | -ethyl- | —NH—C(O)— | cyclohexyl | 2-(amino-carbonyl)-phenyl |
| 544 | -ethyl- | —NH—C(O)— | cyclohexyl | 2-biphenyl |
| 545 | -ethyl- | —NH—C(O)— | cyclohexyl | 2-fluoro-6-methoxy-phenyl |
| 556 | -ethyl- | —C(O)—NH— | 2-adamantyl | 2-methoxy-phenyl |
| 567 | -ethyl- | —NH—C(O)— | 3-cyano-phenyl | 5-pyrimidinyl |
| 568 | -ethyl- | —NH—C(O)— | 3-cyano-phenyl | n-penten-1-yl |
| 569 | -ethyl- | —NH—C(O)— | n-propyl | 5-pyrimidinyl |
| 570 | -ethyl- | —NH—C(O)— | n-propyl | 4-pyridyl |
| 571 | -ethyl- | —NH—C(O)— | n-propyl | n-penten-1-yl |
| 572 | -ethyl- | —NH—C(O)— | t-butyl | 5-pyrimidinyl |
| 573 | -ethyl- | —NH—C(O)— | t-butyl | 4-pyridyl |
| 574 | -ethyl- | —NH—C(O)— | t-butyl | n-penten-1-yl |
| 575 | -ethyl- | —NH—C(O)— | cyclohexyl | 5-pyrimidinyl |
| 576 | -ethyl- | —NH—C(O)— | cyclohexyl | 4-pyridyl |

TABLE 4-continued

| | | | | |
|---|---|---|---|---|
| 577 | -ethyl- | —NH—C(O)— | cyclohexyl | n-penten-1-yl |
| 578 | -ethyl- | —NH—C(O)— | cyclopentyl-methyl- | phenyl |
| 580 | -ethyl- | —NH—C(O)— | cyclopentyl-methyl- | n-penten-1-yl |
| 582 | -ethyl- | —NH—C(O)— | cyclopentyl-methyl- | 3-(methyl-carbonyl)-phenyl |
| 583 | -ethyl- | —NH—C(O)— | cyclopentyl-methyl- | 3-hydroxymethyl-phenyl |
| 584 | -ethyl- | —NH—C(O)— | cyclopentyl-methyl- | 3-trifluoromethyl-phenyl |
| 586 | -ethyl- | —NH—C(O)— | 3-(2,5-dimethyl-furyl) | phenyl |
| 587 | -ethyl- | —NH—C(O)— | 3-(2,5-dimethyl-furyl) | n-penten-1-yl |
| 588 | -ethyl- | —NH—C(O)— | 3-(2,5-dimethyl-furyl) | 3-(methyl-carbonyl)-phenyl |
| 589 | -ethyl- | —NH—C(O)— | 3-(2,5-dimethyl-furyl) | 3-hydroxymethyl-phenyl |
| 590 | -ethyl- | —NH—C(O)— | 3-(2,5-dimethyl-furyl) | 3-trifluoromethyl-phenyl |
| 591 | -ethyl- | —NH—C(O)— | 4-(methyl-carbonyl-amino)-phenyl | phenyl |
| 592 | -ethyl- | —NH—C(O)— | 4-(methyl-carbonyl-amino)-phenyl | n-penten-1-yl |
| 593 | -ethyl- | —NH—C(O)— | 4-(methyl-carbonyl-amino)-phenyl | 3-hydroxymethyl-phenyl |
| 594 | -ethyl- | —NH—C(O)— | 4-(methyl-carbonyl-amino)-phenyl | 3-trifluoromethyl-phenyl |
| 595 | -ethyl- | —NH—C(O)— | benzyl | phenyl |
| 596 | -ethyl- | —NH—C(O)— | benzyl | n-penten-1-yl |
| 598 | -ethyl- | —NH—C(O)— | benzyl | 3-(methyl-carbonyl)-phenyl |
| 599 | -ethyl- | —NH—C(O)— | benzyl | 3-hydroxymethyl-phenyl |
| 600 | -ethyl- | —NH—C(O)— | benzyl | 3-trifluoromethyl-phenyl |
| 610 | -ethyl- | —C(O)—NH— | cyclohexyl | 2-methoxy-phenyl |
| 623 | -ethyl- | —NH—C(O)— | cyclohexyl | 4-fluoro-phenyl |
| 624 | -ethyl- | —NH—C(O)— | cyclohexyl | 4-fluoro-phenyl |
| 625 | -ethyl- | —NH—C(O)— | cyclohexyl | 3-chloro-phenyl |
| 626 | -ethyl- | —NH—C(O)— | cyclohexyl | 4-chloro-phenyl |
| 627 | -ethyl- | —NH—C(O)— | cyclohexyl | 3-methyl-phenyl |
| 628 | -ethyl- | —NH—C(O)— | cyclohexyl | 4-methyl-phenyl |
| 629 | -ethyl- | —NH—C(O)— | cyclohexyl | 2,6-difluoro-phenyl |
| 630 | -ethyl- | —NH—C(O)— | cyclohexyl | 2-methoxy-5-methyl-phenyl |
| 631 | -ethyl- | —NH—C(O)— | cyclohexyl | 2-methoxy-5-fluoro-phenyl |
| 635 | -ethyl- | —C(O)—NH— | 2-adamantyl | 2-fluoro-phenyl |
| 642 | -ethyl- | —NH—C(O)— | cyclobutyl | 2-fluoro-phenyl |
| 643 | -ethyl- | —NH—C(O)— | cyclopentyl | 2-fluoro-phenyl |
| 644 | -ethyl- | —NH—C(O)— | 1-adamantyl | 2-fluoro-phenyl |
| 645 | -ethyl- | —NH—C(O)— | n-propyl | 2-fluoro-phenyl |
| 646 | -ethyl- | —NH—C(O)— | t-butyl | 2-fluoro-phenyl |
| 647 | -ethyl- | —NH—C(O)— | isopentyl | 2-fluoro-phenyl |
| 648 | -ethyl- | —NH—C(O)— | 3-n-heptyl | 2-fluoro-phenyl |
| 649 | -ethyl- | —NH—C(O)— | cyclobutyl | 2-chloro-phenyl |
| 650 | -ethyl- | —NH—C(O)— | cyclopentyl | 2-chloro-phenyl |
| 651 | -ethyl- | —NH—C(O)— | 1-adamantyl | 2-chloro-phenyl |
| 652 | -ethyl- | —NH—C(O)— | n-propyl | 2-chloro-phenyl |
| 653 | -ethyl- | —NH—C(O)— | t-butyl | 2-chloro-phenyl |
| 654 | -ethyl- | —NH—C(O)— | isopentyl | 2-chloro-phenyl |
| 655 | -ethyl- | —NH—C(O)— | 3-n-heptyl | 2-chloro-phenyl |
| 656 | -ethyl- | —NH—C(O)— | cyclobutyl | 2-methyl-phenyl |
| 657 | -ethyl- | —NH—C(O)— | cyclopentyl | 2-methyl-phenyl |
| 658 | -ethyl- | —NH—C(O)— | 1-adamantyl | 2-methyl-phenyl |
| 659 | -ethyl- | —NH—C(O)— | n-propyl | 2-methyl-phenyl |
| 660 | -ethyl- | —NH—C(O)— | t-butyl | 2-methyl-phenyl |
| 661 | -ethyl- | —NH—C(O)— | isopentyl | 2-methyl-phenyl |
| 662 | -ethyl- | —NH—C(O)— | 3-n-heptyl | 2-methyl-phenyl |
| 663 | -ethyl- | —NH—C(O)— | cyclobutyl | 2-naphthyl |
| 664 | -ethyl- | —NH—C(O)— | cyclopentyl | 2-naphthyl |
| 665 | -ethyl- | —NH—C(O)— | 1-adamantyl | 2-naphthyl |
| 666 | -ethyl- | —NH—C(O)— | n-propyl | 2-naphthyl |
| 667 | -ethyl- | —NH—C(O)— | t-butyl | 2-naphthyl |

TABLE 4-continued

| | | | | |
|---|---|---|---|---|
| 668 | -ethyl- | —NH—C(O)— | isopentyl | 2-naphthyl |
| 669 | -ethyl- | —NH—C(O)— | 3-n-heptyl | 2-naphthyl |
| 670 | -ethyl- | —NH—C(O)— | cyclobutyl | 3-quinolinyl |
| 671 | -ethyl- | —NH—C(O)— | cyclopentyl | 3-quinolinyl |
| 672 | -ethyl- | —NH—C(O)— | 1-adamantyl | 3-quinolinyl |
| 673 | -ethyl- | —NH—C(O)— | n-propyl | 3-quinolinyl |
| 674 | -ethyl- | —NH—C(O)— | t-butyl | 3-quinolinyl |
| 675 | -ethyl- | —NH—C(O)— | isopentyl | 3-quinolinyl |
| 676 | -ethyl- | —NH—C(O)— | 3-n-heptyl | 3-quinolinyl |
| 678 | -ethyl- | —NH—C(O)— | 3,3,3-trifluoro-n-propyl | 2-methyl-phenyl |
| 679 | -ethyl- | —NH—C(O)— | 3,3,3-trifluoro-isobutyl | 2-methyl-phenyl |
| 680 | -ethyl- | —NH—C(O)— | 3,3,3-trifluoro-n-propyl | 2-fluoro-phenyl |
| 681 | -ethyl- | —NH—C(O)— | 3,3,3-trifluoro-isobutyl | 2-fluoro-phenyl |
| 682 | -ethyl- | —NH—C(O)— | 3,3,3-trifluoro-n-propyl | 2-chloro-phenyl |
| 683 | -ethyl- | —NH—C(O)— | 3,3,3-trifluoro-isobutyl | 2-chloro-phenyl |
| 684 | -ethyl- | —NH—C(O)— | 3,3,3-trifluoro-n-propyl | phenyl |
| 685 | -ethyl- | —NH—C(O)— | 3,3,3-trifluoro-isobutyl | phenyl |
| 686 | -ethyl- | —NH—C(O)— | 3,3,3-trifluoro-n-propyl | 2-naphthyl |
| 687 | -ethyl- | —NH—C(O)— | 4-tetrahydropyranyl | 2-fluoro-phenyl |
| 688 | -ethyl- | —NH—C(O)— | 4-trifluoromethyl-cyclohexyl | 2-fluoro-phenyl |
| 689 | -ethyl- | —NH—C(O)— | 4-tetrahydropyranyl | 2-chloro-phenyl |
| 690 | -ethyl- | —NH—C(O)— | 4-trifluoromethyl-cyclohexyl | 2-chloro-phenyl |
| 691 | -ethyl- | —NH—C(O)— | 4-(1-methylcarbonyl)-piperidinyl | 2-chloro-phenyl |
| 692 | -ethyl- | —NH—C(O)— | 1-(3-methoxy-cyclohexyl) | 2-chloro-phenyl |
| 693 | -ethyl- | —NH—C(O)— | 4-tetrahydropyranyl | 2-methyl-phenyl |
| 694 | -ethyl- | —NH—C(O)— | 4-trifluoromethyl-cyclohexyl | 2-methyl-phenyl |
| 695 | -ethyl- | —NH—C(O)— | 4-(1-methylcarbonyl)-piperidinyl | 2-methyl-phenyl |
| 696 | -ethyl- | —NH—C(O)— | 3-methoxy-cyclohexyl | 2-methyl-phenyl |
| 697 | -ethyl- | —NH—C(O)— | 4-tetrahydropyranyl | 2-methoxy-phenyl |
| 698 | -ethyl- | —NH—C(O)— | 4-trifluoromethyl-cyclohexyl | 2-methoxy-phenyl |
| 699 | -ethyl- | —NH—C(O)— | 4-tetrahydropyranyl | 2-fluoro-6-methoxy-phenyl |
| 700 | -ethyl- | —NH—C(O)— | 4-trifluoromethyl-cyclohexyl | 2-fluoro-6-methoxy-phenyl |
| 701 | -ethyl- | —NH—C(O)— | 4-trifluoromethyl-cyclohexyl | phenyl |
| 702 | -ethyl- | —NH—C(O)— | 4-(1-methylcarbonyl)-piperidinyl | phenyl |
| 703 | -ethyl- | —NH—C(O)— | 3-methoxy-cyclohexyl | phenyl |
| 704 | -ethyl- | —NH—C(O)— | 4-trifluoromethyl-cyclohexyl | 1-cyclohexenyl |
| 705 | -ethyl- | —NH—C(O)— | 4-(1-methylcarbonyl)-piperidinyl | 1-cyclohexenyl |
| 706 | -ethyl- | —NH—C(O)— | 3-methoxy-cyclohexyl | 1-cyclopentenyl |

TABLE 4-continued

| | | | | |
|---|---|---|---|---|
| 707 | -ethyl- | —NH—C(O)— | 4-trifluoro-methyl-cyclohexyl | 1-cyclopentenyl |
| 716 | 1-(S)-cyclohexyl-n-propyl- | —C(O)—N(CH$_3$)— | 4-(2-phenyl-thiazolyl)-methyl- | 2-methoxy-phenyl |
| 717 | 1-(S)-cyclohexyl-n-propyl- | —C(O)—N(CH$_3$)— | 4-(1-phenyl-pyrazolyl)-methyl- | 2-methoxy-phenyl |
| 718 | 1-(S)-cyclohexyl-n-propyl- | —C(O)—N(CH$_3$)— | 5-(3-methyl-isoxazolyl)-methyl- | 2-methoxy-phenyl |
| 719 | 1-(S)-cyclohexyl-n-propyl- | —C(O)—N(CH$_3$)— | 3-(5-phenyl-isoxazolyl)-methyl- | 2-methoxy-phenyl |
| 720 | 1-(S)-cyclohexyl-n-propyl- | —C(O)—N(CH$_3$)— | 2-cyanoethyl- | 2-methoxy-phenyl |
| 721 | 1-(S)-cyclohexyl-n-propyl- | —C(O)—N(CH$_3$)— | phenylethyl- | 2-methoxy-phenyl |
| 722 | 1-(S)-cyclohexyl-n-propyl- | —C(O)—N(CH$_3$)— | 4-(2-phenyl-thiazolyl)-methyl- | 2-fluoro-phenyl |
| 723 | 1-(S)-cyclohexyl-n-propyl- | —C(O)—N(CH$_3$)— | 5-(3-methyl-isoxazolyl)-methyl- | 2-fluoro-phenyl |
| 724 | 1-(S)-cyclohexyl-n-propyl- | —C(O)—N(CH$_3$)— | 3-(5-phenyl-isoxazolyl)-methyl- | 2-fluoro-phenyl |
| 725 | 1-(S)-cyclohexyl-n-propyl- | —C(O)—N(CH$_3$)— | 2-cyanoethyl- | 2-fluoro-phenyl |
| 726 | 1-(S)-cyclohexyl-n-propyl- | —C(O)—N(CH$_3$)— | 4-methyl-piperidinyl | 2-fluoro-phenyl |
| 727 | 1-(S)-cyclohexyl-n-propyl- | —C(O)—N(CH$_3$)— | phenylethyl- | 2-fluoro-phenyl |

TABLE 5

Compound of formula (I)

| ID No. | R$^{10}$ | A$^1$ | Q$^1$ | R$^2$ | R$^3$ |
|---|---|---|---|---|---|
| 617 | H | -ethyl- | —C(O)—NH— | 2-adamantyl | 2-methoxy-phenyl |
| 620 | F | -ethyl- | —C(O)—NH— | 2-adamantyl | 2-methoxy-phenyl |

TABLE 6

Compounds of Formula (I)

| ID No. | R$^2$ | (L$^1$)$_b$ | R$^3$ |
|---|---|---|---|
| 32 | cyclohexyl | —C(OH)— | phenyl |
| 36 | cyclohexyl | —CH$_2$— | phenyl |

Representative compounds of formula (III) are as listed in Tables 7-8, below.

TABLE 7

Compounds of formula (III)

| ID No | R$^6$ | R$^7$ | L$^3$ | R$^8$ |
|---|---|---|---|---|
| 44 | n-propyl | -phenyl- | -3-NH—C(O)— | cyclohexyl |
| 49 | n-propyl | -phenyl- | -3-N(cyclohexyl)-C(O)O— | benzyl |
| 53 | n-propyl | -phenyl- | -3-NH— | cyclohexyl |
| 55 | n-propyl | -phenyl- | -3-NH— | cyclohexyl-methyl- |
| 56 | n-propyl | -phenyl- | -3-N(CN)— | cyclohexyl-methyl- |
| 60 | n-propyl | -phenyl- | -3-NH—C(O)— | phenyl |
| 61 | n-propyl | -phenyl- | -3-NH—SO$_2$— | phenyl |
| 67 | n-propyl | -phenyl- | -3-NH—C(O)O— | benzyl |
| 95 | 4-hydroxy-n-butyl | -phenyl- | -3-NH— | cyclohexyl-methyl- |
| 126 | 4-hydroxy-n-butyl | -phenyl- | -3-NH—SO$_2$— | phenyl |
| 203 | n-propyl | —CH$_2$-phenyl- | -3-NH—SO$_2$— | phenyl |
| 225 | n-propyl | -phenyl-3-CH$_2$— | —NH—SO$_2$— | phenyl |
| 237 | n-propyl | -phenyl- | -3-NH—SO$_2$— | methyl |
| 238 | n-propyl | -phenyl- | -3-NH—SO$_2$— | isopropyl |
| 239 | n-propyl | -phenyl- | -3-NH—SO$_2$— | n-butyl |

TABLE 7-continued

Compounds of formula (III)

$$R^8-L^3-R^7-O-[\text{quinazoline scaffold}]-N(R^6)-C(NH_2)=N$$

| ID No | R⁶ | R⁷ | L³ | R⁸ |
|---|---|---|---|---|
| 240 | n-propyl | -phenyl- | -3-NH—SO₂— | 3-thienyl |
| 241 | n-propyl | -phenyl- | -3-NH—SO₂— | 2-thienyl |
| 242 | n-propyl | -phenyl- | -3-NH—SO₂— | 4-(3,5-dimethyl-isoxazolyl) |
| 243 | n-propyl | -phenyl- | -3-NH—SO₂— | 2,4,6-trimethyl-phenyl |
| 244 | n-propyl | -phenyl- | -3-NH—SO₂— | 2-naphthyl |
| 245 | n-propyl | -phenyl- | -3-NH—SO₂— | 3-benzothienyl |
| 246 | n-propyl | -phenyl- | -3-NH—SO₂— | 4-(methyl-carbonyl-amino)-phenyl |
| 247 | n-propyl | -phenyl- | -3-NH—SO₂— | 4-benzo[2,3,1]-thiadiazolyl |
| 248 | n-propyl | -phenyl- | -3-NH—SO₂— | 2,5-dimethoxy-phenyl |
| 249 | n-propyl | -phenyl- | -3-NH—SO₂— | 3,4-dimethoxy-phenyl |
| 250 | n-propyl | -phenyl- | -3-NH—SO₂— | 2-(methyl-sulfonyl)-phenyl |
| 251 | n-propyl | -phenyl- | -3-NH—SO₂— | 2-(5-(2-pyridyl)-thienyl) |
| 252 | n-propyl | -phenyl- | -3-NH—SO₂— | 3-trifluoromethoxy-phenyl |
| 253 | n-propyl | -phenyl- | -3-NH—SO₂— | 1-(5-(dimethyl-amino)-naphthyl) |
| 254 | n-propyl | -phenyl- | -3-NH—SO₂— | 2-(5-(3-(2-methyl-thiazolyl)-thienyl)) |
| 255 | n-propyl | -phenyl- | -3-NH—SO₂— | 2-(5-(5-trifluoro-methyl)-isoxazolyl)-thienyl) |
| 269 | n-propyl | -phenyl- | -3-NH—SO₂— | benzyl |
| 270 | n-propyl | -phenyl- | -3-NH—SO₂— | 3-cyano-phenyl |
| 271 | n-propyl | -phenyl- | -3-NH—SO₂— | 3-methoxy-phenyl |
| 272 | n-propyl | -phenyl- | -3-NH—SO₂— | 4-methoxy-phenyl |
| 273 | n-propyl | -phenyl- | -3-NH—SO₂— | 2-methoxy-4-methyl-phenyl |
| 274 | n-propyl | -phenyl- | -3-NH—SO₂— | 1-naphthyl |
| 275 | n-propyl | -phenyl- | -3-NH—SO₂— | 6-(2,3-dihydro-benzo[1,4]dioxanyl) |
| 276 | n-propyl | -phenyl- | -3-NH—SO₂— | 3-(2-methoxy-carbonyl)-thienyl) |
| 277 | n-propyl | -phenyl- | -3-NH—SO₂— | 2-trifluoromethyl-phenyl |
| 278 | n-propyl | -phenyl- | -3-NH—SO₂— | 2-(5-(5-isoxazolyl)-thienyl)) |
| 279 | n-propyl | -phenyl- | -3-NH—SO₂— | 5-carboxy-2-methoxy-phenyl |
| 280 | n-propyl | -phenyl- | -3-NH—SO₂— | 4-biphenyl |
| 281 | n-propyl | -phenyl- | -3-NH—SO₂— | 1-naphthyl-ethyl- |
| 282 | n-propyl | -phenyl- | -3-NH—SO₂— | 3-bromo-phenyl |
| 283 | n-propyl | -phenyl- | -3-NH—SO₂— | 4-trifluoromethoxy-phenyl |
| 284 | n-propyl | -phenyl- | -3-NH—SO₂— | 2-(5-bromo-thienyl) |
| 285 | n-propyl | -phenyl- | -3-NH—SO₂— | 2-(4-phenyl-sulfonyl)-thienyl |
| 296 | n-propyl | -phenyl-3-CH₂— | —NH— | benzyl |
| 305 | n-propyl | -phenyl-3-CH₂— | —NH— | 3-hydroxy-benzyl |
| 335 | n-propyl | -phenyl-3-CH₂— | —NH— | 2-methoxy-benzyl |
| 340 | n-propyl | -phenyl-3-CH₂— | —NH— | 2,6-dimethoxy-benzyl |
| 344 | n-propyl | -phenyl-3-CH₂— | —NH— | 2,4,6-trimethyl-benzyl |
| 355 | 5-hydroxy-n-pentyl | -phenyl- | -3-NH—SO₂— | 2-methoxy-4-methyl-phenyl |
| 380 | 5-hydroxy-n-pentyl | -phenyl- | -3-NH—SO₂— | 2,6-dimethoxy-benzyl |
| 383 | 5-hydroxy-n-pentyl | -phenyl- | -3-NH—SO₂— | 2,4,6-trimethyl-phenyl |
| 423 | n-propyl | -phenyl- | -3-C(O)—NH— | 2,4,6-trimethyl-benzyl |
| 430 | n-propyl | -phenyl-3-CH₂— | —NH— | phenyl-n-propyl- |
| 431 | n-propyl | -phenyl-3-CH₂— | —NH— | phenylethyl- |
| 464 | n-propyl | -phenyl-3-CH₂— | —N(CH₃)— | 2,4,6-trimethyl-benzyl |
| 500 | n-propyl | -phenyl- | -3-NH— | 2,4,6-trimethyl-benzyl |
| 501 | n-propyl | -phenyl- | -3-NH— | 2,6-dimethoxy-benzyl |
| 502 | n-propyl | -phenyl- | -3-NH— | 4-methoxy-benzyl |
| 507 | n-propyl | -phenyl- | -3-NH— | benzyl |
| 533 | n-propyl | -phenyl-3-CH₂— | —NH—C(O)— | 2,4,6-trimethyl-phenyl |
| 729 | n-propyl | -phenyl- | -3-NH— | 4-methyl-benzyl |
| 755 | n-propyl | -phenyl- | -3-NH—C(O)— | 3-(N-methyl-N-cyclohexyl-amino-carbonyl)-n-propyl |

TABLE 8

Compounds of formula (III)

$$R^8-L^3-R^7-(L^2)_d-[\text{quinazoline scaffold}]-N(R^6)-C(NH_2)=N$$

| ID No | R⁶ | (L²)_d | R⁷ | L³ | R⁸ |
|---|---|---|---|---|---|
| 345 | n-propyl | —S— | -phenyl- | -3-NH—SO₂— | phenyl |
| 385 | n-propyl | absent | -phenyl-2-CH₂— | —NH—SO₂— | phenyl |
| 387 | n-propyl | —S(O)— | -phenyl- | -3-NH—SO₂— | phenyl |
| 397 | n-propyl | absent | -phenyl- | -3-NH—SO₂— | phenyl |
| 497 | n-propyl | —S— | -phenyl- | -3-NH—SO₂— | 2,4,6-trimethyl-phenyl |

Representative compounds of formula (II) are as listed in Tables 9-13, below.

TABLE 9

Compounds of Formula (II)

$$R^3-O-[\text{quinazoline scaffold}]-N(\text{R ring})-Q^3-R^2$$

| ID No. | (R) | Q³ | R² | R³ |
|---|---|---|---|---|
| 72 | —(S)-cyclopentyl- | -2-(R)—C(O)—N(CH₃)— | cyclohexyl | phenyl |
| 77 | —(S)-cyclopentyl- | -3-(R)—C(O)—N(CH₃)— | cyclohexyl | phenyl |
| 81 | -(R)-cyclohexyl- | -2-(S)—C(O)—N(CH₃)— | cyclohexyl | phenyl |

TABLE 9-continued

Compounds of Formula (II)

| ID No. | R | Q³ | R² | R³ |
|---|---|---|---|---|
| 87 | -(S)-cyclohexyl- | -2-(R)—C(O)—N(CH₃)— | cyclohexyl | phenyl |
| 93 | -3-pyrrolidinyl- | -1-C(O)O— | t-butyl | phenyl |
| 94 | -phenyl- | -3-C(O)—N(CH₃)— | cyclohexyl | phenyl |
| 118 | -9-fluorenyl- | -2-C(O)—N(CH₃)— | cyclohexyl | phenyl |
| 119 | -3-pyrrolidinyl- | -1-C(O)— | cyclohexyl | phenyl |
| 120 | -3-pyrrolidinyl- | -1-C(O)— | cyclopentyl | phenyl |
| 124 | -9-fluorenyl- | -1-C(O)—N(cyclohexyl)- | cyclohexyl | phenyl |
| 125 | -9-fluorenyl- | -4-C(O)—N(CH₃)— | cyclohexyl | phenyl |
| 145 | -1-indanyl- | -6-C(O)—N(CH₃)— | cyclohexyl | phenyl |
| 146 | -1-(5-methoxy-indanyl)- | -3-CH₂—C(O)—N(CH₃)— | cyclohexyl | phenyl |
| 147 | -9-fluorenyl- | -4-C(O)—N(cyclohexyl)- | cyclohexyl | phenyl |
| 353 | -4-piperidinyl- | -1-C(O)O— | ethyl | (3-(2-methoxy-4-methyl-phenyl)-sulfonyl-amino)-phenyl |
| 362 | -4-piperidinyl- | -1-C(O)O— | ethyl | 3-(2,4,6-trimethyl-phenyl-sulfonyl-amino)-phenyl |
| 376 | -4-piperidinyl- | -1-C(O)O— | ethyl | 3-(phenyl-sulfonyl-amino-phenyl) |
| 499 | -4-piperidinyl- | -1-C(O)O— | t-butyl | phenyl |
| 510 | -3-azepinyl- | -1-C(O)O— | t-butyl | phenyl |
| 522 | -4-piperidinyl- | -1-C(O)— | cyclohexyl | phenyl |
| 523 | -4-piperidinyl- | -1-C(O)— | 4-n-heptyl | phenyl |
| 524 | -4-piperidinyl- | -1-C(O)— | 1-adamantyl | phenyl |
| 550 | -3-azepinyl- | -1-C(O)— | 1-adamantyl | phenyl |
| 551 | -3-azepinyl- | -1-C(O)— | cyclohexyl | phenyl |
| 552 | -3-azepinyl- | -1-C(O)— | 4-n-heptyl | phenyl |
| 611 | -3-piperidinyl- | -1-C(O)— | cyclohexyl | phenyl |
| 612 | -3-piperidinyl- | -1-C(O)— | 4-n-heptyl | phenyl |
| 613 | -3-piperidinyl- | -1-C(O)— | isopentyl | phenyl |

TABLE 10

Compounds of Formula (II)

| ID No | (A²)c | R | Q³ | R² | R³ |
|---|---|---|---|---|---|
| 62 | -methyl- | -phenyl- | -3-C(O)—N(CH₃)— | cyclohexyl | phenyl |
| 89 | -methyl- | -4-pyridyl- | -2-C(O)—N(CH₃)— | cyclohexyl | phenyl |
| 97 | -methyl- | -phenyl- | -4-C(O)—N(CH₃)— | cyclohexyl | phenyl |
| 98 | -methyl- | -phenyl- | -3-C(O)—N(cyclohexyl)- | cyclohexyl | phenyl |
| 100 | -methyl- | -trans-cyclohexyl- | -4-C(O)—N(CH₃)— | cyclohexyl | phenyl |
| 110 | -methyl- | -phenyl- | -3-C(O)—N(CH₃)— | cyclohexyl | 3-(phenyl-sulfonyl-amino)-phenyl |
| 132 | —CH(phenyl)- | -phenyl- | -3-C(O)—N(cyclohexyl)- | cyclohexyl | phenyl |
| 136 | —CH(phenyl)- | -phenyl- | -3-C(O)—N(CH₃)— | cyclohexyl | phenyl |
| 187 | -methyl- | -phenyl- | -3-C(O)—N(4-methyl-cyclohexyl)- | 4-methyl-cyclohexyl | phenyl |
| 188 | -methyl- | -phenyl- | -3-C(O)—NH— | 4-(amino-sulfonyl)-phenyl-ethyl- | phenyl |
| 192 | -methyl- | -phenyl- | -3-C(O)—N(isopropyl)- | cyclohexyl | phenyl |
| 193 | -methyl- | -phenyl- | -3-C(O)— | 2-deca-hydro-iso-quinolinyl | phenyl |
| 197 | -methyl- | -phenyl- | -3-C(O)—N(n-propyl)- | cyclopropyl-methyl- | phenyl |
| 198 | -methyl- | -phenyl- | -3-C(O)—N(2-ethyl-n-hexyl)- | 2-ethyl-n-hexyl | phenyl |
| 204 | -1-ethyl-methyl- | -phenyl- | -3-C(O)—N(CH₃)— | cyclohexyl | phenyl |

TABLE 10-continued

Compounds of Formula (II)

$$R^3-O-\text{[benzene ring]}-CH_2-N(A^2)_c-R-Q^3-R^2$$
(with 2-amino group on fused ring, N in ring)

| ID No | (A²)c | R | Q³ | R² | R³ |
|---|---|---|---|---|---|
| 209 | -methyl- | -phenyl- | -3-C(O)—N(CH₃)— | cyclohexyl | 3-methyl-phenyl |
| 211 | -methyl- | -phenyl- | -3-C(O)—N(isobutyl)- | isobutyl | phenyl |
| 212 | -methyl- | -phenyl- | -3-C(O)— | 1-deca-hydro-quinolinyl | phenyl |
| 213 | -methyl- | -phenyl- | -3-C(O)—NH— | 4-methyl-cyclohexyl | phenyl |
| 222 | -methyl- | -phenyl- | -3-C(O)—NH— | 2-(1-methyl-pyrrolidinyl)-ethyl- | phenyl |
| 223 | -methyl- | -phenyl- | -3-C(O)—N(CH₃)— | 4-(1-methyl-piperidinyl) | phenyl |
| 224 | -methyl- | -phenyl- | -3-NH—C(O)O— | t-butyl | phenyl |
| 228 | -methyl- | -phenyl- | -3-C(O)—N(CH₃)— | cyclohexyl | 3,5-dimethyl-phenyl |
| 229 | -methyl- | -phenyl- | -3-C(O)—N(CH₃)— | cyclohexyl | 3-(methyl-carbonyl-amino)-phenyl |
| 230 | -methyl- | -phenyl- | -3-C(O)—N(CH₃)— | cyclohexyl | 3-pyridyl |
| 231 | -methyl- | -phenyl- | -3-C(O)—N(CH₃)— | cyclohexyl | 3-biphenyl |
| 232 | -methyl- | -phenyl- | -3-C(O)—N(CH₃)— | cyclohexyl | 2-methoxy-phenyl |
| 233 | -methyl- | -phenyl- | -3-C(O)—N(CH₃)— | cyclohexyl | 2-(5,6,7,8-tetrahydro-naphthyl) |
| 234 | -methyl- | -phenyl- | -3-C(O)—N(CH₃)— | cyclohexyl | 2-biphenyl |
| 235 | -methyl- | -phenyl- | -3-C(O)—N(CH₃)— | cyclohexyl | 2-(amino-carbonyl-methyl)-phenyl |
| 236 | -methyl- | -phenyl- | -3-C(O)—N(CH₃)— | cyclohexyl | 3-(phenyloxy)-phenyl |
| 286 | -methyl | -phenyl- | -3-NH—C(O)— | cyclohexyl | phenyl |
| 290 | -methyl- | -phenyl- | -3-NH—C(O)— | t-butyl | phenyl |
| 292 | -methyl- | -phenyl- | -3-C(O)—N(CH₃)— | cyclohexyl | 3-methoxy-phenyl |
| 293 | -methyl- | -phenyl- | -3-C(O)—N(CH₃)— | cyclohexyl | 2-methyl-phenyl |
| 306 | -methyl- | -phenyl-3-CH₂— | —NH—C(O)— | cyclohexyl | phenyl |
| 307 | -methyl- | -phenyl-3-CH₂— | —NH—C(O)— | trifluoro-methyl | phenyl |
| 310 | —CH(cyclo-hexyl-methyl)- | -phenyl- | —C(O)—N(CH₃)— | cyclohexyl | phenyl |
| 315 | -methyl- | -phenyl-3-CH₂— | —NH—C(O)O— | t-butyl | phenyl |
| 316 | -1-phenyl-methyl- | -phenyl- | -3-C(O)—N(CH₃)— | 4-(1-methyl-piperidinyl) | phenyl |
| 336 | -methyl- | -phenyl-3-CH₂— | —NH—C(O)— | 1-adamantyl | phenyl |
| 337 | -methyl- | -phenyl-3-CH₂— | —NH—C(O)— | benzhydryl | phenyl |
| 338 | -methyl- | -phenyl-3-CH₂— | —NH—C(O)— | 4-n-heptyl | phenyl |
| 339 | -methyl- | -phenyl-3-CH₂— | —NH—C(O)— | 3-n-heptyl | phenyl |
| 384 | -methyl- | -4-piperidinyl- | -1-C(O)O— | t-butyl | 3-(phenyl-sulfonyl-amino)-phenyl |
| 396 | -methyl- | -phenyl- | -3-C(O)O— | methyl | 3-(phenyl-sulfonyl-amino)-phenyl |
| 419 | -1-ethyl-methyl- | -phenyl- | -3-C(O)—N(cyclohexyl)- | cyclohexyl | phenyl |
| 424 | -methyl- | -2-furyl- | -5-C(O)—N(CH₃)— | cyclohexyl | phenyl |
| 443 | -methyl- | -phenyl- | -3-C(O)— | 1-piperidinyl | phenyl |
| 451 | -methyl- | -phenyl- | -3-C(O)—NH— | cyclohexyl | phenyl |
| 463 | -methyl- | -phenyl- | -2-C(O)—N(CH₃)— | cyclohexyl | phenyl |

TABLE 10-continued

Compounds of Formula (II)

| ID No | (A²)c | R | Q³ | R² | R³ |
|---|---|---|---|---|---|
| 467 | -methyl- | -phenyl- | -3-C(O)—N(CH₃)— | cyclohexyl | 2-methoxy-5-methyl-phenyl |
| 468 | -methyl- | -phenyl- | -3-C(O)—N(CH₃)— | cyclohexyl | 2-methoxy-6-methyl-phenyl |
| 469 | -methyl- | -phenyl- | -3-C(O)—N(CH₃)— | cyclohexyl | 2-(2-benz-thiazolyl)-5-methoxy-phenyl |
| 470 | -methyl- | -phenyl- | -3-C(O)—N(CH₃)— | cyclohexyl | 2-(2-benzo-thiazolyl)-phenyl |
| 471 | -methyl- | -phenyl- | -3-C(O)—N(CH₃)— | cyclohexyl | 2-(1-pyrrolyl)-phenyl |
| 472 | -methyl- | -phenyl- | -3-C(O)—N(CH₃)— | cyclohexyl | 2-(methyl-sulfonyl)-phenyl |
| 473 | -methyl- | -phenyl- | -3-C(O)—N(CH₃)— | cyclohexyl | 3-(2-quinolinyl)-phenyl |
| 474 | -methyl- | -phenyl- | -3-C(O)—N(CH₃)— | cyclohexyl | 2-methylthio-phenyl |
| 475 | -methyl- | -phenyl- | -3-C(O)—N(CH₃)— | cyclohexyl | 2,6-dimethyl-phenyl |
| 477 | -methyl- | -phenyl- | -3-C(O)—N(CH₃)— | cyclohexyl | 2,6-dimethoxy-phenyl |
| 478 | -methyl- | -phenyl- | -3-C(O)—N(CH₃)— | cyclohexyl | 2-isopropoxy-phenyl |
| 479 | -methyl- | -phenyl- | -3-C(O)—N(CH₃)— | cyclohexyl | 3-(dimethyl-amino)-phenyl |
| 480 | -methyl- | -phenyl- | -3-C(O)—N(CH₃)— | cyclohexyl | 2-allyl-6-methyl-phenyl |
| 481 | -methyl- | -phenyl- | -3-C(O)—N(CH₃)— | cyclohexyl | 2-allyl-6-methoxy-phenyl |
| 482 | -methyl- | -phenyl- | -3-C(O)—N(CH₃)— | cyclohexyl | 2-methyl-6-n-propyl-phenyl |
| 483 | -methyl- | -phenyl- | -3-C(O)—N(CH₃)— | cyclohexyl | 2-(1-pyrrolidinyl-carbonyl)-phenyl |
| 503 | -methyl- | -2-thienyl- | -5-C(O)—N(CH₃)— | cyclohexyl | phenyl |
| 508 | -methyl- | -2-pyridyl- | -4-C(O)—N(CH₃)— | cyclohexyl | phenyl |
| 509 | -methyl- | -4-piperidinyl- | -1-C(O)O— | t-butyl | phenyl |
| 512 | -methyl- | -phenyl- | -3-C(O)—N(CH₃)— | cyclohexyl | 2-cyclopentyl-phenyl |
| 513 | -methyl- | -phenyl- | -3-C(O)—N(CH₃)— | cyclohexyl | 2-biphenyl-methyl- |
| 514 | -methyl- | -phenyl- | -3-C(O)—N(CH₃)— | cyclohexyl | 3-methoxy-benzyl |
| 516 | -methyl- | -phenyl- | -3-C(O)—N(CH₃)— | cyclohexyl | n-pentyl |
| 517 | -methyl- | -phenyl- | -3-C(O)—N(CH₃)— | cyclohexyl | isopentyl |
| 518 | -methyl- | -phenyl- | -3-C(O)—N(CH₃)— | cyclohexyl | isobutyl |
| 519 | -methyl- | -phenyl- | -3-C(O)—N(CH₃)— | cyclohexyl | isopropyl |
| 520 | -methyl- | -phenyl- | -3-C(O)—N(CH₃)— | cyclohexyl | cyclopentyl |
| 521 | -methyl- | -phenyl- | -3-C(O)—N(CH₃)— | cyclohexyl | cyclopentyl-methyl- |
| 525 | -methyl- | -4-piperidinyl- | -1-C(O)— | cyclohexyl | phenyl |
| 526 | -methyl- | -4-piperidinyl- | -1-C(O)— | 4-n-heptyl | phenyl |
| 527 | -methyl- | -4-piperidinyl- | -1-C(O)— | 1-adamantyl | phenyl |
| 534 | -1-cyclohexyl-methyl- | -phenyl- | -3-C(O)—N(CH₃)— | cyclohexyl | phenyl |
| 559 | -1-benzyl-methyl- | -5-oxazolyl- | -4-C(O)—N(CH₃)— | cyclohexyl | phenyl |
| 606 | -1-benzyl-methyl- | -5-oxazolyl- | -4-C(O)—NH— | cyclohexyl | phenyl |
| 640 | -methyl- | -5-oxazolyl- | -4-C(O)—NH— | cyclohexyl | phenyl |
| 641 | -methyl- | -5-oxazolyl- | -4-C(O)—N(CH₃)— | cyclohexyl | phenyl |

TABLE 11

Compounds of formula (II)

| ID No | $(L^1)_b$ | $R^3$ |
|---|---|---|
| 266 | —CH=CH— | phenyl |
| 332 | —CH(CH$_3$)— | phenyl |
| 404 | —S— | 2-methyl-phenyl |
| 405 | —S— | 3-methyl-phenyl |
| 406 | —S— | 2-ethyl-phenyl |
| 407 | —S— | 4-isopropyl-phenyl |
| 408 | —S— | 3,4-dimethyl-phenyl |
| 409 | —S— | 3,5-dimethyl-phenyl |
| 410 | —S— | 4-methoxy-phenyl |
| 411 | —S— | 3,4-dimethoxy-phenyl |
| 412 | —S— | 2-methoxy-phenyl |
| 413 | —S— | 4-methylthio-phenyl |
| 414 | —S— | 1-naphthyl |
| 415 | —S— | 2-naphthyl |
| 416 | —S— | 2-(methylaminocarbonyl)-phenyl |
| 417 | —S— | 4-(methylcarbonylamino)-phenyl |

TABLE 11-continued

Compounds of formula (II)

| ID No | $(L^1)_b$ | $R^3$ |
|---|---|---|
| 432 | —NH— | phenyl |
| 433 | —NH— | 3-methoxy-phenyl |
| 434 | —NH— | 4-methoxy-phenyl |
| 435 | —NH— | 3-methyl-phenyl |
| 436 | —NH— | 2-naphthyl |
| 437 | —NH— | 4-cyclohexyl-phenyl |
| 438 | —NH— | 4-(dimethylamino)-phenyl |
| 439 | —NH— | 4-(4-morpholinyl)-phenyl |
| 440 | —NH— | 3-ethoxy-phenyl |
| 441 | —NH— | 3,4-methylenedioxy-phenyl |
| 442 | —NH— | 4-methylthio-phenyl |
| 476 | —S— | phenyl |
| 549 | —SO— | phenyl |
| 735 | —SO$_2$— | phenyl |

TABLE 12

Compounds of formula (II)

| ID No | $(A^2)_c$ | R | $Q^3$ | $R^2$ | $R^3$ |
|---|---|---|---|---|---|
| 138 | -methyl- | -phenyl- | -3-C(O)—N(CH$_3$)— | cyclohexyl | phenyl |
| 158 | -methyl- | -phenyl- | -3-C(O)—N(CH$_3$)— | cyclohexyl | 2-(t-butyl-amino-sulfonyl)-phenyl |
| 159 | -methyl- | -phenyl- | -3-C(O)—N(CH$_3$)— | cyclohexyl | 4-(3,5-dimethyl-isoxazolyl) |
| 160 | -methyl- | -phenyl- | -3-C(O)—N(CH$_3$)— | cyclohexyl | 2-(t-butyl-carbonyl-amino)-5-methoxy-phenyl |
| 161 | -methyl- | -phenyl- | -3-C(O)—N(CH$_3$)— | cyclohexyl | 4-pyrazolyl |
| 162 | -methyl- | -phenyl- | -3-C(O)—N(CH$_3$)— | cyclohexyl | 4-(amino-carbonyl)-phenyl |
| 163 | -methyl- | -phenyl- | -3-C(O)—N(CH$_3$)— | cyclohexyl | 3-carboxy-phenyl |
| 164 | -methyl- | -phenyl- | -3-C(O)—N(CH$_3$)— | cyclohexyl | 3-thienyl |
| 165 | -methyl- | -phenyl- | -3-C(O)—N(CH$_3$)— | cyclohexyl | 3-methoxy-phenyl |
| 166 | -methyl- | -phenyl- | -3-C(O)—N(CH$_3$)— | cyclohexyl | 3-(methyl-carbonyl-amino)-phenyl |
| 167 | -methyl- | -phenyl- | -3-C(O)—N(CH$_3$)— | cyclohexyl | 2-methoxy-phenyl |
| 168 | -methyl- | -phenyl- | -3-C(O)—N(CH$_3$)— | cyclohexyl | 4-pyridyl |
| 169 | -methyl- | -phenyl- | -3-C(O)—N(CH$_3$)— | cyclohexyl | 2-hydroxy-phenyl |
| 170 | -methyl- | -phenyl- | -3-C(O)—N(CH$_3$)— | cyclohexyl | 3-pyridyl |
| 171 | -methyl- | -phenyl- | -3-C(O)—N(CH$_3$)— | cyclohexyl | 3-biphenyl |
| 172 | -methyl- | -phenyl- | -3-C(O)—N(CH$_3$)— | cyclohexyl | 2-(dimethylamino-methyl)-phenyl |
| 173 | -methyl- | -phenyl- | -3-C(O)—N(CH$_3$)— | cyclohexyl | 2-(amino-carbonyl)-phenyl |
| 174 | -methyl- | -phenyl- | -3-C(O)—N(CH$_3$)— | cyclohexyl | 2-hydroxymethyl-phenyl |
| 175 | -methyl- | -phenyl- | -3-C(O)—N(CH$_3$)— | cyclohexyl | 5-indolyl |
| 176 | -methyl- | -phenyl- | -3-C(O)—N(CH$_3$)— | cyclohexyl | 3-methyl-phenyl |
| 259 | -methyl- | -phenyl- | -3-C(O)—N(CH$_3$)— | cyclohexyl | 2,6-dichloro-phenyl |

TABLE 12-continued

Compounds of formula (II)

[Structure: R³-substituted dihydroquinazoline with -(A²)c-R-Q³-R² substituent and 2-NH₂]

| ID No | (A²)c | R | Q³ | R² | R³ |
|---|---|---|---|---|---|
| 260 | -methyl- | -phenyl- | -3-C(O)—N(CH₃)— | cyclohexyl | 2-chloro-phenyl |
| 261 | -methyl- | -phenyl- | -3-C(O)—N(CH₃)— | cyclohexyl | 2-methyl-phenyl |
| 262 | -methyl- | -phenyl- | -3-C(O)—N(CH₃)— | cyclohexyl | 2,6-dimethyl-phenyl |
| 263 | -methyl- | -phenyl- | -3-C(O)—N(CH₃)— | cyclohexyl | 2-cyano-phenyl |
| 264 | -methyl- | -phenyl- | -3-C(O)—N(CH₃)— | cyclohexyl | 2,6-dimethoxy-phenyl |
| 265 | -methyl- | -phenyl- | -3-C(O)—N(CH₃)— | cyclohexyl | 3-benzothienyl |
| 267 | -methyl- | -phenyl- | -3-C(O)—N(CH₃)— | cyclohexyl | 4-cyclohexyl-phenyl |
| 268 | -methyl- | -phenyl- | -3-C(O)—N(CH₃)— | cyclohexyl | 2-trifluoro-methyl-phenyl |
| 320 | -methyl- | -phenyl- | -3-C(O)—N(CH₃)— | cyclohexyl | 2-ethyl-phenyl- |
| 321 | -methyl- | -phenyl- | -3-C(O)—N(CH₃)— | cyclohexyl | 2-biphenyl |
| 322 | -methyl- | -phenyl- | -3-C(O)—N(CH₃)— | cyclohexyl | 2-methylthio-phenyl |
| 323 | -methyl- | -phenyl- | -3-C(O)—N(CH₃)— | cyclohexyl | 2-(methyl-carbonyl)-phenyl |
| 324 | -methyl- | -phenyl- | -3-C(O)—N(CH₃)— | cyclohexyl | 2-trifluoro-methoxy-phenyl |
| 325 | -methyl- | -phenyl- | -3-C(O)—N(CH₃)— | cyclohexyl | 2-cyanomethyl-phenyl |
| 326 | -methyl- | -phenyl- | -3-C(O)—N(CH₃)— | cyclohexyl | 2-(phenyloxy)-phenyl |
| 327 | -methyl- | -phenyl- | -3-C(O)—N(CH₃)— | cyclohexyl | 2-benzyloxy-phenyl |
| 328 | -methyl- | -phenyl- | -3-C(O)—N(CH₃)— | cyclohexyl | 2-(methyl-carbonyl-amino)-phenyl |
| 329 | -methyl- | -phenyl- | -3-C(O)—N(CH₃)— | cyclohexyl | 2-ethoxy-phenyl |
| 330 | -methyl- | -phenyl- | -3-C(O)—N(CH₃)— | cyclohexyl | 1-naphthyl |
| 331 | -methyl- | -phenyl- | -3-C(O)—N(CH₃)— | cyclohexyl | 2-bromo-phenyl |
| 333 | -methyl- | -phenyl- | -3-C(O)—N(CH₃)— | cyclohexyl | 2-nitro-phenyl |
| 334 | -methyl- | -phenyl- | -3-C(O)—N(CH₃)— | cyclohexyl | 2-fluoro-phenyl |
| 395 | -1-ethyl-methyl- | -phenyl- | -3-C(O)—N(CH₃)— | cyclohexyl | 2-methoxy-phenyl |
| 396 | -methyl- | -phenyl- | -3-C(O)O— | methyl | 3-(phenyl-sulfonyl-amino)-phenyl |
| 418 | -1-ethyl-methyl- | -phenyl- | -3-C(O)—N(cyclo-hexyl)- | cyclohexyl | 2-methoxy-phenyl |

TABLE 13

Compounds of Formula (II)

[Structure: R³-substituted dihydroquinazoline with N-benzyl bearing Q³-R² and 2-NHR¹]

| ID No | R¹ | Q³ | R² | R³ |
|---|---|---|---|---|
| 605 | methoxy | -3-C(O)—N(CH₃)— | cyclohexyl | 2-methoxy-phenyl |
| 607 | methyl-carbonyl | -3-C(O)—N(CH₃)— | cyclohexyl | 2-methoxy-phenyl |

TABLE 14

Intermediates or By-Products

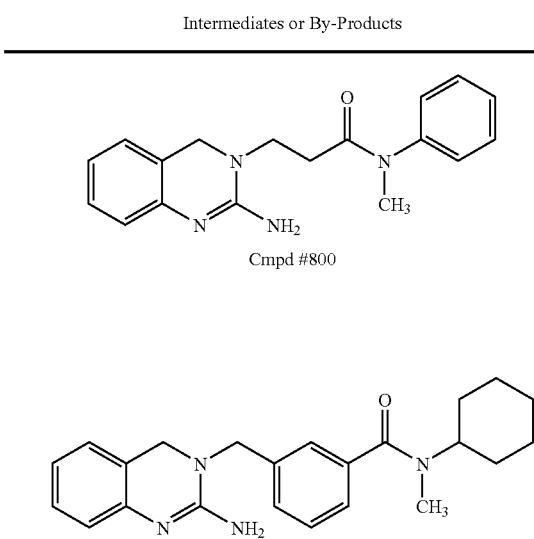

Cmpd #800

Cmpd #801

Table 14 below lists representative intermediates and by-products in the preparation of the compounds of formula (I), formula (II) and/or formula (III) of the present invention.

TABLE 14-continued

Intermediates or By-Products

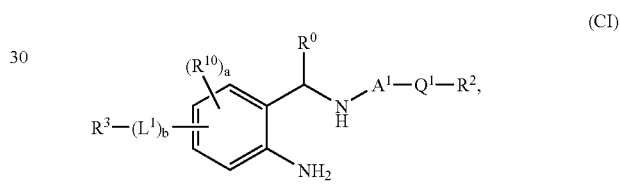

Cmpd #810

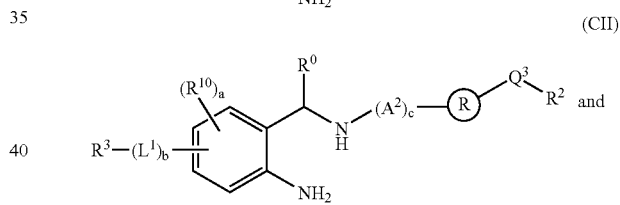

Cmpd #811

The present invention is further directed to compounds of formula (CI), compounds of formula (CII) and compounds of formula (CIII)

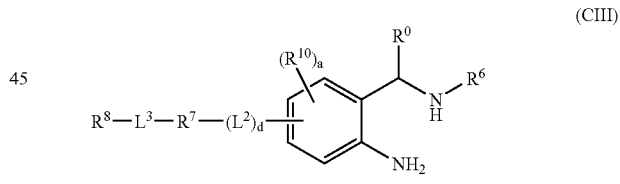

(CI)

(CII)

(CIII)

wherein $R^0$, $R^1$, $R^2$, $R^3$, $R^6$, $R^7$, $R^8$, $R^{10}$, $L^1$, $L^2$, $L^3$, a, b, c, d, $A^1$, $A^2$, $Q^1$, $Q^3$ and

are as herein defined. The compounds of formula (CI), (CII) and (CIII) are useful as intermediates in the preparation of the compounds of formula (I), (II) and/or (III) of the present invention.

As used herein, unless otherwise noted, the term "halogen" shall mean chlorine, bromine, fluorine and iodine.

As used herein, unless otherwise noted, the term "alkyl" whether used alone or as part of a substituent group, includes straight and branched chains. For example, alkyl radicals include methyl, ethyl, n-propyl, isopropyl, n-butyl, isobutyl, sec-butyl, t-butyl, n-pentyl, isopentyl, hexyl, heptyl, octyl, nonyl, decyl, and the like. Similarly, the term "$C_{1-8}$alkyl" shall include straight and branched chains comprising one to eight carbon atoms. The term "alkyl" may also encompass multivalent radicals where indicated in the specification and claims (e.g. $A^1$ and $A^2$ are described as $C_{1-4}$alkyl groups, as shown in the formulas and would be understood by those of ordinary skill the art to be divalent linking groups that may be further substituted, for example —CH$_2$—, —CH$_2$CH$_2$—, —CH$_2$—CH(CH$_3$)—, and the like).

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, the terms "halogen substituted $C_{1-4}$alkyl" and "halogenated $C_{1-4}$alkyl", shall mean a straight or branched chain alkyl group comprising one to four carbon atoms, wherein the alkyl is substituted with one or more, preferably one to five, more preferably one to three halogen atoms. Preferably, the halogen is selected from the group consisting of chloro and fluoro.

Similarly, the terms "halogen substituted $C_{1-4}$alkoxy" and "halogenated $C_{1-4}$alkoxy" shall mean a straight or branched chain alkoxy group comprising one to four carbon atoms, wherein the alkoxy is substituted with one or more, preferably one to five, more preferably one to three halogen atoms. Preferably, the halogen is selected from the group consisting of chloro and fluoro.

As used herein, unless otherwise noted, the term "hydroxy substituted $C_{1-4}$alkyl" shall mean a straight or branched chain $C_{1-4}$alkyl, wherein the $C_{1-4}$alkyl is substituted with one or more, preferably one to three hydroxy groups, more preferably one to two hydroxy groups. Most preferably, the $C_{1-4}$alkyl group is substituted with one hydroxy group. Preferably, wherein the $C_{1-4}$alkyl group has a terminal carbon atom, the hydroxy group is bound at said terminal carbon atom.

As used herein, unless otherwise noted, the term "carboxy substituted $C_{1-4}$alkyl" shall mean a straight or branched chain $C_{1-4}$alkyl, wherein the $C_{1-4}$alkyl is substituted with one or more, preferably one to three carboxy groups, more preferably one to two carboxy groups. Most preferably, the $C_{1-4}$alkyl group is substituted with one carboxy group. Preferably, wherein the $C_{1-4}$alkyl group has a terminal carbon atom, the carboxy group is bound at said terminal carbon atom.

As used herein, unless otherwise noted, "aryl" shall refer to fully conjugated aromatic ring structures such as phenyl, naphthyl, and the like.

As used herein, unless otherwise noted, "$C_{1-4}$aralkyl" shall mean any $C_{1-4}$alkyl group substituted with an aryl group such as phenyl, naphthyl and the like. For example, benzyl, phenylethyl, phenylpropyl, naphthylmethyl, and the like. Unless otherwise noted, the "$C_{1-4}$aralkyl" group is bound through the alkyl portion. For example, phenylethyl- is bound through the terminal carbon atom of the ethyl group (i.e. phenyl-CH$_2$—CH$_2$—).

As used herein, unless otherwise noted, the term "cycloalkyl" shall mean any stable monocyclic, bicyclic, polycyclic, bridged or spiro-bound, saturated ring system. Suitable examples include, but are not limited to, cyclopropyl, cyclobutyl, cyclopentyl, cyclohexyl, cycloheptyl, cyclooctyl, norboranyl, adamantyl, spiropentane, 2,2,2-bicyclooctyl, and the like. Unless otherwise noted, "cycloalkyl" groups do not contain N, O or S heteroatoms.

As used herein, unless otherwise noted, the term "partially unsaturated carbocyclyl" shall mean any stable monocyclic, bicyclic, polycyclic, bridge or spiro-bound ring system containing at least one carbon atom which is not part of an unsaturated bond (i.e. a double or triple bond) or any bicyclic, polycyclic, bridged or spiro-bound, partially aromatic (e.g. benzo-fused) rings system. Suitable examples include, but are not limited to 1,2,3,4-tetrahydro-naphthyl, fluorenyl, 9,10-dihydroanthracenyl, indanyl, and the like. Unless otherwise noted, "partially unsaturated carbocyclyl" groups do not contain N, O or S heteroatoms.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, pyrazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, tetrazolyl, triazolyl, and the like. Preferred heteroaryl groups include furyl, thienyl, imidazolyl, pyridyl, triazolyl, benzimidazolyl and tetrazolyl.

As used herein, the term "heterocycloalkyl" shall denote any five to seven membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic (e.g. benzo-fused) bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure.

Examples of suitable heterocycloalkyl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, tetrahydropyranyl, azepinyl, 2,3-dihydro-1,4-benzodioxanyl, and the like. Preferred heterocycloalkyl groups include piperidinyl, morpholinyl, tetrahydropyranyl (preferably tetrahydropyran-2-yl or tetrahydropyran-6-yl) and azepinyl.

As used herein, unless otherwise noted, the term "spiroheterocyclyl" shall mean any spiro-bound ring structure wherein the spiro-bound ring structure contains at least one heteroartom selected from O, S or N. Suitable examples include, but are not limited to 1,4-dioxaspiro[4.5]decyl, 1-oxa-4-azaspiro[4.5]decyl, 1-thia-4azaspiro[4.5]decyl, 1,4- diazaspiro[4.5]decyl, 1,3-diazaspiro[4.5]dec-2-2nyl and 1-oxa-azaspiro[4.5]dec-2-enyl. Preferred spiro-heterocyclyl groups include

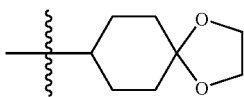

(i.e. 1,4-dioxaspiro[4.5]decyl).

As used herein, the notation "*" shall denote the presence of a stereogenic center.

When a particular group is "substituted" (e.g., cycloalkyl, aryl, heterocycloalkyl, heteroaryl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "aprotic solvent" shall mean any solvent that does not yield a proton. Suitable examples include, but are not limited to DMF, dioxane, THF, acetonitrile, pyridine, dichloroethane, dichloromethane, MTBE, toluene, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to, carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1999.

As used herein, unless otherwise noted, the term "oxygen protecting group" shall mean a group which may be attached to an oxygen atom to protect said oxygen atom from participating in a reaction and which may be readily removed following the reaction. Suitable examples include, but are not limited to methyl, benzyl, trimethylsilyl, tert-butyldimethylsilyl, acetate, 1-ethoxyethyl, and the like. Other suitable nitrogen protecting groups may be found in texts such as T. W. Greene & P. G. M. Wuts, *Protective Groups in Organic Synthesis*, John Wiley & Sons, 1991.

Under standard nomenclature used throughout this disclosure, the terminal portion of the designated side chain is described first, followed by the adjacent functionality toward the point of attachment. Thus, for example, a "phenyl-($C_1$-$C_6$alkyl)-aminocarbonyl-($C_1$-$C_6$alkyl)-" substituent refers to a group of the formula

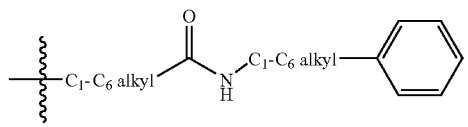

Unless otherwise noted, the position at which substituent groups on the compounds of formula (I), formula (II) and formula (III) are bound to the 2-amino-quinazoline core shall be denoted as follows:

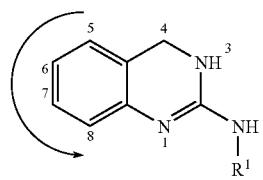

Abbreviations used in the specification, particularly the Schemes and Examples, are as follows:
Ac=Acetyl (i.e. —C(O)—$CH_3$)
ACN=Acetonitrile
AD=Alzheimer's Disease
AgOAc=Silver Acetate
BACE=β-secretase
BH(OAc)$_3$=Triacetoxy Borohydride
BOC or Boc=t-Butoxycarbonyl
(Boc)$_2$O=Boc Anhydride
Cbz=Carbobenzyloxy
DBU=1,8-iazabicyclo[5.4.0]undec-7-ene
DCC=N,N'-Dicyclohexylcarbodiimide
DCE=1,2-Dichloroethane
DCM=Dichloromethane
DEA=diethylamine
DEAD=Diethylazodicarboxylate
DIAD=Diisopropylazodicarboxylate
DIPE=Diisopropyl Ether
DIPCDI=1,3-Diisopropylcarbodiimide
DIPEA or DIEA=Diisopropylethylamine
DMA=N,N-Dimethylacetamide
DMAP=4-N,N-Dimethylaminopyridine
DME=Dimethoxyethane
DMF=N,N-Dimethylformamide
DMSO=Dimethylsulfoxide
dppf=1,1'-Bis(diphenylphosphino)ferrocene
EDC=1-(3-Dimethylaminoproyl)-3-ethylcarbodiimide hydrochoride
EDCI=1-(3-Dimethylaminopropyl)$_3$-ethylcarbodiimide hydrochloride
Et=Ethyl (—$CH_2CH_3$)
Et$_3$N=Triethylamine
Et$_2$O=Diethyl Ether
EtOAc=Ethyl acetate
EtOH=Ethanol HOAc=Acetic acid
HATU=O-(7-Azabenzotriazol-1-yl)-N,N,N'',N'''-Tetramethyl Uronium Hexafluorophosphate
HBTU=O-Benzotriazol-1-yl-N,N,N',N'-tetramethyluronium hexafluorophosphate
HEPES=4-(2-Hydroxyethyl)-1-Piperizine Ethane Sulfonic Acid
HOBT or HOBt=1-Hydroxybenzotriazole
HPLC=High Pressure Liquid Chromatography
LAH=Lithium Aluminum Hydride
μwave=Microwave
MCPBA=2-(4-Chloro-2-methylphenoxy)acetic acid
Me=Methyl
MeCN=Acetonitrile
MeOH=Methanol
MeONH$_2$ HCl=O-methylhydroxylamine hydrochloride
MTBE=Methyl-tert-Butyl Ether
Na(OAc)$_3$BH=Sodium triacetoxyborohydride
NH$_4$OAc=Ammonium Acetate
NMR=Nuclear Magnetic Resonance
OXONE®=Potassium Monopersulfaphate Triple Salt
Pd—C or Pd/C=Palladium on Carbon Catalyst
Pt—C or Pt/C=Platinum on Carbon Catalyst
Pd$_2$(OAc)$_2$=Palladium(II)acetate
Pd$_2$(dba)$_3$=Tris(dibenzylidene acetone)dipalladium(0)
Pd(dppf)Cl$_2$=Dichloro[1,1'-bis(diphenylphosphino)ferrocene]palladium
Pd(PPh$_3$)$_4$=tetrakistriphenylphosphine palladium (0)
Pd(PCy$_3$)$_2$Cl$_2$=Dichlorobis(tricyclohexylphosphine)palladium
PTSA or p-TsOH=p-Toluenesulfonic acid Monohydride
q. s.=Quantum Sufficiat (Quantity Sufficient)
RP-HPLC=Reverse Phase High Pressure Liquid Chromatography
RT or rt=Room temperature
SPE=Solid phase extraction
t-BOC or Boc=Tert-Butoxycarbonyl
TDA-1=Tris(3,6-Dioxaheptyl)amine
TEA=Triethylamine
TEMPO=2,2,6,6-Tetramethyl-1-piperidinyloxy Free Radical
TFA=Trifluoroacetic Acid
THF=Tetrahydrofuran
TLC=Thin Layer Chromatography The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein a compound of the present invention is present an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein a compound of the present invention is a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography or recrystallization. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1999. The protecting groups may be removed at a convenient subsequent stage using methods known from the art.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in *Design of Prodrugs*, ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lacetate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention further comprises pharmaceutical compositions containing one or more compounds of formula (I) and/or formula (II) and/or formula (III) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1-1000 mg and may be given at a dosage of from about 0.1-500 mg/kg/day. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 1000 mg, preferably, from about 0.1 to about 500 mg, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating central nervous system disorders described in the present invention may also be carried out using a pharmaceutical composition comprising any of the compounds as defined herein and a pharmaceutically acceptable carrier. The pharmaceutical composition may contain between about 0.1 mg and 1000 mg, preferably about 50 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, one or more of the compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders of the central nervous system is required.

The daily dosage of the products may be varied over a wide range from 0.01 to 1,000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.01 mg/kg to about 1000 mg/kg of body weight per day. Preferably, the range is from about 0.5 to about 500 mg/kg of body weight per day, most preferably, from about 1.0 to about 250 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

Compounds of formula (I) may be prepared according to the general process outlined in Scheme 1.

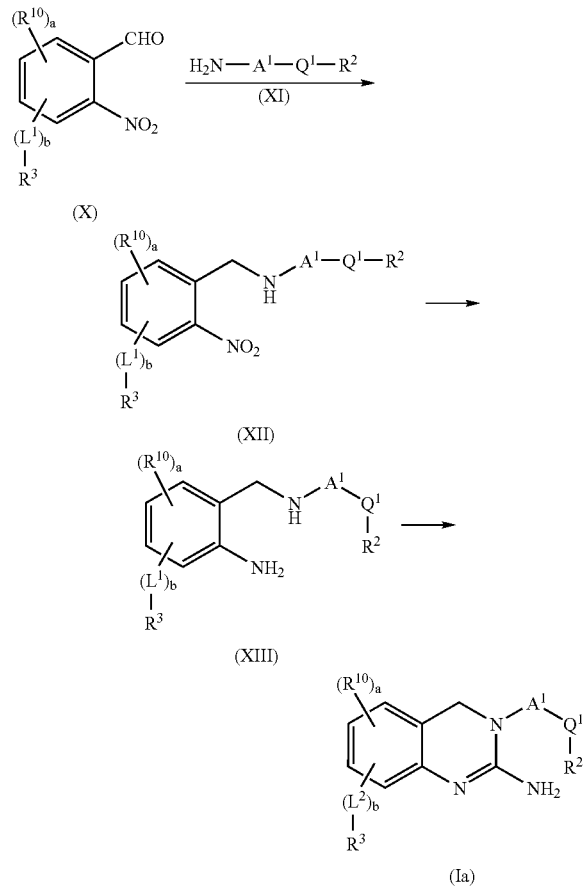

Accordingly, a suitably substituted compound of formula (X), a known compound or compound prepared by known methods, is reacted with a suitably substituted compound of formula (XI), a known compound or compound prepared by known methods, in the presence of a reducing agent such as NaBH(OAc)$_3$, and the like, in an organic solvent such as dichloromethane, 1,2-dichloroethane, THF, acetonitrile, and the like; or in the presence of a reducing agent such as NaBH$_3$CN, NaBH$_4$, and the like, in an organic solvent such as methanol, acetonitrile, and the like; to yield the corresponding compound of formula (XII).

The compound of formula (XII) is reacted with hydrogen gas, in the presence of a catalyst such as Pd on carbon (Pd/C), and the like, in a protic solvent such as methanol, ethanol, and the like, to yield the corresponding compound of formula (XIII). Alternatively, the compound of formula (XII) is reacted with a reducing agent such as stannous chloride, and the like, in an organic solvent such as methanol, ethanol, ethyl acetate, THF and the like, or in acid such as concentrated HCl, and the like; or with a reducing agent such as zinc, in the presence of an acid source such as ammonium chloride, calcium chloride, HBr, and the like, in an organic solvent such as methanol, ethanol, ethyl acetate, and the like, or in a mixture of an organic solvent and water as a co-solvent, or in aqueous acid such as acetic acid, and the like, to yield the corresponding compound of formula (XIII).

The compound of formula (XIII) is reacted with cyanogen bromide, and the like, in an organic solvent such as methanol, ethanol, toluene, and the like, to yield the corresponding compound of formula (Ia). Alternatively, the compound of formula (XIII) is reacted with 2-methyl-2-thiopseudourea, in the presence of an acid such as hydrochloric acid, sulfuric acid, and the like, in an organic solvents such as butanol, and the like, to yield the corresponding compound of formula (Ia).

One skilled in the art will recognize that compounds of formula (I) wherein the amine bound at the 2-position of the core structure is substituted with methyl-carbonyl-may be prepared from the corresponding compound of formula (Ia) above by reacting with a suitably substituted anhydride or chloroformate, in the presence of a base such as TEA, DIPEA, pyridine, DMAP, and the like, in an organic solvent such as DCM, chloroform, THF, and the like.

One skilled in the art will further recognize that compounds of formula (I) wherein the amine bound at the 2-position of the core structure is substituted with hydroxy or methoxy may be prepared from the corresponding compound of formula (Ia) by reacting the compound of formula (XIII) with a reagent such as carbon disulfide, 1,1'-thiocarbonyldiimidazole, thiophosgene, and the like, in the presence of a base such as NaOH, KOH, DIPEA, and the like, in an organic solvent such as methanol, ethanol, acetonitrile, DMF, and the like, or in a mixture of an organic solvent and water, to convert the 2-position amine group on the compound of formula (XIII) to the corresponding thiourea. The thiourea is then reacted with a methylating agent such as methyl iodide, dimethyl sulfide, and the like, in the presence of a base such as NaOH, NaH, DMAP, and the like, in an organic solvent such as DMF, acetone, THF, diethyl ether, and the like, to convert the thiourea to the corresponding thiomethyl compound. The thiomethyl compound is then reacted with N-hydroxylamine or N-methoxyamine, in the presence of a base such as TEA, DIPEA, pyridine, and the like, in an organic solvent such as DMF, acetonitrile, THF, methanol, and the like, optionally in the presence of a thiophilic reagent such as HgCl$_2$, AgOAc, and the like, to yield the corresponding compound of formula (I) wherein R$^1$ is hydroxy or methoxy.

Compounds of formula (I) wherein R$^0$ is methyl or trifluoromethyl may be prepared according to the process outlined in Scheme 1 above by substituting a suitably substituted compound of formula (XIV)

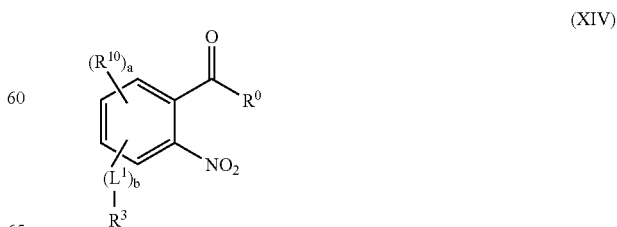

for the compound of formula (X).

Compounds of formula (I) wherein $Q^1$ is —NH—C(O)— may alternatively be prepared according to the process outlined in Scheme 2.

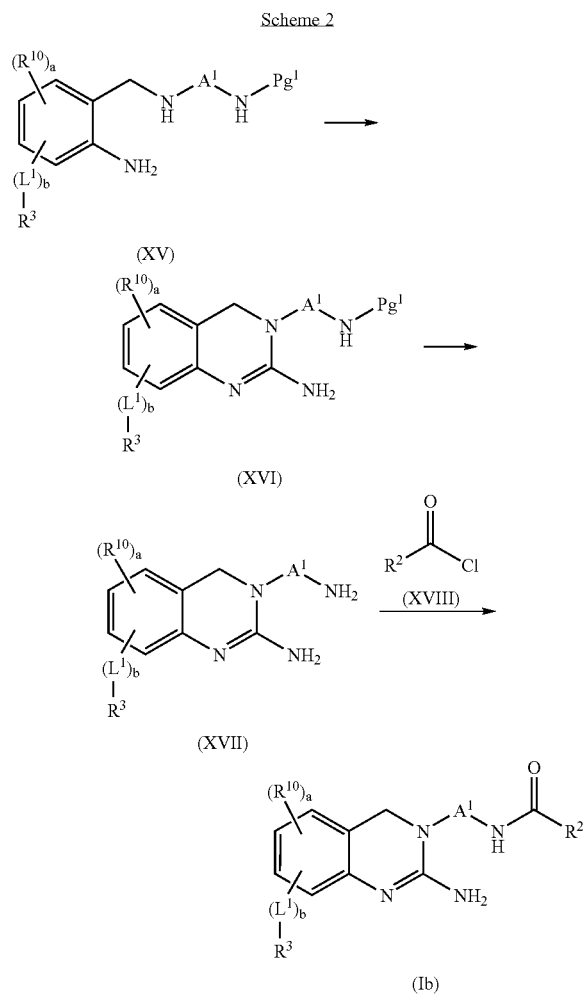

Accordingly, a suitably substituted compound of formula (XV), wherein $Pg^1$ is a suitable nitrogen protecting group such as Cbz, BOC, and the like, preferably BOC, a known compound or compound prepared by known methods, (for example by reacting the compound of formula (X), as defined above, with a compound of the formula $NH_2$-$A^1$-$NHPg^1$ and then reducing the nitro group to the corresponding amine), is reacted with cyanogen bromide, in an organic solvent such as methanol, ethanol, toluene, and the like, to yield the corresponding compound of formula (XVI). Alternatively, the compound of formula (XV) is reacted with 2-methyl-2-thiopsuedourea, in the presence of an acid such as hydrochloric acid, sulfuric acid, and the like, in an organic solvent such as ethanol, butanol, xylene, or dioxane, or in an aqueous solvent such as water to yield the corresponding compound of formula (XVI).

The compound of formula (XVI) is de-protected according to known methods, to yield the corresponding compound of formula (XVII). For example, wherein $Pg^1$ is BOC, the compound of formula (XVI) is de-protected by reacting with an acid such as TFA, HCl, formic acid, and the like; wherein $Pg^1$ is Cbz, the compound of formula (XVI) is de-protected by reacting with a hydrogen source such as $H_{2(g)}$ in the presence of a catalyst. (See for example, *Protective Groups in Organic Chemistry*, ed. J. F. W. McOmie, Plenum Press, 1973; or T. W. Greene & P. G. M. Wuts, *Protective Groups in Organic Synthesis*, John Wiley & Sons, 1999)

The compound of formula (XVII) is reacted with a suitably substituted acid chloride, a compound of formula (XVIII), a known compound or compound prepared by known methods, in the presence of a base such as TEA, DIPEA, pyridine, and the like, in an organic solvent such as dioxane, DCM, chloroform, and the like; to yield the corresponding compound of formula (Ib).

One skilled in the art will recognize that compounds of formula (I) wherein Q is —NH—C(S)—NH— may be similarly prepared according to the process outlined in Scheme 2 above, by reacting the compound of formula (XVII) with a suitably substituted isothiocyanate, a compound of the formula $R^2$—NCS, a known compound or compound prepared by known methods, in an organic solvent such as dioxane, dichloromethane, chloroform, and the like.

One skilled in the art will further recognize that compounds of formula (I) wherein Q is —NH—C(O)—NH— may be similarly prepared according to the process outlined in Scheme 2 above, by reacting the compound of formula (XVII) with a suitably substituted isocyanate, a compound of the formula $R^2$—NCS, a known compound or compound prepared by known methods, in an organic solvent such as dioxane, DCM, chloroform, and the like.

One skilled in the art will further recognize that compounds of formula (I) wherein Q is —NH—C(O)—O— may be similarly prepared according to the process outlined in Scheme 2 above, by reacting the compound of formula (XVII) with a suitably substituted chloroformate, a compound of the formula $R^2$—O—C(O)—Cl, a known compound or compound prepared by known methods, in the presence of a base such as TEA, DIPEA, pyridine, and the like, in an organic solvent such as dioxane, DCM, chloroform, and the like.

One skilled in the art will further recognize that compounds of formula (I) wherein Q is —NH—$SO_2$— may be similarly prepared according to the process outlined in Scheme 2 above, by reacting the compound of formula (XVII) with a suitably substituted sulfonyl chloride, a compound of the formula $R^2$—$SO_2$—Cl, a known compound or compound prepared by known methods, in the presence of a base such as TEA, DIPEA, pyridine, and the like, in an organic solvent such as dioxane, DCM, chloroform, and the like.

Compounds of formula (I) wherein $Q^1$ is —NH— and wherein $R^2$ is selected from the group consisting of $C_{1-8}$alkyl, cycloalkyl-$C_{1-4}$alkyl-, $C_{1-4}$aralkyl, partially unsaturated carbocyclyl-$C_{1-4}$alkyl-, heteroaryl-$C_{1-4}$alkyl- and heterocycloalkyl-$C_{1-4}$alkyl- may alternatively be prepared according to the process outlined in Scheme 3.

Scheme 3

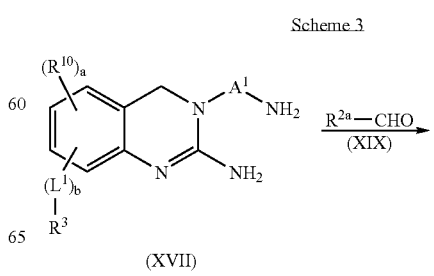

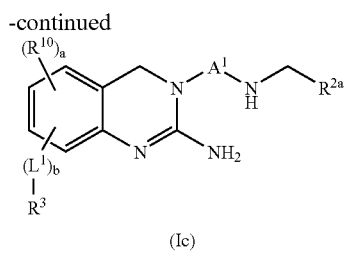

(Ic)

Accordingly, a suitably substituted compound of formula (XVII) is reacted with a suitably substituted aldehyde, a compound of formula (XIX), wherein $R^{2a}$ is $C_{1-7}$alkyl, cycloalkyl-$C_{0-3}$alkyl-, $C_{0-3}$aralkyl, partially unsaturated carbocyclyl-$C_{0-3}$alkyl-, heteroaryl-$C_{0-3}$alkyl- or heterocycloalkyl-$C_{0-3}$alkyl-, a known compound or compound prepared by known methods, in the presence of a reducing agent such as NaBH(OAc)$_3$, and the like, in an aprotic solvent such as DCM, DCE, THF, and the like; or in the presence of a reducing agent such as NaCNBH$_3$, and the like, in an organic solvent such as methanol, ethanol, THF, acetonitrile, and the like, to yield the corresponding compound of formula (Ic).

One skilled in the art will recognize that wherein $R^2$ is selected from the group consisting of —CH($C_{1-4}$alkyl)-($C_{1-4}$alkyl), cycloalkyl-CH($C_{1-4}$alkyl)-, aryl-CH($C_{1-4}$alkyl)-, partially unsaturated carbocyclyl-CH($C_{1-3}$alkyl)-, heteroaryl-CH($C_{1-4}$alkyl)- and heterocycloalkyl-CH($C_{1-4}$alkyl)-, the compound of formula (I) may be prepared according to the process outlined in Scheme 4.

Scheme 4

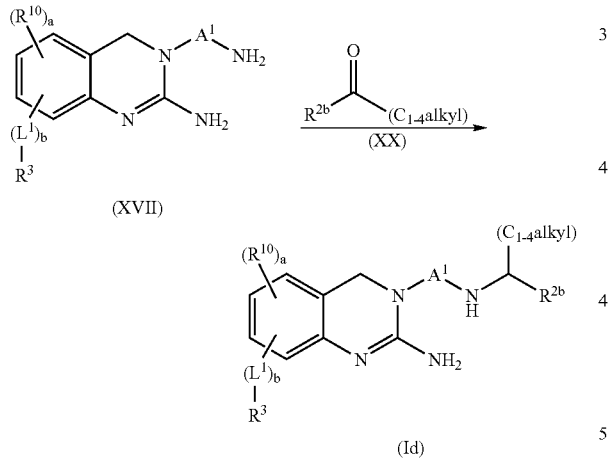

Accordingly, a suitably substituted compound of formula (XVII) is reacted with a suitably substituted ketone, a compound of formula (XX), wherein $R^{2b}$ is selected from ($C_{1-3}$alkyl), cycloalkyl, aryl, partially unsaturated carbocyclyl, heteroaryl or heterocycloalkyl, a known compound or compound prepared by known methods, in the presence of a reducing agent such as NaBH(OAc)$_3$, and the like, in an aprotic solvent such as DCM, DCE, THF, and the like; or in the presence of a reducing agent such as NaCNBH$_3$, and the like, in an organic solvent such as methanol, ethanol, THF, acetonitrile, and the like, to yield the corresponding compound of formula (Id).

One skilled in the art will further recognize that compounds of formula (I) wherein $Q^1$ is NH and $R^2$ is selected from the group consisting of cycloalkyl, partially unsaturated carbocyclyl and heterocycloalkyl may be similarly prepared according to the process outlined in Scheme 4 above, by substituting a suitably substituted ketone (i.e. a cycloalkyl ketone such as cyclohexone; a partially unsaturated carbocyclyl ketone; or a heterocycloalkyl ketone) for the compound of formula (XX).

Compounds of formula (II) may be prepared according to the processes described above by selecting and substituting suitably substituted reagents and intermediates for those disclosed within the schemes.

For example, compounds of formula (II) may be prepared according to the process outlined in Scheme 1 above, by selecting and substituting, a suitably substituted compound of formula (XXI)

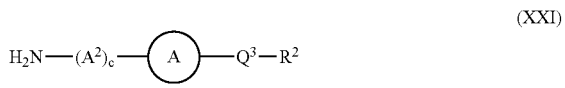

(XXI)

a known compound or compound prepared by known methods, for the compound of (XI).

Compounds of formula (III) wherein d is 1, may be prepared according to the process outlined in Scheme 5.

Scheme 5

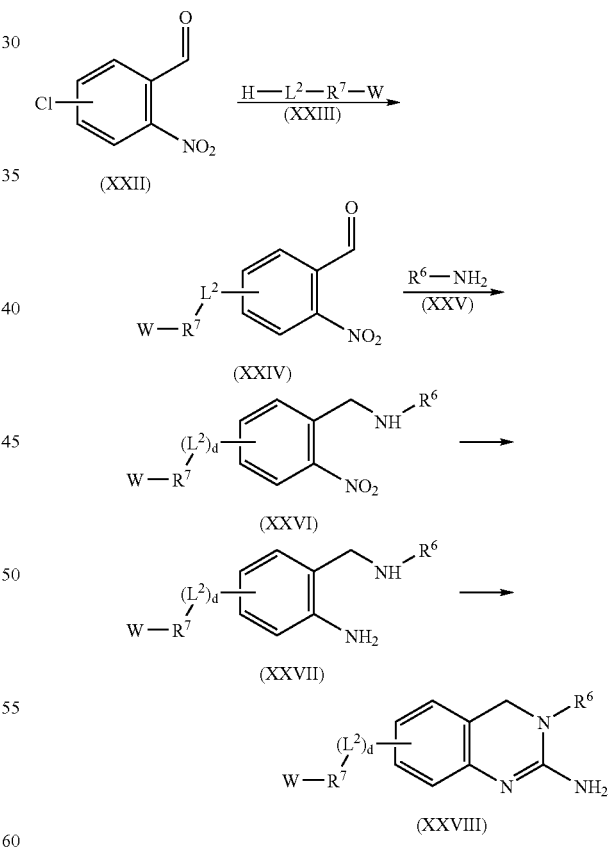

Accordingly, a suitably substituted compound of formula (XXII), a known compound or compound prepared by known methods, is reacted with a suitably substituted compound of formula (XXIII), a known compound or compound prepared by known methods, wherein W is selected from -L$^3$-R$^8$ or a reactive group such as NH$_2$, CN, Br, OH and the like; in the presence of a base such as $K_2CO_3$, $Na_2CO_3$, $Cs_2CO_3$, TEA, DIPEA, pyridine, and the like, in a polar organic solvent such as DMF, DMA, and the like, at an elevated temperature in the range of from about 70° C. to about 150° C., preferably at an elevated temperature in the range of about 80° C. to about 100° C., to yield the corresponding compound of formula (XXIV).

One skilled in the art will recognize that in the process step described above, in the compound of formula (XXII), the Cl may be replaced with F and reacted as described above, to yield the compound of formula (XXIV).

The compound of formula (XXIV) is reacted with a suitably substituted compound of formula (XXV), a known compound or compound prepared by known methods, in an organic solvent such as DCE, DCM, THF, and the like, in the presence of a reducing agent such as $BH(OAc)_3$, $NaCNBH_3$, and the like, to yield the corresponding compound of formula (XXVI).

Alternatively, the compound of formula (XXII) (or the compound of formula (XXII) wherein the Cl is replaced with F) is protected, according to known methods, for example as an acetal of the formula (XXIX)

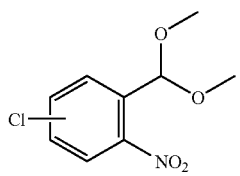

(XXIX)

and then reacted with a suitably substituted compound of formula (XXIII) to yield the corresponding protected version of the compound of formula (XXIV), which is the de-protected and reacted with the compound of formula (XXV), to yield the corresponding compound of formula (XXVI).

The compound of formula (XXVI) is reacted with hydrogen gas, in the presence of a catalyst such as Pd on carbon (Pd/C), and the like, in a protic solvent such as methanol, ethanol, and the like, to yield the corresponding compound of formula (XXVII). Alternatively, the compound of formula (XXVI) is reacted with a reducing agent such as stannous chloride, and the like, in an organic solvent such as methanol, ethanol, ethyl acetate, THF and the like, or in acid such as concentrated HCl, and the like; or with a reducing agent such as zinc, in the presence of an acid source such as ammonium chloride, calcium chloride, HBr, and the like, in an organic solvent such as methanol, ethanol, ethyl acetate, and the like, or in a mixture of an organic solvent and water as a co-solvent, or in aqueous acid such as acetic acid, and the like, to yield the corresponding compound of formula (XXVII).

The compound of formula (XXVII) is reacted with cyanogen bromide, and the like, in an organic solvent such as methanol, ethanol, toluene, and the like, to yield the corresponding compound of formula (XXVIII). Alternatively, the compound of formula (XXVII) is reacted with 2-methyl-2-thiopseudourea, in the presence of an acid such as hydrochloric acid, sulfuric acid, and the like, in an organic solvent such as butanol, and the like, to yield the corresponding compound of formula (XXVIII).

One skilled in the art will recognize that wherein W is -$L^3$-$R^2$, the compound of formula (XXVIII) is the corresponding compound of formula (III).

Wherein the compound of formula (XXVIII), W is other than -$L^3$-$R^2$, the compound of formula (XXVIII) is further reacted with according to known methods to yield the corresponding compound of formula (III).

For example, wherein W is $NH_2$, the compound of formula (XXVIII) is reacted with a suitably substituted aldehyde or cyclic ketone, for example an aldehyde, a compound of the formula $R^8$—CHO or a cyclic ketone such as cyclohexanone, to yield the corresponding compound of formula (III) wherein $L^3$ is —NH—.

Alternatively, wherein W is $NH_2$, the compound of formula (XXVIII) is reacted with a suitably substituted acid, a compound of the formula $R^8$—C(O)—OH, according to known methods, to yield the corresponding compound of formula (III) wherein $L^3$ is —NH—C(O)—.

Alternatively still, wherein W is $NH_2$, the compound of formula (XXVIII) is reacted with a suitably substituted sulfonyl chloride, a compound of the formula $R^8$—$SO_2$—Cl, or a suitably substituted acid chloride, a compound of the formula $R^8$—C(O)—Cl, according to known methods, to yield the corresponding compound of formula (III) wherein $L^3$ is —NH—$SO_2$— or —NH—C(O)—, respectively.

Alternatively still, wherein W is CN, the cyano group on the compound of formula (XXVIII) is reduced according to known methods, to yield the corresponding amine and then further functionalized according to known methods, for example, as described above.

Compounds of formula (III) wherein d is 1 may alternatively be prepared according to the process outlined in Scheme 6.

Scheme 6

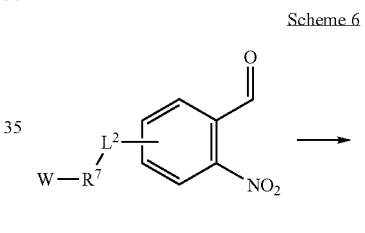

(XXIVa)

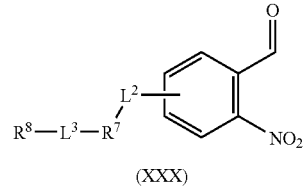

(XXX)

Accordingly, a suitably substituted compound of formula (XXIVa), a compound of formula (XXIV) wherein W is a reactive group such as CN, $NH_2$, Br, OH, and the like, is reacted according to known methods, to yield the corresponding compound of formula (XXX).

For example, wherein W is $NH_2$, the compound of formula (XXIVa) is reacted with a suitably substituted aldehyde or cyclic ketone, for example an aldehyde, a compound of the formula $R^8$—CHO or a cyclic ketone such as cyclohexanone, to yield the corresponding compound of formula (XXX) wherein $L^3$ is —NH—.

Alternatively, wherein W is $NH_2$, the compound of formula (XXIVa) is reacted with a suitably substituted acid, a compound of the formula $R^8$—C(O)—OH, according to known methods, to yield the corresponding compound of formula (XXX) wherein $L^3$ is —NH—C(O)—.

Alternatively still, wherein W is $NH_2$, the compound of formula (XXIVa) is reacted with a suitably substituted sulfonyl chloride, a compound of the formula $R^8$—$SO_2$—Cl, or a suitably substituted acid chloride, a compound of the formula R$^8$—C(O)—Cl, according to known methods, to yield the corresponding compound of formula (XXX) wherein L$^3$ is —NH—SO$_2$— or —NH—C(O)—, respectively.

Alternatively still, wherein W is CN, the cyano group on the compound of formula (XXIVa) is reduced according to known methods, to yield the corresponding amine and then further functionalized according to known methods, for example, as described above.

Alternatively still, wherein W is Br, the compound of formula (XXIVa) is reacted with a suitably substituted amine, a compound of the formula R$^8$—NH$_2$, or a compound of the formula R$^8$—NH—R$^B$, according to known methods, to yield the corresponding compound of formula (XXX) wherein L$^3$ is —NH—R$^8$ or R$^8$—(R$^B$)N—, respectively.

Alternatively still, wherein W is OH, the compound of formula (XXIVa) is converted to the corresponding triflate and then reacted with a suitably substituted amine, a compound of the formula R$^8$—NH$_2$, or of a compound of the formula R$^8$—NH—R$^B$, to yield the corresponding compound of formula (XXX) wherein L$^3$ is —NH—R$^8$ or R$^8$—(R$^B$)N—, respectively.

Wherein the compound of formula (XXIV), W is Br or OH, preferably the compound of formula (XXIV) is reacted according to the process outlined in Scheme 6.

The compound of formula (XXX) is then substituted for the compound of formula (XXIV) in the process outlined in Scheme 5 above, and reacted as disclosed in Scheme 5 above, to yield the corresponding compound of formula (III).

Compounds of formula (III) wherein d is 0 may be prepared according to the processes outlined in Schemes 5 and 6 above by substituting a suitably substituted compound of formula (XXXI)

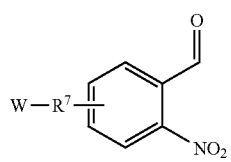

(XXXI)

for the compound of formula (XXIV), a known compound or compound prepared by known methods. For example, the compound of formula (XXXI) may be prepared according to the process outlined in Scheme 7.

Scheme 7

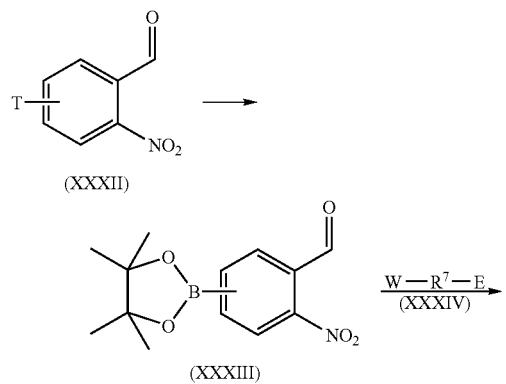

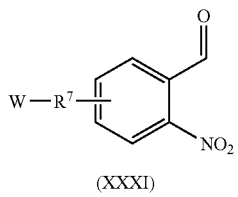

(XXXI)

Accordingly, a suitably substituted compound of formula (XXXII), wherein T is selected from Cl, Br or I, a known compound or compound prepared by known methods, is reacted with pinacol diborane (also known as 4,4,5,5,4',4',5', 5'-octamethyl-[2,2']bi[[1,3,2]dioxaborolanyl]), a known compound, in the presence of a catalyst such as Pd(dppf)Cl$_2$, Pd$_2$(dba)$_3$, and the like, with a base such as potassium carbonate, potassium acetate, and the like, in an organic solvent, such as DMSO, DME, and the like, in the absence or presence of an aqueous co-solvent, such as water, at an elevated temperature in the range of from about 50° C. to about 130° C., preferably at an elevated temperature in the range of from about 80° C. to about 110° C., to yield the corresponding compound of formula (XXXIII).

The compound of formula (XXXIII) is reacted with a suitably substituted compound of formula (XXXIV), wherein E is Br or I, and wherein W is -L$^3$-R$^8$ or a suitable reactive group such as NH$_2$, CN, Br, OH, and the like, a known compound or compound prepared by known methods, (for example as disclosed in Miyaura, N.; Suzuki, A. *Chem. Rev.* 1995, 95, 2457; Suzuki, A. *J. Organomet. Chem.* 1999, 576, 147), in the presence of a catalyst such Pd(PPh$_3$)$_4$, Pd(dppf)Cl$_2$, and the like, in the presence of a base such as Na$_2$CO$_3$, K$_2$CO$_3$, NaHCO$_3$, and the like, in a mixture of an organic solvent such as toluene, DME, THF, MeOH, and the like, and a protic solvent such as water, and the like, at an elevated temperature in the range of from about 60° C. to about 150° C., preferably, at an elevated temperature in the range of from about 100° C. to about 120° C., optionally in the presence of microwave irradiation, to yield the corresponding compound of formula (XXXI).

Compounds of formula (X) are known compounds or compounds which may be prepared according to known methods. Schemes 8-12 below outline processes for the preparation of representative compounds of formula (X).

For example, compounds of formula (X) wherein (L$^1$)$_b$ is —O— and R$^3$ is for example, aryl or heteroaryl, may be prepared according to any of the processes outlined in Scheme 8.

Scheme 8

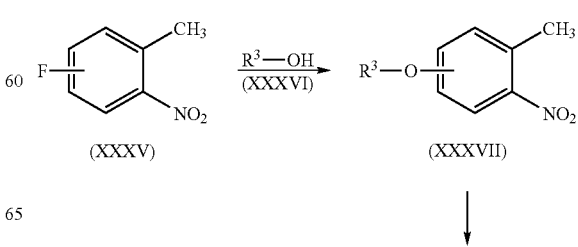

(XXXV)    (XXXVII)

-continued

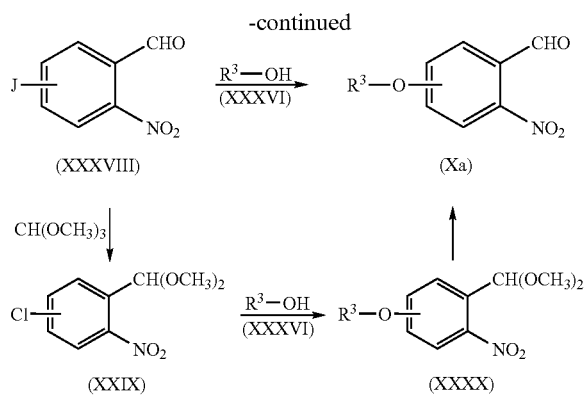

Accordingly, a suitably substituted compound of formula (XXXV), a known compound or compound prepared by known methods, wherein the phenyl ring may be further optionally substituted with one to three $R^{10}$ groups and wherein the F is bound at the carbon of the phenyl ring to which the -$(L^1)_b$-$R^3$ group in the desired compound of formula (I) is to be bound; is reacted with a suitably substituted compound of formula (XXXVI), a known compound or compound prepared by known methods, in the presence of a base such as $K_2CO_3$, $Cs_2CO_3$, and the like, in an organic solvent such as DMF, DMA, and the like, preferably DMF, at an elevated temperature in the range of from about 25° C. to about 150° C., preferably, at an elevated temperature in the range of from about 100° C. to about 120° C., optionally in the presence of microwave irradiation, to yield the corresponding compound of formula (XXXVII).

The compound of formula (XXXVII) is reacted with an electrophilic formyl source such as DMF dimethyl acetal, DMF diethyl acetal, and the like, in an organic solvent such as DMF, DMA, and the like, preferably DMF; or with neat tripiperidinomethane, preferably under vacuum; or with neat tert-butoxy-bis(dimethyl)aminomethane, at an elevated temperature in the range of from about 100° C. to about 150° C., preferably, at an elevated temperature in the range of from about 130° C. to about 140° C., followed by reaction with $NaIO_4$, and the like, in an organic solvent such as THF, DME, and the like, in the presence of water as a co-solvent, to yield the corresponding compound of formula (Xa).

Alternatively, a suitably substituted compound of formula (XXXVIII) wherein J is F, a known compound or compound prepared by known methods, wherein the phenyl ring may be further optionally substituted with one to three $R^{10}$ groups and wherein the F is bound at the carbon of the phenyl ring to which the -$(L^1)_b$-$R^3$ group in the desired compound of formula (I) is to be bound; is reacted with a suitably substituted compound of formula (XXXVI), a known compound or compound prepared by known methods, in the presence of a base such as $K_2CO_3$, $Cs_2CO_3$, and the like, in an organic solvent such as DMF, DMA, and the like, at an elevated temperature in the range of from about 100° C. to about 170° C., preferably, at an elevated temperature in the range of from about 140° C. to about 160° C., to yield the corresponding compound of formula (Xa).

Alternatively, a suitably substituted compound of formula (XXXVIII) wherein J is OH, a known compound or compound prepared by known methods, wherein the phenyl ring may be further optionally substituted with one to three $R^{10}$ groups and wherein the OH is bound at the carbon of the phenyl ring to which the -$(L^1)_b$-$R^3$ group in the desired compound of formula (I) is to be bound; is reacted with a suitably substituted compound of formula (XXXVI), under Mitsonobu conditions, for example, in the presence of a phosphine reagent such as triphenylphosphine, tributylphosphine, and the like and in the presence of an acetylene dicarboxylate such as DEAD, DIAD, and the like, in an organic solvent such as THF, DMF, and the like, to yield the corresponding compound of formula (Xa). Preferably, the Mitsonobu conditions are applied to the preparation of compounds of formula (Xa) wherein $R^3$ is $C_{1-4}$alkyl.

Alternatively still, a suitably substituted compound of formula (XXXVIII) wherein J is Cl or F, a known compound or compound prepared by known methods, wherein the phenyl ring may be further optionally substituted with one to three $R^{10}$ groups and wherein the Cl or F is bound at the carbon of the phenyl ring to which the -$(L^1)_b$-$R^3$ group in the desired compound of formula (I) is to be bound; is reacted with $CH(OCH_3)_3$ in the presence of an acid catalyst such as p-TsOH, $NH_4Cl$, $AlCl_3$, and the like, in an organic solvent such as methanol, THF, and the like, at an elevated temperature, preferably, at about reflux temperature, to yield the corresponding compound of formula (XXXIX).

The compound of formula (XXXIX) is reacted with a suitably substituted compound of formula (XXVI), a known compound or compound prepared by known methods, in the presence of a base such as $K_2CO_3$, $Cs_2CO_3$, and the like, in an organic solvent such as DMF, DMA, and the like, at an elevated temperature in the range of from about 25° C. to about 150° C., preferably, at an elevated temperature in the range of from about 100° C. to about 120° C., to yield the corresponding compound of formula (XXXX).

The compound of formula (XXXX) is hydrolyzed by reacting with an acid such as HCl, $H_2SO_4$, trifluoroacetic acid, and the like, in an organic solvent such as THF, DCM, diethyl ether, and the like, in the presence of water, to yield the corresponding compound of formula (Xa).

Compounds of formula (X) wherein $(L^1)_b$ is —S— may be similarly prepared according to the process described above by reacting a compound of formula (XXXVIII) wherein J is F, with a substituting a suitably substituted compound of the formula $R^3$—SH (i.e. substituting the compound of formula $R^3$—SH for the compound of formula (XXXVI)). The resulting compound may then be optionally, selectively oxidized to yield the corresponding compound of formula (X) wherein the —S— is oxidized to —SO— and/or —$SO_2$—.

Compounds of formula (X) wherein $(L^1)_b$ is —$NR^N$—, may be similarly prepared according to the process outlined in Scheme 7 above, by reacting a compound of formula (XXXVIII) wherein J is Br with a suitably substituted compound of the formula $R^3$—$NHR^N$, in the presence of a catalyst or mixture thereof, such as a 1:3 mixture of $Pd_2(dba)_3$ and dppf, and the like, in an organic solvent such as DMF, DME, toluene, and the like; or a catalyst such as $Pd_2(dba)_3$ or $Pd(dppf)Cl_2$ in the presence or a base such as $Cs_2CO_3$, NaOC$(CH_3)_3$, and the like, in an organic solvent such as toluene, and the like, to yield the corresponding compound of formula (X) wherein $(L^1)_b$ is —$NR^N$—.

Compounds of formula (X) wherein $(L^1)_b$ is —C(O)— may be prepared according to the processes disclosed in European Patent Number EP 0 371 564 B1; Katritzky, A. R., Chassaing, C., Toader, D. and Gill, K., *J. Chem. Research*, (S), 1999, pp 504-505; Katritzky, A. R., Lang, H., Wang, Z., Zhang, Z. and Song, H., *J. Org. Chem.*, 60, 1990, pp 7619-7624; and/or Vetelino, M. G. and Coe, J. W., *Tetrahedron Lett.*, 35(2), 1994, pp 219-22; with suitable modification, as would be clear to one of ordinary skill in art.

Compounds of formula (X) wherein $(L^1)_b$ is —C(S)— may be prepared by reacting the corresponding compound of formula (X) wherein $(L^1)_b$ is —C(O)— with a suitably selected thionating reagent such as $P_2S_5$, Lawesson's reagent, and the like, in an organic solvent such as toluene, benzene, xylene, and the like, at an elevated temperature in the range of from about 70° C. to about 150° C., preferably, at an elevated temperature in the range of from about 80° C. to about 110° C.

Compounds of formula (X) wherein $(L^1)_b$ is —$C_{2-4}$alkenyl- may be prepared by reacting the compound of formula (XXXVIII) wherein J is Br or I with a suitably substituted stannane, or a suitably substituted boronate, in the presence of a catalyst such as $Pd(PPh_3)_4$, and the like, according to known methods (for example, as disclosed in Miyaura, N.; Suzuki, A. *Chem. Rev.* 1995, 95, 2457; Suzuki, A. *J. Organomet. Chem.* 1999, 576, 147).

Alternatively, compounds of formula (X) wherein $(L^1)_b$ is —$C_{2-4}$alkenyl- may be prepared according to the process outlined in Scheme 9.

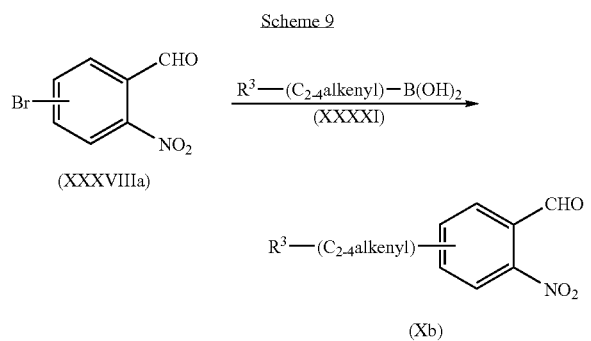

Scheme 9

(XXXVIIIa)

(Xb)

Accordingly, a suitably substituted compound of formula (XXXVIIIa), a compound of formula (XXXVIII) wherein J is Br, a known compound or compound prepared by known methods, is reacted with a suitably substituted compound of formula (XXXXI), wherein $R^3$ is as defined above, preferably, wherein $R^3$ is aryl or alkyl, a known compound or compound prepared by known methods (for example as disclosed in Miyaura, N.; Suzuki, A. *Chem. Rev.* 1995, 95, 2457; Suzuki, A. *J. Organomet. Chem.* 1999, 576, 147), in the presence of a catalyst such $Pd(PPh_3)_4$, $Pd(dppf)Cl_2$, and the like, in the presence of a base such as $Na_2CO_3$, $K_2CO_3$, $NaHCO_3$, and the like, in a mixture of an organic solvent such as toluene, DME, THF, MeOH, and the like, and a protic solvent such as water, and the like, at an elevated temperature in the range of from about 60° C. to about 150° C., preferably, at an elevated temperature in the range of from about 100° C. to about 120° C., optionally in the presence of microwave irradiation, to yield the corresponding compound of formula (Xb).

Compounds of formula (X) wherein $(L^1)_b$ is —$C_{2-4}$alkyl- may be prepared by hydrogenating the corresponding compound of formula (X) wherein $(L^1)_b$ is —$(C_{2-4}$alkenyl)-.

Compounds of formula (X) wherein $(L^1)_b$ is —$CH_2$— or —CH(OH)— may be prepared according to known methods, for example, by reducing the corresponding compound of formula (X) wherein $(L_1)_b$ is —C(O)— with a suitably selected reducing agent, according to known methods.

Compounds of formula (X) wherein $(L^1)_b$ is —CH(OH) may alternatively be prepared according to the process outlined in Scheme 10.

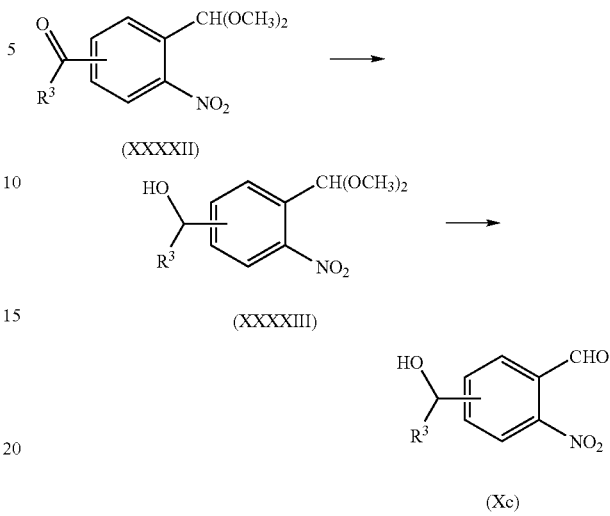

Scheme 10

(XXXXII)

(XXXXIII)

(Xc)

Accordingly, a suitably substituted compound of formula (XXXXII), a known compound or compound prepared by known methods, is reacted with a suitably selected reducing agent, such as sodium borohydride, and the like, in an organic solvent such as methanol, isopropanol, and the like, at a temperature in the range of from about room temperature to about 100° C., preferably, at about room temperature, to yield the corresponding compound of formula (XXXXIII).

The compound of formula (XXXXIII) is hydrolyzed by reacting with a suitably selected acid such as HCl, $H_2SO_4$, trifluoroacetic acid, and the like, in an organic solvent such as THF, DCM, diethyl ether, and the like, in the presence of water, to yield the corresponding compound of formula (Xc).

Compounds of formula (X) wherein $(L^1)_b$ is -(hydroxy substituted $C_{2-4}$alkyl)- may be prepared according to the process outlined in Scheme 11.

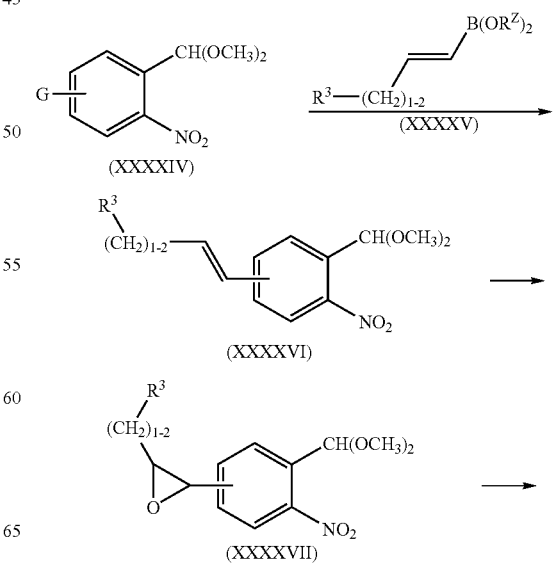

Scheme 11

(XXXXIV)

(XXXXVI)

(XXXXVII)

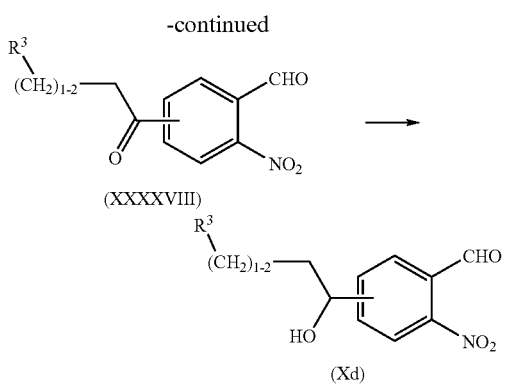

Accordingly, a suitably substituted compound of formula (XXXXIV), wherein G is selected from chloro, bromo or iodo, a known compound or compound prepared by known methods, is reacted with a suitably substituted vinyl boronate ester, a compound of formula (XXXXV) wherein $R^z$ is selected from aryl or heteroaryl, a known compound or compound prepared by known methods (for example as disclosed in Lhermitte, F.; Carboni, B. *SYNLETT* 1996, 377; Matsubara, S.; Otake, Y.; Hashimoto, Y.; Utimoto, K. *Chem. Lett.* 1999, 747; Takai, K.; Shinomiya, N.; Kaihara, H.; Yoshida, N.; Moriwake, T. *SYNLETT* 1995, 963; Deloux, L.; Srebnik, M. *J. Org. Chem.* 1994, 59, 6871), in the presence of a catalyst such as $Pd(PPh_3)_4$, $Pd(dppf)Cl_2$, and the like, (Miyaura, N.; Suzuki, A. *Chem. Rev.* 1995, 95, 2457; Suzuki, A. *J. Organomet. Chem.* 1999, 576, 147), in the presence of a base such as $Na_2CO_3$, $K_2CO_3$, $NaHCO_3$, and the like, in a mixture of an organic solvent such as toluene, DME, THF, MeOH, and the like, and a protic solvent such as water, at an elevated temperature in the range of from about 60° C. to about 150° C., preferably, at an elevated temperature in the range of from about 100° C. to about 120° C., optionally in the presence of microwave irradiation, to yield the corresponding compound of formula (XXXXVI).

The compound of formula (XXXXVI) is reacted with a suitably selected oxidizing agent such as OXONE®, and the like, (Yang, D.; Yip, Y.-C.; Jiao, G.-S.; Wong, M.-K. *Org. Synth.* 2000, 78, 225) in the presence of a catalyst such as tetrahydrothiopyran-4-one, and the like, in the presence of a base such as $Na_2CO_3$, $K_2CO_3$, $NaHCO_3$, and the like, in a mixture of an organic solvent such as MeCN, THF, and the like, and a protic solvent such as water, to yield the corresponding compound of formula (XXXXVII).

Alternatively, the compound of formula (XXXXVI) is reacted with an oxidizing agent, such as MCPBA, (Jung, M. E.; Lam, P. Y.-S.; Mansuri, M. M.; Speltz, L. M. *J. Org. Chem.* 1985, 50, 1087), hydrogen peroxide, and the like, in an in the presence of a base such as $Na_2CO_3$, $K_2CO_3$, $NaHCO_3$, and the like, in an organic solvent such as DCM, DCE, and the like, at a temperature in the range of from about room temperature to about 100° C., preferably, at about room temperature, to yield the corresponding compound of formula (XXXXVII).

The compound of formula (XXXXVII) is reacted with a protic acid such as p-toluenesulfonic acid, methanesulfonic acid, and the like, (Bakke, J. M.; Lorentzen, G. B. *Acta Chem. Scand. B* 1974, 28, 650) in an organic solvent such as benzene, toluene, and the like, at an elevated temperature in the range of from about 80° C. to about 150° C., preferably, at an elevated temperature in the range of from about 80° C. to about 100° C., to yield the corresponding compound of formula (XXXXVIII)

Alternatively, the compound of formula (XXXXVII) is reacted with a Lewis acid such as $BF_3.Et_2O$, and the like, (Baumgarth, M.; Beier, N.; Gericke, R. *J. Med. Chem.* 1998, 41, 3736) in an organic solvent such as DCM, diethyl ether, and the like, at an elevated temperature in the range of from about 40° C. to about 100° C., preferably, at an elevated temperature in the range of from about 40° C. to about 60° C., to yield the corresponding compound of formula (XXXXVIII).

The compound of formula (XXXXVIII) is reacted with a suitably selected reducing agent, such as sodium borohydride, and the like, in an organic solvent such as MeOH, isopropanol, and the like, at a temperature in the range of from about 0° C. to about 100° C., preferably, at about 10° C. to about 40° C., to yield the corresponding compound of formula (Xd). One skilled in the art will recognize that in reacting the compound of formula (XXXXVIII) with a suitably selected reducing agent, the aldehyde on the compound of formula (XXXXVIII) is preferably protected to avoid reduction to the corresponding alcohol.

Compounds of formula (X) wherein $(L^1)_b$ is absent (i.e. b is 0) may be prepared according to the process outlined in Scheme 12.

Scheme 12

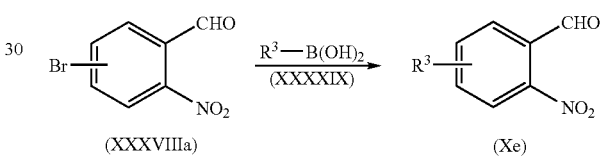

Accordingly, a suitably substituted compound of formula (XXXVIIIa), a compound of formula (XXXVIII) wherein J is Br, a known compound or compound prepared by known methods (For example, 4-bromo-2-nitro-benzaldehyde which may be prepared as disclosed in Jung, M. E. and Dansereau, S. M. K., *Heterocycles*, Vol. 39, 1994, p. 767; or 5-bromo-2-nitro-benzaldehyde, which may be prepared as disclosed in Hu, Y.-Z., Zhang, G., and Thummel, R. P., *Org. Lett.*, Vol. 5, 2003, p. 2251) is reacted with a suitably substituted compound of formula (XXXXIX), wherein $R^3$ is aryl or heteroaryl, a known compound or compound prepared by known methods, in the presence of a catalyst such $Pd(PPh_3)_4$, $Pd(dppf)Cl_2$, and the like, in the presence of a base such as $Na_2CO_3$, $K_2CO_3$, $NaHCO_3$, and the like, in a mixture of an organic solvent such as toluene, DME, THF, MeOH, and the like, and a protic solvent such as water, and the like, at an elevated temperature in the range of from about 60° C. to about 150° C., preferably, at an elevated temperature in the range of from about 100° C. to about 120° C., optionally in the presence of microwave irradiation, to yield the corresponding compound of formula (Xe).

Compounds of formula (XI) are known compounds or compounds which may be prepared by known methods. Schemes 13-17 below, outline representative processes for the preparation of representative compounds of formula (XI).

For example, compounds of formula (XI) wherein $Q^1$ is —C(O)—$NR^4$— may be prepared according to the processes outlined in Scheme 13.

Scheme 13

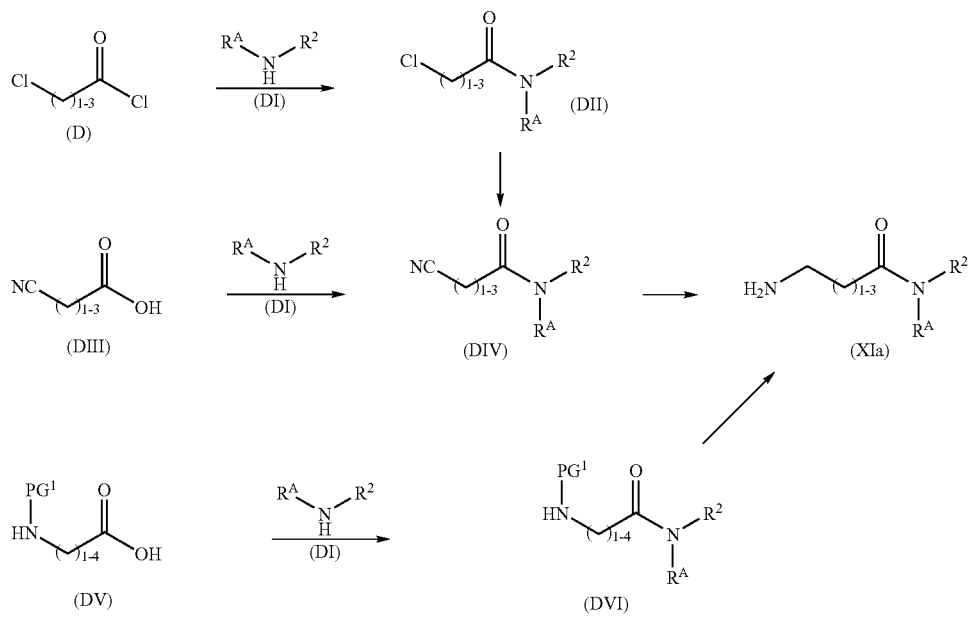

Accordingly, a suitably substituted compound of formula (D), a known compound or compound prepared by known methods, is reacted with a suitably substituted compound of formula (DI), a known compound or compound prepared by known methods, in the presence of a base such as TEA, DIPEA, pyridine, and the like, in an organic solvent such as THF, DCM, chloroform, and the like, to yield the corresponding compound of formula (DII).

The compound of formula (DII) is reacted with NaCN, in an organic solvent such as DMSO, DMF, NMP, and the like, at an elevated temperature in the range of from about 50 to about 160° C., preferably, at an elevated temperature in the range of from about 80 to about 125° C., to yield the corresponding compound of formula (DIV).

The compound of formula (DIV) is reduced according to known methods, for example by reacting with hydrogen gas in the presence of Raney nickel or rhodium, in an organic solvent such as methanol, ethanol, water, and the like, to yield the corresponding compound of formula (XIa).

Alternatively, a suitably substituted compound of formula (DIII), a known compound or compound prepared by known methods, is reacted with a suitably substituted compound of formula (DI), a known compound or compound prepared by known methods, in the presence of a peptide coupling reagent such as HATU, HOBT, DIPCDI, HBTU, and the like, in the presence of a base such as TEA, DIPEA, pyridine, and the like, in an organic solvent such as THF, DMF, and the like, to yield the corresponding compound of formula (DV).

The compound of formula (DIV) is reduced according to known methods, for example by reacting with $H_2$ gas, in the presence of Raney nickel or rhodium, in an organic solvent such as methanol, ethanol, water, and the like, to yield the corresponding compound of formula (XIa).

Alternatively still, a suitably substituted compound of formula (DV), wherein $Pg^1$ is a suitable nitrogen protecting group, such as Cbz, BOC, and the like, a known compound or compound prepared by known methods, is reacted with a suitably substituted compound of formula (DI), a known compound or compound prepared by known methods, in the presence of a peptide coupling reagent such as HATU, HOBT, DIPCDI, HBTU, and the like, in the presence of a base such as TEA, DIPEA, pyridine, and the like, in an organic solvent such as THF, DMF, and the like, to yield the corresponding compound of formula (DVI).

The compound of formula (DVI) is de-protected according to known methods, for example by hydrogenolysis (wherein $PG^1$ is Cbz) or acid cleavage (wherein $PG^1$ is BOC), to yield the corresponding compound of formula (XIa).

One skilled in the art will recognize that for compounds of formula (XI) wherein $Q^1$ is —C(O)—$NR^4$— and wherein the $A^1$ group (i.e. the —($C_{1-4}$alkyl)- group) is substituted as herein defined, may be similarly prepared according to the processes outlined in Scheme 12.

For example, compounds of formula (XI) wherein the —($C_{1-4}$alkyl)- (the $A^1$ group) is substituted at carbon atom bound directly to the core of the desired compound of formula (I) may be prepared by substituting a suitably substituted compound of formula (DVII)

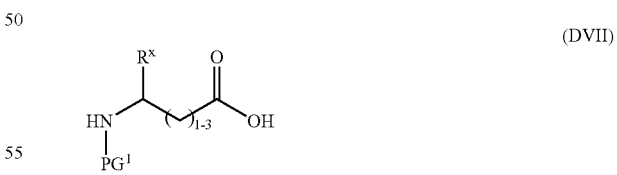

(DVII)

wherein $R^X$ is the substituent on the $A^1$ group as defined herein, for the compound of formula (DV) above.

Similarly, compounds of formula (XI) wherein alternate carbon atoms of the $A^1$ group are substituted may be similarly prepared by selecting and substituting suitably substituted starting reagents for the compound of formula (D), (DIII) or (DV).

Alternatively, compound of formula (XI) wherein $Q^1$ is —C(O)—$NR^4$— and the $A^1$ group (i.e. the —($C_{1-4}$alkyl)- group) is substituted at carbon atom bound directly to the nitrogen atom on the core of the desired compound of formula (I) may be prepared according to the process outlined in Scheme 14.

Scheme 14

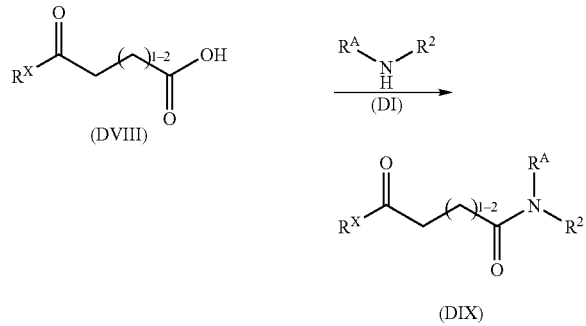

Accordingly, a suitably substituted compound of formula (DVIII), a known compound or compound prepared by known methods (for example by reacting dihydro-furan-2,5-dione or dihydro-pyran-2,6-dione with a compound of the formula $R^X$—MgCl or $R^X$—MgBr, optionally in the presence of a catalyst such as CuI, in an organic solvent such as THF) is reacted with a suitably substituted compound of formula (DI), a known compound or compound prepared by known methods, in the presence of a peptide coupling reagent such as HATU, HOBT, DIPCDI, HBTU, and the like, in the presence of a base such as TEA, DIPEA, pyridine, and the like, in an organic solvent such as THF, DMF, and the like, to yield the corresponding compound of formula (DIX).

The compound of formula (DIX) is then substituted for the compound of formula (XI) and further reacted according to the processes described above, to yield the corresponding compound of formula (I).

Compounds of formula (XI) wherein $Q^1$ is —$NR^4$— may be prepared by known methods, for example, according to the process outlined in Scheme 15.

Scheme 15

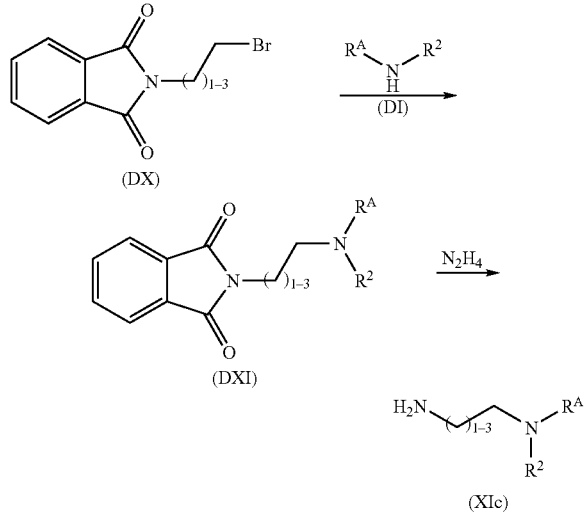

Accordingly, a suitably substituted compound of formula (DX), a known compound or compound prepared by known methods, is reacted with a suitably substituted compound of formula (DI), a known compound or compound prepared by known methods, in the presence of a base such as TEA, DIPEA, pyridine, and the like, in an organic solvent such as THF, DMF, and the like, to yield the corresponding compound of formula (DXI).

The compound of formula (DXI) is reacted with $N_2H_4$, and the like, in an organic solvent such a ethanol, DMF, and the like, to yield the corresponding compound of formula (XIc).

One skilled in the art will recognize that compounds of formula (XI) wherein $Q^1$ is —$NR^4$—C(O)— may be prepared from the corresponding compound of formula (DXI) wherein -$A^1$-$Q^1$-H is —($C_{1-4}$alkyl)-$NR^4$—H, by reacting with a suitably substituted acid chloride of the formula $R^2$—C(O)Cl, in the presence of a base such as TEA, DIPEA, pyridine, and the like, preferably, the base is present in amount equal to about one equivalent, in an organic solvent such as dioxane, DCM, THF, and the like.

One skilled in the art will further recognize that compounds of formula (XI) wherein -$Q^1$-$R^2$ is selected from —$NR^4$—$R^2$, —$NR^4$—C(O)—$R^2$ or —$NR^4$—C(O)—$R^2$ and wherein the $A^1$ group (i.e. the ($C_{1-4}$alkyl) group)) is optionally substituted, may be similarly prepared according to the processes outlined in Scheme 15 above, by selecting and substituting suitably substituted starting reagents.

Alternatively, compounds of formula (XI) wherein $Q^1$-$R^2$ is —$NR^4$—$R^2$ and wherein the $A^1$ group (i.e. the ($C_{1-4}$alkyl) group)) is optionally substituted, may be similarly prepared according to the processes outlined in Scheme 16.

Scheme 16

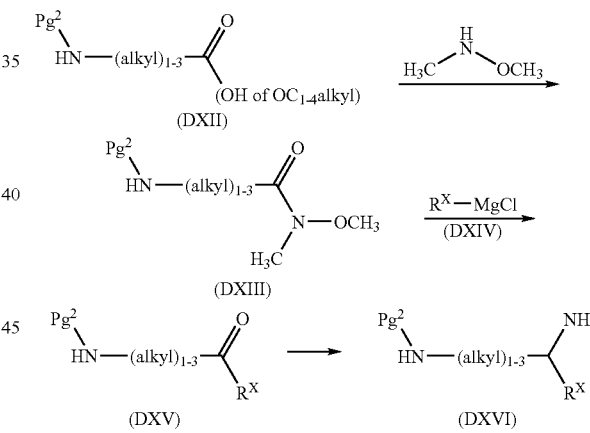

Accordingly, a suitably substituted compound of formula (DXII), a known compound or compound prepared by known methods, is reacted with NH(CH₃)(OCH₃), in the presence of a coupling agent such as (CH₃)₃Al (for compounds of formula (DXII) wherein W is $C_{1-4}$alkyl), or a coupling agent such as DCC, EDC, and the like, in an organic solvent such as DCM, DMF, and the like, to yield the corresponding compound of formula (DXIII).

The compound of formula (DXIII) is reacted with a suitably substituted compound of formula (DXIV), a known compound or compound prepared by known methods, in an organic solvent such as THF, diethyl ether, and the like, to yield the corresponding compound of formula (DXV).

The compound of formula (DXV) is reacted NH₄OAc, NH₄Cl, and the like, in the presence of a reducing agent such as NaBH₃CN, and the like, in a organic solvent such as methanol, ethanol, and the like; or reacted with NH₄O₂CCF₃, NH$_4$OAc, and the like, in the presence of a reducing agent such as NaBH(OAc)$_3$, and the like, in an organic solvent such as DCE, THF, acetonitrile, and the like; to yield the corresponding compound of formula (DXVI).

The compound of formula (DXVI) is then reacted according to the processes disclosed herein (for Example as in Scheme 1) and de-protected to yield the corresponding, desired compound.

One skilled in the art will recognize that the compound of formula (XId) may be further, optionally reacted according to known methods (for example by reacting with a suitably substituted compound of the formula) to further substitute the de-protected amine as desired.

One skilled in the art will recognize that compounds of formula (XI) wherein -Q$^1$-R$^2$ is —NH—C(O)—R$^2$ and wherein the A$^1$ group (i.e. the (C$_{1-4}$alkyl) group)) is optionally substituted may be prepared from the corresponding compound of formula (DXV) according to the process outlined in Scheme 17.

Scheme 17

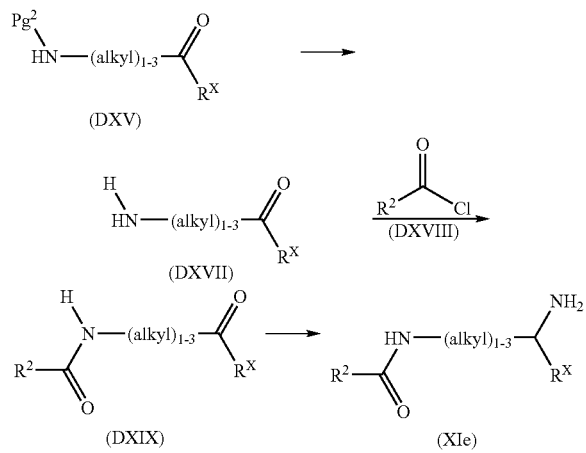

Accordingly, a suitably substituted compound of formula (DXV) is is de-protected according to known methods, to yield the corresponding compound of formula (DXVII).

The compound of formula (DXVII) is reacted with a suitably substituted acid chloride, a compound of the formula (DXVIII), a known compound or compound prepared by known methods, in the presence of a base such as TEA, DIPEA, pyridine, and the like, in an organic solvent such as dioxane, DCM, THF, and the like, to yield the corresponding compound of formula (DXIX).

The compound of formula (DXIX) is reacted with NH$_4$OAc, NH$_4$Cl, and the like, in the presence of a reducing agent such as NaBH$_3$CN, and the like, in a organic solvent such as methanol, ethanol, and the like; or reacted with NH$_4$O$_2$CCF$_3$, NH$_4$OAc, and the like, in the presence of a reducing agent such as NaBH(OAc)$_3$, and the like, in an organic solvent such as DCE, THF, acetonitrile, and the like; to yield the corresponding compound of formula One skilled in the art will further recognize that compounds of formula (XI) wherein -A$^1$-Q$^1$-R$^2$ is —(C$_{1-4}$alkyl)-NH—C(O)—OR$^2$, compounds of formula (XI) wherein -A$^1$-Q$^1$-R$^2$ is —(C$_{1-4}$alkyl)-NH—C(S)—NH—R$^2$ and compounds of formula (XI) wherein -A$^1$-Q$^1$-R$^2$ is —(C$_{1-4}$alkyl)-NH—C(O)—NH—R$^2$ may be similarly prepared according to known methods, by modifying the process described in Scheme 2.

One skilled in the art will further recognize that compounds of formula (XI) wherein Q$^1$ is other than one of the substituent groups specifically exemplified above, for example wherein Q$^1$ is selected from —O—, —S—, —OC(O)—, —NR$^A$—SO—, —NR$^A$—SO$_2$—, —SO—NR$^A$—, —SO$_2$—NR$^A$—, —OC(O)—NR$^A$—, NR$^A$—SO$_2$—O—, —O—SO$_2$—NR$^A$ or —NR$^A$—SO$_2$—NR$^B$—, may be similarly prepared according to known methods.

Compounds of formula (XI) wherein the A$^1$ group (i.e. the —(C$_{1-4}$alkyl)-group) is substituted at the carbon atom closest to the core structure is substituted and wherein a single enantiomer is desired (or wherein an enantiomeric excess of a single enantiomers is desired) may alternatively be prepared by chiral separation of the corresponding racemic mixture.

Compounds of formula (XI) wherein the A$^1$ group (i.e. the —(C$_{1-4}$alkyl)-group) is substituted at the carbon atom closest to the core structure is substituted and wherein a single enantiomer is desired (or wherein an enantiomeric excess of a single enantiomers is desired) may alternatively be prepared according to any of the process as disclosed in Burk, M. J.; Gross, M. F.; Martinez, J. P. *J. Am. Chem. Soc.* 1995, 117, 9375; Smrcina, M.; Majer, P.; Majerová, E.; Guerassina, T. A.; Eissenstat, M. A. *Tetrahedron* 1997, 53, 12867; and/or Hintermann, T.; Gademann, K.; Jaun, B. Seebach, D. *Helv. Chim. Acta* 1998, 81, 983

One skilled in the art will further recognize that the processes described in Schemes 8-17 may be modified, for example, by selecting and substituting suitable starting materials and/or reagents, to yield corresponding compounds for the preparation of compounds of formula (II) and/or compounds of formula (III).

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

3-Amino-N-cyclohexyl-N-methyl-propionamide

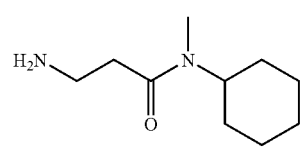

A mixture of 2-cyano-N-cyclohexyl-N-methyl-acetamide (3.96 g, 0.022 mol), a known compound, (which may be prepared as disclosed in Osdene, Thomas S. et al. Journal of Medicinal Chemistry (1967), 10(2), 165-7; Osdene, Thomas S.; Santilli, Arthur A. U.S. Pat. No. 3,138,595) and Raney nickel (3 g) in NH$_3$/MeOH (300 mL) was hydrogenated at normal pressure. After 2 equivalents of hydrogen were consumed, the catalyst was removed by filtration. The filtrate was evaporated, and toluene was added to the residue and then evaporated to yield a residue.

Example 2

3-(5-Benzoyl-2-nitro-benzylamino)-N-cyclohexyl-N-methyl-propionamide

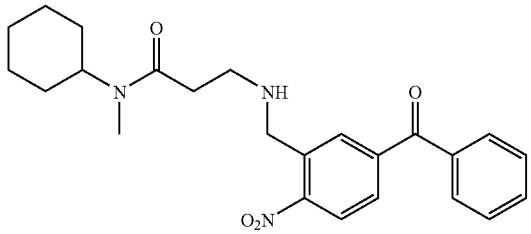 [SMILES: CN(C(=O)CCNCc1cc(C(=O)c2ccccc2)ccc1[N+](=O)[O-])C1CCCCC1]

A mixture of 5-benzoyl-2-nitro-benzaldehyde (10 g, 0.0390 mol), a known compound (which may be prepared as disclosed in European Patent EP 371564) and 3-amino-N-cyclohexyl-N-methyl-propionamide (7.5 g, 0.0410 mol) in 1,2-dichloroethane (250 mL) was stirred at room temperature under nitrogen. Sodium triacetoxyborohydride (8.7 g, 0.0410 mol) was added, and the reaction mixture was stirred for 6 h at room temperature. Saturated NaHCO₃ solution (200 mL) was then added. The organic layer was separated, dried, and evaporated. The resulting residue was purified by column chromatography on silica gel (eluent: 99:1 CH₂Cl₂:MeOH). The purest fractions were combined, and the solvent was evaporated to yield a residue.

Example 3

3-(2-Amino-5-benzoyl-benzylamino)-N-cyclohexyl-N-methyl-propionamide

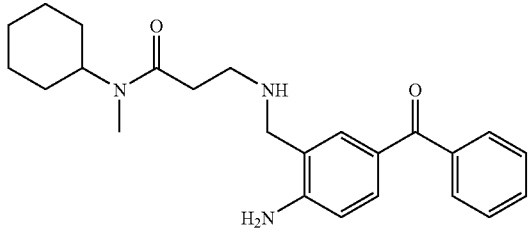

A mixture of 3-(5-benzoyl-2-nitro-benzylamino)-N-cyclohexyl-N-methyl-propionamide (9 g, 0.02 mol), 10% palladium on carbon (2 g), and thiophene solution (2 mL) in MeOH (250 mL) was hydrogenated until 3 equivalents of hydrogen were consumed. The reaction mixture was filtered through Dicalite, and the filtrate was concentrated to yield a residue.

Example 4

3-(2-Amino-6-benzoyl-4H-quinazolin-3-yl)-N-cyclohexyl-N-methyl-propionamide (Compound #1)

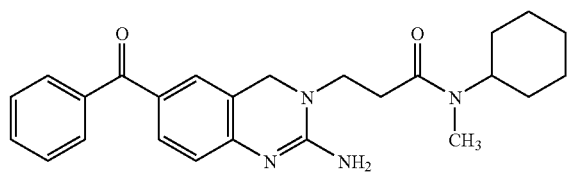 [SMILES: CN(C(=O)CCN1Cc2cc(C(=O)c3ccccc3)ccc2N=C1N)C1CCCCC1]

To a solution of 3-(2-amino-5-benzoyl-benzylamino)-N-cyclohexyl-N-methyl-propionamide (3.94 g, 0.0100 mol) in methanol (200 mL) was added cyanogen bromide (1.16 g, 0.0110 mol). The resulting mixture was stirred at room temperature over the weekend and then was heated at reflux for 5 h. The solvent was evaporated to yield a residue that was crystallized from EtOAc (100 mL). The resulting precipitate was filtered and dried to yield crude product that was recrystallized from 2-propanol (50 mL) to yield the title compound, 3-(2-amino-6-benzoyl-4H-quinazolin-3-yl)-N-cyclohexyl-N-methyl-propionamide.

mp 198.1° C.

Example 5

2-(Dimethoxymethyl)-1-nitro-4-phenoxy-benzene

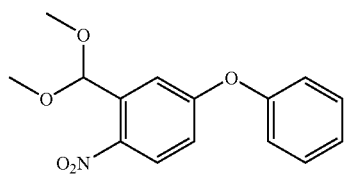 [SMILES: COC(OC)c1cc(Oc2ccccc2)ccc1[N+](=O)[O-]]

A mixture of 4-chloro-2-dimethoxymethyl-1-nitrobenzene (11.55 g, 0.0500 mol), phenol (4.70 g, 0.0500 mol), and potassium carbonate (8.16 g, 0.0600 mol) in DMA (100 mL) was stirred at 150° C. for 6 h. After cooling, the reaction mixture was poured into water and treated with diisopropyl ether. The organic layer was separated, washed with 10% aqueous KOH solution, dried (MgSO₄), filtered, and concentrated. The resulting residue was purified by column chromatography on silica gel using as eluent CH₂Cl₂:petroleum ether (40:60, 60:40, 100:0 gradient). The product containing fractions were combined and evaporated to yield a residue which was dissolved in CH₂Cl₂ and washed with 10% aqueous KOH solution to remove the remaining phenol. Drying and evaporation yielded a residue.

Example 6

2-Nitro-5-phenoxy-benzaldehyde

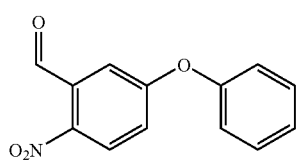 [SMILES: O=Cc1cc(Oc2ccccc2)ccc1[N+](=O)[O-]]

To a solution of 2-(dimethoxymethyl)-1-nitro-4-phenoxy-benzene (7.4 g, 0.0256 mol) in THF (80 mL) was added 12 N HCl (10 mL) and water (20 mL). The resulting mixture was stirred at room temperature for 2 days. Water was then added, and the mixture was extracted with diisopropyl ether. The organic layer was separated, washed with 10% aqueous

Example 7

N-Methyl-3-(2-nitro-5-phenoxy-benzylamino)-N-phenyl-propionamide

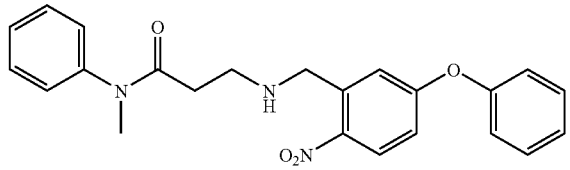 [SMILES: CN(C(=O)CCNCc1cc(Oc2ccccc2)ccc1[N+](=O)[O-])c1ccccc1]

2-Nitro-5-phenoxy-benzaldehyde (2.14 g, 0.00882 mol) was added to a solution of 3-amino-N-cyclohexyl-N-methyl-propionamide (1.5 g, 0.00882 mol) in 100 mL of 1,2-dichloroethane, and the mixture was stirred at 80° C. for 1 hour. Sodium triacetoxyborohydride (2.87 g, 0.00882 mol) was added at room temperature, and the reaction mixture was stirred for 15 h. Additional sodium triacetoxyborohydride (1 g) was added, and the reaction mixture was stirred another 20 h at room temperature. To the reaction mixture was added 10% aqueous NaOH solution (50 mL), and the mixture was extracted with $CH_2Cl_2$. The organic layer was separated, dried ($MgSO_4$), filtered, and concentrated to yield a residue which was purified by column chromatography over silica gel using 97:3 $CH_2Cl_2$:MeOH as the eluent. The product containing fractions were combined and evaporated to yield a side product (MW 638). The residue was further purified by column chromatography over silica gel using 97:3 $CH_2Cl_2$:MeOH. The product containing fractions were combined and evaporated to yield a residue. The fractions containing impure product were combined and evaporated to yield a second residue, which was purified by silica gel chromatography to yield additional desired product.

Example 8

3-(2-Amino-5-phenoxy-benzylamino)-N-methyl-N-phenyl-propionamide

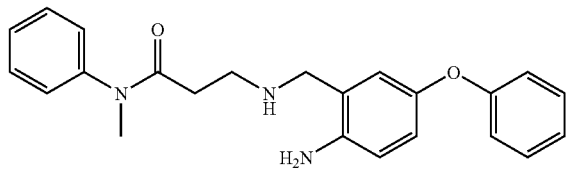

A mixture of N-methyl-3-(2-nitro-5-phenoxy-benzylamino)-N-phenyl-propionamide (2 g, 0.0049 mol), 10% palladium on carbon (1 g), and thiophene solution (1 mL) in 150 mL of MeOH was hydrogenated until 3 equivalents of hydrogen were consumed. The reaction mixture was filtered, and the filtrate was concentrated. The resulting residue was purified by column chromatography on a Biotage. The product containing fractions were collected and concentrated to yield a residue.

Example 9

3-(2-Amino-6-phenoxy-4H-quinazolin-3-yl)-N-cyclohexyl-N-methyl-propionamide (Compound # 20)

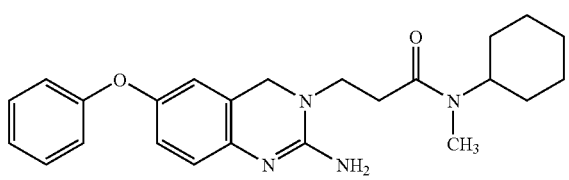 [SMILES: CN(C(=O)CCN1Cc2cc(Oc3ccccc3)ccc2N=C1N)C1CCCCC1]

A solution of 3-(2-amino-5-phenoxy-benzylamino)-N-methyl-N-phenyl-propionamide (diamine) (1.4 g, 0.0037 mol) and cyanogen bromide (0.58 g, 0.0055 mol) in 70 mL of ethanol was refluxed for 3 h. The solvent was evaporated to yield a residue, which was crystallized from EtOAc (100 mL). The resulting precipitate was dissolved in ethanol and stirred for 3 h. The resulting precipitate was collected by filtration, washed with ethanol, and dried to yield the title product, pure 3-(2-amino-6-phenoxy-4H-quinazolin-3-yl)-N-cyclohexyl-N-methyl-propionamide.

Example 10

(3-Dimethoxymethyl-4-nitro-phenyl)-morpholin-4-yl-phenyl-acetonitrile

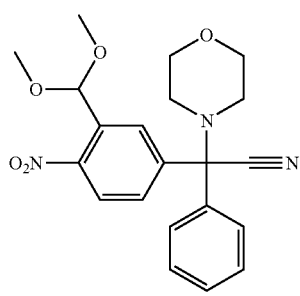 [SMILES: COC(OC)c1cc(C(C#N)(c2ccccc2)N2CCOCC2)ccc1[N+](=O)[O-]]

NaH (0.975 mol) was washed with hexane. After the hexane was decanted off, the NaH was stirred in DMF (1950 mL) at room temperature. Morpholin-4-yl-phenyl-acetonitrile (0.70 mol) in DMF (300 mL) was added dropwise under $N_2$ gas. The reaction mixture was stirred at room temperature for 2 hours. The reaction mixture was cooled in an ice bath and 4-chloro-2-dimethoxymethyl-1-nitrobenzene (0.86 mol) in DMF (150 mL) was added dropwise. The reaction mixture was stirred at 0° C. for 2 hours and at room temperature overnight. The reaction mixture was poured on ice/water and extracted with diisopropyl ether. The organic layer washed with water, dried ($MgSO_4$) and evaporated to yield the title compound as a solid.

Example 11

(3-Dimethoxymethyl-4-nitro-phenyl)-phenyl-methanone

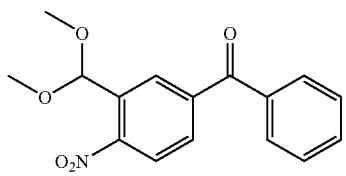 [SMILES: COC(OC)c1cc(C(=O)c2ccccc2)ccc1[N+](=O)[O-]]

A solution of the residue prepared as in Example 10 (0.7 mol) in 70% acetic acid (1500 mL) was stirred and refluxed for 30 min. The reaction mixture was poured on ice/water and extracted with diisopropyl ether. The organic layer was washed with alkalic water and water. The organic layer was dried (MgSO$_4$) and evaporated to a residue. The aqueous layers that contained product were further extracted with DCM. The organic layer was dried (MgSO$_4$) and evaporated to yield a residue. The residues from above were purified on a glass filter over silica gel (eluent: DCM). The pure fractions were collected and evaporated to yield the title compound as a solid.

Example 12

5-Benzoyl-2-nitrobenzaldehyde

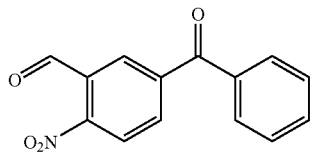 [SMILES: O=Cc1cc(C(=O)c2ccccc2)ccc1[N+](=O)[O-]]

A mixture of the solid prepared as in Example 11 (0.0659 mol) and 5N HCl (40 mL) in chloroform (80 mL) was stirred at room temperature overnight. Then, the reaction mixture was refluxed for 4 hours. After cooling, the organic layer was separated. The organic layer was made alkaline by adding dropwise NH$_4$OH. The organic layer was washed with water, dried (MgSO$_4$) and evaporated. The residue was crystallized from diisopropyl ether/ethyl acetate (50 mL/20 mL). The precipitate was filtered off, washed with diisopropyl ether/ethyl acetate and diisopropyl ether and dried in vacuo at 50° C. to yield the title compound as a beige solid.

mp 96.7° C.

Note: The title compound may alternatively be prepared according to the procedure disclosed in EP 0371564 A2.

Example 13

2-amino-5-benzoylbenzaldehyde

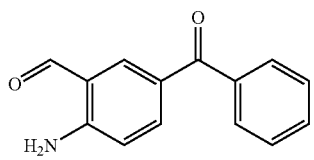 [SMILES: Nc1ccc(C(=O)c2ccccc2)cc1C=O]

A mixture of 5-benzoyl-2-nitrobenzaldehyde (0.01 mol) in toluene was hydrogenated at room temperature and normal pressure with 5% Pd/C (2 g) as a catalyst in the presence of 4% thiophene solution (2 mL). After uptake of H$_2$ gas (3 equiv.), the catalyst was filtered off and the filtrate was evaporated (water bath at 50° C.). The residue was dissolved in diethyl ether (10 mL) and crystallized out at room temperature. The crystals were filtered off, washed with a small amount of diethyl ether and diisopropyl ether, then dried (vacuum, 40° C.) to yield the title compound as a solid.

mp 124.9° C.

Example 14

Cyclohexanecarboxylic acid [2-(2-amino-5-benzoyl-benzylamino)-ethyl]-amide

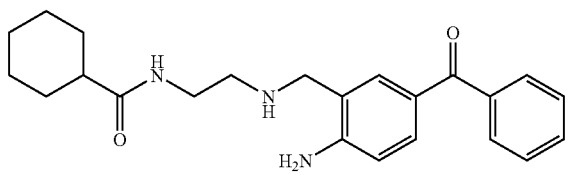 [SMILES: Nc1ccc(C(=O)c2ccccc2)cc1CNCCNC(=O)C1CCCCC1]

A mixture of 2-amino-5-benzoylbenzaldehyde (0.007 mol) and cyclohexanecarboxylic acid (2-amino-ethyl)-amide (0.007 mol) in methanol was hydrogenated at 50° C. with 10% Pd/C (0.5 g) as a catalyst in the presence of thiophene solution (1 mL). After uptake of H$_2$ gas (1 equiv.) the catalyst was filtered off and the solvent evaporated. The residue was purified by column chromatography over silica gel (Biotage column) (eluent:CH$_2$Cl$_2$:methanol gradient). The desired fractions were collected and the solvent evaporated to yield the title compound as a residue.

Example 15

Cyclohexanecarboxylic acid [2-(2-amino-6-benzoyl-4H-quinazolin-3-yl)-ethyl]-amide (Compound #7)

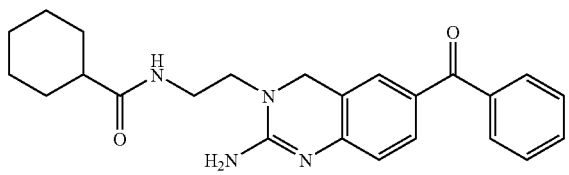 [SMILES: NC1=Nc2ccc(C(=O)c3ccccc3)cc2CN1CCNC(=O)C1CCCCC1]

A mixture of cyclohexanecarboxylic acid [2-(2-amino-5-benzoyl-benzylamino)-ethyl]-amide (0.0032 mol) in ethanol (30 mL) was stirred at room temperature. Cyanogen bromine (0.0048 mol) was added. The reaction mixture was stirred and refluxed for 2 hours, then cooled and stirred overnight at room temperature resulting in a precipitate. The precipitate was filtered off, washed with diisopropyl ether and dried to yield the title compound as a residue.

Example 16

2-Nitro-5-phenoxy-benzaldehyde

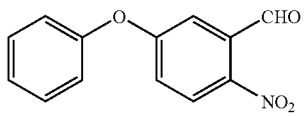 [SMILES: O=Cc1cc(Oc2ccccc2)ccc1[N+](=O)[O-]]

Step A:

To a solution of 5-fluoro-2-nitro-toluene (38.2 g, 0.25 mol) in 200 mL of DMF was added phenol (23.5 g, 0.25 mol) and $K_2CO_3$ (43.0 g, 0.31 mol) and the mixture was heated at 140° C. overnight. The mixture was cooled to room temperature, then most of the DMF was evaporated in vacuo. The residue was dissolved in EtOAc, washed with water (2×) and brine and then dried ($K_2CO_3$). The solution was filtered, and the solvent was evaporated in vacuo to yield a dark brown oil. The crude product was purified by Kugelrohr distillation, and after a small forerun (80-90° C.), 4-phenoxy-2-nitrotoluene was collected as a viscous yellow oil (mp 120-130° C.) that crystallized on standing.

Step B:

A mixture of 2-nitro-5-phenoxytoluene (57.3 g, 0.25 mol) prepared in Step A above and dimethylformamide dimethyl acetal (43.1 mL, 0.324 mol) in DMF (259 mL) was heated overnight at 140° C. The mixture was cooled to room temperature, and the solvent was evaporated in vacuo. The residue was dissolved in THF (500 mL) and transferred to a 3 L 3-neck flask equipped with an overhead stirrer. The mixture was diluted with 500 mL of water, and $NaIO_4$ (160 g, 0.75 mol) was added in portions (slight exotherm). The mixture was stirred overnight at room temperature. The solids were filtered and washed well with EtOAc. The filtrate was washed 3× with saturated aqueous $NaHCO_3$ solution, and then dried ($MgSO_4$). The solution was filtered and the solvent was evaporated in vacuo. The crude product was chromatographed (10-40% $CH_2Cl_2$:hexane) to yield 2-nitro-5-phenoxy-benzaldehyde as a yellow crystalline solid.

Example 17

2-Nitro-5-phenoxy-benzaldehyde

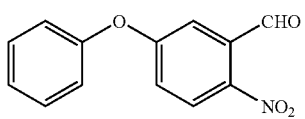 [SMILES: O=Cc1cc(Oc2ccccc2)ccc1[N+](=O)[O-]]

A mixture of 5-fluoro-2-nitrobenzaldehyde (15.00 g, 0.089 mol), phenol (9.12 g, 0.098 mol), and $K_2CO_3$ (13.5 g, 0.089 mol) in 200 mL of DMF was heated at 120° C. for 50 min. The reaction mixture was cooled and concentrated in vacuo. To the residue was added EtOAc (500 mL) and $H_2O$ (500 mL). The layers were separated, and the EtOAc extract was concentrated. The residue was purified on silica gel using 20% EtOAc-hexane as eluent. The product containing fractions were combined and concentrated to yield a yellow oil which solidified on standing. This material was dissolved in a minimal quantity of EtOAc and hexane, and the resulting solution was cooled in a dry ice acetone bath. Filtration yielded 2-nitro-5-phenoxy-benzaldehyde as a light yellow solid. The filtrate was concentrated in vacuo to yield additional 2-nitro-5-phenoxy-benzaldehyde.

Example 18

Cyclohexanecarboxylic acid [2-(2-amino-6-phenoxy-4H-quinazolin-3-yl)-ethyl]-amide (Compound #111)

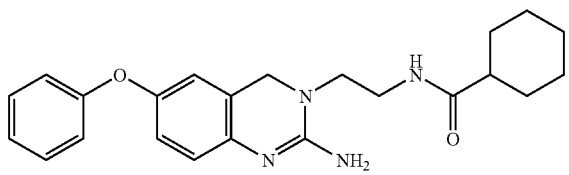 [SMILES: NC1=Nc2ccc(Oc3ccccc3)cc2CN1CCNC(=O)C1CCCCC1]

Step A

A solution of 2-nitro-5-phenoxybenzaldehyde (1.4 g, 5.8 mmol) and N-tert-butoxycarbonylethylenediamine (1.4 g, 8.75 mmol) in 60 mL of DCE was stirred at room temperature for 40 minutes. Then, $NaBH(OAc)_3$ (1.86 g, 8.75 mmol) was added, and the mixture was stirred at room temperature overnight. The reaction was quenched by the addition of 3N NaOH. The organic layer was washed with brine and then was concentrated in vacuo to yield a crude product. The crude product was purified by flash chromatography (40% EtOAc/hexane) to yield a residue.

$MH^+=388$

Step B

A solution of the compound prepared in Step A above (2.0 g, 5.2 mmol) in 100 mL of EtOH was hydrogenated (40 psi) overnight with 10% Pd/C. The catalyst was removed by filtration, and the filtrate was concentrated in vacuo to yield a residue.

Step C

To a solution of the residue prepared in Step B above (0.44 g, 1.18 mmol) EtOH (15 mL) was added BrCN (0.13 g, 1.3 mmol). The reaction mixture was stirred at room temperature for 1 h and then heated at reflux for 3 h. The solvent was evaporated in vacuo, and the residue was purified by reverse phase HPLC to yield a white solid.

$MH^+=383$

Step D

A solution of the white solid prepared in Step C above (0.13 g, 0.28 mmol) 10 mL of TFA was stirred at room temperature overnight. The solvent was evaporated in vacuo to yield a residue.

Step E

To a solution of the residue prepared in Step D above (0.088 g, 0.17 mmol) in 5 mL of dioxane was added TEA (0.14 g, 0.41 mmol) followed by cyclohexylcarbonyl chloride (0.02 g 0.14 mmol). The reaction mixture was stirred overnight at room temperature. The solvent was evaporated in vacuo and the product was purified by reverse phase HPLC to yield the title compound, cyclohexanecarboxylic acid [2-(2-amino-6-phenoxy-4H-quinazolin-3-yl)-ethyl]-amide as a white solid.

$MH^+=393$

¹H NMR (300 MHz, CDCl₃): δ1.15-1.64 (m, 10H), 2.04 (m, 1H), 3.50 (m, 4H), 4.57 (s, 2H), 6.88-7.41 (m, 8H), 7.87-7.90 (m, 3H).

Example 19

Cyclohexanecarboxylic acid [2-(2-amino-6-phenoxy-4H-quinazolin-3-yl)-2-cyclohexyl-ethyl]-amide (Compound #294)

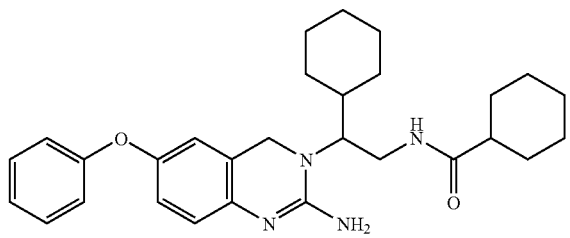 [SMILES: NC1=Nc2ccc(Oc3ccccc3)cc2CN1C(CNC(=O)C1CCCCC1)C1CCCCC1]

Step A

To a suspension of N,O-dimethylhydroxylamine HCl (0.443 g, 4.5 mmol) in 100 mL of CH₂Cl₂ cooled to −10° C., was added a 1.2M solution of Al(CH₃)₃ in hexane (2.19 mL, 4.39 mmol). The resulting reaction mixture was warmed to room temperature and stirred for 30 min, and then re-cooled to 0° C. A solution of N-(tert-butoxycarbonyl) glycine methyl ester (0.23 g 1.46 mmol) in 2 mL of CH₂Cl₂ was then added. The reaction mixture was allowed to warm to room temperature and stirred overnight. The reaction was quenched by addition of 1M KHSO₄ (5 mL), and the aqueous layer was extracted with two additional portions of CH₂Cl₂. The combined extracts were washed with brine and dried over Na₂SO₄. The solution was filtered, and the solvent was evaporated in vacuo to yield a white solid.

Step B

To a solution of the white solid prepared as in Step A (2.8 g, 12.8 mmol) in 50 mL of THF cooled in an ice bath, was added 2.0M cyclohexyl magnesium chloride solution in diethyl ether (38.4 mL, 76.8 mmol) and the reaction mixture was warmed to room temperature and stirred for 1 h. The reaction mixture was quenched with saturated NH₄Cl and extracted with EtOAc (3×). The combined organic layers were washed with brine and dried over MgSO₄. The solution was filtered and the solvent was evaporated in vacuo to yield crude product which was used in the following step without further purification.

Step C

To a solution of the crude product prepared in Step B above (3.5 g) in 40 mL of MeOH was added NH₄OAc (24.0 g, 0.33 mol), and the mixture was stirred at room temperature for 5 h. Next, NaCNBH₃ (1.2 g, 19.0 mmol) was added and the reaction was stirred overnight at room temperature. The solvent was evaporated in vacuo, and the residue was dissolved in water and extracted with Et₂O (3×). The combined extracts were washed with brine and the solvent was evaporated in vacuo to yield an oil.

Step D

To a solution of 2-nitro-5-phenoxybenzaldehyde (1.56 g, 6.4 mmol) and the crude product prepared in Step C above in 100 mL of CH₂Cl₂ was added NaBH(OAc)₃ (2.0 g, 9.6 mmol). The reaction mixture was stirred overnight at room temperature. The reaction was quenched with 2N NaOH, and the layers were separated. The aqueous layer was extracted with CH₂Cl₂ (2×). The combined extracts were washed with brine and dried over MgSO₄. The solution was filtered and the solvent was evaporated in vacuo to yield an oil. Flash chromatography (1 to 10% EtOAc in CH₂Cl₂) of the oil yielded a residue.

MH⁺=470

Step E

A solution of the product prepared in Step D above (1.03 g, 2.19 mmol) and Pd/C (200 mg) in 100 mL of EtOH was hydrogenated at 40 psi for 3 h. The solution was filtered through Dicalite, and the filtrate was concentrated to a 30 mL solution.

Step F

To the solution prepared in Step E was added BrCN (0.26 g, 2.5 mmol), and the reaction mixture was stirred overnight at room temperature. The next day, the reaction mixture was heated at reflux for 90 min, and then the solvent was evaporated in vacuo. The crude product was purified by reverse phase HPLC to yield an off-white solid.

MH⁺=465

Step G

A solution of the off-white solid prepared in Step F above (0.86 g, 1.49 mmol) in 15 mL of TFA was stirred at room temperature for 5 h. The excess TFA was evaporated to yield an oil.

Step H

To a solution of the oil prepared in Step G above (0.06 g, 0.12 mmol) in 7 mL of dioxane was added TEA (37.6 mg, 0.37 mmol) followed by addition of cyclohexylcarbonyl chloride (0.018 g, 0.12 mmol). The reaction mixture was stirred overnight at room temperature. The solvent was evaporated in vacuo yield the title compound, cyclohexanecarboxylic acid [2-(2-amino-6-phenoxy-4H-quinazolin-3-yl)-2-cyclohexyl-ethyl]-amide as a white solid.

MH⁺=475

¹H NMR (300 MHz, DMSO-d₆): δ1.13-2.51 (m, 22H), 3.43 (m, 2H), 3.86 (m, 1H), 4.40 (d, J=15.2 Hz, 1H), 4.41 (d, J=15.5 Hz, 1H), 6.93-7.41 (m, 8H), 7.77 (m, 3H).

Example 20

Cyclohexanecarboxylic acid [2-(2-amino-6-phenoxy-4H-quinazolin-3-yl)-2-(R)-cyclohexyl-ethyl]-amide (Compound #485)

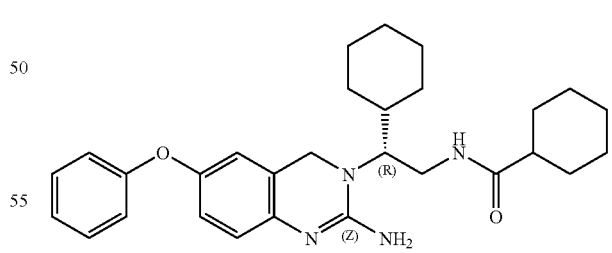

Step A

To a solution of tert-butoxycarbonylamino-(R)-cyclohexyl-acetic acid (2.57 g, 10.0 mmol), (Boc)₂O (2.83 g, 13.0 mmol), and NH₄CO₃ (1.0 g, 12.6 mmol) in 50 mL of acetonitrile was added 0.05 mL of pyridine, and the reaction mixture was stirred at room temperature overnight. Water (50 mL) was added, and the reaction mixture was concentrated to ½ the original volume. The suspension was filtered, and a white solid was collected and washed with water.

Step B

The white solid prepared in Step A above, (0.65 g) was suspended in CH$_2$Cl$_2$ (20 mL), and 10 mL of TFA was added. The reaction mixture was stirred at room temperature for 3 h. The solvent was evaporated in vacuo to yield a residue.

Step C

A solution of the residue prepared in Step B above (0.66 g, 2.44 mmol) and 2-nitro-5-phenoxybenzaldehyde (0.4 g, 1.63 mmol) in 40 mL of THF was stirred for 30 min. Then NaBH(OAc)$_3$ (0.521 g, 2.44 mmol) was added, and the reaction mixture was stirred overnight at room temperature. The reaction mixture was quenched with 1N NaOH and extracted with EtOAc (3×). The combined extracts were washed with brine and dried over MgSO$_4$. The solution was filtered, and the filtrate was evaporated in vacuo to yield a residue.

Step D

To a solution of the residue prepared in Step C above (0.31 g, 0.8 mmol) in 10 mL of THF was added 4.0 mL of BH$_3$.THF, and the mixture was heated at reflux overnight. The reaction was cooled in ice and quenched with 1.5 mL of HCl, and the resultant mixture heated at reflux for 90 min. The solution was basified with 3N NaOH and extracted with CH$_2$Cl$_2$ (3×). The combined extracts were washed with brine, dried over Na$_2$SO$_4$, filtered and then evaporated in vacuo to yield an oil. Flash chromatography (3-5% MeOH in CHCl$_3$) yielded a yellow oil.

MH$^+$=370

Step E

To a solution of the yellow oil prepared in Step D above (0.44 g, 1.2 mmol) and TEA (0.35 mL, 2.5 mmol) in CH$_2$Cl$_2$ (10 mL) was added cyclohexanecarbonyl chloride (0.21 g, 1.4 mmol). The resulting mixture was stirred overnight at room temperature. Next, the reaction mixture was diluted with additional CH$_2$Cl$_2$ and washed with water, and then brine, and then dried over Na$_2$SO$_4$. The solution was filtered, and the solvent was evaporated in vacuo to yield a crude product. Flash chromatography of the crude product (5-15% EtOAc in CH$_2$Cl$_2$) yielded a yellow foam.

MH$^+$=480

Step F

A solution of the yellow foam prepared in Step E above (0.78 g, 1.63 mmol) in 100 mL of EtOH and 30 mL of THF was hydrogenated (40 psi) overnight with 10% Pd/C. The catalyst was removed by filtration and BrCN (0.19 g, 1.63 mmol) was added. The reaction mixture was stirred at room temperature. The solvent was evaporated in vacuo and the residue was purified by reverse phase HPLC to yield the title compound as a brown solid.

MH$^+$=475

Example 21

4-(2-Amino-6-phenoxy-4H-quinazolin-3-yl)-4,N-dicyclohexyl-N-methyl-butyramide (Compound #85)

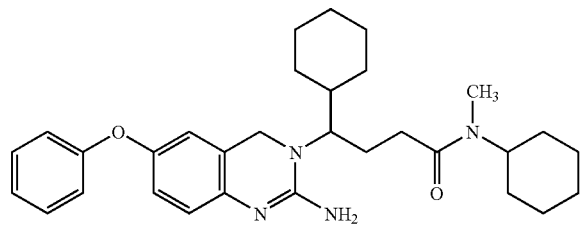 [SMILES: CN(C(=O)CCC(C1CCCCC1)N1Cc2cc(Oc3ccccc3)ccc2N=C1N)C1CCCCC1]

Step A

A solution of succinic anhydride (1 g, 0.01 mol) and CuI (0.2 g, 0.001 mol) in THF (20 mL) was cooled to −20° C. Cyclohexyl magnesium chloride (2.0M in diethyl ether, 6 mL, 0.012 mol) was added slowly to the reaction mixture. (A purple color formed, but it disappeared after the addition was finished.) The cooling bath was removed, and the reaction mixture was stirred one hour at room temperature. H$_2$O (50 mL) and HCl (1N, 30 mL) were then added to the reaction mixture. A precipitate formed which was collected by filtration. CH$_2$Cl$_2$ (200 mL) was added into the filtrate. The layers were separated; the organic layer was washed with saturated Na$_2$SO$_3$ solution and NaCl solution. The organic layer was dried with MgSO$_4$ and evaporated to yield a colorless oil.

$^1$H NMR (300 MHz, CDCl$_3$): δ1.23-1.33 (m, 6H), 1.65-1.88 (m, 4H), 2.40 (m, 1H), 2.59-2.64 (m, 4H).

Step B

To a solution of the colorless oil prepared in Step A above (1.1 g, 6 mmol) in CH$_2$Cl$_2$ (50 mL), was added isobutyl chloroformate (1 mL, 6.3 mmol) at 0° C. followed by addition of TEA (2.5 mL, 18 mmol) and N-methylcyclohexylamine (1 mL, 6.6 mmol). The reaction mixture was stirred at room temperature overnight. NaCl solution (100 mL) was then added. The layers were separated, and the aqueous layer was extracted with CH$_2$Cl$_2$. The organic layers were combined, dried with MgSO$_4$, and evaporated. Purification by flash column chromatography (1:1 hexane:EtOAc) yielded a brown oil.

MH$^+$ 280.1

$^1$H NMR (300 MHz, CDCl$_3$): δ1.23-1.78 (m, 21H), 2.5 (m, 1H), 2.58-2.8 (m, 4H), 2.85 (s, 3H), 3.66 (m, 0.4×1H), 4.39 (m, 0.6×1H).

Step C

To a solution of NH$_4$OAc (0.83 g, 11 mmol) and sodium cyanoborohydride (0.045 g, 8 mmol) in MeOH (20 mL) was slowly added a solution of the brown oil prepared in Step B above (0.2 g, 0.7 mmol) in MeOH (5 mL). The reaction mixture was then stirred at room temperature overnight. The MeOH was evaporated, and CH$_2$Cl$_2$ (100 mL) was added followed by 1N HCl (5 mL). The mixture was stirred 5 min, and then basified with 1N NaOH (6 mL). The CH$_2$Cl$_2$ layer was dried with MgSO$_4$, and then evaporated to yield an oil.

MH$^+$ 281.1

$^1$H NMR (300 MHz, CDCl$_3$): δ1.0-1.75 (m, 21H), 2.2-2.3 (m, 1H), 2.4-2.7 (m, 4H), 2.77 (s, 3H), 3.6 (m, 0.4×1H), 4.3 (m, 0.6×1H).

Step D

To a solution of the oil prepared in Step C above (0.3 g, 1.1 mmol), 2-nitro-5-phenoxybenzaldehyde (0.27 g, 1.1 mmol), and acetic acid (0.07 mL, 1.1 mmol) in CH$_2$Cl$_2$ (10 mL) was added NaCNBH$_3$ (0.07 g, 1.2 mmol). The reaction mixture was then stirred at room temperature for 8 h. 1N HCl (10 mL) was then added, and the reaction mixture was stirred for 5 min and then was basified by 1N NaOH (15 mL). The solution was extracted with CH$_2$Cl$_2$ (50 mL×2). The organic layer was dried with MgSO$_4$ and evaporated to yield an oil which was purified on a column (1:1 hexane:EtOAc) to yield a yellow oil.

MH$^+$ 508.5

$^1$H NMR (300 MHz, CDCl$_3$): δ1.0-1.8 (m, 24H), 2.2-2.3 (m, 2H), 2.78 (s, 0.4×3H), 2.80 (s, 0.6×3H), 3.57 (m, 0.4×1H), 4.0 (m, 2H), 4.5 (m, 1H), 4.37 (m, 0.6×1H), 6.86 (m, 1H), 7.07 (d, J=8.33 Hz, 2H), 7.2-7.38 (m, 2H), 7.42-7.44 (m, 2H), 7.97 (d, J=8.9 Hz, 1H).

Step E

To a solution of the yellow oil prepared in Step D above (0.34 g, 6.7 mmol) in MeOH (10 mL) was added 0.05 g of 10% Pd on activated carbon under N$_2$. The mixture was subjected to hydrogenation at 30 psi for one hour. The catalyst was filtered out, and the MeOH was evaporated to yield an oil.

MH$^+$ 478.4

$^1$H NMR (300 MHz, CDCl$_3$): δ1.1-1.77 (m, 24H), 2.05-2.19 (m, 2H), 2.78 (s, 0.4×3H), 2.79 (s, 0.6×3H), 3.5 (m, 0.4×1H), 3.75 (s, 2H), 4.44 (m, 0.6×1H), 6.7 (d, J=8.04 Hz, 1H), 6.8 (m, 2H), 6.93 (d, J=7.9 Hz, 1H), 7.02 (t, J=7.3 Hz, 1H), 7.3 (m, 3H).

Step F

A mixture of the oil prepared in Step E above (0.2 g, 0.4 mmol) and BrCN (0.044 g, 0.4 mmol) was refluxed in EtOH (10 mL) overnight. The EtOH was evaporated. Diethyl ether (1 mL) and hexane (5 mL) were added to the residue, and the mixture was stirred at room temperature for 30 min. The suspension was filtered, and the title compound was collected as a solid HBr salt.

MH$^+$ 503.7

$^1$H NMR (300 MHz, CD$_3$OD): δ1.1-1.9 (m, 22H), 2.15-2.28 (m, 2H), 2.5 (m, 1H) 2.74 (s, 0.4×3H), 2.78 (s, 0.6×3H), 3.47 (m, 0.4×1H), 3.97 (m, 1H), 4.3 (m, 0.6×1H), 4.4 (m, 2H), 6.9-7.1 (m, 5H), 7.12 (m, 1H), 7.35 (t, J=7.76 Hz, 2H).

Example 22

4-(2-Amino-6-phenoxy-4H-quinazolin-3-yl)-4-(S)-, N-dicyclohexyl-N-methyl-butyramide (Compound #346)

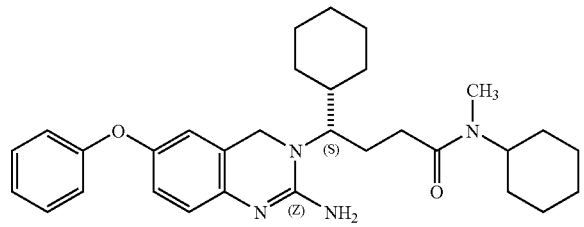

Step A

To an ice cooled solution of Boc-D-cyclohexylglycine (3.7 g, 0.014 mol), HOBT (2.5 g, 0.018 mol) and N,O-dimethylhydroxylamine HCl (1.8 g, 0.019 mol) in CH$_2$Cl$_2$ (100 mL) was added TEA (3.9 mL, 0.028 mol) followed by addition of 1,3-dimethylamino propyl-3-ethylcarbodiimide (EDC, 3.6 g, 0.018 mol). The mixture was warmed to room temperature and stirred overnight. EtOAc (300 mL) was then added to the reaction mixture. The reaction mixture was washed with citric acid solution, aqueous NaHCO$_3$ solution, and NaCl solution. The organic layer was dried with MgSO$_4$ and evaporated to yield an oil. The crude oil was used in the following step without further purification.

MH$^+$ 301.1

$^1$H NMR (300 MHz, CDCl$_3$): 0.93-1.07 (m, 4H), 1.36 (s, 9H), 1.54-1.68 (m, 6H), 3.15 (s, 3H), 3.71 (s, 3H), 4.51 (m, 1H), 5.06 (m, 1H).

Step B

To an ice cooled solution of the oil prepared in Step A above (4.6 g, 0.015 mol) in THF (200 mL) was slowly added LiAlH$_4$ (1 M in THF, 18 mL). The ice bath was removed, and the reaction mixture was stirred at room temperature for 30 min and then was cooled to 0° C. again. A solution of NaHSO$_4$ in water (5 mL) was then added slowly to the reaction mixture while maintaining the temperature below 5° C. The mixture was extracted with EtOAc (200 mL×2), and the combined organic layers were washed with dilute citric acid solution, saturated aqueous NaHCO$_3$, and saturated aqueous NaCl solution, and then dried with Na$_2$SO$_4$ and evaporated to yield a colorless oil. The crude oil was used in the following step without further purification.

MH$^+$ 242.1

$^1$H NMR (300 MHz, CDCl$_3$): δ0.93-1.07 (m, 4H), 1.38 (s, 9H), 1.54-1.68 (m, 6H), 4.16 (m, 1H), 5.02 (m, 1H), 9.7 (m, 1H).

Step C

To an ice cooled solution of triethylphosphonoacetate (6.3 mL, 0.039 mol) in THF (300 mL) was added NaH (60% dispersion in mineral oil, 1 g, 0.025 mol) in portions. The resulting mixture was stirred at room temperature for 30 minutes and then was cooled to 0° C. again. A solution of the oil prepared in Step B above (3.1 g, 0.013 mol) in THF (50 mL) was then added. The reaction mixture was stirred for 5 min at 0° C. and then for another 20 min at room temperature. The reaction mixture was quenched with water, and aqueous NaCl solution was added. The reaction mixture was extracted with EtOAc (200 mL×2), dried with MgSO$_4$, and evaporated. The crude product was purified by column chromatography (1:1 EtOAc:heptane) to yield an oil, which turned into a white solid upon standing.

$^1$H NMR (300 MHz, CDCl$_3$): δ0.93-1.07 (m, 4H), 1.3 (t, J=7.3 Hz, 3H), 1.40 (s, 9H), 1.6-1.85 (m, 6H), 4.1 (m, 1H), 4.2 (m, 2H), 4.5 (m, 1H), 5.86 (dd, J=15.6 Hz, J=1.57 Hz, 1H), 5.86 (dd, J=15.6, 5.5 Hz, 1H).

Step D

To a solution of the white solid prepared in Step C above (4.0 g, 0.013 mol) in MeOH (50 mL) was added 0.4 g of 10% Pd/C under N$_2$. The reaction mixture was hydrogenated at 10 psi for one hour. The catalyst was removed by filtration, and the MeOH was evaporated to yield a solid.

MH$^+$ 314.2

$^1$H NMR (300 MHz, CDCl$_3$): δ0.96-1.2 (m, 6H), 1.25 (t, J=7.1 Hz, 3H), 1.43 (s, 9H), 1.55-1.85 (m, 6H), 2.2 (m, 2H), 3.4 (m, 1H), 4.1 (m, 2H), 4.32 (m, 1H).

Step E

A solution of the solid prepared in Step D above (3.5 g, 0.012 mol) and LiOH (0.29 g, 0.012 mol) in THF:H$_2$O (30 mL:30 mL) was stirred at room temperature overnight. Citric acid (2.8 g, 0.014 mol) in H$_2$O (10 mL) was added. The reaction mixture was extracted with EtOAc (100 mL×2), dried with MgSO$_4$, and evaporated to yield a solid.

M$^-$ 284.1

$^1$H NMR (300 MHz, CDCl$_3$): δ0.96-1.1 (m, 6H), 1.36 (s, 9H), 1.5-1.8 (m, 6H), 2.3 (m, 2H), 3.33 (m, 1H), 4.22 (m, 1H).

Step F

To an ice cooled solution of the solid prepared in Step E above (3.4 g, 0.012 mol), HOBT (2.1 g, 0.015 mol) and N-methylcyclohexylamine (2 mL, 0.015 mol) in CH$_2$Cl$_2$ (100 mL) was added TEA (3.3 mL, 0.024 mol) followed by addition of EDC (2.9 g, 0.015 mol). The reaction mixture was warmed to room temperature and stirred overnight. EtOAc (300 mL) was added to the reaction mixture. The resulting solution was washed with aqueous citric acid solution, aqueous NaHCO$_3$ solution, and aqueous NaCl solution. The organic layer was dried with MgSO$_4$ and evaporated to yield a light brown oil. The crude oil product was used in the following step without further purification.

MH$^+$ 381.3

¹H NMR (300 MHz, CDCl₃): δ0.96-1.37 (m, 12H), 1.42 (d, J=1.7 Hz, 9H), 1.63-1.84 (m, 13H), 2.8 (s, 3H), 3.4 (m, 1H), 3.52 (m, 0.4×1H), 4.48 (m, 0.6×1H).

Step G

A solution of the oil prepared in Step F above (1 g, 2.6 mmol) in 20% TFA:CH₂Cl₂ (50 mL) was stirred at room temperature for 1 hour. The solvent and most of the TFA was evaporated under reduced pressure. EtOAc (100 mL) was added to the residue. The resulting solution was washed with aqueous NaHCO₃ solution and NaCl solution, then dried with MgSO₄, and evaporated to yield a brown oil.

MH⁺ 281.2

¹H NMR (300 MHz, CDCl₃): δ1.1-1.9 (m, 25H), 2.5 (m, 1H), 2.79 (s, 0.4×3H), 2.85 (s, 0.6×3H), 3.5 (m, 0.4×1H), 4.3 (m, 0.6×1H).

Step H

To a solution of the oil prepared in Step G above (0.6 g, 2.1 mmol), 2-nitro-5-phenoxybenzaldehyde (0.6 g, 2.3 mmol) and acetic acid (0.15 mL, 2.1 mmol) in DCE (50 mL), was added NaBH₃CN (0.2 g, 3.2 mmol). The reaction mixture was stirred at room temperature overnight, and then 1N NaOH (10 mL) was added. The reaction mixture was extracted with CH₂Cl₂ (50 mL×2). The combined organic layers were dried with MgSO₄ and evaporated to yield a residue which was purified by column chromatography (1:1 hexane:EtOAc) to yield an oil.

MH⁺ 508.5

¹H NMR (300 MHz, CDCl₃): δ0.96-1.99 (m, 23H), 2.34 (m, 3H), 2.79 (s, 0.4×3H), 2.79 (s, 0.6×3H), 3.59 (m, 0.4×1H), 4.0 (m, 2H), 4.4 (m, 0.6×1H), 6.83 (m, 1H), 7.07 (d, J=8.28 Hz, 2H), 7.2 (d, J=7.5 Hz, 2H), 7.43 (t, J=8.24 Hz, 2H), 7.97 (d, J=8.25 Hz, 1H).

Step I

To a solution of the oil prepared in Step H above (0.78 g, 1.5 mmol) in MeOH (50 mL), was added 0.1 g 10% Pd/C under N₂. The reaction mixture was hydrogenated at 30 psi for one hour. The catalyst was removed by filtration, and the MeOH was evaporated. Preparative TLC yielded an oil.

MH⁺ 478.6

¹H NMR (300 MHz, CDCl₃): δ0.96-2.0 (m, 23H), 2.3 (m, 3H), 2.78 (s, 0.4×3H), 2.79 (s, 0.6×3H), 3.75 (m, 0.4×1H), 3.75 (s, 2H), 4.42 (m, 0.6×1H), 6.64 (dd, J=1.5 Hz, J=8.27 Hz, 1H), 6.78 (m, 2H), 6.89 (d, J=7.84 Hz, 2H), 6.97 (t, J=6.43 Hz, 1H), 7.25 (m, 2H).

Step J

A mixture of the oil prepared in Step I above (0.56 g, 1.2 mmol) and BrCN (0.13 g, 1.23 mmol) in EtOH (20 mL) was stirred at room temperature overnight. The EtOH was evaporated, and diethyl ether (50 mL) was added. The reaction mixture was stirred at room temperature for 30 min and then was filtered to yield the title compound as its HBr salt as a light brown solid.

MH⁺ 503.7

¹H NMR (300 MHz, CDCl₃): δ0.9-2.18 (m, 25H), 2.5-2.6 (m, 1H), 2.81 (s, 0.4×3H), 2.87 (s, 0.6×3H), 3.51 (m, 0.4× 1H), 4.16 (m, 2H), 4.3 (m, 0.6×1H), 6.72 (s, 1H), 6.91-6.97 (m, 2H), 7.11 (t, J=7.4 Hz, 1H), 7.25 (d, J=10 Hz, 2H), 7.31 (t, J=7.6 Hz, 2H).

Example 23

4-[2-Amino-6-(2-methoxy-phenyl)-4H-quinazolin-3-yl]-4-(S)-cyclohexyl-N-methyl-N-phenethyl-butyramide (Compound #721)

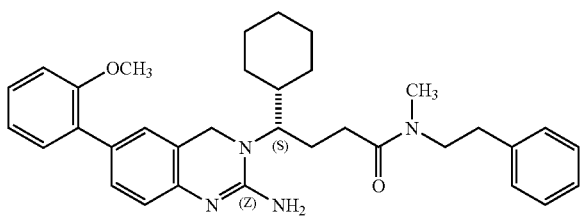

Step A

D-Benzyloxycarbonylamino-cyclohexyl-acetic acid (13.3 g, 45.6 mmol), HOBT (6.8 g, 50.1 mmol), and N,O-dimethylhydroxylamine hydrochloride (4.9 g, 50.1 mmol) were dissolved in CH₂Cl₂ (50 mL) with stirring. The resulting solution was cooled in an ice-bath, and then TEA (13.3 mL, 95.7 mmol) and DCC (50.1 mL, 50.1 mmol, 1 M in CH₂Cl₂) were added. The reaction mixture was stirred at 0° C. for 1 h, then at room temperature for 4 h, and again cooled to 0° C. The resulting white precipitate (dicyclohexylurea) was filtered off, and the filtrate washed with 1N NaOH (2×), 10% citric acid (aqueous) (2×), and brine. The organic layer was dried (Na₂SO₄) and concentrated. Column chromatography (10% EtOAc:heptane to 60% EtOAc:heptane) yielded a white solid.

(M+H): 355.2

Step B

To an ice-bath cooled solution of the solid prepared in Step A above (14.1 g, 0.042 mol) in Et₂O (300 mL) was added LiAlH₄ (53 mL, 0.053 mmol, 1M in THF). The reaction mixture was stirred for 5 minutes. Then the cooling bath was removed, and the reaction mixture was stirred an additional 30 minutes while warming to room temperature before a solution of NaHSO₄ (8.9 g, 73.8 mmol) in H₂O (0.33M) was added. The layers were separated, and the aqueous layer was extracted with Et₂O (3×100 mL). The organic layer was washed with 1N HCl (3×50 mL), saturated aqueous NaHCO₃ solution (50 mL), and brine (50 mL), and then dried (Na₂SO₄), and concentrated. The resulting product, an oil, was stored at −20° C. and used within 1 h without further purification.

(M+H): 276.2

Step C (Dimethoxy-phosphoryl)-acetic acid tert-butyl ester (25 mL, 126 mmol) was dissolved in THF (400 mL) and cooled in an ice-bath with stirring. The addition of NaH (3.4 g, 84 mmol, 60% dispersion in mineral oil) led to a gelatinous mass. The cooling bath was removed and then the slurry was heated and stirred at 30° C. for 20 minutes. The reaction mixture was cooled again in an ice-bath, and a solution of the product prepared in Step B above (~42 mmol) in THF (250 mL) was added. The reaction mixture was stirred for 5 minutes at 0° C. and then for 35 minutes while warming to room temperature. The reaction mixture was quenched with brine (250 mL). EtOAc (250 mL) was then added, and the organic layer was separated. The aqueous layer was extracted with EtOAc (2×100 mL), dried (Na$_2$SO$_4$), and concentrated. Column chromatography (heptane to 30% EtOAc:heptane) yielded a white solid.

(M+H): 374.2

Step D

To a nitrogen degassed/blanked solution of the white solid prepared in Step C above (9.55 g, 25.5 mmol) in MeOH (200 mL) was added 10% Pd/C (1 g) in water (1.5 mL). The reaction mixture was evacuated and flushed three times with H$_2$, and then shaken on a Parr apparatus at room temperature for 3 h under H$_2$ (38 psi). The reaction mixture was filtered through Celite® and concentrated under reduced pressure to yield a white solid that was used without further purification.

(M+H): 242.2

Step E

To a round-bottomed flask containing the white solid prepared in Step D above (5.5 g, 22.8 mmol) in DCE (150 mL) was added 5-bromo-2-nitrobenzaldehyde (5.24 g, 22.8 mmol). After stirring at room temperature for 30 minutes, NaBH(OAc)$_3$ (9.7 g, 45.6 mmol) was added, and the reaction mixture was stirred at room temperature for 18 h. The reaction was quenched with 1N NaOH (100 mL). The layers were separated, and the aqueous layer was extracted with DCM (3×25 mL). The combined organic layers were dried over MgSO$_4$, filtered, and concentrated in vacuo to constant weight. Column chromatography (heptanes to 15% EtOAc/heptanes) yielded a yellow oil.

(M+H): 455.2

Step F

To a stirred solution of the yellow oil prepared in Step E above (4 g, 8.8 mmol) in DCM (50 mL) was added TFA (50 mL). The resulting solution was stirred for 2 h at room temperature, concentrated to a residue, stored for 2 h at <1 mmHg, and used in the following step without further purification.

(M+H): 399.1

Step G

To a −10° C. solution of the residue prepared in Step F above (8.8 mmol) in THF (50 mL) and water (30 mL) was added 4N NaOH (10 mL, 40 mmol) and di-tert-butyl dicarbonate (8.1 mL, 35.2 mmol). The cooling bath was removed, and the solution was heated to 40° C. with stirring for 20 h. The solution was concentrated to the aqueous layer, cooled to 0° C., and the pH was adjusted to 2 with 2N HCl. The aqueous layer was extracted with DCM (3×30 mL) and the combined organic layers were dried and concentrated. Column chromatography (heptanes to 30% EtOAc:heptanes) yielded an off-white solid that was used in the following step without further purification.

(M+H): 499.1

Step H

To a microwave vessel containing the off-white solid prepared in Step G above (50 mg, 0.1 mmol) in DCM (0.5 mL) was added TEA (0.11 mL, 0.8 mmol), N-methylphenethylamine (27 mg, 0.2 mmol) and 2-chloro-1,3-dimethylimidazolium chloride (43 mg, 0.25 mol) in DCM (0.5 mL). The resulting solution was stirred at room temperature for 24 h, quenched with water (0.1 mL), and then concentrated under vacuum to yield a residue that was used directly without further purification.

Step I

To the residue prepared in Step H above was added 2-methoxyphenylboronic acid (23 mg, 0.15 mmol) in EtOH (0.5 mL), potassium carbonate (21 mg, 0.15 mmol) in water (0.05 mL) and bis(diphenyl-phosphino)ferrocene dichloropalladium (8.2 mg, 0.01 mmol). The reaction mixture was degassed with nitrogen for 1 minute and then irradiated (µw) at 120° C. for 6 minutes. The residue was suspended in EtOAc, loaded on a 1 g silica SPE cartridge and then eluted with 15 mL of EtOAc. The eluent was concentrated in vacuo to yield a residue that was used directly in the following step without further purification.

Step J

To the residue prepared in Step I above was added NH$_4$Cl (27 mg, 0.5 mmol) in EtOH (0.65 mL) and zinc dust (131 mg, 2.0 mmol). The reaction mixture was irradiated (µw) at 80° C. for 10 minutes, cooled to room temperature, and filtered through a 70 micron polypropylene frit and used directly as a solution in the following step.

Step K

To the EtOH solution prepared in Step J above was added cyanogen bromide (0.1 mL, 0.5 mmol, 5M in acetonitrile), and the resulting solution was stirred for 36 h at room temperature. The reaction was quenched with 3M NaOH (0.1 mL), was stirred for 5 minutes and then concentrated in vacuo. The resulting residue was suspended in EtOAc with 1% TEA and loaded on a 2 g silica SPE cartridge and then eluted with 15 ml of EtOAc with 1% TEA. The eluent was concentrated in vacuo. The resulting residue was purified by preparative RP-HPLC to yield the title compound as a tan solid as the corresponding TFA salt.

(M+H): 539.3

Example 24

Cyclopentanecarboxylic acid [2-(2-amino-6-o-tolyl-4H-quinazolin-3-yl)-ethyl]-amide (Compound #657)

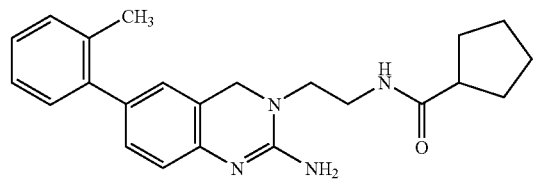 [SMILES: Cc1ccccc1-c1ccc2c(c1)CN(CCNC(=O)C1CCCC1)C(N)=N2]

Step A

To a single-neck 1-L round bottom flask was charged concentrated sulfuric acid (440 mL). The flask was chilled in an ice-water bath, and potassium nitrate (57.3 g, 0.567 mol) was added slowly in one portion, and the reaction mixture was stirred for 10 min. 3-Bromobenzaldehyde (100 g, 0.540 mol) was then added over a 15 min period, and the reaction mixture was stirred in the ice-water bath for 45 min. The reaction mixture was poured onto 2 L of crushed ice, and the ice was allowed to melt while stirring. The aqueous slurry was extracted with dichloromethane (3×400 mL), and the combined organic phases were washed with brine (200 mL), dried (MgSO$_4$), and concentrated in vacuo to yield a solid (a mixture of the desired product as well as other nitration isomers). This material was split into two portions, and each portion was dissolved in dichloromethane/heptane (2:1, 400 mL) and loaded onto a Biotage 75 L (800 g silica gel) column. The columns were eluted with heptane (2 L) and 1:19 ethyl acetate-heptane (10 L) to yield the desired compound as a solid.

mp 69-71° C.

Elemental analysis for C$_7$H$_4$BrNO$_3$:

Calc'd: % C 36.55, % H 1.74, % N 6.09, % Br 34.74

Found: % C 36.68, % H 1.68, % N 5.88, % Br 35.01

HPLC: $R_t$=3.273 min; ABZ+PLUS, 3 μm, 2.1×50 mm. Gradient: A=water (0.1% TFA), B=MeCN (0.1% TFA) @ 0.75 mL/min. Initial: A:B, 90:10. t=0.00-4.00 min (A:B, 10:90), t=4.00-4.10 min (A:B, 0:100), t=4.10-6.00 min (A:B, 0:100).

Step B

A three-neck 2 L round bottom flask was charged with the solid prepared in Step A above (30 g, 0.130 mol), 2-(aminoethyl)-carbamic acid tert-butyl ester (20.9 g, 0.130 mol), and DCE (700 mL). The reaction mixture was stirred for 1 h, and then NaBH(OAc)$_3$ (68.9 g, 0.325 mol) was added. The reaction mixture was heated at 40° C. (exotherm observed, 47° C.) for 3.5 h. The reaction mixture was then cooled to 30° C. and quenched with 3M sodium hydroxide (exotherm observed, 39° C.). The reaction mixture was diluted with water (500 mL), and the layers were separated. The aqueous phase was extracted with dichloromethane (3×400 mL), and the combined organic phases were dried (MgSO$_4$) and concentrated in vacuo to yield crude product as a residual oil. The residual oil was dissolved in 1:2 heptane-dichloromethane (400 mL) and loaded onto a Biotage 75 L column (800 g silica gel). The column was eluted with heptane (4 L), then ethyl acetate-heptane, 1:9 (2 L), 1:4 (4 L), 2:3 (2 L), and 1:1 (4 L) to yield first an unidentified by-product (4 g, 18514-163B) followed by the desired product as an oil that solidified to a yellow solid upon standing.

mp 43-46° C.

Mass spectrum (Electrospray, positive mode): m/z=373/375 (M$^+$)

HPLC: $R_t$=2.321 min; ABZ+PLUS, 3 μm, 2.1×50 mm. gradient: A=water (0.1% TFA), B=MeCN (0.1% TFA) @ 0.75 mL/min. initial: A:B, 90:10. t=0.00-4.00 min (A:B, 10:90), t=4.00-4.10 min (A:B, 0:100), t=4.10-6.00 min (A:B, 0:100)

Step C

A 2 L Parr shaker bottle was charged with a slurry of 3.0 g of 5% platinum (sulfided) on carbon in tetrahydrofuran (25 mL) followed by a solution of the yellow solid prepared in Step B above (27.9 g, 74.5 mmol) in THF (600 mL). The bottle was agitated under hydrogen gas (20-25 psi) for 5 h. The system required frequent re-pressurization during the initial 30 minutes of the reaction. The catalyst was removed by filtration through Celite®, and the filtrate was concentrated to yield a residue. The residue was used without further purification.

Mass Spectrum (Electrospray, positive mode): m/z=343/345 (M+)

HPLC: $R_t$=2.426 min; ABZ+PLUS, 3 μm, 2.1×50 mm. Gradient: A=water (0.1% TFA), B=MeCN (0.1% TFA) @ 0.75 mL/min. Initial: A:B, 90:10. t=0.00-4.00 min (A:B, 10:90), t=4.00-4.10 min (A:B, 0:100), t=4.10-6.00 min (A:B, 0:100)

Step D

A 3 L one-necked flask equipped with magnetic stirrer and a nitrogen inlet was charged with the residue prepared in Step C above (26 g, 75.5 mmol) in EtOH (600 mL). The reaction mixture was cooled in an ice bath and a solution of cyanogen bromide in MeCN (5M, 15.1 mL, 75.5 mmol) was added in one portion. The reaction mixture was warmed to room temperature, stirred for 4 days and then brought to reflux for 3 h. The reaction mixture was cooled to room temperature, poured into water (1.2 L), basified with 3M aqueous sodium hydroxide, and stirred in an ice-water bath for 2 h. The resulting solid was collected by filtration, washed with 1:9 water:EtOH (250 mL), and dried to yield a solid.

mp 199-205° C., decomp.

Mass spectrum (Electrospray, positive mode): m/z=368/370 (M+)

Elemental analysis: ($C_{15}H_{21}BrN_4O_2$):

Cal'd: %C 48.79, %H 5.73, %N 15.17, %Br 21.64

Found: %C 49.63, %H 5.81, %N 15.30, %Br 21.22

Karl-Fisher: 0.14% (w/w) water

HPLC: $R_t$=7.967 min; Agilent Eclipse XDB-C8, 5 μm, 4.6×150 mm. Gradient: A=water (0.1% TFA), B=MeCN (0.1% TFA) @ 1.0 mL/min. Initial: A:B, 90:10. t=0.00-0.50 min (A:B, 90:10), t=0.50-11.50 min (A:B, 5:95), t=11.50-12.50 min (A:B, 5:95)

Step E

To a reaction vessel containing the solid prepared in Step D above (66 mg, 0.18 mmol) was added 50% TFA:DCM (1.4 mL). The reaction mixture was stirred at 40° C. for 2 h and then was concentrated in vacuo to yield a residue, which was taken into the next step without further purification.

Step F

To the residue isolated in Step E was added chloroform (0.5 mL), TEA (138 μL, 0.99 mmol), and cyclopentanecarbonyl chloride (24 mg, 0.18 mmol) in chloroform (0.2 mL). The mixture was stirred at room temperature overnight and then was concentrated in vacuo. To the residue was added methanol (0.2 mL) and the solution was concentrated to furnish a residue.

Step G

To a reaction vessel containing the residue prepared in Step F above was added o-tolylboronic acid (37 mg, 0.27 mmol) in EtOH (1 mL), K$_2$CO$_3$ (50 mg, 0.36 mmol) in water (0.2 mL), and [1,1'-Bis(diphenylphosphino)ferrocene]dichloropalladium (II) (7 mg, 0.008 mmol). The reaction mixture was irradiated (microwave) at 120° C. for 6 min and then was concentrated in vacuo. The residue was taken up in 1% TEA:EtOAc (0.8 mL) and water (0.35 mL). The solution was absorbed onto diatomaceous earth and eluted with 1% TEA:EtOAc. The eluate was concentrated to a residue and then was purified by reverse-phase chromatography to yield the title compound, cyclopentanecarboxylic acid [2-(2-amino-6-o-tolyl-4H-quinazolin-3-yl)-ethyl]-amide as a trifluoroacetate salt as an oil.

MS m/z (MH$^+$) calcd 377.23, found 377.4

Example 25

3-[2-Amino-6-(2-methoxy-phenyl)-4H-quinazolin-3-ylmethyl]-N-cyclohexyl-N-methyl-benzamide (Compound #167)

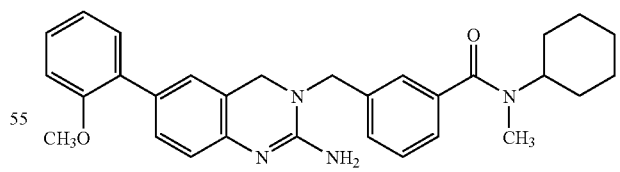

Step A

To a flask containing 3-cyanobenzoic acid (10 g, 0.068 mol) in DCM (300 mL) was added DIEA (47 mL, 0.27 mol) and N-methylcyclohexylamine (13.3 mL, 0.1 mol) with stirring. The resulting solution was cooled to approximately 0° C., and then 2-chloro-1,3-dimethylimidazolium chloride (23 g, 0.14 mol) was added with stirring. After 5 minutes, the cooling bath was removed and the solution was warmed to room temperature over 4 h. The reaction mixture was quenched with 100 mL of water, transferred to a separatory funnel, shaken, and the layers were separated. The aqueous layer was extracted with DCM (2×100 mL) and the combined organics were dried over Na$_2$SO$_4$, filtered, concentrated to a residue, and placed under vacuum (~1 mmHg) for 1 h.

Step B

The residue prepared in Step A above was transferred to a Parr bottle with EtOH (250 mL) and then was degassed and blanked with nitrogen before 12N aqueous HCl (28 mL, 0.34 mol) and 10% Pd/C (1.6 g) slurried in water were added. The resulting slurry was exposed to 50 psi of H$_2$ for 14 h at room temperature using standard Parr techniques and then degassed with nitrogen for 5 minutes and filtered through a pad of Celite®. The resulting solution was concentrated to the aqueous layer and transferred to a separatory funnel with water (100 mL) and DCM (50 mL). The layers were separated and the aqueous layer was extracted with DCM (2×25 mL). The combined organic layers were extracted with 0.5N HCl (25 mL), and the layers were separated. The combined aqueous layers were adjusted to pH>9 with 3N NaOH and extracted with DCM (5×50 mL). The combined organic layers were dried over Na$_2$SO$_4$, filtered, concentrated to a residue, and placed under vacuum (~1 mmHg) for 1 day.

MS m/z (MH$^+$) calcd 247.2, found 247.3

Step C

To a round-bottomed flask containing the residue prepared in Step B above (6.7 g, 0.032 mol) in DCE (175 mL) was added 5-bromo-2-nitrobenzaldehyde (7.4 g, 0.032 mol). After stirring at room temperature for 30 min, NaBH(OAc)$_3$ (13.7 g, 0.065 mol) was added, and the reaction mixture was stirred at room temperature for 18 h. The reaction mixture was quenched with 1N NaOH (100 mL). The layers were separated, and the aqueous layer was extracted with DCM (3×25 mL). The combined organic layers were dried over MgSO$_4$, filtered, and concentrated in vacuo to constant weight to yield a residue which was used in the following step without further purification.

MS m/z (MH$^+$) calcd 460.1, found 460.4

Step D

To a solution of the residue prepared in Step C above (27 mg, 0.059 mmol) in EtOH (0.5 mL) was added K$_2$CO$_3$ (12.3 mg, 0.089 mmol) in water (0.025 mL), 2-methoxyphenylboronic acid (13.5 mg, 0.089 mmol) and bis(diphenyl-phosphino)ferrocene dichloropalladium (4.9 mg, 0.006 mmol). The reaction mixture was irradiated (μw) at 100° C. for 10 min. After cooling to room temperature, the solution was used directly in the following step.

MS m/z (MH$^+$) calcd 488.3, found 488.6

Step E

To the solution prepared in Step D above was added SnCl$_2$ (56 mg, 0.30 mmol) in EtOH (0.2 mL), and the resulting solution was stirred at room temperature for 36 h. The reaction mixture was quenched with water (0.1 mL) and TEA (0.2 mL), stirred for 5 minutes, and concentrated to a residue. The residue was suspended in 1% TEA in EtOAc and loaded on a 2 g silica SPE cartridge and then eluted with 15 ml of 1% TEA in EtOAc. The eluent was concentrated in vacuo to yield a residue which was used directly in the next step without further purification.

MS m/z (MH$^+$) calcd 458.3, found 458.7

Step F

The residue prepared in Step E above was dissolved in EtOH (0.75 mL), and cyanogen bromide (0.047 mL, 0.24 mmol, 5M in MeCN) was added. The resulting solution was stirred for 18 h at room temperature. The reaction mixture was quenched with 3M NaOH (0.1 mL), stirred for 5 minutes, and concentrated in vacuo. The residue was suspended in DCM: water (1 mL:0.1 mL), and the inorganic materials were removed by SLE (solid liquid extraction) cartridge. After concentration, the resulting residue was purified by preparative RP-HPLC to yield the title compound, 3-(2-amino-6-phenoxy-4H-quinazolin-3-ylmethyl)-N-cyclohexyl, N-methyl-benzamide as an oil.

MS m/z (MH$^+$) calcd 483.3, found 483.6

Example 26

3-(2-Amino-6-phenoxy-4H-quinazolin-3-ylmethyl)-N-cyclohexyl-N-methyl-benzamide (Compound #62)

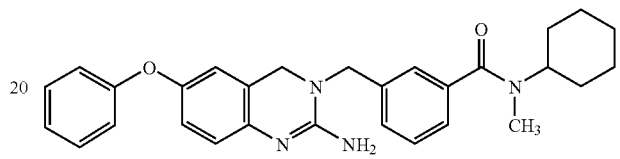

Step A

To a solution of 3-(tert-butoxycarbonylamino-methyl)-benzoic acid (1.00 g, 3.98 mmol) in 21 mL of DMF was added 1,1'-carbonyldiimidazole (0.645 g, 3.98 mmol). After 1.5 h of stirring at room temperature, N-methylcyclohexylamine (0.98 mL, 7.50 mmol) was added. After another 2 h of stirring, 50 mL of water was added to the reaction mixture. The reaction mixture was then extracted with diethyl ether. The diethyl ether extracts were combined, washed with water (2×) and brine (2×), dried over Na$_2$SO$_4$. After filtration, the diethyl ether solution was concentrated in vacuo to yield an oil.

MS m/z (MH$^+$)=347

Step B

To a solution of the oil prepared in Step A above (0.402 g, 1.17 mmol) in CH$_2$Cl$_2$ (40 mL), was added TFA (4.0 mL). The reaction mixture was stirred overnight, and then 3N NaOH solution (35-40 mL) was added with vigorous stirring. The organic layer was separated, dried over Na$_2$SO$_4$, filtered, and evaporated to yield an oil.

MS m/z (MH$^+$)=247

Step C

A solution of the oil prepared in Step B above (0.051 g, 0.21 mmol) and 2-nitro-5-phenoxybenzaldehyde (0.051 g, 0.21 mmol) in 1 mL of DCE was stirred for 10 minutes. Then NaBH(OAc)$_3$ (0.062 g, 0.29 mmol) was added. The reaction mixture was stirred overnight at room temperature, and then 3N NaOH solution was added with vigorous stirring. The organic layer was separated, dried over Na$_2$SO$_4$, filtered, and evaporated to yield a thick oil.

MS m/z (MH$^+$)=474

Step D

A mixture of the oil prepared in Step C above (0.049 g, 0.10 mmol) and tin(II) chloride dihydrate (0.124 g, 0.55 mmol) in 0.4 mL of EtOH was refluxed for 1 hour. The reaction mixture was cooled and saturated NaHCO$_3$ solution and EtOAc were added with thorough mixing. The organic layer was separated, dried over Na$_2$SO$_4$, filtered, and evaporated to yield a glassy solid.

MS m/z (MH$^+$)=444

Step E

A solution of the glassy solid prepared in Step D above (0.037 g, 0.084 mmol) and cyanogen bromide (0.013 g, 0.12 mmol) in 2 mL of EtOH was refluxed for 2 h. The reaction mixture was cooled and evaporated. The residue was triturated with diethyl ether and filtered to yield the title compound as a brown solid.

MS m/z (MH+)=468

Example 27

4-{[4-(2-Amino-6-phenoxy-4H-quinazolin-3-yl)-4-(S)-cyclohexyl-butyryl]-methyl-amino}-cyclohexanecarboxylic acid (Compound #714)

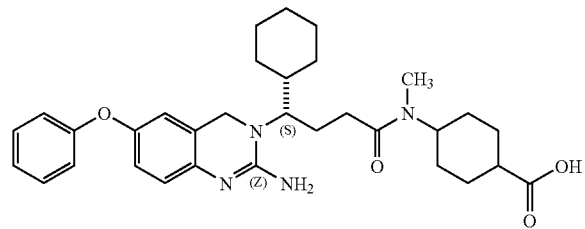

Step A

A solution of 4-cyclohexanonecarboxylic acid ethyl ester (6 g, 35 mmol), methylamine.HCl salt (2.4 g, 35 mmol), triethylamine (0.15 mL, 3 mol %) and wet 5% Pd/C (0.18 g, 3% wt) in MeOH (100 mL) was placed into a hydrogenation bottle. The reaction mixture was subjected to hydrogenation at 60 psi and 50° C. overnight. The catalyst was removed by filtration, and the MeOH was evaporated. The residue was stirred in EtOAc:hexane (1:1) for 30 min. The suspension was filtered, and a white solid was collected as its HCl salt.

MS m/z (MH+)=186.2

Step B

To an ice cooled solution of 4-tert-butoxycarbonylamino-4-(S)-cyclohexyl-butyric acid (3.8 g, 0.014 mol; prepared as in Example 22, Steps A-E) in CH$_2$Cl$_2$ (200 mL), was added the amine (3.2 g, 0.0144 mol) prepared in Step A, HOBT (2.4 g, 0.017 mol) and TEA (5.5 mL, 0.042 mol) followed by addition of 1,3-dimethylamino propyl-3-ethylcarbodiimide (EDC) (3.3 g, 0.017 mol). The reaction mixture was allowed to warm to room temperature and was stirred overnight. EtOAc (300 mL) was then added to the reaction mixture. The resulting mixture was washed with citric acid solution, aqueous NaHCO$_3$, and brine. The organic layer was collected, dried (MgSO$_4$) and evaporated to yield an oil. The crude oil was used in the next step without further purification.

MS m/z (MH+)=453.1

Step C

A solution of the material (6 g, 13 mmol) isolated in Step B in 20% TFA-CH$_2$Cl$_2$ (100 mL) was stirred at room temperature for 3 h. The solvent and most of TFA was evaporated, and EtOAc (200 mL) was added to the residue. The EtOAc extract was washed with aqueous NaHCO$_3$ solution and brine and then dried (MgSO$_4$) and evaporated to yield a light brown oil.

MS m/z (MH+)=353.3

Step D

To a solution of the oil (4.8 g, 13.6 mmol) from Step C in DCE (200 mL) was added 2-nitro-5-phenoxybenzaldehyde (3.9 g, 16 mmol), acetic acid (0.9 mL), and NaBH(OAc)$_3$ (4.7 g, 20 mmol). The reaction mixture was stirred overnight, and then extracted with EtOAc (2×200 mL). The organic layers were combined, dried (Mg$_2$SO$_4$), and evaporated. Purification on a silica gel column (1:1 heptane:EtOAc) yielded an oil.

MS m/z (MH+)=580.4

Step E

To a solution of the oil (2.9 g, 5 mmol) isolated in Step D in MeOH (100 mL) was added 10% Pd/C (0.29 g) on activated carbon under N$_2$. The reaction mixture was subjected to hydrogenation at 5 psi for 2 h. The catalyst was removed by filtration, and then the MeOH was evaporated. Purification on flash silica gel (100% EtOAc) yielded a solid.

MS m/z (MH+)=550.7

Step F

A solution of the solid isolated (2.2 g, 4.1 mmol) in Step E and BrCN (3M in CH$_2$Cl$_2$, 1.4 mL, 4.3 mmol) in EtOH (50 mL) was stirred at room temperature overnight. The EtOH was evaporated to yield a residue which was purified on silica gel (10% 1M NH$_3$ in MeOH:CH$_2$Cl$_2$) to yield a solid.

MS m/z (MH+)=575.3

Step G

A solution of the solid (1.75 g, 3 mmol) isolated in Step F in MeOH (20 mL) and 1N NaOH (3.2 mL, 3.2 mmol) was stirred at room temperature over the weekend. Mass spectral analysis indicated that starting material was still left so additional 1N NaOH (3 mL) was added. The solution was stirred at room temperature for 6 h. Citric acid (1.4 g, 6.6 mmol) was added, and the reaction mixture was stirred for 1 h. The solvent was evaporated to yield crude product. 1.2 g of the crude product was purified by HPLC to yield title compound, 4-{[4-(2-Amino-6-phenoxy-4H-quinazolin-3-yl)-4-cyclohexyl-butyryl]-methyl-amino}-cyclohexanecarboxylic acid, as a white solid.

MS m/z (MH+)=547.4

$^1$H NMR (300 MHz, CD$_3$OD): δ0.91-1.25 (m, 4H), 1.51-1.76 (m, 10H), 2.02-2.21 (m, 8H), 2.57-2.76 (m, 1H), 2.81 (s, 3H), 3.5 (m, 0.4×1H), 3.73 (s, 2H), 4.15 (m, 2H), 4.4 (m, 0.6×1H), 6.72 (s, 1H), 6.94 (d, J=7.78 Hz, 2H), 7.10 (t, J=7.44 Hz, 1H), 7.2-7.36 (m, 4H).

Example 28

(S)-enantiomer of 4-(2-Amino-6-phenoxy-4H-quinazolin-3-yl)-4,N-dicyclohexyl-N-(2-hydroxy-ethyl)-butyramide (Compound #736)

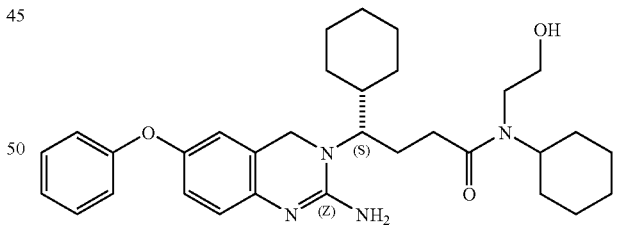

Step A

To an ice cooled solution of Boc-D-cyclohexylglycine (10 g, 39 mmol), N,O-dimethylhydroxyamine.HCl salt (4.6 g, 46 mmol) and HOBT (7 g, 51 mmol) in CH$_2$Cl$_2$ (200 mL), TEA (11 mL) was added followed by addition of EDC (10 g, 51 mmol). The reaction mixture was allowed to warm to room temperature and was then stirred overnight. EtOAc (300 mL) was added. The reaction mixture was then washed with citric acid solution, NaHCO$_3$ solution, and NaCl solution. The organic layer was collected, dried with MgSO$_4$ and evaporated to yield a colorless oil. The crude product was used without further purification.

MH+ 301.2

Step B

To an ice cooled solution of the oil isolated in Step A above (12.3 g, 40 mmol) in THF (100 mL) was slowly added LAH (1M solution in THF, 45 mL) so as to keep the reaction temperature below about 5° C. The ice bath was removed, and the reaction mixture was stirred at room temperature for 20 min. A solution of NaHSO$_4$ (7.3 g) in water (10 mL) was slowly added to quench the reaction. The reaction mixture was then filtered through Celite®. EtOAc (300 mL) was added to the filtrate, and the organic layer was washed with NaCl solution, dried with MgSO$_4$ and evaporated to yield an oil. The crude product was used without further purification.

MH$^+$ 242.2

Step C

To an ice cooled solution of trimethyl phosphonoacetate (19 mL, 0.11 mol) in THF (200 mL) was added 60% NaH (3.1 g, 0.08 mol) in portions. The ice bath was removed, and the reaction mixture was stirred at room temperature for 30 min. The reaction mixture was cooled to 0° C. again before a solution of the oil isolated in Step B (9 g, 37 mmol) in THF (200 mL) was added. The reaction mixture was stirred at room temperature for another 20 min. Water (100 mL) was added, and most of the THF was evaporated. The product was extracted into EtOAc (400 mL), and the organic layer was washed with NaCl solution and dried with MgSO$_4$. Column chromatography (1:1 heptane:EtOAc) yielded a white solid.

$^1$H NMR (300 MHz, CDCl$_3$): δ1.1-1.3 (m, 7H), 1.44 (s, 9H), 1.6-1.8 (m, 5H), 3.73 (s, 3H), 4.17 (m, 0.6×1H), 4.58 (m, 0.4×1H), 5.9 (dd, J=1.4 Hz, J=15.6 Hz, 1H), 6.88 (dd, J=5.6 Hz, J=15.6 Hz, 1H).

Step D

To a solution of the white solid isolated in Step C (9 g, 30 mmol) in MeOH (100 mL) was added 10% Pd on activated carbon (1 g) under N$_2$. The reaction mixture was hydrogenated at 20 psi for 4 hours. The catalyst was removed by filtration, and the MeOH was evaporated to yield a white solid.

$^1$H NMR (300 MHz, CDCl$_3$): δ0.9-1.3 (m, 7H), 1.43 (s, 9H), 15-1.8 (m, 6H), 2.37 (t, J=7.52 Hz, 2H), 3.4 (m, 1H), 3.67 (s, 3H), 4.29 (m, 1H).

Step E

To a solution of the solid isolated in Step D (9 g) in MeOH (100 mL) was added 1N NaOH (31 mL). The reaction mixture was stirred at room temperature overnight. Citric acid (7 g) was added, and the MeOH was removed in vacuo. The product was extracted into EtOAc (300 mL). The organic layer was washed with NaCl solution and then dried with MgSO$_4$ to yield a white solid.

MH$^-$ 284.1

Step F

To an ice cooled solution of N-cyclohexylethanolamine (0.55 g, 3.9 mmol) in CH$_2$Cl$_2$ (200 mL), the solid isolated in Step E (1.0 g, 3.5 mmol), HOBT (0.62 g, 4.5 mmol), TEA (1.0 mL) were added followed by EDC (0.87 g, 4.5 mmol). The reaction mixture was allowed to warm to room temperature and was stirred overnight. EtOAc (300 mL) was added to the reaction mixture. The reaction mixture was washed with citric acid solution, NaHCO$_3$ solution, and NaCl solution. The organic layer was collected, dried with MgSO$_4$, and evaporated to yield an oil. The crude oil product was used without further purification.

MH$^+$ 411.4

Step G

A solution of the oil isolated in Step F (1.5 g, 3.6 mmol) in 20% TFA:CH$_2$Cl$_2$ (60 mL) was stirred at room temperature for one hour. The solvent and most of the TFA was evaporated, and EtOAc (200 mL) was added. The reaction mixture was washed with NaHCO$_3$ solution and NaCl solution. The organic layer was dried with MgSO$_4$ and evaporated to yield a light brown oil.

MH$^+$ 311.0

Step H

To a solution of the oil isolated in Step G (0.4 g, 1.3 mmol) and 2-nitro-5-phenoxybenzaldehyde (0.31 g, 1.3 mmol) in 1,2-dichloroethane (50 mL), NaBH(OAc)$_3$ (0.37 g, 2.0 mmol) was added. The reaction mixture was stirred at room temperature overnight. A solution of 1N NaOH was added, and the reaction mixture was extracted with EtOAc (2×200 mL). The organic layer was dried with MgSO$_4$ and evaporated. Purification by column chromatography (1:1 heptane/EtOAc) yielded an oil.

MH$^+$ 538.4

Step I

To a solution of the oil isolated in Step H (0.07 gm, 0.13 mmol) in MeOH (10 mL) was added a catalytic amount of 10% palladium on activated carbon under N$_2$. The reaction mixture was subjected to hydrogenation at 5 psi for one hour. The catalyst was filtered out, and the MeOH was evaporated to yield a residue. Purification by preparative TLC (100% EtOAc) yielded an oil.

MH$^+$ 508.3

Step J

To a solution of the oil isolated in Step 1 (0.03 g, 0.06 mmol), BrCN (3M in CH$_2$Cl$_2$, 0.02 mL) in EtOH (5 mL) was added. The reaction mixture was stirred at room temperature overnight. The EtOH was evaporated to yield an oil which was stirred in diethyl ether (50 mL) for 30 min. A solid formed, and was collected by filtration. The product was isolated as a solid, as its corresponding HBr salt.

MH$^+$ 533.3

$^1$H NMR (300 MHz, CDCl$_3$): δ0.9-1.9 (m, 22H), 2.0-2.2 (m, 1H), 2.3-2.5 (m, 2H), 3.3-3.8 (m, 5H), 4.1-4.3 (m, 3H), 6.72 (s, 1H), 6.91 (d, J=8.54 Hz, 2H), 7.15 (d, J=8.25 MHz, 1H), 7.2 (m, 2H) 7.34 (t, J=7.8 Hz, 2H).

Example 29

S-enantiomer of 4-(2-Amino-6-phenoxy-4H-quinazolin-3-yl)-N-cyclohexyl-4-(1,4-dioxa-spiro[4.5]dec-8-yl)-N-methyl-butyramide (Compound #730)

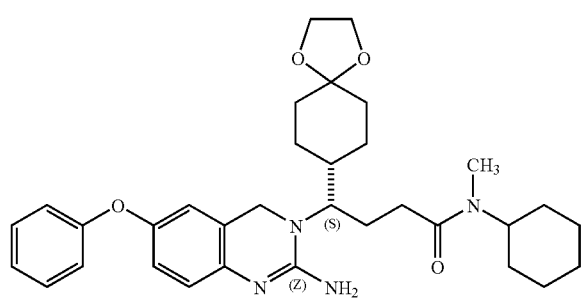

Step A

A solution of N-benzyloxycarbonyl-α-phosphonoglycine trimethyl ester (5 g, 15 mmol) and DBU (2.3 mL, 15 mmol) in THF (50 mL) was stirred at room temperature for 10 min before adding dropwise a solution of 1,4-cyclohexanedione monoethylene ketal (2.4 g, 15 mmol) in THF (20 mL). The reaction mixture was stirred at room temperature overnight before adding 5% HCl (50 mL). The reaction mixture was extracted with EtOAc (3×100 mL). The combined organic layers were washed with aqueous NaCl solution, dried with MgSO$_4$, and evaporated. Column chromatography (1:1 hexane:EtOAc) yielded a light yellow oil which turned into a solid upon standing.

MH$^+$ 362.1

Step B

A solution of the solid isolated in Step B (3.2 g, 8.8 mmol) and R, R-(+)-BPE (1,2-bis(phospholano)ethane)-Rh catalyst (0.03 g) in MeOH (60 mL) was placed into a Parr high pressure reactor and subjected to hydrogenation under 410 psi for three days. The MeOH was removed, and column chromatography (1:1 hexane:EtOAc) yielded an oil which turned to a solid overnight.

MH$^+$ 364.2

Step C

To a solution of the solid isolated in Step B (2.8 g, 8 mmol) in MeOH (50 mL) was added 1N NaOH (8 mL, 8 mmol). The solution was stirred at room temperature overnight. Citric acid (3.1 g, 17 mmol) was added, and the reaction mixture was stirred another 10 min. The MeOH was evaporated, and the resulting solution was extracted with EtOAc (200 mL). The organic layer was washed by aqueous NaHCO$_3$ solution and aqueous NaCl solution and then was dried with MgSO$_4$. Evaporation yielded an oil, which turned to a solid upon standing.

MH$^-$ 348.1

Step D

To an ice-cooled solution of the solid isolated in Step C (2.8 g, 8 mmol), N,O-dimethylhydroxylamine.HCl salt (0.86 gm, 8.8 mmol) and HOBT (1.5 g, 11 mmol) in CH$_2$Cl$_2$ (100 mL) was added TEA (3 mL) followed by addition of EDC (2.2 g, 11 mmol). The reaction mixture was allowed to warm to room temperature and was stirred overnight. EtOAc (100 mL) was added to the reaction mixture which was then washed with citric acid solution, NaHCO$_3$ solution, and NaCl solution. The organic layer was then dried with MgSO$_4$ and evaporated to yield an oil. The crude oil product was used without further purification.

MH$^+$ 393.3

Step E

To an ice cooled solution of the oil isolated in Step D (2.8 g, 7.1 mmol) in THF (50 mL) was slowly added LAH (1M solution in THF, 7.2 mL) in order to keep the reaction temperature below 5° C. The ice bath was removed, and the reaction mixture was stirred at room temperature for 20 min. A solution of NaHSO$_4$ (1.1 g) in water (3 mL) was slowly added to quench the reaction. The reaction mixture was then filtered through Celite®. EtOAc (100 mL) was added, and the organic layer was washed with NaCl solution, dried with MgSO$_4$, and evaporated to yield an oil. The crude oil product was used without further purification.

MH$^+$ 334.1

Step F

To an ice cooled solution of trimethyl phosphonoacetate (3.5 mL, 21 mmol) in THF (200 mL) was added 60% NaH (0.6 g, 14 mmol) in portions. The ice bath was removed and the reaction mixture was stirred at room temperature for 30 min. The reaction mixture was cooled to 0° C. again before a solution of the oil isolated in Step E (2.3 g, 7 mmol) in THF (100 mL) was added. The ice bath was removed, and the reaction mixture was stirred at room temperature for another 20 min. Water (50 mL) was added, and most of the THF was evaporated. The aqueous solution was extracted with EtOAc (200 mL), and the organic layer was washed with NaCl solution and dried with MgSO$_4$. Purification by column chromatography (1:1 heptane/EtOAc) yielded a white solid.

MH$^+$ 390.2

Step G

A solution of the white solid isolated in Step F (1.7 g, 4.4 mmol), 10% Pd/C (1.1 g), Boc anhydride (1.0 g, 4.4 mmol), 1,4-cyclohexadiene (3 mL, 44 mmol) in EtOH (50 mL) was stirred at room temperature for 3 hours. The catalyst was removed by filtration, and EtOH was evaporated to yield a colorless oil.

MH$^+$ 358.2

Step H

The oil (1.1 g) isolated in Step G was dissolved in MeOH (20 mL) before adding 1N NaOH (3.0 mL). The reaction mixture was stirred at room temperature overnight and then was acidified with citric acid (1.2 g). The MeOH was removed by vacuum. The product was extracted into EtOAc (100 mL). The organic layer was washed with NaCl solution, dried with MgSO$_4$, and concentrated to yield a yellow oil.

MH$^-$ 342.1

Step I

To an ice cooled solution of the oil isolated in Step H (0.82 g, 2.4 mmol), N-methylcyclohexylamine (0.35 mL, 2.7 mmol), HOBT (0.42 g, 3.1 mmol) in CH$_2$Cl$_2$ (50 mL), was added TEA (0.7 mL) followed by addition of EDC (0.62 g, 3.1 mmol). The reaction mixture was allowed to warm to room temperature and was stirred overnight. EtOAc (100 mL) was added. The reaction solution was washed with citric acid solution, NaHCO$_3$ solution, and NaCl solution. The organic layer was separated, dried with MgSO$_4$, and evaporated to yield a brown oil which was used without further purification.

MH$^+$ 439.3, MH+339.1 (M−Boc)

Step J

A solution of the oil isolated in Step I (1.0 g, 2.3 mmol) in 20% TFA-CH$_2$Cl$_2$ (60 mL) was stirred at room temperature for one hour. The solvent was evaporated along with most of the TFA, and EtOAc (100 mL) was added. The reaction mixture was washed with NaHCO$_3$ solution and NaCl solution. The organic layer was dried with MgSO$_4$ and evaporated to yield a brown oil.

MH$^+$ 339.0

Step K

To a solution of the oil isolated in Step J (0.4 g, 1.1 mmol) and 2-nitro-5-phenoxy-benzaldehyde (0.3 g, 1.2 mmol) in 1,2-dichloroethane (20 mL), was added NaBH(OAc)$_3$ (0.44 g, 2.1 mmol). The reaction mixture was stirred at room temperature overnight. A solution of 1N NaOH was then added. The reaction mixture was extracted with EtOAc (100 mL). The organic layer was dried with MgSO$_4$ and evaporated. Column chromatography (1:1 heptane:EtOAc) yielded an oil.

MH$^+$ 566.5

Step L

To a solution of the oil isolated in Step K in MeOH (10 mL) was added 10% Pd/C (0.02 g) under N$_2$. The reaction mixture was subjected to hydrogenation at 5 psi for one hour. The catalyst was filtered out, and the MeOH was evaporated to yield a residue. Purification by preparative TLC (100% EtOAc) yielded an oil.

MH$^+$ 536.4

Step M

To a solution of the oil isolated in Step L (0.06 g, 0.1 mmol) in EtOH (5 mL) was added BrCN (3M in CH$_2$Cl$_2$, 0.04 mL). The reaction mixture was stirred at room temperature overnight. The EtOH was evaporated to yield an oil that was stirred in diethyl ether (50 mL) for 30 min. A precipitate formed, and the suspension was filtered to yield the title compound as a solid, as its HBr salt.

MH+ 561.3

¹H NMR (300 MHz, CD₃OD): δ0.9-1.8 (m, 22H), 2.3-2.5 (m, 6H), 3.21 (s, 3H), 3.81 (s, 2H), 6.86 (m, 4H), 7.03 (m, 2H), 7.24 (m, 2H)

Example 30

(S)-enantiomer of 4-(2-Amino-6-phenoxy-4H-quinazolin-3-yl)-N-cyclohexyl-N-methyl-4-(4-oxo-cyclohexyl)-butyramide (Compound #732)

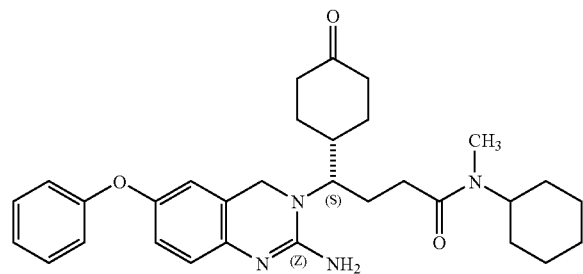

A solution of the compound prepared as in Example 29 (0.06 g, 0.1 mmol) in 1N HCl (1 mL) and THF (1 mL) was stirred at room temperature overnight. The THF was evaporated, and the crude product was dissolved in a small amount of MeOH. Purification by preparative HPLC yielded the title compound as a solid, as its corresponding TFA salt.

MH+ 517.2

¹H NMR (300 MHz, CDCl₃): δ1.2-1.8 (m, 20H), 2.1-2.4 (m, 4H), 2.8 (d, J=15 Hz, 3H), 3.44 (m, 0.4×1H), 4.23 (s, 2H), 4.4 (m, 0.6×1H), 6.72 (s, 1H), 6.95 (d, J=7.61 Hz, 2H), 7.12 (d, 1H), 7.27-7.34 (m, 4H).

Example 31

4-(2-Amino-6-phenoxy-4H-quinazolin-3-yl)-N-cyclohexyl-4-(4-hydroxy-cyclohexyl)-N-methyl-butyramide (Compound #632)

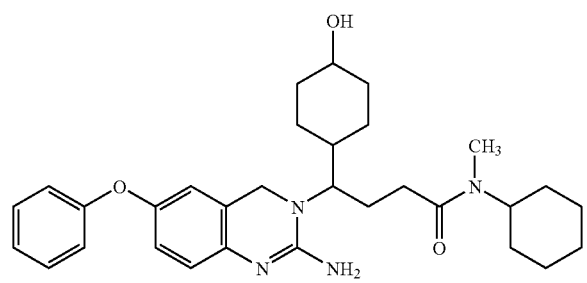 [SMILES: CN(C(=O)CCC(C1CCC(O)CC1)N1Cc2cc(Oc3ccccc3)ccc2N=C1N)C1CCCCC1]

Step A

A solution of the compound prepared as in Example 29, Step A (4.0 g, 11 mmol), 10% Pd/C (4 g), Boc anhydride (3.6 g, 16 mmol), and 1,4-cyclohexadiene (10.4 mL, 0.1 mol) in EtOH (60 mL) was stirred at room temperature for 2 hours. The catalyst was removed by filtration, and the EtOH was evaporated to yield a residue. The residue was purified by column chromatography (1:1 hexane:EtOAc) to yield a colorless oil.

MH+ 330.0, MH+ 230.2 (M−Boc)

Step B

To a solution of the oil isolated in Step A (1 g, 3 mmol) in MeOH (20 mL) was added 1N NaOH (5 mL, 5 mmol). The reaction mixture was stirred at room temperature overnight. The MeOH was evaporated, and the product was extracted into EtOAc (200 mL). The organic layer was washed with dilute HCl solution, NaHCO₃ solution, aqueous NaCl solution, dried with MgSO₄, and evaporated to yield an oil.

MH⁻ 314

Step C

To an ice-cooled solution of the oil isolated in Step B (1.0 g, 3 mmol), N,O-dimethylhydroxyamine.HCl salt (0.6 g, 6 mmol) and HOBT (0.78 g, 6 mmol) in CH₂Cl₂ (50 mL), was added TEA (1.3 mL) followed by addition of EDC (1.2 g, 6 mmol). The reaction mixture was allowed to warm to room temperature and was then stirred overnight. EtOAc (100 mL) was added, and the reaction mixture was washed with citric acid solution, NaHCO₃ solution, and NaCl solution. The organic layer was dried with MgSO₄ and evaporated to yield an oil. The crude oil product was used without further purification.

MH+ 359.1, MH+ 259.1 (M−Boc)

Step D

To an ice cooled solution of the oil isolated in Step C (1.2 g, 3.3 mmol) in THF (50 mL) was slowly added LAH (1M solution in THF, 4 mL) while keeping the temperature below 5° C. The ice bath was removed, and the reaction mixture was stirred at room temperature for 20 min. A solution of NaHSO₄ (0.9 g) in water (3 mL) was slowly added to quench the reaction. The reaction mixture was then filtered through Celite®. EtOAc (100 mL) was added and the organic layer was washed with NaCl solution, dried with MgSO₄ and evaporated to yield an oil. The crude product was used without further purification.

MH+ 300.1, MH+ 200.1 (M−Boc)

Step E

To an ice cooled solution of trimethyl phosphonoacetate (5.5 mL, 33 mmol) in THF (200 mL) was added 60% NaH (1.4 g, 22 mmol) in portions. The ice bath was removed, and the reaction mixture was stirred at room temperature for 30 min. The reaction mixture was cooled to 0° C. again before a solution of the oil isolated in Step D (3.4 g, 11 mmol) in THF (100 mL) was added. The cooling bath was removed, and the reaction mixture was stirred at room temperature for another 20 min. Water (50 mL) was then added, and most of the THF was evaporated. The product was extracted into EtOAc (200 mL), and the organic layer was washed with NaCl solution, dried with MgSO₄, and evaporated. Purification by column chromatography (1:1 heptane:EtOAc) yielded a white solid.

¹H NMR (300 MHz, CDCl₃): δ1.1-1.8 (m, 12H), 3.73 (s, 3H), 3.93 (m, 1H), 4.25 (m, 0.6×1H), 4.68 (m, 0.4×1H), 5.9 (dd, J=1.6 Hz, J=14 Hz, 1H), 6.85 (dd, J=5.1 Hz, J=15 Hz, 1H).

Step F

To a solution of the white solid isolated in Step E (2.0 g) in MeOH (50 mL) was added 10% Pd/C (0.2 g) under N₂, and the reaction mixture was hydrogenated at 30 psi for three hours. The catalyst was removed by filtration, and the MeOH was evaporated to yield an oil.

MH+ 358.2, MH+ 258.1 (M−Boc)

Step G

To a solution of the oil isolated in Step F (1.15 g, 3.2 mmol) in MeOH (15 mL) was added 1N NaOH (5 mL, 5 mmol). The reaction mixture was stirred at room temperature overnight. The MeOH was evaporated, and the product was extracted into EtOAc (100 mL). The organic layer was washed with dilute HCl solution, NaHCO₃ solution, and aqueous NaCl solution, dried with MgSO₄, and evaporated to yield a colorless oil.

MH⁺ 344.1, MH⁻ 342.0

Step H

To an ice cooled solution of N-methylcyclohexylamine (0.4 mL, 3.0 mmol), the oil isolated in Step G (0.95 g, 2.8 mmol), and HOBT (0.41 g, 3.0 mmol) in CH₂Cl₂ (50 mL), was added TEA (0.77 mL) followed by addition of EDC (0.58 g, 3.0 mmol). The reaction mixture was allowed to warm to room temperature and then was stirred overnight. EtOAc (100 mL) was added. The organic solution was washed with citric acid solution, NaHCO₃ solution, and NaCl solution. The organic layer was separated and dried with MgSO₄ and then was evaporated to yield a brown oil. The crude oil product was used without further purification.

MH⁺ 439.3, MH⁺ 339.2 (M−Boc)

Step I

A solution of the oil isolated in Step H (1.1 g, 2.5 mmol) in 20% TFA:CH₂Cl₂ (50 mL) was stirred at room temperature for one hour. The solvent and most of TFA was evaporated, and EtOAc (100 mL) was added. The EtOAc solution was washed with NaHCO₃ solution and NaCl solution. The organic layer was dried with MgSO₄ and evaporated to yield a brown oil.

MH⁺ 339.2

Step J

To a solution of the oil isolated in Step I (0.74 g, 2.1 mmol), 2-nitro-5-phenoxybenzaldehyde (0.55 g, 2.2 mmol), and HOAc (0.15 mL) in 1,2-dichloroethane (20 mL) was added NaBH₃CN (0.20 g, 3.2 mmol). The reaction mixture was stirred at room temperature overnight. The reaction mixture was poured into 1N NaOH (10 mL) and extracted with EtOAc (100 mL). The organic layer was dried with MgSO₄ and evaporated. Purification by column chromatography (1:1 heptane:EtOAc) yielded a colorless oil.

MH⁺ 566.2

Step K

A solution of the oil isolated in Step J (0.41 g, 0.72 mmol) in 1N HCl (2 mL) in THF (5 mL) was stirred at room temperature overnight. EtOAc (50 mL) and NaHCO₃ solution (20 mL) were added to the reaction mixture. The organic layer was separated, dried with MgSO₄ and evaporated to yield a colorless oil.

MH⁺ 522.3

Step L

To a solution of the oil isolated in Step K (0.14 g, 0.27 mmol) in MeOH (5 mL) was added NaBH₄ (0.01 g, 0.27 mmol). The reaction mixture was stirred at room temperature for one hour. The MeOH was evaporated, and EtOAc (50 mL) was added to the residue. The EtOAc solution was then washed with NaCl solution, dried with MgSO₄, and evaporated to yield a colorless oil.

MH⁺ 524.6

Step M

To a solution of the oil isolated in Step L (0.14 g) in MeOH (10 mL), 10% Pd/C (0.01 g) was added under N₂. The mixture was hydrogenated at 5 psi for one hour. The catalyst was removed by filtration, and the MeOH was evaporated to yield an oil.

MH⁺ 494.3

Step N

The oil (0.1 g) isolated in Step M was re-dissolved in EtOH (5 mL). BrCN (3M in CH₂Cl₂, 0.02 mL) was added, and the reaction mixture was stirred at room temperature overnight. The EtOH was evaporated to yield an oil which was stirred in diethyl ether (50 mL) for 30 min. The resulting solid was collected and recrystallized from ethyl ether/ethyl acetate (3:1) to yield the title compound as an off-white solid, as its HBr salt.

MH⁺ 519.5

¹H NMR (300 MHz, CDCl₃): δ0.9-2.1 (m, 22H), 2.6-2.7 (m, 1H), 2.84 (s, 0.63×3H), 3.3-3.5 (m, 2H), 4.19 (d, J=5.7 Hz, 2H), 6.72 (s, 1H), 6.98 (d, J=7.7 Hz, 2H), 7.12 (m, 1H), 7.2-7.3 (m, 3H), 8.18 (s, 1H)

Example 32

(S)-enantiomer of 4-(2-Amino-6-phenoxy-4H-quinazolin-3-yl)-N-cyclohexyl-N-methyl-4-(tetrahydro-pyran-4-yl)-butyramide (Compound #709)

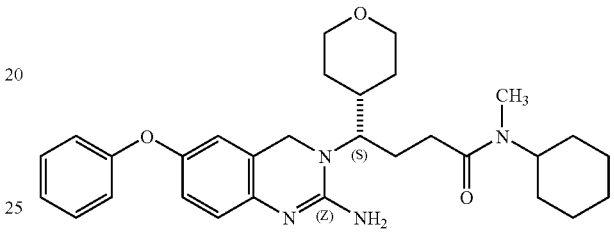

Step A

To a solution of N-benzyloxycarbonyl-α-phosphonoglycine trimethyl ester (6.6 g, 20 mmol) and 1,1,3,3-tetramethylguanidine (3.3 mL, 27 mmole) in THF (50 mL) was added dropwise a solution of tetrahydro-4H-pyran-4-one (2 g, 20 mmol) in THF (30 mL). The reaction mixture was stirred at room temperature overnight, and then 5% HCl (50 mL) was added. The reaction mixture was then extracted with EtOAc (200 mL and then 100 mL portions). The combined organic layers were washed with aqueous NaCl solution, dried with MgSO₄, and evaporated. The residue was recrystallized twice from EtOAc and hexane to yield a white solid.

MH⁺ 306.0

Step B

A solution of the solid isolated in Step A (4 g; 13 mmol) and R, R-(+)-BPE (1,2-bis(phospholano)ethane)-Rh catalyst (0.08 g) in MeOH (60 mL) was placed into a Parr high pressure reactor and subjected to hydrogenation under 410 psi for three days. The MeOH was removed by evaporation, and the residue was purified on a column (1:1 hexane:EtOAc) to yield an oil which turned to solid on standing overnight.

MH⁺ 308.1

Step C

To a solution of the solid isolated in Step B (4.5 g, 14.5 mmol) in MeOH (30 mL) was added 1N NaOH (14.5 mL, 14.5 mmol). The reaction mixture was stirred at room temperature overnight. The MeOH was evaporated, and resulting solution was extracted with EtOAc (200 mL). The organic layer was washed with dilute aqueous HCl solution, NaHCO₃ solution, and NaCl solution, dried with MgSO₄, and evaporated to yield a colorless oil.

MH⁺ 394.1, MH⁻ 392.0

Step D

To an ice cooled solution of the oil isolated in Step C (3.8 g, 13 mmol), N, O-dimethylhydroxylamine.HCl salt (1.4 g, 15 mmol), and HOBT (2 g, 16 mmol) in CH₂Cl₂ (100 mL) was added TEA (3.6 mL) followed by addition of EDC (3.0 g, 16 mmol). The reaction mixture was allowed to warm to room temperature and was stirred overnight. EtOAc (100 mL) was added, and the reaction mixture was then washed with citric acid solution, NaHCO₃ solution, and NaCl solution. The organic layer was separated, dried with MgSO₄, and evaporated to yield a colorless oil. The crude oil product was used without further purification.

MH⁺ 337.1

Step E

To an ice cooled solution of the oil isolated in Step D (4.3 g, 13 mmol) in THF (200 mL) was slowly added LAH (1M solution in THF, 14 mL) while keeping the temperature below 5° C. The ice bath was removed, and the reaction mixture was stirred at room temperature for 20 min. A solution of NaHSO₄ (1.5 g) in water (5 mL) was slowly added to quench the reaction. The reaction mixture was then filtered through Celite®. Then, EtOAc (200 mL) was added, and the organic layer was washed with NaCl solution, dried with MgSO₄ and evaporated to yield an oil. The crude oil product was used without further purification.

MH⁺ 278.0

Step F

To an ice cooled solution of trimethyl phosphonoacetate (6.4 mL, 13 mmol) in THF (200 mL) was added 60% NaH in mineral oil (1.1 g, 26 mmol) in portions. The ice bath was removed, and the reaction mixture was stirred at room temperature for 30 min. The solution was cooled to 0° C. again before a solution of the oil isolated in Step E (3.8 g, 13 mmol) in THF (100 mL) was added. The cooling bath was removed, and the reaction mixture was stirred at room temperature for another 20 min. Water (50 mL) was added, and most of THF was evaporated. The product was extracted into EtOAc (200 mL), and the organic layer was washed with NaCl solution, dried with MgSO₄, and evaporated to yield a residue. Purification by column chromatography (1:1 heptane:EtOAc) yielded an oil which turned to a white solid upon standing.

MH⁺ 334.1

Step H

A solution of the solid isolated in Step G (2.7 g, 8 mmol), 10% Pd/C (2.7 g), Boc anhydride (1.83 g, 8 mmol), and 1,4-cyclohexadiene (7.5 mL, 80 mmol) in EtOH (50 mL) was stirred at room temperature for 3 hours. The catalyst was removed by filtration, and the EtOH was evaporated to yield an oil MH⁺ 302.2, MH⁺ 202.2 (M−Boc)

Step I:

A solution of the oil isolated in Step H (2.5 g, 8 mmol) in MeOH (20 mL) and 1N NaOH (8.0 mL) was stirred at room temperature overnight. Then the pH was adjusted to about pH 2 by the addition of dilute HCl solution. The MeOH was removed in vacuo, and the product was extracted into EtOAc (100 mL). The organic layer was washed with NaCl solution, dried with MgSO₄, and evaporated to yield an oil.

MH⁻ 286.1

Step J

To an ice cooled solution of N-methylcyclohexylamine (1.1 mL, 8 mmol), the oil isolated in Step 1 (2.1 g, 7.3 mmol), and HOBT (1.1 g, 8 mmol) in CH₂Cl₂ (100 mL) was added TEA (2 mL) followed by addition of EDC (1.5 g, 8 mmol). The reaction mixture was allowed to warm to room temperature and then was stirred overnight. Then, EtOAc (100 mL) was added. The organic solution was washed by citric acid solution, NaHCO₃ solution, and NaCl solution. The organic layer was dried with MgSO₄ and evaporated to yield a brown oil. The crude oil product was used without further purification.

MH⁺ 383.2, MH⁺ 283.1 (M−Boc)

Step K

A solution of the oil isolated in Step J (2.44 g, 6.4 mmol) in 20% TFA:CH₂Cl₂ (50 mL) was stirred at room temperature for 30 min. The solvent and most of the TFA was evaporated to give a residue to which EtOAc (100 mL) was added. The reaction mixture was washed with NaHCO₃ solution and NaCl solution. The organic layer was dried with MgSO₄ and evaporated to yield a brown oil.

MH⁺ 283.2

Step L

To a solution of the oil isolated in Step K (1.3 g, 4.6 mmol), 2-nitro-5-phenoxybenzaldehyde (1.2 g, 4.9 mmol) and HOAc (0.28 mL) in 1,2-dichloroethane (20 mL), was added NaBH(OAc)₃ (0.57 g, 9 mmol). The reaction mixture was stirred at room temperature overnight. The reaction mixture was poured into 1N NaOH (10 mL), and the resulting mixture was extracted with EtOAc (100 mL). The organic layer was dried with MgSO₄ and evaporated to yield a residue. The residue was purified by column chromatography (1:1 heptane/EtOAc) to yield a colorless oil.

MH⁺ 510.1

Step M

To a solution of the oil isolated in Step L (0.6 g, 1.2 mmol) in MeOH (20 mL) was added 10% Pd/C (0.06 g) under N₂. The mixture was hydrogenated at 10 psi for two hours. The catalyst was removed by filtration, and the MeOH was evaporated. Purification by preparative TLC (100% EtOAc) yielded a colorless oil.

(MH⁺ 480.2)

Step N

The oil isolated in Step M was dissolved in EtOH (5 mL), and BrCN (3M solution in CH₂Cl₂, 0.16 mL) was added. The reaction mixture was stirred at room temperature overnight, and then the EtOH was evaporated. The resulting residue was stirred in diethyl ether (50 mL) for 30 min. The resulting solid was collected and recrystallized from diethyl ether/ethyl acetate (4:1) to yield the title compound as a yellow solid as its HBr salt.

MH⁺ 519.5

¹H NMR (300 MHz, CDCl₃): δ1.1-2.0 (m, 18H), 2.15-2.21 (m, 1H), 2.60-2.71 (m, 1H), 2.82 (s, 0.37×3H), 2.90 (s, 0.63× 3H), 3.18-3.51 (m, 3H), 3.83-4.00 (m, 2H), 6.77 (s, 1H), 6.91 (d, J=8 Hz, 2H), 7.11 (t, J=5.8 Hz, 1H), 7.27 (m, 3H), 8.22 (s, 1H).

Example 33

(S)-enantiomer of 4-(2-Amino-6-phenoxy-4H-quinazolin-3-yl)-5-hydroxy-pentanoic acid cyclohexyl-methyl-amide (Compound #558)

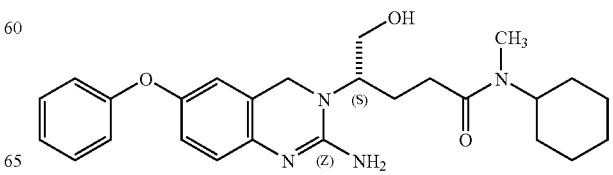

Step A

To an ice cooled solution of N-methylcyclohexylamine (3.4 mL, 26 mmol), N-carbobenzyloxy-D-glutamic acid methyl ester (6 g, 20 mmol), and HOBT (3.6 g, 26 mmol) in CH$_2$Cl$_2$ (200 mL), was added TEA (6 mL) followed by the addition of EDC (6.0 g, 30 mmol). The reaction mixture was allowed to warm to room temperature and stirred overnight. EtOAc (200 mL) was added to the reaction mixture. The resulting solution was washed by citric acid solution, NaHCO$_3$ solution, and NaCl solution. The organic layer was separated, dried with MgSO$_4$, and evaporated to yield an oil. The crude oil product was used without further purification.

MH$^+$ 391.2

Step B

LiBH$_4$ (2M solution in THF, 20 mL, 40 mmol) was added to a solution of the oil isolated in Step A (8 g, 20 mmol) in THF (100 mL). The resulting solution was refluxed under N$_2$ for 8 hours and then was stirred at room temperature overnight. Most of THF was removed under vacuum, and EtOAc (300 mL) was added to the residue. The EtOAc layer was washed by aqueous NaCl solution, dried with MgSO$_4$, and evaporated to yield a colorless oil.

MH$^+$ 363.1

Step C

To a solution of the oil isolated in Step B (7.5 g, 20 mmol) in MeOH (100 mL) was added 10% Pd/C (0.8 g) under N$_2$. The reaction mixture was hydrogenated at 5 psi for 20 hours. The catalyst was removed by filtration, and the MeOH was evaporated to yield a colorless oil.

MH$^+$ 229.2

Step D

To a solution of the oil isolated in Step C (6 g, 26 mmol), 2-nitro-5-phenoxybenzaldehyde (6.4 g, 26 mmol) and HOAc (1.6 mL) in 1,2-dichloroethane (150 mL), was added NaBH$_3$CN (2.5 g, 40 mmol). The reaction mixture was stirred at room temperature over the weekend. Then the reaction mixture was poured into 1N NaOH (50 mL) and extracted with EtOAc (2×100 mL). The organic extracts were combined, dried with MgSO$_4$, and evaporated to yield a residue. Purification by column chromatography (1:1 heptane:EtOAc) yielded a yellow oil.

MH$^+$ 456.1

Step E

To a solution of the oil isolated in Step D (6.3 g, 20 mmol) in MeOH (100 mL) was added 10% Pd/C (0.6 g) under N$_2$. The reaction mixture was hydrogenated at 5 psi for 3 hours. The catalyst was removed by filtration, and the MeOH was evaporated to yield a brown oil.

MH$^+$ 426.3

Step F

A solution of the oil isolated in Step E (0.5 g, 1.2 mmol) and BrCN (3M solution in CH$_2$Cl$_2$, 0.4 mL) in EtOH (50 mL) was stirred at room temperature overnight. The EtOH was evaporated to yield an oil which was stirred in diethyl ether (100 mL) for one hour. The resulting solid was collected to yield the title compound as a solid as its HBr salt.

MH$^+$ 451.2

$^1$H NMR (300 MHz, CDCl$_3$): δ1.0-1.9 (m, 12H), 2.35 (m, 2H), 2.75 (d, J=3.22 Hz, 3H), 3.4 (m, 1H), 3.6-3.8 (m, 2H), 4.27-4.36 (m, 2H), 4.6 (d, J=14.5 Hz, 1H), 6.73 (d, J=2.15 Hz, 1H), 6.83 (m, 1H), 6.94 (d, J=7.7 Hz, 2H), 7.1 (m, 2H), 7.3 (t, J=8.04 Hz, 2H).

Example 34

(S)-enantiomer of 2-(2-Amino-6-phenoxy-4H-quinazolin-3-yl)-pentanedioic acid bis-(cyclohexyl-methyl-amide) (Compound #634)

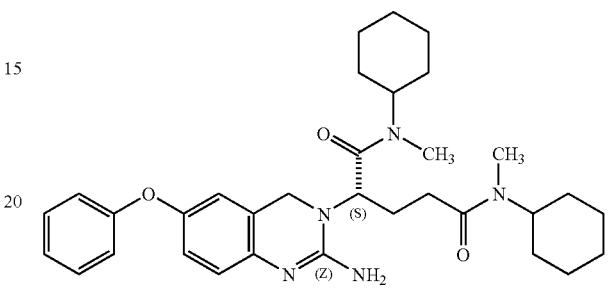

Step A

To a solution of the material prepared as in Example 33, Step A (7.5 g, 19 mmol) in MeOH (40 mL) was added 1N NaOH (24 mL, 24 mmol). The reaction mixture was stirred at room temperature overnight and then was acidified with citric acid (10 g). The MeOH was removed by vacuum. The resulting solution was extracted with EtOAc (2×200 mL). The combined organic layers were washed with NaCl solution, dried with MgSO$_4$, and concentrated to yield an oil.

MH$^-$ 375.0

Step B

To an ice cooled solution of N-methylcyclohexylamine (0.31 mL, 2.2 mmol), the oil isolated in Step A (0.8 g, 2.1 mmol), and HOBT (0.4 g, 3 mmol) in CH$_2$Cl$_2$ (50 mL), was added TEA (0.6 mL) followed by addition of EDC (0.6 g, 3 mmol). The reaction mixture was allowed to warm to room temperature and then was stirred overnight. EtOAc (100 mL) was then added, and the reaction mixture was washed with citric acid solution, NaHCO$_3$ solution, and NaCl solution. The organic layer was dried with MgSO$_4$ and evaporated to yield an oil. The crude oil product was used without further purification.

MH$^+$ 472.5

Step C

To a solution of the oil isolated in Step B (1.0 g, 2.1 mmol) in MeOH (40 mL) was added 10% Pd/C (0.1 g) under N$_2$. The mixture was hydrogenated at 5 psi overnight. The catalyst was removed by filtration, and MeOH was evaporated to yield a colorless oil.

MH$^+$ 338.3

Step D

To a solution of the oil isolated in Step D (0.7 g, 21 mmol), 2-nitro-5-phenoxybenzaldehyde (0.5 g, 21 mmol) and HOAc (0.12 mL) in 1,2-dichloroethane (20 mL), was added NaBH$_3$CN (0.25 g, 4 mmol). The reaction mixture was stirred at room temperature over the weekend. The reaction mixture was poured into 1N NaOH (50 mL) and extracted with EtOAc (100 mL). The organic layer was dried over MgSO$_4$ and evaporated to yield a residue. The residue was purified on a column (1:1 heptane:EtOAc) to yield an oil.

MH$^+$ 565.6

Step E

To a solution of the oil isolated in Step D (0.56 g, 1 mmol) in MeOH (20 mL), 10% Pd/C (0.05 g) was added. The reaction mixture was hydrogenated at 5 psi for 2 hours. The catalyst was removed by filtration, and the MeOH was evaporated. Purification by preparative TLC yielded a colorless oil.

MH+ 535.3

Step F

A solution of the oil isolated in Step E (0.15 g, 0.3 mmol) and BrCN (3M solution in $CH_2Cl_2$, 0.1 mL) in EtOH (10 mL) was stirred at room temperature overnight. The EtOH was evaporated, and the resulting oil was stirred in diethyl ether (50 mL) for one hour. The resulting solid was collected to yield the title compound as a solid as its HBr salt.

MH+ 560.3

$^1$H NMR (300 MHz, CDCl$_3$): δ1.0-2.1 (m, 22H), 2.35 (m, 2H), 2.63 (s, 3H), 2.82 (s, 3H), 2.7-2.9 (m, 2H), 3.4 (m, 1H), 3.99 (m, 1H), 4.3 (m, 2H), 4.86 (m, 1H), 6.6-7.3 (m, 8H).

Example 35

3-[2-Amino-6-(3-methyl-butoxy)-4H-quinazolin-3-ylmethyl]-N-cyclohexyl-N-methyl-benzamide (Compound #517)

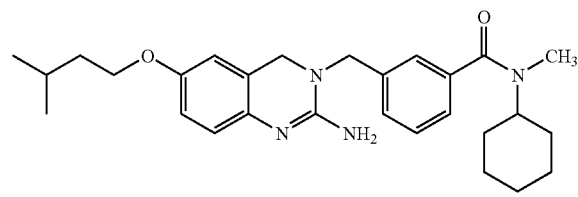 [SMILES: CC(C)CCOc1ccc2c(c1)CN(Cc1cccc(C(=O)N(C)C3CCCCC3)c1)C(N)=N2]

Step A

To a reaction vessel containing isoamyl alcohol (44 mg, 0.5 mmol), triphenylphosphine (197 mg, 0.75 mmol) in THF (1 mL), and 5-hydroxy-2-nitrobenzaldehyde (125 mg, 0.75 mmol) in THF (1 mL) was added diisopropylazodicarboxylate (148 μL, 0.75 mmol) at 0° C. The reaction mixture was allowed to warm to room temperature and then was stirred at 25° C. for 3 h. The solvent was removed in vacuo, and the resulting residue was purified by reverse-phase chromatography to yield an oil.

Step B

To a solution of the oil isolated in Step A (62 mg, 0.26 mmol) in DCE (0.75 mL) was added 3-aminomethyl-N-cyclohexyl-N-methyl-benzamide (79 mg, 0.32 mmol) in DCE (0.75 mL) followed by addition of HOAc (15 μL). The reaction mixture was stirred at 25° C. for 30 min, and then NaBH(OAc)$_3$ (93 mg, 0.44 mmol) in DMF (0.3 mL) was added. The reaction mixture was stirred at 25° C. for 20 h. After quenching with $H_2O$, the solvent was removed in vacuo to yield crude product.

Step C

To a solution of the crude product isolated in Step B in ethanol (2 mL) was added zinc dust (588 mg, 9 mmol) and NH$_4$Cl (120 mg, 2.25 mmol). The reaction mixture was irradiated (μwave) at 85° C. for 10 min. The insolubles were removed by filtration and washed with ethanol (1 mL).

Step D

To the filtrate isolated in Step C was added cyanogen bromide (0.36 mL, 1.8 mmol, 5M solution in CH$_3$CN). The reaction mixture was stirred at 25° C. for 18 h. After quenching with 3M NaOH (0.4 mL), the reaction mixture was concentrated. The resulting residue was taken up in 1% TEA:CH$_2$Cl$_2$ (0.8 mL) and H$_2$O (0.35 mL). The solution was absorbed onto diatomaceous earth and eluted with 1% triethylamine/ethyl acetate. The eluate was concentrated to a residue and purified by reverse-phase chromatography to yield the title compound as an oil, as its corresponding trifluoroacetate salt.

MS m/z (MH+) calcd 463.3, found 463.5

Example 36

N-Cyclohexyl-3-[2-methoxyamino-6-(2-methoxyphenyl)-4H-quinazolin-3-ylmethyl]-N-methyl-benzamide (Compound #605)

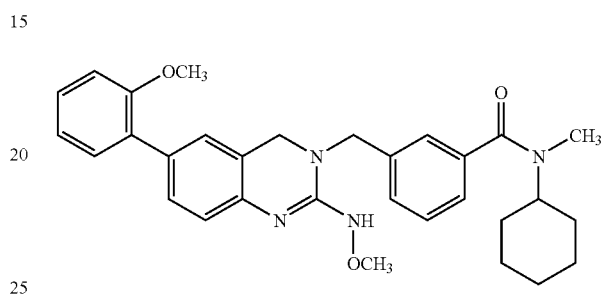

Step A

To a round-bottomed flask containing KNO$_3$ (14.3 g, 0.14 mol) in H$_2$SO$_4$ (109 mL) was added 3-bromobenzaldehyde (25 g, 0.14 mol), over 15 min, at 0° C. The reaction mixture was vigorously stirred at 0° C. for 20 min, poured onto crushed ice (600 mL), and extracted with DCM (3×). The combined organic layers were dried, filtered, and concentrated in vacuo. The residue was recrystallized from EtOAc/hexane to yield a yellow solid.

Step B

To a flask containing 3-cyanobenzoic acid (10 g, 0.068 mol) in DCM (300 mL) was added diisopropyl ethylamine (47 mL, 0.27 mol) and N-methylcyclohexylamine (13.3 mL, 0.1 mol) with stirring. The resulting solution was cooled to approximately 0° C., and then 2-chloro-1,3-dimethylimidazolium chloride (23 g, 0.14 mol) was added with stirring. After 5 minutes the cooling bath was removed and the reaction mixture was stirred toward room temperature for 4 h. The reaction was quenched with 100 mL of water, transferred to a separatory funnel, mixed, and the layers were separated. The aqueous layer was extracted with DCM (2×100 mL), and the combined organic layers were dried over Na$_2$SO$_4$, filtered, concentrated to a residue, and placed under vacuum (~1 mm Hg) for 1 h to yield a residue.

Step C

The residue prepared in Step B was transferred to a Parr bottle with EtOH (250 mL) and then degassed and blanked with nitrogen before 12N HCl$_{(aq)}$ (28 mL, 0.34 mol) and 10% Pd/C (1.6 g) slurried in water were added. The slurry was exposed to 50 psi of H$_2$ for 14 h at room temperature using standard Parr techniques and then degassed with nitrogen for 5 minutes and filtered through a pad of Celite®. The reaction mixture was then concentrated to the aqueous layer and transferred to a separatory funnel with water (100 mL) and DCM (50 mL). The layers were separated and the aqueous layer was extracted with DCM (2×25 mL). The combined organic layers were extracted with 0.5N HCl (25 mL). The layers were separated, and the combined aqueous layers were adjusted to pH>9 with 3N NaOH and extracted with DCM (5×50 mL). The combined organics were dried over Na$_2$SO$_4$, filtered, concentrated to a residue, and placed under vacuum (~1 mm

143

Hg) for 1 day. This two-step procedure yielded a residue contaminated by diisopropyl ethyl amine but of sufficient purity for subsequent chemical transformations.

MS m/z (MH$^+$) calcd 247.2, found 247.3

Step D

To a round-bottomed flask containing the residue isolated in Step C (6.7 g, 0.032 mol) in DCE (175 mL) was added the material isolated in Step A (7.4 g, 0.032 mol). After stirring at room temperature for 30 min, NaBH(OAc)$_3$ (13.7 g, 0.065 mol) was added, and the reaction mixture was stirred at room temperature for 18 h. The reaction was quenched with 1N NaOH (100 mL). The layers were separated and the aqueous layer was extracted with DCM (3×25 mL). The combined organic layers were dried over MgSO$_4$, filtered, and concentrated in vacuo to constant weight. The resulting residue (14.7 g) was greater than 95% pure by LC/MS analysis and used in subsequent reactions without further purification.

MS m/z (MH$^+$) calcd 460.1, found 460.4

Step E

To a solution of the residue isolated in Step D (543 mg, 1.18 mmol) in ethyl alcohol (5 mL) was added potassium carbonate (245 mg, 1.77 mmol) in water (0.25 mL), 2-methoxyphenylboronic acid (269 mg, 1.77 mmol), and bis(diphenylphosphino)ferrocene dichloropalladium (96 mg, 0.118 mmol). The reaction mixture was irradiated (μwave) at 100° C. for 10 min. After cooling to room temperature, the resulting solution was used directly in the following step.

MS m/z (MH$^+$) calcd 488.3, found 488.6

Step F

To the above filtered solution from Step E was added NH$_4$Cl (0.63 g, 11.8 mmol) and Zn (1.5 g, 23.6 mmol). The reaction slurry was irradiated (μwave) at 80° C. for 15 min. After cooling to room temperature, the reaction mixture was filtered and concentrated. The resulting residue was purified by column chromatography on silica gel (10% EtOAc/heptane containing 1% Et$_3$N) to 60% EtOAc/heptane containing 1% Et$_3$N) to yield a white solid.

MS m/z (MH$^+$) calcd 458.3, found 458.7

Step G

To a round bottom flask fitted with a reflux condenser was added the solid isolated in Step F (0.122 g, 0.267 mmol) dissolved in ethanol (4 mL) and carbon disulfide (6 mL). The resulting solution was heated at reflux for 4 h, cooled to room temperature, and concentrated. The resulting residue was purified by column chromatography on silica gel (2% EtOAc/heptane to 30% EtOAc/heptane) to yield a white solid.

HRMS (ES-TOF) calcd. for C$_{30}$H$_{34}$N$_3$O$_2$S m/z 500.2372 (M+H), found: 500.2

Step H

To a solution of the solid isolated in Step G (42.7 mg, 0.09 mmol) in CH$_3$CN (0.2 mL) was added CH$_3$I (0.021 mL, 0.34 mmol). The resulting solution was stirred at room temperature for 3 h, concentrated to a residue, and dried for 1 h at <1 mmHg to yield a residue.

Step I

To the residue isolated in Step H dissolved in MeOH (0.2 mL) was added MeONH$_2$·HCl (0.016 g, 0.19 mmol), NaHCO$_3$ (0.016 g, 0.19 mmol), and AgOAc (0.016 mg, 0.10 mmol). The resulting solution was stirred at 70° C. for 2 h, cooled to room temperature and concentrated. The resulting residue was suspended in water (1 mL) and extracted with EtOAc (4×0.5 mL). The combined organic layers were dried (Na$_2$SO$_4$) and concentrated. The resulting residue was purified by preparative RP-HPLC to yield an oil, which was determined to be pure product, as well as an additional residue, which was determined to be 70% pure.

HRMS (ES-TOF) calcd. for C$_{31}$H$_{37}$N$_4$O$_3$ m/z 513.2866 (M+H), found: 513.3

144

Example 37

Butane-1-sulfonic acid [2-(2-amino-6-phenoxy-4H-quinazolin-3-yl)-ethyl]-amide (Compound #135)

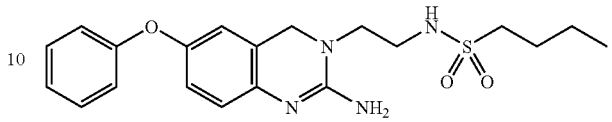

To a solution of the intermediate prepared as in Example 18, Step D (0.16 mmol) in 5 mL of dioxane was added TEA (42 mg, 0.48 mmol) followed by n-butyl sulfonyl chloride (22 mg, 0.14 mmol). The reaction mixture was stirred at room temperature for 3 days. The solvent was removed in vacuo, and the resulting residue was purified on a Gilson to yield the title compound as a yellow solid.

MH$^+$ 430.2

$^1$H NMR (300 MHz, DMSO-d$_6$): δ0.86 (t, J=7.21 Hz, 3H), 1.36 (q, J=7.20 Hz, 2H), 3.00 (t, J=7.67 Hz, 2H), 3.23-3.55 (m, 4H), 4.62 (s, 2H), 6.90-7.41 (m, 9H), 7.80 (br s, 2H).

Example 38

1-Adamantan-1-yl-3-[2-(2-amino-6-phenoxy-4H-quinazolin-3-yl)-ethyl]-urea (Compound #206)

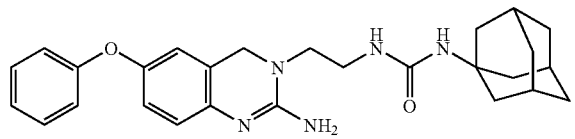 [SMILES: NC1=Nc2ccc(Oc3ccccc3)cc2CN1CCNC(=O)NC12CC3CC(CC(C3)C1)C2]

To a solution of the intermediate prepared as in Example 18, Step D (16.3 mg, 0.137 mmol) in dioxane (5 mL) was added TEA (0.28 mL, 0.41 mmol) followed by 1-adamantyl isocyanate (26.3 mg, 0.137 mmol). The reaction mixture was stirred overnight at room temperature. The solvent was removed in vacuo, and the resulting residue was purified by HPLC to yield the title compound as a white solid.

MH$^+$ 430.2

$^1$H NMR (300 MHz, DMSO-d$_6$): δ1.58-1.96 (m, 15H), 3.24-3.43 (m, 4H), 4.59 (s, 2H), 5.83 (s, 1H), 5.88 (t, 1H), 6.87-7.41 (m, 8H), 7.90 (s, 2H).

Example 39

1-Adamantan-1-yl-3-[2-(2-amino-6-phenoxy-4H-quinazolin-3-yl)-ethyl]-thiourea (Compound #214)

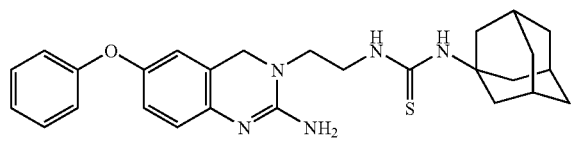 [SMILES: NC1=Nc2ccc(Oc3ccccc3)cc2CN1CCNC(=S)NC12CC3CC(CC(C3)C1)C2]

To a solution of the intermediate prepared as in Example 18, Step D (0.133 mmol) in dioxane (5 mL) was added TEA (0.27 mL, 0.40 mmol) followed by 1-adamantyl isothiocyanate (25.7 mg, 0.133 mmol). The reaction mixture was stirred overnight at room temperature. The solvent was removed in vacuo, and HLPC analysis of the resulting residue indicated mainly unreacted amine was present. The material was redissolved in dioxane (5 mL) and then TEA (0.27 mL, 0.40 mmol) was added followed by 1-adamantyl isothiocyanate (25.7 mg, 0.133 mmol). The reaction mixture was refluxed for 3 h and then was stirred at room temperature overnight. The solvent was removed in vacuo, and the resulting residue was purified by HPLC to yield the title compound as a white solid.

MH$^+$ 476.2

$^1$H NMR (300 MHz, DMSO-d$_6$): δ1.59-2.06 (m, 15H), 3.69 (m, 4H), 4.61 (s, 2H), 6.89-7.40 (m, 10H), 7.82 (s, 2H).

Example 40

[2-(2-Amino-6-phenoxy-4H-quinazolin-3-yl)-ethyl]-carbamic acid isopropyl ester (Compound #220)

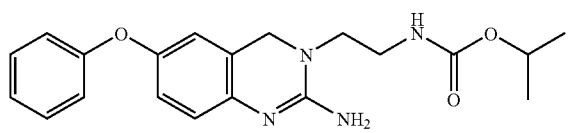 [SMILES: CC(C)OC(=O)NCCN1Cc2cc(Oc3ccccc3)ccc2N=C1N]

To a solution of the intermediate prepared as in Example 18, Step D (0.133 mmol) in dioxane (5 mL) was added TEA (40.3 mg, 0.40 mmol) followed by isopropyl chloroformate (0.133 mL, 0.133 mmol) as a 1.0M solution in toluene. The reaction mixture was stirred overnight at room temperature. The solvent was removed in vacuo to yield a residue that was purified by HPLC to yield the title compound as a white solid.

MH$^+$ 369.1

$^1$H NMR (300 MHz, DMSO-d$_6$): δ1.11 (d, J=6.22 Hz, 6H), 3.29 (m, 4H), 4.58 (s, 3H), 4.64 (m, 1H), 6.88-7.41 (m, 9H), 7.85 (s, 2H).

Example 41

3-[3-(Cyclohexyl-methyl-amino)-propyl]-6-phenoxy-3,4-dihydro-quinazolin-2-ylamine (Compound #428)

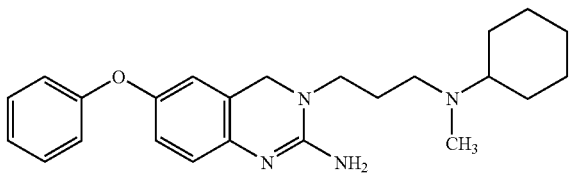 [SMILES: CN(CCCN1Cc2cc(Oc3ccccc3)ccc2N=C1N)C1CCCCC1]

Step A

To a solution of N-(3-bromopropyl)phthalimide (1.61 g, 6 mmol) in 10 mL of DMF was added N-methylcyclohexylamine (2.04 g, 18 mmol). The reaction mixture was heated at 100° C. for 4 h. The reaction mixture was cooled to room temperature and concentrated in vacuo. To the resulting residue was added water (10 mL). The resulting solution was extracted with EtOAc (3×30 mL). The organic extracts were combined, washed with brine, and evaporated to yield a brown oil.

MH$^+$ 301.1

Step B

A solution of the oil isolated in Step A (1.61 g, 5.32 mmol) and hydrazine monohydrate (0.532 g, 10.64 mmol) in methanol was refluxed 3 h. The reaction mixture was concentrated, and water (50 mL) was added to the residue. The resulting solution was acidified with 1N HCl. The reaction mixture was then extracted with EtOAc (4×50 mL). The aqueous layer was basified with NaHCO$_3$ and then was extracted with EtOAc (3×50 mL). The EtOAc extracts were combined, dried (Na$_2$SO$_4$), and concentrated to a residue. The residue did not have the molecular weight of the desired product so the aqueous layer was basified with aqueous ammonia. The resulting solution was extracted with EtOAc (3×50 mL). The organic extracts were combined, washed with brine, dried (Na$_2$SO$_4$), and concentrated to yield a clear oil.

MH$^+$ 171.3

Step C

A solution of the oil isolated in Step B (0.28 g, 1.6 mmol) and 2-nitro-5-phenoxybenzaldehyde (0.27 g, 1.1 mmol) in DCE was stirred for 30 minutes. Then NaBH(OAc)$_3$ (0.34 g, 1.6 mmol) was added, and the reaction mixture was stirred overnight. The reaction mixture was quenched with 1N NaOH (4 mL), and then water (10 mL) was added. The resulting solution was extracted with CH$_2$Cl$_2$ (3×15 mL). The CH$_2$Cl$_2$ extracts were combined, washed with brine, dried (MgSO$_4$), and concentrated to a residue. Purification by flash chromatography 5% (2N NH$_3$ in MeOH) in CHCl$_3$ yielded a yellow oil.

MH$^+$ 398.3

Step D

A solution of the oil isolated in Step C (0.31 g) and palladium on carbon (60 mg) in EtOH (50 mL) was hydrogenated at 40 psi in a Parr shaker for 3 h. The reaction mixture was filtered, and the filtrate was concentrated under reduced pressure to yield a residue.

MH$^+$ 368.3

Step E

To a solution of the residue isolated in Step D (0.78 mmol) in EtOH (20 mL) was added cyanogen bromide in 1 mL of EtOH. The reaction mixture was stirred at room temperature overnight and then refluxed for 3 h. The reaction mixture was cooled and filtered to yield the title compound as an off-white solid.

MH$^+$ 393.2

$^1$H NMR (300 MHz, DMSO-d$_6$): δ0.90-2.00 (m, 12H), 2.70 (d, 3H), 2.90-3.40 (m, 5H), 4.61 (s, 2H), 6.90-7.42 (m, 8H), 7.89 (br s, 2H).

Example 42

[2-(2-Amino-6-phenoxy-4H-quinazolin-3-yl)-ethyl]-methyl-carbamic acid tert-butyl ester (Compound #425)

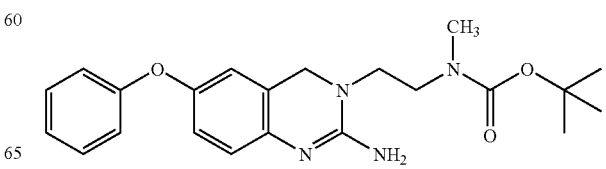

Step A

A solution of N-(2-aminoethyl)-N-methyl carbamic acid tert-butyl ester (0.33 g, 1.90 mmol) and 2-nitro-5-phenoxybenzaldehyde (0.31 g, 1.27 mmol) in DCE was stirred for 30 minutes. Then NaBH(OAc)$_3$ (0.40 g, 1.90 mmol) was added, and the reaction mixture was stirred overnight. The reaction mixture was quenched with 1N NaOH (4 mL), and then water (10 mL) was added. The resulting solution was extracted with CH$_2$Cl$_2$ (3×15 mL). The CH$_2$Cl$_2$ extracts were combined, washed with brine, dried (MgSO$_4$), and concentrated to a residue. Purification by flash chromatography yielded an oil.

MH$^+$ 401.5

Step B

A solution of the oil isolated in Step A (0.40 g) and palladium on carbon (80 mg) in EtOH was hydrogenated at 45 psi in a Parr shaker for 3 h. The reaction mixture was filtered, and the filtrate was concentrated under reduced pressure to yield a residue.

MH$^+$ 372.3

Step C

To a solution of the residue isolated in Step B (0.36 g, 0.97 mmol) in EtOH (20 mL) was added cyanogen bromide (0.113 g, 1.07 mmol) in 1 mL of EtOH. The reaction mixture was stirred at room temperature overnight and then refluxed for 3 h. The reaction mixture was cooled and concentrated to yield a residue. Purification by reverse phase HPLC yielded the title compound as a white solid.

MH$^+$ 397.2

$^1$H NMR (300 MHz, DMSO-d$_6$): δ1.20 (d, 9H), 2.81 (s, 3H), 3.30 (m, 4H), 4.56 (s, 2H), 6.92-7.40 (m, 8H), 7.84 (br s, 2H)

Example 43

Cyclohexanecarboxylic acid [2-(2-amino-6-phenoxy-4H-quinazolin-3-yl)-ethyl]-methyl-amide (Compound #426)

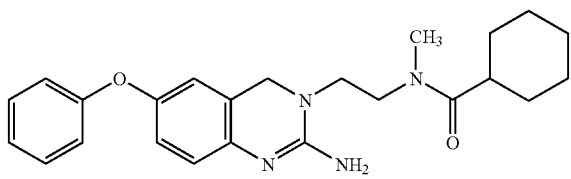 [SMILES: CN(CCN1Cc2cc(Oc3ccccc3)ccc2N=C1N)C(=O)C1CCCCC1]

Step A

A solution of the solid prepared as in Example 40, Step C (0.153 g) in TFA (15 mL) was stirred at room temperature for 3 h. The resulting solution was concentrated in vacuo to yield a residue.

Step B

To a solution of the residue isolated in Step A (0.26 mmol) and TEA (80 mg, 0.79 mmol) in dioxane (10 mL) was added cyclohexanecarbonyl chloride (38.0 mg, 0.26 mmol). The reaction mixture was stirred overnight at room temperature. The resulting solution was concentrated in vacuo to yield a residue. The residue was purified by HPLC to yield the title compound as a white solid.

MH$^+$ 407.3

$^1$H NMR (300 MHz, DMSO-d$_6$): δ1.00-2.00 (m, 11H), 3.01 (br s, 3H), 3.5 (m, 4H), 4.60 (s, 2H), 6.80-7.40 (m, 8H), 7.9 (br s, 2H)

Example 44

4-(2-Amino-6-phenoxy-4H-quinazolin-3-yl)-piperidine-1-carboxylic acid tert-butyl ester (Compound #499)

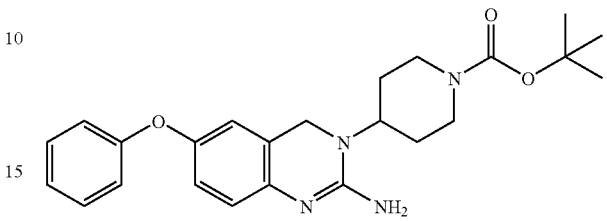

Step A

A solution of 4-amino-1-Boc-piperidine (0.60 g, 3.0 mmol) and 2-nitro-5-phenoxybenzaldehyde (0.48 g, 2.0 mmol) in DCE was stirred for 30 minutes. Then NaBH(OAc)$_3$ (0.64 g, 3.0 mmol) was added, and the reaction mixture was stirred overnight. The reaction mixture was quenched with 1N NaOH (10 mL), and the resulting solution was extracted with CH$_2$Cl$_2$ (2×20 mL). The CH$_2$Cl$_2$ extracts were combined, washed with brine, dried (MgSO$_4$), and concentrated to a residue. Purification by flash chromatography (10% to 40% EtOAc-hexanes) yielded an oil.

Step B

A solution of the oil isolated in Step A (0.67 g) and palladium on carbon (130 mg) in EtOH was hydrogenated at 40 psi in a Parr shaker for 3 h. The reaction mixture was filtered, and the filtrate was concentrated under reduced pressure to yield a residue.

Step C

To a solution of the residue isolated in Step B (0.97 mmol) in EtOH was added cyanogen bromide (0.183 g, 1.73 mmol). The reaction mixture was stirred at room temperature overnight and then refluxed for 1 h. The reaction mixture was cooled and concentrated to yield a residue. Recrystallization of the residue from EtOH yielded the title compound as an off-white solid.

MH$^+$ 423.2

$^1$H NMR (300 MHz, DMSO-d$_6$): δ1.41 (s, 9H), 1.69 (m, 4H), 2.81 (m, 2H), 4.09 (m, 3H), 4.48 (s, 2H), 6.95-7.42 (m, 8H), 7.88 (s, 2H)

Example 45

[[4-(2-Amino-6-phenoxy-4H-quinazolin-3-yl)-piperidin-1-yl]-cyclohexyl-methanone (Compound #522)

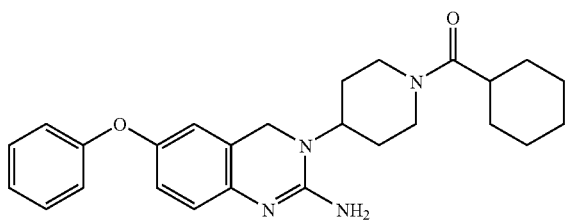 [SMILES: NC1=Nc2ccc(Oc3ccccc3)cc2CN1C1CCN(C(=O)C2CCCCC2)CC1]

Step A

A solution of the solid prepared as in Example 44, Step C (0.350 g) in TFA (20 mL) was stirred at room temperature for 5 h. The resulting solution was concentrated in vacuo to yield a residue.

Step B

To a solution of the residue isolated in Step A (0.23 mmol) and TEA (70 mg) in dioxane (5 mL) was added cyclohexanecarbonyl chloride (34 mg). The reaction mixture was stirred overnight at room temperature. The resulting solution was concentrated in vacuo to yield the title compound as a yellow solid.

MH+ 433.2

$^1$H NMR (300 MHz, DMSO-d$_6$): 61.00-2.01 (m, 15H), 3.4 (m, 2H), 4.1 (m, 2H), 4.5 (m, 3H), 6.9-7.4 (m, 8H), 7.9 (br s, 2H)

Example 46

(R)-enantiomer of cyclohexanecarboxylic acid [2-(2-amino-6-phenoxy-4H-quinazolin-3-yl)-1-cyclohexyl-ethyl]-amide (Compound #636)

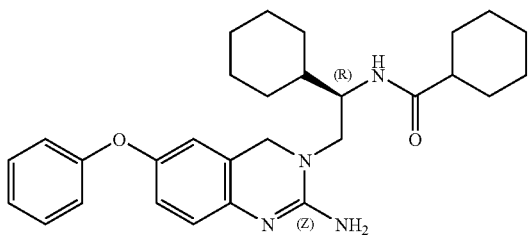 [SMILES: NC1=Nc2ccc(Oc3ccccc3)cc2CN1C[C@H](NC(=O)C1CCCCC1)C1CCCCC1]

Step A

To a solution of 5-fluoro-2-nitrobenzoic acid (6.1 g, 33.0 mmol) in toluene (10 mL) was added thionyl chloride (8.0 mL, 110 mmol). The reaction mixture was refluxed for 3.5 h. The solvent was then evaporated, and the resulting residue was poured into 28% aqueous ammonia solution (30 mL). A yellow solid formed which was extracted into ethyl acetate. The ethyl acetate solution was washed with brine, dried (Na$_2$SO$_4$), and concentrated to yield a residue. The residue was recrystallized from ethyl acetate and hexanes to yield a yellow solid.

Step B

A solution of the yellow solid isolated in Step A (6.13 g, 33.3 mmol), phenol (3.14 g, 33.4 mmol), and K$_2$CO$_3$ (5.52 g, 40.0 mmol) in DMF (30 mL) was heated at 130° C. for 2 h. The DMF was evaporated to yield a yellow solid that was washed with hexane. Purification by HPLC yielded a yellow solid.

Step C

To a solution of the yellow solid isolated in Step B (4.0 g, 15.5 mmol) in THF (10 mL) was added BH$_3$.THF (1M solution in THF, 80 mL). The reaction mixture was refluxed overnight. The reaction mixture was cooled to 0° C., and then concentrated HCl (20 mL) was added. The resulting solution was refluxed 1 h and then cooled. The THF was evaporated, and NaOH solution (100 mL) was added. The resulting solution was extracted with CH$_2$Cl$_2$ (3×100 mL). The organic extracts were combined, washed with brine (100 mL), and dried (MgSO$_4$). Concentration yielded crude product that was purified by column chromatography (100% EtOAc) to yield a residue.

Step D

To a mixture of N-Boc-D-cyclohexylglycine (2.40 g, 9.33 mmol) and N,O-dimethylhydroxylamine.hydrochloride (0.91 g, 9.4 mmol) was added DMF (10 mL) and TEA (1.9 g, 18.66 mmol) followed by HBTU (3.6 g, 9.4 mmol). The reaction mixture was stirred at room temperature overnight. The reaction was quenched with water (50 mL) and then was extracted with EtOAc (3×50 mL). The organic extracts were combined, washed with brine (3×50 mL) and concentrated to an oil containing some solid. $^1$H NMR indicated that the product was contaminated with HBTU. The crude material was dissolved in EtOAc (60 mL) and was washed with 1N HCl (10 mL), water (3×10 mL), and brine (30 mL). The resulting solution was dried and concentrated to yield a residue.

Step E

A solution of LAH (0.37 g, 9.6 mmol) in 20 mL of THF was cooled to about 0° C. Then a solution of the residue isolated in Step D (2.23 g, 7.4 mmol) in THF (20 mL) was added, and the reaction mixture was warmed to room temperature. The reaction mixture was stirred at room temperature for 20 min and then was re-cooled to 0° C. The reaction was quenched with a solution of NaHSO$_4$ (1.8 g) in water (10 mL). The reaction mixture was then extracted with EtOAc (3×50 mL). The organic extracts were combined, washed with brine, dried (MgSO$_4$), and concentrated under reduced pressure to yield a residue.

Step F

A solution of the residue isolated in Step E (1.54 g, 7.4 mmol) and the residue isolated in Step C (1.82 g, 7.4 mmol) in DCE was stirred for 30 minutes. Then NaBH(OAc)$_3$ (1.57 g, 7.4 mmol) was added, and the reaction mixture was stirred overnight. The reaction mixture was quenched with 1N NaOH (10 mL). The resulting solution was extracted with CH$_2$Cl$_2$ (3×30 mL). The CH$_2$Cl$_2$ extracts were combined, washed with brine (1×30 mL), dried (MgSO$_4$), and concentrated to a residue. Purification by flash chromatography (30% EtOAc-hexanes) yielded an orange oil.

MH+ 470.2

Step G

A solution of the oil isolated in Step F (1.88 g) and palladium on carbon (20 mg) in EtOH was hydrogenated at 45 psi in a Parr shaker for 3 h. The reaction mixture was filtered through Celite®, and the filtrate was concentrated under reduced pressure to yield a residue.

MH+ 440

Step H

To a solution of the residue isolated in Step G (2.5 mmol) in EtOH (30 mL) was added cyanogen bromide (0.278 g, 2.6 mmol). The reaction mixture was stirred at room temperature for 1 h and then was refluxed for 3 h. The reaction mixture was cooled and concentrated to yield a residue. Recrystallization of the residue from EtOH yielded a solid. A second recrystallization was done to yield a second crop of product.

Step I

A solution of the solid isolated in Step H (0.24 g) in TFA (10 mL) was stirred at room temperature for 5 h. The solution was concentrated in vacuo to yield a residue.

Step J

To a solution of the residue isolated in Step 1 (0.22 mmol) and TEA (55.1 mg, 0.55 mmol) in dioxane (10 mL) was added cyclohexanecarbonyl chloride (33 mg, 0.22 mol). The reaction mixture was stirred for 2 h at room temperature. The solution was concentrated in vacuo to yield the title compound as a white solid.

MH+ 475.5

$^1$H NMR (300 MHz, DMSO-$d_6$): δ1.00-2.00 (m, 22H), 3.4 (m, 2H), 4.0 (m, 1H), 4.5 (d, J=15.2 Hz, 2H), 4.6 (d, J=15.2 Hz, 2H), 6.8-7.4 (m, 9H), 7.83 (br s, 2H)

Example 47

3-[1-(2-Amino-6-phenoxy-4H-quinazolin-3-yl)-propyl]-N-cyclohexyl-N-methyl-benzamide (Compound #204)

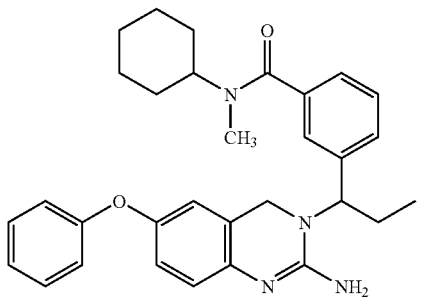 [SMILES: CCC(c1cccc(C(=O)N(C)C2CCCCC2)c1)N1Cc2cc(Oc3ccccc3)ccc2N=C1N]

Step A

A mixture of 3-propionylbenzoic acid (0.194 g, 1.09 mmol), HBTU (0.413 g, 1.09 mmol), and N-ethylmorpholine (0.38 g, 3.38 mmol) in DMF (20 mL) was stirred for 15 minutes. Then N-methylcyclohexylamine (0.351 g, 3.11 mmol) was added, and the reaction mixture was stirred over the weekend. With thorough mixing, 75 mL of 1N HCl and EtOAc were added. The layers were separated, and the organic layer was washed three times with saturated aqueous NaCl solution. The organic layer was dried (Na$_2$SO$_4$), filtered and yield a a thick oil.

MH$^+$ 274.2

Step B

A solution of the oil isolated in Step A (0.34 g, 1.25 mmol) and hydroxylamine (0.062 g, 1.88 mmol, 50% solution in water) in EtOH (10 mL) was refluxed for 2.5 h. The reaction mixture was then cooled and diluted with water (75 mL). The resulting mixture was extracted with EtOAc. The organic layer was separated, dried (Na$_2$SO$_4$), filtered, and evaporated to yield a residue.

Step C

A solution of the residue isolated in Step B (0.388 g, 1.35 mmol) and zinc (4.39 g) in HOAc (35 mL) was stirred overnight. After overnight stirring, the reaction mixture was filtered through Dicalite. The filtrate was evaporated to yield a residue. The residue was treated with excess 3N NaOH, and the resulting solution was extracted with diethyl ether. The diethyl ether extract was dried (Na$_2$SO$_4$), filtered, and evaporated to yield an oil.

MH$^+$ 275.2

Step D

A solution of the oil isolated in Step C (0.187 g, 0.68 mmol) and 2-nitro-5-phenoxybenzaldehyde (0.165 g, 0.68 mmol) in DCE (3.5 mL) was stirred for 15 minutes. Then NaBH(OAc)$_3$ (0.200 g, 0.94 mmol) was added, and the reaction mixture was stirred overnight. To the reaction mixture was added 3N NaOH until the pH was basic. The resulting solution was mixed thoroughly with CH$_2$Cl$_2$. The layers were separated, and the organic layer was dried (Na$_2$SO$_4$), filtered, and evaporated to yield a thick residue.

MH$^+$ 502.5

Step E

A solution of the residue isolated in Step D (0.337 g, 0.67 mmol) and stannous chloride monohydrate (0.833 g, 3.69 mmol) in EtOH (4 mL) was refluxed for 2 h. The solution was cooled, and aqueous sodium bicarbonate solution was added. EtOAc was added to this mixture, and the mixture was filtered through Dicalite. The organic layer was separated, dried (Na$_2$SO$_4$), filtered, and evaporated to yield a thick brown oil.

MH$^+$ 427.5

Step F

To a solution of the oil (0.068 g, 0.14 mmol) prepared in Step E in EtOH (4 mL) was added cyanogen bromide (0.025 g, 0.24 mmol). The reaction mixture was refluxed for 2 h. After cooling, the reaction mixture was evaporated to yield a clear brown glass. The glass was triturated three times with diethyl ether. Filtration yielded the title compound as a tan solid.

Example 48

2-(2-Amino-6-phenoxy-4H-quinazolin-3-yl methyl)-N-cyclohexyl-N-methyl-isonicotinamide (Compound #508)

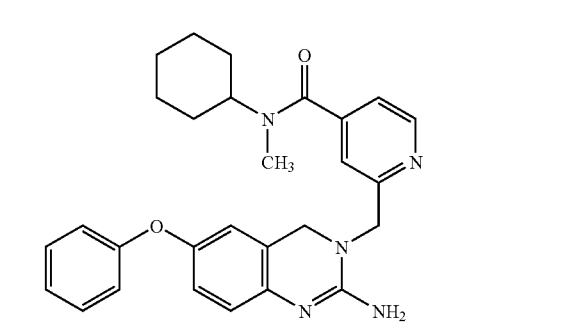 [SMILES: CN(C(=O)c1ccnc(CN2Cc3cc(Oc4ccccc4)ccc3N=C2N)c1)C1CCCCC1]

Step A

A mixture of 2-cyano-4-pyridinecarboxylic acid (0.500 g, 3.38 mmol), HBTU (1.28 g, 3.38 mmol), and N-ethylmorpholine (1.21 g, 10.48 mmol) in DMF (35 mL) was stirred for 15 minutes. Then N-methylcyclohexylamine (1.089 g, 9.64 mmol) was added, and the reaction mixture was stirred overnight. Water (300 mL) was added to the reaction mixture. The resulting solution was extracted with EtOAc. The layers were separated, and the organic layer was washed three times with saturated aqueous NaCl solution. The organic layer was dried (Na$_2$SO$_4$), filtered and evaporated to yield a dark oil.

MH$^+$ 244.1

Step B

Following the procedure described in *J. Med. Chem.* 1985, 28, 164, a solution of the oil isolated in Step A (0.77 g), 10% palladium on carbon (0.260 g), and concentrated HCl (0.680 mL) in EtOH (30 mL) was hydrogenated at 35 psi on a Parr shaker. After 2 h, hydrogen uptake ceased, and the reaction was stopped. The reaction mixture was filtered and evaporated to yield a tan solid. The tan solid was slurried in CH$_2$Cl$_2$, and then 3N NaOH was added with thorough mixing. The layers were separated, and the organic layer was dried (K$_2$CO$_3$), filtered, and evaporated to yield a light brown oil.

MH$^+$ 248.2

Step C

A solution of the oil isolated in Step B (0.242 g, 1.0 mmol) and 2-nitro-5-phenoxybenzaldehyde (0.238 g, 1.0 mmol) in DCE (10 mL) was stirred for 15 minutes. Then NaBH(OAc)$_3$ (0.317 g, 1.5 mmol) was added, and the reaction mixture was stirred overnight. To the reaction mixture was added 3N NaOH with thorough mixing. The CH$_2$Cl$_2$ layer was separated, and the organic layer was dried (Na$_2$SO$_4$), filtered, and evaporated to yield a thick orange oil.

MH$^+$ 475.2

Step D

A solution of the oil isolated in Step C (0.484 g, 1.02 mmol) and 10% palladium on carbon (0.081 g) in EtOH (60 mL) was hydrogenated at 35 psi on a Parr shaker. After 2.5 h, the reaction mixture was filtered and evaporated to yield a thick brown oil.

MH$^+$ 445.2

Step E

To a solution of the oil (0.404 g, 0.91 mmol) prepared in Step D in EtOH (13 mL) was added cyanogen bromide (0.551 mL, 2.76 mmol) as a 5M solution in MeCN. The reaction mixture was stirred at room temperature overnight and then evaporated to yield a residue. The residue was triturated several times with diethyl ether to yield a tan solid. Of this material, 100 mg was purified on flash silica gel using 90:10 CH$_2$Cl$_2$:(0.5M NH$_3$ in MeOH) to yield a residue. This residue was dissolved in CH$_2$Cl$_2$, and the resulting solution was washed with 3N NaOH solution. The organic layer was dried (Na$_2$SO$_4$) and filtered. To the filtrate was added TFA (1 mL), and the solution was evaporated to yield the title compound as a dark residue.

MH$^+$ 470.0

Example 49

5-(2-Amino-6-phenoxy-4H-quinazolin-3-ylmethyl)-furan-2-carboxylic acid cyclohexyl-methyl-amide (Compound #424)

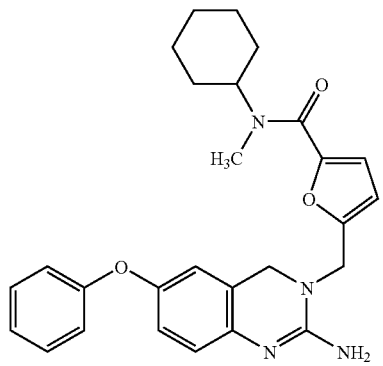 [SMILES: CN(C(=O)c1ccc(CN2Cc3cc(Oc4ccccc4)ccc3N=C2N)o1)C1CCCCC1]

Step A

A mixture of 5-formyl-2-furancarboxylic acid (0.153 g, 1.09 mmol), HBTU (0.413 g, 1.09 mmol), and N-ethylmorpholine (0.38 g, 3.38 mmol) in DMF (20 mL) was stirred for 15 minutes. Then N-methylcyclohexylamine (0.351 g, 3.11 mmol) was added, and the reaction mixture was stirred overnight. With thorough mixing, 75 mL of 1N HCl and EtOAc were added. The layers were separated, and the organic layer was washed three times with saturated aqueous NaCl solution. The organic layer was dried (Na$_2$SO$_4$), filtered, and evaporated to yield a thick oil.

MH$^+$ 236.1

Step B

A solution of the oil isolated in Step A (0.257 g, 1.25 mmol) and hydroxylamine (0.062 g, 1.88 mmol, 50% solution in water) in EtOH (10 mL) was refluxed for 2 h. The reaction mixture was cooled and diluted with water (75 mL). The resulting mixture was extracted with EtOAc. The organic layer was separated, dried (Na$_2$SO$_4$), filtered, and evaporated to yield a dark oil.

MH$^+$ 251.1

Step C

A solution of the oil isolated in Step B (0.235 g) and zinc (3.06 g) in HOAc (25 mL) was stirred overnight. After overnight stirring, the reaction mixture was filtered through Dicalite. The filtrate was evaporated to yield a residue. The residue was treated with 3N NaOH and CH$_2$Cl$_2$ with thorough mixing. The organic layer was separated, dried (Na$_2$SO$_4$), filtered, and evaporated to yield a thick residue.

MH$^+$ 237.1

Step D

A solution of the residue isolated in Step C (0.240 g, 1.02 mmol) and 2-nitro-5-phenoxybenzaldehyde (0.248 g, 1.02 mmol) in DCE (5.5 mL) was stirred for 15 minutes. Then NaBH(OAc)$_3$ (0.300 g, 1.42 mmol) was added, and the reaction mixture was stirred overnight. To the reaction mixture was added 3N NaOH and CH$_2$Cl$_2$ with thorough mixing. The layers were separated, and the organic layer was dried (Na$_2$SO$_4$), filtered, and evaporated to yield a thick oil.

MH$^+$ 464.2

Step E

A solution of the oil isolated in Step D (0.500 g, 1.08 mmol) and 10% palladium on carbon (0.086 g) in EtOH (50 mL) was hydrogenated at 34 psi on a Parr shaker. After 2 h, the reaction mixture was filtered and evaporated to yield a semisolid.

MH$^+$ 434.2

Step F

To a solution of the semisolid (0.175 g, 0.4 mmol) prepared in Step E in EtOH (5 mL) was added cyanogen bromide (0.242 mL, 1.21 mmol) as a 5M solution in MeCN. The reaction mixture was stirred over the weekend and then evaporated to yield a residue. The residue was triturated several times with diethyl ether and then filtered to yield a white solid. Of this material, 90 mg was purified on flash silica gel using 98:2 to 90:10 CH$_2$Cl$_2$:(0.5M NH$_3$ in MeOH) to yield a residue. This residue was dissolved in CH$_2$Cl$_2$, and TFA (0.5 mL) was added. The resulting solution was evaporated and triturated several times with diethyl ether to yield the title compound as a cream-colored solid.

MH$^+$ 459.4

Example 50

9-(2-Amino-6-phenoxy-4H-quinazolin-3-yl)-9H-fluorene-2-carboxylic acid cyclohexyl-methyl-amide (Compound #125)

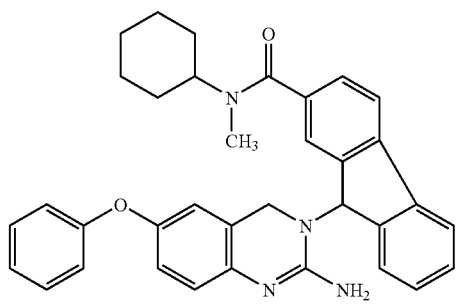 [SMILES: CN(C(=O)c1ccc2c(c1)C(N1Cc3cc(Oc4ccccc4)ccc3N=C1N)c1ccccc1-2)C1CCCCC1]

Step A

A mixture of 9-oxo-9H-fluorene-2-carboxylic acid (0.448 g, 2.18 mmol), HBTU (0.826 g, 2.18 mmol), and N-ethylmorpholine (0.780 g, 6.76 mmol) in DMF (22 mL) was stirred for 30 minutes. Then N-methylcyclohexylamine (0.702 g, 6.22 mmol) was added, and the reaction mixture was stirred for 3 h. With thorough mixing, 50 mL of 1N HCl and EtOAc were added. The layers were separated, and the organic layer was washed with water and with saturated aqueous NaCl solution and then again with water and aqueous NaCl solution. The organic layer was dried ($Na_2SO_4$), filtered and evaporated to yield a solid.

$MH^+$ 319.9

Step B

A solution of the solid isolated in Step A (0.682 g, 3.13 mmol) and hydroxylamine (0.155 g, 4.70 mmol, 50% solution in water) in EtOH (24 mL) was refluxed for 4 h. The reaction mixture was cooled and diluted with water (130 mL). The resulting mixture was extracted with EtOAc. The organic layer was separated, dried ($Na_2SO_4$), filtered, and evaporated to yield a solid.

$MH^+$ 335.13

Step C

A solution of the solid isolated in Step B (0.562 g, 1.68 mmol) and zinc (5.47 g) in HOAc (30 mL) was stirred overnight. After overnight stirring, the reaction mixture was filtered through Filter Aid. The filtrate was evaporated to yield a residue. To the residue was added 3N NaOH (30 mL), and the resulting solution was extracted with diethyl ether. The diethyl ether extract was dried ($Na_2SO_4$), filtered, and evaporated to yield a thick light green residue.

$MH^+$ 321.2

Step D

A solution of the residue isolated in Step C (0.378 g, 1.18 mmol) and 2-nitro-5-phenoxybenzaldehyde (0.287 g, 1.18 mmol) in DCE (5 mL) was stirred for 15 minutes. Then $NaBH(OAc)_3$ (0.380 g, 1.79 mmol) was added, and the reaction mixture was stirred overnight. To the reaction mixture was added 3N NaOH and $CH_2Cl_2$ with thorough mixing. The layers were separated, and the organic layer was washed with saturated aqueous NaCl solution, dried ($Na_2SO_4$), filtered, and evaporated to yield a clear green oil.

$MH^+$ 548.5

Step E

A solution of the oil isolated in Step D (0.707 g, 1.29 mmol) and stannous chloride monohydrate (1.60 g, 7.10 mmol) in EtOH (6 mL) was refluxed for 3 h. The resulting solution was cooled, and excess aqueous sodium bicarbonate solution and EtOAc were added, and the resulting mixture was filtered through Filter Aid. The organic layer was separated, dried ($Na_2SO_4$), filtered, and evaporated to yield a thick clear residue.

$MH^+$ 518.3

Step F

To a solution of the residue (0.450 g, 0.87 mmol) prepared in Step E in EtOH (4 mL) was added cyanogen bromide (0.136 g, 1.29 mmol). The reaction mixture was refluxed for 2.5 h. After cooling, the reaction mixture was evaporated to yield a thick dark residue. This residue was triturated five times with diethyl ether. Filtration yielded a tan solid. Of this material, 0.200 g was purified on a Gilson HPLC to yield the title compound as a white solid.

$MH^+$ 543.6

Example 51

3-(2-Amino-6-phenoxy-4H-quinazolin-3-yl)-N-bicyclo[2.2.1]hept-2-yl-3-cyclohexyl-propionamide (Compound #400)

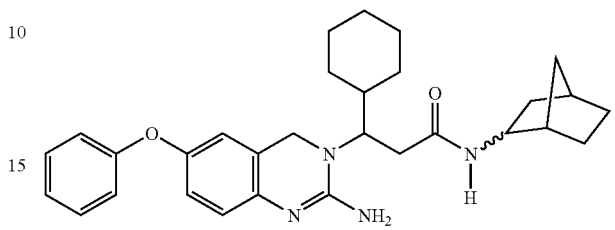

Step A

A mixture of malonic acid (10.4 g, 0.1 mol), cyclohexane carboxaldehyde (11.2 g, 0.1 mol), and ammonium acetate (11.6 g, 0.15 mol) in EtOH (1000 mL) was refluxed overnight. The reaction was cooled to room temperature, and the product was collected as a white solid.

Step B

A solution of the solid isolated in Step A (1.4 g, 5.0 mmol), 2-norbornylamine (0.6 g, 5.0 mmol), HBTU (1.9 g, 5.0 mmol), and TEA (0.5 g, 5.0 mmol) in DMF was stirred for 3 days. The reaction mixture was diluted with water, and a precipitate formed. A white solid was collected by filtration and allowed to air-dry overnight. The solid was dissolved in $CH_2Cl_2$, dried ($Na_2SO_4$), and filtered. To the resulting solution was added TFA (5 mL). The solvent was evaporated in vacuo to yield a residue which was dissolved in isopropanol. To this solution was added excess $K_2CO_3$. The suspension was filtered, and the filtrate was concentrated in vacuo to yield a yellow oil.

Step C

A solution of the oil isolated in Step B (1.1 g, 4.1 mmol) and 2-nitro-5-phenoxybenzaldehyde (0.98 g, 4.0 mmol) in DCE (40 mL) was stirred for 1 hour. Then $NaBH(OAc)_3$ (1.3 g, 6.0 mmol) was added, and the reaction mixture was stirred for three days. The reaction mixture was quenched with 3N NaOH. The resulting solution was extracted with $CH_2Cl_2$. The $CH_2Cl_2$ extracts were combined, dried ($K_2CO_3$), and concentrated to yield a residue. Purification by flash chromatography 0 to 2% (1.0M $NH_3$ in MeOH) in $CH_2Cl_2$ yielded a residue.

Step D

A solution of the residue isolated in Step C (0.15 g) and palladium on carbon in EtOH was hydrogenated at 50 psi in a Parr shaker for 90 minutes. The catalyst was removed by filtration, and the filtrate was concentrated under reduced pressure to a volume of 10 mL.

Step E

To the solution prepared in Step D was added cyanogen bromide (0.05 g, 0.4 mmol). The reaction mixture was stirred at room temperature overnight. The suspension was filtered to yield the title compound a solid.

$MH^+$ 487

$^1$H NMR (300 MHz, DMSO-$d_6$): δ0.55-0.70 (br d, 0.5H), 0.75-0.85 (br d, 0.5H), 0.90-1.82 (m, 20.5H), 1.98 (br d, J=14.7 Hz, 1H), 2.11 (br s, 0.5H), 3.15-4.0 (br m, 2H), 4.10-

4.25 (br m, 1H), 4.21-4.50 (m, 2H), 6.93 (s, 1H), 6.95-7.05 (m, 4H), 7.15 (br t, J=7.2 Hz, 1H), 7.40 (t, 7.3 Hz, 2H), 7.78 (br s, 3H).

Example 52

(R)-Enantiomer of cyclohexanecarboxylic acid [2-(2-amino-6-phenoxy-4H-quinazolin-3-yl)-propyl]-amide (Compound #495)

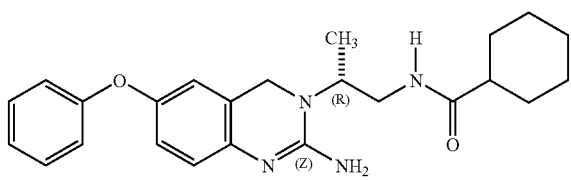 [SMILES: C[C@H](CNC(=O)C1CCCCC1)N1Cc2cc(Oc3ccccc3)ccc2N=C1N]

Step A

A solution of L-alanamide (0.93 g, 7.5 mmol) and 2-nitro-5-phenoxybenzaldehyde (1.2 g, 5.0 mmol) in THF was stirred for 1 hour. Then NaBH(OAc)$_3$ (1.6 g, 7.5 mmol) was added, and the reaction mixture was stirred overnight. The reaction mixture was diluted with EtOAc and 3N NaOH. The layers were separated, and the EtOAc extract was washed with brine, dried (K$_2$CO$_3$), and concentrated to a residue. Purification by flash chromatography 1.0 to 2.0% (0.5M NH$_3$ in MeOH) in CH$_2$Cl$_2$ yielded a residue.

Step B

To a solution of the residue (0.54 g, 1.7 mmol) isolated in Step B in THF (20 mL) was added BH$_3$.THF (1.0M solution in THF, 7.6 mL), and the mixture was heated at reflux overnight. After 24 h of heating, additional BH$_3$.THF (1.0M solution in THF, 5 mL) was added to the reaction mixture. After 16 h, the reaction mixture was cooled, and 1N HCl was added. The resulting mixture was basified with Na$_2$CO$_3$ and extracted with EtOAc. The combined extracts were washed with brine, dried (K$_2$CO$_3$), filtered, and then evaporated in vacuo to yield an oil. Flash chromatography 2.5-7.5% (0.5N NH$_3$ in MeOH) in CH$_2$Cl$_2$ yielded an oil.

Step C

A solution of the oil isolated in Step B (0.27 g, 0.9 mmol) and TEA (0.125 mL, 0.9 mmol) in CH$_2$Cl$_2$ (5 mL) was cooled to 0° C. Then, cyclohexanecarbonyl chloride (0.13 g, 0.9 mmol) was added. The reaction mixture was warmed to room temperature and was stirred overnight. Additional cyclohexanecarbonyl (20 µL) chloride was added. The reaction mixture was stirred for 2 h. Then, 3N NaOH solution was added. The layers were separated, and the organic layer was dried (K$_2$CO$_3$), filtered, and evaporated in vacuo to yield a residue. Flash chromatography 5-25% (0.5N NH$_3$ in MeOH) in CH$_2$Cl$_2$ yielded a residue.

Step D

A solution of the residue isolated in Step C (0.25 g) and 10% palladium on carbon in EtOH was hydrogenated at 50 psi in a Parr shaker for 3 hours. The catalyst was removed by filtration, and the filtrate was concentrated under reduced pressure to a volume of 5 mL.

Step E

To the solution prepared in Step D was added cyanogen bromide (0.1 g). The reaction mixture was stirred at room temperature for 4 days. The solvent was evaporated to yield a residue which was divided into two portions and purified by reversed phase HPLC using 30:70 MeCN:water with 0.1% TFA as the eluent to yield the title compound as a white powder.

MH$^+$ 407

$^1$H NMR (300 MHz, DMSO-d$_6$): δ0.98-1.38 (m, 6H), 1.20 (d, J=6.5 Hz, 3H), 1.40-1.72 (m, 5H), 1.90-2.10 (br m, 1H), 3.08 (dt, J=4.8 Hz, 1H), 4.12-4.32 (br m, 1H), 4.43 (s, 2H), 6.90 (s, 1H), 6.92-7.02 (m, 4H), 7.13 (t, J=7.4 Hz, 1H), 7.38 (t, 7.6 Hz, 2H), 7.38 (br t, 1H), 8.06 (br s, 2H)

Example 53

N-Adamantan-2-yl-3-(2-amino-6-phenoxy-4H-quinazolin-3-yl) propionamide (Compound #221)

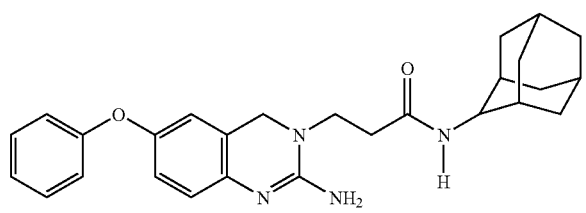 [SMILES: NC1=Nc2ccc(Oc3ccccc3)cc2CN1CCC(=O)NC1C2CC3CC(C2)CC1C3]

Step A

To a solution of N-Boc β-alanine (4.7 g, 25.0 mmol), 2-adamantanamine hydrochloride (4.7 g, 25.0 mmol), and TEA (5.0 g, 50.0 mmol) in DMF (75 mL) was added HBTU (9.5 g, 55.0 mmol). The reaction mixture was stirred overnight. The reaction mixture was diluted with water, and extracted with EtOAc (2×). The organic layers were combined and washed with water and brine and dried over K$_2$CO$_3$. Evaporation yielded a residue.

Step B

To a solution of the residue isolated in Step A (4.7 g, 25.0 mmol) in CH$_2$Cl$_2$ was added TFA (10 mL). The reaction mixture was concentrated to a residue. To the residue was added EtOAc and water followed by solid Na$_2$CO$_3$; The layers were separated, and the aqueous layer was extracted twice with EtOAc. The organic layers were combined, washed with brine, dried (K$_2$CO$_3$), filtered, and evaporated to yield a residue.

Step C

A solution of the residue isolated in Step B (0.55 g, 2.5 mmol) and 2-nitro-5-phenoxybenzaldehyde (0.49 g, 2.0 mmol) in DCE was stirred for 1 hour. Then NaBH(OAc)$_3$ (0.63 g, 3.0 mmol) was added, and the reaction mixture was stirred overnight. The reaction mixture was quenched with 3N NaOH. The resulting solution was extracted with CH$_2$Cl$_2$. The CH$_2$Cl$_2$ extracts were combined, dried (K$_2$CO$_3$), and concentrated to a residue. Purification by flash chromatography 0.5 to 2.0% (0.5M NH$_3$ in MeOH) in CH$_2$Cl$_2$ yielded a residue.

Step D

A solution of the residue isolated in Step E (0.8 g) and 10% palladium on carbon in EtOH was hydrogenated at 55 psi in a Parr shaker overnight. The catalyst was removed by filtration, and the filtrate was concentrated under reduced pressure to a volume of 20 mL.

Step E

To the solution prepared in Step D was added cyanogen bromide (0.26 g, 2.5 mmol). The reaction mixture was stirred overnight. The reaction mixture was filtered to yield a white solid. The filtrate was evaporated to yield a residue that was recrystallized from MeCN to yield a solid that was combined with the collected solid from the reaction mixture. These were combined and recrystallized from $CH_3CN$ to yield the title compound as a white solid.

MH+ 445

$^1$H NMR (300 MHz, DMSO-$d_6$): δ1.41 (d, J=12.2 Hz, 1H), 1.55-1.92 (m, 13H), 2.61 (t, J=6.0 Hz, 2H), 3.69 (t, J=5.5 Hz, 2H), 3.82 (d, J=6.6 Hz, 1H), 4.55 (s, 2H), 6.67 (s, 1H), 6.90-7.05 (m, 4H), 7.13 (t, J=7.3 Hz, 1H), 7.39 (t, 7.9 Hz, 2H), 7.96 (d, J=7.4 Hz, 1H), 8.00 (br s, 2H)

Elemental analysis for $C_{27}H_{32}N_4O_2 \cdot 1.0$ HBr:
Calculated: C, 61.71; H, 6.33; N, 10.66
Found: C, 61.77; H, 6.36; N, 10.57

Example 54

N-Adamantan-2-yl-3-[2-amino-7-(2-methoxy-phenyl)-4H-quinazolin-3-yl]-propionamide (Compound #617)

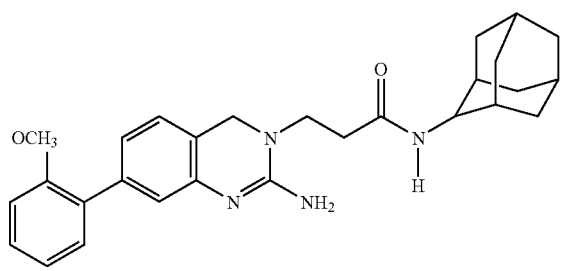 [SMILES: COc1ccccc1-c1ccc2c(c1)N=C(N)N(CCC(=O)NC1C3CC4CC(C3)CC1C4)C2]

Step A

To a solution of 4-bromo-2-nitrotoluene (2.16 g, 10.0 mmol) and 2-methoxyphenyl boronic acid in EtOH (50 mL) was added $K_2CO_3$ (1.8 g, 13.0 mmol) in water (1.8 mL) followed by Pd(dppf)$Cl_2$ (0.5 g, 0.065 mmol). The reaction mixture was refluxed 4 h. The reaction mixture was cooled, filtered through Dicalite, and concentrated to yield a residue. The residue was purified by flash chromatography using 5% to 20% $CH_2Cl_2$ in heptane to yield a yellow solid.

Step B

A mixture of the solid isolated in Step A (0.82 g, 3.4 mmol) dimethylformamide dimethyl acetal (0.6 mL, 4.4 mmol) in of DMF (4 mL) was heated for 2 h at 210° C. The mixture was cooled to room temperature, and the solvent was evaporated in vacuo to yield a residue.

Step C

The residue isolated in Step B was dissolved in THF (75 mL). The mixture was diluted with water (75 mL) and $NaIO_4$ (4.3 g, 20.4 mol) was added. The reaction mixture was stirred overnight at room temperature. The solids were filtered and washed well with EtOAc. The filtrate was washed 3× with saturated aqueous $NaHCO_3$ solution, and then dried (MgSO$_4$). The solution was filtered and the solvent was evaporated in vacuo. The crude product was chromatographed to yield an off-white solid.

Step D

A solution of the solid isolated in Step C (0.32 g, 1.25 mmol), the residue isolated in Example 53, Step B as its TFA salt (0.50 g, 1.5 mmol), and TEA (1.25 mmol) in DCE was stirred for 1 h. Then NaBH(OAc)$_3$ (0.33 g, 32.5 mmol) was added, and the reaction mixture was stirred overnight. The reaction mixture was quenched with 3N NaOH. The resulting solution was extracted with $CH_2Cl_2$. The $CH_2Cl_2$ extracts were combined, dried ($K_2CO_3$), and concentrated to a residue. Purification by flash chromatography 1.0 to 2.5% (0.5M $NH_3$ in MeOH) in $CH_2Cl_2$ yielded a yellow glass.

Step E

A solution of the yellow glass isolated in Step D (0.24 g, 0.51 mmol) and 10% palladium on carbon in EtOH was hydrogenated at 55 psi in a Parr shaker for 3 h. The catalyst was removed by filtration, and the filtrate was concentrated under reduced pressure to a volume of 5 mL.

Step F

To the solution prepared in Step F was added cyanogen bromide (0.08 g, 0.75 mmol). The reaction mixture was stirred overnight. The reaction mixture was filtered to yield a white solid. The filtrate was evaporated to yield a residue that was purified by reversed phase HPLC (35% MeCN in $H_2O$ with 0.1% TFA) to yield the title compound as a white powder.

MH+ 459

$^1$H NMR (300 MHz, DMSO-$d_6$): δ1.42 (d, J=12.7 Hz, 1H), 1.60-1.85 (m, 11H), 1.88 (d, J=12.0 Hz, 2H), 2.64 (br t, 2H), 3.65-3.80 (m, 2H), 3.76 (s, 3H), 3.80-3.90 (m, 1H), 4.61 (s, 2H), 7.00-7.28 (m, 6H), 7.37 (t, 6.9 Hz, 2H), 7.97 (d, J=7.5 Hz, 1H), 8.03 (br s, 2H).

Example 55

4-(2-Amino-6-phenoxy-4H-quinazolin-3-yl)-heptanedioic acid bis-(cyclohexyl-methyl-amide) (Compound #84)

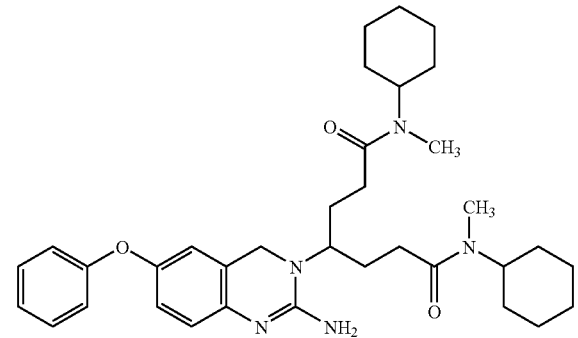 [SMILES: CN(C(=O)CCC(CCC(=O)N(C)C1CCCCC1)N1Cc2cc(Oc3ccccc3)ccc2N=C1N)C1CCCCC1]

Step A

To a cold mixture of 4-ketopimelic acid (1.7415 g 10.0 mmol) and triethylamine (7.00 mL, 50.2 mmol) in DMF (10 mL) was added diphenylphosphorylazide (5.1 mL, 23.7 mmol) and N-methylcyclohexyl amine. The reaction mixture was stirred at ambient temperature 40 h. The reaction was diluted with $H_2O$ (50 mL) and extracted with EtOAc (2×100 mL). The organic extracts were washed with water (4×50 mL), 1N aqueous HCl (2×50 mL), $H_2O$ (2×50 mL), dried ($Na_2SO_4$), filtered, and concentrated in vacuo to yield an oil. The crude oil was combined with product synthesized previously on a 1 mmol scale and purified by flash chromatography on silica gel (2% MeOH in $CHCl_3$) to yield a residue.

MH+ 365

Step B

To a stirred solution of the residue isolated in Step A (1.1449 g, 3.14 mmol) and ammonium acetate (2.4874 g, 32.3 mmol) in anhydrous methanol (30 mL) was added sodium cyanoborohydride (196.7 mg, 3.13 mmol). The resulting mixture was stirred for 72 hours and then was treated with 1N aqueous HCl to destroy excess borohydride reagent. The reaction mixture was basified with 3N aqueous NaOH, and the aqueous mixture was extracted with $CHCl_3$ (2×50 mL). The organic extracts were dried ($Na_2SO_4$), filtered, and concentrated to yield a colorless oil which was taken forward without further purification.

Step C

A mixture of 2-nitro-5-phenoxybenzaldehyde (760.2 mg, 3.13 mmol) and the oil isolated in Step B (1.1421 g, 3.12 mmol) in MeOH (30 mL) was stirred at room temperature for 2 days and then was cooled to 0° C. and treated with $NaBH_4$ (0.12 g, 3.17 mmol) and then stirred for another 20 h at room temperature. Aqueous $NH_4Cl$ was added to destroy excess borohydride reagent. The aqueous mixture was extracted into $CHCl_3$ (2×50 mL). The organic solution was dried ($Na_2SO_4$), filtered, and concentrated in vacuo to yield a yellow oil. The crude oil was purified by column chromatography (silica gel, 2% MeOH in $CHCl_3$) to yield a residue.

Step D

A heterogenous mixture of the oil isolated in Step C (162.5 mg, 0.27 mmol), and 10% Pd/C (20 mg) in EtOH (25 mL) was shaken under 55 psi of $H_2$ gas at room temperature for 20 h. The reaction mixture was filtered through a bed of Celite®, and the filter cake was rinsed with EtOH (25 mL). The organic filtrate was evaporated. The residue was purified by preparative TLC (2 tapered plates; 90:10:1 $CHCl_3$:MeOH:concentrated $NH_4OH$) to yield a yellow oil.

Step E

A mixture of the oil isolated in Step D (69.7 mg, 0.124 mmol) and cyanogen bromide (19.2 mg, 0.181 mmol) in EtOH (5 mL) was stirred at reflux for 6 h and then at room temperature for 60 h. The solvent was removed in vacuo, and remaining residue was triturated with $Et_2O$. The solvent was decanted and the remaining HBr salt was dried under high vacuum at room temperature overnight to yield the title compounds as a tan amorphous solid.

$MH^+$=588

$^1H$ NMR (300 MHz, $CDCl_3$) δ1.00-2.10 (m, 24H), 2.20-2.35 (m, 4H), 2.60-2.80 (m, 6H), 3.30-3.45 (m, 1H), 4.10-4.25 (m, 3H), 4.30-4.45 (m, 1H), 6.70 (s, 1H), 7.05-7.15 (m, 1H), 7.20-7.30 (m, 2H), 7.35-7.50 (m, 2H), 11.5 (br s, 1H).

Example 56

3-(2-Amino-6-phenoxy-4H-quinazolin-3-yl)-pentanedioic acid bis-(cyclohexyl-methyl-amide) (Compound #107)

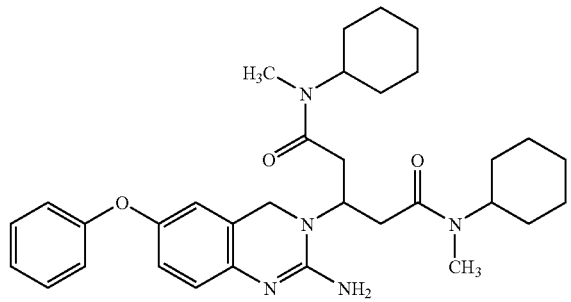 [SMILES: CN(C(=O)CC(CC(=O)N(C)C1CCCCC1)N1Cc2cc(Oc3ccccc3)ccc2N=C1N)C1CCCCC1]

Step A

To a cold (−60° C.) solution of 1,3-diamino-2-hydroxypropane (947.1 mg, 10.0 mmol) and triethylamine (3.5 mL, 25.1 mmol) in a 4:1 THF:$CH_2Cl_2$ mixture (50 mL) was added cyclohexanecarbonyl chloride (2.90 mL, 21.7 mmol). The reaction was allowed to warm to room temperature over a two-hour period. The heterogenous mixture was diluted with $CH_2Cl_2$ (20 mL) and was stirred overnight. Thereafter, the mixture was washed with $H_2O$ (50 mL), aqueous $Na_2CO_3$ (50 mL), and $H_2O$ (50 mL), and then dried ($Na_2SO_4$), filtered, and concentrated to a residue. The residue was purified by column chromatography (silica gel, 6% MeOH in $CHCl_3$) to yield a white solid.

Step B

To a stirred mixture of the solid isolated in Step A (2.1783 g, 7.03 mmol) and triethylamine (10.0 mL, 71.7 mmol) in DMSO (20 mL) was added sulfur trioxide pyridine complex (3.3662 g, 21.1 mmol) in DMSO (20 mL) under a $N_2$ atmosphere. The reaction mixture was stirred for 60 h and then was diluted with ice water (100 mL) and extracted into $CHCl_3$ (2×75 mL). The organic extracts were combined and washed with aqueous citric acid (2×1 25 mL), aqueous $Na_2CO_3$ (1×150 mL), $H_2O$ (100 mL), dried ($Na_2SO_4$), filtered, and concentrated to yield an off-white solid.

Step C

To a solution of the solid isolated in Step B (924.2 mg. 3.00 mmol) in MeOH (40 mL) was added $NH_4OAc$ (4.7890 g, 62.1 mmol). The mixture was stirred at room temperature for 1 h and then was treated with $NaBH_3CN$ (185.6 mg, 2.95 mmol). The reaction mixture was then stirred for 1 day and then quenched with 1N aqueous HCl solution (25 mL) and then was basified to pH 9.0 with $Na_2CO_3$ and extracted into $CHCl_3$ (2×50 mL). The organic solution was dried ($Na_2SO_4$), filtered, and concentrated. The residue was purified by column chromatography (silica gel, 8% MeOH in $CHCl_3$ to 90:10:1 $CHCl_3$:MeOH:concentrated $NH_4OH$) to yield an off-white solid.

Step D

A mixture of 5-phenoxy-2-nitrobenzaldehyde (217.1 mg, 0.893 mmol) and the solid isolated in Step C (274.8 mg, 0.889 mmol) was stirred in MeOH (15 mL) at room temperature for 18 h. The resulting suspension was diluted with MeOH (5 mL), dissolved with gentle warming and treated with $NaBH_4$ (38.8 mg, 1.02 mmol). The reaction mixture was stirred for one additional hour and then quenched with aqueous $NH_4Cl$ followed by extraction into $CHCl_3$ (2×50 mL). The organic solution was dried ($Na_2SO_4$), filtered, and evaporated to yield a residue that was carried on to the next chemical step.

Step E

The residue isolated in Step D (274.5 mg) and 10% Pd/C (31.4 mg) in absolute EtOH (30 mL) was shaken under 55 psi of $H_2$ at room temperature for 3 h. The reaction was filtered through a bed of Celite®, and the filter cake was rinsed with solvent (50 mL). The organic filtrate was evaporated and purified by preparative TLC (3 tapered silica gel plates, 3 to 5% MeOH in $CHCl_3$) to yield a tan amorphous solid.

Step F

A mixture of the solid isolated in Step E (109.2 mg, 0.215 mmol) and BrCN (25.8 mg, 0.243 mmol) in EtOH (6 mL) was stirred at reflux for 18 h. The solvent was removed in vacuo, and the remaining residue was triturated with $Et_2O$. The solvent was decanted and the resulting HBr salt was dried under high vacuum at room temperature overnight to yield the title compound as a tan amorphous solid.

$MH^+$=532

$^1H$ NMR (300 MHz, DMSO-$d_6$) δ1.00-1.35 (m, 10H), 1.50-1.70 (m, 2H), 1.90-2.10 (m, 2H), 3.15-3.25 (m, 2H), 3.45-3.55 (m, 2H), 4.25-4.35 (m, 1H), 4.40 (s, 2H), 6.85 (s,

1H), 6.90-7.05 (m, 4H), 7.10-7.15 (m, 1H), 7.35-7.45 (m, 2H), 7.75-7.80 (m, 2H), 7.85-7.95 (m, 2H), 10.5 (s, 1H)

Example 57

5-[1-(2-Amino-6-phenoxy-4H-quinazolin-3-yl)-2-phenyl-ethyl]-oxazole-4-carboxylic acid cyclohexylamide (Compound #606)

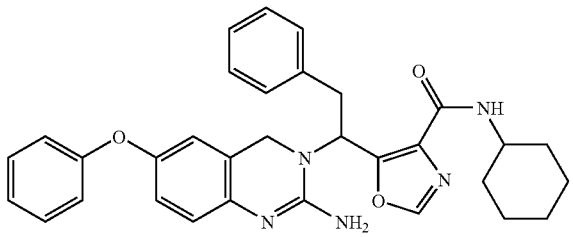 [SMILES: NC1=Nc2ccc(Oc3ccccc3)cc2CN1C(Cc1ccccc1)c1ocnc1C(=O)NC1CCCCC1]

Step A

To a cold (0° C.) mixture of DL-N-Cbz-phenylalanine (12.02 g, 40.0 mmol) and potassium carbonate sesquihydrate (26.50 g, 160 mmol) in anhydrous DMF was added diphenylphosphorylazide (13.5 mL, 62.6 mmol) and methyl isocyanoacetate (7.5 mL, 82.5 mmol). The resulting mixture was stirred at room temperature for 96 h and then was diluted with H$_2$O (600 mL). The precipitated solid was collected by filtration. The crude solid was dissolved in CHCl$_3$ (200 mL) and washed with aqueous NaCl. The organic solution was dried (Na$_2$SO$_4$), filtered, and evaporated to yield a solid. The solid was carried on to the next step without further manipulation.
MH$^+$=381

Step B

To a cold (0° C.) solution of the solid isolated in Step A (7.60 g, 20.0 mmol) in 2:1 THF:H$_2$O (300 mL) was added LiOH (526.3 mg, 21.9 mmol). The mixture was stirred for 18 h, acidified to about pH 3 with aqueous citric acid, and extracted into CHCl$_3$ (2×1 50 mL). The organic solution was dried (Na$_2$SO$_4$), filtered, and concentrated to yield a white amorphous solid that was carried on to the next step without further purification.

Step C

To a cold (0° C.) mixture of the solid isolated in Step B (1.8339 g, 5.00 mmol) and N,N-diisopropylethylamine (4.4 mL, 25.2 mmol) in DMF (12 mL) was added diphenylphosphorylazide (1.3 mL, 6.03 mmol) and cyclohexylamine (0.74 mL, 6.47 mmol). The reaction mixture was stirred for 20 h at room temperature and then was diluted with aqueous NaCl and extracted into CHCl$_3$ (2×100 mL). The organic solution was washed with H$_2$O (5×100 mL), dried (Na$_2$SO$_4$), filtered, and concentrated to a residue. The residue was purified by column chromatography (silica gel, 3% MeOH in CHCl$_3$). Trituration of the resulting gum with Et$_2$O yielded a white solid.

Step D

A mixture of the solid isolated in Step C (1.6532 g, 3.70 mmol) and 10% Pd/C (332.4 mg) in MeOH (120 mL) was shaken under 55 psi of hydrogen gas at room temperature for 5 h. The reaction mixture was filtered through a bed of Celite®. The filter cake was rinsed with MeOH (50 mL). The filtrate was concentrated and the residue was purified by column chromatography (silica gel, 6% MeOH in CHCl$_3$) to yield a light yellow oil.

Step E

To a solution of 5-phenoxy-2-nitrobenzaldehyde (267.0 mg, 1.10 mmol) and the oil isolated in Step D (381.0 mg, 1.22 mmol) in 1,2-dichloroethane was added sodium triacetoxyborohydride (362.1 mg, 1.71 mmol). The reaction mixture was stirred at room temperature for 18 h and then quenched with aqueous NaHCO$_3$ and extracted into CHCl$_3$ (2×40 mL). The organic solution was dried (Na$_2$SO$_4$), filtered, and concentrated. The residue was purified by column chromatography (silica gel, 3% MeOH in CHCl$_3$) to yield a light yellow gum.

Step F

A mixture of the gum isolated in Step E (532.6 mg, 0.970 mmol) and 10% Pd/C (110.4 mg) in EtOH (70 mL) was shaken under 55 psi of hydrogen gas at room temperature for 4 h. The reaction mixture was filtered through a bed of Celite®. The filter cake was rinsed with MeOH (50 mL). The filtrate was concentrated and the residue was purified by column chromatography (silica gel, 2% MeOH in CHCl$_3$) to yield a flaky brown solid.

Step G

To a solution of the solid isolated in Step F (304.1 mg, 0.596 mmol) in EtOH (10 mL) was added cyanogen bromide (83.1 mg, 0.784 mmol). The resulting mixture was stirred at room temperature for 1.5 d, refluxed for 1 h, and then concentrated to a residue. The residue was purified by preparative thin layer chromatography (5 tapered silica gel plates; 90:10:1 CHCl$_3$:MeOH:concentrated NH$_4$OH) to yield the title compound as a free base.

The free base was dissolved in CHCl$_3$ (3 mL), acidified with 1N HCl (0.6 mL) in Et$_2$O and further diluted with Et$_2$O (75 mL). The HCl salt was collected by filtration and dried under vacuum at room temperature to yield the title compound as an amorphous solid, as its HCl salt.
MH$^+$=536

$^1$H NMR (300 MHz, DMSO-d$_6$) δ1.10-1.80 (m, 10H), 3.30-3.60 (m, 2H), 3.65-3.85 (m, 1H), 4.25-4.35 (m, 1H), 5.05-5.15 (m, 1H), 5.90-6.10 (m, 1H), 6.90-7.10 (m, 4H), 7.15-7.30 (m, 7H), 7.50-7.60 (m, 2H), 8.35-8.50 (br s, 2H), 8.65-8.75 (m, 2H), 11.1 (s, 1H)

Example 58

4-(2-Amino-6-phenoxy-4H-quinazolin-3-yl)-N-cyclohexyl-4-(cis-4-hydroxy-cyclohexyl)-N-methyl-butyramide (Compound #731)

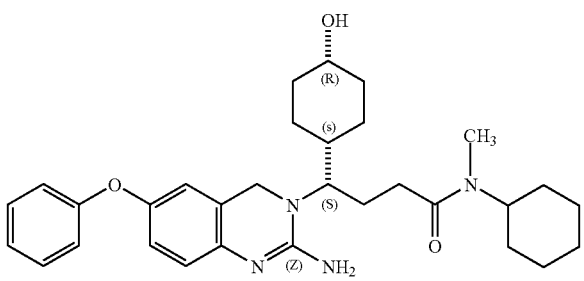

Step A

Following the procedure described in PCT Publication WO 02/76450, a 500 mL round bottom flask was charged with anhydrous MeOH (200 mL). The flask was placed in an ice bath, cooled to 0° C., and treated with acetyl chloride (10 mL, 140 mmol) followed by D-(+)-4-hydroxyphenylglycine (10.01 g, 59.8 mmol). The reaction mixture was stirred at room temperature for 18 h, then at 40° C. for 5 h and then concentrated to an oil. The oil was redissolved in MeOH (250 mL) and the solution concentrated to yield a solid. The moist solid was washed with $Et_2O$, dried in vacuum oven at 40° C. for 5 h to yield an off white solid. This material was carried on directly to the next step.

Step B

A suspension of D-(+)-4-hydroxyphenylglycine methyl ester (12.9620 g, 59.8 mmol) in $CH_2Cl_2$ (150 mL) was treated with diisopropyl ether (15 mL, 86.0 mmol), di-tert-butyl dicarbonate (15.1740 g, 69.5 mmol) in DCM (50 mL) and N,N-diisopropylethylamine (12.0 mL, 68.8 mmol). The resulting mixture was stirred for 60 h at room temperature and then was concentrated to a residue. The residue was dissolved in EtOAc (250 mL), washed with $H_2O$ (2×100 mL), saturated $NaHCO_3$ (1×100 mL), brine (1×100 mL), dried ($Na_2SO_4$), filtered, and concentrated to a gummy residue. The gum was triturated with 1:4 $Et_2O$: hexanes (200 mL) to yield a solid.

Step C

A solution of the solid (5.0550 g, 0.018 mol) isolated in Step B in HOAc (90 mL) was prepared with slight heating. Then $PtO_2$ (403.2 mg) was added, and the reaction was shaken under 50 psi of $H_2$ gas for 2 h at room temperature. Acetic acid was evaporated by azeotropic removal using benzene as a cosolvent. The oily residue was diluted with EtOAc (100 mL), washed with saturated aqueous $NaHCO_3$ (100 mL), brine (100 mL) and $H_2O$ (100 mL). The organic solution was dried ($Na_2SO_4$), filtered, and concentrated to a thick oil which solidified upon standing. The solid was purified by gradient column chromatography (silica gel; 10% to 60% EtOAc in heptane) on the Isco to yield the cis and trans isomers of tert-butoxycarbonylamino-(4-hydroxy-cyclohexyl)-acetic acid methyl ester as solids.

Step D

A mixture of the cis isomer isolated in Step C (998.0 mg, 3.48 mmol) and lithium hydroxide (179.5 mg, 7.49 mmol) in 70:33 $THF:H_2O$ (103 mL) was stirred at room temperature for 6 h. The reaction mixture was made acidic by addition of citric acid (1.61 g), and then $H_2O$ (25 mL) was added. The reaction mixture was extracted with $CHCl_3$ (2×75 mL). The organic solution was dried ($Na_2SO_4$), filtered, and concentrated to yield a foam which was carried on to the next chemical step without further purification.

Step E

To a cooled (10° C.) suspension of the foam prepared in Step D (887.7 mg, 3.25 mmol), N,O-dimethylhydroxylamine.HCl (438.2 mg, 4.49 mmol) and N-hydroxybenzotriazole hydrate (607.9 mg, 4.50 mmol) in $CH_2Cl_2$ (30 mL) was added triethylamine (2.0 mL, 14.3 mmol) and 1-[(3-dimethylamino)propyl]-3-ethylcarbodiimide.HCl (866.2 mg, 4.52 mmol). The reaction was allowed to warm to room temperature and then was stirred overnight. The reaction mixture was diluted with $CH_2Cl_2$ (125 mL), washed with brine (3×50 mL), aqueous citric acid (2×50 mL), dried ($Na_2SO_4$), filtered, and concentrated to a residue. The residue was purified by column chromatography (silica gel; 7% MeOH in $CHCl_3$) to yield a residue.

Step F

To a cooled (0° C.) solution of the residue isolated in Step E (500.3 mg, 1.58 mmol) in THF (22 mL) was added 1M $LiAlH_4$ in THF (3.8 mL, 3.8 mmol) in a dropwise manner over a 6 minute period. The resulting mixture was stirred for 10 minutes at 0° C., then was allowed to warm to room temperature during a 20 minute interval and then was recooled in an ice bath for 20 minutes. The cooled reaction mixture was treated with $NaHSO_4$ (602.4 mg) in $H_2O$ (10 mL) and aqueous citric acid (30 mL). The reaction mixture was extracted into EtOAc (2×50 mL), and the organic solution was washed with $H_2O$ (50 mL), dried ($Na_2SO_4$), filtered and concentrated to yield a crude residue, which was carried onto next step.

Step G

To an ice cold (0° C.) solution of trimethylphosphonoacetate (0.90 mL, 6.24 mmol) in THF (20 mL) was added 60% NaH in mineral oil (unwashed; 194.6 mg, 4.86 mmol) in three portions. The heterogeneous mixture was further diluted with THF (10 mL) and was stirred at room temperature for 2.5 h. The reaction mixture was cooled in ice bath for 15 minutes and then was treated with the residue isolated in Step F (530.5 mg) in THF (30 mL). The ice bath was removed and the reaction mixture was allowed to warm to room temperature over a 45-minute interval. The reaction was quenched with aqueous citric acid solution (50 mL) and extracted into EtOAc (2×50 mL). The organic solution was dried ($Na_2SO_4$), filtered, and concentrated. The residue was purified by column chromatography (silica gel; 70% EtOAc in heptane) to yield a white solid.

Step H

A heterogeneous mixture of the solid isolated in Step G (286.5 mg, 0.915 mmol), and 10% Pd/C (72 mg) in MeOH (65 mL) was shaken over 50 psi of $H_2$ gas at room temperature for 4 h. The reaction mixture was filtered through a bed of Celite®, and the filter cake was rinsed with $CHCl_3$/MeOH (50 mL). The organic filtrate was concentrated to yield a solid. The reaction was repeated with additional solid prepared as in Step G (177.4 mg) to yield additional solid product. Both batches were combined and carried onto the next step without further manipulation.

Step I

A mixture of the compound isolated in Step H (400.0 mg, 1.27 mmol) and lithium hydroxide (65.8 mg, 2.75 mmol) in 7:3 $THF:H_2O$ (40 mL) was stirred for 3 h and then was allowed to stand at room temperature for 20 h. The reaction mixture was treated with citric acid (764.2 mg, 3.98 mmol) and water (25 ml) and then was stirred for 15 minutes and then was extracted into $CHCl_3$ (3×50 mL). The organic solution was washed with $H_2O$ (50 mL), dried ($Na_2SO_4$), filtered and concentrated to yield a white solid.

Step J

To a cooled (10° C.) suspension of the solid isolated in Step 1 (331.6 mg, 1.10 mmol), triethylamine (0.21 mL, 1.50 mmol) and N-hydroxybenzotriazole hydrate (204.6 mg, 1.51 mmol) in DMF (10 mL) was added N-methyl-cyclohexylamine (0.20 mL, 1.52 mmol), triethylamine (0.29 mL, 2.08 mmol) and 1-[(3-dimethylamino)propyl]-3-ethylcarbodiimide.HCl (289.3 mg, 1.51 mmol). After the reaction stirred at 0° C. for 1 h, the ice bath was removed, and the reaction was allowed to warm to room temperature and then was stirred for an additional 18 h. The reaction mixture was diluted with $CHCl_3$ (75 mL), washed with $H_2O$ (4×75 mL), dried ($Na_2SO_4$), filtered, and concentrated to a residue. The residue was purified by column chromatography (silica gel; 6% MeOH in $CHCl_3$) to yield a residue.

Step K

A solution of the residue isolated in Step J (382.4 mg, 0.966 mmol) in $CH_2Cl_2$ (15 mL) was treated with trifluoroacetic acid (3 mL) and stirred for 2 h at room temperature. The reaction mixture was concentrated to give a residue, which was basified with aqueous $NaHCO_3$, extracted into $CHCl_3$ (12×40 mL). The organic extracts were dried ($Na_2SO_4$), filtered, and evaporated to yield an oil.

Step L

A mixture of 2-nitro-5-phenoxybenzaldehyde (189.9 mg, 0.781 mmol) and the oil isolated in Step K (231.2 mg, 0.781 mmol) in MeOH (15 mL) was stirred at room temperature for 40 h and then was cooled in an ice bath for 30 minutes. The reaction mixture was treated with NaBH₄ (65.5 mg, 1.73 mmol) and was stirred for 1 h at room temperature. The reaction was quenched with aqueous NH₄Cl (50 mL) and then was extracted into CHCl₃ (2×50 mL). The organic solution was dried (Na₂SO₄), filtered, and concentrated. The residue was purified by column chromatography (silica gel, 6% MeOH in CHCl₃) to yield a yellow gum.

Step M

A heterogenous mixture of the yellow gum (345.7 mg, 0.660 mmol) isolated in Step L and 10% Pd/C (74.5 mg) in EtOH (70 mL) was shaken over 53 psi of H₂ gas at room temperature for 4 h. The reaction mixture was filtered through a bed of Celite®, and the filter cake was rinsed with EtOH (50 mL). The organic filtrate was concentrated to a yellow flaky solid that was carried onto the next step without further manipulation.

Step N

To a solution of the solid isolated in Step M (290.2 mg, 0.5886 mmol) in EtOH (10 mL) was added 3M cyanogen bromide in CH₂Cl₂ (200 µL, 0.600 mmol) at room temperature. The resulting mixture was stirred at room temperature for 20 h, and then was treated with additional cyanogen bromide solution (25 µL) and was heated at 55° C. for 4 h. The reaction mixture was concentrated to a residue that was purified by preparative TLC (4 tapered silica gel plates; 80:18:2 CHCl₃:MeOH:NH₄OH) to yield the title compound as a beige solid as its free base.

A solution of the free base (135.0 mg) in CHCl₃ (3 mL) was acidified with 1N HCl (0.5 mL) in Et₂O and was further diluted with Et₂O (75 mL). The HCl salt was collected by filtration and dried in the vacuum oven at 50° C. to yield the title compound a residue, as a 6:4 mixture of rotamers, as HCl salt.

MH⁺=519

¹H NMR (300 MHz, DMSO-d₆) δ1.00-2.10 (m, 21H), 2.15-2.25 (m, 1H), 2.40-2.60 (m, 1H), 2.75 (s, 0.4×1H), 2.85 (s, 0.6×1H), 3.40-3.50 (m, 1H), 4.00 (br s, 1H), 4.20-4.45 (m, 4H), 6.65 (s, 1H), 6.80-6.90 (m, 3H), 7.10-7.15 (m, 1H), 7.20-7.25 (m, 1H), 7.35-7.40 (m, 2H), 8.25 (br s, 2H), 11.70-11.75 (m, 1H)

Example 59

(S)-enantiomer of 4-cis-{[4-(2-Amino-6-phenoxy-4H-quinazolin-3-yl)-4-cyclohexyl-butyryl]-methyl-amino}-cyclohexanecarboxylic acid (Compound #739)

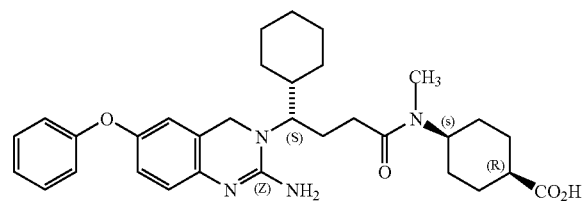

Step A

To a stirred solution of cis-4-(tert-butoxycarbonylamino) cyclohexane carboxylic acid (7.19 g, 29.6 mmole) in THF (100 mL) at 0° C., lithium aluminum hydride pellets (6.73 g, 177 mmole) were added slowly. After the addition of lithium aluminum hydride, the solution was stirred at room temperature for 2 h. Then, the solution was heated at reflux overnight. After cooling to room temperature, potassium sodium tartrate tetrahydrate and water were added to terminate the reaction. The solution was filtered through a pad of Celite®. Ethanol was used to wash the pad. The filtrate was evaporated, and the residue was dissolved in 6N hydrochloric acid (50 mL). The solution was concentrated to yield a colorless oil which was used directly in the next step without further purification.

MH⁺=144.0

Step B

To a stirred solution of the (S)-enantiomer of 4-tert-butoxycarbonylamino-4-cyclohexyl-butyric acid (prepared as in Example 28, Step E) (10.07 g, 35.3 mmole), the oil isolated in Step A (9.51 g, 52.9 mmole), and DIPEA (18.5 mL, 106.2 mmole) in DMF (100 mL), HBTU (9.51 g, 25.1 mmole) was added. After stirring at room temperature overnight, the solution was diluted with diethyl ether (300 mL). The solution was extracted with 1N HCl (80 mL) three times, and once with water, and dried over magnesium sulfate. The solution was concentrated to yield a colorless oil.

MH⁺=411.1

Step C

A stirred mixture of the oil isolated in Step B (13.20 g, 32.1 mmole) in aqueous 15% sodium bicarbonate solution (150 mL), sodium bromide (0.661 g, 6.4 mmole), and TEMPO (0.1005 g, 6.4 mmole) in acetone (400 mL) was cooled to 0° C., and trichloroisocyanuric acid (14.94 g, 64.3 mmole) was added slowly over 30 min. The solution then was warmed to room temperature and was stirred at this temperature for 24 hours. The solution was filtered through Celite®. The organic solvent was evaporated. Sodium carbonate (5.0 g) was added. The solution was washed with ethyl acetate once and then was acidified with 1N HCl. The resulting solution was extracted with ethyl acetate three times. The combined organic extracts were dried over magnesium sulfate. The solvent was evaporated to yield a colorless oil.

MH⁺=425.3

Step D

To a stirred solution of the oil isolated in Step C (7.4 g, 17.4 mmole) in dichloromethane (100 mL), trifluoroacetic acid (100 mL) was added. The solution was stirred at room temperature for 1 hour and then was concentrated. Water (50 mL) was added. Sodium bicarbonate was added until there was no bubbling from the solution. The resulting mixture was extracted with ethyl acetate three times. The combined organic phases were dried over magnesium sulfate. The solvent was evaporated to yield a white solid which was used directly in the next reaction.

Step E

To a stirred solution of the solid isolated in Step D in dichloromethane (100 mL), 2-nitro-5-phenoxy-benzaldehyde (3.85 g, 15.8 mmole), acetic acid (4.0 mL) and 4 Å molecular sieves (5.0 g) were added. After stirring at room temperature for 20 min, the solution was cooled to 0° C., and sodium triacetoxyborohydride (3.36 g, 15.8 mmole) was added slowly into the solution. The solution was stirred at this temperature for 7-8 hours, and then was allowed to warm up overnight. The solution was filtered through a pad of Celite®. The filtrate was concentrated. The residue was treated with 1N HCl (30 mL). The solution was extracted with ethyl acetate twice. The combined organic phases were washed with aqueous 1N NaOH solution twice. The combined aqueous extracts were acidified by adding 1N HCl. The solution was extracted with ethyl acetate twice. The combined organic phases was dried over magnesium sulfate. The solvent was evaporated to yield a slightly colored solid.

MH⁺=552.3

Step F

To a solution of the solid isolated in Step E (2.80 g, 3.6 mmole) in a solvent mixture of THF (40 mL) and ethanol (60 mL), 10% palladium on carbon (1.24 g) was added. The solution was subjected to hydrogenation for 1 hour at 30 psi. The solution was filtered through a pad of Celite® to yield a solution.

Step G

To the solution obtained in Step F, cyanogen bromide (3M in dichloromethane, 2.5 mL, 7.6 mmole) was added. The solution was stirred at room temperature overnight and then was concentrated. Water (100 mL) was added. Sodium bicarbonate was added until no more bubbling was observed. The solution was extracted with ethyl acetate twice. The combined organic phases were dried over magnesium sulfate. After removing the solvent, the residue was purified over silica gel column eluted with a mixture of dichloromethane and methanol from 99:1 to 70:30 to yield the title compound as a white solid.

MH$^+$=547.5

$^1$H NMR (300 MHz, DMSO), δ0.83-2.27 (m, 24H), 2.54 (s, 3H), 3.32 (s, 2H), 3.79 (m, 1H), 4.35-4.41 (m, 3H), 6.95-7.16 (m, 6H), 7.35-7.41 (m, 2H), 8.04 (br s, 1H)

Example 60

(S)-Enantiomer of 4-cis-{[4-(2-Amino-6-phenoxy-4H-quinazolin-3-yl)-4-(tetrahydro-pyran-4-yl)-butyryl]-methyl-amino}-cyclohexanecarboxylic acid (Compound #745)

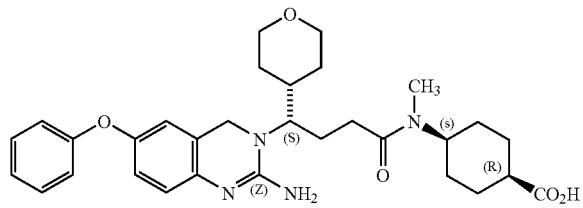

Step A

A stirred solution of the oil isolated in Example 59, Step A (6.69 g, 27.5 mmole) in 15% aqueous sodium bicarbonate solution (80 mL), sodium bromide (0.566 g, 5.5 mmole), and TEMPO (0.0859 g, 5.5 mmole) in acetone (200 mL) was cooled to 0° C., and trichloroisocyanuric acid (12.78 g, 55.0 mmole) was added slowly over 30 min. The reaction mixture then was warmed to room temperature and was stirred at this temperature for 24 hours and then was filtered through Celite®. The organic solvent was evaporated. Sodium carbonate (5.0 g) was added. The solution was washed with ethyl acetate once and then was acidified with 1N HCl. The resulting solution was extracted with ethyl acetate three times. The combined organic extracts were dried over magnesium sulfate. The solvent was evaporated to yield a white solid.

MH$^-$=256.1

Step B

Acetyl chloride (4.0 mL, 55 mmole) was added slowly to methanol at 0° C., and the mixture was stirred at this temperature for 30 min. The solid isolated in Step A (7.31 g, 28.4 mmole) was added. The solution was warmed to room temperature. After stirring at room temperature for 1 hour, the solution was heated at reflux overnight. The solvent was evaporated. The residue was recrystallized from acetone and diethyl ether to yield a white solid.

MH$^+$=172.2

Step C

To a stirred solution of the (S)-enantiomer of 4-tert-butoxycarbonylamino-4-(tetrahydro-pyran-4-yl)-butyric acid (Example 32, Step I) (0.74 g, 2.57 mmole), the solid isolated in Step B (0.59 g, 2.84 mmole), and DIPEA (1.8 mL, 10.3 mmole) in DMF (10 mL), HBTU (1.27 g, 3.3 mmole) was added. After stirring at room temperature overnight, the solution was diluted with diethyl ether (50 mL). The solution was washed with 1N HCl (20 mL) three times and once with water, and dried over magnesium sulfate. The solution was concentrated to yield a slightly colored oil.

MH$^+$=441.2

Step D

To a stirred solution of the oil isolated in Step C (1.23 g, 2.8 mmole) in dichloromethane (25 mL), trifluoroacetic acid (25 mL) was added. The solution was stirred at room temperature for 2 hours and then was concentrated. Water (50 mL) was added. Sodium bicarbonate was added until there was no bubbling from the solution. The resulting mixture was extracted with ethyl acetate three times. The combined organic phases were dried over magnesium sulfate. The solvent was evaporated to yield a black oil.

Step E

To a stirred solution of the solid isolated in Step D (0.28 g, 1.15 mmole) in dichloromethane (10 mL), 2-nitro-5-phenoxy-benzaldehyde (0.39 g, 1.15 mmole), acetic acid (0.2 mL), and 4 Å molecular sieves (0.9 g) were added. After stirring at room temperature for 1 hour, the solution was cooled to 0° C., and sodium triacetoxyborohydride was added slowly into the solution. The solution was stirred at this temperature for 8 hours and then was allowed to warm up overnight. The solution was filtered through a pad of Celite®, and the filtrate was concentrated. The residue was dissolved in ethyl acetate, and the solution was washed with aqueous 1N NaOH solution twice and once with water and then was dried over magnesium sulfate. The solvent was evaporated to yield a slightly colored solid.

MH$^+$=568

Step F

To a solution of the solid isolated in Step E (0.47 g, 0.83 mmole) in ethanol (50 mL), 10% palladium on carbon (0.37 g) was added. The mixture was subjected to hydrogenation for 1 hour at 30 psi. The reaction mixture was filtered through a pad of Celite® to yield a solution.

Step G

To the solution obtained in Step F, cyanogen bromide (3M in dichloromethane, 0.42 mL, 1.26 mmole) was added. The solution was stirred at room temperature overnight and then was concentrated. The residue was purified on HPLC to yield a white solid as its TFA salt.

MH$^+$=563.2

Step H

To a stirred solution of the solid isolated in Step G (0.045 g, 0.066 mmole) in a solvent mixture of THF (1.0 mL), methanol (1.0 mL), and water (1.0 mL), aqueous 1N NaOH (0.6 mL) was added. The solution was stirred at room temperature for 58 hours. The reaction mixture was neutralized with 1N HCl and then was purified by HPLC to yield the title compound as a white solid as its TFA salt.

MH$^+$=549.3

$^1$H NMR (300 MHz, DMSO), δ1.30-2.27 (m, 18H), 2.55 (m, 4H), 3.24 (m, 2H), 3.88 (m, 3H), 4.39-4.45 (m, 2H), 6.96-7.04 (m, 5H), 7.11-7.16 (m, 1H), 7.36-7.39 (m, 2H), 7.93 (s, 2H), 10.76 (s, 1H), 12.1 (s, 1H).

Example 61

(S)-Enantiomer of 4-cis-[[4-(2-Amino-6-phenoxy-4H-quinazolin-3-yl)-4-cyclohexyl-butyryl]-(2-hydroxy-ethyl)-amino]-cyclohexanecarboxylic acid (Compound #749)

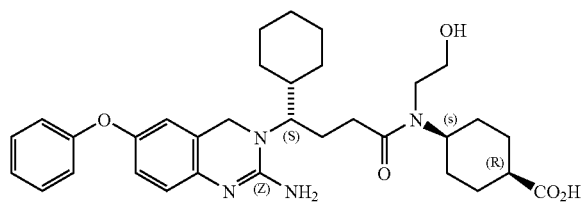

Step A

A solution of cis-4-aminocyclohexanecarboxylic acid HCl salt (10.27 g, 71.7 mmole), benzyl alcohol (36.4 mL, 351.7 mmole), and p-toluenesulfonic acid monohydrate (16.37 g, 86.0 mmole) in toluene (500 mL) was refluxed in a round bottom flask fitted with a condenser and Dean-Stark trap for 24 hours. Then the reaction mixture was cooled to 0° C., and diethyl ether was added. A white precipitate was produced and was collected by filtration. The precipitate was dissolved in ethyl acetate (400 mL). The organic solution was washed with aqueous sodium carbonate solution three times and saturated aqueous sodium chloride once and then dried over magnesium sulfate. The solvent was removed to yield a colorless oil.

$MH^+=234.0$

Step B

To a stirred solution of the oil isolated in Step A (6.25 g, 26.8 mmole) in methanol (100 mL) was added benzyloxyacetaldehyde (3.76 mL, 26.8 mmole). After stirring at room temperature for one hour, the solution was cooled to 0° C. Sodium borohydride (1.01 g, 26.7 mmole) was added slowly to the solution. After the solution was stirred at 0° C. for one hour, 2N HCl (30 mL) was added. The solution was washed with diethyl ether twice and then was basified by adding solid sodium carbonate. The aqueous phase was extracted with ethyl acetate twice. The combined organic phases were washed with saturated sodium bicarbonate twice and saturated sodium chloride once and then was dried over magnesium sulfate. The solvent was removed to yield a colorless oil.

$MH^+=368.3$

Step C

To a stirred solution of the (S)-enantiomer of 4-tert-butoxycarbonylamino-4-cyclohexyl-butyric acid (prepared as in Example 28, Step E) (2.67 g, 10.3 mmole), the oil isolated in Step B (3.78 g, 10.3 mmole), and DIPEA (3.3 mL, 34.5 mmole) in DMF (50 mL), HBTU (4.61 g, 12.1 mmole) was added. After stirring at room temperature overnight, the solution was diluted with diethyl ether (200 mL). The solution was extracted with 1N HCl (20 mL) three times and once with water and dried over magnesium sulfate. This material was purified on a silica gel column with 10:90 to 60:40 ethyl acetate:heptane to yield a colorless oil.

$MH^+=635.4$

Step D

To a stirred solution of the oil isolated in Step C (4.34 g, 6.8 mmole) in dichloromethane (20 mL), trifluoroacetic acid (20 mL) was added. The solution was stirred at room temperature for 2 hours and then was concentrated. Water (50 mL) was added. Sodium bicarbonate was added until there was no more bubbling from the solution. The resulting mixture was extracted with ethyl acetate three times. The combined organic phases were dried over magnesium sulfate. The solvent was evaporated to yield a colorless oil which was used directly in the next reaction.

Step E

To a solution of the solid isolated in Step D in ethanol (60 mL), 10% palladium on carbon (1.2 g) was added. The solution was subjected to hydrogenation for 4 hours at 50 psi. The solution was filtered through a pad of Celite® to yield a white solid.

$MH^+=355.2$

Step F

To a stirred solution of the solid isolated in Step E (0.47 g, 1.3 mmole) and 2-nitro-5-phenoxy-benzaldehyde (0.29 g, 1.2 mmole) in dichloromethane (40 mL), acetic acid (0.2 mL) and 4 Å molecular sieves (1.0 g) were added. After stirring at room temperature for 30 min, the solution was cooled to 0° C., and sodium triacetoxyborohydride (0.51 g, 2.4 mmole) was added slowly into the solution. The solution was stirred at this temperature for 8 hours, and then was allowed to warm up overnight. The filtrate was concentrated, and the residue was treated with ethyl acetate (100 mL). The solution was filtered through a pad of Celite®. The filtrate was washed with saturated aqueous sodium bicarbonate solution three times and once with brine and then was dried over magnesium sulfate. The solvent was evaporated to yield a colorless oil.

$MH^+=582.3$

Step G

To a solution of the solid isolated in Step F (1.36 g, 2.3 mmole) in a solvent mixture of THF (10 mL) and ethanol (60 mL), 10% palladium on carbon (1.4 g) was added. The solution was subjected to hydrogenation for 30 minutes at 30 psi. The solution was filtered through a pad of Celite® to yield a solution. The solvent was removed, and the residue was dissolved in ethyl acetate. The solution was extracted with saturated sodium bicarbonate solution twice and dried over magnesium sulfate. The solvent was removed to yield a residue that was used directly in the next step.

Step H

To the residue obtained in Step G, cyanogen bromide (3M in dichloromethane, 0.42 mL, 1.26 mmole) was added. The solution was stirred at room temperature overnight and then was concentrated. The residue was purified by HPLC to yield the title compound as a white solid, as its TFA salt.

$MH^+=577.3$ $^1$H NMR (300 MHz, DMSO), δ1.30-2.49 (m, 25H), 3.28 (m, 2H), 3.30 (m, 3H), 3.82 (m, 1H), 4.34-4.49 (m, 2H), 6.97-7.07 (m, 5H), 7.14-7.16 (m, 1H), 7.36-7.40 (m, 2H), 7.93 (s, 2H), 10.77 (s, 1H), 12.1 (s, 1H)

Example 62

(S)-Enantiomer of 4-cis-[[4-(2-Amino-6-phenoxy-4H-quinazolin-3-yl)-4-(tetrahydro-pyran-4-yl)-butyryl]-(2-hydroxy-ethyl)-amino]-cyclohexanecarboxylic acid (Compound #750)

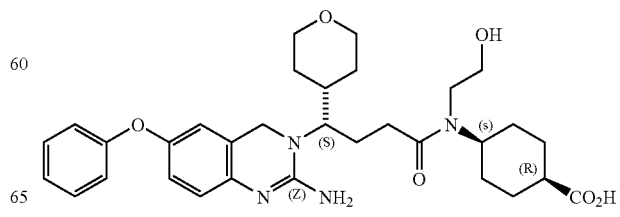

Step A

To an ice cooled solution of (S)-enantiomer of 4-tert-butoxycarbonylamino-4-(tetrahydro-pyran-4-yl)-butyric acid (2.4 g, 8 mmol), prepared as in Example 32, Step I, cis-4-(2-benzyloxyethylamino)cyclohexanecarboxylic acid benzyl ester (3.0 g, 8.1 mmol), prepared by as in Example 61, Step B, HOBT (1.4 g, 10 mmol) in $CH_2Cl_2$ (100 mL), TEA (2.3 mL, 16 mmol) was added followed by 1,3-dimethylamino propyl-3-ethylcarbodiimide (2.0 g, 10 mmol). The mixture was allowed to warm to room temperature and then was stirred overnight. Then, EtOAc (200 mL) was added, and this solution was washed with citric acid solution, $NaHCO_3$ solution, and NaCl solution. The organic layer was separated, dried with $MgSO_4$, and evaporated to yield an oil. The crude product (oil) was purified by column chromatography (1:1 hexane:EtOAc) to yield a colorless oil.

$MH^+$ 637.3

Step B

A solution of the colorless oil isolated in Step A (4.8 g, 7.5 mmol) in 5% $TFA:CH_2Cl_2$ (100 mL) was stirred at room temperature overnight. An additional 2 mL of TFA was added, and the solution was stirred at room temperature for another hour. The solvent and most of TFA was evaporated to yield a residue. To the residue was added EtOAc (300 mL). The resulting solution was washed with aqueous $NaHCO_3$ and NaCl solutions. The organic layer was separated, dried with $MgSO_4$, and evaporated to yield a light brown oil.

$MH^+$ 537.2

Step C

A solution of the oil isolated in Step B (1.9 g, 3.5 mmol), 2-nitro-5-phenoxybenzaldehyde (0.86 g, 3.5 mmol) in 1,2-dichloroethane (100 mL) was stirred at room temperature for 4 h. Then, $NaBH(OAc)_3$ (1.3 g, 6.1 mmol) was added, and the reaction mixture was stirred at room temperature overnight. The solution was poured into saturated $NaHCO_3$ solution and then was extracted with EtOAc (2×200 mL). The organic layer was dried with $MgSO_4$ and evaporated. Column chromatography (1:1 heptane:EtOAc) yielded a yellow oil.

$MH^+$ 764.1

Step D

To a solution of the oil isolated in Step C (1.45 g, 1.9 mmol) in MeOH (250 mL), zinc dust (16.7 g) and $NH_4Cl$ (2.0 g, 38 mmol) were added. The resulting mixture was refluxed for 4 h. The residual zinc was removed by filtration through Celite®. After the MeOH was removed, EtOAc (300 mL) was added, the solution was washed with aqueous $NaHCO_3$ and NaCl solutions. The organic layer was dried with $MgSO_4$ and evaporated to yield a light brown oil.

$MH^+$ 734.4

Step E

A solution of the oil isolated in Step D (0.67 g, 0.9 mmol) and BrCN (3M in $CH_2Cl_2$, 0.31 mL, 0.93 mmol) in EtOH (20 mL) was stirred at room temperature overnight. The EtOH was evaporated to yield a crude residue, as its HBr salt, which was used directly in next reaction.

$MH^+$ 759.9

Step F

A solution of the residue isolated in Step E (0.35 g, 0.42 mmol) and 10% Pd on carbon (0.18 g) in EtOH (100 mL) was subjected to hydrogenation at 10 psi for 48 h. The reaction mixture then was filtered through Celite®, and the filtrate was concentrated to yield a residue. Purification by HPLC yielded the title compound as a residue, as its TFA salt.

$MH^+$ 579.1

$^1H$ NMR (300 MHz, $CD_3OD$): δ0.91-1.25 (m, 4H), 1.51-1.76 (m, 10H), 2.02-2.21 (m, 8H), 3.3-3.61 (m, 8H), 3.9-3.99 (m, 2H), 4.05-4.15 (m, 2H), 6.74 (s, 1H), 6.95 (d, J=7.84 Hz, 2H), 6.99-7.06 (m, 2H), 7.11 (m, 1H), 7.35 (m, 2H).

In addition to the desired title compound, HPLC separation yielded the (S)-enantiomer of 4-[[4-(2-Amino-6-phenoxy-4H-quinazolin-3-yl)-4-(tetrahydro-pyran-4-yl)-butyryl]-(2-benzyloxy-ethyl)-amino]-cyclohexanecarboxylic acid (Compound #751):

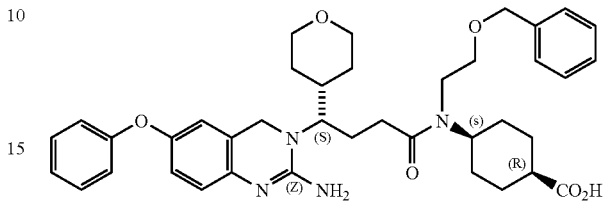

$MH^+$ 669.2, $MH^-$ 667.4

$^1H$ NMR (300 MHz, $CD_3OD$): δ1.17-1-33 (m, 4H), 1.46-1.68 (m, 6H), 1.76-1.89 (m, 4H), 2.18-2.27 (m, 2H), 2.6-2.8 (m, 6H), 3.13-3.29 (m, 2H), 3.43-3.54 (m, 1H), 3.53-3.54 (d, J=5.16 Hz, 2H), 3.94-4.02 (m, 1H), 4.06 (d, J=5.16 Hz, 2H), 4.46 (s, 2H), 6.68 (d, J=2.33 Hz, 1H), 6.94 (d, J=7.03 Hz, 2H), 7.10-7.21 (m, 2H), 7.28-7.3 (m, 8H).

Example 63

(S)-4-tert-Butoxycarbonylamino-5-methyl-hexanoic acid (Smrcina, M., Majer, P., Majerová, E., Guerassina, T. A., Eissenstat, M. A., *Tetrahedron*, 1997, 53 (38), 12867)

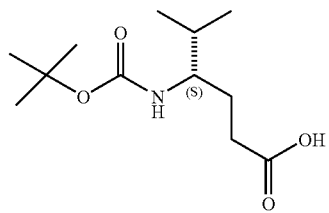

Step A: (R)-[1-(2,2-Dimethyl-4,6-dioxo-[1,3]dioxane-5-carbonyl)-2-methyl-propyl]-carbamic acid, tert-butyl ester A 5 L four-necked flask (equipped with mechanical stirrer, nitrogen inlet, thermocouple, and glass stopper) was charged with Boc-D-Valine (143.6 g, 0.661 mol) and dichloromethane (2.8 L). The reaction was chilled to ~3° C. in an ice bath, and then 4-N,N-dimethylaminopyridine (124.6 g, 1.02 mol) and Meldrum's acid (104.8 g, 0.727 mol) were added to the reaction. To the reaction mixture was then added 1-[3-(dimethylaminopropyl)]-3-ethylcarbodiimide hydrochloride (EDCI, 139.4 g, 0.727 mol) over a five-minute period, and then the reaction mixture was allowed to warm to room temperature over 18 h (overnight). The reaction mixture was washed with 5% (w/w) aqueous potassium bisulfate (4×600 mL), dried ($MgSO_4$), and the solution was used directly in the next step without concentration or purification. A small portion was concentrated and displayed the following analytical data.

Mass Spectrum (Electrospray, Negative mode): m/z=342 (M−1).

HPLC: R$_t$=5.051 min; ABZ+PLUS, 3 μm, 2.1×50 mm
Gradient: A=water (0.1% TFA), B=ACN (0.1% TFA) @ 0.75 mL/min
Initial: A:B, 90:10.t=0.00-4.00 min (A:B, 10:90), t=4.00-4.10 min (A:B, 0:100), t=4.10-6.00 min (A:B, 0:100)

Step B: (S)-[1-(2,2-Dimethyl-4,6-dioxo-[1,3]dioxan-5-ylmethyl)-2-methyl-propyl]-carbamic acid tert-butyl ester In a 5 L one-neck flask four-necked flask (equipped with mechanical stirrer, nitrogen inlet, thermocouple, and glass stopper), was charged the solution of (R)-[1-(2,2-dimethyl-4,6-dioxo-[1,3]dioxane-5-carbonyl)-2-methyl-propyl]-carbamic acid, tert-butyl ester in dichloromethane prepared in Step A above, (~3.2 L). The reaction was chilled to ~3° C. in an ice bath, and acetic acid was added (437 g, 7.27 mol). The reaction mixture was then treated with sodium borohydride granules (62.5 g, 1.65 mol), which were added in portions over 1 h. During the addition the reaction temperature increased to ~9° C. and was stirred at that temperature 1.5 h and then was split into two portions. Each portion was poured into brine (1 L), stirred (magnetically) for 20 minutes, and partitioned. Each organic phase was washed with brine (3×750 mL) and distilled water (2×500 mL). The combined organic phases were dried (MgSO$_4$) and concentrated to yield crude product. The crude product was dissolved in heptane-dichloromethane (~1:1) and loaded onto a Biotage 150M cartridge (2.5 kg silica gel) and then eluted with heptane (2 L), 15:85 (14 L), 3:7 (16 L), and 1:1 ethyl acetate-heptane (8 L) to give two main fractions. The first fraction yielded the desired material contaminated with minor impurities.
Melting Point: 108-112° C.
Optical Rotation: [α]$_D$=−10.2° (c 4.15, MeOH, 23° C.)
The second fraction yielded additional product, which displayed the following analytical data.
Melting Point: 115-117° C.
Optical Rotation: [α]$_D$=−11.2° (c 4.18, MeOH, 23° C.)
Mass Spectrum (Electrospray, Negative mode): m/z=328 (M−1)
HPLC: R$_t$=3.700 min; ABZ+PLUS, 3 μm, 2.1×50 mm
Gradient: A=water (0.1% TFA), B=ACN (0.1% TFA) @0.75 mL/min
Initial: A:B, 90:10.t=0.00-4.00 min (A:B, 10:90), t=4.00-4.10 min (A:B, 0:100), t=4.10-6.00 min (A:B, 0:100)

Step C: (S)-2-Isopropyl-5-oxo-pyrrolidine-1-carboxylic acid, tert-butyl ester

In a 3 L, one-necked flask (equipped with a magnetic stir bar and a condenser with nitrogen inlet) was charged (S)-[1-(2,2-dimethyl-4,6-dioxo-[1,3]dioxan-5-ylmethyl)-2-methyl-propyl]-carbamic acid, tert-butyl ester prepared in Step B above (147 g, 0.446 mol) and toluene (1.4 L). The reaction mixture was heated to reflux for 4 h then cooled to room temperature and concentrated in vacuo to yield crude product as a residual oil. The crude product was dissolved in heptane (~200 mL) and loaded onto a Biotage 75 L (800 g silica gel) and eluted with heptanes (1 L), 1:9 (7 L), and 1:3 ethyl acetate-heptane (2 L) to yield the product as an oil.
Optical Rotation: [α]$_D$=−71.90 (c 1.05, CHCl$_3$, 23° C.); lit value (R)+77.4° (c 1.4, CHCl$_3$)
Optical Rotation: [α]$_D$=−72.2° (c 0.983, MeOH, 23° C.)
Elemental Analysis: C$_{12}$H$_{21}$NO$_3$:
Calculated: % C=63.41, % H=9.31, % N=6.16
Found: % C=63.51, % H=9.35, % N=6.41

Step D: (S)-4-tert-Butoxycarbonylamino-5-methyl-hexanoic acid

A 2 L, one-necked flask (equipped with a magnetic stir bar and a nitrogen inlet) was charged with (S)-2-isopropyl-5-oxo-pyrrolidine-1-carboxylic acid, tert-butyl ester prepared in Step C above (77.4 g, 0.341 mol) and acetone (260 mL). To this solution was added 1M aqueous sodium hydroxide (408 mL, 0.408 mol), and the reaction mixture was stirred 30 minutes. The acetone was removed in vacuo and the resulting aqueous slurry was acidified, with vigorous stirring, by addition of solid sodium bisulfate (55 g, 0.45 mol) and diluted to 1 L with deionized water. The slurry was stirred for 2 h and the resulting white solid was collected by filtration, washed with deionized water, and dried in a vacuum oven to yield the product as a white solid.
Melting Point: 107-109° C.
Optical rotation: [α]$_D$=−6.400 (c 4.13, MeOH, 23° C.);
lit value (R)+2.9° (c 1.4, EtOH)
Mass Spectrum (Electrospray, Positive mode): m/z=267.9 (M+Na)
Elemental Analysis: C$_{12}$H$_{23}$NO$_4$:
Calculated: % C=58.75, % H=9.45, % N=5.71
Found: % C=58.84, % H=9.21, % N=5.60
The opposite enantiomer was prepared in an identical fashion starting from Boc-L-Valine and gave the following analytical data.
Melting Point: 91-95° C.
Optical rotation: [α]$_D$=+5.49° (c 3.16, MeOH, 23° C.)
Mass Spectrum (Electrospray, Positive mode): m/z=268.0 (M+Na)
Karl Fisher Titration: 0.20% (w/w); indicated 0.3 mol eq. hydrate.
Elemental Analysis: C$_{12}$H$_{23}$NO$_4$.0.3H$_2$O:
Calculated: % C=57.49, % H=9.49, % N=5.59
Found: % C=57.78, % H=10.04, % N=5.21

Example 64

(S)-4-tert-Butoxycarbonylamino-5-methyl-hexanoic acid, benzyl ester

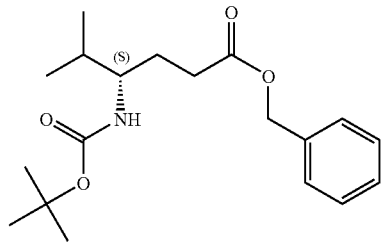

A 50 mL, one-neck round bottom flask (equipped with a magnetic stirrer and a nitrogen inlet) was charged with (S)-4-tert-butoxycarbonylamino-5-methyl-hexanoic acid prepared as in Example 63 above (500 mg, 2.04 mmol), cesium carbonate (1.99 g, 6.11 mmol), benzyl chloride (773 mg, 6.11 mmol), and tetrahydrofuran (15 mL). The reaction was stirred at room temperature for three days (weekend) and then was heated to a mild reflux for 6 h. The reaction mixture was poured into saturated aqueous sodium bicarbonate (100 mL)

and extracted with ethyl ether (2×100 mL). The combined organics were dried and concentrated to give 1 g of crude product. The residue was dissolved in heptane-dichloromethane (9:1, ~7 mL) and eluted through a 12 g Isco silica gel cartridge to yield the title compound as a solid.

Melting Point: 94-96° C.
Optical rotation: $[\alpha]_D=-8.52°$ (c 4.08, MeOH, 23° C.)
Mass Spectrum (Electrospray, Positive mode): m/z=357.9 (M+Na)
Elemental Analysis: $C_{19}H_{29}NO_4$:
Calculated: % C=68.03, % H=8.71, % N=4.18
Found: % C=68.06, % H=8.97, % N=4.07
HPLC: $R_t$=4.157 min; ABZ+PLUS, 3 μm, 2.1×50 mm
Gradient: A=water (0.1% TFA), B=ACN (0.1% TFA) @ 0.75 mL/min.
Initial: A:B, 90:10
t=0.00-4.00 min (A:B, 10:90), t=4.00-4.10 min (A:B, 0:100), t=4.10-6.00 min (A:B, 0:100)
Chiral HPLC: $R_t$=5.865 min; Chiralpak AD, 10 μm, 4.6× 250 mm
Isocratic: Hexane:Iso-Propanol (9:1)

The small amount of the enantiomer was synthesized as a reference and had the following characteristics (19415-84A).

Melting Point: 94-96° C.
Mass Spectrum (Electrospray, Positive mode): m/z=357.9 (M+Na)
HPLC: $R_t$=4.208 min; ABZ+PLUS, 3 μm, 2.1×50 mm
Gradient: A=water (0.1% TFA), B=ACN (0.1% TFA) @ 0.75 mL/min
Initial: A:B, 90:10
t=0.00-4.00 min (A:B, 10:90), t=4.00-4.10 min (A:B, 0:100), t=4.10-6.00 min (A:B, 0:100)
Chiral HPLC: $R_t$=11.376 min; Chiralpak AD, 10 μm, 4.6× 250 mm.
Isocratic: Hexane:Iso-Propanol (9:1)

Evaluation of the chiral HPLC indicated an enantiomeric excess of ~97.3% for each isomer. This indicates that there is little to no racemization in this synthetic route.

Example 65

3-(3-Dimethoxymethyl-4-nitro-phenoxy)-phenylamine

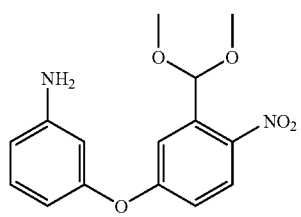 [SMILES: COC(OC)c1cc(Oc2cccc(N)c2)ccc1[N+](=O)[O-]]

3-Aminophenol (0.050 mol) was dissolved in DMA (100 mL). $K_2CO_3$ (0.060 mol) was added. 4-Chloro-2-dimethoxymethyl-1-nitrobenzene (0.050 mol) was added, and the reaction mixture was stirred overnight at 100° C. and then for 2 hours at 120° C. The reaction mixture was poured into water and this mixture was extracted with diisopropyl ether. The separated organic layer was dried, filtered and the solvent evaporated. The residue was purified by column chromatography over silica gel (eluent: $CH_2Cl_2$:$CH_3OH$ 100:0 (to remove unreacted 4-chloro-2-dimethoxymethyl-1-nitrobenzene) up to 70:30). The desired fractions were collected and the solvent was evaporated to yield a residue.

Example 66

N-[3-(3-Dimethoxymethyl-4-nitro-phenoxy)-phenyl]-benzenesulfonamide

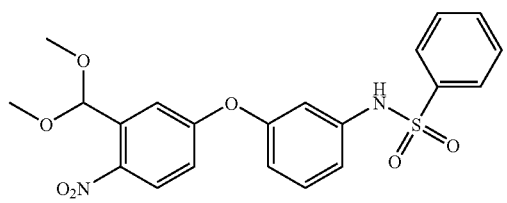 [SMILES: COC(OC)c1cc(Oc2cccc(NS(=O)(=O)c3ccccc3)c2)ccc1[N+](=O)[O-]]

A mixture of 3-(3-dimethoxymethyl-4-nitro-phenoxy) phenylamine (0.013 mol) in THF (100 mL) and TEA (200 mL) was stirred at room temperature and a mixture of benzenesulfonyl chloride (0.013 mol) in THF (50 mL) was added dropwise, then the reaction mixture was stirred overnight at room temperature and again overnight at 60° C. The solvent was evaporated and the residue was stirred in $H_2O$. After extraction with $CH_2Cl_2$, the organic layer was separated, dried, filtered off and the solvent was evaporated. The residue was purified by Biotage column chromatography (eluent: $CH_2Cl_2$ 100%). The purest product fractions were collected and the solvent was evaporated to yield the title compound as a residue.

Example 67

N-[3-(3-Formyl-4-nitro-phenoxy)-phenyl]-benzenesulfonamide

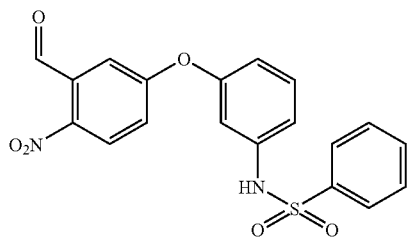 [SMILES: O=Cc1cc(Oc2cccc(NS(=O)(=O)c3ccccc3)c2)ccc1[N+](=O)[O-]]

A mixture of N-[3-(3-dimethoxymethyl-4-nitrophenoxy)-phenyl]-benzenesulfonamide (0.0083 mol) in THF (12 mL) was stirred at room temperature, then 12N HCl (6 mL) and water (6 mL) were added and the reaction mixture was stirred for 48 hours at room temperature. The mixture was stirred in $H_2O$ and extracted with diisopropyl ether. The organic layer was separated, washed with a 10% $NaHCO_3$ solution, separated again, dried, filtered, and the solvent was evaporated. The obtained residue was stirred in diisopropyl ether, and then the desired product was filtered off and dried to yield the title compound as a solid.

Example 68

N-[3-(4-Nitro-3-propylaminomethyl-phenoxy)-phenyl]-benzenesulfonamide

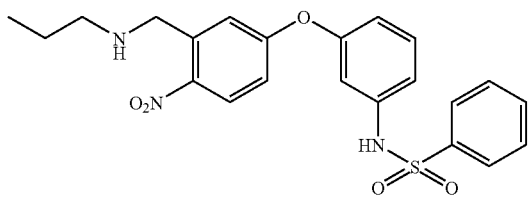 [SMILES: CCCNCc1cc(Oc2cccc(NS(=O)(=O)c3ccccc3)c2)ccc1N]

Under $N_2$, a mixture of N-[3-(3-formyl-4-nitrophenoxy)-phenyl]-benzenesulfonamide (0.0060 mol) and propylamine (0.0085 mol) in DCE (50 mL) was stirred at room temperature, then $NaBH(OAc)_3$ (0.0080 mol) was added and the reaction mixture was stirred overnight at room temperature. A saturated $NaHCO_3$ solution (50 mL) was added and the layers were separated. The organic layer was dried, filtered off and the solvent was evaporated. The residue was purified over silica gel filter (eluent: 98:2 $CH_2Cl_2$:$CH_3OH$). The purest product fractions were collected and the solvent was evaporated to yield the title compound as a residue.

Example 69

N-[3-(4-Amino-3-propylaminomethyl-phenoxy)-phenyl]-benzenesulfonamide

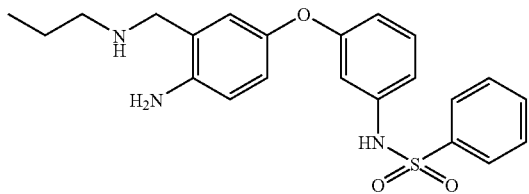

A mixture of N-[3-(4-nitro-3-propylaminomethyl-phenoxy)-phenyl]-benzenesulfonamide (0.0045 mol) in methanol (100 mL) was hydrogenated with 10% Pd/C (0.5 g) as a catalyst in the presence of thiophene solution (1 mL). After uptake of $H_2$ gas (3 equiv.), the reaction mixture was filtered over Dicalite and the filtrate was evaporated to yield the title compound as a residue.

Example 70

N-[3-(2-Amino-3-propyl-3,4-dihydro-quinazolin-6-yloxy)-phenyl]-benzenesulfonamide

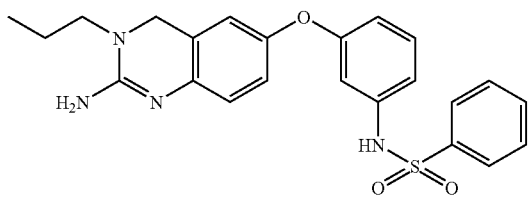 [SMILES: CCCN1Cc2cc(Oc3cccc(NS(=O)(=O)c4ccccc4)c3)ccc2N=C1N]

A mixture of N-[3-(4-amino-3-propylaminomethyl-phenoxy)-phenyl]-benzenesulfonamide (0.0044 mol) in ethanol (50 mL) was stirred at room temperature and cyanogen bromide (0.0064 mol) was added, then the reaction mixture was stirred and refluxed for 4 hours. After cooling, the precipitate was filtered off and was stirred in boiling $CH_3CN$ with $CH_3OH$. The resulting solids were filtered off, washed with diisopropyl ether and dried to yield the title compound as a solid.

Example 71

3-(3-Dimethoxymethyl-4-nitrophenoxy)-benzonitrile

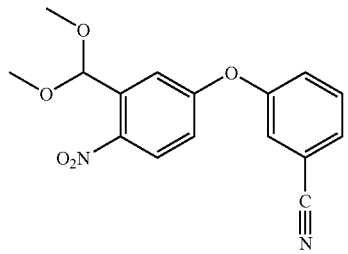 [SMILES: COC(OC)c1cc(Oc2cccc(C#N)c2)ccc1[N+](=O)[O-]]

A mixture of 3-hydroxybenzonitrile (0.129 mol) in N,N-dimethyl-acetamide (200 mL) was stirred at room temperature and $K_2CO_3$ (0.147 mol) was added, then 4-chloro-2-dimethoxymethyl-1-nitrobenzene (0.086 mol) was added and the reaction mixture was stirred for 24 hours at 130° C. The solvent was evaporated and the residue was stirred in $H_2O$. After extraction with $CH_2Cl_2$, the organic layer was separated, dried, filtered off and the solvent was evaporated. The residue was purified over a silica gel filter (eluent: $CH_2Cl_2$ 100%). The purest product fractions were collected and the solvent was evaporated to yield the title compound as residue.

Example 72

3-(3-Formyl-4-nitrophenoxy)-benzonitrile

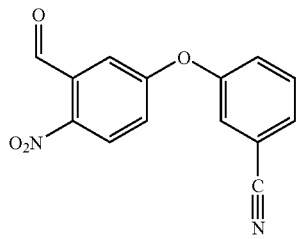 [SMILES: N#Cc1cccc(Oc2ccc([N+](=O)[O-])c(C=O)c2)c1]

A mixture of 3-(3-dimethoxymethyl-4-nitro-phenoxy)-benzonitrile (0.068 mol) in water (55 mL) was stirred at room temperature, and then 12N HCl (55 mL) and THF (140 mL) were added, and the reaction mixture was stirred overnight at room temperature. The mixture was stirred in $H_2O$ and extracted with diisopropyl ether. The organic layer was separated, washed with a 10% $NaHCO_3$ solution, separated again, dried, filtered off and the solvent was evaporated. The obtained residue was stirred in diisopropyl ether, and then the desired product was filtered off and dried to yield the title compound as a solid.

Example 73

3-(4-Nitro-3-propylaminomethyl-phenoxy)-benzonitrile

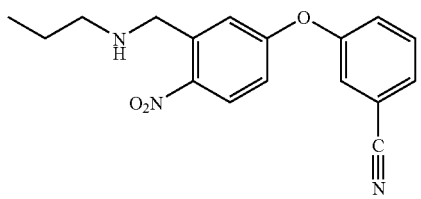 [SMILES: CCCNCc1cc(Oc2cccc(C#N)c2)ccc1[N+](=O)[O-]]

Under N$_2$, a mixture of 3-(3-formyl-4-nitrophenoxy)-benzonitrile (0.056 mol) and propylamine (0.059 mol) in DCE (450 mL) was stirred at room temperature, and then NaBH(OAc)$_3$ (0.063 mol) was added, and the reaction mixture was stirred overnight at room temperature. A saturated NaHCO$_3$ solution was added, and the layers were separated. The organic layer was dried, filtered off and the solvent was evaporated. The residue was purified over silica gel filter (eluent: 99:1 CH$_2$Cl$_2$:CH$_3$OH). The purest product fractions were collected and the solvent was evaporated to yield the title compound as a residue.

Example 74

3-(4-Amino-3-propylaminomethyl-phenoxy)-benzonitrile

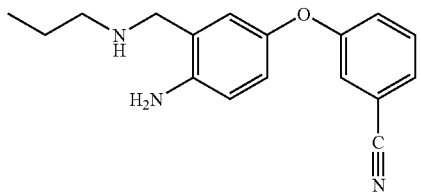 [SMILES: CCCNCc1cc(Oc2cccc(C#N)c2)ccc1N]

A mixture of 3-(4-nitro-3-propylaminomethyl-phenoxy)-benzonitrile (0.045 mol) in methanol (250 mL) was hydrogenated with 10% Pd/C (2 g) as a catalyst in the presence of thiophene solution (2 mL). After uptake of H$_2$ gas (3 equiv.), the reaction mixture was filtered over Dicalite and the filtrate was evaporated. The residue was purified by column chromatography over silica gel (eluent: 98:2 CH$_2$Cl$_2$:CH$_3$OH). The purest product fractions were collected and the solvent was evaporated to yield the title compound as a residue.

Example 75

3-(2-Amino-3-propyl-3,4-dihydro-quinazolin-6-yloxy)-benzonitrile

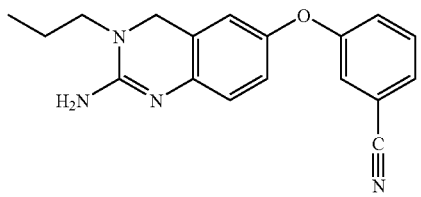 [SMILES: CCCN1Cc2cc(Oc3cccc(C#N)c3)ccc2N=C1N]

A mixture of 3-(4-amino-3-propylaminomethyl-phenoxy)-benzonitrile (0.032 mol) in ethanol (400 mL) was stirred at room temperature, and cyanogen bromide (0.038 mol) was added, and then the reaction mixture was stirred and refluxed for 2 hours. After cooling, the precipitate was filtered off, washed with diisopropyl ether and dried to yield crude product as a solid.

The filtrate was evaporated and the obtained residue was crystallized from CH$_3$CN:diisopropyl ether, then the precipitate was filtered off, washed with diisopropyl ether, and dried to yield an additional crop of the title compound as a solid.

Example 76

[6-(3-Cyano-phenoxy)-3-propyl-3,4-dihydro-quinazolin-2-yl]-carbamic acid tert-butyl ester

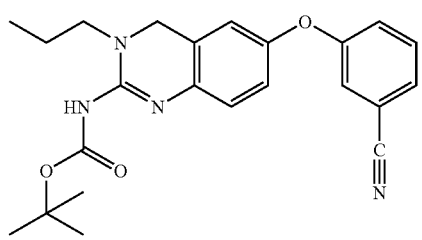 [SMILES: CCCN1Cc2cc(Oc3cccc(C#N)c3)ccc2N=C1NC(=O)OC(C)(C)C]

A mixture of 3-(2-amino-3-propyl-3,4-dihydro-quinazolin-6-yloxy)-benzonitrile (0.021 mol) and TEA (2.5 g) in THF (400 mL) was stirred at 5° C., then t-butoxycarbonyl anhydride (0.023 mol) was added, and the reaction mixture was stirred over the weekend at room temperature. The solvent was evaporated, then the residue was stirred in H$_2$O and the mixture was extracted with CH$_2$Cl$_2$. The organic layer was separated, dried, filtered off and the solvent was evaporated. The residue was purified by column chromatography over silica gel (eluent: 99:1 CH$_2$Cl$_2$:CH$_3$OH). The purest product fractions were collected and the solvent was evaporated to yield the title compound as residue.

Example 77

[6-(3-Aminomethyl-phenoxy)-3-propyl-3,4-dihydro-quinazolin-2-yl]-carbamic acid tert-butyl ester

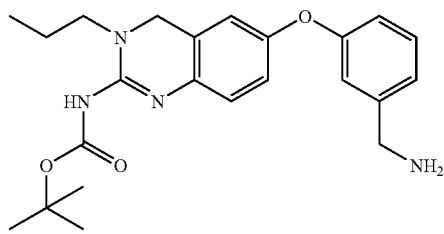 [SMILES: CCCN1Cc2cc(Oc3cccc(CN)c3)ccc2N=C1NC(=O)OC(C)(C)C]

A mixture of [6-(3-cyano-phenoxy)-3-propyl-3,4-dihydro-quinazolin-2-yl]-carbamic acid tert-butyl ester (0.0197 mol) in a solution of ammonia in methanol (250 mL) was hydrogenated at 14° C. with Raney nickel (1 g) as a catalyst. After uptake of H$_2$ gas (2 equiv.), the reaction mixture was filtered over Dicalite and the filtrate was evaporated to yield the title compound as a residue.

Example 78

(3-Propyl-6-{3-[(2,4,6-trimethyl-benzylamino)-methyl]-phenoxy}-3,4-dihydro-quinazolin-2-yl)-carbamic acid tert-butyl ester

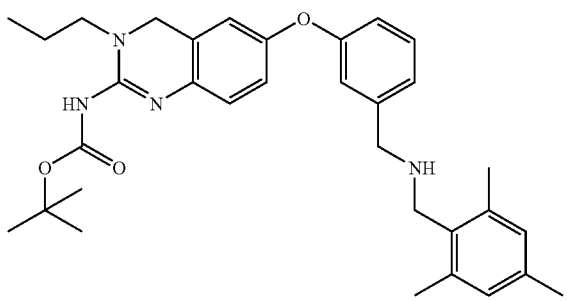 [SMILES: CCCN1Cc2cc(Oc3cccc(CNCc4c(C)cc(C)cc4C)c3)ccc2N=C1NC(=O)OC(C)(C)C]

Under $N_2$, a mixture of [6-(3-aminomethyl-phenoxy)-3-propyl-3,4-dihydro-quinazolin-2-yl]-carbamic acid tert-butyl ester (0.0007 mol) and 2,4,6-trimethyl-benzaldehyde (0.0007 mol) in DCE (10 mL) was stirred at room temperature, then NaBH(OAc)$_3$ (0.2 g) was added, and the reaction mixture was stirred overnight at room temperature. A saturated NaHCO$_3$ solution was added, and the layers were separated. The organic layer was dried, filtered off and the solvent was evaporated. The residue was purified by Biotage column chromatography (gradient eluent: CH$_2$Cl$_2$:CH$_3$OH). The purest product fractions were collected and the solvent was evaporated to yield the title compound as a residue.

Example 79

3-Propyl-6-{3-[(2,4,6-trimethyl-benzylamino)-methyl]-phenoxy}-3,4-dihydro-quinazolin-2-ylamine

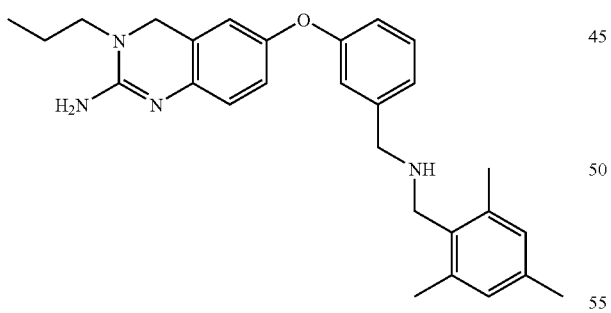

A mixture of (3-propyl-6-{3-[(2,4,6-trimethyl-benzylamino)-methyl]-phenoxy}-3,4-dihydro-quinazolin-2-yl)-carbamic acid tert-butyl ester (0.00041 mol) in trifluoroacetic acid (1 mL) and DCM (10 mL) was stirred overnight at room temperature and the solvent was evaporated. The obtained residue was decomposed in diisopropyl ether/CH$_3$CN, then the desired product was filtered off and dried to yield the title compound as a solid.

mp 184.5° C.

Example 80

3-(3-Dimethoxymethyl-4-nitro-phenylsulfanyl)-phenylamine

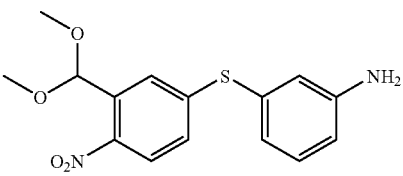 [SMILES: COC(OC)c1cc(Sc2cccc(N)c2)ccc1[N+](=O)[O-]]

K$_2$CO$_3$ (0.085 mol) was added to a mixture of 3-aminothiophenol (0.075 mol) in DMA (150 mL), then 4-chloro-2-dimethoxymethyl-1-nitrobenzene (0.050 mol) was added and the reaction mixture was stirred for 2 hours at 80° C. H$_2$O was added and the mixture was extracted with diisopropyl ether. The crude product was purified by column chromatography (eluent: 70:30 CH$_2$Cl$_2$:hexane up to 99:1 CH$_2$Cl$_2$:CH$_3$OH). The product fractions were collected and the solvent was evaporated to yield the title compound as a residue which contained about 10% of an impurity. (The product was used in subsequent steps without further purification.)

Example 81

N-[3-(3-Dimethoxymethyl-4-nitro-phenylsulfanyl)-phenyl]-benzenesulfonamide

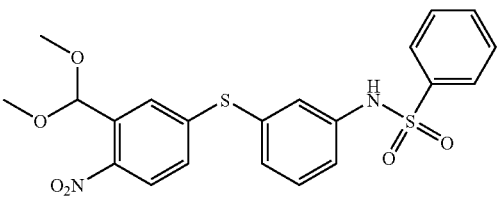 [SMILES: COC(OC)c1cc(Sc2cccc(NS(=O)(=O)c3ccccc3)c2)ccc1[N+](=O)[O-]]

A mixture of 3-(3-dimethoxymethyl-4-nitro-phenylsulfanyl)-phenylamine (0.0384 mol) and TEA (0.0576 mol) in THF (q.s.) was stirred at 5° C., and benzenesulfonyl chloride (0.0384 mol) was added dropwise at 5° C., then the reaction mixture was reacted at room temperature and purified by column chromatography over silica gel (eluent: CH$_2$Cl$_2$). The product fractions were collected and the solvent was evaporated to yield the title compound as a residue. (The product was used in subsequent steps without further purification.)

Example 82

N-[3-(3-Formyl-4-nitro-phenylsulfanyl)-phenyl]-benzenesulfonamide

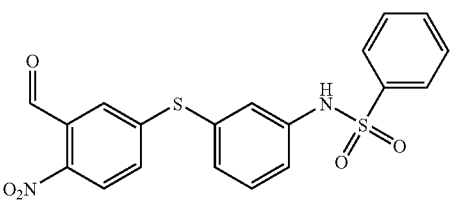 [SMILES: O=Cc1cc(Sc2cccc(NS(=O)(=O)c3ccccc3)c2)ccc1[N+](=O)[O-]]

A mixture of N-[3-(3-dimethoxymethyl-4-nitro-phenyl-sulfanyl)-phenyl]-benzenesulfonamide (0.027 mol) in 12N HCl (25 mL), THF (75 mL) and water (50 mL) was stirred overnight at room temperature, and then the mixture was extracted with ethyl acetate. The extract was washed with water and with a saturated aqueous Na₂CO₃ solution. The solvent was evaporated and the residue was purified by column chromatography over silica gel (eluent: CH₂Cl₂). The product fractions were collected and the solvent evaporated to yield the title compound as a residue.

Example 83

N-[3-(4-Nitro-3-propylaminomethyl-phenylsulfanyl)-phenyl]-benzenesulfonamide

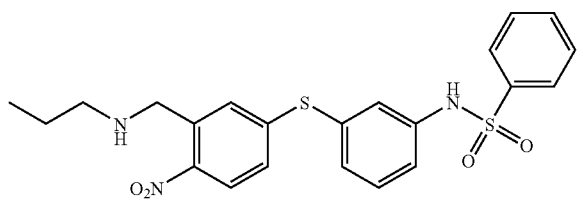

A mixture of N-[3-(3-formyl-4-nitro-phenylsulfanyl)-phenyl]-benzenesulfonamide (0.0027 mol), propylamine (0.003 mol) and NaBH(OAc)₃ (0.0041 mol) in DCE (60 mL) was reacted overnight at room temperature. Then a 10% NaOH solution was added and the mixture was extracted with CH₂Cl₂. The extract was dried (MgSO₄) and then purified by column chromatography over silica gel (eluent: 1:0 to 7:1 CH₂Cl₂:CH₃OH). The product fractions were collected and the solvent was evaporated to yield the title compound as a residue.

Example 84

N-[3-(4-Amino-3-propylaminomethyl-phenylsulfanyl)-phenyl]-benzenesulfonamide

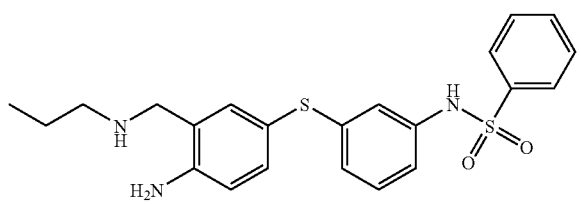 [SMILES: CCCNCc1cc(Sc2cccc(NS(=O)(=O)c3ccccc3)c2)ccc1[N+](=O)[O-]]

A mixture of N-[3-(4-nitro-3-propylaminomethyl-phenylsulfanyl)-phenyl]-benzenesulfonamide (0.0016 mol) in methanol (50 mL) was hydrogenated with 10% Pd/C (0.1 g) as a catalyst. After uptake of H₂ gas (3 equiv.), the catalyst was filtered off and the filtrate was evaporated to yield the title compound as a residue. (The product was used in subsequent steps without further purification.)

Example 85

N-[3-(2-Amino-3-propyl-3,4-dihydro-quinazolin-6-ylsulfanyl)-phenyl]-benzenesulfonamide

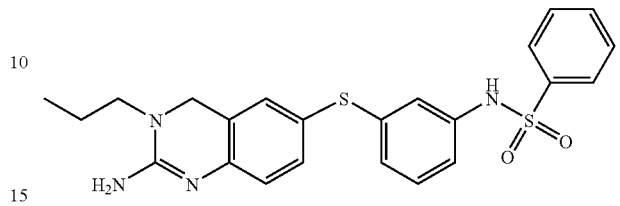

A mixture of N-[3-(4-Amino-3-propylaminomethyl-phenylsulfanyl)-phenyl]-benzenesulfonamide (0.0016 mol) and cyanogen bromide (0.0020 mol) in ethanol (q.s.) was reacted overnight at room temperature and then the organic solvent (EtOH) was evaporated. The obtained concentrate was warmed in EtOH and then cooled. The mixture was filtered and the collected residue was recrystallized from EtOH to yield the title compound as a solid.

mp 196.8-274° C.

Example 86

N-[2-(2-Bromo-phenyl)-ethyl]-benzenesulfonamide

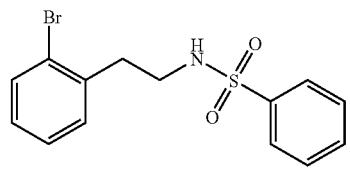 [SMILES: O=S(=O)(NCCc1ccccc1Br)c1ccccc1]

Benzenesulfonyl chloride (0.011 mol) was slowly added dropwise at room temperature to a mixture of 2-bromophenylethylamine (0.01 mol) and TEA (0.013 mol) in THF (50 mL). Then the reaction mixture was stirred overnight at room temperature, and the solvent was evaporated. The obtained residue was washed with H₂O and extracted with CH₂Cl₂. The organic layer was separated, dried (MgSO₄), filtered off and the solvent was evaporated. The residue was stirred in diethyl ether, then the desired product was filtered off and dried (vac.) to yield the title compound as an oil.

Example 87

2-Nitro-5-(4,4,5,5-tetramethyl-[1,3,2]dioxaborolan-2-yl)-benzaldehyde

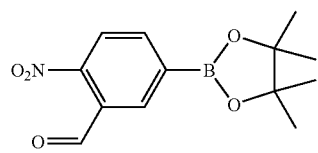 [SMILES: CC1(C)OB(c2ccc([N+](=O)[O-])c(C=O)c2)OC1(C)C]

A mixture of Pd$_2$(dba)$_3$ (0.0007 mol) and tricyclohexylphosphine (0.0029 mol) in dry dioxane (200 mL) was stirred under N$_2$ for 30 min, and then 2-nitro-4-bromobenzaldehyde (0.040 mol), pinacol diborane (4,4,4',4',5,5,5',5'-octamethyl-2,2'-bi-1,3,2-dioxaborolane) (0.044 mol), and potassium acetate (0.060 mol) were added and the reaction mixture was stirred for 16 hours under N$_2$ at 80° C. The mixture was cooled to room temperature and the solvent was evaporated. The obtained residue was washed with H$_2$O and extracted with CH$_2$Cl$_2$. The organic layer was separated, dried (MgSO$_4$), filtered off and the solvent was evaporated. The residue was purified by short column chromatography over silica gel (eluent: 100% CH$_2$Cl$_2$). The purest product fractions were collected and the solvent was evaporated. The residue was stirred in hexane, and then the resulting precipitate was filtered off and dried to yield the title compound as a residue.

Example 88

N-[2-(3'-Formyl-4'-nitro-biphenyl-2-yl)-ethyl]-benzenesulfonamide

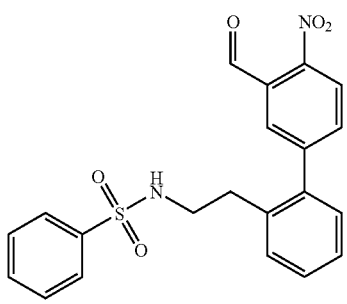 [SMILES: O=Cc1cc(-c2ccccc2CCNS(=O)(=O)c2ccccc2)ccc1[N+](=O)[O-]]

A mixture of 2-nitro-5-(4,4,5,5-tetramethyl-[1,3,2]dioxaborolan-2-yl)-benzaldehyde (0.001 mol), N-[2-(2-bromophenyl)-ethyl]-benzenesulfonamide (0.0012 mol) and Pd(PCy$_3$)$_2$Cl$_2$ (0.00005 mol) in DME (5 mL) and 1M Na$_2$CO$_3$ (2 mL) in a reaction vial was stirred for 3 hours at 80° C., then DME was removed under a stream of N$_2$ and the resulting mixture was extracted with CH$_2$Cl$_2$. The mixture was filtered through Extrelut, and the organic layer was blown dry, then the desired product was isolated by FAST-synthesis to yield the title compound as a residue.

Example 89

N-[2-(4'-Nitro-3'-propylaminomethyl-biphenyl-2-yl)-ethyl]-benzenesulfonamide

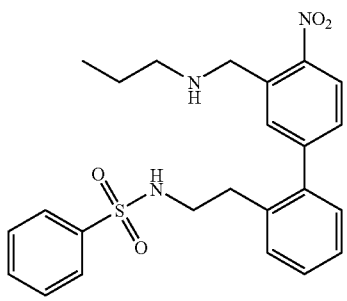 [SMILES: CCCNCc1cc(-c2ccccc2CCNS(=O)(=O)c2ccccc2)ccc1[N+](=O)[O-]]

NaBH(OAc)$_3$ (0.0031 mol) was added to a mixture of N-[2-(3'-formyl-4'-nitro-biphenyl-2-yl)-ethyl]-benzenesulfonamide (0.0021 mol) and propylamine (0.0023 mol) in DCE (2 mL), and the reaction mixture was stirred overnight under N$_2$. The excess of NaBH(OAc)$_3$ was decomposed with CH$_3$OH, and the solvent was evaporated. The residue was purified by Biotage column chromatography (eluent: 95:5 CH$_2$Cl$_2$:CH$_3$OH). The purest product fractions were collected and then the solvent was evaporated and co-evaporated with toluene to yield the title compound as a residue.

Example 90

N-[2-(4'-Amino-3'-propylaminomethyl-biphenyl-2-yl)-ethyl]-benzenesulfonamide

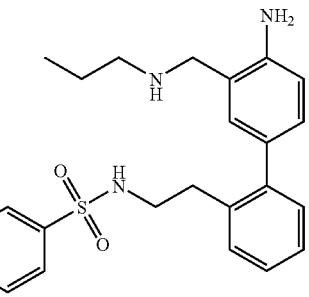

A mixture of N-[2-(4'-nitro-3'-propylaminomethyl-biphenyl-2-yl)-ethyl]-benzenesulfonamide (0.00031 mol) in methanol (50 mL) was hydrogenated with 10% Pd/C (0.100 g) as a catalyst in the presence of thiophene solution (0.5 mL). After uptake of H$_2$ gas (3 equiv.), the reaction mixture was filtered over Dicalite and the filtrate was evaporated to yield the title compound as a residue. (The compound was used without further purification, immediately in the next reaction step.)

Example 91

N-{2-[2-(2-Amino-3-propyl-3,4-dihydro-quinazolin-6-yl)-phenyl]-ethyl}-benzenesulfonamide

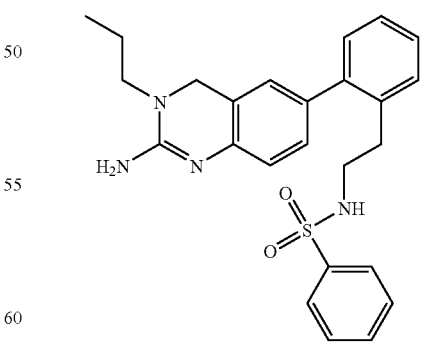

Cyanogen bromide (0.00034 mol) was added to a mixture of N-[2-(4'-amino-3'-propylaminomethyl-biphenyl-2-yl)-ethyl]-benzenesulfonamide (0.00031 mol) in ethanol (1 mL) in a Fast-tube, and then the reaction mixture was stirred overnight at room temperature. The solvent was evaporated and the residue was purified by high-performance liquid chromatography. The purest product fractions were collected and the solvent was evaporated to yield the title compound as a residue.

Example 92

[3-(3-Dimethoxymethyl-4-nitro-phenoxy)-phenyl]-carbamic acid benzyl ester

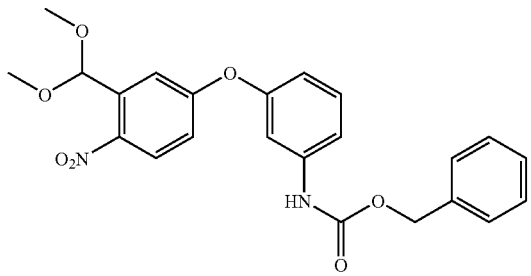 [SMILES: COC(OC)c1cc(Oc2cccc(NC(=O)OCc3ccccc3)c2)ccc1[N+](=O)[O-]]

A mixture of 3-(3-dimethoxymethyl-4-nitro-phenoxy)-phenylamine (0.14 mol), prepared as in Example 65, and diisopropyl ether (0.16 mol) in DCM (1000 mL) was cooled to 10° C., and carbonochloridic acid phenylmethyl ester (also known as benzyl chloroformate) (0.16 mol) was added dropwise, then the reaction mixture was stirred overnight at room temperature and washed with $H_2O$. The organic layer was separated, dried ($MgSO_4$), filtered off and the solvent was evaporated. The residue was purified by column chromatography (eluent: 100% $CH_2Cl_2$). The product fractions were collected and the solvent was evaporated to yield the title compound as a residue.

Example 93

[3-(3-Formyl-4-nitro-phenoxy)-phenyl]-carbamic acid benzyl ester

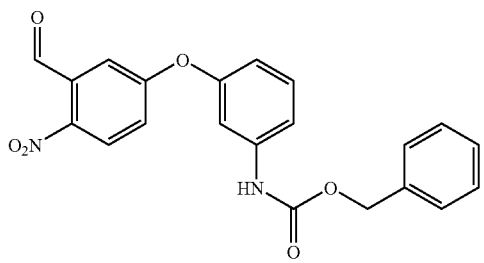 [SMILES: O=Cc1cc(Oc2cccc(NC(=O)OCc3ccccc3)c2)ccc1[N+](=O)[O-]]

12N HCl (33 mL) and water (66 mL) were added to a mixture of [3-(3-dimethoxymethyl-4-nitro-phenoxy)-phenyl]-carbamic acid benzyl ester (0.14 mol) in THF (400 mL) and the reaction mixture was stirred for 48 hours at room temperature. The mixture was diluted with $H_2O$ (500 mL) and extracted 2 times with diisopropyl ether. The organic layer was separated, dried ($MgSO_4$), filtered off and the solvent was evaporated. The resulting product was removed with a spatula and dried under vacuum to yield the title compound as a residue.

Example 94

[3-(4-Nitro-3-propylaminomethyl-phenoxy)-phenyl]-carbamic acid benzyl ester

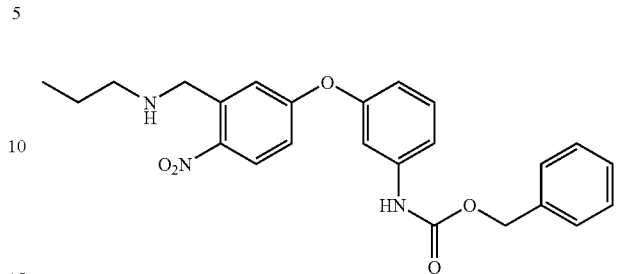

A mixture of [3-(3-formyl-4-nitro-phenoxy)-phenyl]-carbamic acid benzyl ester (0.038 mol) in DCE (300 mL) was cooled in an ice bath to 15° C., then propylamine (0.042 mol), followed by $NaBH(OAc)_3$ (0.057 mol) which was added portionwise. The reaction mixture was stirred overnight at room temperature and the mixture was washed with a saturated $NaHCO_3$ solution. The organic layer was separated, dried ($MgSO_4$), filtered off and the solvent was evaporated. The residue was purified by column chromatography over silica gel (eluent: 90:10 $CH_2Cl_2$:$CH_3OH$). The product fractions were collected and the solvent was evaporated, then co-evaporated with toluene to yield the title compound as a residue.

Example 95

[3-(4-Amino-3-propylaminomethyl-phenoxy)-phenyl]-carbamic acid benzyl ester

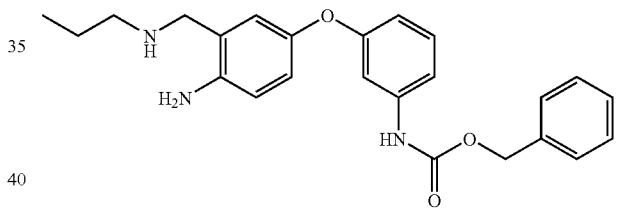

A mixture of [3-(4-nitro-3-propylaminomethyl-phenoxy)-phenyl]-carbamic acid benzyl ester (0.033 mol) in THF (200 mL) was hydrogenated with 10% Pt/C (2 g) as a catalyst in the presence of thiophene solution (2 mL). After uptake of $H_2$ gas (3 equiv.), the reaction mixture was filtered through Dicalite, and the filtrate was evaporated. The residue was purified by column chromatography (eluent: 90:10 $CH_2Cl_2$:($CH_3OH$:$NH_3$)). The product fractions were collected, and the solvent was evaporated to yield the title compound as an oil.

Example 96

[3-(2-Amino-3-propyl-3,4-dihydro-quinazolin-6-yloxy)-phenyl]-carbamic acid benzyl ester

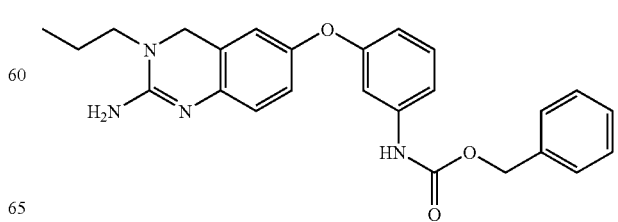

A mixture of [3-(4-Amino-3-propylaminomethyl-phenoxy)-phenyl]-carbamic acid benzyl ester (0.032 mol) and cyanogen bromide (0.035 mol) in ethanol (250 mL) was stirred and refluxed for 2 hours, then the reaction mixture was cooled to room temperature and the solvent was evaporated. The residue was converted into its free base with a NaOH solution and the resulting mixture was extracted with $CH_2Cl_2$. The organic layer was separated and the solvent was evaporated, then the residue was stirred in diisopropyl ether, filtered off and dried under vacuum to yield the title compound as a solid.

Example 97

[6-(3-Benzyloxycarbonylamino-phenoxy)-3-propyl-3,4-dihydro-quinazolin-2-yl]-carbamic acid tert-butyl ester

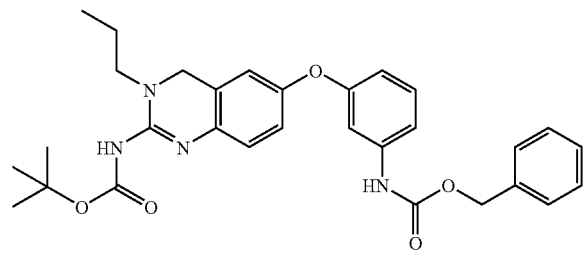 [SMILES: CCCN1Cc2cc(Oc3cccc(NC(=O)OCc4ccccc4)c3)ccc2N=C1NC(=O)OC(C)(C)C]

A mixture of [3-(2-amino-3-propyl-3,4-dihydro-quinazolin-6-yloxy)-phenyl]-carbamic acid benzyl ester (0.011 mol) in DCM (100 mL) was cooled to 5° C. Then, a solution of t-butoxycarbonyl anhydride (0.013 mol) in DCM (20 mL) was added dropwise, and the reaction mixture was stirred overnight at room temperature. Extra t-butoxycarbonyl anhydride (q.s.) was added and the resulting mixture was stirred for 3 hours at 30° C. The solvent was evaporated and the obtained residue was stirred in diisopropyl ether. Finally, the resulting precipitate was filtered off and dried under vacuum to yield the title compound as a solid.

Example 98

[6-(3-Amino-phenoxy)-3-propyl-3,4-dihydro-quinazolin-2-yl]-carbamic acid tert-butyl ester

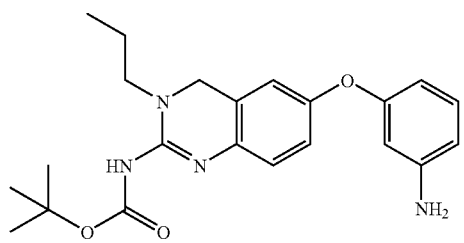 [SMILES: CCCN1Cc2cc(Oc3cccc(N)c3)ccc2N=C1NC(=O)OC(C)(C)C]

A mixture of [6-(3-benzyloxycarbonylamino-phenoxy)-3-propyl-3,4-dihydro-quinazolin-2-yl]-carbamic acid tert-butyl ester (0.008 mol) in methanol (150 mL) was hydrogenated with 10% Pd/C (1 g) as a catalyst. After uptake of $H_2$ gas (1 equiv.), the reaction mixture was filtered over Dicalite and the filtrate was evaporated. The residue was stirred in diisopropyl ether and the resulting precipitate was filtered off and dried to yield the title compound as a solid.

Example 99

{3-Propyl-6-[3-(2,4,6-trimethyl-benzylamino)-phenoxy]-3,4-dihydro-quinazolin-2-yl}-carbamic acid tert-butyl ester

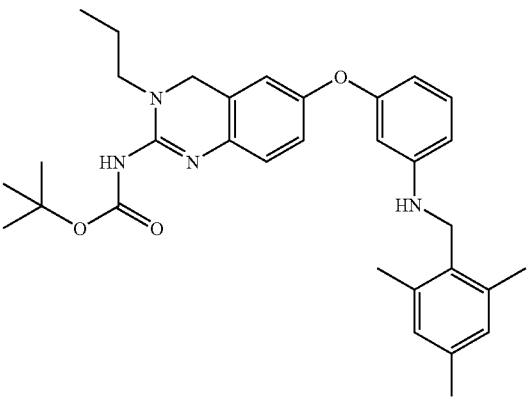 [SMILES: CCCN1Cc2cc(Oc3cccc(NCc4c(C)cc(C)cc4C)c3)ccc2N=C1NC(=O)OC(C)(C)C]

2,4,6-Trimethyl-benzaldehyde (0.0005 mol) was added to a mixture of [6-(3-amino-phenoxy)-3-propyl-3,4-dihydro-quinazolin-2-yl]-carbamic acid tert-butyl ester (0.0005 mol) in DCE (3 mL) and the mixture was stirred for 5 min. at room temperature, and then $NaBH(OAc)_3$ (0.0006 mol) was added and the reaction mixture was stirred overnight at room temperature. The excess $NaBH(OAc)_3$ was decomposed with $CH_3OH$, and the solvent was evaporated. The obtained residue was purified by Biotage column chromatography (eluent: 100% $CH_2Cl_2$). The purest product fractions were collected and then the solvent was evaporated and co-evaporated with toluene to yield the title compound as a residue.

Example 100

3-Propyl-6-[3-(2,4,6-trimethyl-benzylamino)-phenoxy]-3,4-dihydro-quinazolin-2-ylamine

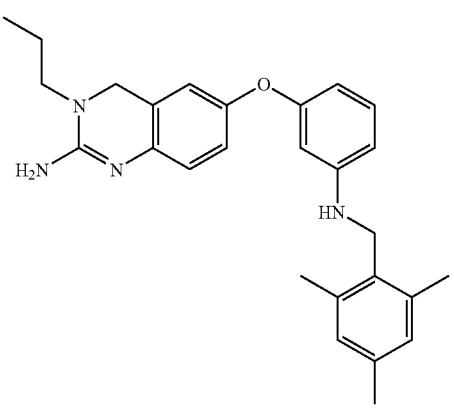 [SMILES: CCCN1Cc2cc(Oc3cccc(NCc4c(C)cc(C)cc4C)c3)ccc2N=C1N]

A mixture of {3-propyl-6-[3-(2,4,6-trimethyl-benzylamino)-phenoxy]-3,4-dihydro-quinazolin-2-yl}-carbamic acid tert-butyl ester (0.0001 mol) in 10% TFA in DCM (6 mL)

Example 101

4-Chloro-2-dimethoxymethyl-1-nitro-benzene

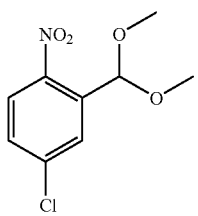

A mixture of 5-chloro-2-nitro-benzaldehyde (0.0792 mol), trimethoxy-methane (0.126 mol) and PTSA (0.00079 mol) in methanol (80 mL) was refluxed until the 5-chloro-2-nitro-benzaldehyde had completely reacted. The mixture was cooled, $Na_2CO_3$ was added, and the reaction mixture was stirred for 5 min. The mixture was filtered and the filtrate was evaporated under reduced pressure to yield the title compound as a residue.

Example 102

(3-Dimethoxymethyl-4-nitro-phenyl)-phenyl-methanone

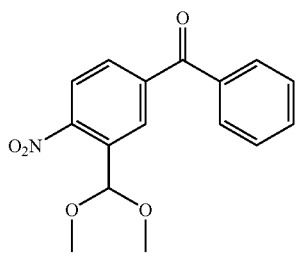 [SMILES: COC(OC)c1cc(C(=O)c2ccccc2)ccc1[N+](=O)[O-]]

Phenyl-acetonitrile (0.0793 mol) in DMA (100 ml) was stirred at room temperature and 50% NaH (0.0793 mol) was added portionwise. The mixture was stirred at room temperature until the evolution of $H_2$ had ceased. TDA-1 (0.004 mol) was added and 4-chloro-2-dimethoxymethyl-1-nitro-benzene (0.0793 mol) in DMA (30 mL) was added dropwise. The mixture was stirred at 60° C. and at 100° C. overnight. 50% NaH (0.0793 mol) was added again and the mixture was stirred further at room temperature. The mixture was poured carefully on ice/water and brought to about pH 6-7 with $CH_3COOH$. The product was extracted with $CH_2Cl_2$. The organic layer was dried ($MgSO_4$) and evaporated. DMA was evaporated by use of high vacuum pump to yield the title compound as a residue.

A mixture of the title compound prepared as described above and $K_2CO_3$ (0.0939 mol) in DMA (420 mL) was stirred at room temperature with air bubbling through the solution overnight. The mixture was poured in water and extracted with $CH_2Cl_2$. The organic layer was dried ($MgSO_4$) and evaporated. The residue (26.4 g) was purified on a glass filter over silica gel (eluent: hexane:$CHCl_3$ 20:80). The pure fractions were collected and evaporated to yield the title compound as a residue.

Example 103

5-Benzoyl-2-nitro-benzaldehyde

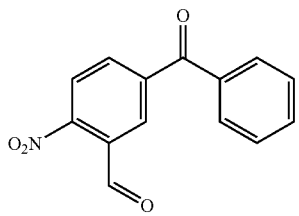 [SMILES: O=Cc1cc(C(=O)c2ccccc2)ccc1[N+](=O)[O-]]

A mixture of (3-dimethoxymethyl-4-nitro-phenyl)-phenyl-methanone (0.0659 mol) and 5N HCl (40 mL) in $CH_3Cl$ (80 mL) was stirred at room temperature overnight. Then the mixture was refluxed for 4 h. After cooling, the organic layer was separated. The organic layer was alkalized by adding dropwise $NH_4OH$. The organic layer was washed with water, dried ($MgSO_4$) and evaporated. The residue (14.6 g) was crystallized from diisopropyl ether/EtOAc (50 mL:20 mL). The precipitate was filtered off, washed with diisopropyl ether/EtOAc, diisopropyl ether and dried in vacuo at 50° C. to yield the title compound as a residue.

Example 104

(4-Amino-3-{[3-(cyclohexyl-methyl-amino)-propylamino]-methyl}-phenyl)-phenyl-methanone

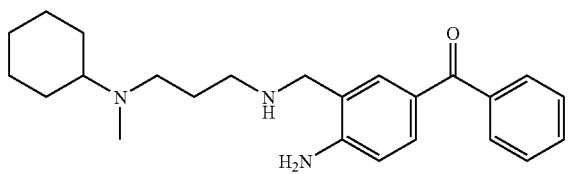 [SMILES: CN(CCCNCc1cc(C(=O)c2ccccc2)ccc1N)C1CCCCC1]

A mixture of 5-benzoyl-2-nitrobenzaldehyde (0.0058 mol) in THF (100 ml) was hydrogenated with 10% Pd/C (1 g) as a catalyst in the presence of 4% thiophene solution (1 mL). After uptake of $H_2$ (3 equiv), the mixture was put in an autoclave. N-cyclohexyl, N-methyl-propane-1,3-diamine (0.01 mol) and $CaH_2$ (0.5 g) were added and the mixture was reacted under 10 atm of $CO_2$ and 50 atm of $H_2$ at 50° C. for 16 hours. When the reaction was complete, the mixture was purified over silica gel on a glass filter (eluent: 90:10 $CH_2Cl_2$:($CH_3OH:NH_3$)). The product fractions were collected and the solvent was evaporated to yield the title compound as a residue.

Example 105

{2-Amino-3-[3-(cyclohexyl-methyl-amino)-propyl]-3,4-dihydro-quinazolin-6-yl}-phenyl-methanone
(Compound #15)

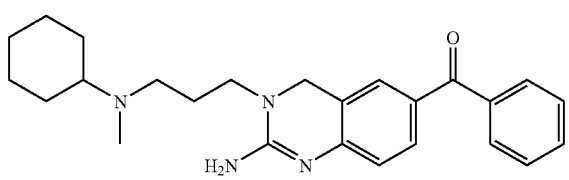 [SMILES: CN(CCCN1Cc2cc(C(=O)c3ccccc3)ccc2N=C1N)C1CCCCC1]

was stirred in a reaction vial for 1 hour at room temperature and then the solvent was evaporated. The obtained residue was crystallized from $CH_3CN$, and then the desired product was filtered off, washed with diisopropyl ether and dried under vacuum to yield the title compound as a solid.

mp 238° C.

A mixture of (3-{[3-(Cyclohexyl-methyl-amino)-propylamino]-methyl}-4-nitro-phenyl)-phenyl-methanone (0.0037 mol) in ethanol (40 mL) was stirred at room temperature. Cyanogen bromide (0.0055 mol) was added, and the reaction mixture was stirred and refluxed for 4 hours, then cooled and the resulting precipitate was filtered off and dried. This fraction was recrystallized from $CH_3CN$, then filtered off and recrystallized from methanol, filtered off, washed with diisopropyl ether, then dried to yield the title compound as a solid.

Example 106

3-(2-Amino-6-benzoyl-4H-quinazolin-3-yl)-N-cyclohexyl-N-methyl-propionamide

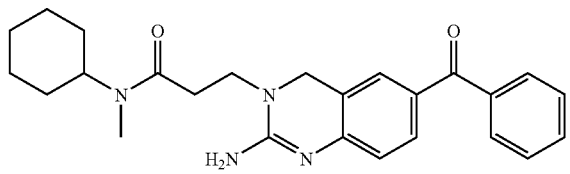 [SMILES: CN(C(=O)CCN1Cc2cc(C(=O)c3ccccc3)ccc2N=C1N)C1CCCCC1]

A mixture of 3-(2-amino-5-benzoyl-benzylamino)-N-cyclohexyl-N-methyl-propionamide (0.017) prepared as described in Example 3 in ethanol (250 mL) was stirred at room temperature and cyanogen bromide (0.027 mol) was added. The reaction mixture was stirred and refluxed for 3 hours, then cooled. The solvent was evaporated and the residue was crystallized from $CH_3CN$. The precipitate was filtered off and dried to yield the title compound as a residue.

Example 107

3-(2-Amino-6-benzoyl-4H-quinazolin-3-yl)-N-cyclohexyl-N-methyl-propionamide

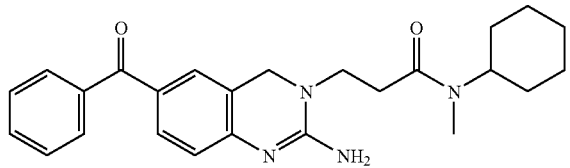 [SMILES: CN(C(=O)CCN1Cc2cc(C(=O)c3ccccc3)ccc2N=C1N)C1CCCCC1]

Cyanogen bromide (0.011 mol) was added to a solution of 3-(2-amino-5-benzoyl-benzylamino)-N-cyclohexyl-N-methyl-propionamide (0.01 mol) in methanol (200 mL), stirred at room temperature. The reaction solution was stirred over a weekend at room temperature, then stirred and refluxed for an additional 5 h. The solvent was evaporated to yield a residue. The residue was crystallized from ethyl acetate (100 mLI). The resulting precipitate was filtered off and dried. The product fraction was recrystallized from 2-propanol (50 mL). The crystals were filtered off and dried to yield the title compound as a residue.

Example 108

3-[2-Amino-6-(hydroxy-phenyl-methyl)-4H-quinazolin-3-yl]-N-cyclohexyl-N-methyl-propionamide

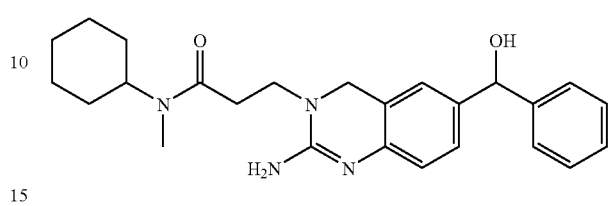

A mixture of 3-(2-amino-6-benzoyl-4H-quinazolin-3-yl)-N-cyclohexyl-N-methyl-propionamide (0.0056 mol) in methanol (60 mL) and THF (30 mL) was stirred at room temperature. Then, $NaBH_4$ (0.0056 mol) was added and the reaction mixture was stirred for 30 min at room temperature. The solvent was evaporated, and the residue was stirred in $H_2O$ and then extracted with $CH_2Cl_2$. The organic layer was separated and dried, and the solvent was evaporated. The residue was purified by column chromatography over silica gel (eluent: 94:6 $CH_2Cl_2$:($CH_3OH$:$NH_3$)). The purest product fractions were collected and the solvent was evaporated to yield the title compound as a residue.

Example 109

3-(2-Amino-6-benzyl-4H-quinazolin-3-yl)-N-cyclohexyl-N-methyl-propionamide

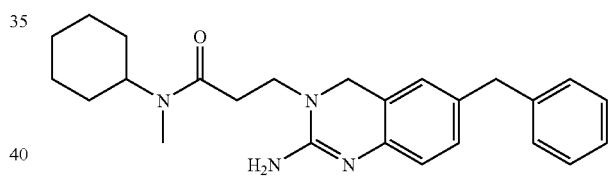

A mixture of 3-[2-amino-6-(hydroxy-phenyl-methyl)-4H-quinazolin-3-yl]-N-cyclohexyl-N-methyl-propionamide (0.0012 mol) in methanol (40 mL) and HCl/2-propanol (0.5 mL) was hydrogenated at 50° C. with 10% Pd/C (0.4 g) as a catalyst. After uptake of $H_2$ (1 equiv.), the reaction mixture was filtered over Dicalite and the solvent was evaporated. The residue was triturated under diisopropyl ether, then the resulting solids were filtered off and dried to yield the title compound as a solid.

Example 110

3-(3-Dimethoxymethyl-4-nitro-phenoxy)-phenylamine

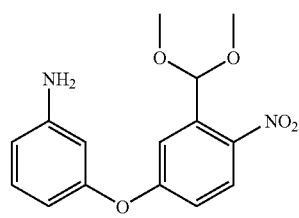 [SMILES: COC(OC)c1cc(Oc2cccc(N)c2)ccc1[N+](=O)[O-]]

K$_2$CO$_3$ (0.17 mol) and then 4-chloro-2-dimethoxymethyl-1-nitro-benzene (0.1 mol) was added to a solution of 3-amino-phenol (0.15 mol) in DMA (200 mL) and the reaction mixture was stirred at 130° C. for 24 hours. The mixture was poured out into water and extracted with diisopropyl ether. The extract was purified by column chromatography over silica gel (eluent: CH$_2$Cl$_2$:CH$_3$OH 100:0 to 65:35). The product fractions were collected and the solvent was evaporated to yield the title compound as a residue.

Example 111

3-(3-Dimethoxymethyl-4-nitro-phenoxy)-phenylamine

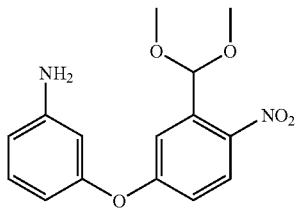 [SMILES: COC(OC)c1cc(Oc2cccc(N)c2)ccc1[N+](=O)[O-]]

3-Amino-phenol (0.050 mol) was dissolved in DMA (100 ml). K$_2$CO$_3$ (0.050 mol) was added. 4-Chloro-2-dimethoxymethyl-1-nitro-benzene (0.050 mol) was added and the reaction mixture was stirred overnight at 100° C., then for 2 hours at 120° C. The reaction mixture was poured out into water and this mixture was extracted with diisopropyl ether. The separated organic layer was dried, filtered and the solvent evaporated. The residue was purified by column chromatography over silica gel (eluent: CH$_2$Cl$_2$:CH$_3$OH 100:0 (to remove starting material) up to 70:30). The desired fractions were collected and the solvent was evaporated to yield the title compound as a residue.

Example 112

Cyclohexyl-[3-(3-dimethoxymethyl-4-nitro-phenoxy)-phenyl]-amine

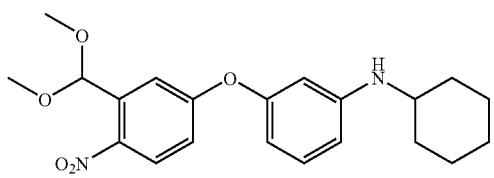 [SMILES: COC(OC)c1cc(Oc2cccc(NC3CCCCC3)c2)ccc1[N+](=O)[O-]]

3-(3-Dimethoxymethyl-4-nitro-phenoxy)-phenylamine (0.0125 mol) was dissolved in DCE (150 mL), and cyclohexanone (0.0125 mol) was added, followed by NaBH(OAc)$_3$ (0.0187 mol). The reaction mixture was stirred overnight at room temperature. Some extra NaBH(OAc)$_3$ was added, and the reaction mixture was stirred overnight at room temperature. A 10% NaOH solution (150 mL) was added, and this mixture was extracted with diisopropyl ether. The separated organic layer was dried (MgSO$_4$) and filtered, and the solvent was evaporated. The residue was purified by column chromatography over silica gel (eluent: 20:80 up to 5:95 hexane: CH$_2$Cl$_2$). The product fractions were collected and the solvent was evaporated to yield the title compound as a residue.

Example 113

Cyclohexyl-[3-(3-dimethoxymethyl-4-nitro-phenoxy)-phenyl]-carbamic acid benzyl ester

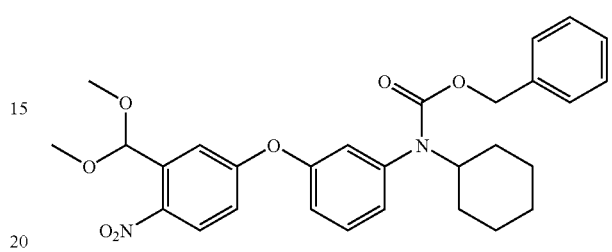

A mixture of cyclohexyl-[3-(3-dimethoxymethyl-4-nitro-phenoxy)-phenyl]-amine (0.00868 mol) and Na$_2$CO$_3$ (0.02083 mol) in H$_2$O (15 mL) and THF (75 mL) was stirred at 5° C. A solution of benzyl chloroformate (0.0104 mol) in THF (25 mL) was added dropwise over 15 min at 5° C. The resultant reaction mixture was stirred for 21 hours at room temperature. This mixture was extracted with diisopropyl ether. The separated organic layer was dried (MgSO$_4$) and filtered, and the solvent was evaporated. The residue (0.00633 mol A) was reacted again with benzyl chloroformate (1.3 g, 0.0076 mol) and TEA (1.53 g, 0.0152 mol) in DCM (70 mL) under the same conditions as above. The residue was purified by column chromatography over silica gel (eluent: 95:5 CH$_2$Cl$_2$:hexane). The product fractions were collected and the solvent was evaporated to yield the title compound as a residue.

Example 114

Cyclohexyl-[3-(3-formyl-4-nitro-phenoxy)-phenyl]-carbamic acid benzyl ester

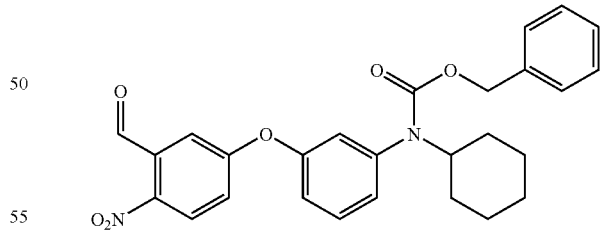

Cyclohexyl-[3-(3-dimethoxymethyl-4-nitro-phenoxy)-phenyl]-carbamic acid benzyl ester (0.0027 mol) was dissolved in THF (12 mL). Water (6 mL) and 12N HCl (3 mL) were added and the reaction mixture was stirred for 42 hours at room temperature. Water was added. This mixture was extracted with diisopropyl ether. The organic layer was separated, washed with a 10% aqueous NaHCO$_3$ solution and then with water, dried (MgSO$_4$) and filtered. The solvent was then evaporated to yield a residue that was used in the next reaction step without further purification.

Example 115

Cyclohexyl-[3-(4-nitro-3-propylaminomethyl-phenoxy)-phenyl]-carbamic acid benzyl ester

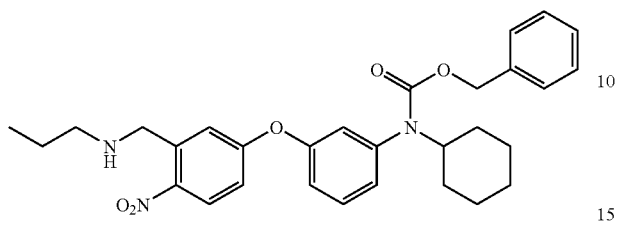

A mixture of propylamine (0.00356 mol) in DCE (70 mL) was stirred at room temperature. Cyclohexyl-[3-(3-formyl-4-nitro-phenoxy)-phenyl]-carbamic acid benzyl ester (0.00274 mol) was added. NaBH(OAc)$_3$ (0.00438 mol) was added. The reaction mixture was stirred overnight at room temperature. A 10% NaOH solution was added and this mixture was extracted with diisopropyl ether. The separated organic layer was dried (MgSO$_4$), filtered and the solvent evaporated. The residue was purified by column chromatography over silica gel (eluent: 100:0 to 96:4 CH$_2$Cl$_2$:CH$_3$OH). The product fractions were collected and the solvent was evaporated to yield the title compound as a residue.

Example 116

[3-(4-Amino-3-propylaminomethyl-phenoxy)-phenyl]-cyclohexyl-carbamic acid benzyl ester

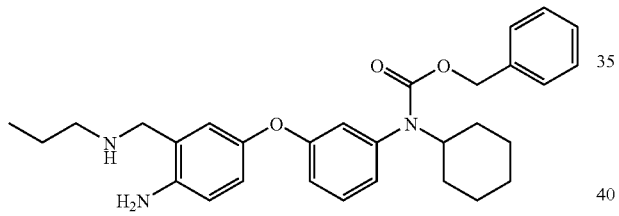

A mixture of cyclohexyl-[3-(4-nitro-3-propylaminomethyl-phenoxy)-phenyl]-carbamic acid benzyl ester (0.00181 mol) in methanol (50 mL) was hydrogenated with 5% Pt/C (0.5 g) as a catalyst in the presence of thiophene solution (1 mL). After uptake of H$_2$ (3 equiv), the catalyst was filtered off and the filtrate was evaporated to yield the title compound as a residue which was used in subsequent reactions without further purification.

Example 117

[3-(2-Amino-3-propyl-3,4-dihydro-quinazolin-6-yloxy)-phenyl]-cyclohexyl-carbamic acid benzyl ester

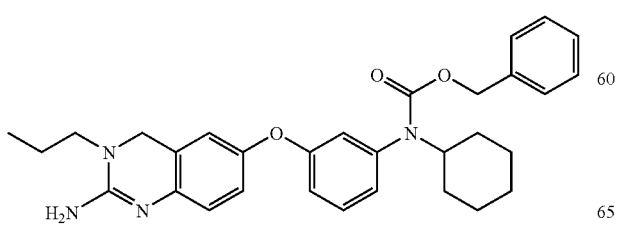

A mixture of [3-(4-amino-3-propylaminomethyl-phenoxy)-phenyl]-cyclohexyl-carbamic acid benzyl ester (0.0018 mol) and cyanogen bromide (0.00234 mol) in ethanol (60 mL) was stirred and refluxed for 3 hours and then was cooled. The ethanol solvent was evaporated. The residue was triturated under diisopropyl ether and ethanol, filtered off, and dried to yield the title compound as a solid.

Example 118

Cyclohexylmethyl-[3-(3-dimethoxymethyl-4-nitro-phenoxy)-phenyl]-amine

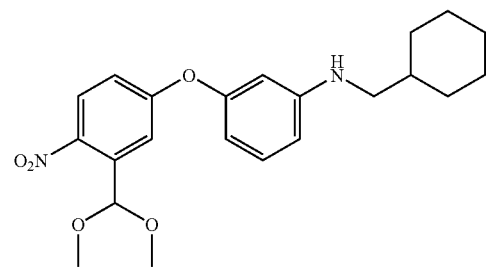 [SMILES: COC(OC)c1cc(Oc2cccc(NCC3CCCCC3)c2)ccc1[N+](=O)[O-]]

The reaction was completed under N$_2$. Cyclohexanecarboxaldehyde (0.01 mol) and then NaBH(OAc)$_3$ (0.015 mol) were added to a solution of 3-(3-dimethoxymethyl-4-nitro-phenoxy)-phenylamine (0.01 mol) in DCE (130 mL). The reaction mixture was stirred overnight at room temperature and washed with a saturated NaHCO$_3$ solution. The organic layer was separated, dried (MgSO$_4$) and filtered, and the solvent was evaporated to yield the title compound as a residue.

Example 119

5-[3-(Cyclohexylmethyl-amino)-phenoxy]-2-nitro-benzaldehyde

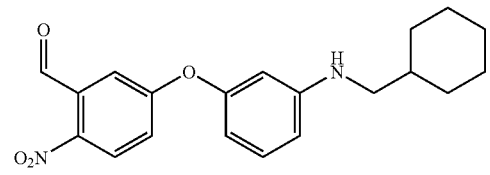 [SMILES: O=Cc1cc(Oc2cccc(NCC3CCCCC3)c2)ccc1[N+](=O)[O-]]

12N HCl (2 mL) and H$_2$O (4 mL) were added to a mixture of cyclohexylmethyl-[3-(3-dimethoxymethyl-4-nitro-phenoxy)-phenyl]-amine (0.0055 mol) in THF (17 mL), and the reaction mixture was stirred overnight at room temperature. H$_2$O was added, and the mixture was extracted with diisopropyl ether. The organic layer was washed with a 10% NaHCO$_3$ solution, dried (MgSO$_4$), filtered off and the solvent was evaporated. The residue was purified by short column chromatography (eluent: 100% CH$_2$Cl$_2$). The purest product fractions were collected and the solvent was evaporated to yield the title compound as a residue.

Example 120

Cyclohexylmethyl-[3-(4-nitro-3-propylaminomethyl-phenoxy)-phenyl]-amine

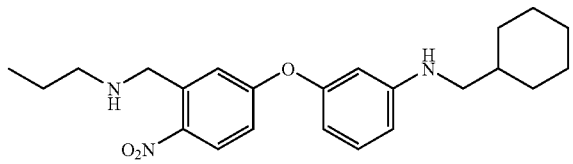 [SMILES: CCCNCc1cc(Oc2cccc(NCC3CCCCC3)c2)ccc1N]

NaBH(OAc)$_3$ (0.0080 mol) was added to a mixture of propylamine (0.0054 mol) and 5-[3-(cyclohexylmethyl-amino)-phenoxy]-2-nitro-benzaldehyde (0.00054 mol) in DCE (100 mL). Then the reaction mixture was stirred overnight at room temperature and washed with a saturated NaHCO$_3$ solution. The organic layer was separated, dried (MgSO$_4$), and filtered, and the solvent was evaporated. The residue was purified by column chromatography (eluent: 100% CH$_2$Cl$_2$). The purest product fractions were collected and the solvent was evaporated to yield the title compound as a residue.

Example 121

2-Amino-5-[3-[(cyclohexylmethyl)amino]phenoxy]-N-propyl-benzenemethamine

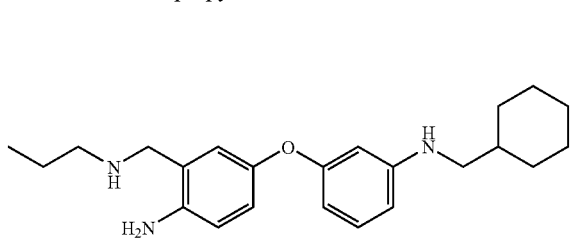

A mixture of cyclohexylmethyl-[3-(4-nitro-3-propylaminomethyl-phenoxy)-phenyl]-amine (0.0037 mol) in methanol (50 mL) was hydrogenated with 10% Pd/C (0.5 g) as a catalyst in the presence of thiophene solution (0.5 mL). After uptake of H$_2$ (3 equiv.), the reaction mixture was filtered over Dicalite and the filtrate was evaporated. The residue was purified by column chromatography (eluent: 98:2 CH$_2$Cl$_2$:CH$_3$OH). The purest product fractions were collected and the solvent was evaporated to yield the title compound as a residue.

Example 122

6-[3-(Cyclohexylmethyl-amino)-phenoxy]-3-propyl-3,4-dihydro-quinazolin-2-ylamine and [3-(2-Amino-3-propyl-3,4-dihydro-quinazolin-6-yloxy)-phenyl]-cyclohexylmethyl-cyanamide

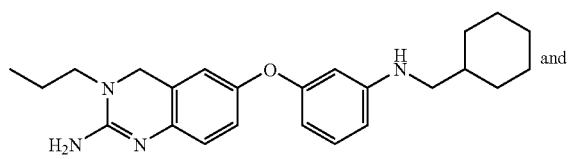

and

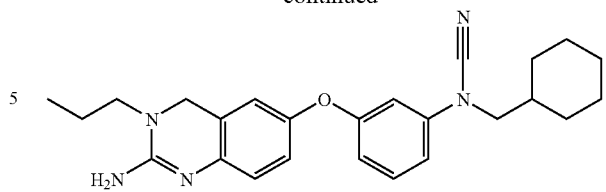

Cyanogen bromide (0.0030 mol) was added to a mixture of 2-amino-5-[3-[(cyclohexylmethyl)amino]phenoxy]-N-propyl-benzenemethamine (0.0027 mol) in ethanol (100 mL) and the reaction mixture was stirred for 2 hours, and the solvent was evaporated. The residue was converted into the free base with aqueous NaHCO$_3$ solution, and the mixture was extracted with CH$_2$Cl$_2$. The organic layer was separated, dried (MgSO$_4$), and filtered, and the solvent was evaporated. The residue was separated by reversed-phase high-performance liquid chromatography over RP-18, then two product fractions were collected and the solvent was evaporated to yield the title compounds, each as a white solid.

Example 123

3-(2-Amino-5-benzoyl-benzylamino)-N-cyclohexyl-N-methyl-propionamide

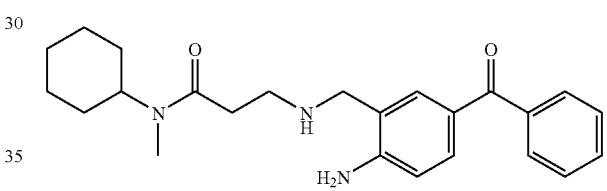

3-(5-Benzoyl-2-nitro-benzylamino)-N-cyclohexyl-N-methyl-propionamide (0.01 mol) was converted into its corresponding free base. A mixture of the free base (0.01 mol) in methanol (200 mL) was hydrogenated under atmospheric conditions, with 5% Pt/C (2 g) as a catalyst in the presence of 4% thiophene solution (1 mL). After uptake of H$_2$ (3 equiv.), the catalyst was filtered off and the filtrate was evaporated. Toluene was added to the residue, then evaporated again to yield the title compound as a residue.

Example 124

(3-Dimethoxymethyl-4-nitro-phenyl)-phenyl-methanone

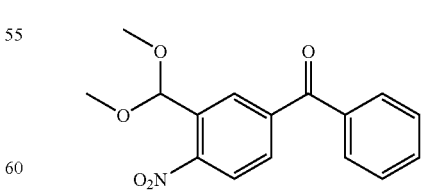

(3-Dimethoxymethyl-4-nitro-phenyl)-morpholin-4-yl-phenyl-acetonitrile (0.7 mol) in CH$_3$CO$_2$H (1500 ml) was stirred and refluxed for 30 min. The mixture was poured on ice/water and extracted with diisopropyl ether. The organic layer was washed with alkalic water and water. The organic layer was dried (MgSO$_4$) and evaporated to yield a residue. The aqueous layers which contained product were extracted with CH$_2$Cl$_2$. The organic layer was dried (MgSO$_4$) and evaporated to yield a residue. The combined residues were purified on a glass filter over silica gel (eluent: CH$_2$Cl$_2$). The pure fractions were collected and evaporated to yield the title compound as a residue.

Example 125

3-(3-Dimethoxymethyl-4-nitro-phenoxy)-phenylamine

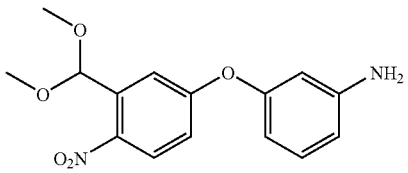

K$_2$CO$_3$ (0.34 mol), followed by 4-chloro-2-dimethoxymethyl-1-nitro-benzene (0.2 mol) was added to a solution of 3-amino-phenol (0.3 mol) in DMA (400 mLI) and the reaction mixture was stirred overnight at 130° C. The mixture was cooled to room temperature and the solvent was evaporated. The residue was taken up in H$_2$O and the mixture was extracted with CH$_2$Cl$_2$. The organic layer was separated, dried (MgSO$_4$), filtered off and the solvent was evaporated. The residue was purified by column chromatography (eluent: CH$_2$Cl$_2$ 100%). The product fractions were collected and the solvent was evaporated to yield the title compound as a residue.

Example 126

3-(3-Dimethoxymethyl-4-nitro-phenoxy)-phenylamine

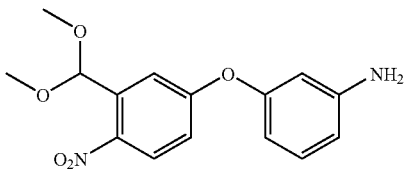

K$_2$CO$_3$ (0.076 mol) was added to a mixture of 3-amino-phenol (0.069 mol) in ethanol (200 mL) and the mixture was stirred for 10 min at room temperature, then 4-chloro-2-dimethoxymethyl-1-nitro-benzene (0.046 mol) was added and the reaction mixture was stirred for 16 hours at reflux temperature. The mixture was allowed to reach room temperature and the solvent was evaporated. The residue was washed with water and extracted 2 times with CH$_2$Cl$_2$. The organic layer was separated, dried (MgSO$_4$), filtered off and the solvent was evaporated. The residue was purified by column chromatography over silica gel (eluent: CH$_2$Cl$_2$ 100%). The purest product fractions were collected and the solvent was evaporated to yield the title compound as a residue.

Example 127

N-[3-(3-Dimethoxymethyl-4-nitro-phenoxy)-phenyl]-benzenesulfonamide

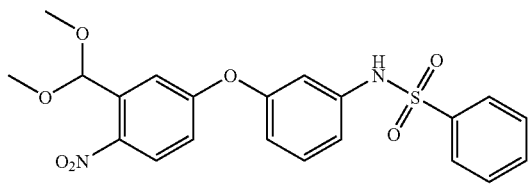

A mixture of 3-(3-dimethoxymethyl-4-nitro-phenoxy)-phenylamine (0.013 mol) in THF (100 mL) and TEA (200 mL) was stirred at room temperature and a mixture of benzenesulfonyl chloride (0.013 mol) in THF (50 mL) was added dropwise, then the reaction mixture was stirred overnight at room temperature and again overnight at 60° C. The solvent was evaporated and the residue was stirred in H$_2$O. After extraction with CH$_2$Cl$_2$, the organic layer was separated, dried, filtered off and the solvent was evaporated. The residue was purified by Biotage column chromatography (eluent: CH$_2$Cl$_2$ 100%). The purest product fractions were collected and the solvent was evaporated to yield the title compound as a residue.

Example 128

Ethenesulfonic acid cyclohexyl-methyl-amide

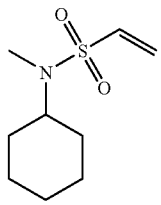

A mixture of N-methylcyclohexylamine (0.048 mol) and TEA (0.053 mol) in DCM (200 mL) was cooled in an ice bath to 5° C., and then a solution of 2-chloro-ethanesulfonyl chloride (0.048 mol, 97%) in DCM (20 mL) was added dropwise. The reaction mixture was stirred for 2 hours at room temperature and then was washed with H$_2$O. The organic layer was separated, dried (MgSO$_4$), and filtered, and the solvent was evaporated to yield the title compound as a residue.

Example 129

2-Amino-ethanesulfonic acid cyclohexyl-methyl-amide

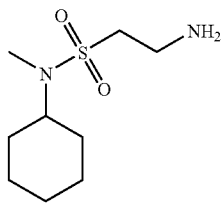

Ethenesulfonic acid cyclohexyl-methyl-amide (0.0167 mol) was reacted with a mixture of methanol/ammonia (10 mL) in an autoclave for 16 hours at room temperature, and then the solvent was evaporated. The residue was purified by column chromatography (eluent: 90:10 $CH_2Cl_2$:($CH_3OH$: $NH_3$)). The purest product fractions were collected and the solvent was evaporated to yield the title compound as a residue.

Example 130

2-(5-Benzoyl-2-nitro-benzylamino)-ethanesulfonic acid cyclohexyl-methyl-amide

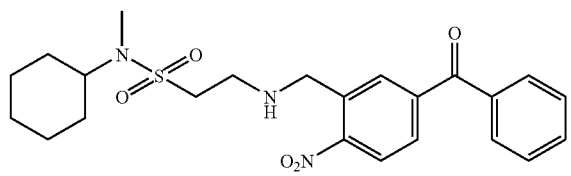 [SMILES: CN(C1CCCCC1)S(=O)(=O)CCNCc1cc(C(=O)c2ccccc2)ccc1N]

NaBH(OAc)$_3$ (0.014 mol) was added to a mixture of 2-amino-ethanesulfonic acid cyclohexyl-methyl-amide (0.0091 mol) and 5-benzoyl-2-nitro-benzaldehyde (0.0091 mol) in DCE (150 mL). The reaction mixture was then stirred overnight at room temperature and then washed with saturated NaHCO$_3$ solution. The organic layer was separated, dried (MgSO$_4$), and filtered, and the solvent was evaporated. The residue was purified by column chromatography (eluent: 100% $CH_2Cl_2$). The purest product fractions were collected and the solvent was evaporated to yield the title compound as a residue.

Example 131

2-(2-Amino-5-benzoyl-benzylamino)-ethanesulfonic acid cyclohexyl-methyl-amide

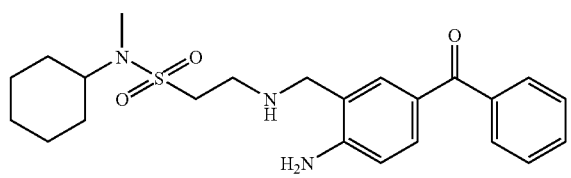

A mixture of 2-(5-benzoyl-2-nitro-benzylamino)-ethanesulfonic acid cyclohexyl-methyl-amide (0.009 mol) in methanol (150 mL) was hydrogenated with 10% Pd/C (1 g) as a catalyst in the presence of thiophene solution (1 mL). After uptake of H$_2$ (3 equiv.), the catalyst was filtered off, and the filtrate was evaporated. The residue was purified by column chromatography over Biotage (eluent: 98:2 $CH_2Cl_2$:$CH_3OH$). The purest product fractions were collected and the solvent was evaporated to yield the title compound as a residue.

Example 132

2-(2-Amino-6-benzoyl-4H-quinazolin-3-yl)-ethanesulfonic acid cyclohexyl-methyl-amide

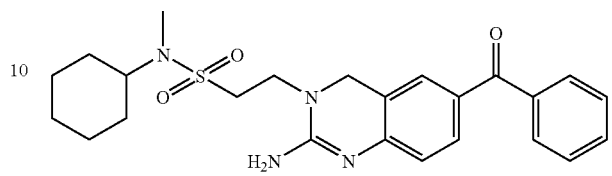

A mixture of 2-(2-amino-5-benzoyl-benzylamino)-ethanesulfonic acid cyclohexyl-methyl-amide (0.0054 mol) and cyanogen bromide (0.0080 mol) in ethanol (100 mL) was stirred and refluxed for 2 hours, and then the reaction mixture was cooled to room temperature. After filtration, the filter residue was washed with diisopropyl ether and dried under vacuum to yield the title compound as a solid.

Example 133

3-(3-Dimethoxymethyl-4-nitro-phenoxy)-benzonitrile

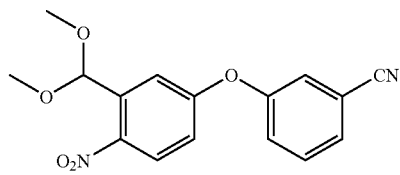 [SMILES: COC(OC)c1cc(Oc2cccc(C#N)c2)ccc1[N+](=O)[O-]]

A mixture of 3-cyanophenol (0.38 mol) in ethanol (600 mL) was stirred at room temperature and K$_2$CO$_3$ (0.29 mol) was added. 5-fluoro-2-nitrobenzaldehyde (0.18 mol) was added, and the reaction mixture was stirred and refluxed for 4 hours. The solvent was evaporated, and the residue was stirred in water and extracted with $CH_2Cl_2$. The organic layer was separated, dried, filtered off and the solvent was evaporated. The residue was triturated under diisopropyl ether, and then the formed solids were filtered off and dried to yield the title compound.

Example 134

3-(3-Formyl-4-nitro-phenoxy)-benzonitrile

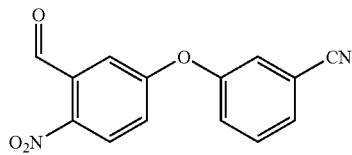 [SMILES: N#Cc1cccc(Oc2ccc([N+](=O)[O-])c(C=O)c2)c1]

A mixture of 3-(3-dimethoxymethyl-4-nitro-phenoxy)-benzonitrile (0.068 mol) in THF (140 ml) was stirred at room temperature, then 12N HCl (55 ml) and water (55 ml) were added and the reaction mixture was stirred overnight at room temperature. The mixture was stirred in H$_2$O and extracted

Example 135

3-(4-Nitro-3-propylaminomethyl-phenoxy)-benzonitrile

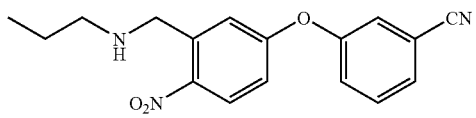 [SMILES: CCCNCc1cc(Oc2cccc(C#N)c2)ccc1[N+](=O)[O-]]

The following reaction was completed under N$_2$. A mixture of 3-(3-formyl-4-nitro-phenoxy)-benzonitrile (0.056 mol) and propylamine (0.059 mol) in DCE (450 ml) was stirred at room temperature, then NaBH(OAc)$_3$ (0.063 mol) was added. The reaction mixture was stirred overnight at room temperature. A saturated NaHCO$_3$ solution was added and the layers were separated. The organic layer was dried, filtered off and the solvent was evaporated. The residue was purified over silica gel filter (eluent: CH$_2$Cl$_2$/CH$_3$OH 99/1). The purest product fractions were collected and the solvent was evaporated to yield the title compound as a residue.

Example 136

3-(4-Amino-3-propylaminomethyl-phenoxy)-benzonitrile

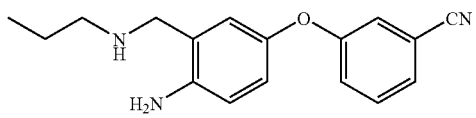

A mixture of 3-(4-nitro-3-propylaminomethyl-phenoxy)-benzonitrile (0.045 mol) in methanol (250 ml) was hydrogenated with 10% Pd/C (2 g) as a catalyst in the presence of thiophene solution (2 ml). After uptake of H$_2$ (3 equiv.), the reaction mixture was filtered over dicalite and the filtrate was evaporated. The residue was purified by column chromatography over silica gel (eluent: CH$_2$Cl$_2$/CH$_3$OH 98/2). The purest product fractions were collected and the solvent was evaporated to yield the title compound as a residue.

Example 137

3-(2-Amino-3-propyl-3,4-dihydro-quinazolin-6-yloxy)-benzonitrile

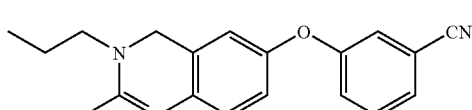

A mixture of 3-(4-Amino-3-propylaminomethyl-phenoxy)-benzonitrile (0.032 mol) in ethanol (400 ml) was stirred at room temperature and cyanogens bromide (0.038 mol) was added. The reaction mixture was stirred and refluxed for 2 hours. After cooling, the precipitate was filtered off, washed with DIPE and dried to yield the title compound.

The filtrate was evaporated and the obtained residue was crystallised from CH$_3$CN/DIPE, then the precipitate was filtered off, washed with DIPE and dried to yield residue.

Example 138

3-(2-Amino-3-propyl-3,4-dihydro-quinazolin-6-yloxy)-benzoic acid

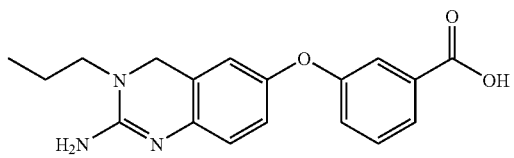 [SMILES: CCCN1Cc2cc(Oc3cccc(C(=O)O)c3)ccc2N=C1N]

A mixture of 3-(2-amino-3-propyl-3,4-dihydro-quinazolin-6-yloxy)-benzonitrile (0.0013 mol), prepared as described in Example 75, in concentrated H$_2$SO$_4$ (5 mL) and water (5 mL) was stirred and refluxed for 2 hours. The reaction mixture was then cooled, and the resulting solids were filtered off. The obtained filter residue was washed with ice-water and dried to yield the title compound as a solid.

Example 139

3-(2-Amino-3-propyl-3,4-dihydro-quinazolin-6-yloxy)-benzoyl chloride

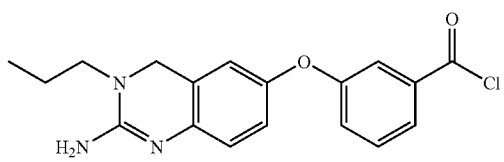 [SMILES: CCCN1Cc2cc(Oc3cccc(C(=O)Cl)c3)ccc2N=C1N]

A mixture of 3-(2-amino-3-propyl-3,4-dihydro-quinazolin-6-yloxy)-benzoic acid (0.0009 mol) in SOCl$_2$ (2 mL) and DCM (10 mL) was stirred for 2 hours at room temperature and then the solvent was evaporated. The obtained residue was stirred in toluene and the solvent was evaporated again to yield the title compound as a residue.

Example 140

3-(2-Amino-3-propyl-3,4-dihydro-quinazolin-6-yloxy)-N-(2,4,6-trimethyl-benzyl)-benzamide

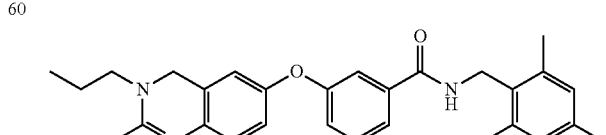

A mixture of 3-(2-amino-3-propyl-3,4-dihydro-quinazolin-6-yloxy)-benzoyl chloride (0.0008 mol) in DCM (20 mL) was stirred at 0° C. and 2,4,6-trimethylbenzylamine (0.0013 mol) was added. Then TEA (q.s.) was added, and the reaction mixture was stirred at room temperature. The mixture was stirred in H$_2$O and the organic layer was separated. The remaining layer was washed again with H$_2$O, then the organic layer was separated, dried, and filtered, and the solvent was evaporated. The residue was purified by column chromatography over silica gel (gradient eluent: CH$_2$Cl$_2$:(CH$_3$OH:NH$_3$)). The purest product fractions were collected, and the solvent was evaporated. The residue was triturated under diisopropyl ether:CH$_3$CN, and then the resulting solids were filtered off and dried to yield the title compound as a solid.

Example 141

4-Chloro-2-dimethoxymethyl-1-nitro-benzene

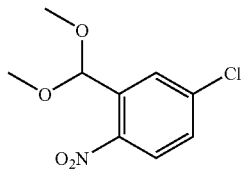

A mixture of 5-chloro-2-nitro-benzaldehyde (0.0792 mol), trimethoxy-methane (0.126 mol) and PTSA (0.00079 mol) in methanol (80 m) was refluxed until the 5-chloro-2-nitro-benzaldehyde had completely reacted. The mixture was cooled, Na$_2$CO$_3$ was added and stirred for 5 min. The mixture was filtered off and the filtrate was evaporated under reduced pressure to yield the title compound as a residue.

Example 142

3-(3-Dimethoxymethyl-4-nitro-phenylsulfanyl)-phenylamine

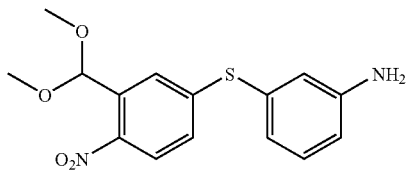 [SMILES: COC(OC)c1cc(Sc2cccc(N)c2)ccc1[N+](=O)[O-]]

K$_2$CO$_3$ (0.085 mol) was added to a mixture of 3-aminobenzenethiol (0.075 mol) in DMA (150 mL). Then 4-chloro-2-dimethoxymethyl-1-nitrobenzene (0.050 mol) was added and the reaction mixture was stirred for 2 hours at 80° C. H$_2$O was added and the mixture was extracted with diisopropyl ether. The crude product was purified by column chromatography (eluent: 70:30 CH$_2$Cl$_2$/hexane up to 99:1 CH$_2$Cl$_2$:CH$_3$OH). The product fractions were collected, and the solvent was evaporated to yield the title compound as a residue.

Example 143

N-[3-(3-Dimethoxymethyl-4-nitro-phenylsulfanyl)-phenyl]-benzenesulfonamide

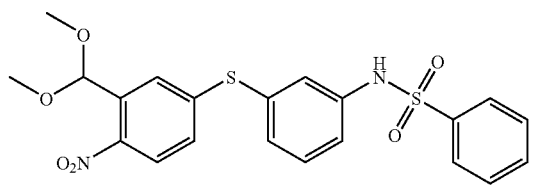

A mixture of 3-(3-dimethoxymethyl-4-nitro-phenylsulfanyl)-phenylamine (0.0384 mol) and TEA (0.0578 mol) in THF (q.s.) was cooled to 5° C., and phenylsulfonyl chloride (0.0384 mol) was added dropwise at 5° C. Then, the reaction mixture was reacted at room temperature, and purified by column chromatography over silica gel (eluent: CH$_2$Cl$_2$). The product fractions were collected and the solvent was evaporated to yield the title compound as a residue.

Example 144

N-[3-(3-Formyl-4-nitro-phenylsulfanyl)-phenyl]-benzenesulfonamide

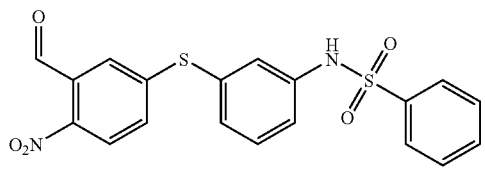 [SMILES: O=Cc1cc(Sc2cccc(NS(=O)(=O)c3ccccc3)c2)ccc1[N+](=O)[O-]]

A mixture of N-[3-(3-dimethoxymethyl-4-nitro-phenylsulfanyl)-phenyl]-benzenesulfonamide (0.027 mol) in 12N HCl (25 mL), THF (75 mL), and water (50 mL) was stirred overnight at room temperature, and then the mixture was extracted with EtOAc. The extract was washed with H$_2$O and then with a saturated Na$_2$CO$_3$ solution. The solvent was evaporated, and the residue was purified by column chromatography over silica gel (eluent: CH$_2$Cl$_2$). The product fractions were collected and the solvent was evaporated to yield the title compound as a residue.

Example 145

N-[3-(3-Formyl-4-nitro-benzenesulfinyl)-phenyl]-benzenesulfonamide

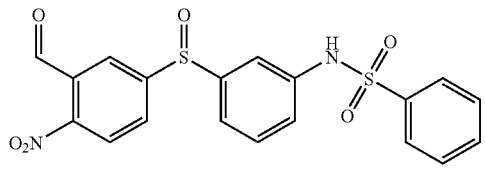 [SMILES: O=Cc1cc(S(=O)c2cccc(NS(=O)(=O)c3ccccc3)c2)ccc1[N+](=O)[O-]]

A mixture of N-[3-(3-formyl-4-nitro-phenylsulfanyl)-phenyl]-benzenesulfonamide (0.0034 mol) and 3-Chlorobenzenecarboperoxoic acid (also known as MCPBA or meta-chloroperbenzoic acid) (0.7 g; 75%) in CHCl$_3$ (q.s.) was stirred for 4 hours at room temperature. Then a NaHCO$_3$ solution was added, and the reaction mixture was stirred. The organic layer was separated, dried, and filtered, and the solvent was evaporated. The residue was purified by column chromatography over Biotage (gradient eluent: CH$_2$Cl$_2$: CH$_3$OH). The purest product fractions were collected, and the solvent was evaporated to yield the title compound as a residue.

Example 146

N-[3-(4-Nitro-3-propylaminomethyl-benzenesulfinyl)-phenyl]-benzenesulfonamide

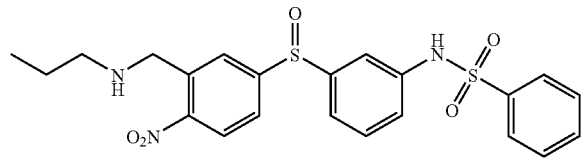

The following reaction was run under N$_2$. A mixture of N-[3-(3-formyl-4-nitro-benzenesulfinyl)-phenyl]-benzenesulfonamide (0.0023 mol) and propylamine (0.0025 mol) in DCE (50 mL) was stirred at room temperature and NaBH(OAc)$_3$ (0.8 g) was added. The reaction mixture was stirred overnight at room temperature, and then a NaHCO$_3$ solution was added. The organic layer was separated, dried, and filtered, and the solvent was evaporated to yield the title compound as a residue.

Example 147

N-[3-(4-Amino-3-propylaminomethyl-benzenesulfinyl)-phenyl]-benzenesulfonamide

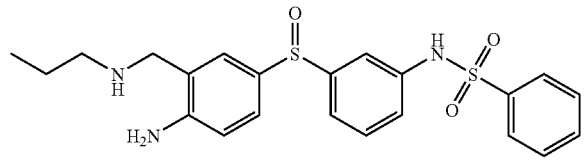 [SMILES: CCCNCc1cc(S(=O)c2cccc(NS(=O)(=O)c3ccccc3)c2)ccc1[N+](=O)[O-]]

A mixture of N-[3-(4-nitro-3-propylaminomethyl-benzenesulfinyl)-phenyl]-benzenesulfonamide (0.0019 mol) in methanol (100 mL) was hydrogenated with 10% Pd/C (0.5 g) as a catalyst. After uptake of H$_2$ (3 equiv.), the reaction mixture was filtered over Dicalite, and the filtrate was evaporated. The residue was filtered over silica gel (eluent: 95:5 CH$_2$Cl$_2$: CH$_3$OH), and then the purest product fractions were collected, and the solvent was evaporated to yield the title compound as a residue.

Example 148

N-[3-(2-Amino-3-propyl-3,4-dihydro-quinazoline-6-sulfinyl)-phenyl]-benzenesulfonamide

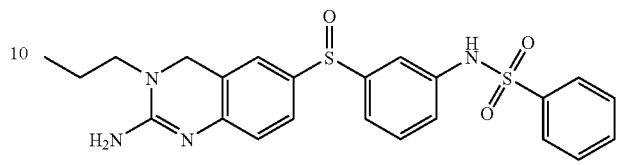

A mixture of N-[3-(4-amino-3-propylaminomethyl-benzenesulfinyl)-phenyl]-benzenesulfonamide (0.00090 mol) and cyanogen bromide (0.00094 mol) in ethanol (30 mL) was stirred overnight at room temperature, and then the solvent was evaporated. The residue was triturated under diisopropyl ether, and the solids were filtered off. The residue was converted into the free base with a NaOH solution. The mixture was extracted with CH$_2$Cl$_2$, but the product stayed in the aqueous layer so the mixture was desalted with NaCl to yield an oil. The solvent was decanted, and the remaining oil was triturated under CH$_3$CN. The resulting solids were filtered off, washed with diisopropyl ether, and dried to yield the title compound as a solid.

Example 149

2-[4-(2-Amino-6-phenoxy-4H-quinazolin-3-yl)-4S-(tetrahydro-pyran-4-yl)-butyrylamino]-3R-tert-butoxy-propionic acid and 2-[4-(2-Amino-6-phenoxy-4H-quinazolin-3-yl)-4S-(tetrahydro-pyran-4-yl)-butyrylamino]-3R-hydroxy-propionic acid

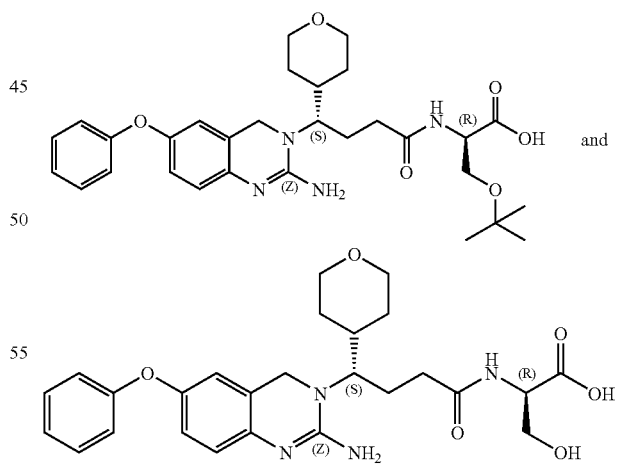

Step A:

To an ice cooled solution of H-D-Ser(t-Butyl)OCH$_3$.HCl, 4-tert-butoxycarbonylamino-4-(4-tetrahydropyranyl)-butyric acid (0.5 g, 1.8 mmol) and HOBT (0.32 g, 2.4 mmol) in CH$_2$Cl$_2$ (50 mL), TEA (0.7 mL) was added followed by addition of 1,3-dimethylamino propyl-3-ethylcarbodiimide (EDC, 0.45 g, 2.4 mmol). The reaction mixture was allowed to warm to room temperature and stirred overnight. Ethyl acetate (200 mL) was added. The solution was washed with dilute-HCl acid solution (about 0.1N, 50 mL), saturated aqueous $NaHCO_3$, and aqueous NaCl solution. The organic layer was dried with $MgSO_4$. After filtration, the EtOAc was evaporated to yield 3-(R)-tert-butoxy-2-[4-tert-butoxycarbonylamino-4S-(tetrahydro-pyran-4-yl)-butyrylamino]-propionic acid methyl ester as a a crude oil.

$MH^+$ 444.9

Step B:

A solution of the oil isolated in Step A (0.8 g, 1.8 mmol) in TFA (5% in $CH_2Cl_2$, 50 mL) was stirred at room temperature 4 hours. The solvent and most of the TFA was evaporated, and EtOAc (100 mL) was added. The organic extract was washed with aqueous $NaHCO_3$ solution and brine. The organic layer was dried with $MgSO_4$, filtered, and evaporated to yield 2-[4-amino-4-(S)-(tetrahydro-pyran-4-yl)-butyrylamino]-3-(R)-tert-butoxy-propionic acid methyl ester as an oil.

$MH^+$ 345.0

Step C:

A solution of the oil isolated in Step C (0.5 g, 1.4 mmol) and 2-nitro-5-phenoxy-benzaldehyde (0.35 g, 1.4 mmol) in methylene chloride (50 mL) was stirred at room temperature for 5 hours, and then $NaBH(OAc)_3$ (0.6 g, 2.8 mmol) was added. The reaction mixture was stirred at room temperature 3 hours. The reaction mixture was then poured into EtOAc (100 mL). The organic layer was washed with brine, dried with $MgSO_4$, filtered, and evaporated. Purification by column chromatography (1:1 heptane/EtOAc) yielded 3-(R)-tert-butoxy-2-[4-(2-nitro-5-phenoxy-benzylamino)-4-(S)-(tetrahydro-pyran-4-yl)-butyrylamino]-propionic acid methyl ester as an oil.

$MH^+$ 571.9

Step D:

To a solution of the oil isolated in Step C (0.37 g, 0.65 mmol) in MeOH (10 mL) was added 0.05 g of 10% Pd on activated carbon under $N_2$. The reaction mixture was subjected to hydrogenation under 5 psi for 2 hour. The catalyst was removed by filtration, and the filtrate was evaporated to yield 2-[4-(2-amino-5-phenoxy-benzylamino)-4-(S)-(tetrahydro-pyran-4-yl)-butyrylamino]-3-(R)-tert-butoxy-propionic acid methyl ester as an oil.

$MH^+$ 542.0

Step E:

To a solution of the oil isolated in Step D (0.29 g, 0.53 mmol) was added BrCN (3M in $CH_2Cl_2$, 0.18 mL) in EtOH (20 mL) was stirred at room temperature overnight. The EtOH was evaporated to yield an oil which was stirred in diethyl ether (50 mL) for 30 min. The precipitate which formed was collected to yield 2-[4-(2-amino-6-phenoxy-4H-quinazolin-3-yl)-4-(S)-(tetrahydro-pyran-4-yl)-butyrylamino]-3-(R)-tert-butoxy-propionic acid methyl ester as a solid, as its corresponding HBr salt.

$MH^+$ 567.9

Step F:

To a solution of the solid isolated in Step E (0.4 g, 0.7 mmol) in MeOH (20 mL) and water (1 mL) was added LiOH (0.04 g, 1.7 mmol). The solution was stirred at room temperature overnight and then was acidified (pH=2) with citric acid. The MeOH was removed by vacuum to yield a crude oil which was purified by Gilson HPLC to yield 2-[4-(2-amino-6-phenoxy-4H-quinazolin-3-yl)-4-(S)-(tetrahydro-pyran-4-yl)-butyrylamino]-3-(R)-tert-butoxy-propionic acid as a TFA salt.

$MH^+$ 553.8

$^1H$ NMR (300 MHz, $CDCl_3$): δ1.17 (s, 9H), 1.60-2.40 (m, 9H), 3.28-3.36 (m, 2H), 3.62 (m, 1H), 3.83-3.97 (m, 4H), 4.14 (d, J=14.4 Hz, 1H), 4.32 (d, J=14.4 Hz, 1H), 4.48 (m, 1H), 6.73 (d, J=2.3 Hz, 1H), 6.95 (m, 3H), 7.1 (m, 2H), 7.30 (t, J=7.6 Hz, 2H)

Step G:

A solution of the salt isolated in Step H (0.4 g) in 30% $TFA/CH_2Cl_2$ (5 mL) was stirred at room temperature overnight. The solvent was evaporated to yield a crude oil which was purified by Gilson HPLC to yield 2-[4-(2-amino-6-phenoxy-4H-quinazolin-3-yl)-4S-(tetrahydro-pyran-4-yl)-butyrylamino]-3R-hydroxy-propionic acid as a TFA salt.

$MH^+$ 497.9

$^1H$ NMR (300 MHz, $CDCl_3$): δ1.27-1.36 (m, 4H), 1.67-1.78 (m, 4H), 2.17-0.46 (m, 3H), 3.23-3.34 (m, 2H), 3.85-3.95 (m, 5H), 3.83-3.97 (m, 4H), 4.15 (d, =14.3 Hz, 1H), 4.33 (d, J=14.3 Hz, 1H), 4.48 (m, 1H), 6.73 (d, J=2.0 Hz, 1H), 0.95 (m, 4H), 7.11 (t, J=7.38 Hz, 1H), 7.3 (m, 2H).

Example 150

2-{[4-(2-Amino-6-phenoxy-4H-quinazolin-3-yl)-4S-(tetrahydro-pyran-4-yl)-butyryl]-methyl-amino}-3R-benzyloxy-propionic acid

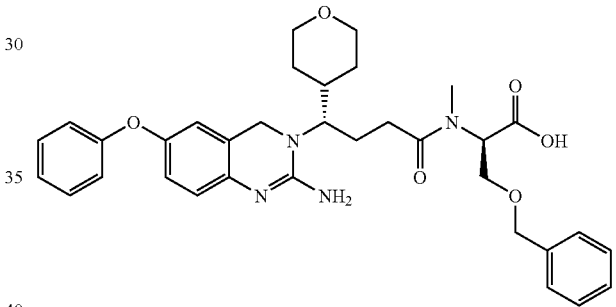

Step A:

A solution of Boc-D-Ser(Benzyl)-OH (1 g, 3.4 mmol), $CH_3I$ (2M in diethyl ether, 16 mL) in DMF (16 mL) was cooled to 0° C. before NaH (60% wt., 0.31 g, 7.2 mmol) was added. The reaction mixture was stirred under 0° C. for 5 h before overnight storage in freezer. Additional $CH_3I$ (2M in diethyl ether, 5 mL) was added and stirring was continued for 5 h. The reaction was quenched with water and acidified to pH 3 with HCl before extraction with diethyl ether (4×100 mL). The organic layer was dried with $MgSO_4$ and evaporated to yield 3R-benzyloxy-2-(tert-butoxycarbonyl-methyl-amino)-propionic acid as a crude oil.

$MH^+$ 210.0 ($MH^+$–Boc)

Step B:

A solution of the oil isolated in Step A (1.1 g, 3.4 mmol), concentrated $H_2SO_4$ (0.7 mL) in MeOH (50 mL) was refluxed for 24 h. Additional $H_2SO_4$ (1 mL) was added, and the reaction mixture was refluxed for an additional 5 h. The MeOH was removed under vacuum. To the reaction mixture was then added $CH_2Cl_2$ (100 mL), and the aqueous layer was basified with $NH_4OH$. The layers were separated, and the aqueous layer was extracted with $CH_2Cl_2$ (2×100 mL). The organic layers were combined, dried with $MgSO_4$, filtered, and evaporated to yield 3R-benzyloxy-2-methylamino-propionic acid methyl ester as an oil.

$MH^+$ 223.9

Step C:

To an ice cooled solution of the oil isolated in Step C (0.7 g, 3 mmol), 4-tert-butoxycarbonylamino-4-cyclohexyl-butyric acid (0.76 g, 3 mmol) and HOBT (0.6 g, 4.4 mmol) in $CH_2Cl_2$ (100 mL), TEA (0.87 mL, 7 mmol) was added followed by addition of 1,3-dimethylamino propyl-3-ethylcarbodiimide (EDC, 0.8 g, 4.2 mmol). The reaction mixture was allowed to warm to room temperature and stirred overnight. The reaction mixture was acidified by adding aqueous citric acid solution. This mixture was then extracted by EtOAc (2×100 mL). The organic layers were combined, dried with $MgSO_4$ and evaporated to yield 3R-benzyloxy-2-{[4-tert-butoxycarbonylamino-4S-(tetrahydro-pyran-4-yl)-butyryl]-methyl-amino}-propionic acid methyl ester as an oil.

$MH^+$ 492.9

Step D:

A solution of the oil isolated in Step C (1.5 g, 3 mmol) in TFA (10% in $CH_2Cl_2$, 100 mL) was stirred at room temperature for 5 hours. The solvent and most of TFA was evaporated to yield a solution which was basified with aqueous saturated $NaHCO_3$ solution and extracted with $CH_2Cl_2$ (2×100 mL). The organic layers were combined, dried with $MgSO_4$ and evaporated to yield 2-{[4-amino-4S-(tetrahydro-pyran-4-yl)-butyryl]-methyl-amino}-3R-benzyloxy-propionic acid methyl ester as an oil.

$MH^+$ 392.9

Step E:

A solution of the oil isolated in Step D (0.5 g, 1.3 mmol), 2-nitro-5-phenoxy-benzaldehyde (0.33 g, 1.3 mmol) in methylene chloride (50 mL) was stirred at room temperature overnight. $NaBH(OAc)_3$ (0.58 g, 2.6 mmol) was added, and the reaction mixture was stirred at room temperature for 5 hours. The reaction mixture was then poured into EtOAc (100 mL). The organic layer was washed with brine, dried with $MgSO_4$, filtered, and evaporated. Column chromatography (1:1 heptane:EtOAc) yielded 3R-benzyloxy-2-{methyl-[4-(2-nitro-5-phenoxy-benzylamino)-4S-(tetrahydro-pyran-4-yl)-butyryl]-amino}-propionic acid methyl ester as an oil.

$MH^+$ 620.8

Step F:

To a solution of the oil isolated in Step E (0.5 g, 0.8 mmol) in MeOH (10 mL) was added 0.1 g of 10% Pd on activated carbon under $N_2$. The reaction mixture was subjected to hydrogenation under 5 psi for 2 h. The catalyst was removed by filtration, and the filtrate was evaporated to yield 2-{[4-(2-amino-5-phenoxy-benzylamino)-4S-(tetrahydro-pyran-4-yl)-butyryl]-methyl-amino}-3R-benzyloxy-propionic acid methyl ester as an oil.

$MH^+$ 590.8

Step G:

A solution of the oil isolated in Step F (0.48 g, 0.8 mmol), BrCN (3M in $CH_2Cl_2$, 0.41 mL) in EtOH (50 mL) was stirred at room temperature overnight. The EtOH was evaporated. The resulting oil was stirred in diethyl ether (50 mL) for 30 min, and the precipitate that formed was collected to yield 2-{[4-(2-amino-6-phenoxy-4H-quinazolin-3-yl)-4S-(tetrahydro-pyran-4-yl)-butyryl]-methyl-amino}-3R-benzyloxy-propionic acid methyl ester as a solid, as its corresponding HBr salt.

$MH^+$ 615.8

Step H:

To a solution of the solid isolated in Step G (0.24 g, 0.4 mmol) in MeOH (30 mL) was added 1N NaOH (0.6 mL). The reaction mixture was stirred at room temperature overnight before acidification with citric acid. The methanol was evaporated to yield a crude oil which was purified by Gilson HPLC to yield 2-{[4-(2-amino-6-phenoxy-4H-quinazolin-3-yl)-4S-(tetrahydro-pyran-4-yl)-butyryl]-methyl-amino}-3R-benzyloxy-propionic acid as its TFA salt.

$MH^+$ 601.7

$^1H$ NMR (300 MHz, $CDCl_3$): δ1.18-2.18 (m, 11H), 2.9 (s, 3H), 3.27-3.36 (m, 2H), 3.8-4.0 (m, 4H), 4.18-4.25 (m, 2H), 4.50 (d, J=11.87 Hz, 1H), 4.55 (d, J=11.87 Hz, 1H), 6.7 (d, 1H, J=2.6 Hz), 6.8-7.0 (m, 4H), 7.1-7.2 (m, 2H), 7.28-7.33 (m, 6H).

Example 151

4-{[4-(2-Amino-6-phenoxy-4H-quinazolin-3-yl)-4S-cyclohexyl-butyryl]-methyl-amino}-S,R-cyclohexanecarboxylic acid amide

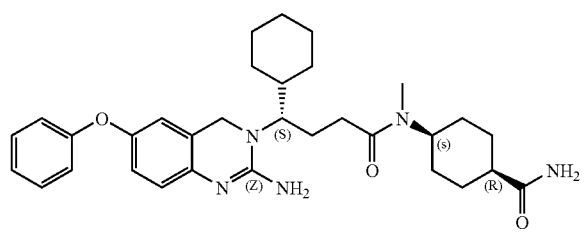

Step A:

To a stirred solution of 4-{[4-(2-Amino-6-phenoxy-4H-quinazolin-3-yl)-4S-cyclohexyl-butyryl]-methyl-amino}-S,R-cyclohexanecarboxylic acid (1.51 g, 2.3 mmol) and triethylamine (0.95 mL, 6.8 mmol) in dichloromethane (50 mL), di-tert-butyl dicarbonate (1.25 g, 5.7 mmol) was added. The reaction mixture was then stirred at room temperature overnight. N,N-diisopropylethylamine (1.0 mL, 5.8 mmol) was added. The reaction mixture was stirred for another 48 h at room temperature. Dichloromethane (50 mL) was added. The reaction mixture was washed with aqueous hydrochloric acid (1.0 M) twice and water one time, then dried over magnesium sulfate. The solution was filtered and concentrated to yield a white solid. The solid was dissolved in THF (20 mL). Sodium hydroxide (1 N, 3.8 mL, 3.8 mmol) was added. The solution was stirred at room temperature overnight. The solution was acidified to pH 4 by adding aqueous hydrochloric acid solution (1.0 N). The solution was extracted with ethyl acetate twice. The combined ethyl acetate extracts were washed with water and dried over magnesium sulfate. The solution was filtered and concentrated to yield 4-{[4-(2-tert-butoxycarbonylamino-6-phenoxy-4H-quinazolin-3-yl)-4S-cyclohexyl-butyryl]-methyl-amino}-S,R-cyclohexanecarboxylic acid as a white solid.

$MH^+$=647.4.

Step B:

To a stirred solution of the white solid isolated in Step A (0.104 g, 0.16 mmole), ammonium chloride (0.017 g, 0.32 mmole), and N,N-diisopropylethylamine (0.08 mL, 0.48 mmole) in DMF (1.0 mL), HBTU (0.073 g, 0.19 mmole) was added. After stirring at room temperature overnight, the reaction mixture was diluted with diethyl ether (3.0 mL). The reaction mixture was extracted with aqueous hydrochloric acid (1.0 N) twice, water one time, and dried over sodium sulfate. The reaction mixture was filtered and concentrated to a residue. The residue was dissolved in dichloromethane (1.0 mL). Trifluoacetic acid (1.0 mL) was added. The resulting solution was stirred at room temperature for 1 hour. The solution was then concentrated to a residue. The residue was purified by HPLC to yield 4-{[4-(2-amino-6-phenoxy-4H- quinazolin-3-yl)-4S-cyclohexyl-butyryl]-methyl-amino}-S,R-cyclohexanecarboxylic acid amide as a white solid.

MH$^{30}$=546.7.

$^1$H NMR (300 MHz, DMSO) δ7.83 (s, 1H), 7.39 (m, 1H), 6.90-7.20 (m, 5H), 6.74 (m, 1H), 4.30-4.47 (m, 2H), 3.50-3.90 (broad m, 3H), 2.00-2.40 (m, 5H), 1.00-2.00 (m, 21H).

Example 152

4-(2-Amino-6-phenoxy-4H-quinazolin-3-yl)-4S,N-dicyclohexyl-N-(1H-tetrazol-5-ylmethyl)-butyramide

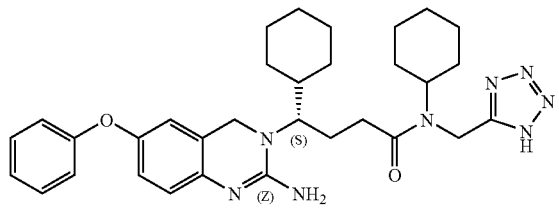

Step A:

To a stirred solution of N-phthaloylglycine (11.92 g, 58 mmol) in dichloromethane (200 mL) at room temperature, oxalyl chloride (7.5 mL, 87 mmol) was added. DMF (two drops) was then added. The resulting solution was concentrated after stirring four hours at room temperature. Dichloromethane (100 mL, dry) was then added to the residue. Benzylamine (9.5 mL, 87 mmol) was added slowly into the resulting solution. Triethylamine (12 mL, 87 mmol) was then added slowly into the solution. Dichloromethane (200 mL) and methanol (50 mL) were added 30 min after the completed addition of triethylamine. The resulting solution was extracted with 2 N HCl solution twice, 1N NaOH solution one time and 1N HCl one time, and then dried over MgSO$_4$. The solution was filtered and concentrated to yield N-benzyl-2-(1,3-dioxo-1,3-dihydro-isoindol-2-yl)-acetamide as a white solid.

MH$^+$=294.9.

Step B:

Dissolution of the white solid isolated in Step A (8.02 g, 27.2 mmol) in acetonitrile (100 mL) was achieved by heating to reflux. After the solution was cooled to 0° C., NaN$_3$ (2.30 g, 35.4 mmol) and trifluoromethanesulfonic anhydride (10 g, 35.4 mmol) were added. The resulting solution was then stirred at room temperature overnight. Dichloromethane (200 mL) was added. The resulting solution was washed with saturated sodium bicarbonate solution three times and brine one time and then dried over MgSO$_4$. The solution was filtered and concentrated to yield 2-(1-benzyl-1H-tetrazol-5-ylmethyl)-isoindole-1,3-dione as a white solid.

MH$^+$=320.0.

Step C:

To a stirred solution of the solid isolated in Step B (7.88 g, 24.7 mmol) in ethanol (300 mL), hydrazine (1.58 g, 49.3 mmol) was added. The reaction mixture was then refluxed four hours. After cooling down to room temperature, the white solid from the solution was removed by filtration. The filtrate was concentrated. Acetonitrile (50 mL) was added to the residue. The precipitate from the solution was removed by filtration. The filtrate was concentrated to yield a colorless oil which was treated with 1N HCl in diethyl ether to yield C-(1-benzyl-1H-tetrazol-5-yl)-methylamine as a white solid, as its corresponding HCl salt.

MH$^+$=190.1.

Step D:

To a stirred solution of the solid isolated in Step C (3.27 g, 14.5 mmol) in methanol (100 mL), sodium acetate (1.43 g, 17.4 mmol) and cyclohexanone (1.65 mL, 15.9 mmol) were added. The resulting solution was concentrated, and then THF (50 mL) and dichloromethane (50 mL) were added. The solution was cooled to 0° C., and sodium triacetoxyborohydride (6.14 g, 29 mmol) was added. The resulting solution was stirred at this temperature for six hours and then at room temperature for six hours. The reaction mixture was concentrated to a residue. The residue was dissolved in 1 N hydrochloric acid solution (50 mL). The resulting solution was extracted with diethyl ether once. Sodium bicarbonate was added slowly into the aqueous solution until no more bubbling from the solution was observed. The solution was extracted with ethyl acetate three times. The combined ethyl acetate extracts were dried over MgSO$_4$. The solution was concentrated to yield (1-benzyl-1H-tetrazol-5-ylmethyl)-cyclohexyl-amine as a colorless oil.

MH$^+$=272.1.

Step E:

To a stirred solution of 4-tert-butoxycarbonylamino-4-cyclohexyl-butyric acid (2.63 g, 9.2 mmole), the oil isolated in Step D (2.50 g, 9.2 mmole), and N,N-diisopropylethylamine (3.2 mL, 18.4 mmole) in DMF (50 mL), HBTU (4.19 g, 11.0 mmole) was added. After stirring at room temperature overnight, the solution was diluted with diethyl ether (200 mL). The solution was extracted with water three times and dried over magnesium sulfate. The solution was then concentrated to yield {3-[(1-benzyl-1H-tetrazol-5-ylmethyl)-cyclohexyl-carbamoyl]-1 S-cyclohexyl-propyl}-carbamic acid tert-butyl ester as a colorless oil.

MH$^+$=539.2.

Step F:

To a stirred solution of the oil isolated in Step E (2.34 g, 4.3 mmol) in THF (50 mL) and ethanol (50 mL), Pd(OH)$_2$ (3.25 g, 20% on carbon) was added. The solution was hydrogenated at 50 psi at room temperature for five hours. The solution was filtered and concentrated to yield a white solid. MH$^+$=449.0. To a solution of the white solid. (1.29 g, 2.9 mmole) in dichloromethane (21 mL) was added trifluoroacetic acid (21 mL). The resulting solution was stirred at room temperature for 1 hour and then concentrated to yield 4-amino-4S,N-dicyclohexyl-N-(1H-tetrazol-5-ylmethyl)-butyramide as a residue as its corresponding TFA salt.

Step G:

To a stirred solution of the material isolated in Step G (0.66 g) in methanol (30 mL), 2-nitro-5-phenoxy-benzaldehyde (0.318 g, 1.3 mmole), and sodium acetate (0.32 g, 3.9 mmol) were added. The resulting solution was concentrated to dryness. Dichloromethane (30 mL), THF (30 mL) and 4 Å molecular sieves (4 g) were added. After stirring at room temperature for 1 h, the resulting solution was cooled to 0° C. Sodium triacetoxyborohydride (0.55 g, 2.6 mmol) was added slowly into the solution. The solution was stirred at 0° C. for 8 h and then warmed to room temperature overnight. Diethyl ether (200 mL) was added. The resulting solution was filtered and extracted with saturated sodium bicarbonate solution three times and dried over magnesium sulfate. The solution was filtered and concentrated to yield 4S,N-dicyclohexyl-4-(2-nitro-5-phenoxy-benzylamino)-N-(1H-tetrazol-5-ylmethyl)-butyramide as a slightly colored oil.

MH$^+$=575.8.

Step H:

To a solution of the oil isolated in Step H (0.35 g, 0.6 mmole) in ethanol (20 mL) and THF (20 mL), 10% palladium on carbon (0.27 g) was added. The resulting solution was subjected to hydrogenation for 1 hour at 20 psi. The resulting solution was filtered. Cyanogen bromide (3 M in dichloromethane, 0.30 mL, 0.9 mmole) was added. The solution was stirred at room temperature overnight. The solution was then concentrated to a residue. The residue was purified by HPLC to yiled 4-(2-amino-6-phenoxy-4H-quinazolin-3-yl)-4S,N-dicyclohexyl-N-(1H-tetrazol-5-ylmethyl)-butyramide as a white solid, as its corresponding TFA salt.

$MH^+$=570.9

$^1$H NMR (300 MHz, DMSO), δ7.85 (s, 2H), 6.73-7.41 (m, 8H), 4.63 (s, 2H), 4.35-4.50 (m, 2H), 3.79-3.82 (m, 2H), 2.00-2.45 (m, 3H), 1.00-2.00 (m, 23H).

Example 153

{[4-(2-Amino-6-phenoxy-4H-quinazolin-3-yl)-4S-cyclohexyl-butyryl]-cyclohexyl-amino}-acetic acid

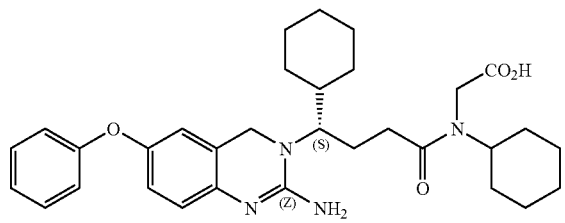

Step A:

Following the procedure of Example 152, Step D, except substituting aminoacetonitrile hydrochloride salt for the product of Example 152, Step C, cyclohexylamino-acetonitrile, as a white solid was prepared.

$MH^+$=139.1.

Step B:

Following the procedure of Example 152, Step E, except substituting the product of Example 153, Step A, for the product of Example 152, Step D, [3-(cyanomethyl-cyclohexyl-carbamoyl)-1 S-cyclohexyl-propyl]-carbamic acid tert-butyl ester as a slightly colored oil was prepared.

$MH^+$=406.4.

Step C:

To a stirred solution of the oil isolated In Step B (6.10 g, 15.0 mmole) in dichloromethane (20 mL), trifluoroacetic acid (20 mL) was added. The resulting solution was stirred at room temperature for 2 h. The solution was then concentrated. Hydrochloric acid solution (1 N, 10 mL) was added to the residue. The resulting solution was extracted with diethyl ether one time. Sodium bicarbonate was added until there was no more bubbling observed from the aqueous solution. The aqueous solution was extracted with ethyl acetate three times. The combined ethyl acetate extracts were dried over magnesium sulfate. The resulting solution was filtered and concentrated to yield [(4-amino-4S-cyclohexyl-butyryl)-cyclohexyl-amino]-acetic acid as a grey solid.

$MH^+$=324.0

Step D:

To a stirred solution of the solid isolated in Step C (3.40 g, 10.5 mmole), 2-nitro-5-phenoxy-benzaldehyde (2.71 g, 11.1 mmole) in THF (20 mL), dichloromethane (40 mL) and 4 Å molecular sieves (6 g) were added. After stirring at room temperature for 1 h, the solution was cooled to 0° C. Sodium triacetoxy-borohydride (4.72 g, 22.3 mmol) was added slowly into the solution. The resulting solution was stirred at 0° C. for 8 h and then warmed to room temperature overnight. Diethyl ether (200 mL) was added. The resulting solution was filtered through a pad of Celite. The filtrate was extracted with 1 N HCl solution three times. The combined aqueous HCl extracts were neutralized by adding solid sodium bicarbonate. The aqueous solution was extracted with ethyl acetate twice. The combined ethyl acetate extracts were dried over magnesium sulfate. The solution was filtered and concentrated to yield {cyclohexyl-[4-Scyclohexyl-4-(2-nitro-5-phenoxy-benzylamino)-butyryl]-amino}-acetic acid as a slightly colored oil.

$MH^+$=551.0.

Step E:

Following the procedure of Example 152, Step H, except substituting the product of Step D above for the product of Example 152, Step G, {[4-(2-amino-6-phenoxy-4H-quinazolin-3-yl)-4S-cyclohexyl-butyryl]-cyclohexyl-amino}-acetic acid was prepared as a white solid.

$MH^+$=546.0

$^1$H NMR (300 MHz, DMSO), δ10.80 (s, 1H), 7.91 (s, 1H), 6.96-7.47 (m, 8H), 4.35-4.50 (m, 2H), 3.81-3.87 (m, 3H), 2.00-2.45 (m, 5H), 1.00-2.00 (m, 23H).

Example 154

3-(2-Amino-6-phenoxy-4H-quinazolin-3-yl)-N-(4-cyano-cyclohexyl)-3S-cyclohexyl-N-methyl-propionamide

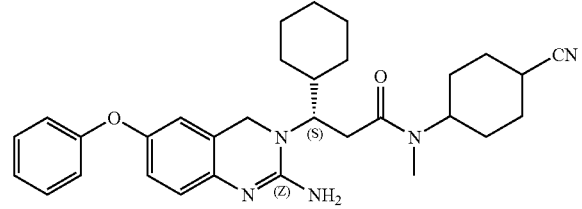

Step A:

To a stirred solution of Boc-D-cyclohexylglycine (4.25 g, 16.5 mmol) and triethyl amine (2.7 ml, 19.8 mmol) in THF (100 mL) at 0° C., ethyl chloroformate was added. The resulting solution was stirred at this temperature for 1 hr. Diazomethane in diethyl ether, freshly prepared from N-methyl-N-nitrosourea (6.0 g, 58.2 mmol), was added slowly into the solution. The solution was stirred at 0° C. for two hours and then at room temperature overnight. Ethyl acetate (100 mL) was added. The solution was washed with aqueous hydrochloric acid (1.0 N) once, saturated sodium bicarbonate solution once, and then was dried over magnesium sulfate. The solution was filtered and concentrated to yield a white solid.

$^1$H NMR (300 MHz, CDCl$_3$), δ5.40 (br s, 1H), 5.12 (br m, 1H), 4.04 (br m, 1H), 0.98-1.76 (m, 11H), 1.43 (s, 9H).

Step B

To a stirred solution of the white solid (4.99 g, 17.6 mmol) isolated in Step A in a solvent mixture of THF (100 mL) and water (10 mL) at 0° C., silver trifluoroacetate (0.78 g, 3.5 mmol) in triethyl amine (7.3 mL, 52.7 mmol) was added. The resulting solution was stirred at room temperature in the dark for four hours. Diethyl ether (100 mL) was then added. The resulting solution was extracted with aqueous sodium hydroxide (1.0 N) three times. The combined aqueous phases were acidified with 2 N HCl solution. The resulting solution was extracted with ethyl acetate three times. The combined ethyl acetate extracts were dried over magnesium sulfate. The solution was filtered and concentrated to yield 3-tert-butoxycarbonylamino-3-cyclohexyl-propionic acid as a slightly colored solid.

$^1$H NMR (300 MHz, CDCl$_3$), δ5.63 (broad s, 1H), 3.74 (broad m, 1H), 2.57 (broad m, 2H), 0.98-1.76 (m, 11H), 1.44 (s, 9H).

Step C:
Following the procedure of Example 152, Step E, except substituting the solid from Step B above for 4-tert-butoxycarbonylamino-4-cyclohexyl-butyric acid and N-(4-cyanocyclohexyl), N-methylamine hydrochloride for the oil isolated in Example 152, Step D, a slightly colored oil was obtained.
MH+=292.0

Following Example 153, Step C, except substituting the slightly colored oil for the solid isolated in Example 153, Step B, 3-amino-N-(4-cyano-cyclohexyl)-3S-cyclohexyl-N-methyl-propionamide was prepared as a slightly colored oil.
Step D:
Following the procedure of Example 153, Step D, except substituting the oil isolated in Step C above for the solid isolated in Example 153, Step C, (1.63 g, 89%) N-(4-cyanocyclohexyl)-3S-cyclohexyl-N-methyl-3-(2-nitro-5-phenoxy-benzylamino)-propionamide was prepared as a slightly colored solid.
$^1$H NMR (300 MHz, CDCl$_3$), δ8.14 (m, 1H), 6.90-7.50 (m, 7H), 4.96 (s, 2H), 2.89 (s, 3H), 2.50-2.83 (m, 3H), 2.07 (m, 2H), 1.08-1.79 (m, 15H).
Step E:
Following the procedure of Example 152, Step H, except substituting the oil isolated in Step D above for the oil isolated in Example 152, Step G, 3-(2-amino-6-phenoxy-4H-quinazolin-3-yl)-N-(4-cyano-cyclohexyl)-3S-cyclohexyl-N-methyl-propionamide was prepared as a white solid.
MH+=513.9
$^1$H NMR (300 MHz, DMSO), δ8.00 (broad s, 2H), 6.89-7.43 (m, 8H), 4.09-4.51 (m, 3H), 2.77 (s, 3H), 2.60-2.95 (m, 4H), 1.00-2.00 (m, 19H).

Example 155

1-[4-(2-Amino-6-phenoxy-4H-quinazolin-3-yl)-4S-cyclohexyl-butyryl]-octahydro-indole-2S-carboxylic acid

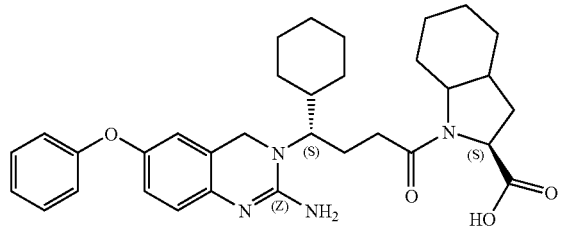

Step A:
To a stirred solution of Boc-L-octahydroindole-2S-carboxylic acid (0.98 g, 3.64 mmol) in a solvent mixture of dichloromethane (20 mL) and methanol (3.0 mL) at 0° C., (trimethylsilyl)diazomethane (2.0 M in hexane, 5.5 mL, 10.9 mmol) was added. The resulting solution was stirred at room temperature for two hours. The solution was then concentrated to a residue. The residue was dissolved in dichloromethane (11 mL). TFA (11 mL) was then added. The resulting solution was stirred at room temperature for one hour. The solution was then concentrated. Water (20 mL) was added followed by excess solid sodium bicarbonate. The resulting solution was extracted with ethyl acetate three times. The combined organic extracts were dried over magnesium sulfate. The solution was filtered and concentrated to yield octahydro-indole-2S-carboxylic acid methyl ester as a colorless oil.
MH+=184.1
Step B:
Following the procedure of Example 152, Step E, except substituting the oil isolated in Step A above for the oil isolated in Example 152, Step D, 1-(4-tert-butoxycarbonylamino-4-cyclohexyl-butyryl)-octahydro-indole-2S-carboxylic acid methyl ester was prepared as a slightly colored oil.
MH+=450.9.
Step C:
Following the procedure of Example 153, Step C, except substituting the oil isolated in Step B above for the oil isolated in Example 153, Step B, 1-(4-amino-4-cyclohexyl-butyryl)-octahydro-indole-2S-carboxylic acid methyl ester was prepared as a grey solid.
MH+=351.2
Step D:
Following the procedure of Example 153, Step D substituting the solid isolated in Step C above for the solid isolated in Example 3, Step C, 1-[4-S-cyclohexyl-4-(2-nitro-5-phenoxy-benzylamino)-butyryl]-octahydro-indole-2S-carboxylic acid methyl ester was prepared as a slightly colored oil.
MH+=578.2.
Step E:
Following the procedure of Example 152, Step H, except substituting the oil isolated in Step D above for the oil isolated in Example 152, Step G, 1-[4-(2-amino-6-phenoxy-4H-quinazolin-3-yl)-4S-cyclohexyl-butyryl]-octahydro-indole-2S-carboxylic acid methyl ester was prepared as a white solid.
MH+=573.3.
Step F:
To a stirring solution of the solid isolated in Step E (0.1365 g, 0.20 mmol) in a solvent mixture of THF (1.0 mL) and methanol (1.0 mL), aqueous sodium hydroxide solution (1.0 M, 0.6 mL, 0.60 mmol) was added. The resulting solution was stirred at room temperature for three hours. The solution was then acidified with aqueous hydrochloric acid (2.0 M). The solution was purified by HPLC to yield 1-[4-(2-Amino-6-phenoxy-4H-quinazolin-3-yl)-4S-cyclohexyl-butyryl]-octahydro-indole-2S-carboxylic acid as a white solid.
MH+=559.3
$^1$H NMR (300 MHz, DMSO) δ10.96 (s, 1H), 8.03 (s, 2H), 7.34-7.62 (m, 2H), 6.95-7.23 (m, 6H), 4.10-4.50 (m, 3H), 3.71-3.81 (m, 1H), 3.05-3.09 (m, 1H), 0.73-2.34 (m, 28H).

Example 156

4-(2-Amino-6-phenoxy-4H-quinazolin-3-yl)-4S,N-dicyclohexyl-N-[2R-(3R,4S,5S-trihydroxy-6R-hydroxymethyl-tetrahydro-pyran-2-yloxy)-ethyl]-butyramide

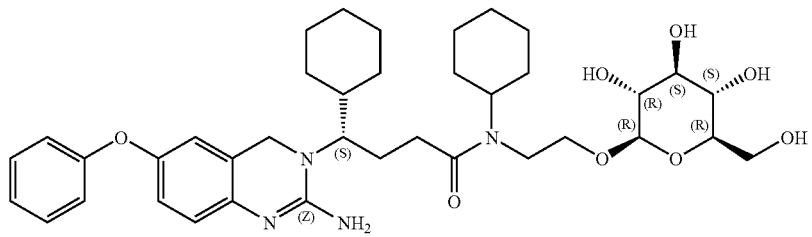

Step A:

2-Cyclohexylamino-ethanol (11.6 g, 81 mmol) was taken into a mixture of 1:1 dioxane:water (200 mL), and sodium carbonate (8.6 g, 81 mmol) was then added. The resulting solution was cooled with an ice bath and Boc-anhydride (18.6 mL, 81 mmol) in dioxane (50 mL) was added. The reaction mixture was stirred at room temperature overnight, and then was quenched with water and extracted with ethyl acetate. The organic layer was washed with 1N HCl, saturated NaHCO$_3$, and brine and then was dried over sodium sulfate. The solvent was removed in vacuo to yield a clear oil.

$^1$H NMR (300 MHz, DMSO): 61.0-1.3 (m, 4H), 1.4 (s, 9H), 1.45-1.8 (m, 6H), 3.1 (s, 2H), 3.4 (m, 2H), 3.7 (s, 1H), 4.6 (m, 1H).

Step B:

The oil from Step A (4.67 g, 19.2 mmol) and β-D-glucose pentaacetate (15 g, 38 mmol) were taken up in dry DCM (50 mL). The reaction mixture was cooled with an ice bath and boron trifluoride-diethyl etherate (23.86 mL, 190 mmol) was added slowly. The reaction mixture was stirred at room temperature overnight. The reaction was complete, and the Boc group had been removed. The reaction mixture was poured into ice water and extracted with DCM. The DCM extracts were combined and washed with cold saturated NaHCO$_3$ and brine and then was dried over sodium sulfate. The solvent was removed in vacuo to yield a residue which was purified on normal phase column with 95/5 DCM/MeOH to yield an oil.

$^1$H NMR (300 MHz, CDCl$_3$): δ 1.0-1.3 (m, 5H), 1.6-1.9 (m, 6H), 1.95 (s, 3H), 1.98 (s, 3H), 2.05 (s, 3H), 2.1 (s, 3H), 2.38 (m, 1H), 2.75 (m, 2H), 3.64 (m, 2H), 3.94 (m, 1H), 4.12 (m, 1H), 4.26 (m, 1H), 4.55 (d, 1H), 4.98 (t, 1H), 5.1 (t, 1H), 5.2 (t, 1H).

Step C:

To a solution of the oil from Step B (3.0 g, 6.3 mmol) in DMF (35 mL) was added 4-tert-butoxycarbonylamino-4-cyclohexyl-butyric acid (1.85 g, 6.3 mmol), HOBt (1.06 g, 7.9 mmol), EDC (1.5 g, 7.9 mmol) and DIPEA (1.6 mL, 9.5 mmol). The reaction mixture was stirred at room temperature overnight. The reaction was quenched with water, and the reaction mixture was extracted with ethyl acetate. The ethyl acetate extract was washed with saturated NaHCO$_3$ and brine and then was dried over sodium sulfate. The solvent was evaporated, and the residue was purified on a normal phase column with 95/5 DCM/MeOH to yield a light yellow oil.

MH$^+$ 741.0

Step D:

The oil from Step C (2.0 g, 2.7 mmol) was taken into DCM (20 mL) and then TFA (10 mL) was added. The reaction mixture was stirred for 2 hours at room temperature. The reaction mixture was quenched with saturated NaHCO$_3$ and extracted with ethyl acetate. The ethyl acetate extract was washed with brine and dried over sodium sulfate. The solvent was removed in vacuo to yield a residue which was used in the next step without further purification.

MH$^+$ 641.0

Step E:

The product from Step D (1.0 g, 1.56 mmol) and 2-nitro-5-phenoxy-benzaldehyde (0.42 g, 1.56 mmol) were taken into methanol (20 mL) and stirred at room temperature overnight. The reaction mixture was cooled with an ice bath. A sodium borohydride pellet (0.18 g, 4.8 mmol) was added, and the reaction mixture effervesced. After 1 h, the reaction was quenched with acetic acid to neutral pH. Ethyl acetate was added, and the resulting solution was washed with saturated solution NaHCO$_3$ and brine and then dried over sodium sulfate. The solvent was removed in vacuo to yield a residue which was purified on a normal phase column with 98/2 DCM/MeOH to yield a residue.

MH$^+$ 867.9

Step F:

The residue from E (0.5 g, 0.57 mmol) was taken into ethanol (15 mL) and 10% Pd/C (0.10 g) was added. The reaction mixture was stirred under H$_2$ for 4 hours. The reaction mixture was then filtered through Celite. The solvent was removed to yield a residue as crude material.

MH$^+$ 837.9

Step G:

The crude material from Step F (0.5 g, 0.57 mmol) was taken up in ethanol (8 mL), and then 3M cyanogen bromide in DCM (0.288 mL, 0.86 mmol) was added. The reaction mixture was stirred at 80° C. for 2.5 hours. The reaction mixture was quenched with saturated NaHCO$_3$ solution and then extracted with ethyl acetate. The organic extract was washed with brine and dried over sodium sulfate. The solvent was removed in vacuo to yield a residue which was purified on a normal phase column with 97.5/2.5 DCM/MeOH to yield a white solid.

MH$^+$ 863.0

Step H:

To a solution of the white solid prepared in Step G (0.10 g, 0.12 mmol) in methanol (4 mL) was added hydrazine monohydrate (75 µL, 2.4 mmol). The reaction mixture was stirred at room temperature for 2.5 hours. The solvent was removed in vacuo, and the residue was purified on the HPLC. The desired fractions were made basic with saturated NaHCO$_3$ and extracted with ethyl acetate. The ethyl acetate extracts were washed with brine and dried over sodium sulfate. The solvent was removed in vacuo, and the residue was taken into isopropanol (4 mL) and 1N HCl was added, followed by addition of water (8 mL). The resulting solution was frozen and lyophilized to yield the title compound as a white powder.

MH$^+$ 695.4

$^1$H NMR (300 MHz, CDCl$_3$): δ 0.8-1.3 (m, 10H), 1.32-1.75 (m, 12H), 1.8-2.8 (m, 5H), 3.2-4.5 (m, 16H), 6.65 (s, 1H), 6.8 (m, 3H), 7.1 (m, 2H), 7.30 (r, 2H), 7.9 (s, 2H), 10.6 (s, 1H)

Example 157

(3-{[4-(2-Amino-6-phenoxy-4H-quinazolin-3-yl)-4S-cyclohexyl-butyryl]-cyclohexyl-amino}-propyl)-carbamic acid 3R,4R,S5,6S-tetrahydroxy-tetrahydro-pyran-2R-ylmethyl ester

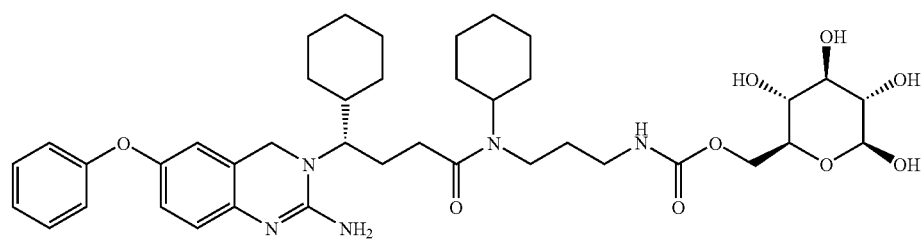 [SMILES: NC1=Nc2ccc(Oc3ccccc3)cc2CN1[C@@H](CCC(=O)N(CCCNC(=O)OC[C@@H]1O[C@H](O)[C@@H](O)[C@H](O)[C@H]1O)C1CCCCC1)C1CCCCC1]

Step A:

Imidazole-1-carboxylic acid 3,4,5,6-tetrakis-benzyloxy-tetrahydro-pyran-2-ylmethyl ester (0.114 g, 0.18 mmol), synthesized according to the prodecure disclosed in *Org. Biomol. Chem.*, 2003, 1, 767-771, was taken up in THF (10 mL) under $N_2$. 1,3-diaminopropane (0.067 mL, 0.72 mmol) and triethylamine (0.278 mL, 1.8 mmol) were added, and the reaction mixture was stirred at room temperature for 1 hour. The reaction was quenched with water, and the resulting solution was extracted with ethyl acetate. The organic extract was washed with water and brine and then dried over sodium sulfate, filtered, and concentrated in vacuo to yield a yellow oil which was taken to the next step without further purification.

$MH^+$ 641.0

Step B:

The yellow oil from Step A (0.10 g, 0.16 mmol) and cyclohexanone (0.032 mL, 0.32 mmol) were taken up THF (10 mL). The reaction mixture was then stirred at room temperature for 1 hour. Sodium triacetoxyborohydride (0.135 g, 0.64 mmol) was added, and the reaction mixture was stirred at room temperature overnight. Ethyl acetate was added, and the resulting solution was washed with saturated aqueous $NaHCO_3$ solution and brine, then dried over sodium sulfate, filtered, and concentrated in vacuo to yield an oil which was taken to the next step without further purification.

$MH^+$ 723.0

Step C:

To a solution of the oil from Step B (2.58 g, 3.6 mmol) in DMF (35 mL) was added (S)-4-t-butoxycarbonylamino-4-cyclohexylbutyric acid (1.27 g, 4.5 mmol), HOBT (0.73 g 5.4 mmol), EDC (1.0 g, 5.4 mmol), and DIPEA (1.25 mL, 7.2 mmol). The reaction mixture was stirred at room temperature overnight. The reaction was quenched with water, and the resulting mixture was extracted with ethyl acetate. The organic extract was washed with saturated aqueous $NaHCO_3$ and brine, then dried over sodium sulfate, filtered, concentrated and the residue purified on a normal phase column with 99:1 DCM:MeOH to yield a light yellow oil.

$MH^+$ 989.9

Step D:

The oil from Step C (1.58 g, 0.16 mmol) was taken into DCM (20 mL) and then TFA (10 mL) was added. The solution was stirred for 2 hours at room temperature and then quenched with saturated aqueous $NaHCO_3$. The resulting mixture was extracted with ethyl acetate. The organic extracts were washed with brine, dried over sodium sulfate, filtered, and concentrated in vacuo to yield crude product which was used in the next step without further purification.

$MH^+$ 890.0

Step E:

The crude product from Step D (1.4 g, 1.6 mmol) and 2-nitro-5-phenoxy-benzaldehyde (0.48 g, 2.0 mmol) were taken into methanol (20 mL) and stirred at room temperature for 2 hours. A sodium borohydride pellet (0.30 g, 6.7 mmol) was added, and the reaction was observed to effervesce. After 30 minutes, the reaction was quenched with water. The resulting solution was extracted with ethyl acetate. The organic extract was washed with saturated aqueous $NaHCO_3$ and brine, dried over sodium sulfate, filtered, and concentrated in vacuo to yield a residue. The residue was purified on a normal phase column with 98:2 DCM:MeOH to yield product.

$MH^+$ 1116.8

Step F:

The product from Step E (0.35 g, 0.3 mmol) was taken into a 50:50 ethanol/ethyl acetate solvent mixture (15 mL) and then 10% Pd/C (0.080 g) was added. The reaction was stirred under a $H_2$ balloon for 1 hour. The solution was filtered through Celite. The filtrate was concentrated to yield crude product.

$MH^+$ 1086.8

Step G:

The crude product from Step F (0.32 g, 0.3 mmol) was taken up into ethanol (4 mL) and then 3M cyanogen bromide in DCM (0.157 mL, 0.45 mmol) was added. The reaction was stirred at 80° C. for 2.5 hours. The reaction was quenched with saturated aqueous $NaHCO_3$, and the resulting mixture was extracted with ethyl acetate. The organic extracts were washed with brine, dried over sodium sulfate, filtered, and concentrated in vacuo to yield a residue. The residue was purified on a normal phase column with 97.5:2.5 DCM:MeOH to yield product.

$MH^+$ 1111.8

Step H:

The product from Step G (0.40 g, 0.36 mmol) was taken into a 4:3:3 EtOAc:toluene:MeOH solvent mixture (20 mL) and then 10% Pd/C (200 mg) was added. $H_2$ was added, and the reaction mixture was shaken under 50 psi overnight. The catalyst was filtered off and solvent was removed in vacuo. The reaction was repeated five more times. The catalyst was filtered off and solvent was removed in vacuo to yield a residue. The residue was purified by HPLC to yield the corresponding TFA salt, which was basified with saturated aqueous $NaHCO_3$ followed by addition of HCl to yield the title compound as a white powder.

$MH^+$ 752.0

$^1H$ NMR (300 MHz, DMSO): δ 0.9-1.3 (m, 8H), 1.4-1.85 (m, 16H), 2.0-2.4 (m, 3H), 2.85-3.6 (m, 13H), 3.75-4.5 (m, 5H), 4.85 (s, 1H), 6.97 (m, 5H), 7.15 (t, 1H), 7.40 (t, 2H), 7.98 (s, 2H), 10.9 (m, 1H)

Example 158

BACE Assay-1

The following standards are reagents were used in this assay: Sodium Citrate trisodium salt dihydrate (Sigma), Citric Acid monohydrate (Merck), PEG8000 (Sigma), MCA-substrate (Bachem), β-secretase (BACE) (Panvera), 96-well plate zwart (Costar (Elscolab)), StatVal (Bachem).

The following standard assay buffer solution was prepared and used in this assay: 0.05 M, pH 5.0 mixture of sodium citrate trisodium salt dihydrate (9.56 g), citric acid monohydrate (3.68 g) and PEG8000 (0.50 g).

The MCA-substrate stock solution was prepared by mixing 10 mg MCA-substrate with 5 mL DMSO for a final solution concentration of 2.0 mg/mL. The substrate work solution was prepared by mixing 0.1 mL substrate in 1.90 mL assay buffer for a final concentration of 0.05 mM. The β-secretase (BACE) work solution was prepared by mixing 8 μL BACE in 2 mL assay buffer for a final concentration of 10 μg/mL.

Test compounds were dissolved in DMSO at various concentrations in the range of $3.3 \times 10^{-3}$ M to $1.5 \times 10^{-6}$ M.

The screen procedure for this assay was as follows. 60 μL of assay buffer was pippeted into each well of a 96-well plate. To each well was then pipetted 1 μL of test compound at the selected concentration. To each well was then added 20 μL of the β-secretase work solution and 20 μL of the MCA-substrate stock solution. Each well was mixed for a few second and the $T_0$ measured with fluoroscan Ex320/Em405. The plates were then incubated for 1 hour at room temperature and the T60 measured with fluoroscan Ex320/Em405.

The procedure for the blank was as follows. 80 μL of assay buffer was pipetted into each well to be used as a blank control. To each well was then added 1 µL of DMSO and 20 µL of MCA-substrate solution in each well. The $T_0$ was measured with fluoroscan Ex320/Em405, the plate was incubated for 1 hour at room temperature and the T60 was then measured with fluoroscan Ex320/Em405.

The procedure for the positive control was as follows. 60 µL of assay buffer was pipetted into each well to be used as a positive control. To each well was then added 1 µL of DMSO, 20 µL of BACE work solution and 20 µL of MCA-substrate stock solution. The $T_0$ was measured with fluoroscan Ex320/Em405, the plate was incubated for 1 hour at room temperature and the T60 was then measured with fluoroscan Ex320/Em405.

For test compounds, measured at multiple concentrations, the measured $T_0$ and $T_{60}$ values were used to calculate an $IC_{50}$ value using Graphpad Software (or PIR).

Example 159

BACE Assay-2

The following reagents were used in this assay: sodium acetate, PEG8000 (Sigma), DMSO, HEPES, FS1 substrate [R(AedensE)EEVNLDAEFK-(DabcylK)R] (SEQ ID NO: 1), β-secretase(BACE) (Panvera), and 96-well plate (HE microplate, Molecular Devices).

The following assay buffers were prepared and used in this assay: (1) enzyme assay buffer (0.05 M sodium acetate, pH5, 0.1% PEG8000 (w/v)), (2) substrate assay buffer (0.05 M sodium acetate, pH5), and (3) compound vehicle (30% DMSO in 50 mM HEPES, pH 7.4).

The FS1-substrate stock solution was prepared in DMSO as a 10 mg/mL solution. The FS1-substrate working solution was prepared by diluting the 10 mg/mL stock solution with substrate assay buffer to a final concentration of 300 µg/mL. The β-secretase (BACE) working solution was prepared by diluting a 0.83 mg/mL BACE stock solution with enzyme assay buffer to a final concentration of 4 µg/mL.

Test compounds were dissolved in DMSO at 10 mM. Compounds were further diluted in compound vehicle to various concentrations in the range of 675 µM to 13.5 nM (13.5×final compound concentration in Ki plate).

The procedure for this assay was as follows: 15 µL of BACE working solution was pipetted into each well of a 96-well plate. To each well was then pipetted 2 µL of test compound at the selected concentration. Test compound and BACE were then mixed with a pipettor and incubated for 20 min at room temperature. To each well was then added 10 µL of the FS1 substrate working solution. The fluorescence for each well was then measured on a Polarstar fluorometer (Ex 390 nm/Em 520 nm) for 20 min at room temperature, reading fluorescence at 1 min intervals.

The procedure for the positive control was as follows: 15 µL of BACE working solution was pipetted into each well to be used as a positive control. To each well was then pipetted 2 µL of vehicle. Vehicle and BACE were then mixed with a pipettor and incubated for 20 min at room temperature. To each well was then added 10 µL of the FS1 substrate working solution. The fluorescence was then measured on a Polarstar fluorometer (Ex 390 nm/Em 520 nm) for 20 min at room temperature, reading fluorescence at 1 min intervals.

For test compounds, measured at multiple concentrations, the measured $T_0$ and $T_{60}$ values were used to calculate an $IC_{50}$ value using Graphpad Software (or PIR). For test compounds, $K_i$ inhibition was determined as follows: For each compound concentration and positive control, rate of cleavage of substrate ($V_i$, where i=compound concentration in µM) was determined as Δ Fluorescence/Δ time (min). Cleavage rates ($V_i$) were plotted as a function of inhibitor concentration in µM [I]. The $K_i$ was then determined by fitting the following equation to the graph of [I] vs $V_i$ $$Y = aV_{max}/(50+24*(1+X/K_i)),$$

where 50=substrate concentration (µM) and 24=$K_m$ of substrate (µM).

Representative compounds of the present invention were tested according to procedures described in Example 158 and 159 above with measured $IC_{50}$ and $K_i$ values as listed in Table 15 below. The procedure used to determine a particular value is defined within the header row in parentheses (for example (158) indicates that the $IC_{50}$ values in that column were determined using the procedure described in Example 158).

TABLE 15

BACE in vitro Assay Results

| ID No. | $IC_{50}$ µM (158) | $IC_{50}$ µM (159) | Ki µM (159) |
|---|---|---|---|
| 1 | 2.1 | 6.1 | 0.91 |
| 2 | 26 | | |
| 3 | 4.0 | | |
| 4 | 2.5 | | |
| 5 | 5.1 | | |
| 6 | 9.1 | | |
| 7 | 1.4 | 5.3 | 0.24 |
| 8 | 3.1 | 15 | 1.2 |
| 10 | 3.7 | | |
| 12 | 10 | | |
| 13 | 16 | | |
| 15 | 2.3 | | 4.0 |
| 18 | 91 | | |
| 19 | 0.18 | 1.6 | 0.38 |
| 20 | 0.48 | 2.1 | 0.34 |
| 22 | 12 | | |
| 23 | 4.9 | 10 | 1.1 |
| 24 | 1.8 | | |
| 25 | 5.5 | | |
| 27 | 1.2 | 3.0 | 0.66 |
| 30 | 11 | 20 | 2.3 |
| 31 | 2.3 | | |
| 32 | 14 | | |
| 35 | 33 | | |
| 36 | 2.3 | | |
| 37 | 12 | | |
| 39 | 1.3 | | |
| 40 | 9.8 | | |
| 41 | 5.1 | | |
| 42 | 15 | | |
| 43 | 7.2 | | |
| 44 | 6.1 | | 3.3 |
| 45 | 2.7 | | |
| 46 | 0.60 | 2.1 | 0.6 |
| 47 | 4.2 | | |
| 48 | 4.0 | | |
| 49 | 0.80 | 2.8 | 0.84 |
| 50 | 1 | 11 | 0.53 |
| 51 | 2.2 | 13 | 1.2 |
| 53 | 1.0 | 6.8 | 0.82 |
| 54 | 2.3 | | |
| 55 | 0.28 | 2.4 | 0.79 |
| 56 | 0.97 | 5.4 | 0.77 |
| 57 | 1.4 | | |
| 60 | 5.6 | | |
| 61 | 0.20 | 0.44 | 0.23 |
| 62 | | 0.52 | 0.14 |
| 62 | 0.055 | 0.37 | 0.18 |
| 65 | | | |
| 67 | 0.68 | 3.9 | 0.81 |
| 71 | 2.6 | | |
| 75 | 0.66 | | |
| 80 | | 0.94 | 0.12 |
| 80 | 0.11 | | |
| 84 | 0.47 | 3.1 | 0.76 |

TABLE 15-continued

BACE in vitro Assay Results

| ID No. | IC$_{50}$ μM (158) | IC$_{50}$ μM (159) | Ki μM (159) |
|---|---|---|---|
| 85 | 0.021 | | 0.025 |
| 85 | | | 0.030 |
| 86 | 0.048 | | 0.13 |
| 89 | | 0.4 | |
| 90 | 0.074 | | 0.22 |
| 91 | 0.60 | | 0.32 |
| 95 | 0.31 | | |
| 96 | 0.78 | | |
| 98 | 0.20 | 2.3 | 1.1 |
| 101 | | 11 | |
| 103 | | 3.6 | 4.0 |
| 106 | 0.15 | | 0.23 |
| 107 | 0.82 | 4.581 | 1.2 |
| 108 | 0.32 | 0.954 | 0.076 |
| 110 | 0.053 | 1.239 | 0.4 |
| 111 | 0.10 | 0 | 0.082 |
| 111 | | | 0.067 |
| 112 | 0.12 | 0 | 0.59 |
| 113 | 0.99 | | |
| 114 | 0.079 | | 0.27 |
| 121 | 0.58 | | 0.32 |
| 122 | 0.19 | | 0.17 |
| 123 | 1.2 | | 0.3 |
| 126 | 0.24 | | |
| 127 | 0.16 | | 0.18 |
| 128 | 0.072 | | 0.13 |
| 129 | 0.10 | | 0.12 |
| 130 | 0.45 | | 0.21 |
| 131 | 0.10 | | 0.17 |
| 133 | 0.15 | | |
| 134 | | | 0.37 |
| 135 | 0.89 | | 0.29 |
| 136 | | | 0.5 |
| 137 | | | 0.73 |
| 138 | 0.023 | | 0.06 |
| 140 | | | 0.32 |
| 141 | 0.15 | | 0.08 |
| 148 | | | 0.25 |
| 149 | | | 0.21 |
| 150 | | | 0.46 |
| 151 | | | 0.23 |
| 152 | | | 0.3 |
| 154 | | | 0.61 |
| 158 | | | 0.81 |
| 159 | 0.89 | | 0.28 |
| 160 | 0.54 | | 0.12 |
| 164 | 0.11 | | 0.1 |
| 165 | 0.19 | | 0.28 |
| 167 | | | 0.03 |
| 167 | 0.014 | | 0.05 |
| 169 | 0.058 | | 0.08 |
| 170 | | | 0.77 |
| 173 | | | 0.47 |
| 174 | 0.085 | | 0.07 |
| 176 | | | 0.2 |
| 177 | | | 0.56 |
| 178 | 0.19 | | 0.11 |
| 179 | | | 1.04 |
| 183 | 0.058 | | 0.19 |
| 192 | | | 0.22 |
| 196 | 0.015 | | 0.11 |
| 199 | | | 0.51 |
| 201 | | | 0.4 |
| 203 | 4.7 | | |
| 204 | 0.062 | | 0.23 |
| 205 | | | 0.32 |
| 206 | 0.078 | | 0.27 |
| 209 | | | 0.29 |
| 211 | | | 0.69 |
| 214 | 0.19 | | 0.1 |
| 215 | 0.23 | | 0.4 |
| 216 | | | 0.52 |
| 218 | 0.13 | | 0.1 |
| 219 | 0.31 | | 0.17 |
| 220 | 0.45 | | 0.2 |
| 221 | 0.023 | | 0.025 |
| 221 | 0.011 | | 0.029 |
| 225 | 2.9 | | |
| 227 | 0.043 | | 0.065 |
| 231 | | | 3.8 |
| 237 | >10 | | |
| 238 | 8.9 | | |
| 239 | 0.35 | | |
| 240 | 0.89 | | |
| 241 | 0.49 | | |
| 242 | >10 | | |
| 243 | 0.033 | | |
| 244 | 2.1 | | |
| 245 | 0.17 | | |
| 246 | >10 | | |
| 247 | 1.7 | | |
| 248 | 6.9 | | |
| 249 | 5.2 | | |
| 250 | >10 | | |
| 251 | >10 | | |
| 252 | 1.0 | | |
| 253 | >10 | | |
| 254 | >10 | | |
| 255 | >10 | | |
| 257 | 0.083 | | 0.056 |
| 258 | 0.39 | | 0.33 |
| 259 | 0.25 | | 0.25 |
| 260 | 0.15 | | 0.21 |
| 261 | | | 0.42 |
| 262 | | | 0.66 |
| 263 | | | 0.77 |
| 264 | | | 0.78 |
| 265 | | | 1.1 |
| 268 | | | 0.65 |
| 269 | 0.35 | | |
| 270 | 2.37 | | |
| 271 | 0.39 | | |
| 272 | 0.52 | | |
| 273 | 0.17 | | |
| 274 | >10 | | |
| 275 | >10 | | |
| 276 | >10 | | |
| 277 | 0.70 | | |
| 278 | >10 | | |
| 279 | >10 | | |
| 280 | 11 | | |
| 281 | 1.6 | | |
| 282 | >10 | | |
| 283 | >10 | | |
| 284 | 0.87 | | |
| 285 | >10 | | |
| 288 | >10 | | |
| 292 | | | 1.0 |
| 293 | | | 1.1 |
| 294 | 0.016 | | 0.020 |
| 295 | 0.016 | | 0.030 |
| 296 | 0.90 | | |
| 297 | 0.066 | | 0.12 |
| 298 | 0.22 | | 0.23 |
| 301 | 0.15 | | 0.21 |
| 302 | 0.050 | | 0.14 |
| 303 | 0.062 | | 0.24 |
| 304 | | | 0.56 |
| 305 | 1.4 | | |
| 311 | 0.020 | | 0.05 |
| 312 | 0.039 | | 0.039 |
| 317 | 0.39 | | 0.18 |
| 318 | 0.25 | | 0.19 |
| 319 | 0.053 | | 0.074 |
| 322 | 0.14 | | 0.29 |
| 324 | | | 0.52 |
| 325 | 0.089 | | 0.1 |
| 326 | | | 0.42 |
| 328 | | | 0.33 |
| 329 | 0.012 | | 0.02 |

TABLE 15-continued

BACE in vitro Assay Results

| ID No. | IC$_{50}$ μM (158) | IC$_{50}$ μM (159) | Ki μM (159) |
|---|---|---|---|
| 330 | 0.048 | | 0.21 |
| 331 | 0.089 | | 0.19 |
| 333 | | | 0.49 |
| 334 | | | 0.068 |
| 335 | 0.24 | | |
| 340 | 2.0 | | |
| 342 | 0.082 | | 0.19 |
| 343 | 0.041 | | 0.065 |
| 344 | 0.058 | | |
| 345 | 0.028 | | |
| 346 | 0.021 | | 0.013 |
| 346 | 0.027 | | 0.0082 |
| 346 | 0.021 | | 0.012 |
| 353 | 0.35 | | |
| 355 | 2.6 | | |
| 362 | 0.53 | | |
| 365 | | | 0.10 |
| 366 | | | 0.067 |
| 367 | | | 0.12 |
| 376 | 0.17 | | |
| 380 | 0.71 | | |
| 383 | 0.65 | | |
| 384 | 0.13 | | |
| 385 | 0.28 | | |
| 386 | | | 0.033 |
| 386 | 0.41 | | 0.17 |
| 387 | 3.3 | | |
| 388 | | | 0.063 |
| 389 | | | 0.028 |
| 390 | | | 0.57 |
| 391 | 0.054 | | 0.10 |
| 392 | 0.093 | | 0.16 |
| 393 | 0.15 | | 0.29 |
| 394 | 0.87 | | |
| 396 | 0.20 | | |
| 397 | 3.98 | | |
| 404 | | | 0.78 |
| 418 | | | 0.035 |
| 419 | | | 0.29 |
| 421 | 0.054 | | |
| 423 | 5.8 | | |
| 424 | | | 0.40 |
| 425 | 0.14 | | 0.074 |
| 426 | | | 0.53 |
| 428 | | | 0.23 |
| 430 | 2.8 | | |
| 431 | 0.80 | | |
| 432 | | | 0.86 |
| 444 | | | 0.58 |
| 450 | 0.011 | | 0.019 |
| 464 | 1.3 | | |
| 476 | 0.067 | | 0.28 |
| 484 | 1.1 | | 0.74 |
| 485 | 0.012 | | 0.017 |
| 487 | 0.36 | | 0.26 |
| 487 | 0.36 | | |
| 495 | 0.25 | | 0.10 |
| 497 | 0.011 | | |
| 500 | 0.16 | | |
| 501 | 3.4 | | |
| 502 | 0.18 | | |
| 506 | 0.030 | | 0.018 |
| 506 | 0.030 | | 0.0075 |
| 507 | 0.081 | | |
| 508 | | | 0.15 |
| 511 | | | 0.10 |
| 515 | | | 0.13 |
| 530 | | | 0.13 |
| 533 | 0.17 | | |
| 534 | | | 0.18 |
| 535 | | | 0.076 |
| 536 | | | 0.086 |
| 537 | | | 0.041 |
| 538 | | | 0.44 |
| 545 | | | 0.14 |
| 556 | | | 0.044 |
| 558 | | | 0.16 |
| 561 | | | 0.016 |
| 562 | | | 0.026 |
| 563 | | | 0.020 |
| 564 | 0.018 | | 0.011 |
| 578 | | | 0.18 |
| 583 | | | 0.49 |
| 595 | | | 0.33 |
| 601 | | | 0.027 |
| 602 | | | 0.056 |
| 603 | | | 0.033 |
| 605 | | | 0.54 |
| 610 | | | 0.076 |
| 618 | | | 0.19 |
| 619 | | | 0.011 |
| 625 | | | 0.27 |
| 627 | | | 0.16 |
| 629 | | | 0.13 |
| 632 | | | 0.0084 |
| 634 | | | 0.054 |
| 635 | | | 0.014 |
| 638 | | | 0.23 |
| 647 | | | 0.033 |
| 654 | | | 0.046 |
| 657 | | | 0.032 |
| 692 | | | 0.13 |
| 693 | | | 0.17 |
| 709 | | | 0.0065 |
| 710 | | | 0.30 |
| 711 | | | 0.45 |
| 712 | | | 0.10 |
| 714 | | | 0.029 |
| 714 | | | 0.022 |
| 720 | | | 0.30 |
| 721 | | | 0.22 |
| 723 | | | 0.23 |
| 725 | | | 0.45 |
| 727 | | | 0.43 |
| 728 | | | 0.38 |
| 729 | | | 0.33 |
| 730 | | | 0.054 |
| 731 | | | 0.087 |
| 732 | | | 0.010 |
| 736 | | | 0.013 |
| 739 | | | 0.005 |
| 740 | | | 0.037 |
| 742 | | | 0.168 |
| 744 | | | 0.031 |
| 745 | | | 0.01 |
| 746 | | | 0.035 |
| 747 | | | 0.088 |
| 748 | | | 0.372 |
| 749 | | | 0.017 |
| 750 | | | 0.005 |
| 751 | | | 0.025 |
| 752 | | | 0.221 |
| 753 | | | 0.656 |
| 755 | 0.21 | 1.9 | 0.270 |
| 761 | | | 0.175 |
| 762 | | | 0.111 |
| 764 | | | 0.061 |
| 768 | | | 0.013 |
| 771 | | | 0.173 |
| 773 | | | 0.028 |
| 774 | | | 0.003 |
| 776 | | | 0.107 |
| 779 | | | 0.045 |
| 781 | | | 0.038 |
| 782 | | | 0.015 |
| 783 | | | 0.301 |

TABLE 15-continued

BACE in vitro Assay Results

| ID No. | IC$_{50}$ μM (158) | IC$_{50}$ μM (159) | Ki μM (159) |
|---|---|---|---|
| 784 | | | 0.298 |
| 785 | | | 0.198 |
| 786 | | | 0.101 |
| 787 | | | 0.038 |
| 800 | 17 | | |

Example 160

BACE FS1% Inhibition Assay

The following reagents were used in this assay: sodium acetate, PEG8000 (Sigma), DMSO, HEPES, FS1 substrate [R(AedensE)EEVNLDAEFK-(DabcylK)R] (SEQ ID NO: 1), β-secretase(BACE) (Panvera), and 96-well plate (HE microplate, Molecular Devices).

The following assay buffers were prepared and used in this assay: (1) enzyme assay buffer (0.05 M sodium acetate, pH5, 0.1% PEG8000 (w/v)), (2) substrate assay buffer (0.05 M sodium acetate, pH5), and (3) compound vehicle (30% DMSO in 50 mM HEPES, pH 7.4).

The FS1-substrate stock solution was prepared in DMSO as a 10 mg/mL solution. The FS1-substrate working solution was prepared by diluting the 10 mg/mL stock solution with substrate assay buffer to a final concentration of 300 μg/mL. The β-secretase (BACE) working solution was prepared by diluting a 0.83 mg/mL BACE stock solution with enzyme assay buffer to a final concentration of 4 μg/mL.

Test compounds were dissolved in DMSO to 10 mM. Compounds were further diluted in vehicle to various concentrations in the range of 405 μM to 4.05 μM (13.5×final compound concentration in screening plate).

The screening procedure for this assay was as follows: 15 μL of BACE working solution was pipetted into each well of a 96-well plate. To each well was then pipetted 2 μL of test compound at the selected concentration. Test compound and BACE were then mixed with a pipettor and incubated for 20 min at room temperature. To each well was then added 10 μL of the FS1 substrate working solution. The plates were then incubated for 1 hour at room temperature. The fluorescence for each well was then measured on an LJL analyst (Ex 360 nm/Em 530 nm).

The procedure for the blank was as follows. 15 μL of assay buffer was pipetted into each well to be used as a blank control. To each well was then added 2 μL of vehicle and 10 μL of FS1-substrate working solution. The plates were then incubated for 1 hour at room temperature. The fluorescence was measured on an LJL analyst (Ex 360 nm/Em 530 nm).

The procedure for the positive control was as follows: 15 μL of BACE working solution was pipetted into each well to be used as a positive control. To each well was then pipetted 2 μL of vehicle. Vehicle and BACE were then mixed with a pipettor and incubated for 20 min at room temperature. To each well was then added 10 μL of the FS1 substrate working solution. The plates were then incubated for 1 hour at room temperature. The fluorescence (Fl) was then measured on an LJL analyst (Ex 360 nm/Em 530 nm).

For test compounds, % inhibition was determined at each concentration as follows:

$$\% \text{ Inhibition} = \frac{[Fl(\text{compound}) - Fl(\text{negative control})]}{[Fl(\text{positive control}) - Fl(\text{negative control})]}.$$

% Inhibition values of less than 30% were indistinguishable from control are listed as ≦30% in the Table below. % Inhibition values greater than 100% were indistinguishable from 100% within the error of the measurement.

Representative compounds of the present invention were tested according to procedure described in Example 160 above with results as listed in Table 16 below.

TABLE 16

| | % Inhibition (FS) | | | | |
|---|---|---|---|---|---|
| ID No. | 30 μM | 10 μM | 3 μM | 1 μM | 0.3 μM |
| 1 | 108 | 81 | 59 | <30 | <30 |
| 85 | | | 117 | 112 | 96 |
| 90 | | 124 | 106 | | |
| 91 | | 117 | 68 | | |
| 98 | | | 114 | 93 | 49 |
| 105 | | | <30 | <30 | <30 |
| 106 | | 114 | 103 | | |
| 110 | | | 84 | 30 | <30 |
| 114 | | 126 | 109 | | |
| 115 | | 105 | 40 | | |
| 116 | | 81 | 39 | | |
| 118 | | 91 | 48 | | |
| 119 | | 75 | 42 | | |
| 120 | | 34 | <30 | | |
| 121 | | 117 | 103 | | |
| 122 | | 123 | 101 | | |
| 123 | | 116 | 71 | | |
| 124 | | 67 | 56 | | |
| 125 | | 80 | 42 | | |
| 127 | | 102 | 79 | | |
| 128 | | 108 | 97 | | |
| 129 | | 113 | 113 | | |
| 130 | | 123 | 101 | | |
| 131 | | 130 | 115 | | |
| 132 | | 118 | 54 | | |
| 134 | | 104 | 70 | | |
| 135 | | 118 | 89 | | |
| 136 | | 133 | 85 | | |
| 137 | | 107 | 82 | | |
| 138 | | | 114 | 113 | 98 |
| 139 | | 61 | <30 | | |
| 140 | | 101 | 79 | | |
| 141 | | 102 | 100 | | |
| 142 | | 38 | <30 | | |
| 143 | | 32 | <30 | | |
| 144 | | 59 | 39 | | |
| 145 | | 37 | <30 | | |
| 146 | | 39 | <30 | | |
| 147 | | 71 | <30 | | |
| 148 | | | 114 | 62 | 35 |
| 149 | | | 111 | 71 | 32 |
| 150 | | | 90 | <30 | <30 |
| 151 | | 104 | 79 | | |
| 152 | | 107 | 85 | | |
| 154 | | 79 | 56 | | |
| 155 | | 49 | <30 | | |
| 156 | | 40 | <30 | | |
| 157 | | 50 | <30 | | |
| 158 | | | 60 | <30 | <30 |
| 158 | | | 79 | 53 | <30 |
| 159 | | | 92 | 65 | 34 |
| 160 | | | 102 | 78 | 51 |
| 161 | | <30 | <30 | | <30 |
| 162 | | <30 | <30 | | <30 |
| 163 | | <30 | 33 | | <30 |
| 164 | | 109 | 96 | | 67 |

TABLE 16-continued

% Inhibition (FS)

| ID No. | 30 μM | 10 μM | 3 μM | 1 μM | 0.3 μM |
|---|---|---|---|---|---|
| 165 | | | 101 | 72 | <30 |
| 166 | | | 74 | 37 | <30 |
| 167 | | | 113 | 112 | 100 |
| 167 | | | 118 | 110 | 91 |
| 168 | | | <30 | <30 | <30 |
| 169 | | | 109 | 104 | 80 |
| 170 | | | 67 | 49 | <30 |
| 171 | | | 42 | 31 | <30 |
| 172 | | | <30 | <30 | <30 |
| 173 | | | 76 | 53 | <30 |
| 174 | | | 111 | 106 | 85 |
| 175 | | | 37 | <30 | <30 |
| 176 | | | 111 | 97 | 66 |
| 177 | | | 102 | 80 | <30 |
| 178 | | | 107 | 93 | 50 |
| 179 | | | 85 | 54 | <30 |
| 180 | | | 77 | <30 | <30 |
| 181 | | | 32 | <30 | <30 |
| 182 | | | 38 | <30 | <30 |
| 183 | | | 106 | 93 | 48 |
| 184 | | | 31 | <30 | <30 |
| 187 | | | 39 | <30 | <30 |
| 188 | | | <30 | <30 | <30 |
| 189 | | | <30 | <30 | <30 |
| 190 | | | 101 | 86 | 51 |
| 191 | | | 88 | 46 | <30 |
| 192 | | | 110 | 92 | 38 |
| 193 | | | 67 | 34 | <30 |
| 194 | | | 38 | 42 | <30 |
| 195 | | | <30 | <30 | <30 |
| 196 | | | 120 | 96 | 65 |
| 197 | | | 32 | <30 | <30 |
| 198 | | | <30 | <30 | <30 |
| 199 | | | 82 | <30 | <30 |
| 200 | | | <30 | <30 | <30 |
| 201 | | | 66 | <30 | <30 |
| 202 | | | <30 | <30 | <30 |
| 204 | | | 107 | 66 | <30 |
| 204 | | | 115 | 97 | 54 |
| 205 | | | 90 | 47 | <30 |
| 206 | | | 106 | 62 | <30 |
| 207 | | | 108 | 90 | 48 |
| 208 | | | 67 | <30 | <30 |
| 209 | | | 103 | 58 | <30 |
| 210 | | | <30 | <30 | <30 |
| 211 | | | 68 | <30 | <30 |
| 212 | | | 32 | <30 | <30 |
| 213 | | | <30 | <30 | <30 |
| 214 | | | 101 | 70 | <30 |
| 215 | | | 106 | 71 | 39 |
| 216 | | | 91 | 45 | <30 |
| 217 | | | 56 | <30 | <30 |
| 218 | | | 114 | 101 | 75 |
| 219 | | | 108 | 85 | 51 |
| 220 | | | 102 | 72 | 103 |
| 221 | | | 118 | 115 | 100 |
| 221 | | | 121 | 119 | 110 |
| 222 | | | <30 | <30 | <30 |
| 223 | | | <30 | <30 | <30 |
| 224 | | | <30 | <30 | <30 |
| 226 | | | 54 | <30 | <30 |
| 227 | | | 116 | 109 | 86 |
| 228 | | | 40 | 49 | <30 |
| 229 | | | <30 | 35 | <30 |
| 230 | | | <30 | 33 | <30 |
| 231 | | | 75 | 71 | <30 |
| 232 | | | 31 | <30 | <30 |
| 233 | | | 36 | 32 | <30 |
| 234 | | | 43 | 57 | <30 |
| 235 | | | <30 | 46 | <30 |
| 236 | | | 49 | 37 | <30 |
| 257 | | | 111 | 105 | 67 |
| 258 | | | 72 | 46 | <30 |
| 259 | | | 97 | 66 | <30 |
| 260 | | | 112 | 86 | 53 |
| 261 | | | 110 | 87 | 51 |
| 262 | | | 95 | 63 | 39 |
| 263 | | | 92 | 60 | 20 |
| 264 | | | 92 | 63 | 26 |
| 265 | | | 92 | 55 | <30 |
| 266 | | | <30 | 34 | <30 |
| 267 | | | 38 | 39 | <30 |
| 268 | | | 71 | <30 | <30 |
| 286 | | | 36 | <30 | <30 |
| 290 | | | <30 | <30 | <30 |
| 292 | | | 83 | 49 | <30 |
| 293 | | | 81 | 44 | <30 |
| 294 | | | 118 | 109 | 94 |
| 295 | | | 116 | 106 | 79 |
| 297 | | | 109 | 76 | <30 |
| 298 | | | 110 | 75 | <30 |
| 299 | | | <30 | <30 | <30 |
| 300 | | | 77 | <30 | <30 |
| 301 | | | 106 | 82 | <30 |
| 302 | | | 108 | 72 | <30 |
| 303 | | | 109 | 70 | <30 |
| 304 | | | 100 | 46 | <30 |
| 306 | | | 46 | <30 | <30 |
| 307 | | | <30 | <30 | <30 |
| 310 | | | 57 | <30 | <30 |
| 311 | | | 118 | 108 | 74 |
| 312 | | | 115 | 103 | 74 |
| 313 | | | 31 | <30 | <30 |
| 314 | | | 85 | 45 | <30 |
| 315 | | | 33 | <30 | <30 |
| 316 | | | <30 | <30 | <30 |
| 320 | | | <30 | <30 | −31 |
| 321 | | | <30 | <30 | −33 |
| 322 | | | 95 | <30 | <30 |
| 323 | | | 45 | <30 | <30 |
| 324 | | | 87 | 55 | <30 |
| 325 | | | 110 | 86 | <30 |
| 326 | | | 79 | 35 | <30 |
| 327 | | | 48 | <30 | <30 |
| 328 | | | 92 | 61 | <30 |
| 329 | | | 118 | 109 | 92 |
| 330 | | | 114 | 66 | <30 |
| 331 | | | 108 | 60 | <30 |
| 332 | | | <30 | <30 | <30 |
| 333 | | | 78 | <30 | <30 |
| 334 | | | 118 | 103 | 74 |
| 395 | | | 118 | 107 | 69 |
| 398 | | | <30 | <30 | <30 |
| 400 | | | 94 | <30 | <30 |
| 401 | | | 52 | <30 | <30 |
| 402 | | | 99 | 53 | <30 |
| 403 | | | 66 | <30 | <30 |
| 404 | | | 67 | 32 | <30 |
| 405 | | | 118 | 106 | 43 |
| 406 | | | 50 | <30 | <30 |
| 407 | | | 48 | <30 | <30 |
| 408 | | | 95 | 34 | <30 |
| 409 | | | 72 | <30 | <30 |
| 410 | | | 50 | 39 | <30 |
| 411 | | | 55 | <30 | <30 |
| 412 | | | 49 | <30 | <30 |
| 413 | | | 53 | <30 | <30 |
| 414 | | | 27 | <30 | <30 |
| 415 | | | 63 | <30 | <30 |
| 416 | | | −3 | <30 | <30 |
| 417 | | | 78 | <30 | <30 |
| 418 | | | 119 | 89 | 54 |
| 419 | | | 109 | 64 | 38 |
| 420 | | | 53 | <30 | <30 |
| 421 | | | 111 | 71 | <30 |
| 424 | | | 94 | 50 | <30 |
| 425 | | | 111 | 85 | 46 |
| 426 | | | 86 | 34 | <30 |
| 427 | | | 62 | 26 | <30 |
| 428 | | | 98 | 60 | <30 |
| 429 | | | <30 | <30 | <30 |
| 432 | | | 84 | 41 | <30 |

TABLE 16-continued

| ID No. | 30 μM | 10 μM | 3 μM | 1 μM | 0.3 μM |
|---|---|---|---|---|---|
| 433 | | | 88 | 33 | <30 |
| 434 | | | <30 | <30 | <30 |
| 435 | | | 85 | <30 | <30 |
| 436 | | | 50 | 37 | <30 |
| 437 | | | 38 | <30 | <30 |
| 438 | | | <30 | <30 | <30 |
| 439 | | | <30 | <30 | <30 |
| 440 | | | 72 | 35 | <30 |
| 441 | | | 48 | 29 | <30 |
| 442 | | | 101 | 58 | <30 |
| 443 | | | 67 | 39 | <30 |
| 444 | | | 30 | <30 | <30 |
| 450 | | | 121 | 112 | 97 |
| 451 | | | <30 | <30 | <30 |
| 452 | | | 78 | 42 | <30 |
| 463 | | | <30 | <30 | <30 |
| 465 | | | <30 | <30 | <30 |
| 466 | | | 53 | <30 | <30 |
| 467 | | | <30 | <30 | <30 |
| 468 | | | <30 | <30 | <30 |
| 469 | | | <30 | <30 | <30 |
| 470 | | | 31 | <30 | <30 |
| 471 | | | 38 | <30 | <30 |
| 472 | | | <30 | <30 | <30 |
| 473 | | | <30 | <30 | <30 |
| 474 | | | <30 | <30 | <30 |
| 475 | | | <30 | <30 | <30 |
| 476 | | | 102 | 66 | 19.86 |
| 477 | | | <30 | <30 | <30 |
| 478 | | | 46 | <30 | <30 |
| 479 | | | 81 | <30 | <30 |
| 480 | | | 38 | <30 | <30 |
| 481 | | | 32 | <30 | <30 |
| 482 | | | 43 | <30 | <30 |
| 483 | | | <30 | <30 | <30 |
| 484 | | | 62 | <30 | <30 |
| 485 | | | 123 | 112 | 100 |
| 486 | | | <30 | <30 | <30 |
| 487 | | | 93 | 44 | 38 |
| 487 | | | 95 | 32 | <30 |
| 488 | | | <30 | <30 | <30 |
| 490 | | | <30 | <30 | <30 |
| 491 | | | 44 | <30 | <30 |
| 491 | | | <30 | <30 | <30 |
| 493 | | | 49 | <30 | <30 |
| 494 | | | <30 | <30 | <30 |
| 495 | | | 106 | 75 | <30 |
| 499 | | | <30 | <30 | <30 |
| 503 | | | 90 | <30 | <30 |
| 504 | | | 96 | 31 | <30 |
| 506 | | | 128 | 115 | 106 |
| 508 | | | 113 | 74 | 31 |
| 509 | | | 41 | <30 | <30 |
| 510 | | | 37 | <30 | <30 |
| 511 | | | 113 | 85 | 34 |
| 512 | | | 51 | <30 | <30 |
| 513 | | | <30 | <30 | <30 |
| 514 | | | <30 | <30 | <30 |
| 515 | | | 110 | 66 | 41 |
| 516 | | | <30 | <30 | <30 |
| 517 | | | 40 | <30 | <30 |
| 518 | | | <30 | <30 | <30 |
| 519 | | | <30 | <30 | <30 |
| 520 | | | 33 | <30 | <30 |
| 521 | | | <30 | <30 | <30 |
| 522 | | | 79 | <30 | <30 |
| 523 | | | 58 | <30 | <30 |
| 524 | | | 44 | <30 | <30 |
| 525 | | | 70 | <30 | <30 |
| 526 | | | 98 | 36 | <30 |
| 527 | | | 51 | <30 | <30 |
| 528 | | | 41 | <30 | <30 |
| 529 | | | 66 | <30 | <30 |
| 530 | | | 118 | 80 | <30 |
| 532 | | | 68 | <30 | <30 |
| 534 | | | 126 | 103 | 54 |
| 535 | | | 116 | 86 | 57 |
| 536 | | | 118 | 83 | 61 |
| 537 | | | 125 | 106 | 83 |
| 538 | | | 100 | 53 | <30 |
| 539 | | | <30 | <30 | <30 |
| 540 | | | 84 | 30 | <30 |
| 541 | | | <30 | <30 | <30 |
| 542 | | | 73 | <30 | <30 |
| 543 | | | <30 | <30 | <30 |
| 544 | | | 51 | <30 | 32 |
| 545 | | | 118 | 77 | 55 |
| 549 | | | 71 | 30 | <30 |
| 550 | | | 67 | <30 | <30 |
| 551 | | | <30 | <30 | <30 |
| 552 | | | 36 | <30 | <30 |
| 553 | | | 49 | <30 | <30 |
| 554 | | | 42 | <30 | <30 |
| 555 | | | 46 | <30 | <30 |
| 556 | | | 126 | 118 | 103 |
| 557 | | | <30 | <30 | <30 |
| 558 | | | 115 | 92 | 42 |
| 559 | | | <30 | <30 | <30 |
| 561 | | | 125 | 118 | 114 |
| 562 | | | 128 | 118 | 106 |
| 563 | | | 127 | 119 | 101 |
| 564 | | | 129 | 119 | 112 |
| 567 | | | <30 | <30 | <30 |
| 568 | | | <30 | <30 | <30 |
| 569 | | | <30 | <30 | <30 |
| 570 | | | <30 | <30 | <30 |
| 571 | | | <30 | <30 | <30 |
| 573 | | | <30 | <30 | <30 |
| 574 | | | <30 | <30 | <30 |
| 575 | | | <30 | <30 | <30 |
| 576 | | | <30 | <30 | <30 |
| 577 | | | <30 | <30 | <30 |
| 578 | | | <30 | <30 | <30 |
| 578 | | | 97 | 64 | 31 |
| 580 | | | <30 | <30 | <30 |
| 582 | | | <30 | <30 | <30 |
| 583 | | | 86 | 56 | 40 |
| 584 | | | 56 | <30 | <30 |
| 586 | | | 59 | <30 | <30 |
| 587 | | | <30 | <30 | <30 |
| 588 | | | <30 | <30 | <30 |
| 589 | | | <30 | <30 | <30 |
| 590 | | | <30 | <30 | <30 |
| 591 | | | <30 | <30 | <30 |
| 592 | | | <30 | <30 | <30 |
| 593 | | | <30 | <30 | <30 |
| 594 | | | <30 | <30 | <30 |
| 595 | | | 104 | 70 | 32 |
| 596 | | | <30 | <30 | <30 |
| 598 | | | 36 | <30 | <30 |
| 599 | | | 65 | <30 | <30 |
| 600 | | | 41 | <30 | <30 |
| 601 | | | 121 | 115 | 105 |
| 602 | | | 121 | 113 | 78 |
| 603 | | | 122 | 114 | 101 |
| 605 | | | 111 | 72 | 47 |
| 606 | | | 56 | <30 | <30 |
| 607 | | | 123 | 116 | 94 |
| 610 | | | 119 | 106 | 75 |
| 611 | | | <30 | 36 | <30 |
| 612 | | | <30 | 34 | <30 |
| 613 | | | <30 | 31 | 36 |
| 614 | | | <30 | <30 | <30 |
| 615 | | | <30 | <30 | <30 |
| 616 | | | <30 | <30 | <30 |
| 617 | | | 41 | 34 | <30 |
| 618 | | | 104 | 70 | <30 |
| 619 | | | 125 | 118 | 119 |
| 620 | | | 37 | <30 | <30 |
| 623 | | | 82 | <30 | <30 |
| 624 | | | 78 | 38 | <30 |
| 625 | | | 95 | 54 | <30 |

TABLE 16-continued

% Inhibition (FS)

| ID No. | 30 μM | 10 μM | 3 μM | 1 μM | 0.3 μM |
|---|---|---|---|---|---|
| 626 | | | 56 | <30 | <30 |
| 627 | | | 105 | 75 | 39 |
| 628 | | | 32 | <30 | <30 |
| 629 | | | 102 | 72 | <30 |
| 630 | | | 48 | <30 | <30 |
| 631 | | | 48 | <30 | <30 |
| 632 | | | 117 | 118 | 115 |
| 633 | | | 70 | 30 | <30 |
| 634 | | | 114 | 88 | 46 |
| 635 | | | 119 | 115 | 104 |
| 636 | | | 30 | <30 | <30 |
| 637 | | | 73 | <30 | <30 |
| 638 | | | 116 | 101 | 74 |
| 639 | | | 48 | <30 | <30 |
| 640 | | | <30 | <30 | <30 |
| 641 | | | 48 | <30 | <30 |
| 642 | | | 96 | 63 | 37 |
| 643 | | | 110 | 92 | 74 |
| 644 | | | 104 | 72 | 46 |
| 645 | | | 91 | 57 | 67 |
| 646 | | | 97 | 72 | 52 |
| 647 | | | 113 | 100 | 79 |
| 648 | | | 104 | 74 | 39 |
| 649 | | | 95 | 65 | 34 |
| 650 | | | 112 | 94 | 72 |
| 651 | | | 96 | 51 | <30 |
| 652 | | | 91 | 63 | 31 |
| 653 | | | 101 | 82 | 46 |
| 654 | | | 111 | 102 | 83 |
| 655 | | | 104 | 79 | 45 |
| 656 | | | 104 | 87 | 56 |
| 657 | | | 111 | 103 | 88 |
| 658 | | | 100 | 62 | <30 |
| 659 | | | 100 | 69 | 43 |
| 660 | | | 105 | 86 | 63 |
| 661 | | | 106 | 98 | 68 |
| 662 | | | 109 | 97 | 66 |
| 663 | | | <30 | <30 | <30 |
| 664 | | | <30 | <30 | <30 |
| 665 | | | <30 | <30 | 35 |
| 666 | | | <30 | <30 | 37 |
| 667 | | | <30 | <30 | 33 |
| 668 | | | <30 | <30 | <30 |
| 669 | | | 32 | <30 | <30 |
| 670 | | | 44 | <30 | <30 |
| 671 | | | <30 | 30 | <30 |
| 672 | | | <30 | <30 | <30 |
| 673 | | | <30 | <30 | 34 |
| 674 | | | 41 | <30 | 36 |
| 675 | | | <30 | <30 | 35 |
| 676 | | | 44 | <30 | 33 |
| 678 | | | 99 | 88 | 51 |
| 679 | | | 103 | 99 | 78 |
| 680 | | | 90 | 75 | 42 |
| 681 | | | 103 | 100 | 67 |
| 682 | | | 97 | 77 | 39 |
| 683 | | | 102 | 86 | 64 |
| 684 | | | 78 | 38 | 33 |
| 685 | | | 101 | 90 | 50 |
| 686 | | | 80 | 73 | <30 |
| 687 | | | 87 | 50 | <30 |
| 688 | | | 81 | 36 | <30 |
| 689 | | | 102 | 82 | 33 |
| 690 | | | 52 | <30 | <30 |
| 691 | | | 51 | <30 | <30 |
| 692 | | | 116 | 90 | 46 |
| 693 | | | 109 | 83 | 47 |
| 694 | | | 84 | <30 | <30 |
| 695 | | | 54 | <30 | <30 |
| 696 | | | 104 | 72 | <30 |
| 697 | | | 63 | <30 | <30 |
| 698 | | | 64 | <30 | <30 |
| 699 | | | 93 | 64 | 31 |
| 700 | | | 85 | 36 | <30 |
| 701 | | | 54 | <30 | <30 |
| 702 | | | <30 | <30 | <30 |
| 703 | | | 83 | 46 | <30 |
| 704 | | | <30 | <30 | <30 |
| 705 | | | <30 | <30 | <30 |
| 706 | | | <30 | <30 | <30 |
| 707 | | | <30 | <30 | <30 |
| 709 | | | 139 | 143 | 141 |
| 710 | | | 126 | 68 | <30 |
| 711 | | | 113 | 43 | <30 |
| 712 | | | 134 | 104 | 39 |
| 714 | | | 138 | 126 | 100 |
| 714 | | | 138 | 129 | 98 |
| 716 | | | 72 | <30 | <30 |
| 717 | | | 72 | 39 | 33 |
| 718 | | | 114 | 30 | <30 |
| 719 | | | 81 | <30 | 31 |
| 720 | | | 138 | 93 | 72 |
| 721 | | | 127 | 66 | 60 |
| 722 | | | 78 | 35 | 35 |
| 723 | | | 111 | 63 | 47 |
| 724 | | | 65 | <30 | 38 |
| 725 | | | 126 | 74 | 33 |
| 726 | | | 46 | <30 | <30 |
| 727 | | | 137 | 80 | 46 |
| 728 | | | 97 | 58 | 43 |
| 729 | | | 100 | 61 | 33 |
| 730 | | | 114 | 109 | 93 |
| 731 | | | 132 | 114 | 56 |
| 732 | | | 133 | 135 | 135 |
| 736 | | | 135 | 134 | 125 |
| 737 | | | 97 | 34 | 22 |
| 738 | | | 61 | 28 | 14 |
| 739 | | | 105 | 104 | 99 |
| 740 | | | 104 | 98 | 82 |
| 741 | | | −25 | −38 | −48 |
| 742 | | | 101 | 63 | 17 |
| 743 | | | 130 | 125 | 107 |
| 744 | | | 112 | 108 | 91 |
| 745 | | | 114 | 114 | 115 |
| 746 | | | 112 | 104 | 85 |
| 747 | | | 104 | 74 | 41 |
| 748 | | | 97 | 71 | 20 |
| 749 | | | 115 | 112 | 113 |
| 750 | | | 116 | 114 | 115 |
| 751 | | | 116 | 112 | 112 |
| 752 | | | 109 | 81 | 45 |
| 753 | | | 93 | 47 | 13 |
| 754 | | | 89 | 35 | 8 |
| 755 | | 79 | 59 | | |
| 760 | | | 89 | 44 | <30 |
| 761 | | | 112 | 91 | 51 |
| 762 | | | 113 | 102 | 74 |
| 763 | | | 109 | 84 | <30 |
| 764 | | | 116 | 110 | 87 |
| 765 | | | 97 | 56 | <30 |
| 766 | | | <30 | <30 | <30 |
| 767 | | | 106 | 71 | <30 |
| 768 | | | 126 | 120 | 122 |
| 769 | | | 107 | 61 | <30 |
| 770 | | | <30 | <30 | <30 |
| 771 | | | 105 | 79 | 46 |
| 773 | | | 119 | 111 | 102 |
| 774 | | | 124 | 120 | 122 |
| 775 | | | 111 | 62 | <30 |
| 776 | | | 117 | 95 | 41 |
| 777 | | | 123 | 97 | 38 |
| 778 | | | 113 | 77 | <30 |
| 779 | | | 120 | 107 | 102 |
| 780 | | | 109 | 97 | 69 |
| 781 | | | 121 | 109 | 106 |
| 782 | | | 113 | 107 | 104 |
| 783 | | | 121 | 110 | 109 |
| 784 | | | 120 | 108 | 107 |
| 785 | | | 107 | 91 | 71 |
| 786 | | | 114 | 105 | 97 |
| 787 | | | 121 | 109 | 108 |
| 788 | | | 118 | 114 | 110 |

TABLE 16-continued

| | | % Inhibition (FS) | | |
|---|---|---|---|---|
| ID No. | 30 µM | 10 µM | 3 µM | 1 µM | 0.3 µM |
| 789 | | | 106 | 99 | 80 |
| 801 | | | <30 | <30 | <30 |
| 802 | | | 50 | <30 | <30 |
| 803 | | | <30 | <30 | <30 |
| 804 | | | <30 | <30 | <30 |
| 805 | | | <30 | <30 | <30 |
| 806 | | | <30 | <30 | <30 |
| 807 | | | <30 | <30 | <30 |
| 808 | | | <30 | <30 | <30 |
| 809 | | | 32 | <30 | <30 |
| 810 | | | <30 | <30 | <30 |
| 811 | | | <30 | <30 | <30 |

Example 161

BACE % Inhibition Assay

The following reagents were used in this assay: sodium acetate, PEG8000 (Sigma), DMSO, HEPES, (Aedens)-EVNLDAEF-(Dabcyl K-amide) (SEQ ID NO: 2) substrate, β-secretase(BACE) (Panvera), and 96-well plate (HE microplate, Molecular Devices).

The following assay buffers were prepared and used in this assay: (1) enzyme assay buffer (0.05 M sodium acetate, pH5, 0.1% PEG8000 (w/v)), (2) substrate assay buffer (0.05 M sodium acetate, pH5), and (3) compound vehicle (30% DMSO in 50 mM HEPES, pH 7.4).

The substrate stock solution was prepared in DMSO as a 10 mg/mL solution. The substrate working solution was prepared by diluting the 10 mg/mL stock solution with substrate assay buffer to a final concentration of 300 µg/mL. The β-secretase (BACE) working solution was prepared by diluting a 0.83 mg/mL BACE stock solution with enzyme assay buffer to a final concentration of 4 µg/mL.

Test compounds were dissolved in DMSO to 10 mM. Compounds were further diluted in vehicle to various concentrations in the range of 405 µM to 4.05 µM (13.5×final compound concentration in screening plate).

The screening procedure for this assay was as follows: 15 µL of BACE working solution was pipetted into each well of a 96-well plate. To each well was then pipetted 2 µL of test compound at the selected concentration. Test compound and BACE were then mixed with a pipettor and incubated for 20 min at room temperature. To each well was then added 10 µL of the substrate working solution. The plates were then incubated for 1 hour at room temperature. The fluorescence for each well was then measured on an LJL analyst (Ex 360 nm/Em 530 nm).

The procedure for the blank was as follows. 15 µL of assay buffer was pipetted into each well to be used as a blank control. To each well was then added 2 µL of vehicle and 10 µL of substrate working solution. The plates were then incubated for 1 hour at room temperature. The fluorescence was measured on an LJL analyst (Ex 360 nm/Em 530 nm).

The procedure for the positive control was as follows: 15 µl of BACE working solution was pipetted into each well to be used as a positive control. To each well was then pipetted 2 µL of vehicle. Vehicle and BACE were then mixed with a pipettor and incubated for 20 min at room temperature. To each well was then added 10 µL of the substrate working solution. The plates were then incubated for 1 hour at room temperature. The fluorescence (Fl) was then measure on an LJL analyst (Ex 360 nm/Em 530 nm).

For test compounds, % inhibition was determined at each concentration as follows:

$$\% \text{ Inhibition} = \frac{[Fl(\text{compound}) - Fl(\text{negative control})]}{[Fl(\text{positive control}) - Fl(\text{negative control})]}$$

% Inhibition values of less than 30% were indistinguishable from control are listed as ≦30% in the Table below.

Representative compounds of the present invention were tested according procedure described in Example 161 above with results as listed in Table 17 below. The % error in the measurements was ±10%.

TABLE 17

| | | % Inhibition | | | |
|---|---|---|---|---|---|
| ID No. | 30 µM | 10 µM | 3 µM | 1 µM | 0.3 µM |
| 1 | 61 | 44 | 24 | | |
| 1 | | 61 | 38 | 31 | <30 |
| 7 | | 87 | 76 | | |
| 15 | | 69 | 42 | | |
| 19 | | 92 | 67 | | |
| 20 | | 83 | 68 | | |
| 23 | | 76 | 47 | | |
| 27 | | 81 | 63 | | |
| 30 | | 48 | 32 | | |
| 44 | | 31 | <30 | | |
| 46 | | 82 | 66 | | |
| 49 | | 90 | 56 | | |
| 50 | | 34 | <30 | | |
| 51 | | 56 | <30 | | |
| 53 | | 82 | 34 | | |
| 55 | | 95 | 62 | | |
| 56 | | 79 | 35 | | |
| 61 | | 87 | 75 | | |
| 62 | | 82 | 62 | | |
| 62 | | 82 | 73 | | |
| 65 | | <30 | <30 | | |
| 67 | | 71 | 44 | | |
| 72 | | <30 | <30 | | |
| 77 | | <30 | <30 | | |
| 79 | | <30 | <30 | | |
| 80 | | 80 | 61 | | |
| 81 | | <30 | <30 | | |
| 84 | | 63 | 38 | | |
| 85 | | 93 | 81 | | |
| 86 | | 80 | 72 | | |
| 87 | | <30 | <30 | | |
| 88 | | <30 | <30 | | |
| 89 | | 81 | 77 | | |
| 93 | | <30 | <30 | | |
| 94 | | <30 | <30 | | |
| 97 | | 53 | <30 | | |
| 98 | | 99 | 76 | | |
| 100 | | <30 | <30 | | |
| 101 | | 64 | 45 | | |
| 103 | | 74 | 56 | | |
| 105 | | <30 | <30 | | |
| 107 | | 78 | 48 | | |
| 108 | | 90 | 73 | | |
| 109 | | 58 | <30 | | |
| 110 | | 96 | 75 | | |
| 111 | | 94 | 84 | | |
| 111 | | | 115 | 96 | 63 |
| 112 | 92 | 88 | | | |
| 317 | | 107 | 66 | <30 | |
| 318 | | 103 | 70 | 32 | |
| 319 | | 120 | 95 | 61 | |
| 336 | | <30 | <30 | <30 | |
| 337 | | <30 | <30 | <30 | |
| 338 | | <30 | <30 | <30 | |
| 339 | | <30 | <30 | <30 | |
| 341 | | 72 | <30 | <30 | |
| 342 | | 119 | 93 | 50 | |
| 343 | | 118 | 101 | 81 | |

TABLE 17-continued

| | % Inhibition | | | |
|---|---|---|---|---|
| ID No. | 30 μM | 10 μM | 3 μM | 1 μM | 0.3 μM |
| 346 | | | 126 | 121 | 110 |
| 346 | | | 123 | 122 | 115 |
| 365 | | | 113 | 86 | <30 |
| 366 | | | 119 | 113 | 64 |
| 367 | | | 111 | 80 | <30 |
| 386 | | | 122 | 112 | 80 |
| 386 | | | 107 | 53 | <30 |
| 388 | | | 119 | 119 | 107 |
| 389 | | | 120 | 112 | 85 |
| 390 | | | 102 | 50 | <30 |
| 391 | | | 115 | 93 | 35 |
| 392 | | | 120 | 116 | 75 |
| 393 | | | 113 | 52 | <30 |

Example 162

BACE Assay (CEREP)

This assay was run by CEREP (Catalog Ref. 761-B, Reffered to SOP No. 1C131; ERMOLIEFF, J., LOY, J. A., KOELSCH, G. and TANG, J., Proteolytic activation of recombinant pro-memapsin 2 (pro-β-secretase) studied with new fluorogenic substrates, Biochemistry, (2000) Vol. 39, p. 12450).

More specifically the assay, run at 50 μL in a 96 well plate, evaluated the effect of test compound on the activity of the human BACE-1 quantified by measuring the formation of Mca-S-E-V-N-L-NH$_2$ (SEQ ID NO: 3) from Mca-S-E-V-N-L-D-A-E-F-R-K(Dnp)-R-R-NH$_2$ (SEQ ID NO: 4), using a recombinant enzyme.

The test compound, reference compound or water (control) were added to a buffer containing 0.09 M sodium acetate (pH 4.5) and 0.25 μg BACE-1. Compound interference with the fluorimetric detection method due to autofluorescence was then checked by measurements at the wavelengths defined to evaluate the enzyme activity. Thereafter, the reaction was initiated by adding 7.5 μM of the substrate Mca-S-E-V-N-L-D-A-E-F-R-K(Dnp)-R-R-NH$_2$ (SEQ ID NO: 4) and the mixture was incubated for 60 mm at 37° C. For control basal measurement, the substrate was omitted from the reaction mixture. Immediately after the incubation, the fluorescence intensity emitted by the reaction product Mca-S-E-V-N-L-NH$_2$ (SEQ ID NO: 3) was measured at λex=320 nm and λem=405 nm using a microplate reader (Ultra, Tecan). The standard inhibitory reference compound was OM99-2, which was tested in each experiment at several concentrations to obtain an inhibition curve from which its IC$_{50}$ value was calculated.

Representative compounds of the present invention were tested according to procedure described in Example 162 above with results as listed in Table 18 below.

TABLE 18

| | % Inhibition and IC$_{50}$ | | |
|---|---|---|---|
| ID No. | 1 μM | 0.3 μM | IC$_{50}$ (μM) |
| 62 | | | 0.38 |
| 154 | | | >1.0 |
| 346 | 99 | | 0.18 |
| 788 | | 97 | 0.16 |
| 789 | | 94 | 0.078 |
| 790 | | 98 | 0.093 |
| 795 | | 98 | 0.15 |
| 796 | | 97 | 0.19 |
| 797 | | 95 | 0.12 |
| 798 | | 95 | 0.074 |

Example 163

As a specific embodiment of an oral composition, 100 mg of the Compound #346, prepared as in Example 22 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of formula (I)

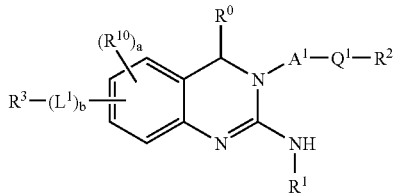

wherein
$R^0$ is selected from the group consisting of hydrogen, methyl, and $CF_3$;
$R^1$ is selected from the group consisting of hydrogen, hydroxy, methyl, ethyl, trifluoromethyl, 2,2,2-trifluoroethyl, methoxy, ethoxy and methyl-carbonyl;
$A^1$ is selected from the group consisting of $C_{1-4}$alkyl; wherein the $C_{1-4}$alkyl is optionally substituted with one or more $R^X$ substituents;
wherein each $R^X$ is independently selected from the group consisting of hydroxy, oxo, $C_{1-8}$alkyl, $C_{1-8}$alkoxy, hydroxy substituted $C_{1-6}$alkyl, amino substituted $C_{1-6}$alkyl, cycloalkyl, cycloalkyl-$C_{1-4}$alkyl-, biphenyl, aryl, $C_{1-4}$aralkyl, heteroaryl, heteroaryl-$C_{1-4}$alkyl-, heterocycloalkyl, heterocycloalkyl-$C_{1-4}$alkyl-, spiro-heterocyclyl and —$(C_{1-4}$alkyl$)_n$-$Q^2$-$R^4$;
wherein the $R^X$ cycloalkyl, aryl, heteroaryl, heterocycloalkyl or spiro-heterocyclyl group, whether alone or as part of a substituent group is optionally substituted with one or more substituents independently selected from the group consisting of fluoro, chloro, hydroxy, oxo, carboxy, $C_{1-4}$alkyl, $C_{1-4}$alkoxy, —C(O)O—($C_{1-4}$alkyl), hydroxy substituted $C_{1-4}$alkyl, fluoro substituted $C_{1-4}$alkyl, fluoro substituted $C_{1-4}$alkoxy, 5-tetrazolyl and 1-(1,4-dihydro-tetrazol-5-one);
wherein n is an integer from 0 to 1;
wherein $Q^2$ is selected from the group consisting of —O—, —S—, —C(O)—, —C(S)—, —C(O)O—, —OC(O)—, —$NR^G$—, —$NR^G$—C(O)—, —C(O)—$NR^G$—, —$NR^G$—$SO_2$—, —$SO_2$—$NR^G$—, —$NR^G$—SO—, —SO—$NR^G$, —$NR^G$C(O)O—, —OC(O)—$NR^G$—, —O—$SO_2$—$NR^G$—, —$NR^G$—$SO_2$—O—, —$NR^G$—C(O)—$NR^H$—, —$NR^G$—C(S)—$NR^H$— and —$NR^G$—$SO_2$—$NR^H$—;
wherein each $R^G$ and $R^H$ is independently selected from the group consisting of hydrogen, $C_{1-8}$alkyl, hydroxy substituted $C_{1-4}$alkyl, $C_{1-4}$aralkyloxy substituted $C_{1-4}$alkyl, cycloalkyl, aryl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;
wherein the independently selected $R^G$ and $R^H$ cycloalkyl aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, $C_{1-4}$alkyl, $C_{1-4}$alkoxy, $C_{1-4}$alkoxy-carbonyl, nitro, cyano, amino, $C_{1-4}$alkylamino, di($C_{1-4}$alkyl)amino, —$SO_2$—N($R^J R^K$), 5-tetrazolyl and 1-(1,4-dihydro-tetrazol-5-one);
wherein each $R^J$ and $R^K$ is independently selected from the group consisting of hydrogen and $C_{1-4}$alkyl;

wherein $R^4$ is selected from the group consisting of hydrogen, $C_{1-4}$alkyl, hydroxy substituted $C_{1-4}$alkyl, fluoro substituted $C_{1-4}$alkyl, cycloalkyl, aryl, biphenyl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;
wherein the $R^4$ cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, —C(O)O—$C_{1-4}$alkyl, —C(O)—$C_{1-4}$alkyl, $C_{1-4}$alkyl, fluoro substituted $C_{1-4}$alkyl, $C_{1-4}$alkoxy, nitro, cyano, amino, $C_{1-4}$alkylamino, di($C_{1-4}$alkyl)amino and phenyl;
wherein the phenyl is optionally substituted with one or more substituent independently selected from the group consisting of halogen, hydroxy, oxo, carboxy, C(O)O—$C_{1-4}$alkyl, C(O)—$C_{1-4}$alkyl, $C_{1-4}$alkyl, fluoro substituted $C_{1-4}$alkyl, $C_{1-4}$alkoxy, nitro, cyano, amino, $C_{1-4}$alkylamino, di($C_{1-4}$alkyl)amino and —$SO_2$—N($R^E R^F$);
wherein each $R^E$ and $R^F$ is independently selected from the group consisting of hydrogen and $C_{1-4}$alkyl;
$Q^1$ is selected from the group consisting of —O—, —S—, —C(O)—, —C(S)—, —C(O)O—, —OC(O)—, —$NR^A$—, —$NR^A$—C(O)—, —C(O)—$NR^A$—, —$NR^A$C(S)—, —C(S)—$NR^A$—, —$NR^A$—$SO_2$—, —$SO_2$—$NR^A$—, —$NR^A$—SO—, —SO—$NR^A$, —$NR^A$—C(O)O—, —OC(O)—$NR^A$—, —O—$SO_2NR^A$—, —$NR^A$—$SO_2$—O—, —$NR^A$—C(O)—$NR^B$—, —$NR^A$—C(S)—$NR^B$— and —$NR^A SO_2$—$NR^B$—;
wherein each $R^A$ and $R^B$ is independently selected from the group consisting of hydrogen, $C_{1-8}$alkyl, hydroxy substituted $C_{1-4}$alkyl, $C_{1-4}$aralkyloxy substituted $C_{1-4}$alkyl, cycloalkyl, aryl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl and spiro-heterocyclyl;
wherein the independently selected $R^A$ and $R^B$ cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, $C_{1-4}$alkyl, $C_{1-4}$alkoxy, $C_{1-4}$alkoxy-carbonyl, nitro, cyano, amino, $C_{1-4}$alkylamino, di($C_{1-4}$alkyl)amino, —$SO_2$—N($R^C R^D$), 5-tetrazolyl and 1-(1,4-dihydro-tetrazol-5-one);
wherein each $R^C$ and $R^D$ is independently selected from the group consisting of hydrogen and $C_{1-4}$alkyl;
$R^2$ is selected from the group consisting of $C_{1-10}$alkyl, cycloalkyl, aryl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;
wherein the $R^2$ $C_{1-10}$alkyl, cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, —C(O)—$C_{1-4}$alkyl, —C(O)—$C_{1-4}$aralkyl, —C(O)O—$C_{1-4}$alkyl, —C(O)O—$C_{1-4}$aralkyl, —$C_{1-4}$alkyl-C(O)O—$C_{1-4}$alkyl, —$C_{1-4}$alkyl-S—$C_{1-4}$alkyl, —C(O)—N($R^L R^M$), —$C_{1-4}$alkyl-C(O)—N($R^L R^M$), —$NR^L$—C(O) $C_{1-4}$alkyl, —$SO_2$—N($R^L R^M$), —$C_{1-4}$alkyl-$SO_2$—N($R^L R^M$), $C_{1-6}$alkyl, fluoro substituted $C_{1-4}$alkyl, hydroxy substituted $C_{1-4}$alkyl, carboxy substituted $C_{1-4}$alkyl, $C_{1-4}$alkoxy, —O—$C_{1-4}$aralkyl, —O-(tetrahydropyranyl), —NH—C(O)—O—$CH_2$-(tetrahydropyranyl), —N($CH_3$)—C(O)O—$CH_2$-(tetrahydropyranyl), nitro, cyano, amino, $C_{1-4}$alkylamino, di($C_{1-4}$alkyl)amino, phenyl, 5-tetrazolyl and 1-(1,4-dihydro-tetrazol-5-one);

wherein the phenyl or tetrahydropyranyl is optionally substituted with one or more substituent independently selected from the group consisting of halogen, hydroxy, oxo, carboxy, —C(O)O—$C_{1-4}$alkyl, —C(O)—$C_{1-4}$alkyl, —O—C(O)—$C_{1-4}$alkyl, —$C_{1-4}$alkyl-OC(O)—$C_{1-4}$alkyl, —O—$C_{1-4}$aralkyl, $C_{1-4}$alkyl, fluoro substituted $C_{1-4}$alkyl, hydroxy substituted $C_{1-4}$alkyl, $C_{1-4}$alkoxy, nitro, cyano, amino, $C_{1-4}$alkylamino and di($C_{1-4}$alkyl)amino;

wherein each $R^L$ and $R^M$ is independently selected from the group consisting of hydrogen and $C_{1-4}$alkyl;

b is an integer from 0 to 1;

$L^1$ is selected from the group consisting of —O—, —$S(O)_{0-2}$—, —$NR^N$—, —C(O)—, —C(S)—, —$C_{1-4}$alkyl-, -(hydroxy substituted $C_{1-4}$alkyl)- and —($C_{2-4}$alkenyl)-;

wherein $R^N$ is selected from the group consisting of hydrogen and $C_{1-4}$alkyl;

$R^3$ is selected from the group consisting of $C_{2-6}$alkenyl, cycloalkyl, partially unsaturated carbocyclyl, aryl, biphenyl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;

wherein the $R^3$ cycloalkyl, partially unsaturated carbocyclyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, $C_{1-4}$alkyl, hydroxy substituted $C_{1-4}$alkyl, halogen substituted $C_{1-4}$alkyl, cyano substituted $C_{1-4}$alkyl, $C_{2-4}$alkenyl, $C_{2-4}$alkynyl, halogen substituted $C_{1-4}$alkoxy, nitro, cyano, —$R^5$, —O—$R^5$, —S—$R^5$, —$SO_2$—$R^5$, —$SO_2$—$NR^P$—$R^5$, —$NR^P$—$SO_2$—$R^5$, —$NH_2$, —$N(R^P)$—$R^5$, —C(O)—$R^5$, —C(O)—$NH_2$, —C(O)—$NR^P$—$R^5$, —$NR^P$—C(O)—$R^5$ and —$NR^P$—C(O)O—$R^5$;

wherein $R^5$ is selected from the group consisting of $C_{1-4}$alkyl, aryl, $C_{1-4}$aralkyl, partially unsaturated carbocyclyl, cycloalkyl, cycloalkyl-$C_{1-4}$alkyl-, partially unsaturated carbocyclyl-$C_{1-4}$alkyl-, heteroaryl, heteroaryl-$C_{1-4}$alkyl-, heterocycloalkyl and heterocyclyl-$C_{1-4}$alkyl-;

wherein the $R^5$ aryl, partially unsaturated carbocyclyl, cycloalkyl, heteroaryl or heterocycloalkyl, whether alone or as part of a substituent group is optionally substituted with one or more substituent independently selected from the group consisting of $C_{1-4}$alkyl, $C_{1-4}$alkoxy, halogen, hydroxy, carboxy, amino, $C_{1-4}$alkylamino, di($C_{1-4}$alkyl)amino, cyano and nitro;

wherein each $R^P$ is selected from the group consisting of hydrogen, $C_{1-8}$alkyl, hydroxy substituted $C_{1-4}$alkyl, $C_{1-4}$aralkyloxy substituted $C_{1-4}$alkyl, cycloalkyl, aryl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl and spiro-heterocyclyl;

wherein the $R^P$ cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, $C_{1-4}$alkyl, $C_{1-4}$alkoxy, $C_{1-4}$alkoxy-carbonyl, nitro, cyano, amino, $C_{1-4}$alkylamino, di($C_{1-4}$alkyl)amino, —$SO_2$—$N(R^S R^T)$, 5-tetrazolyl and 1-(1,4-dihydro-tetrazol-5-one);

wherein each $R^S$ and $R^T$ is independently selected from the group consisting of hydrogen and $C_{1-4}$alkyl;

a is an integer from 0 to 3;

each $R^{10}$ is independently selected from the group consisting of hydroxy, halogen, $C_{1-4}$alkyl, $C_{1-4}$alkoxy, halogen substituted $C_{1-4}$alkyl, halogen substituted $C_{1-4}$alkoxy, —C(O)—$NR^V R^W$, —$SO_2 NR^V R^W$, —C(O)—$C_{1-4}$alkyl and —$SO_2$—$C_{1-4}$alkyl;

wherein each $R^V$ and $R^V$ is independently selected from the group consisting of hydrogen and $C_{1-4}$alkyl; alternatively $R^V$ and $R^W$ are taken together with the N atom to which they are bound to form a 5 to 6 membered saturated, partially unsaturated or aromatic ring structure;

provided that the halogens on the halogen substituted $C_{1-4}$alkyl or the halogen substituted $C_{1-4}$alkoxy are selected from the group consisting of chloro and fluoro;

or a pharmaceutically acceptable salt thereof.

2. A compound as in claim 1 wherein $R^0$ is selected from the group consisting of hydrogen and methyl;

$R^1$ is selected from the group consisting of hydrogen, hydroxy, methyl, trifluoromethyl, methoxy and methylcarbonyl;

$A^1$ is selected from the group consisting of $C_{1-4}$alkyl; wherein the $C_{1-4}$alkyl is optionally substituted with one to two $R^X$ substituents;

wherein each $R^X$ is independently selected from the group consisting of hydroxy, oxo, $C_{1-8}$alkyl, $C_{1-8}$alkoxy, hydroxy substituted $C_{1-4}$alkyl, cycloalkyl, cycloalkyl-$C_{1-4}$alkyl, biphenyl, aryl, $C_{1-4}$aralkyl, heteroaryl, heteroaryl-$C_{1-4}$alkyl-, heterocycloalkyl, heterocycloalkyl-$C_{1-4}$alkyl-, spiro-heterocyclyl and —$(C_{1-4}$alkyl$)_n$-$Q^2$-$R^4$;

wherein the $R^X$ cycloalkyl, aryl, heteroaryl or heterocycloalkyl group, whether alone or as part of a substituent group is optionally substituted with one or more substituents independently selected from the group consisting of fluoro, chloro, hydroxy, oxo, carboxy, $C_{1-4}$alkyl, $C_{1-4}$alkoxy, hydroxy substituted $C_{1-4}$alkyl, fluoro substituted $C_{1-4}$alkyl, fluoro substituted $C_{1-4}$alkoxy, 5-tetrazolyl and 1-(1,4-dihydro-tetrazol-5-one);

wherein n is an integer from 0 to 1;

wherein $Q^2$ is selected from the group consisting of —O—, —C(O)—, —C(O)O—, —OC(O)—, —$NR^G$—, —$NR^G$—C(O)— and —C(O)—$NR^G$—;

wherein $R^G$ is selected from the group consisting of hydrogen, $C_{1-8}$alkyl, hydroxy substituted $C_{1-4}$alkyl, $C_{1-4}$aralkyloxy substituted $C_{1-4}$alkyl, cycloalkyl, aryl, heteroaryl, heterocycloalkyl and $C_{1-4}$aralkyl;

wherein the $R^G$ cycloalkyl, aryl, heteroaryl or heterocycloalkyl, whether alone or as part of a substituent group is optionally substituted with one to two substituents independently selected from the group consisting of halogen, hydroxy, oxo, carboxy, $C_{1-4}$alkyl, $C_{1-4}$alkoxy, $C_{1-4}$alkoxy-carbonyl, nitro, cyano, amino, $C_{1-4}$alkylamino, di($C_{1-4}$alkyl)amino, —$SO_2 N(R^J R^K)$, 5-tetrazolyl and 1-(1,4-dihydro-tetrazol-5-one);

wherein each $R^J$ and $R^K$ is independently selected from the group consisting of hydrogen and $C_{1-4}$alkyl;

wherein $R^4$ is selected from the group consisting of $C_{1-4}$alkyl, hydroxy substituted $C_{1-4}$alkyl, fluoro substituted $C_{1-4}$alkyl, cycloalkyl, aryl, biphenyl, heteroaryl, heterocycloalkyl and $C_{1-4}$aralkyl;

wherein the $R^4$ cycloalkyl, aryl, heteroaryl or heterocycloalkyl, whether alone or as part of a substituent group is optionally substituted with one to two substituents independently selected from the group consisting of halogen, hydroxy, oxo, carboxy, C(O)O—$C_{1-4}$alkyl, C(O)—$C_{1-4}$alkyl, $C_{1-4}$alkyl, fluoro substituted $C_{1-4}$alkyl, $C_{1-4}$alkoxy, nitro, cyano, amino, $C_{1-4}$alkylamino, di($C_{1-4}$alkyl)amino and phenyl;

wherein the phenyl is optionally substituted with one to two substituent independently selected from the group consisting of halogen, hydroxy, oxo, carboxy, —C(O)O—$C_{1-4}$alkyl, —C(O)—$C_{1-4}$alkyl, $C_{1-4}$alkyl, fluoro substituted $C_{1-4}$alkyl, $C_{1-4}$alkoxy, nitro, cyano, amino, $C_{1-4}$alkylamino and di($C_{1-4}$alkyl)amino;

$Q^1$ is selected from the group consisting of —O—, —S—, —C(O)—, —C(S)—, —C(O)O—, —OC(O)—, —C(O)—NH—, —C(O)—N(CH$_3$)—, —C(O)—N(CH$_2$CH$_3$)—, —C(O)—N(CH$_2$CH$_2$OH)—, —C(O)—N($C_{1-4}$alkyl))-, —C(O)—N(cycloalkyl)-, —C(O)—N(CH$_2$CH$_2$—O—$C_{1-4}$aralkyl)-, —NH—, —N($C_{1-4}$alkyl)-, —NH—C(O)—, —N($C_{1-4}$alkyl)-C(O)—, —NH—C(O)O—, —N($C_{1-4}$alkyl)-C(O)O—, —NH—SO$_2$—, —SO$_2$—NH—, —NH—C(O)—NH—, NH—C(S)—NH— and —NH—SO$_2$—NH—;

$R^2$ is selected from the group consisting of $C_{1-10}$alkyl, cycloalkyl, aryl, heteroaryl, heterocycloalkyl, cycloalkyl-$C_{1-4}$alkyl-, $C_{1-4}$aralkyl, -heteroaryl-$C_{1-4}$alkyl-, heterocycloalkyl-$C_{1-4}$alkyl- and spiro-heterocyclyl;

wherein the $R^2$ $C_{1-10}$alkyl, cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, —C(O)—$C_{1-4}$alkyl, —C(O)—$C_{1-4}$aralkyl, —C(O)O—$C_{1-4}$alkyl, —C(O)O—$C_{1-4}$aralkyl, —C(O)—N($R^L R^M$), —$C_{1-4}$alkyl-C(O)O—$C_{1-4}$alkyl, —$C_{1-4}$alkyl-C(O)—N($R^L R^M$), —NR$^L$—C(O)$C_{1-4}$alkyl, $C_{1-6}$alkyl, fluoro substituted $C_{1-4}$alkyl, hydroxy substituted $C_{1-4}$alkyl, carboxy substituted $C_{1-4}$alkyl, $C_{1-4}$alkoxy, —O—$C_{1-4}$aralkyl, —O-(tetrahydropyranyl), —NH—C(O)—O—CH$_2$-(tetrahydropyranyl), nitro, cyano, amino, $C_{1-4}$alkylamino, di($C_{1-4}$alkyl)amino phenyl and 5-tetrazolyl;

wherein the phenyl or tetrahydropyranyl is optionally substituted with one to two substituent independently selected from the group consisting of halogen, hydroxy, oxo, carboxy, —OC(O)—$C_{1-4}$alkyl, —$C_{1-4}$alkyl-OC(O)—$C_{1-4}$alkyl, $C_{1-4}$alkyl, fluoro substituted $C_{1-4}$alkyl, hydroxy substituted $C_{1-4}$alkyl, $C_{1-4}$alkoxy, nitro, cyano, amino, $C_{1-4}$alkylamino and di($C_{1-4}$alkyl)amino;

wherein each $R^L$ and $R^M$ is independently selected from the group consisting of hydrogen and $C_{1-4}$alkyl;

b is an integer selected from 0 to 1;

$L^1$ is selected from the group consisting of —O—, —S(O)O$_2$—, —C(O)—, —C(S)—, —$C_{1-4}$alkyl- and (hydroxy substituted $C_{1-4}$alkyl)-;

$R^3$ is selected from the group consisting of $C_{2-6}$alkenyl, cycloalkyl, partially unsaturated carbocyclyl, aryl, $C_{1-4}$aralkyl, biphenyl, heteroaryl and heterocycloalkyl;

wherein the $R^3$ cycloalkyl, partially unsaturated carbocyclyl, aryl, heteroaryl or heterocycloalkyl, whether alone or as part of a substituent group is optionally substituted with one to two substituents independently selected from the group consisting of halogen, hydroxy, oxo, carboxy, $C_{1-4}$alkyl, hydroxy substituted $C_{1-4}$alkyl, halogen substituted $C_{1-4}$alkyl, cyano substituted $C_{1-4}$alkyl, $C_{2-4}$alkenyl, $C_{2-4}$alkynyl, halogen substituted $C_{1-4}$alkoxy, nitro, cyano, —R$^5$, —O—R$^5$, —C(O)O—R$^5$ and —SO$_2$—NR$^P$—R$^5$;

wherein $R^5$ is selected from the group consisting of $C_{1-4}$alkyl, aryl, $C_{1-4}$aralkyl, cycloalkyl and cycloalkyl-$C_{1-4}$alkyl-;

wherein the $R^5$ aryl, whether alone or as part of a substituent group is optionally substituted with one to two substituent independently selected from the group consisting of $C_{1-4}$alkyl, $C_{1-4}$alkoxy, halogen, hydroxy, carboxy, amino, $C_{1-4}$alkylamino, di($C_{1-4}$alkyl)amino, cyano and nitro;

wherein $R^P$ is selected from the group consisting of hydrogen, $C_{1-8}$alkyl, hydroxy substituted $C_{1-4}$alkyl, $C_{1-4}$aralkyloxy substituted $C_{1-4}$alkyl, cycloalkyl, aryl, heteroaryl, heterocycloalkyl and $C_{1-4}$aralkyl;

wherein the $R^P$ cycloalkyl, aryl, heteroaryl or heterocycloalkyl, whether alone or as part of a substituent group is optionally substituted with one to two substituents independently selected from the group consisting of halogen, hydroxy, oxo, carboxy, $C_{1-4}$alkyl, $C_{1-4}$alkoxy, $C_{1-4}$alkoxy-carbonyl, nitro, cyano, amino, $C_{1-4}$alkylamino, di($C_{1-4}$alkyl)amino, —SO$_2$N($R^S R^T$), 5-tetrazolyl and 1-(1,4-dihydro-tetrazol-5-one);

wherein each $R^S$ and $R^T$ is independently selected from the group consisting of hydrogen and $C_{1-4}$alkyl;

a is an integer from 0 to 1;

$R^{10}$ is selected from the group consisting of hydroxy, halogen, $C_{1-4}$alkyl, $C_{1-4}$alkoxy, halogen substituted $C_{1-4}$alkyl, halogen substituted $C_{1-4}$alkoxy;

provided that the halogens on the halogen substituted $C_{1-4}$alkyl and the halogen substituted $C_{1-4}$alkoxy are selected from the group consisting of fluoro and chloro;

or a pharmaceutically acceptable salt thereof.

3. A compound as in claim 2 wherein $R^0$ is hydrogen;

$R^1$ is hydrogen;

$A^1$ is selected from the group consisting of $C_{1-4}$alkyl; wherein the $C_{1-4}$alkyl is optionally substituted with one to two $R^X$ substituents;

wherein each $R^X$ is independently selected from the group consisting of $C_{1-8}$alkyl, hydroxy substituted $C_{1-4}$alkyl, cycloalkyl, aryl, $C_{1-4}$aralkyl, biphenyl, heterocycloalkyl, spiro-heterocyclyl and —($C_{1-4}$alkyl)$_n$-Q$^2$-R$^4$;

wherein the $R^X$ cycloalkyl or aryl, whether alone or as part of a substituent group is optionally substituted with one to two substituents independently selected from the group consisting of fluoro, chloro, hydroxy, oxo, $C_{1-4}$alkyl and $C_{1-4}$alkoxy;

wherein n is an integer from 0 to 1;

wherein $Q^2$ is selected from the group consisting of —C(O)—, —C(O)—NR$^G$— and —NR$^G$—C(O)—;

wherein $R^G$ is selected from the group consisting of hydrogen and $C_{1-4}$alkyl;

wherein $R^4$ is selected from the group consisting of cycloalkyl and heterocycloalkyl;

$Q^1$ is selected from the group consisting of —O—, —C(O)—, —C(O)O—, —C(O)—NH—, —C(O)—N(CH$_3$)—, —C(O)—N(CH$_2$CH$_3$)—, —C(O)—N(CH$_2$CH$_2$OH)—, —C(O)—N($C_{1-4}$alkyl))-, —C(O)—N(cycloalkyl)-, —C(O)—N(CH$_2$CH$_2$—O—$C_{1-4}$aralkyl)-, —NH—, —N($C_{1-4}$alkyl), —NH—C(O)—, —N($C_{1-4}$alkyl)-C(O)—, —NH—C(O)O—, —N($C_{1-4}$alkyl)-C(O)O—, —NH—SO$_2$—, —NH—C(O)—NH— and NH—C(S)—NH—;

$R^2$ is selected from the group consisting of $C_{1-10}$alkyl, cycloalkyl, cycloalkyl-alkyl, aryl, $C_{1-4}$aralkyl, heteroaryl, heterocycloalkyl, spiro-heterocyclyl and heteroaryl-$C_{1-4}$alkyl-;

wherein the $R^2$ $C_{1-10}$alkyl, aryl, cycloalkyl, heteroaryl or heterocycloalkyl, whether alone or as part of a substituent group is optionally substituted with one to two substituent independently selected from the group consisting of $C_{1-5}$alkyl, $C_{1-4}$alkoxy, —O—$C_{1-2}$aralkyl, —O—(tetrahydropyranyl), —NH—C(O)—O—CH$_2$—(tetrahydropyranyl), halogen, trifluoromethyl, amino, cyano, hydroxy, oxo, carboxy, phenyl, —C(O)—$C_{1-4}$alkyl, —C(O)O—$C_{1-2}$aralkyl, —C(O)—N($R^L R^M$), —C(O)—N($C_{1-4}$alkyl)(cycloalkyl), —NH—C(O)—$C_{1-4}$alkyl, —C(O)O—$C_{1-4}$alkyl, —$C_{1-2}$alkyl-C(O)O—$C_{1-4}$alkyl, carboxy substituted $C_{1-2}$alkyl and 5-tetrazolyl;

wherein the phenyl or tetrahydropyranyl is optionally substituted with one to two substituents independently selected from the group consisting of hydroxy, halogen, cyano, $C_{1-4}$alkyl, $C_{1-4}$alkoxy, hydroxy substituted $C_{1-2}$alkyl, —OC(O)—$C_{1-2}$alkyl, —$C_{1-2}$alkyl-OC(O)—$C_{1-2}$alkyl, amino, $C_{1-4}$alkylamino and di($C_{1-4}$alkyl)amino;

wherein $R^L$ and $R^M$ are each independently selected from the group consisting of hydrogen, methyl and ethyl;

b is an integer from 0 to 1;

$L^1$ is selected from the group consisting of —O—, —C(O)—, —CH$_2$— and —C(OH)—;

$R^3$ is selected from the group consisting of $C_{2-6}$alkenyl, aryl, biphenyl, partially unsaturated carbocyclyl and heteroaryl;

wherein the $R^3$ aryl or heteroaryl group is optionally substituted with one to two substituents independently selected from the group consisting of hydroxy, halogen, $C_{1-4}$alkyl, $C_{1-4}$alkoxy, —S—$C_{1-4}$alkyl, hydroxy substituted $C_{1-4}$alkyl, halogen substituted $C_{1-4}$alkyl, —C(O)—NH$_2$, —C(O)—$C_{1-4}$alkyl, —NH—$C_{1-4}$alkyl-cycloalkyl, —NH—C(O)—$C_{1-4}$alkyl, —NH—C(O)—O—$C_{1-4}$aralkyl, —SO$_2$—NH—$C_{1-4}$alkyl and —SO$_2$—NH-phenyl;

a is an integer from 0 to 1;

$R^{10}$ is selected from the group consisting of halogen;

or a pharmaceutically acceptable salt thereof.

4. A compound as in claim 3 wherein $R^0$ is hydrogen;

$R^1$ is hydrogen;

$A^1$ is selected from the group consisting of methyl, ethyl, 1-methyl-ethyl, (1)-(R)-methyl-ethyl, (1)-(S)-methyl-ethyl, 1-n-propyl-ethyl, (1)-(R)-n-propyl-ethyl, (1)-(S)-n-propyl-ethyl, 1-isopropyl-ethyl, (1)-(R)-isopropyl-ethyl, (1)-(S)-isopropyl-ethyl, 1-cyclohexyl-ethyl, (1)-(R)-cyclohexyl-ethyl, (1)-(S)-cyclohexyl-ethyl, 1-phenyl-ethyl, 1-(4-hydroxybenzyl)-ethyl, (1)-(R)-(4-hydroxybenzyl)-ethyl, (1)-(S)-(4-hydroxybenzyl)-ethyl, n-propyl, 1-hydroxymethyl-n-propyl, (1)-(R)-hydroxymethyl-n-propyl, (1)-(S)-hydroxymethyl-n-propyl, 1-(dimethyl)-n-propyl, 1-(n-propyl)-n-propyl, 1-isopropyl-n-propyl, (1)-(S)-isopropyl-n-propyl, (1)-(R)-isopropyl-n-propyl, 1-(n-pentyl)-n-propyl, 1-n-octyl-n-propyl, 1-cyclohexyl-n-propyl, (1)-(R)-cyclohexyl-n-propyl, (1)-(S)-cyclohexyl-n-propyl, 1-phenyl-n-propyl, 1-(4-chlorophenyl)-n-propyl, 1-(4-methylphenyl)-n-propyl, 1-(4-methoxyphenyl)-n-propyl, 1-(4-biphenyl)-n-propyl, 1-(N-piperidinycarbonyl-n-propyl)-n-propyl, 1-(4-tetrahydropyranyl)-n-propyl, (1)-(R)-(4-tetrahydropyranyl)-n-propyl, (1)-(S)-(4-tetrahydropyranyl)-n-propyl, 1-(4-hydroxy-cyclohexyl)-n-propyl, 1-(N-methyl-N-cyclohexyl-aminocarbonyl)-n-propyl, (1)-(R)—(N-methyl-N-cyclohexyl-aminocarbonyl)-n-propyl, (1)-(S)—(N-methyl-N-cyclohexyl-aminocarbonyl)-n-propyl, 1-(1,4-dioxaspiro[4.5]decane)-n-propyl, (1)-(R)-(1,4-dioxaspiro[4.5]decane)-n-propyl, (1)-(S)-(1,4-dioxaspiro[4.5]dec-8-yl)-n-propyl, (1)-(R)-((4R)-hydroxycyclohexyl)-n-propyl, 1-(cylcohexan-4-one)-n-propyl, (1)-(R)-(cylcohexan-4-one)-n-propyl, (1)-(S)-(cylcohexan-4-one)-n-propyl, 1-pyranyl-n-propyl, (1)-(S)-pyranyl-n-propyl, n-butyl, 1-propyl-n-butyl, 1-phenyl-n-butyl, 1-(cyclohexylcarbonylaminomethyl)-ethyl, 1-(N-cyclohexyl-N-methyl-aminocarbonylethyl)-n-propyl, 1-(2-methyl-piperidinylcarbonyl-n-propyl)-n-propyl and 1-(4-methyl-piperidinylcarbonyl-n-propyl)-n-propyl;

$Q^1$ is selected from the group consisting of —O—, —C(O)—, —C(O)O—, —C(O)—NH—, —C(O)—N(CH$_3$)—, —C(O)—N(CH$_2$CH$_3$)—, —C(O)—N(CH$_2$CH$_2$OH)—, —C(O)—N(isopropyl)-, —C(O)—N(cyclohexyl)-, —C(O)—N(CH$_2$CH$_2$—O-benzyl)-, —NH—, —N(CH$_3$)—, —N(CH$_2$CH$_3$)—, —NH—C(O)—, —N(CH$_3$)—C(O)—, —NH—C(O)O—, —N(CH$_3$)—C(O)O—, —NH—SO$_2$—, —NH—C(O)—NH— and NH—C(S)—NH—;

$R^2$ is selected from the group consisting of methyl, ethyl, n-propyl, isopropyl, t-butyl, isobutyl, isopentyl, 3-n-heptyl, n-nonyl, amino-methyl, carboxy-methyl-, 2-amino-ethyl, 2-cyano-ethyl, 4-carboxy-n-butyl, 3-n-heptyl, 4-n-heptyl, 3-amino-n-propyl, 3,3,3-trifluoro-n-propyl, 3,3,3-trifluoro-isobutyl, 1-(1-carboxy-2-hydroxy-ethyl), 1-(S)-(1-carboxy-2-hydroxy-ethyl), 1-(R)-(1-carboxy-2-hydroxy-ethyl), 1-(1-carboxy-2-t-butoxy-ethyl), 1-(R)-(1-carboxy-2-t-butoxy-ethyl), 1-(1-carboxy-2-benzyloxy-ethyl), 1-(S)-(1-carboxy-2-benzyloxy-ethyl), 1-(R)-(1-carboxy-2-benzyloxy-ethyl), 1-(1-methoxy-carbonyl-2-benzyloxy-ethyl), 1-(S)-(1-methoxy-carbonyl-2-benzyloxy-ethyl), 1-(R)-(1-methoxy-carbonyl-2-benzyloxy-ethyl), cyclopropyl, cyclobutyl, cyclopentyl, cyclohexyl, cycloheptyl, 2-phenyl-cyclopropyl, cyclopentyl-methyl, cyclopentyl-ethyl, 1-(1-aminocarbonyl-cyclopropyl), 4-hydroxy-cyclohexyl, 4-carboxy-cyclohexyl, cis-(4-carboxy)-cyclohexyl, trans-(4-carboxy)-cyclohexyl, 3-carboxy-cyclohexyl, cis-(3-carboxy)-cyclohexyl, 4-cyano-cyclohexyl, 4-methoxy-carbonyl-cyclohexyl, 3-methoxy-carbonyl-cyclohexyl, cis-(3-methoxy-carbonyl)-cyclohexyl, 4-ethoxy-carbonyl-cyclohexyl, (1)-(S)-((4R)-methoxy-carbonyl-cyclohexyl, (1)-(R)-((4S)-methoxy-carbonyl-cyclohexyl, 2-methyl-cyclohexyl, 4-methyl-cyclohexyl, 4-n-pentyl-cyclohexyl, 4-t-butyl-cyclohexyl, (1)-(S)-2-(R)-methyl-cyclopentyl, 3-methoxy-cyclohexyl, 1-(1-(4-chlorophenyl)-cyclopentyl), 4-trifluoromethyl-cyclohexyl, 4-oxo-cyclohexyl, 1-(4-benzyloxy-carbonyl-cyclohexyl), 1-(S)-(4-(S)-benzyloxy-carbonyl-cyclohexyl), 1-(4-amino-carbonyl-cyclohexyl), 1-(S)-(4-(S)-amino-carbonyl-cyclohexyl), 1-(4-methylamino-carbonyl-cyclohexyl), 1-(S)-(4-(S)-methylamino-carbonyl-cyclohexyl), 1-(4-(5-tetrazolyl)-cyclohexyl), phenyl, benzyl, phenyl-ethyl, 3-carboxy-methyl-benzyl, 3-methoxy-carbonyl-methyl-benzyl, 4-carboxy-phenyl, 3-cyano-phenyl, 4-methyl-phenyl, 4-t-butyl-phenyl, 4-n-butyl-phenyl, 2-methoxy-phenyl, 3-methoxy-phenyl, 4-dimethylamino-phenyl, 4-(methylcarbonylamino)-phenyl, 1-naphthyl-methyl, 1-(1,2,3,4-tetrahydro-naphthyl), 4-biphenyl, benzhydryl, 1-adamantyl, 2-adamantyl, 2-(R)-adamantyl, 2-(S)-adamantyl, N-piperidinyl, 1-(2-carboxy-piperidinyl), 1-(S)-2-carboxy-piperidinyl), 1-(2-methoxy-carbonyl-piperidinyl), 1-(S)-2-methoxy-carbonyl-piperidinyl), 1-(2-methyl-piperidinyl), 1-(4-methyl-piperidinyl), 1-(4-isopropyl-piperidinyl), 4-(1-methylcarbonyl)-piperidinyl), 3-(2,5-dimethyl-furyl), 4-tetrahydropyranyl, 4-(2-phenyl-thiazolyl)-methyl, 4-(1-phenyl-pyrazolyl)-methyl, 5-(3-methyl-isoxazolyl)-methyl, 3-(5-phenyl-isoxazolyl)-methyl, 1-(2-carboxy-pyrrolidinyl), 1-(S)-2-carboxy-pyrrolidinyl), 1-(2-(N-methyl-N-cyclohexylaminocarbonyl)-pyrrolidinyl), 1,4-dioxaspiro[4.5]dec-8-yl, 2-(bicyclo[2.2.1]heptyl), 1-(3-n-pentyl-bicyclo[2.2.2]-octyl, 2-bicyclo[2.2.2]octyl, 2-(R)-bicyclo[2.2.2]octyl, 2-(S)-bicyclo[2.2.2]octyl, 5-tetrazolyl-methyl, 2-imidazolyl-methyl, 5-imidazolyl-methyl, 4-pyridyl-methyl, 3-(1,2,4-triazolyl)-methyl, 1-(2-carboxy-octahydroindolyl), 1-(S)-2-carboxy-octahydroindolyl), 1-(2-methoxy-carbonyl-octahydroindolyl), 1-(S)-2-methoxy-carbonyl-octahydroindolyl), 2R-(3R,4S,5R-tri(methyl-carbonyloxy)-6R-(methyl-carbonyloxy-methyl)-tetrahydropyranyl)oxy-ethyl, 2R-(3S,4S,5R-trihydroxy-6R-(hydroxy-methyl)-tetrahydropyranyl)oxy-ethyl and 3-(2R-(3S,4S,5R,6R-tetrahydroxy-tetrahydropyrantl)-methoxy-carbonyl-amino)-n-propyl;

b is an integer from 0 to 1;

$L^1$ is selected from the group consisting of —O—, —C(O)—, —CH$_2$— and —C(OH)—;

$R^3$ is selected from the group consisting of n-penten-1-yl, phenyl, 2-hydroxy-phenyl, 2-chloro-phenyl, 3-chloro-phenyl, 4-chloro-phenyl, 2-fluoro-phenyl, 4-fluorophenyl, 2,6-difluoro-phenyl, 2-methyl-phenyl, 3-methyl-phenyl, 4-methyl-phenyl, 2-methoxy-phenyl, 4-methoxy-phenyl, 3,5-dimethoxy-phenyl, 2,6-dimethoxy-phenyl, 2-isopropyl-phenyl, 2-methylthiophenyl, 2-fluoro-6-methoxy-phenyl, 2-methoxy-5-methyl-phenyl, 2-methoxy-5-fluoro-phenyl, 3-(hydroxymethyl)-phenyl, 3-trifluoromethyl-phenyl, 2-(methylcarbonylamino)-phenyl, 2-(t-butylaminosulfonyl)-phenyl, 2-(aminocarbonyl)-phenyl, 2-(methylsulfonylamino)-phenyl, 2-(methylcarbonyl)-phenyl, 3-(benzyloxycarbonylamino)-phenyl, 3-(N-(cyclohexylmethyl)-amino)-phenyl, 3-(phenylsulfonylamino)-phenyl, 2-naphthyl, 1-cyclohexenyl, 1-cyclopentenyl, 2-biphenyl, 5-pyrimidinyl, 4-pyridyl, 3-quinolinyl and 3-(6-fluoro-benzo[d]isoxazolyl);

a is an integer from 0 to 1;

$R^{10}$ is fluoro;

or a pharmaceutically acceptable salt thereof.

5. A compound as in claim 4

$R^0$ is hydrogen;

$R^1$ is hydrogen;

$A^1$ is selected from the group consisting of -ethyl-, -n-butyl-, -n-propyl-, 1-(R)-methyl-ethyl-, 1-n-propyl-ethyl-, 1-cyclohexyl-ethyl-, 1-(R)-cyclohexyl-ethyl-, 1-cyclohexyl-n-propyl, 1-(S)-cyclohexyl-n-propyl, 1-(R)-cyclohexyl-n-propyl, 1-(n-propyl)-n-propyl, 1-(n-propyl)-n-butyl-, 1-(R)-isopropyl-n-propyl, 1-(S)-isopropyl-n-propyl, 1-(4-chlorophenyl)-n-propyl, 1-(4-methylphenyl)-n-propyl, 1-(4-methoxyphenyl)-n-propyl, 1-(phenyl)-ethyl-, 1-(cyclohexyl-carbonyl-amino-methyl)-ethyl and 1-(N-cyclohexyl-N-methyl-aminocarbonyl-ethyl)-n-propyl;

$Q^1$ is selected from the group consisting of —C(O)—NH—, —C(O)—N(CH$_3$)—, —C(O)—N(cyclohexyl)-, —NH—C(O)—, —NH—C(O)O—, —N(CH$_3$)—C(O)O—, —NH—C(O)—NH—, —NH—C(S)—NH and —NH—SO$_2$—;

$R^2$ is selected from the group consisting of isopropyl, n-butyl, t-butyl, 1-ethyl-n-pentyl, isopentyl, 3-n-heptyl, 4-n-heptyl, cyclobutyl, cyclopentyl, cyclohexyl, cycloheptyl, cyclopentyl-methyl-, 2-methyl-cyclohexyl, 3-methoxy-cyclohexyl, phenyl, phenylethyl-, 4-(1-methyl-piperidinyl), 1-(1-(4-chlorophenyl)-cyclopentyl), 1-adamantyl and 2-adamantyl;

b is an integer from 0 to 1;

$L^1$ is selected from the group consisting of —C(O)— and —O—;

$R^3$ is selected from the group consisting of phenyl, 2-methoxyphenyl, 3-(benzyloxy-carbonyl-amino)-phenyl, 3-(N-(cyclohexyl-methyl)-amino)-phenyl and 3-(phenyl-sulfonyl-amino)-phenyl;

a is 0;

or a pharmaceutically acceptable salt thereof.

6. A compound as in claim 5

$R^0$ is hydrogen;

$R^1$ is hydrogen;

$A^1$ is selected from the group consisting of ethyl-, n-butyl-, 1-(R)-methyl-ethyl-, 1-n-propyl-ethyl-, 1-cyclohexyl-ethyl-, 1-(R)-cyclohexyl-ethyl-, 1-cyclohexyl-n-propyl, 1-(S)-cyclohexyl-n-propyl, 1-(n-propyl)-n-propyl, 1-(n-propyl)-n-butyl-, 1-(R)-isopropyl-n-propyl, 1-(S)-isopropyl-n-propyl, 1-(4-chlorophenyl)-n-propyl, 1-(4-methylphenyl)-n-propyl and 1-(4-methoxyphenyl)-n-propyl;

$Q^1$ is selected from the group consisting of —O(O)—NH—, —C(O)—N(CH$_3$)—, —C(O)—N(cyclohexyl)-, —NH—C(O)—, —NH—C(O)O—, —N(CH$_3$)—C(O)O—, —NH—C(O)—NH— and —NH—C(S)—NH;

$R^2$ is selected from the group consisting of isopropyl, t-butyl, 1-ethyl-n-pentyl, isopentyl, 3-n-heptyl, 4-n-heptyl, cyclopentyl, cyclohexyl, cycloheptyl, cyclopentyl-methyl-, 2-methyl-cyclohexyl, phenyl, 4-(1-methyl-piperidinyl), 1-(1-(4-chlorophenyl)-cyclopentyl), 1-adamantyl and 2-adamantyl;

b is an integer from 0 to 1;

$L^1$ is —O—;

$R^3$ is selected from the group consisting of phenyl, 2-methoxyphenyl, 3-(benzyloxy-carbonyl-amino)-phenyl and 3-(phenyl-sulfonyl-amino)-phenyl;

a is 0;

or a pharmaceutically acceptable salt thereof.

7. A compound as in claim 6

$R^0$ is hydrogen;

$R^1$ is hydrogen;

$A^1$ is selected from the group consisting of ethyl-, 1-n-propyl-ethyl-, 1-cyclohexyl-ethyl-, 1-(R)-cyclohexyl-ethyl-, 1-cyclohexyl-n-propyl, 1-(5)-cyclohexyl-n-propyl, 1-(n-propyl)-n-propyl, 1-(R)-isopropyl-n-propyl and 1-(5)-isopropyl-n-propyl;

$Q^1$ is selected from the group consisting of —C(O)—NH—, —C(O)—N(CH$_3$)— and —NH—C(O)—;

$R^2$ is selected from the group consisting of isopentyl, 4-n-heptyl, cyclopentyl, cyclohexyl, cyclopentyl-methyl-, 1-(1-(4-chlorophenyl)-cyclopentyl), 1-adamantyl and 2-adamantyl;

b is an integer from 0 to 1;

257

$L^1$ is —O—;
$R^3$ is selected from the group consisting of phenyl and 2-methoxyphenyl;
a is 0;
or a pharmaceutically acceptable salt thereof.

8. A compound as in claim 4
$R^0$ is hydrogen;
$R^1$ is hydrogen;
$A^1$ is selected from the group consisting of ethyl-, -n-butyl-, -n-propyl-, 1-(R)-methyl-ethyl, 1-n-propyl-ethyl, 1-(R)-n-propyl-ethyl-, 1-(n-propyl)-n-propyl-, 1-(n-propyl)-n-butyl-, 1-isopropyl-ethyl-, 1-(n-pentyl)-n-propyl-, 1-cyclohexyl-ethyl-, 1-(R)-cyclohexyl-ethyl-, 1-(5)-cyclohexyl-ethyl-, 1-phenyl-ethyl, 1-(4-chlorophenyl)-n-propyl-, 1-(4-methoxyphenyl)-n-propyl-, 1-cyclohexyl-n-propyl-, 1-phenyl-n-propyl-, 1-(R)-isopropyl-n-propyl, 1-(S)-isopropyl-n-propyl, 1-(R)-cyclohexyl-n-propyl-, 1-(S)-(cyclohexyl)-n-propyl-, 1-(S)-(hydroxymethyl)-n-propyl-, 1-(4-tetrahydropyranyl)-n-propyl-, 1-(S)-(4-tetrahydropyranyl)-n-propyl-, 1-(4-hydroxy-cyclohexyl)-n-propyl-, 1-(S)-(4-oxo-cyclohexyl)-n-propyl, 1-(S)-(cis-4-hydroxy-cyclohexyl)-n-propyl, 1-(S)—(N-cyclohexyl-N-methyl-amino-carbonyl)-n-propyl-, 1-(N-cyclohexyl-N-methyl-amino-carbonyl-ethyl)-n-propyl- and 1-(S)-(1,4-dioxa-spiro[4.5]dec-8-yl)-n-propyl;
$Q^1$ is selected from the group consisting of —C(O)—NH—, —C(O)—N(CH$_3$)—, —C(O)—N(ethyl)-, —C(O)—N(CH$_2$CH$_2$OH)—, —C(O)—N(cyclohexyl)-, —C(O)—N(hydroxyethyl)-, —C(O)—N(benzyloxy-ethyl)-, —N(CH$_3$)—, —NH—C(O)—, —N(CH$_3$)—C(O)—, —NH—C(O)O—, —N(CH$_3$)—C(O)O—, —NH—C(O)—NH, —NH—C(S)—NH and —NH—SO$_2$—;
$R^2$ is selected from the group consisting of carboxy-methyl, 2-cyanoethyl-, n-propyl, isopropyl, n-butyl, isobutyl, t-butyl, isopentyl, 3-n-heptyl, 4-n-heptyl, 4-carboxy-n-butyl, cyclopropyl, cyclobutyl, cyclopentyl, cyclohexyl, cycloheptyl, cyclopentyl-methyl-, cyclopentyl-ethyl-, 1-(S)-(1-carboxy-2-hydroxy-ethyl), 1-(R)-(1-carboxy-2-hydroxy-ethyl), 1-(R)-(1-carboxy-2-t-butoxy-ethyl), 1-(S)-(1-methoxy-carbonyl-2-benzyloxy-ethyl), 1-(R)-(1-methoxy-carbonyl-2-benzyloxy-ethyl), 1-(S)-(1-carboxy-2-benzyloxy-ethyl), 1-(R)-(-carboxy-2-benzyloxy-ethyl), trans-2-methyl-cyclohexyl-, 1-(1-(4-chlorophenyl)-cyclopentyl), 3-methoxy-cyclohexyl, 4-hydroxy-cyclohexyl, 1-cis-(3-carboxy-cyclohexyl), 4-carboxy-cyclohexyl, (1)-(S)-((4R)-carboxy-cyclohexyl), (1)-(R)-((4S)-carboxy-cyclohexyl), 4-(ethoxy-carbonyl)-cyclohexyl, cis-(4-methoxy-carbonyl)-cyclohexyl, trans-(4-methoxy-carbonyl)-cyclohexyl, 1-4-oxo-cyclohexyl, 1-cis-(4-amino-carbonyl-cyclohexyl), phenyl, 2-methoxyphenyl, 2-methylphenyl, benzyl, phenylethyl-, benzhydryl, 4-(1-isopropyl)-piperidinyl, 4-(1-methyl-piperidinyl), 1-adamantyl, 2-adamantyl, 4-(tetrahydropyranyl), 5-(3-methyl-isoxazolyl)-methyl, 1,4-oxaspiro[4.5]dec-8-yl and 5-tetrazolyl-methyl;
b is an integer from 0 to 1;
$L^1$ is selected from the group consisting of —C(O)— and —(O)—;
$R^3$ is selected from the group consisting of phenyl, 2-hydroxyphenyl, 2-fluorophenyl, 2,6-difluorophenyl, 2-chlorophenyl, 3-chlorophenyl, 2-methylphenyl, 3-methylphenyl, 2-methoxy-phenyl, 2-fluoro-6-methoxyphenyl, 3-hydroxymethyl-phenyl and 3-(phenyl-sulfonyl-amino)-phenyl;
a is 0;
or a pharmaceutically acceptable salt thereof.

258

9. A compound as in claim 8
$R^0$ is hydrogen;
$R^1$ is hydrogen;
$A^1$ is selected from the group consisting of -ethyl-, -n-propyl-, 1-(R)-methyl-ethyl, 1-n-propyl-ethyl, 1-(R)-n-propyl-ethyl-, 1-(n-propyl)-n-propyl-, 1-(n-propyl)-n-butyl-, 1-(n-pentyl)-n-propyl-, 1-cyclohexyl-ethyl-, 1-(R)-cyclohexyl ethyl, 1-phenyl-ethyl, 1-(4-chlorophenyl)-n-propyl-, 1-(4-methoxyphenyl)-n-propyl, 1-cyclohexyl-n-propyl-, 1-phenyl-n-propyl-, 1-(R)-isopropyl-n-propyl, 1-(5)-isopropyl-n-propyl, 1-(R)-cyclohexyl-n-propyl-, 1-(S)-(cyclohexyl)-n-propyl-, 1-(5)-hydroxymethyl)-n-propyl-, 1-(4-tetrahydropyranyl)-n-propyl-, 1-(S)-(4-tetrahydropyranyl)-n-propyl-, 1-(4-hydroxy-cyclohexyl)-n-propyl-, 1-(S)-(4-oxo-cyclohexyl)-n-propyl, 1-(S)-(cis-4-hydroxy-cyclohexyl)-n-propyl, 1-(S)—(N-cyclohexyl-N-methyl-amino-carbonyl)-n-propyl- and 1-(S)-(1,4-dioxa-spiro[4.5]dec-8-yl)-n-propyl;
$Q^1$ is selected from the group consisting of —C(O)—NH—, —C(O)—N(CH$_3$)—, —C(O)—N(ethyl)-, —C(O)—N(CH$_2$CH$_{20}$H)—, —C(O)—N(hydroxyethyl)-, —C(O)—N(benzyloxy-ethyl)-, —N(CH$_3$)—, —NH—C(O)—, —NH—C(O)O—, —N(CH$_3$)—C(O)O— and —NH—C(S)—NH;
$R^2$ is selected from the group consisting of carboxy-methyl, isopropyl, isobutyl, t-butyl, isopentyl, 3-n-heptyl, 4-n-heptyl, 4-carboxy-n-butyl, cyclobutyl, cyclopentyl, cyclohexyl, cycloheptyl, cyclopentyl-methyl-, cyclopentyl-ethyl-, 1-(S)-(1-carboxy-2-hydroxy-ethyl), 1-(R)-(1-carboxy-2-hydroxy-ethyl), 1-(R)-(1-carboxy-2-t-butoxy-ethyl), 1-(S)-(1-methoxy-carbonyl-2-benzyloxy-ethyl), 1-(R)-(1-methoxy-carbonyl-2-benzyloxy-ethyl), 1-(S)-(1-carboxy-2-benzyloxy-ethyl), trans-2-methyl-cyclohexyl-, 1-(1-(4-chlorophenyl)-cyclopentyl), 3-methoxy-cyclohexyl, 4-hydroxy-cyclohexyl, 1-cis-(3-carboxy-cyclohexyl), 4-carboxy-cyclohexyl, (1)-(S)-((4R)-carboxy-cyclohexyl), (1)-(R)-((4S)-carboxy-cyclohexyl), cis-(4-methoxy-carbonyl)-cyclohexyl, trans-(4-methoxy-carbonyl)-cyclohexyl, 1-cis-(4-amino-carbonyl-cyclohexyl), phenyl, 2-methylphenyl, phenylethyl-, 4-(1-methyl-piperidinyl), 1-adamantyl, 2-adamantyl, 4-(tetrahydropyranyl), 5-(3-methyl-isoxazolyl)-methyl and 5-tetrazolyl-methyl;
b is an integer from 0 to 1;
$L^1$ is selected from the group consisting of —C(O)— and —(O)—;
$R^3$ is selected from the group consisting of phenyl, 2-fluorophenyl, 2,6-difluorophenyl, 2-chlorophenyl, 2-methylphenyl, 3-methylphenyl, 2-methoxy-phenyl and 2-fluoro-6-methoxyphenyl;
a is 0;
or a pharmaceutically acceptable salt thereof.

10. A compound as in claim 9
$R^0$ is hydrogen;
$R^1$ is hydrogen;
$A^1$ is selected from the group consisting of -ethyl-, 1-cyclohexyl-ethyl-, 1-(R)-cyclohexyl-ethyl, 1-cyclohexyl-n-propyl-, 1-(R)-isopropyl-n-propyl, 1-(S)-isopropyl-n-propyl, 1-(R)-cyclohexyl-n-propyl-, 1-(S)-(cyclohexyl)-n-propyl-, 1-(4-tetrahydropyranyl)-n-propyl-, 1-(S)-(4-tetrahydropyranyl)-n-propyl-, 1-(4-hydroxy-cyclohexyl)-n-propyl- and 1-(S)-(4-oxo-cyclohexyl)-n-propyl;

Q¹ is selected from the group consisting of —C(O)—NH—, —C(O)—N(CH₃)—, —C(O)—N(hydroxyethyl)-, —C(O)—N(benzyloxy-ethyl)-, —C(O)—N(cyclohexyl)- and —NH—C(O)—;

R² is selected from the group consisting of carboxy-methyl, isobutyl, isopentyl, 1-(1-(R)-carboxy-2-hydroxyethyl), 1-(1-(R)-carboxy-2-t-butoxy-ethyl), 1-(1-(S)-carboxy-2-benzyloxy-ethyl), cyclopentyl, cyclohexyl, 4-carboxy-cyclohexyl, (1)-(S)-((4R)-carboxy-cyclohexyl), 1-adamantyl and 2-adamantyl;

b is an integer from 0 to 1;

L¹ is —(O)—;

R³ is selected from the group consisting of phenyl, 2-fluorophenyl and 2-methoxy-phenyl;

a is 0;

or a pharmaceutically acceptable salt thereof.

11. A compound as in claim 4 wherein
R⁰ is hydrogen; R¹ is hydrogen; A¹ is 1-(S)-cyclohexyl-n-propyl, Q¹ is selected from the group consisting of —C(O)— and —C(O)—N(cyclohexyl)-; R² is selected from the group consisting of 2-imidazolyl-methyl, 5-imidazolyl-methyl, 4-pyridyl-methyl, 2-carboxy-octahydroindolyl, 2R-(3R,4S,5R-tri(methoxy-carbonyl-oxy)-6R-(methyl-carbonyl-oxy-methyl)-tetrahydropyranyl)oxy-ethyl and 2R-(3S,4S,5R-trihydroxy-6R-(hydroxymethyl)-tetrahydropyranyl)oxy-ethyl; b is 1; R³ is phenyl; and a is 0; or a pharmaceutically acceptable salt thereof.

12. A compound of formula (I)

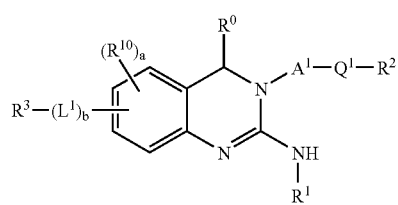

(I)

wherein
R⁰ is selected from the group consisting of hydrogen, methyl and CF₃;

R¹ is selected from the group consisting of hydrogen, hydroxy, methyl, ethyl, trifluoromethyl, 2,2,2-trifluoroethyl, methoxy, ethoxy and methyl-carbonyl;

A¹ is selected from $C_{1-4}$alkyl; wherein the $C_{1-4}$alkyl is optionally substituted with one or more $R^X$ substituents;

wherein each $R^X$ is independently selected from the group consisting of hydroxy, oxo, $C_{1-8}$alkyl, $C_{1-8}$alkoxy, hydroxy substituted $C_{1-6}$alkyl, amino substituted $C_{1-6}$alkyl, cycloalkyl, cycloalkyl-$C_{1-4}$alkyl-, biphenyl, aryl, $C_{1-4}$aralkyl, heteroaryl, heteroaryl-$C_{1-4}$alkyl-, heterocycloalkyl, heterocycloalkyl-$C_{1-4}$alkyl-, spiro-heterocyclyl and —($C_{1-4}$alkyl)$_n$-Q²-R⁴;

wherein the $R^X$ cycloalkyl, aryl, heteroaryl, heterocycloalkyl or spiro-heterocyclyl group, whether alone or as part of a substituent group is optionally substituted with a substituent selected from the group consisting of fluoro, chloro, hydroxy, oxo, carboxy, $C_{1-4}$alkyl, $C_{1-4}$alkoxy, —C(O)—($C_{1-4}$alkyoxy), hydroxy substituted $C_{1-4}$alkyl, fluoro substituted $C_{1-4}$alkyl, fluoro substituted $C_{1-4}$alkoxy, 5-tetrazolyl and 1-(1,4-dihydro-tetrazol-5-one);

wherein n is an integer from 0 to 1;

wherein Q² is selected from the group consisting of —O—, —S—, —C(O)—, —C(S)—, —C(O)O—, —OC(O)—, —NR^G—, —NR^G—C(O)—, —C(O)—NR^G—, —NR^G—SO₂—, —SO₂—NR^G, —NR^G—SO—, —SO—NR^G, —NR^G—C(O)O—, —OC(O)NR^G, —O—SO₂—NR^G—, —NR^G—SO₂—O—, —NR^G—C(O)—NR^H, —NR^GC(S)—NR^H— and —NR^G—SO₂—NR^H—;

wherein each R^G and R^H is independently selected from the group consisting of hydrogen, $C_{1-8}$alkyl, hydroxy substituted $C_{1-4}$alkyl, $C_{1-4}$aralkyloxy substituted $C_{1-4}$alkyl, cycloalkyl, aryl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;

wherein the independently selected R^G and R^H cycloalkyl aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, $C_{1-4}$alkyl, $C_{1-4}$alkoxy, $C_{1-4}$alkoxy-carbonyl, nitro, cyano, amino, $C_{1-4}$alkylamino, di($C_{1-4}$alkyl)amino, —SO₂—N(R^JR^K), 5-tetrazolyl and 1-(1,4-dihydro-tetrazol-5-one);

wherein each R^J and R^K is independently selected from the group consisting of hydrogen and $C_{1-4}$alkyl;

wherein R⁴ is selected from the group consisting of hydrogen, $C_{1-4}$alkyl, hydroxy substituted $C_{1-4}$alkyl, fluoro substituted $C_{1-4}$alkyl, cycloalkyl, aryl, biphenyl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;

wherein the R⁴ cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, —C(O)O—$C_{1-4}$alkyl, —C(O)—$C_{1-4}$alkyl, $C_{1-4}$alkyl, fluoro substituted $C_{1-4}$alkyl, $C_{1-4}$alkoxy, nitro, cyano, amino, $C_{1-4}$alkylamino, di($C_{1-4}$alkyl)amino and phenyl;

wherein the phenyl is optionally substituted with one or more substituent independently selected from the group consisting of halogen, hydroxy, oxo, carboxy, —C(O)O—$C_{1-4}$alkyl, —C(O)—$C_{1-4}$alkyl, $C_{1-4}$alkyl, fluoro substituted $C_{1-4}$alkyl, $C_{1-4}$alkoxy, nitro, cyano, amino, $C_{1-4}$alkylamino, di($C_{1-4}$alkyl)amino and —SO₂—N(R^ER^F);

wherein each R^E and R^F is independently selected from the group consisting of hydrogen and $C_{1-4}$alkyl;

Q¹ is selected from the group consisting of —O—, —S—, —C(O)—, —C(S)—, —C(O)O—, —OC(O)—, —NR^A—, —NR^A—C(O)—, —C(O)—NR^A—, —NR^A—C(S)—, —C(S)—NR^A—, —NR^A—SO₂—, —SO₂NR^A, —NR^A—SO—, —SO—NR^A, —NR^AC(O)O—, —OC(O)—NR^A—, —O—SO₂NR^A—, —NR^A—SO₂O—, —NR^A—C(O)—NR^B—, —NR^AC(S)—NR^B— and —NR^ASO₂—NR^B—;

wherein each R^A and R^B is independently selected from the group consisting of hydrogen, $C_{1-8}$alkyl, hydroxy substituted $C_{1-4}$alkyl, $C_{1-4}$aralkyloxy substituted $C_{1-4}$alkyl, cycloalkyl, aryl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;

wherein the independently selected R^A and R^B cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, $C_{1-4}$alkyl, $C_{1-4}$alkoxy, $C_{1-4}$alkoxy-carbonyl, nitro, cyano, amino, $C_{1-4}$alkylamino, di($C_{1-4}$alkyl)amino, —SO$_2$—N(R$^C$R$^D$), 5-tetrazolyl and 1-(1,4-dihydro-tetrazol-5-one);

wherein each R$^C$ and R$^D$ is independently selected from the group consisting of hydrogen and $C_{1-4}$alkyl;

R$^2$ is selected from the group consisting of $C_{1-10}$alkyl, cycloalkyl, aryl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;

wherein the R$^2$ $C_{1-10}$alkyl, cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, —C(O)—$C_{1-4}$alkyl, —C(O)—$C_{1-4}$aralkyl, —C(O)O—$C_{1-4}$alkyl, —C(O)O—$C_{1-4}$aralkyl, —$C_{1-4}$alkyl-C(O)O—$C_{1-4}$alkyl, —$C_{1-4}$alkyl-S—$C_{1-4}$alkyl, —C(O)—N(R$^L$R$^M$), —$C_{1-4}$alkyl-C(O)—N(R$^L$R$^M$), —NR$^L$—C(O)$C_{1-4}$alkyl, —SO$_2$—N(R$^L$R$^M$), —$C_{1-4}$alkyl-SO$_2$—N(R$^L$R$^M$), $C_{1-6}$alkyl, fluoro substituted $C_{1-4}$alkyl, hydroxy substituted $C_{1-4}$alkyl, carboxy substituted $C_{1-4}$alkyl, $C_{1-4}$alkoxy, nitro, cyano, amino, $C_{1-4}$alkylamino, di($C_{1-4}$alkyl)amino, phenyl, 5-tetrazolyl and 1-(1,4-dihydro-tetrazol-5-one);

wherein the phenyl is optionally substituted with one or more substituent independently selected from the group consisting of halogen, hydroxy, oxo, carboxy, —C(O)O—$C_{1-4}$alkyl, —C(O)—$C_{1-4}$alkyl, $C_{1-4}$alkyl, fluoro substituted $C_{1-4}$alkyl, $C_{1-4}$alkoxy, nitro, cyano, amino, $C_{1-4}$alkylamino and di($C_{1-4}$alkyl)amino;

wherein each R$^L$ and R$^M$ is independently selected from the group consisting of hydrogen and $C_{1-4}$alkyl;

b is an integer from 0 to 1;

L$^1$ is selected from the group consisting of —O—, —S(O)$_{0-2}$—, —NR$^N$—, —C(O)—, —C(S)—, —$C_{1-4}$alkyl-, -(hydroxy substituted $C_{1-4}$alkyl) and —(C$_{2-4}$alkenyl)-;

wherein R$^N$ is selected from the group consisting of hydrogen and $C_{1-4}$alkyl;

R$^3$ is selected from the group consisting of $C_{2-6}$alkenyl, cycloalkyl, partially unsaturated carbocyclyl, aryl, biphenyl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;

wherein the R$^3$ cycloalkyl, partially unsaturated carbocyclyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, $C_{1-4}$alkyl, hydroxy substituted $C_{1-4}$alkyl, halogen substituted $C_{1-4}$alkyl, cyano substituted $C_{1-4}$alkyl, $C_{2-4}$alkenyl, $C_{2-4}$alkynyl, halogen substituted $C_{1-4}$alkoxy, nitro, cyano, —R$^5$, —O—R$^5$, —S—R$^5$, —SO$_2$—R$^5$, —SO$_2$—NR$^P$—R$^5$, —NR$^P$—SO$_2$—R$^5$, —NH$_2$, —N(R$^P$)—R$^5$, —C(O)—R$^5$, —C(O)—NH$_2$, —C(O)—NR$^P$—R$^5$, —NR$^P$—C(O)—R$^5$ and —NR$^P$—C(O)O—R$^5$;

wherein R$^5$ is selected from the group consisting of $C_{1-4}$alkyl, aryl, $C_{1-4}$aralkyl, partially unsaturated carbocyclyl, cycloalkyl, cycloalkyl-$C_{1-4}$alkyl-, partially unsaturated carbocyclyl-$C_{1-4}$alkyl-, heteroaryl, heteroaryl-$C_{1-4}$alkyl-, heterocycloalkyl and heterocyclyl-$C_{1-4}$alkyl-;

wherein the R$^5$ aryl, $C_{1-4}$aralkyl, partially unsaturated carbocyclyl, cycloalkyl, heteroaryl or heterocycloalkyl, whether alone or as part of a substituent group may be optionally substituted with one or more substituent independently selected from the group consisting of $C_{1-4}$alkyl, $C_{1-4}$alkoxy, halogen, hydroxy, carboxy, amino, $C_{1-4}$alkylamino, di($C_{1-4}$alkyl)amino, cyano and nitro;

wherein R$^P$ is selected from the group consisting of hydrogen, $C_{1-8}$alkyl, hydroxy substituted $C_{1-4}$alkyl, $C_{1-4}$aralkyloxy substituted $C_{1-4}$alkyl, cycloalkyl, aryl, heteroaryl, heterocycloalkyl, cycloalkyl-$C_{1-4}$alkyl-, $C_{1-4}$aralkyl, heteroaryl-$C_{1-4}$alkyl-, heterocycloalkyl-$C_{1-4}$alkyl- and spiro-heterocyclyl;

wherein the R$^P$ cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, $C_{1-4}$alkyl, $C_{1-4}$alkoxy, $C_{1-4}$alkoxy-carbonyl, nitro, cyano, amino, $C_{1-4}$alkylamino, di($C_{1-4}$alkyl)amino, —SO$_2$—N(R$^S$R$^T$), 5-tetrazolyl and 1-(1,4-dihydro-tetrazol-5-one);

wherein each R$^S$ and R$^T$ is independently selected from the group consisting of hydrogen and $C_{1-4}$alkyl;

a is an integer from 0 to 3;

each R$^{10}$ is independently selected from the group consisting of hydroxy, halogen, $C_{1-4}$alkyl, $C_{1-4}$alkoxy, halogenated $C_{1-4}$alkyl, halogenated $C_{1-4}$alkoxy, —C(O)—NR$^V$R$^W$, —SO$_2$—NR$^V$R$^W$, —C(O)—$C_{1-4}$alkyl and —SO$_2$—$C_{1-4}$alkyl;

wherein each R$^V$ and R$^W$ is independently selected from the group consisting of hydrogen and $C_{1-4}$alkyl; alternatively R$^V$ and R$^W$ are taken together with the N atom to which they are bound to form a 5 to 6 membered saturated, partially unsaturated or aromatic ring structure;

provided that the halogens on the halogenated $C_{1-4}$alkyl or the halogenated $C_{1-4}$alkoxy are selected from chloro or fluoro;

or a pharmaceutically acceptable salt thereof.

13. A pharmaceutical composition comprising a pharmaceutically acceptable carrier and a compound of claim 1.

* * * * *

UNITED STATES PATENT AND TRADEMARK OFFICE
CERTIFICATE OF CORRECTION

| | | |
|---|---|---|
| PATENT NO. | : 8,383,637 B2 | Page 1 of 1 |
| APPLICATION NO. | : 11/197669 | |
| DATED | : February 26, 2013 | |
| INVENTOR(S) | : Baxter et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1780 days.

Signed and Sealed this
Eighteenth Day of November, 2014

Michelle K. Lee
*Deputy Director of the United States Patent and Trademark Office*